United States Patent [19]

Ogawa et al.

[11] Patent Number: 5,225,402
[45] Date of Patent: Jul. 6, 1993

[54] CARBOSTYRIL DERIVATIVES

[75] Inventors: Hidenori Ogawa; Hisashi Miyamoto, both of Tokushima; Kazumi Kondo, Naruto; Hiroshi Yamashita, Tokushima; Kenji Nakaya, Tokushima; Michiaki Tominaga, Tokushima; Yoichi Yabuuchi, Tokushima, all of Japan

[73] Assignee: Otsuka Pharmaceutical Co., Ltd., Tokyo, Japan

[21] Appl. No.: 762,736

[22] Filed: Sep. 18, 1991

Related U.S. Application Data

[63] Continuation of Ser. No. 478,181, Feb. 9, 1990, abandoned.

[30] Foreign Application Priority Data

Feb. 10, 1989 [JP] Japan ................................ 1-31580
Apr. 21, 1989 [JP] Japan ................................ 1-102699
Jul. 13, 1989 [JP] Japan ................................ 1-181440
Sep. 7, 1989 [JP] Japan ................................ 1-232333

[51] Int. Cl.$^5$ .................. C07H 5/04; C07D 215/227; C07D 295/195; A61K 31/47
[52] U.S. Cl. .................. 514/23; 514/222.8; 514/235.2; 514/63; 514/312; 514/255; 514/303; 514/310; 514/248; 514/259; 536/41; 536/173; 544/58.2; 544/62; 544/128; 544/363; 544/333; 544/284; 544/406; 544/235; 546/14; 546/118; 546/148; 546/157
[58] Field of Search .............. 514/222.8, 235.2, 63, 514/312, 255, 266, 303, 27, 310, 248, 259, 23; 546/157, 118, 14, 148; 544/58.2, 62, 333, 128, 363, 406, 284, 235, 80; 536/4.1, 17.3, 29.11; 540/593

[56] References Cited

U.S. PATENT DOCUMENTS 4,960,883 10/1990 Tanabe et al. .................. 544/363

FOREIGN PATENT DOCUMENTS 236140 9/1987 European Pat. Off. ............ 514/312
3054364 3/1988 Japan .................. 546/157

OTHER PUBLICATIONS

J. Med. Chem., 24(7), 777-782 (1981), "Opiate Receptor Interaction of Compounds Derived from or Structurally Related to Fentanyl".
Klein et al Arch. Pharm. 1974 307(5) 360-6 Chemical Abstracts, vol. 81, 1974 Abstract 77786r.
Lobbezoo, et al. J. Med. Chem. 1981 24 777-782.

*Primary Examiner*—Mukund J. Shah
*Assistant Examiner*—E. C. Ward
*Attorney, Agent, or Firm*—Sughrue, Mion, Zinn, Macpeak & Seas

[57] ABSTRACT

Novel carbostyril derivatives of the formula:

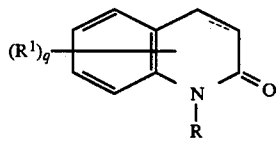

wherein $R^1$ is H, $NO_2$, alkoxy, alkoxycarbonyl, alkyl, halogen, optionally substituted amino, OH, CN, COOH, alkanoyloxy, hydrazinocarbonyl; q is 1 to 3, and R is a group of the formula

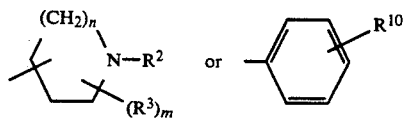

[wherein $R^2$ is H, alkoxycarbonyl, optionally substituted phenoxycarbonyl, phenylalkenyl-CO-, optionally substituted phenylalkanoyl, alkanoyl, alkenyl-CO-, optionally substituted phenyl—$SO_2$—, —$CONR^8R^9$, optionally substituted heterocyclic group—CO—, naphthyl—CO—, thienylalkanoyl, tricyclo[3.3.1.1]alkanoyl,

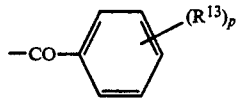

($R^{13}$ is OH, optionally substituted alkoxy, —$NR^{32}R^{33}$, —O—A—(E)$_t$—$NR^4R^5$, —(B)$_t'$$NR^6R^7$, etc.), n is 1 or 2, m is 0 or 1 to 3, $R^3$ is alkyl, $R^{10}$ is —(CO)$_t$—$NR^{11}R^{12}$], and the bond between 3- and 4-position of carbostyril nucleus is single or double bond, which have excellent vasopressin antagonistic activities and are useful as vasodilator, hypotensive agent, water diuretics, platelet agglutination inhibitor, and a vasopressin antagonistic composition containing the compound as the active ingredient.

55 Claims, No Drawings

CARBOSTYRIL DERIVATIVES

This is a continuation of application No. 07/478,181 filed Feb. 9, 1990, now abandoned.

This invention relates to novel carbostyril derivatives which have excellent vasopressin antagonistic activities and are useful as vasodilator, hypotensive agent, water diuretics, platelet agglutination inhibitor.

The carbostyril derivatives of this invention have the following formula:

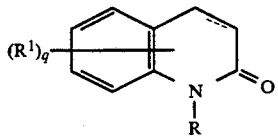
(1)

wherein $R^1$ is hydrogen atom; nitro; a lower alkoxy; a lower alkoxycarbonyl; a lower alkyl; a halogen atom; an amino having optionally one or two substituents selected from a lower alkanoyl, a lower alkyl, benzoyl and a phenyl(lower)alkoxycarbonyl; hydroxy; cyano; carboxy; a lower alkanoyloxy; or hydrazinocarbonyl, q is an integer of 1 to 3 ' and R is a group of the formula:

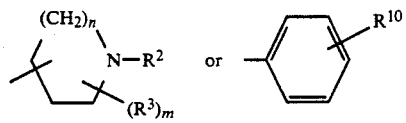

wherein $R^2$ is hydrogen atom; a lower alkoxycarbonyl; a phenoxycarbonyl which phenyl ring may optionally be substituted by one to three substituents selected from nitro and an amino having optionally one or two substituents selected from a lower alkanoyl, a lower alkyl and benzoyl; a phenyl(lower)alkenylcarbonyl; a phenyl(lower)alkanoyl which lower alkanoyl moiety may optionally be substituted by an amino having optionally a lower alkoxycarbonyl substituent; an alkanoyl; an alkenylcarbonyl; a phenylsulfonyl which phenyl ring may optionally be substituted by a lower alkoxy; a group of the formula:

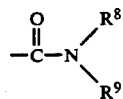

n $R^8$ and $R^9$ are the same or different and are each hydrogen atom or a phenyl which may optionally have one to three substituents selected from a lower alkoxy, a lower alkyl, a halogen atom, an amino having optionally one or two substituents selected from a lower alkyl and a lower alkanoyl, and nitro); a heterocyclic group-substituted carbonyl which heterocyclic group may optionally have one to three substituents selected from a phenyl(lower)alkoxycarbonyl, a phenyl(lower)alkoxy, oxo, a lower alkyl, and a lower alkylenedioxy); a group of the formula:

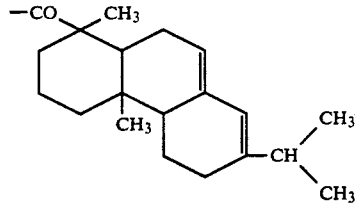

naphthylcarbonyl; thienyl(lower)alkanoyl; tricyclo[3.3.1.1]decanyl(lower)alkanoyl; tricyclo[3.3.1.1-]decanylcarbonyl; or a group of the formula:

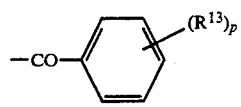

(wherein p is 0 or an integer of 1 to 3, and $R^{13}$ is hydroxy; an alkoxy; an alkoxy which has one or two substituents selected from hydroxy, a lower alkanoyloxy, a tri(lower)alkylammonium, a lower alkoxy, and a group of the formula

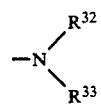

(wherein $R^{32}$ and $R^{33}$ are the same or different and are each hydrogen atom, a lower alkyl, a hydroxy-substituted lower alkyl, a lower alkanoyl, a tetrahydropyranyl(lower)alkyl, phenyl, a phenyl(lower)alkyl (wherein the alkyl moiety may optionally be substituted by hydroxy and the phenyl ring may optionally be substituted by a lower alkoxy), or a pyridyl(lower)alkyl; or $R^{32}$ and $R^{33}$ may bind with the nitrogen atom to which they bond to form a 5- or 6-membered, saturated heterocyclic group which may be intervened or not with nitrogen, oxygen or sulfur atom (wherein the heterocyclic group may optionally be substituted by a member selected from carbamoyl, a lower alkyl, a phenyl(lower)alkyl, phenyl and a hydroxysubstituted lower alkyl)]; a carboxy-substituted alkoxy; a halogen-substituted lower alkoxy; a lower alkoxycarbonylsubstituted alkoxy; a lower alkanoyloxy-substituted lower alkoxy; a lower alkenyloxy-substituted lower alkoxy; a lower alkoxy(lower)alkoxy; a lower alkylsulfonyloxy-substituted lower alkoxy; a benzoyloxy-substituted lower alkoxy; tricyclo[3.3.1.1]decanyl-substituted lower alkoxy; a lower alkoxy(lower)alkoxy which is substituted by one or two substituents selected from hydroxy and an amino being optionally substituted by a lower alkyl; a morpholinylsubstituted lower alkoxy which may optionally be substituted by a lower alkyl or oxo; a benzimidazolylthio-substituted lower alkoxy; a benzimidazolylsulfinyl-substituted lower alkoxy; a group of the formula:

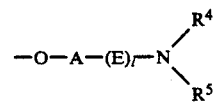

wherein A is an alkylene, l is an integer of 0 or 1, E is —CO— or —OCO—, $R^4$ and $R^5$ are the same or different and are each hydrogen atom; a lower alkyl which may optionally be substituted by hydroxy or cyano; a lower alkenyl; a lower alkynyl; a phenyl(lower)alkyl; a lower alkanoyl which may optionally have one to three substituents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a phenyl(lower)alkyl having optionally a lower alkoxy substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by a lower alkyl group, nitro or an amino having optionally one or two substituents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally substituted by a lower alkyl or a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholinyl wherein the heterocyclic group have optionally a substituent selected from a lower alkyl and phenyl; a piperidinylsubstituted carbonyl which may optionally be substituted by a lower alkanoyl; a lower alkanoyloxy(lower)alkyl; a pyridyl-substituted lower alkyl; or an amino acid residue which can form an amido group with its amino group, or $R_4$ and $R_5$ may bind together with the nitrogen atom to which they bond to form a 5- or 6-membered, saturated or unsaturated heterocyclic group which may be intervened or not with nitrogen, oxygen or sulfur atom, wherein the heterocyclic group may optionally be substituted by a member selected from a phenyl having optionally a substituent selected from a lower alkoxy and a halogen atom, oxo, hydroxy, a lower alkenyl, carboxy, a phenyl(lower)alkyl having optionally a hydroxy substituent on the lower alkyl moiety, a lower alkanoyl, a lower alkyl having optionally a hydroxy substituent, benzoyl, an amido having optionally a lower alkyl substituent, anilinocarbonyl, a benzoyl(lower)alkyl, a lower alkylsulfonyl, piperidinyl, pyrimidinyl, pyridyl, and a lower alkoxycarbonyl); a carbamoyloxy-substituted lower alkoxy; a lower alkylthio-substituted lower alkoxy; a lower alkylsulfonyl-substituted lower alkoxy; a lower alkylsulfinyl-substituted lower alkoxy; an alkenyloxy; phenoxy; a lower alkanoyloxy; a lower alkylsulfonyloxy; a lower alkynyloxy; a phenyl(lower)alkoxy; a cycloalkyl; a cycloalkyloxy; a cycloalkenyloxy; imidazo-[4,5-c]pyridylcarbonyl(lower)alkoxy; a group of the formula:

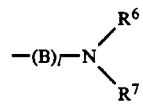

(wherein l is as defined above, B is a lower alkylene or a group of —CO—, and $R^6$ and $R^7$ are the same or different and are each hydrogen atom, a lower alkyl, a lower alkanoyl having optionally one to three halogen substituents, a carboxy(lower)alkyl, a lower alkoxycarbonyl, a lower alkoxycarbonyl(lower)alkyl, a lower alkenyl, an amidosubstituted lower alkyl having optionally a lower alkyl substituent, or a phenyl(lower)alkoxycarbonyl, or $R^6$ and $R^7$ may bind together with nitrogen atom to which they bond to form a 5- or 6-membered, saturated or unsaturated heterocyclic group which may be intervened or not with nitrogen, oxygen or sulfur atom, wherein the heterocyclic group may optionally have a substituent selected from a lower alkoxycarbonyl, a lower alkyl, a lower alkylthio, or oxo); nitro; a halogen atom; a lower alkylsulfonyl; a lower alkyl which may optionally have one to three substituents selected from a halogen atom, hydroxy, phenyl and a lower alkoxy; a cyano-substituted lower alkoxy; an oxilanyl-substituted lower alkoxy; a phthalimido-substituted alkoxy; an amidinosubstituted substituted lower alkoxy, a pyrrolyl-substituted lower alkoxy; cyano; a lower alkoxycarbonyl; amidino; carbamoyl; carboxy; a lower alkanoyl; benzoyl; a lower alkoxycarbonyl(lower)alkyl; a carboxy(lower)alkyl; a lower alkoxy(lower)alkyl; a lower alkanoyloxy(lower)alkyl; hydroxyiminosubstituted lower alkyl; phenyl; a lower alkylthio; a lower alkylsulfinyl; a lower alkenyl having optionally a hydroxy substituent; a lower alkylenedioxy, a lower alkylsilyl; a pyrimidylthio-substituted lower alkoxy; a pyrimidylsulfinylsubstituted lower alkoxy; a pyrmidylsufonyl-substituted lower alkoxy; an imidazolylthio-substituted lower alkoxy which may optionally have a lower alkyl substituent; an imidazolylsulfonyl-substituted lower alkoxy which may optionally have a lower alkyl substituent; an ammonium-lower alkoxy having three substituents selected from lower alkyl, lower alkenyl and oxo; a phenylthio-substituted lower alkoxy which phenyl ring may optionally have a substituent selected from nitro and amino; a phenylsulfonyl-substituted lower alkoxy which phenyl ring may optionally have a substituent selected from nitro and an amino having optionally one or two substituents selected from a lower alkanoyl and lower alkyl; a pyridylthio-substituted lower alkoxy; or a pyridylsuflonyl-substituted lower alkoxy which pyridyl ring may optionally be substituted by oxo), n is an integer of 1 or 2, m is 0 or an integer of 1 to 3, $R^3$ is a lower alkyl, $R^{10}$ is a group of the formula:

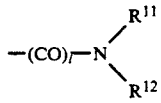

(wherein l is as defined above and R$^{12}$ and R$^{12}$ are the same or different and are each hydrogen atom, a lower alkyl, a phenyl(lower)alkyl, a lower alkenyl, a benzoyl which may optionally have a lower alkoxy substituent, tricyclo[3.3.1.1]decanyl, a phenyl which may optionally have a lower alkoxy substituent, or a cycloalkyl, or R$^{11}$ and R$^{12}$ may bind together with nitrogen atom to which they bond to form a saturated or unsaturated heterocyclic group which may be intervened or not with nitrogen, oxygen or sulfur atom, wherein the heterocyclic group may optionally have a substituent selected from a benzoyl, a lower alkanoyl, a phenyl(lower)alkyl and a phenyl which may optionally be substituted by a lower alkoxy and a lower alkanoyl), the bond between 3- and 4-positions of the carbostyril ring is single bond or double bond, provided that when R$^1$ is hydrogen atom and the l in the formula:

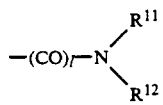

is 0, R$^{11}$ and R$^{12}$ are not simultaneously hydrogen atom.

The carbostyril derivatives of the formula (1) and their salts have excellent vasopressin antagonistic activities and vasodilating activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor and are used for the prophylaxis and treatment of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formula (1) includes specifically the following groups.

The "lower alkoxy" includes a straight chain or branched chain alkoxy group having 1 to 12 carbon atoms, for example, methoxy, ethoxy, propoxy, isopropoxy, butoxy, tertbutoxy, pentyloxy, hexyloxy, heptyloxy, octyloxy, nonyloxy, decyloxy, undecyloxy, dodecyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "halogen atom" includes fluorine atom, chlorine atom, bromine atom and iodine atome.

The "amino having optionally one or two substituents selected from a lower alkanoyl, a lower alkyl and benzoyl" includes an amino having one or two substituents selected from a straight chain or branched chain alkyl group having 1 to 6 carbon atoms, a straight chain or branched chain alkanoyl group having 1 to 6 carbon atoms and benzoyl group, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tertbutylcarbonylamino, N-hexanoylamino, N-ethyl-N-acetylamino, benzoylamino, N-methyl-N-benzoylamino, N-ethyl-N-benzoylamino, and the like.

The "amino having optionally one or two substituents selected from a lower alkanoyl and a lower alkyl" includes an amino having one or two substituents selected from a straight chain or branched chain alkyl group having 1 to 6 carbon atoms and a straight chain or branched chain alkanoyl group having 1 to 6 carbon atoms, for example, amino, methylamino, ethylamino, propylamino, isopropylamino, butylamino, tertbutylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-acetylamino, N-acetylamino, N-formylamino, N-propionylamino, N-butyrylamino, N-isobutyrylamino, N-pentanoylamino, N-tert-butylcarbonylamino, N-hexanoylamino, N-ethyl-N-acetylamino, and the like.

The "phenyl(lower)alkyl" includes a phenylalkyl group wherein the alkyl moiety is a straight chain or branched chain alkyl group having 1 to 6 carbon atoms, for example, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, and the like.

The "amino having optionally one or two substituents selected from a lower alkyl, phenyl and a phenyl(lower)alkyl" includes an amino having one or two substituents selected from a straight chain or branched chain alkyl group having 1 to 6 carbon atoms, phenyl and a phenylalkyl wherein the alkyl moiety is a straight chain or branched chain alkyl group having 1 to 6 carbon atoms, for example, amino, phenylamino, diphenylamino, methylamino, ethylamino, propylamino, isopropylamino, butylamino, tertbutylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-methyl-N-phenylamino, N-ethyl-N-phenylamino, N-benzylamino, N-(2-phenylethyl)amino, N-(1-phenylethyl)amino, N-(3-phenylpropyl)amino, N-(4-phenylbutyl)amino, N-(5-phenylpentyl)amino, N-(6-phenylhexyl)amino, N-(1,1-dimethyl-2-phenylethyl)amino, N-(2-methyl-3-phenylpropyl)amino, N-methyl-N-benzylamino, N-ethyl-N-benzylamino, N-phenyl-N-benzylamino, and the like.

The "alkoxy which has one or two substituents selected from hydroxy, a lower alkanoyloxy, a tri(lower)alkylammonium, a lower alkoxy, and a group of the formula:

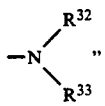

includes an alkoxy group having 1 to 10 carbon atoms which has one or two substituents selected from hydroxy, a straight chain or branched chain alkanoyloxy having 1 to 6 carbon atoms, a trialkylammonium group wherein the alkyl moiety is a straight chain or branched chain alkyl group having 1 to 6 carbon atoms, a straight chain or branched chain alkoxy group, having 1 to 6 carbon atoms, and a group of the formula

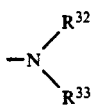

wherein $R^{32}$ and $R^{33}$ are the same or different and are each hydrogen atom, a straight chain or branched chain alkyl group having 1 to 6 carbon atoms, a hydroxy-substituted straight chain or branched chain alkyl group having 1 to 6 carbon atoms, a straight chain or branched chain alkanoyl group having 1 to 6 carbon atoms, a tetrahydropyranylalkyl group (wherein the alkyl moiety is straight chain or branched chain alkyl group having 1 to 6 carbon atoms, phenyl, a phenylalkyl wherein the alkyl moiety is straight chain or branched chain alkyl group having 1 to 6 carbon atoms which may optionally be substituted by hydroxy and the phenyl ring may optionally be substituted by one to three of straight chain or branched chain alkoxy group having 1 to 6 carbon atoms), or a pyridylalkyl wherein the alkyl moiety is straight chain or branched chain alkyl group having 1 to 6 carbon atoms, or $R^{32}$ and $R^{33}$ may bind with the nitrogen atom to which they bond to form a 5- or 6-membered, saturated heterocyclic group which may be intervened or not with nitrogen, oxygen or sulfur atom (wherein the heterocyclic group may optionally be substituted by one to three substituents selected from carbamoyl, a straight chain or branched chain alkyl group having 1 to 6 carbon atoms, a phenylalkyl group wherein the alkyl moiety is a straight chain or branched chain alkyl group having 1 to 6 carbon atoms, phenyl and a hydroxysubstituted alkyl group wherein the alkyl moiety is a straight chain or branched chain alkyl group having 1 to 6 carbon atoms], for example, hydroxymethoxy, 2-hydroxyethoxy, 1-hydroxyethoxy, 3-hydroxypropoxy, 2,3-dihydroxypropoxy, 4-hydroxybutoxy, 3,4-dihydroxybutoxy, 1,1-dimethyl-2-hydroxyethoxy, 5,6-dihydroxyhexyloxy, 5-hydroxypentyloxy, 6-hydroxyhexyloxy, 7-hydroxyheptyloxy, 8-hydroxyoctyloxy, 9-hydroxynonyloxy, 10-hydroxydecyloxy, 6-(3,4-dimethoxybenzylamino)-5-hydroxyhexyloxy, 6-(3-methoxybenzylamino)-5-hydroxyhexyloxy, 6-[2-(2-pyridyl)ethylamino]-5-hydroxyhexyloxy, 6-[N-methyl-N-(2-pyridylethyl)amino]-5-hydroxyhexyloxy, 6-(N-ethyl-N-[2-(2-pyridyl)ethylamino]-5-hydroxyhexyloxy, 6-[N-ethyl-N-(4-pyridylmethyl)amino]-5-hydroxyhexyloxy, 6-(3-pyridylmethylamino)-5-hydroxyhexyloxy, 6-(2-pyridylmethylamino)-5-hydroxyhexyloxy, 6-(diethylmethylammonium)-5-methoxyhexyloxy, 4-(trimethylammonium)-3-hydroxyhexyloxy, 5-(dipropylethylammonium)-4-acetyloxypentyloxy, 7-(2-ethoxybenzylamino)-6-acetyloxyheptyloxy, 8-(3,4,5-trimethoxybenzylamino)-7-ethoxyoctyloxy, 5-[3-(2pyridyl)propyl]-4-acetyloxypentyloxy, 7-[4-(3-pyridyl)butyl]-6-propoxyheptyloxy, 2-methyl-3-hydroxypropoxy, aminomethoxy, 1-aminoethoxy, 2-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, ethylaminomethoxy, propylaminomethoxy, isopropylaminomethoxy, butylaminomethoxy, tert-butylaminomethoxy, pentylaminomethoxy, hexylaminomethoxy, dimethylaminomethoxy, diethylaminomethoxy, dibutylaminomethoxy, dipentylaminomethoxy, dihexylaminomethoxy, N-methyl-N-ethylaminomethoxy, N-methyl-N-propylaminomethoxy, N-methyl-N-butylaminomethoxy, N-methyl-N-hexylaminomethoxy, 1-methylaminoethoxy, 2-ethylaminoethoxy, 3-propylaminopropoxy, 4-butylaminobutoxy, 1,1-dimethyl-2-pentylaminoethoxy, 5-hexylaminopentyloxy, 6-dimethylaminohexyloxy, 7-methylaminoheptyloxy, 8-dimethylaminooctyloxy, 4-dimethylaminobutoxy, 2-diethylaminoethoxy, 1-(N-methyl-N-hexylamino)ethoxy, 3-dihexylaminopropoxy, 6-diethylaminohexyloxy, 4-dibutylaminobutoxy, 9-(N-methyl-N-propylamino)nonyloxy, 2-(N-methyl-N-pentylamino)ethoxy, 7-hydroxy-8-dimethylaminooctyloxy, 2-hydroxy-3-diethylaminopropoxy, 7-hydroxy-8-diethylaminooctyloxy, 2-hydroxy-3-(N-phenyl-N-benzylamino)propoxy, 7-hydroxy-8-ethylaminooctyloxy, 3-hydroxy-4-methylaminobutoxy, 5-hydroxy-6-diethylaminohexyloxy, 3-hydroxy-4-phenylaminobutoxy, 8-hydroxy-9-dimethylaminononyloxy, 4-hydroxy-5-dimethylaminopentyloxy, 9-hydroxy-10-diethylaminodecyloxy, 4-hydroxy-5-methylaminopentyloxy, 4-hydroxy-5-diethylaminopentyloxy, phenylaminomethoxy, diphetnylaminomethoxy, benzylaminomethoxy, 5-hydroxy-6-benzylaminohexyloxy, 5-hydroxy-6-[N-methyl-N-(2-phenylethyl)amino]hexyloxy, 5-hydroxy-6-ethylaminohexyloxy, 5-hydroxy-6-isopropylaminohexyloxy, 5-hydroxy-6-(N-methyl-N-benzylamino)hexyloxy, 5-hydroxy-6-aminohexyloxy, (N-methylN-benzylamino)methoxy, (N-ethyl-N-benzylamino)methoxy, (N-phenyl-N-benzylamino)methoxy, 2-(phenylamino)ethoxy, 3-(2-phentylethylamino)propoxy, 4-(3-phenylpropylamino)butoxy, 1,1-dimethyl-2-(4-phenylbutylamino)ethoxy, 5-(5-phenylpentylamino)pentyloxy, 6-(6-phenylhexylamino)hexyloxy, 7-hydroxy-8-(N-phenyl-N-benzylamino)octyloxy, 8-hydroxy-9-[N-(2-phenylethyl)amino]nonyloxy, 9-hydroxy-10-(N-ethyl-N-benzylamino)decyloxy, acetyloxymethoxy, 2-propionyloxyethoxy, 1-butyryloxyethoxy, 3-acetyloxypropoxy, 4-isobutyryloxybutoxy, 5-pentanoyloxypentyloxy, 6-tert-butylcarbonyloxyhexyloxy, 1,1-dimethyl-2-hexanoyloxyethoxy, 2-methyl-3-acetyloxypropoxy, 7-acetyloxyheptyloxy, 8-acetyloxyoctyloxy, 9-acetyloxynonyloxy, 10-acetyloxydecyloxy, (hydroxymethyl)aminomethoxy, 1-[N,N-di-(2-hydroxyethyl)amino]ethoxy, 2-(3-hydroxypropyl)aminoethoxy, 3-(4-hydroxybutyl)aminopropoxy, 4-(5-hydroxypentyl)aminobutoxy, 5-(6-hydroxyhexyl)aminopentyloxy, 6-[N-(2-hydroxyethyl)-N-methylamino]hexyloxy, 5-hydroxy-6-[N-(2-hydroxyethyl)-N-methylamino]hexyloxy, 5-hydroxy-6-[N,N-di(2-hydroxyethyl)amino]hexyloxy, 6-hydroxy-7-[N-(2-hydroxyethyl)-N-benzylamino]heptyloxy, 7-hdroxy-8-[N-(3-hydroxypropyl)-N-phenylamino]octyloxy, 7-hydroxy-9-{N-(4-hydroxybutyl)-N-[(tetrahydropyranyl-2-yl)methyl]amino]nonyloxy, 8-hydroxy-10-[N-(2-hydroxyethyl)-N-acetylamino]decyloxy, acetylaminomethoxy, 2-(formylamino)ethoxy, 1-(propionylamino)ethoxy, 3-(butyrylamino)propoxy, 4-(isobutyrylamino)butyloxy, 5-(pentanoylamino)pentyloxy, 6-(hexanoylamino)hexyloxy, 5-acetyloxy-6-acetylaminohexyloxy, 5-hydroxy-6-acetylaminohexyloxy, 6-hydroxy-7-(N-methyl-N-acetylamino)heptyloxy, 7-hydroxy-8-(N-benzyl-N-acetylamino)octyloxy, 8-hydroxy-9-(N-phenyl-N- acetylamino)nonyloxy, 9-acetyloxy-10-[N-(tetrahydropyran-2-yl)methyl-N-acetylamino]decyloxy, (tetrahydropyran-2-yl)methylaminomethoxy, 2-[(tetrahydropyran-3-yl)methylamino]ethoxy, 1-[(tetrahydropyran-4-yl)methylamino]ethoxy, 3-[2-(tetrahydropyran-2-yl)ethylamino]propoxy, 4-[3-(tetrahydropyran-2-yl)propylamino]butoxy, 5-[4-(tetrahydropyran-2-yl)butylamino]pentyloxy, 5-hydroxy-6-[N-ethyl-N-(tetrahydropyran-2-yl)meth ylamino]hexyloxy, 6-hydroxy-7-(N-phenyl-N-[5-(tetrahydropyran-2-yl)pentylamino]-heptyloxy, 7-hydroxy-8-{N-benzyl-N-[6-(tetrahydropyran-2-yl)hexylamino)octyloxy, (2-hydroxy-2-phenylethyl)aminomethoxy, 2-[(3-hydroxy-3-phenylpropyl)amino]ethoxy, 3-[(2-hydroxy-4-phenylbutyl)amino]propoxy, 4-[(6-hydroxy-6-phenylhexyl)amino]butoxy, 5-[(2-hydroxy-2-phenylethyl)amino]pentyloxy, 5-hydroxy-6-[(2-hydroxy-2-phenylethyl)amino]hexyloxy, 6-hydroxy-7-[N-(2-hydroxy-2-phenylethyl)-N-methylamino]heptyloxy, 7-hydroxy-8-[N-(2-hydroxy-2-phenylethyl)-N-phenylamino]octyloxy, 8-hydroxy-9-[N-(2-hydroxy-2-phenylethyl)-N-benzylamino]-nonyloxy, 9-hydroxy-10-[N-(2-hydroxy-2-phenylethyl)-N-acetylamino]decyloxy, (piperazin-1-yl)methoxy, 2-(pyrrolidin-1-yl)ethoxy, 3-(piperidin-1-yl)propoxy, 4-morpholinobutoxy, 5-thiomorpholinopentyloxy, 6-(piperazin-1-yl)hexyloxy, 5-hydroxy-6-(4-benzyl-1-piperazinyl)hexyloxy, 5-hydroxy-6-(1-piperazinyl)hexyloxy, 5-hydroxy-6-(4-methyl-1-piperazinyl)hexyloxy, 4-hydroxy-5-(1-pyrrolidinyl)pentyloxy, 4-hydroxy-5-(1-piperidinyl)pentyloxy, 4-hydroxy-5-morpholinopentyloxy, 5-hydroxy-6-(1-pyrrolidinyl)hexyloxy, 5-hydroxy-6-(1piperidinyl)hexyloxy, 5-hydroxy-6-(4-phenyl-1-piperazinyl)hexyloxy, 5-hydroxy-6-(2-carbamoyl-1-pyrrolidinyl)hexyloxy, 7-hydroxy-8-(1-pyrrolidinyl)octyloxy, 5-hydroxy-6-(2-hydroxymethyl-1-pyrrolidinyl)hexyloxy, 7-(2-carbamoyl-morpholino)-6-hydroxyheptyloxy, 8-hydroxy-9-(4-benzyl-1- piperazinyl)nonyloxy, 4-(3-carbamoyl-1-piperidinyl))-3-hydroxybutoxy, 9-hydroxy-10-(4-ethyl-1-piperazinyl)-decyloxy, 6-(4-carbamoyl-1-piperazinyl)-5-hydroxyhexyloxy, and the like.

The "carboxy-substituted alkoxy" includes a carboxy-substituted alkoxy group wherein the alkoxy moiety is a straight chain or branched chain alkoxy group having 1 to 12 carbon atoms, for example, carboxymethoxy, 2-carboxyethoxy, 1-carboxyethoxy, 3-carboxypropoxy, 4-carboxybutoxy, 5-carboxypentyloxy, 6-carboxyhexyloxy, 1,1-dimethyl-2-carboxyethoxy, 2-methyl-3-carboxypropoxy, 7-carboxyheptyloxy, 8-carboxyoctyloxy, 9-carboxynonyloxy, 10-carboxydecyloxy, 11-carboxyundecyloxy, 12-carboxydodecyloxy, and the like.

The "lower alkoxycarbonyl-substituted alkoxy" includes an alkoxycarbonyl-substituted straight chain or branched chain alkoxy group having 1 to 12 carbon atoms wherein the alkoxycarbonyl moiety is a straight chain or branched chain alkoxycarbonyl group having 1 to 6 carbon atoms, for example, methoxycarbonylmethoxy, 3-methoxycarbonylpropoxy, ethoxycarboxymethoxy, 3-ethoxycarbonylpropoxy, 4-ethoxycarbonylbutoxy, 5-isopropoxycarbonylpentyloxy, 6-propoxycarbonylhexyloxy, 1,1-dimethyl-2-butoxycarbonylethoxy, 2-methyl-3-tert-butoxycarbonylpropoxy, 2-pentyloxycarbonylethoxy, hexyloxycarbonylmethoxy, 7-methoxycarbonylheptyloxy, 8-ethoxycarbonyloctyloxy, 9-propoxycarbonylnonyloxy, 10-butoxycarbonyldecyloxy, 11-methoxycarbonylundecyloxy, 12-ethoxycarbonyldodecyloxy, and the like.

The "lower alkanoyloxy-substituted lower alkoxy" includes a straight chain or branched chain alkoxy group having 1 to 6 carbon atoms which is substituted by a straight chain or branched chain alkanoyloxy group having 2 to 6 carbon atoms, for example, acetyloxymethoxy, 2-propionyloxyethoxy, 1-butyryloxyethoxy, 3-acetyloxypropoxy, 4isobutyryloxybutoxy, 5-pentanoyloxypentyloxy, 6-tertbutylcarbonyloxyhexyloxy, 1,1-dimethyl-2-hexanoyloxyethoxy, 2-methyl-3-acetyloxypropoxy, and the like.

The "lower alkenyloxy-substituted lower alkoxy" includes a straight chain or branched chain alkoxy group having 1 to 6 carbon atoms which is substituted by a straight chain or branched chain alkenyloxy group having 2 to 6 carbon atoms, for example, vinyloxymethoxy, 2-allyloxyethoxy, 1-(2-butenyloxy)ethoxy, 3-allyloxypropoxy, 4-(3-butenyloxy)butoxy, 5-(1-methylallyloxy)pentyloxy, 6-(2-pentenyloxy)hexyloxy, 1,1-dimethyl-2-(2-hexenyloxy)ethoxy, 2-methyl-3-allyloxypropoxy, and the like.

The "lower alkoxy(lower)alkoxy" includes a straight chain or branched chain alkoxy group having 1 to 6 carbon atoms which is substituted by a straight chain or branched chain alkoxy group having 1 to 6 carbon atoms, for example, methoxymethoxy, 3-methoxypropoxy, 4-ethoxybutoxy, 6-propoxyhexyloxy, 5-isopropoxypentyloxy, 1,1-dimethyl-2-butoxyethoxy, 2-methyl-3-tert-butoxypropoxy, 2-pentyloxy-ethoxy, hexyloxymethoxy, and the like.

The "lower alkylsulfonyloxy-substituted lower alkoxy" includes a straight chain or branched chain alkoxy group having 1 to 6 carbon atoms which is substituted by a straight chain or branched chain alkylsulfonyloxy group having 1 to 6 carbon atoms, for example, methylsulfonyloxymethoxy, 3-methylsulfonyloxypropoxy, 4-ethylsulfonyloxybutoxy, 2-methylsulfoyloxyethoxy, 6-propylsulfonyloxyhexyloxy, 5-isopropylsulfonyloxypentyloxy, 1,1-dimethyl-2-butylsulfoyloxyethoxy, 2-methyl-3-methlsulfonyloxypropoxy, and the like.

The "benzoyloxy-substituted lower alkoxy" includes a benzoyloxyalkoxy group wherein the alkoxy moiety is a straight chain or branched chain alkoxy group having 1 to 6 carbon atoms, for example, benzoyloxymethoxy, 2-benzoyloxyethoxy, 1-benzoyloxyethoxy, 3-benzoyloxypropoxy, 4-benzoyloxybutoxy, 6-benzoyloxyhexyloxy, 5-benzoyloxypentyloxy, 1,1-dimethyl-2-benzoyloxyethoxy, 2-methyl-3-benzoyloxypropoxy, and the like.

The "tricyclo[3.3.1.1]decanyl-substituted lower alkoxy" includes a tricyclo[3.3.1.1]decanyl-substituted straight chain or branched chain alkoxy group having 1 to 6 carbon atoms, for example, tricyclo[3.3.1.1-]decanylmethoxy, 2-tricyclo[3.3.1.1]decanylethoxy, 1-tricyclo[3.3.1.1]-decanylethoxy, 3-tricyclo[3.3.1.1-]decanylpropoxy, 4-tricyclo[3.3.1.1]decanylbutoxy, 5-tricyclo[3.3.1.1]decanylpentyloxy, 6-tricyclo[3.3.1.1-]decanylhexyloxy, 1,1-dimethyl2-tricyclo[3.3.1.1-]decanylethoxy, 2-methyl-3-tricyclo[3.3.1.1]decanylpropoxy, and the like.

The "lower alkylene" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyl" includes a straight chain or branched chain alkanoyl group having 1 to 6 carbon atoms, for example, formyl, acetyl, propionyl, butyryl, isobutyryl, pentanoyl, tert-butylcarbonyl, hexanolyl, and the like.

The "amino having optionally one or two substituents selected from a lower alkyl, a lower alkanoyl and a phenyl(lower)alkoxycarbonyl" includes an amino having one or two substituents selected from a straight chain or branched chain alkyl group having 1 to 6 carbon atoms, a straight chain or branched chain alkanoyl group having 1 to 6 carbon atoms and a phenylalkoxycarbonyl group wherein the alkoxy moiety is a straight chain or branched chain alkoxy group having 1 to 6 carbon atoms, for example, amino, methylamino, ethylamino, propylamino, isopropylamino, butylamino, tertbutylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, N-benzyloxycarbonylamino, N-(2-phenylethoxycarbonyl)amino, N-(1-phenylethoxycarbonyl)amino, N-(3-phenylpropoxycarbonyl)amino, N-(4-phenylbutoxycarbonyl)amino, N-(5-phenylpentyloxycarbonyl)amino, N-(6-phenylhexyloxycarbonyl)amino, N-(1,1-dimethyl-2-phenylethoxycarbonyl)amino, N-(2-methyl-3-phenylpropoxycarbonyl)amino, N-methyl-N-benzyloxycarbonylamino, N-ethyl-N-benzyloxycarbonylamino, acetylamino, formylamino, propionylamino, butyrylamino, isobutyrylamino, pentanoylamino, tert-butylcarbonylamino, hexanoylamino, N-methyl-N-acetylamino, N-ethyl-N-acetylamino, N-benzyloxycarbonyl-N-acetylamino, and the like.

The "benzoyl which phenyl ring may optionally has a substituent selected from nitro and an amino having optionally one or two substituents selected from a lower alkyl, a lower alkanoyl and a phenyl(lower)alkoxycarbonyl" includes a benzoyl group which phenyl ring may optionally have one to three substituents selected from nitro and an amino having one or two substituents selected from a straight chain or branched chain alkyl group having 1 to 6 carbon atoms, a straight chain or branched chain alkanoyl group having 1 to 6 carbon atoms and a phenylalkoxycarbonyl group wherein the alkoxy moiety is a straight chain or branched chain alkoxy group having 1 to 6 carbon atoms, for example, benzoyl, 2-aminobenzoyl, 4-aminobenzoyl, 4-methylaminobenzoyl, 3-ethylaminobenzoyl, 2-(N-methyl-N-ethylamino)benzoyl, 3-(N-methyl-N-hexylamino)benzoyl, 4-dimethylaminobenzoyl, 4-dipentylaminobenzoyl, 2-isopropylaminobenzoyl, 3-butylaminobenzoyl, 4-(N-methyl-N-benzyloxycarbonylamino)benzoyl, 2-[N-(2-phenylethoxycarbonyl)amino]benzoyl, 2,3-bis(dimethylamino)benzoyl, 3,4-bis(methylamino)benzoyl, 3,4,5-tri(methylamino)benzoyl, 2,6-di(N-methyl-N-benzyloxycarbonylamino)benzoyl, 3-[N-(3-phenylpropoxycarbonyl)amino]benzoyl, 4-[N-(5-phenylpentyloxycarbonyl)amino]benzoyl, 2-[N-(6-phenylhexyloxycarbonyl)amino]benzoyl, 3-[N-(4-phenylbutoxycarbonyl)amino]benzoyl, 4-acetylaminobenzoyl, 3-(N-methyl-N-acetylamino)benzoyl, 2-(N-benzyloxycarbonyl-N-acetylamino)benzoyl, 4-nitrobenzoyl, 4-nitro-3-methylaminobenzoyl, 2,4-dinitrobenzoyl, 2,4,6-trinitrobenzoyl, and the like.

The "lower alkoxycarbonyl" includes a straight chain or branched chain alkoxycarbonyl group having 1 to 6 carbon atoms in the alkoxy moiety, for example, methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, and the like.

The "lower alkoxycarbonyl(lower)alkyl" includes a straight chain or branched chain alkoxycarbonylalkyl group having 1 to 6 carbon atoms in the alkoxy moiety wherein the alkyl moiety is a straight chain or branched chain alkyl group having 1 to 6 carbon atoms, for example, methoxycarbonylmethyl, 3-methoxycarbonylpropyl, ethoxycarbonylmethyl, 4-ethoxycarbonylbutyl, 1-ethoxycarbonylethyl, 1-methoxycarbonylethyl, 6-propoxycarbonylhexyl, 5-isopropoxycarbonylpentyl, 1,1-dimethyl-2-butoxycarbonylethyl, 2-methyl-3-tertbutoxycarbonylpropyl, 2-pentyloxycarbonylethyl, hexyloxycarbonylmethyl, and the like.

The "amido having optionally a lower alkyl substituent" includes an amido having one or two substituents of a straight chain or branched chain alkyl group having 1 to 6 carbon atoms, for example, carbamoyl, methylamido, ethylamido, propylamido, isopropylamido, butylamido, tert-butylamido, pentylamido, hexylamido, dimethylamido, diethylamido, dipropylamido, dibutylamido, dipentylamido, dihexylamido, N-methyl-N-ethylamido, N-ethylN-propylamido, N-methyl-N-butylamido, N-methyl-N-hexylamido, and the like.

The "lower alkylsulfonyl" includes a straight chain or branched chain alkylsulfonyl group having 1 to 6 carbon atoms, for example, methylsulfonyl, ethylsulfonyl, isopropylsulfonyl, butylsulfonyl, tert-butylsulfonyl, pentylsulfonyl, hexylsulfonyl, and the like.

The "5- or 6-membered, saturated or unsaturated heterocyclic group which is formed by binding the groups $R^4$ and $R^5$ together with the nitrogen atom to which they bond and may be intervened or not with nitrogen, oxygen or sulfur atom" includes, for example, pyrrolidinyl, piperidinyl, piperazinyl, morpholino, thiomorpholino, pyrrolyl, pyrazolyl, imidazolyl, imidazolidinyl, 1,2,4-triazolyl, 1,2,3,4-tetrazolyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, and the like.

The "phenyl which may optionally have a substituent selected from a lower alkoxy and a halogen atom" includes a phenyl group which may optionally have one to three substituents selected from a straight chain or branched chain alkoxy group having 1 to 6 carbon atoms and a halogen atom, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, and the like.

The "heterocyclic group which may optionally be substituted by a member selected from a phenyl having optionally a subsitutent selected from a lower alkoxy and a halogen atom, oxo, hydroxy, a lower alkenyl, carboxy, a phenyl(lower)alkyl having optionally a hydroxy substituent on the lower alkyl moiety, a lower alkanoyl, a lower alkyl having optionally a hydroxy substituent, benzoyl, an amido having optionally a lower alkyl substituent, anilinocarbonyl, a benzoyl(lower)alkyl, a lower alkylsulfonyl, piperidinyl, pyrimidinyl, pyridyl, and a lower alkoxycarbonyl" includes the above-mentioned heterocyclic group which may optionally be substituted by one to three substituents selected from a phenyl having optionally one to three subsitutents selected from a straight chain or branched chain alkoxy group having 1 to 6 carbon atoms and a halogen atom, an oxo group, a hydroxy group, a straight chain or branched chain alkenyl group having 2 to 6 carbon atoms, carboxy, a phenylalkyl wherein the alkyl moiety is a straight chain or branched chain alkyl group having 1 to 6 carbon atoms and having optionally a hydroxy substituent, a straight chain or branched chain alkanoyl group having 1 to 6 carbon atoms, a straight chain or branched chain alkyl group having 1 to 6 carbon atoms and having optionally one to three hydroxy substituents, benzoyl, an amido group having optionally one or two substituents of a straight chain or branched chain alkyl group having 1 to 6 carbon atoms, anilinocarbonyl, a benzoylalkyl group wherein the alkyl moiety is a straight chain or branched chain alkyl group having 1 to 6 carbon atoms, a straight chain or branched chain alkylsulfonyl group having 1 to 6 carbon atoms in the alkyl moiety, piperidinyl, pyrimidinyl, pyridyl, and a straight chain or branched chain alkoxycarbonyl group having 1 to 6 carbon atoms, for example, 4-phenylpiperazinyl, 4-(4-methoxyphenyl)piperazinyl, 4-(4-chlorophenyl)piperazinyl, 3-(2-ethoxyphenyl)pyrrolidinyl, 2-(4-isopropoxyphenyl)pyrrolidinyl, 4-(4-pentyloxyphenyl)piperidinyl, 3-(4-hexyloxyphenyl)piperidinyl, 3-(2,3-dimethoxyphenyl)morpholino, 2-(2-methoxyphenyl)morpholino, 3-(3-ethoxyphenyl)thiomorpholino, 2-(3,4,5-trimethoxyphenyl)thiomorpholino, 4-(3,4-dimethoxyphenyl)piperazinyl, 4-(3,4,5-trimethoxyphenyl)piperazinyl, 3-(2-fluorophenyl)pyrrolidinyl, 2-(3-bromophenyl)pyrrolidinyl, 4-(3-iodophenyl)piperidinyl, 3-(4-bromophenyl)piperidinyl, 2-(3,4-dichlorophenyl)morpholino, 3-(3-chlorophenyl)morpholino, 3-(2-bromophenyl)thiomorpholino, 2-(4-fluorophenyl)thiomorpholino, 4-(3,4,5-trichlorophenyl)piperazinyl, 4-(2,6-dichlorophenyl)piperazinyl, 4-benzylpiperazinyl, 3-(2-phenylethyl)pyrrolidinyl, 2-(3-phenylpropyl)pyrrolidinyl, 4-(4-phenylbutyl)piperidinyl, 3-(5phenylpentyl)morpholino, 2-(6-phenylhexyl)thiomorpholino, 4-(2-phenyl-2-hydroxyethyl)piperidinyl, 3-(1-hydroxy-1phenylmethyl)pyrrolidinyl, 2-(3-hydroxy-3-phenylpropyl)pyrrolidinyl, 4-(2-hydroxy-4-phenylbutyl)piperidinyl, 2-(5-hydroxy-5-phenylpentyl)thiomorpholino, 3-(6-hydroxy-6-phenylhexyl)morpholino, 4-acetylpiperazinyl, 3-formylpyrrolidinyl, 2-propionylpyrrolidinyl, 4-butyrylpiperidinyl, 3-pentanoylthiomorpholino, 2-hexanoylmorpholino, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 2-hexylthiomorpholino, 4-benzoylpiperazinyl, 3-benzoylpyrrolidinyl, 3-benzoylmorpholino, 2-benzoylthiomorpholino, 3-benzoylpiperidinyl, 4-anilinocarbonylpiperazinyl, 2-anilinocarbonylpyrrolidinyl, 3-anilinocarbonylpiperidinyl, 2-anilinocarbonylmorpholino, 3-anilinocarbonylthiomorpholino, 4-(benzoylmethyl)piperazinyl, 3-(1-benzoylethyl)pyrrolidinyl, 2-(3-benzoylpropyl)pyrrolidinyl, 4-(4-benzoylbutyl)piperidinyl, 3-(5-benzoylpentyl)morpholino, 2-(6-benzoylhexyl)thiomorpholino, 3-methyl-4-benzoylpiperazinyl, 3-ethyl-4-acetylpiperidinyl, 3-methyl-4-benzylpyrrolidinyl, 3-propyl-4-anilinocarbonylpyrrolidinyl, 3-methyl-5-(benzoylmethyl)morpholino, 3-methyl-5-(2-phenyl-2-hydroxyethyl)thiomorpholino, 4-methylsulfonylpiperazinyl, 4-methoxycarbonylpiperazinyl, 3-ethylsulfonylpyrrolidinyl, 3-ethoxycarbonylpyrrolidinyl, 4-propylsulfonylpiperidinyl, 3-propoxycarbonylpiperidinyl, 3-butylsulfonylmorpholino, 2-pentyloxycarbonylmorpholino, 2-hexylsulfonylthiomorpholino, 3-hexyloxycarbonylthiomorpholino, 4-allylpiperazinyl, 4-ethoxycarbonylpiperidinyl, 4-carboxypiperidinyl, 4-dimethylamidopiperidinyl, 4-carbamoylpiperidinyl, 4-(1-piperidinyl)piperidinyl, 3-hydroxypiperidinyl, 2-carbamoylpyrrolidinyl, 2-hydroxymethylpiperidinyl, 2-hydroxymethylpyrrolidinyl, 3-hydroxymethylpiperidinyl, 3-hydroxypyrrolidinyl, 4-(2-hydroxyethyl)piperidinyl, 2-methoxycarbonylpyrrolidinyl, 2-(2-hydroxyethyl)piperidinyl, (2-pyrimidyl)piperazinyl, (2-pyridyl)piperazinyl, 2-methylimidazolyl, 3-methyl-1,2,4-triazolyl, 5-methyl-1,2,3,4-tetrazolyl, 4-hydroxymethylimidazolyl, 3-allyl-1,2,4-triazolyl, 5-phenyl-1,2,3,4-tetrazolyl, 3-carboxypyrrolyl, 2-hydroxyoxazolidinyl, 2-carbamoylthiazolidinyl, 4-oxothiomorpholino, 4,4-dioxothiomorpholino, and the like.

The "phenyl(lower)alkyl having optionally a hydroxy-substituent on the alkyl moiety and having optionally a lower alkoxy substituent on the phenyl ring" includes a phenylalkyl group wherein the alkyl moiety is a straight chain or branched chain alkyl group having 1 to 6 carbon atoms and having optionally a hydroxy-substituent and the phenyl ring has optionally one to three substituents of a straight chain or branched chain alkoxy group having 1 to 6 carbon atoms, for example, in addition to the abovementioned phenyl(lower)alkyl groups, 1-hydroxy-1-phenylmethyl, 1-phenyl-2-hydroxyethyl, 2-phenyl-2-hydroxyethyl, 3-hydroxy-3-phenylpropyl, 2-hydroxy-4-phenylbutyl, 6-hydroxy6-phenylhexyl, 3,4-dimethoxybenzyl, 3-methoxybenzyl, 1-(2-methoxyphenyl)ethyl, 2-(4-methoxyphenyl)ethyl, 3-(2-ethoxyphenyl)propyl, 4-(3-ethoxyphenyl)butyl, 5-(4-ethoxyphenyl)pentyl, 6-(4-isopropoxyphenyl)hexyl, 1,1-dimethyl-2-(4-pentyloxyphenyl)ethyl, 2-methyl-3-(4-hexyloxyphenyl)propyl, 3-ethoxy-4-methoxybenzyl, 2,3-dimethoxybenzyl, 3,4-diethoxybenzyl, 3,4,5-trimethoxybenzyl, 1-hydroxy-1-(3-methoxyphenyl)methyl, 1-(2,5-dimethoxyphenyl)-2-hydroxyethyl, 2-(2,6-dimethoxyphenyl)-2-hydroxyethyl, 5-hydroxy-5-(3,4-dipentyloxyphenyl)pentyl, and the like.

The "benzoyl(lower)alkyl" includes a benzoylalkyl group wherein the alkyl moiety is a straight chain or branched chain alkyl group having 1 to 6 carbon atoms, for example, benzoylmethyl, 1-benzoylethyl, 2-benzoylethyl, 3-benzoylpropyl, 4-benzoylbutyl, 5-benzoylpentyl, 6benzoylhexyl, 1,1-dimethyl-2-benzoylethyl, 2-methyl-3benzoylpropyl, and the like.

The "carbamoyloxy-substituted lower alkoxy" includes a carbamoyloxy-substituted alkoxy group wherein the alkoxy moiety is a straight chain or branched chain alkoxy group having 1 to 6 carbon atoms, for example, carbamoyloxymethoxy, 2-carbamoyloxyethoxy, 1-carbamoyloxyethoxy, 3-carbamoyloxypropoxy, 4-carbamoyloxybutoxy, 5-carbamoyloxypentyloxy, 6-carbamoyloxyhexyloxy, 1,1-dimethyl-2-carbamoyloxyethoxy, 2-methyl-3-carbamoyloxypropoxy, and the like.

The "lower alkylthio-substituted alkoxy" includes a alkylthio-substituted straight chain or branched chain alkoxy group having 1 to 6 carbon atoms wherein the alkylthio moiety is a straight chain or branched chain alkylthio group having 1 to 6 carbon atoms, for example, methylthiomethoxy, 3-ethylthiopropoxy, 4-methylthiobutoxy, 2-methylthioethoxy, 6-propylthiohexyloxy, 5-isopropylthiopentyloxy, 1,1-dimethyl-2-butylthioethoxy, 2-methyl-3-methylthiopropoxy, and the like.

The "lower alkylsulfonyl-substituted lower alkoxy" includes a straight chain or branched chain alkoxy group having 1 to 6 carbon atoms which is substituted by a straight chain or branched chain alkylsulfonyl group having 1 to 6 carbon atoms, for example, methylsulfonylmethoxy, 3-ethylsulfonylpropoxy, 4-methylsulfonylbutoxy, 2-methylsulfoylethoxy, 6-propylsulfonylhexyloxy, 5-isopropylsulfonylpentyloxy, 1,1-dimethyl-2-butylsulfoylethoxy, 2-methyl-3-methylsulfonylpropoxy, and the like.

The "lower alkylsulfinyl-substituted lower alkoxy" includes a straight chain or branched chain alkoxy group having 1 to 6 carbon atoms which is substituted by a straight chain or branched chain alkylsulfinyl group having 1 to 6 carbon atoms, for example, methylsulfinylmethoxy, 3-ethylsulfinylpropoxy, 4-methylsulfinylbutoxy, 2-methylsulfinylethoxy, 6-propylsulfinylhexyloxy, 5-isopropylsulfinylpentyloxy, 1,1-dimethyl-2-butylsulfinylethoxy, 2-methyl-3-methylsulfinylpropoxy, and the like.

The "lower alkenyloxy" includes a straight chain or branched chain alkenyl group having 2 to 12 carbon atoms and containing one to three double bonds, for example, vinyloxy, allyloxy, 3-methyl-2-butenyloxy, 2-butenyloxy, 3-butenyloxy, 1-methylallyloxy, 2-pentenyloxy, 2-hexenyloxy, 1-heptenyloxy, 1-octenyloxy, 1-nonenyloxy, 1-decenyloxy, 1-undecenyloxy, 1-dodecenyloxy, 2-heptenyloxy, 3-heptenyloxy, 2-methyl4-heptenyloxy, 2-methyl-5-heptenyloxy, 4-methyl-2-heptenyloxy, 3-methyl-1-heptenyloxy, 1,3-heptadienyloxy, 1,4-heptadienyloxy, 1,5-heptadienyloxy, 1,6-heptadienyloxy, 2,4-heptadienyloxy, 2-methyl-2,4-heptadienyloxy, 2,6-dimethyl2,4-heptadienyloxy, 2,5-dimethyl-1,3-heptadienyloxy, 2,4,6-trimethyl-2,4-heptadienyloxy, 2-octenyloxy, 3-octenyloxy, 4octenyloxy, 2-methyl-5-octenyloxy, 2-methyl-6-octenyloxy, 2-methyl-7-octenyloxy, 1,3-octadienyloxy, 1,4-octadienyloxy, 1,5-octadienyloxy, 1,6-octadienyloxy, 1,7-octadienyloxy, 2,4-octadienyloxy, 3,7-octadienyloxy, 4,8-dimethyl-3,7-octadienyloxy, 2,4,6-trimethyl-3,7-octadienyloxy, 3,4-dimethyl-2,5-octadienyloxy, 3,7-dimethyl-2,6-octadienyloxy, 4,8-dimethyl-2,6-octadienyloxy, 2-nonenyloxy, 3-nonenyloxy, 4-nonenyloxy, 2-methyl-5-nonenyloxy, 2-methyl-6-nonenyloxy, 2-methyl-7-nonenyloxy, 2-methyl-8-nonenyloxy, 1,3-nonadienyloxy, 1,4-nonadienyloxy, 1,5-nonadienyloxy, 1,6-nonadienyloxy, 1,7-nonadienyloxy, 1,8-nonadienyloxy, 2,4-nonadienyloxy, 3,7-nonadienyloxy, 4,8-dimethyl-3,7-nonadienyloxy, 2,4,6-trimethyl-3,7-nonadienyloxy, 3,4-dimethyl-2,5-nonadienyloxy, 4,8-dimethyl-2,6-nonadienyloxy, 2-decenyloxy, 3-decenyloxy, 4-decenyloxy, 5-decenyloxy, 2-methyl-6-decenyloxy, 3-methyl-7-decenyloxy, 4-methyl-8-decenyloxy, 5-methyl-9-decenyloxy, 1,3-decadienyloxy, 1,4-decadienyloxy, 1,5-decadienyloxy, 1,6-decadienyloxy, 1,7-decadienyloxy, 1,8-decadienyloxy, 1,9-decadienyloxy, 2-methyl-2,4-decadienyloxy, 3-methyl-2,5-decadienyloxy, 4,8-dimethyl-2,6-decadienyloxy, 2,4,6-trimethyl-3,7-decadienyloxy, 2,9-dimethyl-3,7-decadienyloxy, 2-undecenyloxy, 3-undecenyloxy, 4-undecenyloxy, 5-undecenyloxy, 2-methyl-6-undecenyloxy, 3-methyl-7-undecenyloxy, 4-methyl-8-undecenyloxy, 5-methyl-9-undecenyloxy, 2-methyl-10-undecenyloxy, 1,3-undecadienyloxy, 1,4-undecadienyloxy, 1,5-undecadienyloxy, 1,6-undecadienyloxy, 1,7-undecadienyloxy, 1,8-undecadienyloxy, 1,9-undecadienyloxy, 1,10-undecadienyloxy, 2-methyl-2,4-undecadienyloxy, 3-methyl-2,5-undecadienyloxy, 4,8-dimethyl-2,6-undecadienyloxy, 2,4,6-trimethyl-3,8-undecadienyloxy, 2,9-dimethyl-3,8-undecadienyloxy, 2-dodecenyloxy, 3-dodecenyloxy, 4-dodecenyloxy, 5-dodecenyloxy, 6-dodecenyloxy, 2-methyl-7-dodecenyloxy, 3-methyl-8-dodecenyloxy, 4-methyl-9-dodecenyloxy, 5-methyl-10-dodecenyloxy, 6-methyl-11-dodecenyloxy, 2-methyl-2,4-dodecadienyloxy, 3-methyl-2,5-dodecadienyloxy, 4,8-dimethyl-2,6-dodecadienyloxy, 2,4,6-trimethyl-2,7-dodecadienyloxy, 2,10-dimethyl-2,8-dodecadienyloxy, 2,5-dimethyl-3,7-dodecadienyloxy, 4,8,12-trimethyl-3,7,11-dodecatrienyloxy, 1,3,5-heptatrienyloxy, 2,4,6-octatrienyloxy, 1,3,6-nonatrienyloxy, 2,6,8-dodecatrienyloxy, 1,5,7-undecatrienyloxy, and the like.

The "lower alkanoyloxy" includes a straight chain or branched chain alkanoyloxy group having 1 to 6 carbon atoms, for example, formyloxy, acetyloxy, propionyloxy, butyryloxy, isobutyryloxy, pentanoyloxy, tert-butylcarbonyloxy, hexanoyloxy, and the like.

The "lower alkylsulfonyl" includes a straight chain or branched chain alkylsulfonyloxy group having 1 to 6 carbon atoms, for example, methylsulfonyloxy, ethylsulfonyloxy, isopropylsulfonyloxy, butylsulfoyloxy, tert-butylsulfonyloxy, pentylsulfonyloxy, hexylsulfonyloxy, and the like.

The "lower alkynyloxy" includes a straight chain or branched chain alkynyloxy group having 2 to 6 carbon atoms, for example, ethynyloxy, 2-propynyloxy, 2-butynyloxy, 3-butynyloxy, 1-methyl-2-propynyloxy, 2-pentynyloxy, 2-hexynyloxy, and the like.

The "phenyl(lower)alkoxy" includes a phenylalkoxy group wherein the alkoxy moiety is a straight chain or branched chain alkoxy group having 1 to 6 carbon atoms, for example, benzyloxy, 2-phenylethoxy, 1-phenylethoxy, 3-phenylpropoxy, 4-phenylbutoxy, 5-phenylpentyloxy, 6-phenylhexyloxy, 1,1-dimethyl-2-phenylethoxy, 2-methyl-3-phenylpropoxy, and the like.

The "cycloalkoxy" includes a cycloalkyloxy group having 3 to 8 carbon atoms, for example, cyclopropyloxy, cyclopentyloxy, cyclohexyloxy, cycloheptyloxy, cyclooctyloxy, and the like.

The "cycloalkenyloxy" includes a cycloalkenyloxy group having 3 to 8 carbon atoms, for example, cyclopropenyloxy, cyclobutenyloxy, cyclopentenyloxy, cyclohexenyloxy, cycloheptenyloxy, cyclooctenyloxy, and the like.

The "lower alkanoyl which may optionally have one to three substituents of a halogen atom" includes a straight chain or branched chain alkanoyl group having 1 to 6 carbon atoms which may optionally have one to three substituents of a halogen atom, for example, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkylthio" includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The "5- or 6-membered, saturated or unsaturated heterocyclic group which is formed by binding $R^6$ and $R^7$ together with the nitrogen atom to which they bond and may be intervened or not with nitrogen, oxygen or sulfur atom" includes, for example, pyrrolidinyl, piperidinyl, piperazinyl, morpholino, thiomorpholino, pyrrolyl, pyrazolyl, imidazolyl, imidazolidinyl, pyrrolyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, and the like.

The "heterocyclic group having a substituent selected from a lower alkoxycarbonyl, lower alkyl, lower alkylthio or oxo" includes the above heterocyclic groups which have a substituent selected from a straight chain or branched chain alkoxycarbonyl group having 1 to 6 carbon atoms, a straight chain or branched chain alkyl group having 1 to 6 carbon atoms, a straight chain or branched chain alkylthio group having 1 to 6 carbon atoms, and an oxo group, for example, 4-tert-butoxycarbonylpiperazinyl, 4-methylpiperazinyl, 2-ethylthioimidazolyl, 2-oxopyrrolidinyl, 2-oxo-oxazolidinyl, 3-oxopiperazinyl, 4-methoxycarbonylpiperazinyl, 3-ethoxycarbonylpiperidinyl, 2-propoxycarbonylpyrrolidinyl, 3-pentyloxycarbonylthiomorpholino, 2-hexyloxycarbonylthiomorpholino, 3-ethoxycarbonylpyrrolyl, 3-methoxycarbonylimidazolyl, 3-ethylpiperidinyl, 3-propylpyrrolidinyl, 3-butylpyrrolyl, 2-pentylimidazolyl, 3-hexylmorpholino, 2-methylthiomorpholino, 2-methyloxazolidinyl, 2-ethylthiazolinyl, 3-methylisoxazolinyl, 2-methylthioimidazolyl, 2-propylthioimidazolinyl, 2-butylthioimidazolidinyl, 3-pentylthiopyrrolyl, 3-hexylthiopyrrolinyl, 3-methylthiopyrrolidinyl, 3-ethylthiomorpholino, 2-methylthiomorpholino, 2-methylthioisoxazalidinyl, and the like.

The "lower alkyl which may optionally have one to three substituents selected from a halogen atom, hydroxy, phenyl and a lower alkoxy" includes a straight chain or branched chain alkyl group having 1 to 6 carbon atoms which may optionally have one to three substituents selected from a halogen atom, hydroxy, phenyl and a straight chain or branched chain alkoxy group having 1 to 6 carbon atoms, for example, in addition to the above-mentioned lower alkyl groups, hydroxymethyl, 2-hydroxyethyl, 1-hydroxyethyl, 3-hydroxypropyl, 2,3-dihyroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, benzyl, 1-phenylethyl, 2-phenylethyl, 3-phenylpropyl, 4-phenylbutyl, 1,1-dimethyl-2-phenylethyl, 5-phenylpentyl, 6-phenylhexyl, 2-methyl-3-phenylpropyl, methoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, hexyloxymethyl, dimethoxymethyl, 2,3-dimethoxyethyl, 6,6,5-trimethoxyhexyl, 1-hydroxy-1-phenylmethyl, 1-hydroxy-2-phenylethyl, 1-hydroxy-3-phenylpropyl, 1-methoxy-1-phenylmethyl, and the like.

The "cyano-substituted lower alkoxy" includes a straight chain or branched chain alkoxy group having 1 to 6 carbon atoms which is substituted by cyano group, for example, cyanomethoxy, 2-cyanoethoxy, 1-cyanoethoxy, 3-cyanopropoxy, 4-cyanobutoxy, 5-cyanopentyloxy, 6-cyanohexyloxy, 1,1-dimethyl-2-caynoethoxy, 2-methyl-3-cyanopropoxy, and the like.

The "oxilanyl-substituted lower alkoxy" includes a straight chain or branched chain alkoxy group having 1 to 6 carbon atoms which is substituted by oxilanyl group, for example, glycidoxy, 2-oxilanylethoxy, 1-oxilanylethoxy, 3-oxilanylpropoxy, 4-oxilanylbutoxy, 5-oxilanylpentyloxy, 6-oxilanylhexyloxy, 1,1-dimethyl-2-oxilanylethoxy, 2-methyl-3-oxilanylpropoxy, and the like.

The "phthalimido-substituted alkoxy" includes a straight chain or branched chain alkoxy group having 1 to 12 carbon atoms which is substituted by phthalimido group, for example, phthalimidomethoxy, 2-phthalimidoethoxy, 1-phthalimidoethoxy, 3-phthalimidopropoxy, 4-phthalimidobutoxy, 5-phthalimidopentyloxy, 6-phthalimidohexyloxy, 1,1-dimethyl-2-phthalimidoethoxy, 2-methyl-3-phthalimidopropoxy, 7-phthalimidoheptyloxy, 8-phthalimidooctyloxy, 9-phthalimidononyloxy, 10-phthalimidodecyloxy, 11-phthalimidoundecyloxy, 12-phthalimidododecyloxy, and the like.

The "pyrrolyl-substituted lower alkoxy" includes a straight chain or branched chain alkoxy group having 1 to 6 carbon atoms which is substituted by pyrrolyl group, for example, (1-pyrrolyl)methoxy, 2-(2-pyrrolyl)ethoxy, 1-(3-pyrrolyl)ethoxy, 3-(1-pyrrolyl)propoxy, 4-(1-pyrrolyl)butoxy, 5-(2-pyrrolyl)pentyloxy, 6-(3-pyrrolyl)hexyloxy, 1,1-dimethyl-2-(1-pyrrolyl)ethoxy, 2-methyl-3-(1-pyrrolyl)propoxy, and the like.

The "amidino-substituted lower alkoxy" includes a straight chain or branched chain alkoxy group having 1 to 6 carbon atoms which is substituted by amidino group, for example, amidinomethoxy, 2-amidinoethoxy, 1-amidinoethoxy, 3-amidinopropoxy, 4-amidinobutoxy, 5-amidinopentyloxy, 6-amidinohexyloxy, 1,1-dimethyl-2-amidinoethoxy, 2-methyl-3-amidinopropoxy, and the like.

The "lower alkanoyloxy(lower)alkyl" includes a straight chain or branched chain alkyl group having 1 to 6 carbon atoms which is substituted by a straight chain or branched chain alkanoyloxy group having 2 to 6 carbon atoms, for example, acetyloxymethyl, 2-propionyloxyethyl, 1butyryloxyethyl, 3-acetyloxypropyl, 4-isobutyryloxybutyl, 5-pentanoyloxypentyl, 6-tert-butylcarbonyloxyhexyl, 1,1-dimethyl-2-hexanoyloxyethyl, 2-methyl-3-acetyloxypropyl, and the like.

The "lower alkylsulfinyl" includes a straight chain or branched chain alkylsulfinyl group having 1 to 6 carbon atoms, for example, methylsulfinyl, ethylsulfinyl, isopropylsulfinyl, butylsulfiyl, tert-butylsulfinyl, pentylsulfinyl, hexylsulfinyl, and the like.

The "lower alkenyl having optionally a hydroxysubstituent" include a straight chain or branched chain alkenyl group having 2 to 6 carbon atoms and having optionally a hydroxy-substituent, for example, in addition to the above-mentioned alkenyl groups, 1-hydroxyallyl, 4-hydroxy-1-butenyl, 4-hydroxy-2-butenyl, 2- hydroxy-3-butenyl, 5-hydroxy 2 pentenyl, 6-hydroxy-2-hexenyl, and the like.

The "lower alkylenedioxy" includes a straight chain or branched chain alkylenedioxy group having 1 to 4 carbon atoms, for example, methylenedioxy, ethylenedioxy, trimethylenedioxy, tetramethylenedioxy, and the like.

The lower alkylsilyl includes a silyl group having one to three substituents of a straight chain or branched chain alkyl group having 1 to 6 carbon atoms, for example, methylsilyl, ethylsilyl, propylsilyl, isopropylsilyl, butylsilyl, tert-butylsilyl, pentylsilyl, hexylsilyl, dimethylsilyl, trimethylsilyl, dimethyl-tert-butylsilyl, and the like.

The "amino which may optionally substituted by a lower alkanoyl" includes an amino which may optionally substituted by a straight chain or branched chain alkanoyl group having 1 to 6 carbon atoms, for example, amino, formylamino, acetylamino, propionylamino, butyrylamino, isobutyrylamino, pentanoylamino, tert-butylcarbonylamino, hexanoylamino, and the like.

The "phenoxycarbonyl which may optionally have one to three substituents selected from nitro and an amino having optionally one or two substituents selected from a lower alkanoyl, lower alkyl and benzoyl" includes a phenoxycarbonyl group which may optionally have one to three substituents selected from nitro group and an amino group having optionally one or two substituents selected from a straight chain or branched chain alkanoyl group having 1 to 6 carbon atoms, a straight chain or branched chain alkyl group having 1 to 6 carbon atoms and benzoyl group, for example, phenoxycarbonyl, 2-nitrophenoxycarbonyl, 3-nitrophenoxycarbonyl, 4-nitrophenoxycarbonyl, 3,4-dinitrophenoxycarbonyl, 2,5-dinitrophenoxycarbonyl, 2,6-dinitrophenoxycarbonyl, 3,4,5-trinitrophenoxycarbonyl, 2-aminophenoxycarbonyl, 3-aminophenoxycarbonyl, 4-aminophenoxycarbonyl, 3-acetylaminophenoxycarbonyl, 4-formylaminophenoxycarbonyl, 4-isobutyrylaminophenoxycarbonyl, 2-pentanoylaminophenoxycarbonyl, 3-hexanoylaminophenoxycarbonyl, 3,4-diacetylaminophenoxycarbonyl, 3,4-diaminophenoxycarbonyl, 2,6-diaminophenoxycarbonyl, 2,5-diaminophenoxycarbonyl, 2,4,6-triaminophenoxycarbonyl, 4-acetylaminophenoxycarbonyl, 4-dimethylaminophenoxycarbonyl, 4-benzoylaminophenoxycarbonyl, 3-(N-methylN-benzoylamino)phenoxycarbonyl, 2-(N-ethyl-N-acetylamino)phenoxycarbonyl, and the like.

The "phenyl(lower)alkenylcarbonyl" includes a phenylalkenylcarbonyl group wherein the alkenylcarbonyl moiety is a straight chain or branched chain alkenylcarbonyl group having 3 to 6 carbon atoms, for example, cinnamoyl, 4-phenyl-3-butenoyl, 4-phenyl-2-butenoyl, 5-phenyl-4pentenoyl, 5-phenyl-3-pentenoyl, 5-phenyl-2-pentenoyl, 6-phenyl-5-hexenoyl, 6-phenyl-4-hexenoyl, 6-phenyl-3-hexenoyl, 6-phenyl-2-hexenoyl, 2-methyl-4-phenyl-3-butenoyl, and the like.

The "amino having optionally a lower alkoxycarbonyl substituent" includes an amino being optionally substituted by a straight chain or branched chain alkoxycarbonyl group having 1 to 6 carbon atoms, for example, amino, methoxycarbonylamino, ethoxycarbonylamino, propoxycarbonylamino, isopropoxycarbonylamino, butoxycarbonylamino, tert-butoxycarbonylamino, pentyloxycarbonylamino, hexyloxycarbonylamino, and the like.

The "phenyl(lower)alkanoyl wherein the lower alkanoyl moiety may optionally be substituted by an amino having optionally a lower alkoxycarbonyl substituent" includes a phenylalkanoyl wherein the alkanoyl moiety is a straight chain or branched chain alkanoyl group having 2 to 6 carbon atoms and may optionally be substituted by an amino group which may optionally be substituted by a straight chain or branched chain alkoxycarbonyl group having 1 to 6 carbon atoms, for example, phenylacetyl, 3-phenylpropionyl, 2-phenylpropionyl, 4-phenylbutyryl, 2,2-dimethyl-3phenylpropionyl, 5-phenylpentanoyl, 6-phenylhexanoyl, 3-methyl-4-phenylbutyryl, 2-amino-4-phenylacetyl, 2-tertbutoxycarbonylamino-2-phenylacetyl, 2-methoxycarbonylamino-2-phenylacetyl, 2-ethoxycarbonylamino-3-phenylpropionyl, 2-propoxycarbonylamino-4-phenylbutyryl, 2-pentyloxycarbonylamino-5-phenylpentanoyl, 2-hexyloxycarbonylamino-6-phenylhexanoyl, nd the like.

The "alkanoyl" includes a straight chain or branched chain alkanoyl group having 1 to 12 carbon atoms, for example, in addition to the above-mentioned lower alkanoyl groups, heptanoyl, octanoyl, nonanoyl, decanoyl, undecanoyl, dodecanoyl, neopentanoyl, and the like.

The "alkenylcarbonyl" includes a straight chain or branched chain alkenylcarbonyl group having 2 to 12 carbon atoms and having one to three double bonds, for example, vinylcarbonyl, acrylcarbonyl, 3-methyl-2-butenylcarbonyl, 2-butenylcarbonyl, 1-methylallylcarbonyl, 2-pentenylcarbonyl, 2-hexenylcarbonyl, 1-heptenylcarbonyl, 1-octenylcarbonyl, 1-nonenylcarbonyl, 1-decenylcarbonyl, 1-undecenylcarbonyl, 1-dodecenylcarbonyl, 2-heptenylcarbonyl, 3-heptenylcarbonyl, 2-methyl-4-heptenylcarbonyl, 2-methyl-5-heptenylcarbonyl, 4-methyl-2-heptenylcarbonyl, 3-methyl-1-heptenylcarbonyl, 1,3-heptadienylcarbonyl, 1,4-heptadienylcarbonyl, 1,5-heptadienylcarbonyl, 1,6-heptadienylcarbonyl, 2,4-heptadienylcarbonyl, 2-methyl-2,4-heptadienylcarbonyl, 2,6-dimethyl 2-4-heptadienylcarbonyl, 2,6-dimethyl-1,5-heptadienylcarbonyl, 2,5-dimethyl-1,3-heptadienylcarbonyl, 2,4,6-trimethyl-2,4-heptadienylcarbonyl, 2-octenylcarbonyl, 3-octenylcarbonyl, 4-octenylcarbonyl, 2-methyl-5-octenylcarbonyl, 2-methyl-6-octenylcarbonyl, 2-methyl-7-octenylcarbonyl, 1,3-octadienylcarbonyl, 1,4-octadienylcarbonyl, 1,5-octadienylcarbonyl, 1,6-octadienylcarbonyl, 1,7-octadienylcarbonyl, 2,4-octadienylcarbonyl, 3,7-octadienylcarbonyl, 4,8-dimethyl-3,7-octadienylcarbonyl, 2,4,6-trimethyl-3,7-octadienylcarbonyl, 3,4-dimethyl-2,5octadienylcarbonyl, 4,8-dimethyl-2,6-octadienylcarbonyl, 2-nonenylcarbonyl, 3-nonenylcarbonyl, 4-nonenylcarbonyl, 2-methyl-5-nonenylcarbonyl, 2-methyl-6-nonenylcarbonyl, 2-methyl-7-nonenylcarbonyl, 2-methyl-8-nonenylcarbonyl, 1,3-nonadienylcarbonyl, 1,4-nonadienylcarbonyl, 1,5-nonadienylcarbonyl, 1,6-nonadienylcarbonyl, 1,7-nonadienylcarbonyl, 1,8-nonadienylcarbonyl, 2,4-nonadienylcarbonyl, 3,7-nonadienylcarbonyl, 4,8-dimethyl-3,7-nonadienylcarbonyl, 2,4,6-trimethyl-3,7-nonadienylcarbonyl, 3,4-dimethyl-2,5-nonadienylcarbonyl, 4,8-dimethyl-2,6-nonadienylcarbonyl, 2decenylcarbonyl, 3-decenylcarbonyl, 4-decenylcarbonyl, 5-decenylcarbonyl, 2-methyl-6-decenylcarbonyl, 3-methyl-7-decenylcarbonyl, 4-methyl-8-decenylcarbonyl, 5-methyl-9-decenylcarbonyl, 1,3-decadienylcarbonyl, 1,4-decadienylcarbonyl, 1,5-decadienylcarbonyl, 1,6-decadienylcarbonyl, 1,7-decadienylcarbonyl, 1,8-decadienylcarbonyl, 1,9- decadienylcarbonyl, 2-methyl-2,4-decadienylcarbonyl, 3-methyl-2,5-decadienylcarbonyl, 4,8-dimethyl-2,6-decadienylcarbonyl, 2,4,6-trimethyl-3,7-decadienylcarbonyl, 2,9-dimethyl-3,7-decadienylcarbonyl, 2-undecenylcarbonyl, 3-undecenylcarbonyl, 4-undecenylcarbonyl, 5-undecenylcarbonyl, 2-methyl-6-undecenylcarbonyl, 3-methyl-7-undecenylcarbonyl, 4-methyl-8-undecenylcarbonyl, 5-methyl-9-undecenylcarbonyl, 2-methyl-10-undecenylcarbonyl, 1,3-undecadienylcarbonyl, 1,4-undecadienylcarbonyl, 1,5-undecadienylcarbonyl, 1,6-undecadienylcarbonyl, 1,7-undecadienylcarbonyl, 1,8-undecadienylcarbonyl, 1,9-undecadienylcarbonyl, 1,10-undecadienylcarbonyl, 2-methyl-2,4-undecadienylcarbonyl, 3-methyl-2,5-undecadienylcarbonyl, 4,8-dimethyl-2,6-undecadienylcarbonyl, 2,4,6-trimethyl-3,8-undecadienylcarbonyl, 2,9 dimethyl-3,8-undecadienylcarbonyl, 2-dodecenylcarbonyl, 3-dodecenylcarbonyl, 4-dodecenylcarbonyl, 5-dodecenylcarbonyl, 6-dodecenylcarbonyl, 2-methyl-7-dodecenylcarbonyl, 3-methyl-8-dodecenylcarbonyl, 4-methyl-9-dodecenylcarbonyl, 5-methyl-10-dodecenylcarbonyl, 6-methyl11-dodecenylcarbonyl, 2-methyl-2,4-dodecadienylcarbonyl, 3-methyl-2,5-dodecadienylcarbonyl, 4,8-dimethyl-2,6-dodecadienylcarbonyl, 2,4,6-trimethyl-2,7-dodecadienylcarbonyl, 2,10-dimethyl-2,8-dodecadienylcarbonyl, 2,5-dimethyl-3,7-dodecadienylcarbonyl, 4,8,12-trimethyl-3,7,11dodecatrienylcarbonyl, 1,3,5-heptatrienylcarbonyl, 2,4,6-octatrienylcarbonyl, 1,3,6-nonatrienylcarbonyl, 2,6,8-dodecatrienylcarbonyl, 1,5,7-undecatrienylcarbonyl, and the like.

The "phenylsulfonyl which phenyl ring may optionally have a lower alkoxy substituent" includes a phenylsulfonyl group which phenyl ring may optionally have one to three substituents of a straight chain or branched chain alkoxy group having 1 to 6 carbon atoms, for example, phenylsulfonyl, 2-methoxyphenylsulfonyl, 3-methoxyphenylsulfonyl, 4-methoxyphenylsulfonyl, 2-ethoxyphenylsulfonyl, 3-ethoxyphenylsulfonyl, 4-ethoxyphenylsulfonyl, 4-isopropoxyphenylsulfonyl, 4-pentyloxyphenylsulfonyl, 4-hexyloxyphenylsulfonyl, 3,4-dimethoxyphenylsulfonyl, 3-ethoxy-4-methoxyphenylsulfonyl, 2,3-dimethoxyphenylsulfonyl, 3,4-diethoxyphenylsulfonyl, 2,5-dimethoxyphenylsulfonyl, 2,6-dimethoxyphenylsulfonyl, 3,5-dimethoxyphenylsulfonyl, 3,4-dipentyloxyphenylsulfonyl, 3,4,5-trimethoxyphenylsulfonyl, and the like.

The "phenyl which may optionally have one to three substituents selected from a lower alkoxy, a lower alkyl, a halogen atom, an amino having optionally one or two substituents selected from a lower alkyl and a lower alkanoyl, and nitro" includes a phenyl group which may optionally have one to three substituents selected from a straight chain or branched chain alkoxy group having 1 to 6 carbon atoms, a straight chain or branched chain alkyl group having 1 to 6 carbon atoms, a halogen atom, an amino group having optionally one or two substituents selected from straight chain or branched chain alkyl group having 1 to 6 carbon atoms and a straight chain or branched chain alkanoyl group having 1 to 6 carbon atoms, and a nitro group, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,5-dimethylphenyl, 2,6-dimethylphenyl, 3,4,5-trimethylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-nitrophenyl, 3-nitrophenyl, 4-nitrophenyl, 3,4-dinitrophenyl, 2,5-dinitrophenyl, 2,6-dinitrophenyl, 3,4,5-trinitrophenyl, 2-aminophenyl, 3-aminophenyl, 4-aminophenyl, 3-(N-acetylamino)phenyl, 4-(N-formylamino)phenyl, 4-(N-isobutyrylamino)phenyl, 2-(N-pentanoylamino)phenyl, 3,4-diaminophenyl, 3,4-di(N-acetylamino)phenyl, 3,4,5-triaminophenyl, 2,6-diaminophenyl, 2,5-diaminophenyl, 3,5-di-t-butyl-4-hydroxyphenyl, 3-hydroxy-4-pentyloxyphenyl, 2-hydroxy-5-t-butylphenyl, 3,5-dichloro-4-aminophenyl, 3-amino-4-hydroxyphenyl, 3-acetylamino-4-methoxyphenyl, 3-nitro-4-acetylaminophenyl, 3-nitro4-chlorophenyl, 3-chloro-4-methylphenyl, 3-methoxy-4-methyl5-iodophenyl, 3,4-dimethoxy-5-bromophenyl, 3,5-diiodo-4-methoxyphenyl, 4-dimethylaminophenyl, 3-methylaminophenyl, 2-butylaminophenyl, 4-diethylaminophenyl, 3-dipropylaminophenyl, 2-(N-methyl-N-hexaylamino)phenyl, 4-(N-methyl-Nacetylamino)phenyl, 2,4-dimethylaminophenyl, and the like.

The "heterocyclic group-substituted carbonyl" includes a 5- to 10-membered, monocyclic or dicyclic heterocyclic groups containing one or two hetero atoms selected from nitrogen atom, oxygen atom and/or sulfur atom, for example, 2-pyrrolidinylcarbonyl, 3-pyrrolidinylcarbonyl, 1-piperidinylcarbonyl, 1-piperazinylcarbonyl, morpholinocarbonyl, thiomopholinocarbonyl, 2-tetrahydrofurylcarbonyl, 2-thienylcarbonyl, 3-thienylcarbonyl, 2-pyrrolylcarbonyl, 3-pyrrolylcarbonyl, 2-furoyl, 3-furoyl, 2-pyridylcarbonyl, 3-pyridylcarbonyl, 4-pyridylcarbonyl, 3-pyridazylcarbonyl, 2-thiazolylcarbonyl, 2-oxazolylcarbonyl, 2-imidazolylcarbonyl, 4-pyridazylcarbonyl, 5-pyridazylcarbonyl, 6-pyridazylcarbonyl, 2-pyrimidylcarbonyl, 4-pyrimidylcarbonyl, 5-pyrimidylcarbonyl, 6-pyrimidylcarbonyl, 2-pyradylcarbonyl, 3-pyradylcarbonyl, 6-quinolylcarbonyl, 5-indolylcarbonyl, 6-isoquinolylcarbonyl, 4-cinnolylcarbonyl, 3-quinoxalylcarbonyl, 4,-phthalazylcarbonyl, 5-quinazolylcarbonyl, 3-benzo[b]furanylcarbonyl, 5-benzo[b]thiophenylcarbonyl, 2-oxo-6-quinolylcarbonyl, 2-oxo-4-quinolylcarbonyl, and the like.

The above "heterocyclic group-substituted carbonyl which has one to three substituents selected from a phenyl(lower)alkoxycarbonyl, a phenyl(lower)alkoxy, oxo, a lower alkyl and a lower alkylenedioxy" includes the abovementioned heterocyclic group-substituted carbonyl groups which have one to three substituents selected from a phenylalkoxycarbonyl group wherein the alkoxycarbonyl moiety is a straight chain or branched chain alkoxycarbonyl group having 1 to 6 carbon atoms, a phenylalkoxy group wherein the alkoxy moiety is a straight chain or branched chain alkoxy group having 1 to 6 carbon atoms, an oxo group, a straight chain or branched chain alkyl group having 1 to 6 carbon atoms, and a straight chain or branched chain alkylenedioxy group having 1 to 4 carbon atoms, for example, 1-benzyloxycarbonyl-2-pyrrolidinylcarbonyl, 3-benzyloxycarbonyl-4,5-(1,1-dimethylmethylene)-2-tetrahydrofurylcarbonyl, 4-(2-phenylethoxycarbonyl)-1-piperazinylcarbonyl, 3-methyl-2-thienylcarbonyl, 3-ethyl-2-pyrrolylcarbonyl, 3-propyl-2-furoyl, 4-butyl-2-oxo-6-quinolylcarbonyl, 6-pentyl-2-oxo-4-quinolylcarbonyl, 5-hexyl-2pyrazylcarbonyl, 1,3-dioxo-2-methyl-6-quinazolylcarbonyl, 4,5-methylenedioxy-3-indolyl-carbonyl, 3-(3-phenylpropoxy)morpholinocarbonyl, and the like.

The "thienyl(lower)alkanoyl" includes a thienylalkanoyl wherein the alkanoyl moiety is a straight chain or branched chain alkanoyl group having 2 to 6 carbon atoms, for example, 2-(2-thienyl)acetyl, 3-(3-thienyl)propionyl, 2-(3-thienyl)propionyl, 4-(2-thienyl)butyryl, 2,2-dimethyl-3-(3-thienyl)propionyl, 5-(2-thienyl)pentanoyl, 6-(3-thienyl)hexanoyl, 3-methyl-4-(2-thienyl)butyryl, and the like.

The "tricyclo[3.3.1.1]decanyl(lower)alkanoyl" includes a tricyclo[3.3.1.1]decanylalkanoyl wherein the alkanoyl moiety is a straight chain or branched chain alkanoyl group having 2 to 6 carbon atoms, for example, 2-tricyclo[3.3.1.1]decanylacetyl, 3-tricyclo[3.3.1.1]decanylpropionyl, 2-tricyclo[3.3.1.1decanylpropionyl, 4-tricyclo[3.3.1.1]decanylbutyryl, 2,2,-dimethyl-3-tricyclo[3.3.1.1]decanylpropionyl, 5-tricyclo[3.3.1.1]decanylpentanoyl, 6-tricyclo[3.3.1.1]decanylhexanoyl, 3-methyl-4-tricyclo[3.3.1.1]decanylbutyryl, and the like.

The "benzoyl which phenyl ring may optionally have a lower alkoxy substituent≈ includes a benzoyl which may optionally have one to three substituents of a straight chain or branched chain alkoxy group having 1 to 6 carbon atoms, for example, benzoyl, 2-methoxybenzoyl, 3-methoxybenzoyl, 4-methoxybenzoyl, 2-ethoxybenzoyl, 3-ethoxybenzoyl, 4-butoxybenzoyl, 4-isopropoxybenzoyl, 4-pentyloxybenzoyl, 4-hexyloxybenzoyl, 3,4-dimethoxybenzoyl, 3-ethoxy-4-methoxybenzoyl, 2,3-dimethoxybenzoyl, 2,4-dimethoxybenzoyl, 3,4-diethoxybenzoyl, 2,5-dimethoxybenzoyl, 2,6-dimethoxybenzoyl, 3,5-dimethoxybenzoyl, 3,4-dipentyloxybenzoyl, 2-methoxy-4-methoxybenzoyl, 2,4,6-trimethoxybenzoyl, 3,4,5-trimethoxybenzoyl, and the like.

The "phenyl which may optionally have a lower alkoxy substituent" includes a phenyl group which may optionally have one to three substituents of a straight chain or branched chain alkoxy group having 1 to 6 carbon atoms, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy-4-methoxyphenyl, 2,3-dimethoxydimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, and the like.

The "cycloalkyl" includes a cycloalkyl having 3 to 8 carbon atoms, for example, cyclopropyl, cyclobutyl, cyclopentyl, cyclohexyl, cycloheptyl, cyclooctyl, and the like.

The "saturated or unsaturated heterocyclic group which is formed by binding the groups $R^{11}$ and $R^{12}$ together with the nitrogen atom to which they bond and may be intervened or not with nitrogen, oxygen or sulfur atom" includes, a 5- to 10-membered, saturated or unsaturated, monocyclic or dicyclic heterocyclic group, for example, pyrrolidinyl, piperidinyl, piperazinyl, morpholino, thiomorpholino, pyrrolyl, imidazolyl, pyrazolyl, imidazolidinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, 1,2,3,4-tetrahydroquinolyl, 1,2-dihydroquinolyl, indolyl, isoindolyl, 1,2-dihydroisoquinolyl, 1,2,3,4-tetrahydroisoquinolyl, 1H-indazolyl, 1,2-dihyroquinazolyl, 1,2-dihydrocinnolyl, 1,2-dihydroquinoxalyl, 1,2,3,4-tetrahydroquinazolyl, 1,2,3,4-tetrahydrocinnolyl, 1,2,3,4-tetrahydroquinoxalyl, and the like.

The "phenyl which may optionally have a substituent selected from a lower alkoxy and a lower alkanoyl" includes a phenyl group which may optionally have one to three substituents selected from a straight chain or branched chain alkoxy group having 1 to 6 carbon atoms and a straight chain or branched chain alkanoyl group having 1 to 6 carbon atoms, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3-ethoxy4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 3-methoxy-4-acetylphenyl, 2-acetylphenyl, 3-acetylphenyl, 4-acetylphenyl, 2-formylphenyl, 3-propionylphenyl, 4-isobutyrylphenyl, 2-pentanoylphenyl, 3-hexanoylphenyl, 3,4-diacetylphenyl, 2,5-diacetylphenyl, 3,4,5-triacetylphenyl, and the like.

The "heterocyclic group which may optionally be substituted by a member selected from benzoyl, a lower alkanoyl, a phenyl(lower)alkyl, and a phenyl having optionally a substituent selected from a lower alkoxy and a lower alkanoyl" includes the above heterocyclic groups which may optionally have a substituent selected from benzoyl group, a straight chain or branched chain alkanoyl group having 1 to 6 carbon atoms, a phenylalkyl group wherein the alkyl moiety is a straight chain or branched chain alkyl group having 1 to 6 carbon atoms, and a phenyl group having optionally one to three substituents selected from a straight chain or branched chain alkoxy group having 1 to 6 carbon atoms and a straight chain or branched chain alkanoyl group having 1 to 6 carbon atoms, for example, 3-benzoyl-1-pyrrolidinyl, 4-benzoyl-1-piperidinyl, 4-benzoyl-1-piperazinyl, 4-benzyl-1-piperazinyl, 3-(2-phenylethyl)morpholino, 3-(3-phenylpropyl)thiomorpholino, 3-(4-phenylbutyl)-1-pyrrolyl, 4-acetyl-1-piperidinyl, 4-acetyl-1piperazinyl, 4-formyl-1-piperazinyl, 2-(5-phenylpentyl)-1imidazolyl, 3-(6-phenylpentyl)-1-pyrazolyl, 4-(4-methoxyphenyl)-1-piperazinyl, 4-(4-acetylphenyl)-1-piperazinyl, 4-(3-ethoxyphenyl)-1-piperazinyl, 4-(3-propionylphenyl)-1-piperazinyl, 5-benzyl-1,2,3,4-tetrahydroquinolin-1-yl, 6-(4-butyrylphenyl)-1,2,3,4-tetrahydroisoquinolin-2-yl, 4-(2-propoxyphenyl)-1-indolyl, 5-(3-pentanoylphenyl)-1H-indazol-1-yl, 6-(3-butoxyphenyl)-1,2-dihydroquinazolin-1-yl, 7-(4-hexanoylphenyl)-1,2-dihydrocinnolin-2-yl, 6-(4-hexyloxyphenyl)-1,2,3,4-tetrahydroquinoxalin-1-yl, and the like.

The "alkylene" includes a straight chain or branched chain alkylene group having 1 to 12 carbon atoms, for example, in addition to the above-mentioned alkylene groups, heptamethylene, octamethylene, nonamethylene, decamethylene, undecamethylene, dodecamethylene, and the like.

The "lower alkoxycarbonyl(lower)alkyl wherein the alkyl moiety may optionally be substituted by hydroxy or an amino having optionally a phenyl(lower)alkoxycarbonyl substituent" includes a straight chain or branched chain alkoxycarbonylalkyl group having 1 to 6 carbon atoms in the alkoxy moiety, wherein the alkyl moiety is straight chain or branched chain alkyl group having 1 to 6 carbon atoms and has optionally a substituent selected from a hydroxy group and an amino group having optionally a substituent of a phenylalkoxycarbonyl group wherein the alkoxycarbonyl moiety is a straight chain or branched chain alkoxycarbonyl group having 1 to 6 carbon atoms, for example, 1-hydroxy-1-methoxycarbonylmethyl, 1-methoxycarbonyl-2-hydroxyethyl, 3-hydroxy-3-methoxycarbonylpropyl, 2-hydroxy-4-ethoxycarbonylbutyl, 2-hydroxy-6-propoxycarbonylhexyl, 2-hydroxy- 2-pentyloxycarbonylethyl, 1-hydroxy-1-hexyloxycarbonylmethyl, 5-benzyloxycarbonyl-1-methoxycarbonylpentyl, 5-amino-1-methoxycarbonylpentyl, 3-(2-phenylethoxycarbonylamino)-1-ethoxycarbonylpropyl, 4-amino-1-butyloxycarbonylbutyl, and the like.

The "amino-substituted lower alkanoyl wherein the lower alkanoyl moiety may optionally be substituted by a member selected from a phenyl(lower)alkoxycarbonylamino, hydroxy, a phenyl having optionally a hydroxy substituent, carbamoyl, imidazolyl or a lower alkylthio, and the amino group may optionally have a substituent selected from a lower alkyl having optionally a hydroxy substitutent, a lower alkenyl, a phenyl(lower)alkyl having optionally a lower alkoxy substituent on the phenyl ring, a lower alkylsulfonyl, a lower alkanoyl, or a phenyl(lower)alkoxycarbonyl" includes an amino-substituted straight chain or branched chain alkanoyl group having 2 to 6 carbon atoms, wherein the alkanoyl moiety may optionally be substituted by a member selected from phenylalkoxycarbonylamino wherein the alkoxycarbonyl moiety is a straight chain or branched chain alkoxycarbonyl group having 1 to 6 carbon atoms, a hydroxy group, a phenyl group having optionally one to three hydroxy-substitutents, a carbamoyl group, an imidazolyl group or a straight chain or branched chain alkylthio group having 1 to 6 carbon atoms, and the amino group may optionally have a substituent selected from a straight chain or branched chain alkyl group having 1 to 6 carbon atoms and having optionally one to three hydroxy-substitutents, a straight chain or branched chain alkenyl group having 2 to 6 carbon atoms, a phenylalkyl group wherein the alkyl moiety is a straight chain or branched chain alkyl group having 1 to 6 carbon atoms and the phenyl ring has optionally one to three substituents of a straight chain or branched chain alkoxy group having 1 to 6 carbon atoms, a straight chain or branched chain alkylsulfonyl group having 1 to 6 carbon atoms, a straight chain or branched chain alkanoyl group having 1 to 6 carbon atoms, or a phenylalkoxycarbonyl wherein the alkoxycarbonyl moiety is a straight chain or branched chain alkoxycarbonyl group having 1 to 6 carbon atoms, for example, aminoacetyl, 3-formylaminopropionyl, acetylaminoacetyl, 2-propionylaminopropionyl, 4-butyrylaminobutyryl, 2,2-dimethyl-3-isobutyrylaminopropionyl, 5-pentanoylaminopentanoyl, 6-tert-butylcarbonylaminohexanoyl, 3-methyl-4-hexanoylaminobutyryl, 4-methylthio-2-acetylaminobutyryl, 3-(imidazol-4-yl)-2-acetylaminopropionyl, 2-acetylaminopropionyl, 3-(4-hydroxyphenyl)-2-benzyloxycarbonylaminopropionyl, 4-carbomyl-2-acetylaminobutyryl, 2-acetylaminoisopentanoyl, 5-ethylthio-2-acetylaminopentanoyl, 4-(imidazol-2-yl)-2-propionylaminobutyryl, 6-(2-hydroxyphenyl)-2-butyrylaminohexanoyl, 3-carbamoyl-2-benzyloxycarbonylaminopropionyl, 5- carbamoyl-2-(2-phenylethoxycarbonylamino)pentanoyl, 3-(2,4-dihydroxyphenyl)-2-(3-phenylpropoxycarbonylamino)propionyl, 2,5-dibenzyloxycarbonylaminohexanoyl, 3-(4-hydroxyphenyl)-2-aminopropionyl, dimethylaminoacetyl, 3-hydroxy-2-benzyloxycarbonylaminopropionyl, 2-benzyloxycarbonylaminopropionyl, 2-aminopropionyl, 2-aminoisopentanoyl, 2-aminobutyryl, 4-benzyloxycarbonylaminobutyryl, diethylaminoacetyl, 4-acetylaminobutyryl, 4-dimethylaminobutyryl, 2-hdyroxyacetyl, ethylaminoacetyl, allylaminoacetyl, benzylaminoacetyl, isopropylaminoacetyl, (N-methyl-N-benzylamino)acetyl, [N-methyl-N-(2-hydroxyethyl)amino]acetyl, [N-methyl-N-(4-ethoxybenzyl)-amino]acetyl, 2-benzyloxycarbonylaminoacetyl, methylsulfonylaminoacetyl, (3-methoxybenzyl)aminoacetyl, (N-methyl-N-acetylamino)acetyl, 5-(N-methyl-N-allylamino)pentanoyl, 6-[N-allyl-N-(3,4-dimethoxybenzyl)amino]hexanoyl, and the like.

The "amido-substituted lower alkyl wherein the lower alkyl moiety have optionally a substituent selected from a phenyl having optionally a hydroxy substituent, imidazolyl, carbamoyl or a lower alkylthio, and the amido group may optionally have a lower alkyl substituent" includes an amido-substituted straight chain or branched chain alkyl group having 1 to 6 carbon atoms wherein the alkyl moiety have optionally a substituent selected from a phenyl having optionally one to three hydroxy-substituents, an imidazolyl group, a carbamoyl group or a straight chain or branched chain alkylthio group having 1 to 6 carbon atoms, and the amido group may optionally have one or two substituents of a straight chain or branched chain alkyl group having 1 to 6 carbon atoms, for example, carbamoylmethyl, 2-carbamoylethyl, 1-carbamoylethyl, 3-carbamoylpropyl, 4-carbamoylbutyl, 5-carbamoylpentyl, 6-carbamoylhexyl, 1,2-dimethyl-2-carbamoylethyl, 2-methyl-3-carbamoylpropyl, methylamidomethyl, 1-ethylamidoethyl, 2-propylamidoethyl, 3-isopropylamidopropyl, 4-butylamidobutyl, 5-pentylamidopentyl, 6-hexylamidohexyl, dimethylamidomethyl, (N-ethyl-N-propylamido)methyl, 2-(N-methyl-N-hexylamido)ethyl, 2-(4-hydroxyphenyl)carbamoylethyl, 1-carbamoylisobutyl, 2-(imidazol-4-yl)-1-carbamoylethyl, 1,3-dicarbamoylpropyl, 3-methylthio-1-carbamoylpropyl, 3-(2-hydroxyphenyl)-1-methylamidopropyl, 4-(2,6-dihydroxyphenyl)-1-(N-methyl-N-hexylamido)butyl, 3-(imidazol-2-yl)-1-propylamidopropyl, 1,4-dicarbamoylbutyl, 2-ethylthio-1-butylamidobutyl, 4-pentylthio-1-hexylamidobutyl, and the like.

The "carboxy(lower)alkyl" includes a carboxyalkyl group wherein the alkyl moietyl is a straight chain or branched chain alkyl group having 1 to 6 carbon atoms, for example, carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, 2-methyl-3-carboxypropyl, and the like.

The "lower alkoxy(lower)alkyl" includes a straight chain or branched chain alkoxyalkyl group having 1 to 6 carbon atoms in the alkoxy moiety wherein the alkyl moiety is a straight chain or branched chain alkyl group having 1 to 6 carbon atoms, for example, methoxymethyl, 2-ethoxyethyl, 1-methoxyethyl, 3-methoxypropyl, 4-ethoxybutyl, 6-propoxyhexyl, 5-isopropoxypentyl, 1,1-dimethyl-2-butoxyethyl, 2-methyl-3-tertbutoxypropyl, 2-pentyloxyethyl, hexyloxymethyl, and the like.

The "amino acid residue which is able to form an amido bond with the amino group to which $R^4$ and $R^5$ bind" includes, for example, alanine residue, $N^2$-arginine residue, $N^5$-arginine residue, $N^6$-arginine residue, $N^4$-asparagine residue, aspartic acid residue, $N^5$-glutamine residue, cysteine residue, glutamic acid residue, glycine residue, histidine residue, isoleucine residue, leucine residue, $N^2$-lysine residue, $N^6$-lysine residue, methionine residue, phenylalanine residue, proline residue, serine residue, threonine residue, tryptophane residue, tyrosine residue, valine residue, and the like.

The "hydroxyimino-substituted lower alkyl" includes a hydroxyimino-substituted straight chain or branched chain alkyl group having 1 to 6 carbon atoms, for example, hydroxyiminomethyl, 1-hydroxyiminoethyl, 2-hydroxyiminoethyl, 3-hydroxyiminopropyl, 4-hydroxyiminobutyl, 5-hydroxyiminopentyl, 6-hydroxyiminohexyl, 1,1-dimethyl-2-hydroxyiminoethyl, 2-methyl-3-hydroxyiminopropyl, and the like.

The "halogen-substituted lower alkoxy" includes a straight chain or branched chain alkoxy group having 1 to 6 carbon atoms which is substituted by one to three halogen atoms, for example, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, and the like.

The "phenyl(lower)alkoxycarbonyl" includes a phenylalkoxycarbonyl wherein the alkoxycarbonyl moietyl is a straight chain or branched chain alkoxycarbonyl group having 1 to 6 carbon atoms, for example, benzyloxycarbonyl, 2-phenylethoxycarbonyl, 1-phenylethoxycarbonyl, 3-phenylpropoxycarbonyl, 4-phenylbutoxycarbonyl, 5-phenylpentyloxycarbonyl, 6-phenylhexyloxycarbonyl, 1,1-dimethyl-2-phenylethoxycarbonyl, 2-methyl-3-phenylpropoxycarbonyl, and the like.

The "lower alkoxy(lower)alkoxy which is substituted by one or two substituents selected from hydroxy and an amino being optionally substituted by a lower alkyl" includes an alkoxy-alkoxy group wherein both alkoxy moiety are each a straight chain or branched chain alkoxy group having 1 to 6 carbon atoms which is substituted by one or two substituents selected from hydroxy and an amino being optionally substituted by a straight chain or branched chain alkyl group having 1 to 6 carbon atoms, for example, hydroxymethoxymethoxy, 3-(2-hydroxyethoxy)propoxy, 4-(1-hydroxyethoxy)butoxy, 6-(3-hydroxypropoxy)hexyloxy, 5-(2,3-dihydroxypropoxy)pentyloxy, 1,1-dimethyl-2-(4-hydroxybutoxy)ethoxy, 2-methyl-3-(3,4-dihydroxybutoxy)propoxy, 2-(1,1-dimethyl-2-hydroxyethoxy)ethoxy, (5-hydroxypentyloxy)methoxy, (6-hydroxyhexyloxy)methoxy, (2-methyl-3-hydroxypropoxy)methoxy, aminomethoxymethoxy, 2-(1-aminoethoxy)ethoxy, 1-(2-aminoethoxy)ethoxy, 3-(3-aminopropoxy)propoxy, 4-(4-aminobutoxy)butoxy, 5-(5-aminopentyloxy)pentyloxy, 6-(6-aminohexyloxy)hexyloxy, (1,1-dimethyl-2-aminoethoxy)methoxy, (2-methyl-3-aminopropoxy)methoxy, 1,1-dimethyl-2-(methylaminomethoxy)ethoxy, 2-methyl-3-(ethylaminomethoxy)propoxy, propylaminomethoxymethoxy, 1-(isopropylaminomethoxy)ethoxy, 2-(butylaminomethoxy)ethoxy, 3-(tert-butylaminomethoxy)propoxy, 4-(pentylaminomethoxy)butoxy, 5-(hexylaminomethoxy)pentyloxy, 6-(dimethylaminomethoxy)hexyloxy, 1,1-dimethyl-2-(diethylaminomethoxy)ethoxy, 2-methyl-3-(dipropylaminomethoxy)propoxy, dibutylaminomethoxymethoxy, 1-(dipentylaminomethoxy)ethoxy, 2-(dihexylaminomethoxy)ethoxy, 3-(N-methyl-N-ethylaminomethoxy)propoxy, 4-(N-methyl-N-propylaminomethoxy)butoxy, 5-(N-methyl-N-butylaminomethoxy)pentyloxy, 6-(N-methyl-N-hexylaminomethoxy)hexyloxy, (1-methylaminoethoxy)methoxy, 1-(2-ethylaminoethoxy)ethoxy, 2-(3-propylaminopropoxy)ethoxy, 3-(4-butylaminobutoxy)propoxy, 4-(1,1-dimethyl-2-pentylaminoethoxy)butoxy, 5-(5-hexylaminopentyloxy)pentyloxy, 6-(6-dimethylaminohexyloxy)hexyloxy, 3-(2-diethylaminoethoxy)propoxy, 4-[1-(N-methyl-N-hexylamino)ethoxy]butoxy, 5-(3-dihexylaminopropoxy)pentyloxy, 6-(4-dibutylaminobutoxy)hexyloxy, 3-[2-(N-methyl-N-pentylamino)ethoxy]propoxy, 5-(2-hydroxy-3-dimethylaminopropoxy)pentyloxy, 5-(2-hydroxy-3-diethylaminopropoxy)pentyloxy, 3-(2-hydroxy-3-diethylaminopropoxy)propoxy, 4-(3-hydroxy-4-methylaminobutoxy)butoxy, 5-(4-hydroxy-5-dimethylaminopentyloxy)pentyloxy, 6-(4-hydroxy-5-methylaminopentyloxy)hexyloxy, and the like.

The "morpholinyl-substituted lower alkoxy which may optionally have a substituent selected from a lower alkyl and oxo" includes a morpholinyl-substituted straight chain or branched chain alkoxy group having 1 to 6 carbon atoms which may optionally have one or two substituents selected from a straight chain or branched chain alkyl group having 1 to 6 carbon atoms, and an oxo group, for example, (2-morpholinyl)methoxy, 2-(3-morpholinyl)ethoxy, 1-(3-morpholinyl)ethoxy, 3-(2-morpholinyl)propoxy, 4-(3-morpholinyl)butoxy, 5-(2-morpholinyl)pentyloxy, 6-(3-morpholinyl)hexyloxy, 1,1-dimethyl-2-(3-morpholinyl)ethoxy, 2-methyl-3-(2-morpholinyl)-propoxy, 6-(1-methyl-5-oxo-3-morpholinyl)hexyloxy, (1-ethyl-2-morpholinyl)methoxy, 2-(2-oxo-3-morpholinyl)ethoxy, 1-(2-propyl-3-morpholinyl)ethoxy, 3-(3-butyl-2-morpholinyl)propoxy, 4-(5-pentyl-3-morpholinyl)butoxy, 5-(6-hexyl-2-morpholinyl)pentyloxy, 3-(5-oxo-1-propyl-2-morpholinyl)propoxy, 4-(2-oxo-1-butyl-3-morpholinyl)butoxy, 5-(3-oxo-1-pentyl-6-morpholinyl)pentyloxy, 6-(2-oxo-1-hexyl-5-morpholinyl)hexyloxy, and the like.

The "benzimidazolylthio-substituted lower alkoxy" includes a benzimidazolylthio-substituted straight chain or branched chain alkoxy group having 1 to 6 carbon atoms, for example, (benzimidazol-2-yl)thiomethoxy, 1-(benzimidazol-4-yl)thioethoxy, 2-(benzimidazol-5-yl)thioethoxy, 3-(benzimidazol-6-yl)thiopropoxy, 4-(benzimidazol-2-yl)thiobutoxy, 5-(benzimidazol-7-yl)thiopentyloxy, 6-(benzimidazol-2-yl)thiohexyloxy, 1,1-dimethyl-2-(benzimidazol-2-yl)thioethoxy, 2-methyl-3-(benzimidazol-2-yl)thiopropoxy, and the like.

The "benzimidazolylsulfinyl-substituted lower alkoxy" includes a benzimidazolylsulfinyl-substituted straight chain or branched chain alkoxy group having 1 to 6 carbon atoms, for example, (benzimidazol-2-yl)sulfinylmethoxy, 1-(benzimidazol-4-yl)sulfinylethoxy, 3-(benzimidazol-6-yl)sulfinylpropoxy, 4-(benzimidazol-2-yl)sulfinylbutoxy, 5-(benzimidazol-7-yl)sulfinylpentyloxy, 6-(benzimidazol-2-yl)sulfinylhexyloxy, 1,1-dimethyl-2-(benzimidazol-2-yl)sulfinylethoxy, 2-methyl-3-(benzimidazol-2-yl)sulfinylpropoxy, and the like.

The "tetrahydropyranyl-substituted lower alkyl" includes a tetrahydropyranyl-substituted straight chain or branched chain alkyl group having 1 to 6 carbon atoms, for example, (2-, 3- or 4-tetrahydropyranyl)-methyl, 2-(2-, 3- or 4-tetrahydropyranyl)ethyl, 1-(2-, 3- or 4-tetrahydropyranyl)ethyl, 3-(2-, 3- or 4-tetrahydropyranyl)propyl, 4-(2-, 3- or 4-tetrahydropyranyl)butyl, 5-(2-, 3- or 4-tetrahydropyranyl)pentyl, 6-(2-, 3- or 4-tetrahydropyranyl)hexyl, 1,1-dimethyl-2-(2-, 3- or 4-tetrahydropyranyl)ethyl, 2-methyl-3-(2-, 3- or 4-tetrahydropyranyl)propyl, and the like.

The "5- or 6-membered saturated heterocyclic group which is formed by binding $R^{32}$ and $R^{33}$ together with the nitrogen atom to which they bond with being intervened or not with nitrogen, oxygen or sulfur atom" includes, for example, pyrrolidinyl, piperidinyl, piperazinyl, morpholino, thiomorpholino, and the like.

The "heterocyclic group having a substituent selected from carbamoyl, a lower alkyl, a phenyl(lower)alkyl, phenyl and a hydroxy-substituted lower alkyl" includes the above-mentioned heterocyclic groups which have one to three substituents selected from a carbamoyl group, a straight chain or branched chain alkyl group having 1 to 6 carbon atoms, a phenylalkyl group wherein the alkyl moiety is a straight chain or branched chain alkyl group having 1 to 6 carbon atoms, a phenyl group and a hydroxy-substituted straight chain or branched chain alkyl group having 1 to 6 carbon atoms, for example, 4-phenylpiperazinyl, 2-phenylpyrrolidinyl, 4-phenylpiperidinyl, 3-phenylmorpholino, 3-phenylthiomorpholino, 4-benzylpiperazinyl, 3-(2-phenylethyl)pyrrolidinyl, 2-(3-phenylpropyl)pyrrolidinyl, 4-(4-phenylbutyl)piperidinyl, 3-(5-phenylpentyl)morpholino, 2-(6-phenylhexyl)thiomorpholino, 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 2-hexylthiomorpholino, 4-ethylpiperazinyl, 3-methyl-4-phenylpiperazinyl, 3-ethyl-4-benzylpiperidinyl, 3-methyl-4-benzylpyrrolidinyl, 3-methyl-5-phenylmorpholino, 3-methyl-5-(2-hydroxyethyl)thiomorpholino, 4-(2-hydroxyethyl)piperazinyl, 2-(hydroxymethyl)pyrrolidinyl, 4-(4-hydroxybutyl)piperidinyl, 2-(5-hydroxypentyl)thiomorpholino, 3-(6-hydroxyhexyl)morpholino, 2-methyl-4-(2-hydroxyethyl)pyrrolidinyl, 2-carbamoylpyrrolidinyl, 3-carbamoylpyrrolidinyl, 4-carbamoylpiperazinyl, 3-carbamoylpiperazinyl, 2-carbamoylpiperazinyl, 4-carbamoylpiperidinyl, 3-carbamoylpiperidinyl, 2-carbamoylpiperidinyl, 3-carbamoylmorpholino, 2-carbamoylthiomorpholino, 2-methyl-3-carbamoylpyrrolidinyl, 3-methyl-4-carbamoylpiperidinyl, 2,6-dimethyl-4-carbamoylpiperazinyl, and the like.

The "amino having optionally a phenyl(lower)alkoxycarbonyl substituent" includes an amino group which may optionally have a substituent of a phenylalkoxycarbonyl group wherein the alkoxycarbonyl moiety is a straight chain or branched chain alkoxycarbonyl group having 1 to 6 carbon atoms, for example, amino, benzyloxycarbonylamino, (2-phenylethoxycarbonyl)amino, (1-phenylethoxycarbonyl)amino, (3-phenylpropoxycarbonyl)amino, (4-phenylbutoxycarbonyl)amino, (5-phenylpentyloxycarbonyl)amino, (6-phenylhexyloxycarbonyl)amino, (1,1-dimethyl-2-phenylethoxycarbonyl)amino, (2-methyl-3-phenylpropoxycarbonyl)amino, and the like.

The "phenyl having optionally hydroxy substituent" includes a phenyl group having optionally one to three hydroxy-substituents, for example, phenyl, 4-hydroxyphenyl, 3-hydroxyphenyl, 2-hydroxyphenyl, 2,4-dihydroxyphenyl, 3,4-dihydroxyphenyl, 2,3,4-trihydroxyphenyl, and the like.

The "phenylsulfonyl which phenyl ring may optionally have a substituent selected from a lower alkyl, nitro, and an amino having optionally one or two substituents selected from a lower alkanoyl and lower alkyl" includes a phenylsulfonyl group which phenyl ring may optionally have one to three substitutents selected from a straight chain or branched chain alkyl group having 1 to 6 carbon atoms, a nitro group, an amino group having optionally one or two substituents selected from a straight chain or branched chain alkanoyl group having 1 to 6 carbon atoms and a straight chain or branched chain alkyl group having 1 to 6 carbon atoms, for example, phenylsulfonyl, 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 4-isopropylphenylsulfonyl, 4-butylphenylsulfonyl, 2-pentylphenylsulfonyl, 3-hexylphenylsulfonyl, 2,4-dimethylphenylsulfonyl, 3,4-diethylphenylsulfonyl, 3,4,5-trimethylphenylsulfonyl, 4-aminophenylsulfonyl, 3-aminophenylsulfonyl, 2-aminophenylsulfonyl, 3,4-diaminophenylsulfonyl, 2,5-diaminophenylsulfonyl, 2,4,6-triaminophenylsulfonyl, 4-nitrophenylsulfonyl, 3-nitrophenylsulfonyl, 2-nitrophenylsulfonyl, 2,3-dinitrophenylsulfonyl, 2,6-dinitrophenylsulfonyl, 2,4,6-trinitrophenylsulfonyl, 4-acetylaminophenylsulfonyl, 4-dimethylaminophenylsulfonyl, 3-(N-methyl-N-acetylamino)phenylsulfonyl, 2-methyl-4-aminophenylsulfonyl, 3-nitro-4-methylphenylsulfonyl, 2-ethylaminophenylsulfonyl, 2-methyl-3-diethylaminophenylsulfonyl, and the like.

The "amino-substituted lower alkyl which may optionally have a substituent selected from a lower alkyl and a lower alkanoyl" include a straight chain or branched chain alkyl group having 1 to 6 carbon atoms which is substituted by an amino group having optionally one or two substituents selected from a straight chain or branched chain alkyl group having 1 to 6 carbon atoms and a straight chain or branched chain alkanoyl group having 1 to 6 carbon atoms, for example, aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, (N-ethyl-N-propylamino)methyl, 2-(N-methyl-N-hexylamino)ethyl, 2-(acetylamino)ethyl, 3-(acetylamino)propyl, formylaminomethyl, 1-(propionylamino)ethyl, 4-(butyrylamino)butyl, 5-(pentanoylamino)pentyl, 5-(hexanoylamino)hexyl, 2-(N-methyl-N-acetylamino)ethyl, 1-(N-ethyl-N-acetylamino)ethyl, and the like.

The "piperidinyl having optionally a phenyl(lower)alkyl substituent" includes a piperidinyl which has optionally a substituent of a phenylalkyl group wherein the alkyl moiety is a straight chain or branched chain alkyl group having 1 to 6 carbon atoms, for example, 4-piperidinyl, 3-piperidinyl, 2-piperidinyl, 1-benzyl-4-piperidinyl, 1-(2-phenylethyl)-3-piperidinyl, 2-(3-phenylpropyl)-5-piperidinyl, 3-(4-phenylbutyl)-6-piperidinyl, 4-(5-phenylpentyl)-3-piperidinyl, 5-(6-phenylhexyl)-4-piperidinyl, 2-benzyl-4-piperidinyl, 1-(3-phenylpropyl)-4-piperidinyl, and the like.

The "imidazo[4,5-c]pyridylcarbonyl(lower)alkoxy" includes an imidazo[4,5-c]pyridylcarbonylalkoxy group wherein the alkoxy moiety is a straight chain or branched chain alkoxy group having 1 to 6 carbon atoms, for example, (imidazo[4,5-c]pyridin-2-yl)carbonylmethoxy, 2-(imidazo[4,5-c]pyridin-2-yl)carbonylethoxy, 1-(imidazo[4,5-c]pyridin-4-yl)carbonylethoxy, 3-(imidazo[4,5-c]pyridin-5-yl)carbonylpropoxy, 4-(imidazo[4,5-c]pyridin-7-yl)carbonylbutoxy, 5-(imidazo[4,5-c]pyridin-2-yl)carbonylpentyloxy, 6-(imidazo[4,5-c]pyridin-2-yl)carbonylhexyloxy, 1,1-dimethyl-2-(imidazo[4,5-c]pyridin-2-yl)carbonylethoxy, 2-methyl-3-(imidazo[4,5-c]pyridin-2-yl)carbonylpropoxy, and the like.

The "tri(lower alkyl)ammonium" includes an ammonium group having three of a straight chain or branched chain alkyl group having 1 to 6 carbon atoms, for example, trimethylammonium, triethylammonium, tripropylammonium, triisopropylammonium, tributylammonium, tri(tert-butyl)ammonium, tripentylammonium, trihexylammonium, dimethylethylammonium, diethylpropylammonium, dimethylbutylammonium, diethylmethylammonium, dimethylhexylammonium, dipropylmethylammonium, dibutylethylammonium, methylethylpropylammonium, methylbutylpentylammonium, and the like.

The "pyridyl(lower)alkyl" include a pyridylalkyl group wherein the alkyl moiety is a straight chain or branched chain alkyl group having 1 to 6 carbon atoms, for example, (2-pyridyl)methyl, (3-pyridyl)methyl, (4-pyridyl)methyl, 2-(2-pyridyl)ethyl, 1-(3-pyridyl)ethyl, 3-(4pyridyl)propyl, 4-(2-pyridyl)butyl, 5-(3-pyridyl)pentyl, 6-(4-pyridyl)hexyl, 1,1-dimethyl-2-(2-pyridyl)ethyl, 2-methyl-3-(3-pyridyl)propyl, and the like.

The "lower alkyl which may optionally have a substituent selected from hydroxy and cyano" includes a straight chain or branched chain alkyl group having 1 to 6 carbon atoms which may optionally have one to three substituents selected from a hydroxy group and a cyano group, for example, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 2,3-dihydroxyethyl, 3,4-dihydroxybutyl, 5,6-dihydroxyhexyl, cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl, and the like.

The "lower alkynyl" includes a straight chain or branched chain alkynyl group having 2 to 6 carbon atoms, for example, ethynyl, 2-propynyl, 2-butynyl, 3-butynyl, 1-methyl-2-propynyl, 2-pentynyl, 2-hexynyl, and the like.

The "pyrrolidinylcarbonyl which may optionally be substituted by a phenyl(lower)alkoxycarbonyl on the pyrrolidine group" includes a pyrrolidinylcarbonyl which may optionally be substituted by a phenylalkoxycarbonyl group wherein the alkoxy moiety is a straight chain or branched chain alkoxy group having 1 to 6 carbon atoms, for example, 1-benzyloxycarbonyl-2-pyrrolidinylcarbonyl, 2-pyrrolidinylcarbonyl, 1-pyrrolidinylcarbonyl, 3-pyrrolidinylcarbonyl, 1-(2-phenylethoxycarbonyl)-2-pyrrolidinylcarbgnyl, 2-(1-phenylethoxycarbonyl)-1-pyrrolidinylcarbonyl, 3-(3-phenylpropoxycarbonyl)-2-pyrrolidinylcarbonyl, 1-(4-phenylbutoxycarbonyl)-2-pyrrolidinylcarbonyl, 2-(5-phenylpentyloxycarbonyl)-1-pyrrolidinylcarbonyl, 2-(6-phenylhexyloxycarbonyl)-3-pyrrolidinylcarbonyl, and the like.

The "phenyl(lower)alkoxycarbonylamino" includes a phenylalkoxycarbonylamino wherein the alkoxycarbonyl moiety is a straight chain or branched chain alkoxycarbonyl group having 1 to 6 carbon atoms, for example, N-benzyloxycarbonylamino, N-(2-phenylethoxycarbonyl)amino, N-(1-phenylethoxycarbonyl)amino, N-(3-phenylpropoxycarbonyl)amino, N-(4-phenylbutoxycarbonyl)amino, N-(5-phenylpentyloxycarbonyl)amino, N-(6-phenylhexyloxycarbonyl)amino, N-(1,1-dimethyl-2-phenylethoxycarbonyl)amino, N-(2-methyl-3-phenylpropoxycarbonyl)amino, and the like.

The "lower alkyl having optionally a hydroxysubstituent" includes a straight chain or branched chain alkyl group having 1 to 6 carbon atoms which has optionally one to three hydroxy-substituents, for example, in addition to the above-mentioned lower alkyl groups, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, 3,4-dihydroxybutyl, 5,6-dihydroxyhexyl, and the like.

The "hydroxy-substituted lower alkanoyl" includes a hydroxy-substituted straight chain or branched chain alkanoyl group having 2 to 6 carbon atoms, for example, 2-hydroxyacetyl, 3-hydroxypropionyl, 2-hydroxypropionyl, 4-hydroxybutyryl, 2,2-dimethyl-3-hydroxypropionyl, 5-hydroxypentanoyl, 6-hydroxyhexanoyl, 3-methyl-4-hydroxybutyryl, and the like.

The "lower alkanoyloxy(lower)alkanoyl" includes an alkanoyloxyalkanoyl wherein both alkanoyl moieties are a straight chain or branched chain alkanoyl group having 2 to 6 carbon atoms, for example, 2-acetyloxyacetyl, 3-propionyloxypropionyl, 2-butyryloxypropionyl, 4-pentanoyloxybutyryl, 2,2-dimethyl-3-hexanoyloxypropionyl, 5-acetyloxypentanoyl, 6-propionyloxyhexanoyl, and the like.

The "phenyl(lower)alkyl which phenyl ring may optionally have a lower alkoxy substituent" includes a phenylalkyl group wherein the alkyl moiety is a straight chain or branched chain alkyl group having 1 to 6 carbon atoms and the phenyl ring has optionally one to three substituents of a straight chain or branched chain alkoxy group having 1 to 6 carbon atoms, for example, in addition to the above-mentioned phenyl(lower)alkyl groups, 2-methoxybenzyl, 3-methoxybenzyl, 2-(4-methoxyphenyl)ethyl, 1-(2-ethoxyphenyl)ethyl, 3-(4-isopropoxyphenyl)propyl, 4-(3-pentyloxyphenyl)butyl, 5-(4-hexyloxyphenyl)pentyl, 6-(2-butyloxyphenyl)hexyl, 3,4-dimethoxybenzyl, 3-ethoxy-4-methoxybenzyl, 2,3-dimethoxybenzyl, 2,6-dimethoxybenzyl, 3,4,5-trimethoxybenzyl, and the like.

The "cycloalkenylcarbonyl" includes a cycloalkenylcarbonyl group having 3 to 8 carbon atoms, for example, cyclopropenylcarbonyl, cyclobutenylcarbonyl, cyclopentenylcarbonyl, cyclohexenylcarbonyl, cycloheptenylcarbonyl, cyclooctenylcarbonyl, and the like.

The "pyrimidylthio-substituted lower alkoxy" includes a pyrimidylthio-substituted straight chain or branched chain alkoxy group having 1 to 6 carbon atoms, for example, (2-pyrimidyl)thiomethoxy, 2-(4-pyrimidyl)thioethoxy, 1-(5-pyrimidyl)thioethoxy, 3-(6-pyrimidyl)thiopropoxy, 4-(4-pyrimidyl)thiobutoxy, 5-(2-pyrimidyl)thiopentyloxy, 6-(5-pyrimidyl)thiohexyloxy, 1,1-dimethyl-2-(2-pyrimidyl)thioethoxy, 2-methyl-3-(2-pyrimidyl)thiopropoxy, and the like.

The "pyrimidylsulfinyl-substituted lower alkoxy" includes a pyrimidylsulfinyl-substituted straight chain or branched chain alkoxy group having 1 to 6 carbon atoms, for example, (2-pyrimidyl)sulfinylmethoxy, 2-(4-pyrimidyl)sulfinylethoxy, 1-(5-pyrimidyl)sulfinylethoxy, 3-(6-pyrimidyl)sulfinylpropoxy, 4-(4-pyrimidyl)sulfinylbutoxy, 5-(2-pyrimidyl)sulfinylpentyloxy, 6-(5-pyrimidyl)sulfinylhexyloxy, 1,1-dimethyl-2-(2-pyrimidyl)sulfinylethoxy, 2-methyl-3-(2-pyrimidyl)sulfinylpropoxy, and the like.

The "pyrimidylsulfonyl-substituted lower alkoxy" includes a pyrimidylsulfonyl-substituted straight chain or branched chain alkoxy group having 1 to 6 carbon atoms, for example, (2-pyrimidyl)sulfonylmethoxy, 2-(4-pyrimidyl)sulfonylethoxy, 1-(5-pyrimidyl)sulfonylethoxy, 3-(6-pyrimidyl)sulfonylpropoxy, 4-(4-pyrimidyl)sulfonylbutoxy, 5-(2-pyrimidyl)sulfonylpentyloxy, 6-(5-pyrimidyl)sulfonylhexyloxy, 1,1-dimethyl-2-(2-pyrimidyl)sulfonylethoxy, 2-methyl-3-(2-pyrimidyl)sulfonylpropoxy, and the like.

The "imidazolylthio-substituted lower alkoxy which may optionally have a lower alkyl substituent" includes a imidazolylthio-substituted straight chain or branched chain alkoxy group having 1 to 6 carbon atoms which may optionally have a substituent of a straight chain or branched chain alkyl group having 1 to 6 carbon atoms on the imidazolyl group, for example, (2-imidazolyl)thiomethoxy, 2-(4-imidazolyl)thioethoxy, 1-(5-imidazolyl)thioethoxy, 3-(2-imidazolyl)thiopropoxy, 4-(4-imidazolyl)thiobutoxy, 5-(2-imidazolyl)thiopentyloxy, 6-(5-imidazolyl)thiohexyloxy, 1,1-dimethyl-2-(2-imidazolyl)thioethoxy, 2-methyl-3-(2-imidazolyl)thiopropoxy, (4-methyl-2-imidazolyl)thiomethoxy, 2-(5-ethyl-4-imidazolyl)thioethoxy, 1-(4-propyl-5-imidazolyl)thioethoxy, 3-(1-butyl-2-imidazolyl)thiopropoxy, 4-(2-pentyl-4-imidazolyl)thiobutoxy, 5-(1-methyl-2-imidazolyl)thiopentyloxy, 6-(1-hexyl-5-imidazolyl)thiohexyloxy, 1,1-dimethyl-2-(1-ethyl-2-imidazolyl)thioethoxy, 2-methyl-3-(1-propyl-2-imidazolyl)thiopropoxy, and the like.

The "imidazolylsulfonyl-substituted lower alkoxy which may optionally have a lower alkyl substituent" includes a imidazolylsulfonyl-substituted straight chain or branched chain alkoxy group having 1 to 6 carbon atoms which may optionally have a substituent of a straight chain or branched chain alkyl group having 1 to 6 carbon atoms on the imidazolyl group, for example, (2-imidazolyl)sulfonylmethoxy, 2-(4-imidazolyl)sulfonylethoxy, 1-(5-imidazolyl)sulfonylethoxy, 3-(2-imidazolyl)sulfonylpropoxy, 4-(4-imidazolyl)sulfonylbutoxy, 5-(2-imidazolyl)sulfonylpentyloxy, 6-(5-imidazolyl)sulfonylhexyloxy, 1,1-dimethyl-2-(2-imidazolyl)sulfonylethoxy, 2-methyl-3-(2-imidazolyl)sulfonylpropoxy, (4-methyl-2-imidazolyl)sulfonylmethoxy, 2-(5-ethyl-4-imidazolyl)sulfonylethoxy, 1-(4-propyl-5-imidazolyl)sulfonylethoxy, 3-(1-butyl-2-imidazolyl)sulfonylpropoxy, 4-(2-pentyl-4-imidazolyl)sulfonylbutoxy, 5-(1-methyl-2-imidazolyl)sulfonylpentyloxy, 6-(1-hexyl-5-imidazolyl)sulfonylhexyloxy, 1,1-dimethyl-2-(1-ethyl-2-imidazolyl)sulfonylethoxy, 2-methyl-3-(1-propyl-2-imidazolyl)sulfonylpropoxy, and the like.

The "ammonium-substituted lower alkoxy having three substituents selected from a lower alkyl, a lower alkenyl and oxo" includes an ammonium-substituted straight chain or branched chain alkoxy group having 1 to 6 carbon atoms, which have three substituents selected from a straight chain or branched chain alkyl group having 1 to 6 carbon atoms, a straight chain or branched chain alkenyl group having 2 to 6 carbon atoms, and an oxo group, for example, trimethylammoniummethoxy, 2-(triethylammonium)ethoxy, 1-(tripropylammonium)ethoxy, 3-(tributylammonium)propoxy, 4-(tripentylammonium)butoxy, 5-(triethylammonium)pentyloxy, 6-(trihexylammonium)hexyloxy, 1,1-dimethyl-2-(triallylammonium)ethoxy, 2-methyl-3-(tributenylammonium)propoxy, tri(1-methylallyl)ammonium-methoxy, 2-[tri(2-pentenyl)ammonium]ethoxy, 1-[tri(2-hexenyl)ammonium]ethoxy, 3-(N-allyl-N,N-dimethylammonium)propoxy, 4-(N,N-diallyl-N-methylammonium)butoxy, 5-(N-allyl-N-methylamino)pentyloxy N-oxide, 6-(N-allyl-N-ethylamino)hexyloxy N-oxide, 5-(N-allyl-N-methyl-N-ethylammonium)pentyloxy, and the like.

The "phenylthio(lower)alkoxy which phenyl ring may optionally have a substituent selected from nitro and an amino" includes a phenylthioalkoxy wherein the alkoxy moiety is a straight chain or branched chain alkoxy group having 1 to 6 carbon atoms, and the phenyl ring may optionally have one to three substituents selected from a nitro group and an amino group, for example, phenylthiomethoxy, 2-phenylthioethoxy, 1-phenylthioethoxy, 3-phenylthiopropoxy, 4-phenylthiobutoxy, 5-phenylthiopentyloxy, 6-phenylthiohexyloxy, 1,1-dimethyl-2-phenylthioethoxy, 2-methyl-3-phenylthiopropoxy, (2-nitrophenyl)thiomethoxy, 2-(3-nitrophenyl)thioethoxy, 1-(4-nitrophenyl)thioethoxy, 3-(2,3-dinitrophenyl)thiopropoxy, 4-(3,4-dinitrophenyl)thiobutoxy, 5-(4-nitrophenyl)thiopentyloxy, 6-(2,6-dinitrophenyl)thiohexyloxy, 1,1-dimethyl-2-(2,4,6-trinitrophenyl)thioethoxy, 2-methyl-3-(4-nitrophenyl)thiopropoxy, (2-aminophenyl)thiomethoxy, 2-(3-aminophenyl)thioethoxy, 1-(4-aminophenyl)thioethoxy, 3-(2,3-diaminophenyl)thiopropoxy, 4-(3,4-diaminophenyl)thiobutoxy, 5-(4-aminophenyl)thiopentyloxy, 6-(2,6-diaminophenyl)thiohexyloxy, 1,1-dimethyl-2-(2,4,6-triaminophenyl)thioethoxy, 2-methyl-3-(4-aminophenyl)thiopropoxy, and the like.

The "phenylsulfonyl(lower)alkoxy which phenyl ring may optionally have a substituent selected from nitro and an amino having optionally one or two substituents selected from a lower alkanoyl and a lower alkyl" includes a phenylsulfonylalkoxy wherein the alkoxy moiety is a straight chain or branched chain alkoxy group having 1 to 6 carbon atoms, and the phenyl ring may optionally have one to three substituents selected from a nitro group and an amino group having optionally one or two substituents selected from a straight chain or branched chain alkyl group having 1 to 6 carbon atoms and a straight chain or branched chain alkanoyl group having 1 to 6 carbon atoms, for example, phenylsulfonylmethoxy, 2-phenylsulfonylethoxy, 1-phenylsulfonylethoxy, 3-phenylsulfonylpropoxy, 4-phenylsulfonylbutoxy, 5-phenylsulfonylpentyloxy, 6-phenylsulfonylhexyloxy, 1,1-dimethyl-2-phenylsulfonylethoxy, 2-methyl-3-phenylsulfonylpropoxy, (2-aminophenyl)sulfonylmethoxy, 5-(4-aminophenyl)sulfonylpentyloxy, 2-(4-methylaminophenyl)sulfonylethoxy, 1-(3-ethylaminophenyl)sulfonylethoxy, 3-[2-(N-methyl-N-ethylamino)phenyl] sulfonylpropoxy, 4-[3-(N-methyl-N-hexylamino)phenyl]sulfonylbutoxy, 5-(4-dimethylaminophenyl)sulfonylpentyloxy, 4-dipentylaminophenylsulfonylmethoxy, 2-(2-isopropylaminophenyl)sulfonylethoxy, 1-(3-butylaminophenyl)sulfonylethoxy, 5-(2,4-diaminophenyl)sulfonylpentyloxy, 3-[2,3-bis(dimethylamino)phenyl]sulfonylpropoxy, 4-

[3,4-bis(methylamino)phenyl]sulfonylbutoxy, 5-(2,4,6-triaminophenyl)sulfonylpentyloxy, 6-[3,4,5-tri(methylamino)phenyl]sulfonylhexyloxy, 5-(4-acetylaminophenyl)sulfonylpentyloxy, 3-[4-(N-methyl-N-acetylamino)phenyl]sulfonylpropoxy, 5-(4-nitrophenyl)sulfonylpentyloxy, 2-(4-nitro-3-methylaminophenyl)sulfonylethoxy, 3-(2,4-dinitrophenyl)sulfonylpropoxy, 4-(2,4,6-trinitrophenyl)sulfonylbutoxy, and the like.

The "pyridylthio-substituted lower alkoxy" includes a pyridylthio-substituted straight chain or branched chain alkoxy group having 1 to 6 carbon atoms, for example, (2-pyridyl)thiomethoxy, 2-(3-pyridyl)thioethoxy, 1-(4-pyridyl)thioethoxy, 3-(3-pyridyl)thiopropoxy, 4-(4-pyridyl)thiobutoxy, 5-(2-pyridyl)thiopentyloxy, 5-(4-pyridyl) 6-(3-pyridyl)thiohexyloxy, 1,1-dimethyl-2-(2-pyridyl)thioethoxy, 2-methyl-3-(4-pyridyl)thiopropoxy, and the like.

The "pyridylsulfonyl-substituted lower alkoxy which may optionally have an oxo substituent on the pyridyl ring" includes a pyridylsulfonyl-substituted straight chain or branched chain alkoxy group having 1 to 6 carbon atoms which may optionally have an oxo substituent on the pyridyl ring, for example, (2-pyridyl)sulfonylmethoxy, 2-(3-pyridyl)sulfonylethoxy, 1-(4-pyridyl)sulfonylethoxy, 3-(3-pyridyl)sulfonylpropoxy, 4-(4-pyridyl)sulfonylbutoxy, 5-(2-pyridyl)sulfonylpentyloxy, 5-(4-pyridyl)sulfonylpentyloxy, 6-(3-pyridyl)sulfonylhexyloxy, 1,1-dimethyl-2-(2-pyridyl)sulfonylethoxy, 2-methyl-3-(4-pyridyl)sulfonylpropoxy, 5-(1-oxido-4-pyridyl)sulfonylpentyloxy, (4-oxo-2-pyridyl 2-(1-oxido-3-pyridyl)sulfonylethoxy, 1-(2-oxo-4-pyridyl)sulfonylethoxy, 3-(2-oxo-3-pyridyl)sulfonylpropoxy, 4-(3-oxo-4-pyridyl)sulfonylbutoxy, 5-(1-oxido-2-pyridyl)sulfonylpentyloxy, 6-(1-oxido-3-pyridyl)sulfonylhexyloxy, and the like.

The "cycloalkylcarbonyl having optionally one to three substituents selected from hydroxy and a lower alkanoyloxy" includes a cycloalkylcarbonyl having 3 to 8 carbon atoms which has optionally one to three substituents selected from a hydroxy group and a straight chain or branched chain alkanoyloxy group having 2 to 6 carbon atoms, for example, cyclopropylcarbonyl, cyclobutylcarbonyl, cyclooctylcarbonyl, 2-hydroxycyclopropylcarbonyl, 3-hydroxycyclobutylcarbonyl, 2-hydroxycyclopentylcarbonyl, 3-hydroxycyclopentylcarbonyl, 2,4-dihydroxycyclopentylcarbonyl, 2-hydroxycyclohexylcarbonyl, 3-hydroxycyclohexylcarbonyl, 4-hydroxycyclohexylcarbonyl, 3,4-dihydroxycyclohexylcarbonyl, 2,4-dihydroxycyclohexylcarbonyl, 2,5-dihydroxycyclohexylcarbonyl, 3,4,5-trihydroxycyclohexylcarbonyl, 3-hydroxycycloheptylcarbonyl, 3,4-dihydroxycycloheptylcarbonyl, 2,3,4-trihydroxycycloheptylcarbonyl, 4-hydroxycyclooctylcarbonyl, 4,5-dihydroxycyclooctylcarbonyl, 4,5,6-trihydroxycyclooctylcarbonyl, 2-acetyloxycyclopropylcarbonyl, 3-propionyloxycyclobutylcarbonyl, 2-butyryloxycyclopentylcarbonyl, 3-pentanoyloxycyclopentylcarbonyl, 2,4-dihexanoyloxycyclopentylcarbonyl, 2-acetyloxycyclohexylcarbonyl, 3-propionyloxycyclohexylcarbonyl, 4-butyryloxycyclohexylcarbonyl, 3,4-diacetyloxycyclohexylcarbonyl, 2,4-diacetyloxycyclohexylcarbonyl, 2,5-diacetyloxycyclohexylcarbonyl, 3,4,5-triacetyloxycyclohexylcarbonyl, 3,4-diacetyloxy-5-hyroxycyclohexylcarbonyl, 3-pentanoyloxycycloheptylcarbonyl, 3,4-diacetyloxycycloheptylcarbonyl, 2,3,4-tripropionyloxycycloheptylcarbonyl, 4-hexanoyloxycyclooctylcarbonyl, 4,5-dibutyryloxycyclooctylcarbonyl, 4,5,6-triacetyloxycyclooctylcarbonyl, and the like.

The "tetrahydroypyranyl(lower)alkyl which tetrahydroxypyranyl ring may optionally have one to four substituents selected from hydroxy and a lower alkoxy" includes a tetrahydropyranylalkyl wherein the alkyl moiety is a straight chain or branched chain alkyl group having 1 to 6 carbon atoms, and the tetrahydropyranyl ring may optionally have one to four substituents selected from a hydroxy group and a straight chain or branched chain alkoxy group having 1 to 6 carbon atoms, for example, (2-tetrahydropyranyl)methyl, 2-(3-tetrahydropyranyl)ethyl, 1-(4-tetrahydropyranyl)ethyl, 3-(2-tetrahydropyranyl)propyl, 4-(3-tetrahydropyranyl)butyl, 5-(4-tetrahydropyranyl)pentyl, 6-(2-tetrahydropyranyl)hexyl, 1,1-dimethyl-2-(3-tetrahydropyranyl)ethyl, 2-methyl-3-(4-tetrahydropyranyl)propyl, (3-hydroxy-2-tetrahydropyranyl)methyl, 2-(2,4-dihydroxy-3-tetrahydropyranyl)ethyl, 1-(2,3,5-trihydroxy-4-tetrahydropyranyl)ethyl, 3-(6-methoxy-2-tetrahydropyranyl)propyl, 4-(4-ethoxy-3-tetrahydropyranyl)butyl, 5-(4,6-dimethoxy-4-tetrahydropyranyl)pentyl, 6-(4,5,6-trimethoxy-2-tetrahydropyranyl)hexyl, 1,1-dimethyl-2-(2-propoxy-3-tetrahydropyranyl)ethyl, 2-methyl-3-(6-butoxy-4-tetrahydropyranyl)propyl, (6-pentyloxy-2-tetrahydropyranyl)methyl, 2-(4-hexyloxy-3-tetrahydropyranyl)ethyl, 2-(3,4,5-trihydroxy-6-methoxy-2-tetrahydropyranyl)methyl, 1-(3,4,5,6-tetrahydroxy-2-tetrahydropyranyl)ethyl, 3-(3,4,5,6-tetramethoxy-2-tetrahydropyranyl)propyl, and the like.

The "lower alkanoyl substituted by a 5- or 6membered saturated heterocyclic group selected from pyrrolidinyl, piperazinyl, piperidinyl, and morpholinyl" includes a straight chain or branched chain alkanoyl group having 2 to 6 carbon atoms which is substituted by a 5- or 6-membered saturated heterocyclic group selected from pyrrolidinyl, piperazinyl, piperidinyl, and morpholinyl, for example, 2-(1-pyrrolidinyl)acetyl, 3-(2-pyrrolidinyl)propionyl, 2-(3-pyrrolidinyl)propionyl, 4-(1-pyrrolidinyl)butyryl, 2,2-dimethyl-3-(2-pyrrolidinyl)propionyl, 5-(3-pyrrolidinyl)pentanoyl, 6-(1-pyrrolidinyl)hexanoyl, 2-(1-piperazinyl)acetyl, 3-(2-piperazinyl)propionyl, 2-(3-piperazinyl)propionyl, 4-(1-piperazinyl)butyryl, 2,2-dimethyl-3-(2-piperazinyl)propionyl, 5-(3-piperazinyl)pentanoyl, 6-(1 -piperidinyl)acetyl, 3-(2-piperidinyl)propionyl, 2-(3-piperidinyl)propionyl, 4-(4-piperidinyl)butyryl, 2,2-dimethyl-3-(1-piperidinyl)propionyl, 5-(2-piperidinyl)pentanoyl, 6-(3-piperidinyl)hexanoyl, 2-(1-morpholinyl)acetyl, 3-(2-morpholinyl)propionyl, 2-(3-morpholinyl)propionyl, 4-(1-morpholinyl)butyryl, 2,2-dimethyl-3-(2-morpholinyl)propionyl, 5-(3-morpholinyl)pentanoyl, 6-(1-morpholinyl)hexanoyl, and the like.

The above "heterocyclic group-substituted lower alkanoyl which has a substituent selected from a lower alkyl and phenyl" includes the above heterocyclic group-substituted straight chain or branched chain alkanoyl group having 2 to 6 carbon atoms, which has one to three substituents selected from a straight chain or branched chain alkyl group having 1 to 6 carbon atoms, and a phenyl group, for example, 2-(2-methyl-1-pyrrolidinyl)acetyl, 3-(1-ethyl-2-pyrrolidinyl)propionyl, 2-(1-propyl-3-pyrrolidinyl)propionyl, 4-(3-butyl-1-pyrrolidinyl)butyryl, 2,2-dimethyl-3-(4-pentyl-2-pyrrolidinyl)propionyl, 5-(1-hexyl-3-pyrrolidinyl)pentanoyl, 6-(2,3-dimethyl-1-pyrrolidinyl)hexanoyl, 2-(2,3,4-trimethyl-1-pyrrolidinyl)acetyl, 3-(1-phenyl-2-pyrrolidinyl)propionyl, 2-(1-methyl-2-phenyl-3-pyrrolidinyl)propionyl, 2-(4-methyl-1-piperazinyl)acetyl, 2-(4-phenyl-1-piperazinyl)acetyl, 3-(4-ethyl-2-piperazinyl)propionyl, 2-(4-propyl-3-piperazinyl)propionyl, 4-(4-butyl-1-piperazinyl)butyryl, 2,2-dimethyl-3-(4-pentyl-2-piperazinyl)propionyl, 5-(4-hexyl-3-piperazinyl)pentanoyl, 6-(2,4-dimethyl-1-piperazinyl)hexanoyl, 2-(3,4,5-trimethyl-1-piperazinyl)acetyl, 2-(4-phenyl-3-methyl-1-piperazinyl)acetyl, 2-(4-methyl-1-piperidinyl)acetyl, 3-(1-ethyl-2-piperidinyl)propionyl, 2-(1-propyl-3-piperidinyl)propionyl, 4-(1-butyl-4-piperidinyl)butyryl, 2,2-dimethyl-3-(4-pentyl-1-piperidinyl)propionyl, 5-(1-hexyl-2-piperidinyl)pentanoyl, 6-(1-phenyl-3-piperidinyl)hexanoyl, 2-(2,5-dimethyl-4-phenyl-1-piperidinyl)acetyl, 2-(2,3,4-trimethyl-1-piperidinyl)acetyl, 2-(1,2-dimethyl-4-piperidinyl)acetyl, 2-(3-methyl-1-morpholinyl)acetyl, 3-(1-ethyl-2-morpholinyl)propionyl, 2-(1-propyl-3-morpholinyl)propionyl, 4-(2-butyl-1-morpholinyl)butyryl, 2,2-dimethyl-3-(1-pentyl-2-morpholinyl)propionyl, 5-(2-hexyl-3-morpholinyl)pentanoyl, 6-(3,5-dimethyl-1morpholinyl)hexanoyl, 2-(2,3,5-trimethyl-1-morpholinyl)acetyl, 2-(3-phenyl-1-morpholinyl)acetyl, 2-(2-methyl-3-phenyl-1-morpholinyl)acetyl, and the like.

The "piperidinylcarbonyl which may optionally have a lower alkanoyl substituent" includes a piperidinylcarbonyl which may optionally have a substituent of a straight chain or branched chain alkanoyl group having 1 to 6 carbon atoms, for example, (1-piperidinyl)carbonyl, (2-piperidinyl)carbonyl, (3-piperidinyl)carbonyl, (4-piperidinyl)carbonyl, (1-acetyl-4-piperidinyl)carbonyl, (4-formyl-1-piperidinyl)carbonyl, (3-propionyl-2-piperidinyl)carbonyl, (1-butyryl-4-piperidinyl)carbonyl, (1-pentanoyl-4-piperidinyl)carbonyl, (1-hexanoyl-4-piperidinyl)carbonyl, and the like.

The carbostyril derivatives of the present invention can be prepared by various processes, for example, by the processes shown in the following reaction schemes.

[Reaction Scheme-1]

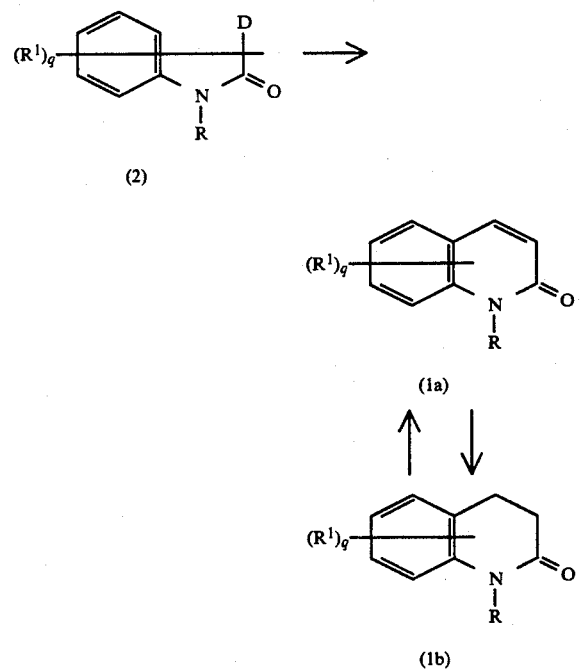

wherein R, q and $R^1$ are the same as defined above, and D is a group of the formula: $-CH=CHR^{14}$ ($R^{14}$ is a lower alkoxy, phenyl or a halogen atom), a group of the formula:

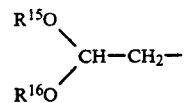

($R^{15}$ and $R^{16}$ are each a lower alkyl), or a group of the formula: $-C\equiv CH$, and the D group may optionally be substituted by the group $R^1$.

The cyclization reaction of the compound of the formula (2) is carried out in an appropriate solvent or without solvent in the presence of an acid. The acid includes any conventional inorganic acids and organic acids, for example, inorganic acids (e.g. hydrochloric acid, hydrobromic acid, sulfuric acid, etc.), Lewis acids (e.g. aluminum chloride, boron trifluoride, titanium tetrachloride, etc.), organic acids (e.g. formic acid, acetic acid, ethanesulfonic acid, p-toluenesulfonic acid, etc.), phosphorus pentoxide, polyphosphoric acid, among which hydrochloric acid, hydrobromic acid and sulfuric acid are preferable. The acid is usually used in at least equivalent amount, preferably in an amount of 10 to 50 times by weight, as much as the amount of the compound (2). The solvent includes any conventional inert solvents, for example, water, lower alcohols (e.g. methanol, ethanol, propanol, etc.), ethers (e.g. dioxane, tetrahydrofuran, etc.), aromatic hydrocarbons (e.g. benzene, chlorobenzene, toluene, etc.), halogenated hydrocarbonss (e.g. methylene chloride, chloroform, carbon tetrachloride, etc.), acetone, dimethylsulfoxide, dimethylformamide, hexamethylphosphoric triamide, and the like. The reaction is usually carried out at a temperature of from about 0 to about 200° C., preferably from room temperature to about 150° C., for about 5 minutes to 6 hours.

The reduction of the compound of the formula (1a) is usually carried out under conventional conditions for the usual catalytic reduction. The catalyst includes metals such as palladium, palladium-carbon, platinum, Raney nickel, etc. The solvent used therein includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.). The reduction reaction can be carried out at atmospheric pressure or under pressure, usually under atmospheric pressure to 20 kg/cm², preferably atmospheric pressure to 10 kg/cm². The reaction temperature is usually in the range of from about 0° C. to about 150° C., preferably from room temperature to about 100° C.

The dehydration reaction of the compound of the formula (1b) is usually carried out in an appropriate solvent with an oxidizing agent. The oxidizing agent includes, for example, benzoquinones (e.g. 2,3-dichloro-5,6-dicyanobenzoquinone, chloranil (=2,3,5,6-tetrachlorobenzoquinone), etc.), halogenating agents (e.g. N-bromosuccinimide, N-chlorosuccinimide, bromine, etc.), hydrogenating catalysts (e.g. selenium oxide, palladium-carbon, palladium black, palladium oxide, Raney nickel, etc.). When a halogenating agent is used, it is usually used in an amount of 1 to 5 moles, preferably 1 to 2 moles, to 1 mole of the compound (1b). When a hydrogenating catalyst is used, it is used in a catalytic amount as usual. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar solvents (e.g. acetic acid, etc.), aprotic polar solvents (e.g. dimethylformamide, dimethylsulfoxide, hexamethylphosphoric triamide, etc.). The reaction is usually carried out at a temperature of from room temperature to about 300° C., preferably from room temperature to about 200° C., for 1 to 40 hours.

[Reaction Scheme-2]

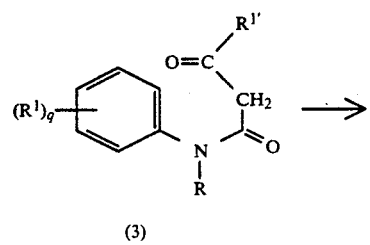

(3)

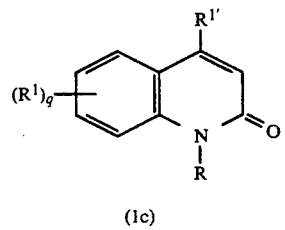

(1c)

wherein $R^1$, q and R are the same as defined above, and $R^{1'}$ is hydrogen atom or a lower alkyl, provided that when $R^{1'}$ is a lower alkyl, q is 1 or 2.

The cyclization reaction of the compound (3) is carried out in an appropriate solvent in the presence of a condensation agent. The condensation agent includes, for example, Lewis acids, such as phosphorus pentoxide, hydrogen fluoride, sulfuric acid, polyphosphoric acid, aluminum chloride, zinc chloride, etc. The solvent includes, for example, halogenated hydrocarbons (e.g. chloroform, dichloromethane, 1,2-dichloroethane, etc.), ethers (e.g. diethyl ether, dioxane, etc.), aromatic hydrocarbons (e.g. nitrobenzene, chlorobenzene, etc.). The condensation agent is usually used in an amount of about 1 to 10 moles, preferably about 3 to 6 moles, to 1 mole of the compound (3). The reaction is usually carried out at a temperature of about 50° C. to about 250° C., preferably about 70° C. to about 200° C., for about 20 minutes to about 6 hours.

[Reaction Scheme-3]

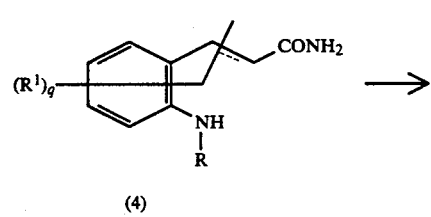

(4)

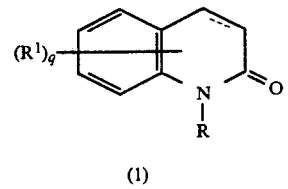

(1)

wherein R, $R^1$, q, and the bond between 3- and 4-positions of the carbonstyril nucleus are the same as defined above.

The cyclization reaction of the compound (4) is carried out in an appropriate solvent or without using a solvent in the presence of an acid. The acid includes, for example, inorganic acids (e.g. hydrochloric acid, sulfuric acid, hydrobromic acid, nitric acid, polyphosphoric acid, etc.), organic acids (e.g. p-toluenesulfonic acid, ethanesulfonic acid, trifluoroacetic acid, etc.). The solvent includes any conventional solvents unless they affect on the reaction, for example, water, lower alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, diphenyl ether, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The reaction is usually carried out at a temperature of from about −20° C. to about 150° C., preferably from about 0° C. to about 150° C., for about 5 minutes to about 30 hours.

[Reaction Scheme-4]

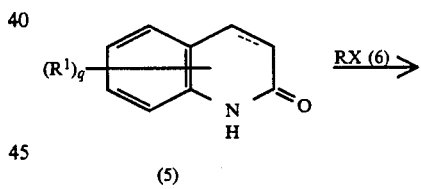

(5)

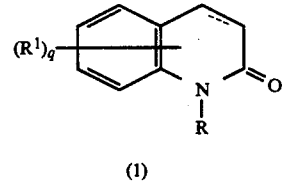

(1)

wherein R, $R^1$, q and the bond between 3- and 4-positions of the carbostyril nucleus are the same as defined above.

The reaction of the compound of the formula (5) and the compound of the formula (6) is usually carried out in an appropriate inert solvent in the presence or absence of a basic compound. The inert solvent includes, for example, aromatic hydrocarbons (e.g. benzene, toluene, xylene, etc.), alcohols (e.g. methanol, ethanol, propanol, butanol, 3-methoxy-1-butanol, ethylcellosolve, methylcellosolve, etc.), pyridine, acetone, N-methylpyrrolidone, dimethylsulfoxide, dimethylformamide, hexamethylphosphoric triamide, etc. The basic compound includes, for example, sodium carbonate, potassium carbonate, sodium hydrogen carbonate, potassium hydrogen carbonate, sodium hydroxide, potassium hydroxide, sodium hydride, potassium hydride, triethylamine, etc.

The amounts of the compound (5) and the compound (6) are not critical, but the compound (6) is usually used at least in equimolar amount, preferably in an amount of 1 to 5 moles to 1 mole of the compound (5). The reaction is usually carried out at a temperature of from room temperature to about 200° C., preferably about 100° C. to about 180° C., for about 3 to 30 hours. In the above reaction, a copper powder may also be used as a catalyst, by which the reaction can proceed advantageously.

[Reaction Scheme-5]

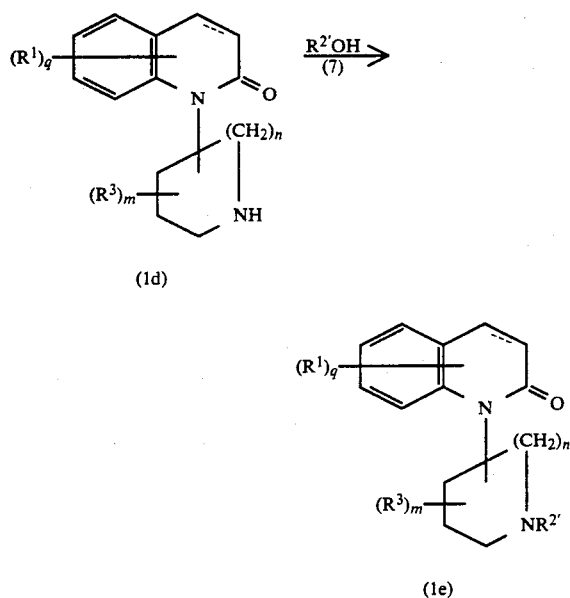

wherein $R^1$, q, $R^3$, m, n and the bond between 3- and 4-positions of the carbostyril nucleus are the same as defined above, and $R^{2'}$ is the same groups as $R^2$ other than hydrogen atom and a group of the formula:

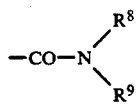

($R^8$ and $R^9$ are the same as defined above).

The process of Reaction Scheme-5 is carried out by reacting a carbostyril derivative of the formula (1d) and a carboxylic acid compound of the formula (7) by a conventional amido bond producing reaction. The amido bond producing reaction can be carried out under the conditions for the conventional amido bond producing reaction, for example, (a) a mixed acid anhydride process, i.e. a process of reacting the carboxylic acid compound (7) with an alkylhalocarboxylic acid to form a mixed acid anhydride and reacting the resultant with the amine compound (1d), (b) an activated ester process, i.e. a process of converting the carboxylic acid compound (7) into an activated ester, such as p-nitrophenyl ester, N-hydroxysuccinimide ester, 1-hydroxybenzotriazole ester, etc., and reacting the resultant with the amine compound (1d), (c) a carbodiimide process, i.e. a process of condensing the carboxylic acid compound (7) and the amine compound (1d) in the presence of an activating agent such as dicyclohexylcarbodiimide, carbonyldiimidazole, etc., (d) other processes, i.e. a process of converting the carboxylic acid compound (7) into a carboxylic anhydride by treating it with a dehydrating agent such as acetic anhydride, and reacting the resultant with the amine compound (1d); a process of reacting an ester of the carboxylic acid compound (7) with a lower alcohol and the amine compound (1d) at a high temperature under high pressure; a process of reacting an acid halide compound of the carboxylic acid compound (7), i.e. a carboxylic acid halide, with the amine compound (1d), and the like.

The mixed acid anhydride used in the above mixed acid anhydride process is obtained by the known Schötten-Baumann reaction, and the reaction product is used without isolation from the reaction mixture for the reaction with the amine compound (1d) to give the desired compound of the formula (1e). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about −20° C. to about 100° C., preferably from about 0° C. to about 50° C., for about 5 minutes to about 10 hours, preferably about 5 minutes to about 2 hours.

The reaction of the thus obtained mixed acid anhydride with the amine compound (1d) is usually carried out at a temperature of from about −20° C. to about 150° C., preferably about 10° C. to about 50° C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (7), the alkylhalocarboxylic acid and the amine (1d) are usually used in each equimolar amount, but preferably, the alkylhalocarboxylic acid and the carboxylic acid compound (7) are used each in an amount of about 1 to 1.5 mole to 1 mole of the amine (1d).

Among the above other processes (d), in case of the process of reacting the carboxylic acid halide with the amine compound (1d), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride. etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, and the like. The amount of the amine compound (1d) and the carboxylic acid halide is not critical, but the carboxylic acid halide is usually used at least in equimolar amount, preferably about 1 to 5 moles to 1 mole of the amine compound (1d). The reaction is usually carried out at a temperature of from about −20° C. to about 180° C., preferably from about 0° C. to about 150° C., for about 5 minutes to about 30 hours.

The amido bond producing reaction in the above Reaction Scheme-5 may also be carried out by reacting the carboxylic acid compound (7) and the amine (1d) in the presence of a condensation agent such as triphenylphosphine, diphenylphosphinyl chloride, phenyl-N-phenylphosphoramide chloridate, diethyl chlorophosphate, diethyl cyanophosphate, bis(2-oxo-3-oxazolidinyl)phosphinic chloride, etc. The reaction is usually carried out in the presence of the solvent and basic compound as used in the above reaction of the carboxylic acid halide and the amine (1d) at a temperature of from about −20° C. to about 150° C., preferably about 0° C. to about 100° C., for about 5 minutes to about 30 hours. The condensation agent and the carboxylic acid compound (7) are used at least in equimolar amount, preferably about 1 to 2 moles, to 1 mole of the amine (1d).

[Reaction Scheme-6]

wherein $R^1$, q, $R^3$, m, n and the bond between 3- and 4-positions of the carbostyril nucleus are the same as defined above, and $R^{8'}$ is the same as $R^8$ other than hydrogen atom.

The reaction of the compound (1d) and the compound (8) can be carried out in the presence or preferably absence of a basic compound in an appropriate solvent or without solvent. The solvent and the basic compound used therein are the same as the solvent and basic compound as used in the reaction of the carboxylic acid halide and the amine (1d) of the above Reaction Scheme-5. The compound (8) is usually used in an amount of about 1 to 5 moles, preferably about 1 to 3 moles, to 1 mole of the compound (1d). The reaction is usually carried out at a temperature of about 0 to 200° C., preferably from room temperature to about 150° C., for about 5 minutes to about 30 hours. In the above reaction, a boron compound (e.g. borone trifluoride etherate, etc.) may be added to the reaction system.

[Reaction Scheme-7]

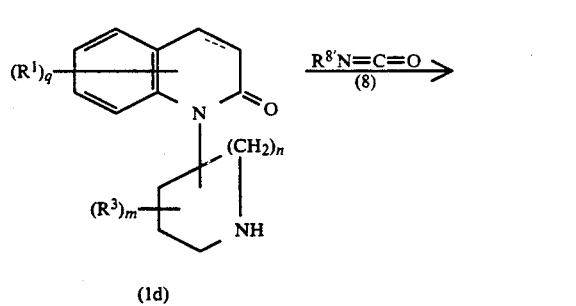

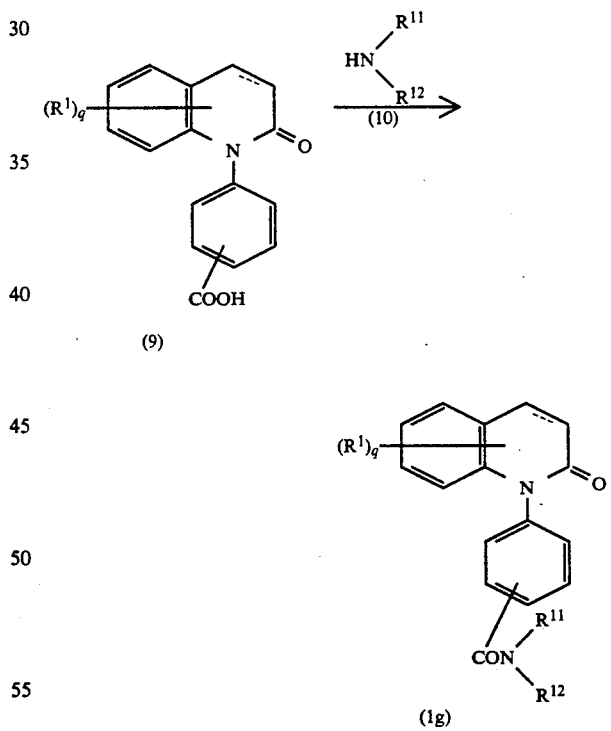

wherein $R^1$, q, $R^{11}$, $R^{12}$ and the bond between 3- and 4-positions of the carbostyril nucleus are the same as defined above.

The reaction of the compound (9) and the compound (10) is carried out under the same conditions as used in the reaction of the compound (1d) and the compound (7) in the above Reaction Scheme-5.

[Reaction Scheme-8]

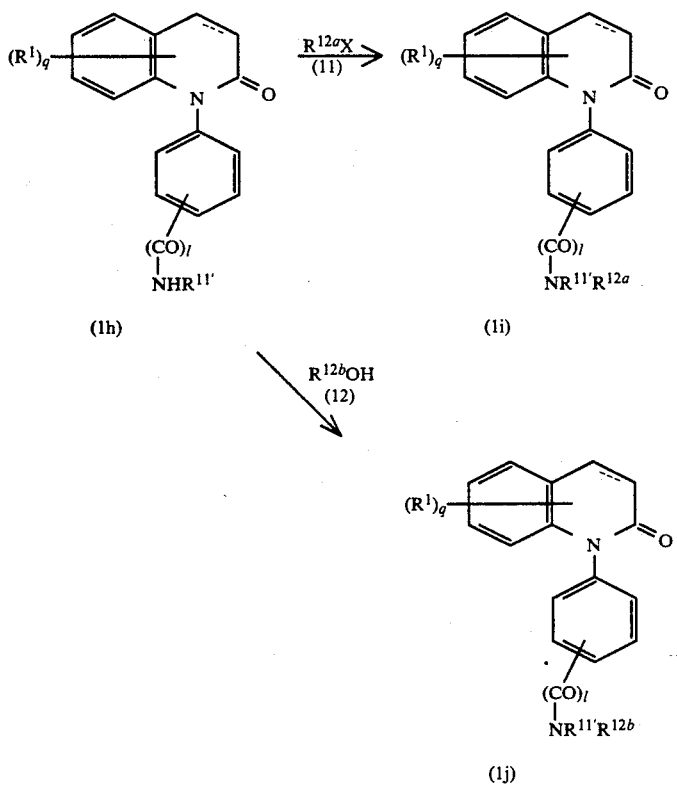

wherein $R^1$, q, X, l and the bond between 3- and 4-positions of carbostyril nucleus are the same as defined above, and $R^{11'}$ is hydrogen atom, a lower alkyl, a phenyl(lower)alkyl, a lower alkenyl, a benzoyl which may optionally have a lower alkoxy substituent, tricyclo[3.3.1.1]decanyl, a phenyl which may optionally have a lower alkoxy substituent, or a cycloalkyl, $R^{12a}$ is a lower alkyl, a phenyl(lower)alkyl, a lower alkenyl, tricyclo[3.3.1.1]decanyl, a phenyl which may optionally have a lower alkoxy substituent, or a cycloalkyl, and $R^{12b}$ is a benzoyl which may optionally have a lower alkoxy substituent.

The reaction of the compound (1h) and the compound (11) is usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), acetic acid, ethyl acetate, acetone, acetonitrile, dimethylsulfoxide, dimethylformamide, hexamethylphosphoric triamide, and the like. The basic compound includes, for example, carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, ethyldiisopropylamine, dimethylaminopyridine, triethylamine, 1,5-diazabicyclo[4.3.0]nonene(5) (DBN), 1,8-diazabicyclo[5.4.0]undecene-7 (DBU), 1,4-diazabicyclo[2.2.2]octane (DABCO), etc.). The amount of the compound (1h) and the compound (11) is not critical, but the compound (11) is usually used at least in equivalent amount, preferably 1 to 5 moles, to 1 mole of the compound (1h). The reaction is usually carried out at a temperature of from about 0° C. to about 200° C., preferably from about 0° C. to about 170° C., for about 30 minutes to about 30 hours.

The reaction of the compound (1h) and the compound (12) is carried out under the same conditions in the reaction of the compound (1d) and the compound (7) in the above Reaction Scheme-5.

In case of the compound of the formula (1) wherein $R^{11}$ and $R^{12}$ combine together with the nitrogen atom to which they bond to form a saturated or unsaturated heterocyclic group which may be intervened or not with nitrogen, oxygen or sulfur atom and said heterocyclic group contains a secondary amino group, the compound can be converted into a compound where said heterocyclic group is substituted on said secondary amino group by a substituent selected from a phenyl(lower)alkyl and a phenyl having optionally a substituent selected from a lower alkoxy and a lower alkanoyl by treating it in the same manner as in the reaction of the compound (1h) and the compound (11) in the above Reaction Scheme-8.

Besides, said compound can also be converted into a compound where the heterocyclic group is substitued on said secondary amine by a substituent selected from benzoyl and a lower alkanoyl by treating it in the same manner as in the reaction of the compound (1h) and the compound (12) in the above Reaction Scheme-8.

[Reaction Scheme-9A]

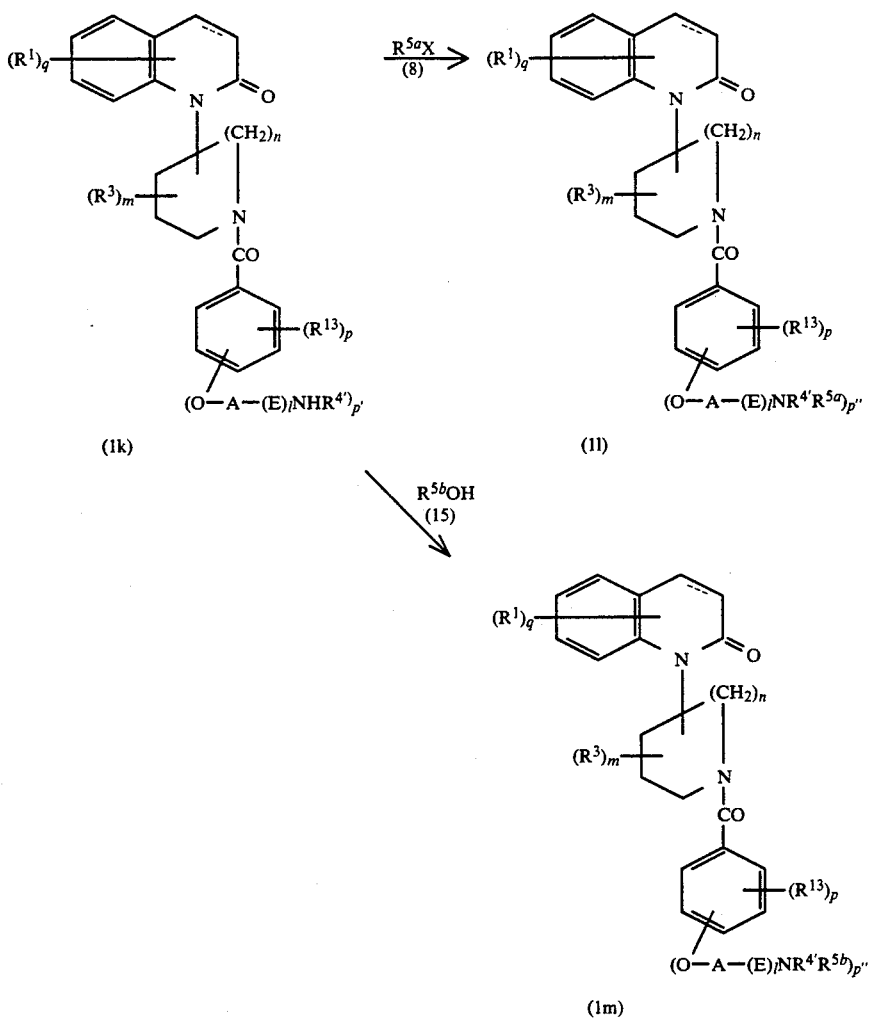

wherein $R^1$, q, $R^3$, m, n, $R^{13}$, p, X, A, E, l, and the bond between 3- and 4-positions of the carbostyril nucleus are the same as defined above, and $R^{4'}$ is hydrogen atom; a lower alkyl which may optionally be substituted by hydroxy or cyano; a lower alkenyl, a lower alkynyl; a phenyl(lower)alkyl; a lower alkanoyl which may optionally have one to three substitutents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a phenyl(lower)alkyl having optionally a lower alkoxy substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by nitro or an amino having optionally one or two substitutents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have substituent selected from a lower alkyl and a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholino wherein the heterocyclic group may optionally have substituent selected from a lower alkyl and phenyl; a piperidinyl-substituted carbonyl which may optionally be substituted by a lower alkanoyl; a lower alkanoyloxy(lower)alkyl; a pyridyl-substituted lower alkyl; or an amino acid residue which can form an amido group with its amino group, $R^{5a}$ is a lower alkyl which may optionally be substituted by hydroxy or cyano; a lower alkenyl; a lower alkynyl; a phenyl(lower)alkyl; phenyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a lower alkylsulfonyl; a phenylsulfonyl which phenyl ring may optionally be substituted by nitro or an amino having optionally one or two substitutents selected from a lower alkyl and a lower alkanoyl; an amido-substituted lower alkyl wherein the lower alkyl moiety have optionally a substituent selected from a phenyl having optionally hydroxy substituent, imidazolyl, carbamoyl or a lower alkylthio, and the amido group may optionally have a lower alkyl substituent; an amino-substituted lower alkyl which may optionally have a substituent selected from a lower alkyl and a lower alkanoyl; anilinocarbonyl; a piperidinyl which may optionally be substituted by a phenyl(-lower)alkyl; a cycloalkyl, a tetrahydropyranyl-substituted lower alkyl wherein the tetrahydropyranyl ring may optionally have one to four substituents selected from hydroxy and a lower alkoxy; a lower alkanoyloxy(lower)alkyl; or a pyridyl-substituted lower alkyl, $R^{5b}$ is a lower alkanoyl which may optionally have one to three substitutents of a halogen atom; a benzoyl which phenyl ring may optionally be substituted by a member selected from nitro and an amino having optionally one or two substituents selected from a lower alkyl, a lower alkanoyl and a phenyl(lower)alkoxycarbonyl; a lower alkoxycarbonyl; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, a phenyl having optionally a hydroxy substitutent, carbamoyl, imidazolyl or a lower alkylthio, and the amino group may optionally have a substituent selected from a lower alkyl having optionally a hydroxy substitutent, a lower alkenyl, a lower alkanoyl, or a phenyl(lower)alkoxycarbonyl; a hydroxy-substituted lower alkanoyl; a lower alkanoyloxy(lower)alkanoyl; a cycloalkenylcarbonyl; a cycloalkylcarbonyl which may optionally have one to three substituents selected from hydroxy and a lower alkanoyloxy; a lower alkanoyl which is substituted by a 5- or 6-membered saturated heterocyclic group selected from pyrrolidinyl, piperazinyl, piperidinyl and morpholino wherein the heterocyclic group may optionally be substituted by a lower alkyl or phenyl; a piperidinyl-substituted carbonyl which may optionally be substituted by a lower alkanoyl; or an amino acid residue which can form an amido group with its amino group, p' and p" are each an integer of 1 to 3, provided that p+p' and p+p" are each an integer not more than 3.

[Reaction Scheme-9B]

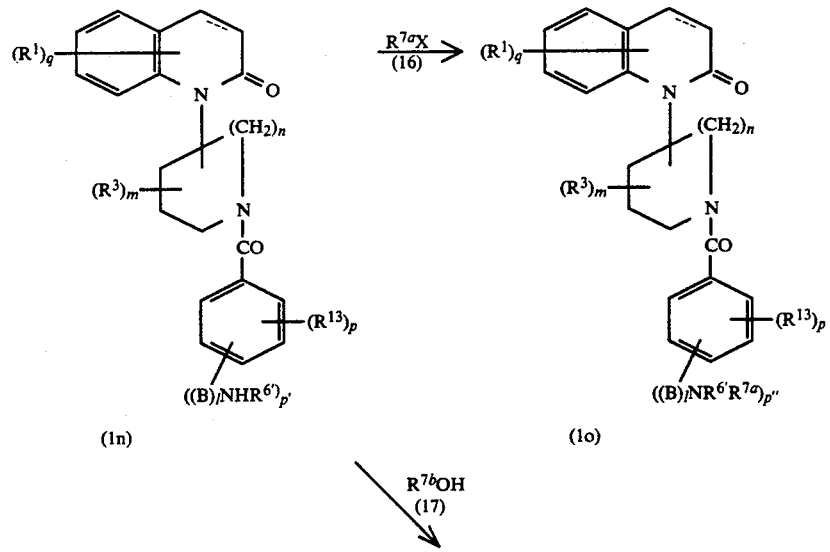

-continued

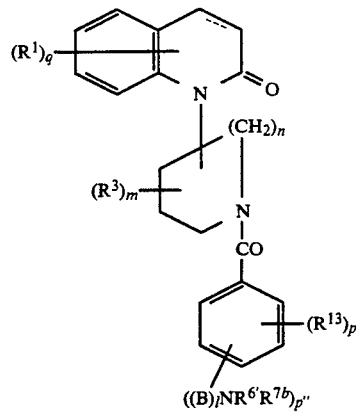

(1p)

wherein $R^1$, q, $R^3$, m, n, $R^{13}$, p, X, B, l, and the bond between 3- and 4-positions of the carbostyril nucleus are the same as defined above, and $R^{6'}$ is hydrogen atom, a lower alkyl, a lower alkanoyl having optionally one to three halogen substituents, a lower alkoxycarbonyl, a carboxy(lower)alkyl, a lower alkoxycarbonyl(lower)alkyl, a lower alkenyl, an amido-substituted lower alkyl having optionally a lower alkyl substituent, or a phenyl(lower)alkoxycarbonyl, $R^{7a}$ is a lower alkyl, a lower alakoxycarbonyl(lower)alkyl, carboxy(lower)alkyl, a lower alkenyl, or an amido-substituted lower alkyl having optionally a lower alkyl substituent, $R^{7b}$ is a lower alkanoyl having optionally one to three halogen substitituents, a lower alkoxycarbonyl, or a phenyl(lower-)alkoxycarbonyl, p' and p" are each an integer of 1 to 3, provided that p+p' and p+p" are each an integer not more than 3.

The reaction of the compound (1k) and the compound (14) in the Reaction Scheme-9A and the reaction of the compound (1n) and the compound (16) in the Reaction Scheme-9B can be carried out under the same conditions as in the reaction of the compound (1h) and the compound (12) in the above Reaction Scheme-8.

Besides, the compound (1m) wherein $R^{5b}$ is a lower alkanoyl or the compound (1p) wherein $R^{7b}$ is a lower alkanoyl having optionally one to three substituents of a halogen atom can also be obtained by reacting the compound (1k) or the compound (1n) with an alkanoylating agent of the formula: $(R^{5b'})_2O$ or $(R^{7b'})_2O$ (wherein $R^{5'}$ is a lower alkanoyl, and $R^{7b'}$ is a lower alkanoyl having optionally one to three substituents of a halogen atom) in an appropriate solvent or without solvent in the presence or absence, preferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, etc. The basic compound includes, for example, tertiary amines (e.g. triethylamine, pyridine, etc.), sodium hydroxide, potassium hydroxide, sodium hydride, and the like. The above reaction can also be carried out in a solvent such as acetic acid in the presence of a mineral acid (e.g. sulfuric acid, etc.). The alkanoylating agent is usually used in an equimolar amount or more, preferably 1 to 10 moles, to 1 mole of the staring compound, and the reaction is usually carried out at a temperature of about 0° C. to about 200° C., preferably from about 0° C. to about 150° C., for about 0.5 to 15 hours.

Moreover, the compound (1l) wherein $R^{5a}$ is a lower alkyl or a phenyl(lower)alkyl) and the compound (1o) wherein $R^{7a}$ is a lower alkyl can also be obtained by reacting the compound (1k) or the compound (1n) with a compound of the formula: $R^{18}$—CO—$R^{19}$ (18) (wherein $R^{18}$ and $R^{19}$ are each hydrogen atom, phenyl, or a lower alkyl), respectively. In case of the compound (1n), however, the compound to be reacted should be the compound (18) wherein $R^{18}$ and $R^{19}$ are other than phenyl. The reaction is usually carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate, etc.), hydrogenating reducing agents (e.g. sodium boro hydride, sodium cyanoboro hydride, lithium aluminum hydride, etc.), catalystic reducing agents (e.g. palladium black, palladium-carbon, platinum oxide, platinum black, Raney nickel, etc.). When formic acid is used as the reducign agent, the reaction is usually carried out at a temperature of from room temperature to about 200° C., preferably about 50° C. to about 150° C., for about 1 to 10 hours. The formic acid is usually used in a large excess amount to the compound (1k) or the compound (1n).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (1k) or the compound (1n). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40% by weight, preferably about 1 to 20% by weight, of the amount of the compound (1k) or the compound (1n). The compound (18) is usually used at least in equivalent amount, preferably equivalent to a large excess amount, to the compound (1k) or the compound (1n).

In case of the compound of the formula (1) wherein $R^6$ and $R^7$ combine together with the nitrogen atom to which they bond to form a 5- or 6-membered, saturated or unsaturated heterocyclic group which may be intervened or not with nitrogen, oxygen or sulfur atom and said heterocyclic group contains a secondary amino group, and/or $R^4$ and $R^5$ combine together with the nitrogen atom to which they bond to form a 5- or 6-membered, saturated heterocyclic group which may be intervened or not with nitrogen, oxygen or sulfur atom and said heterocyclic group contains a secondary amino group, the compound can be converted into a compound where said heterocyclic groups are substituted on said secondary amino group by a substituent selected from a lower alkyl (in case of forming a heterocyclic group by $R^6$ and $R^7$) or a phenyl having optionally a substituent selected from a halogen atom and a lower alkoxy (in case of forming a heterocyclic group by $R^4$ and $R^5$) by treating it in the same manner as in the reaction of the compound (1k) and the compound (14) in the above Reaction Scheme-9A.

Besides, said compound (where $R^6$ and $R^7$ form a heterocyclic group) can also be converted into a compound where the heterocyclic group is substituted on said secondary amino group by a substituent selected from a lower alkoxycarbonyl by treating it in the same manner as in the reaction of the compound (1k) and the compound (15) in the above Reaction Scheme-9A.

[Reaction Scheme-10A]

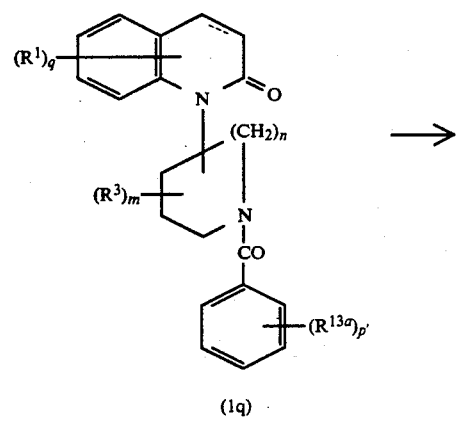

(1q)

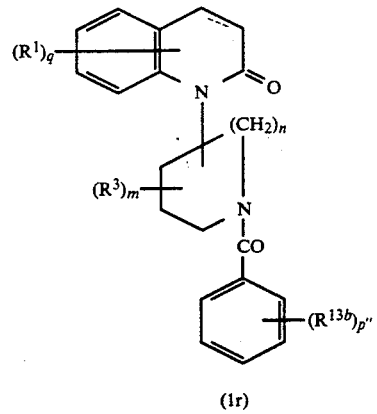

(1r)

wherein $R^1$, q, $R^3$, m, n, p', p", and the bond between 3- and 4-positions of the carbostyril nucleus are the same as defined above, and $R^{13a}$ is the same groups as $R^{13}$ provided that at least one of the $R^{13a}$ is cyano, and $R^{13b}$ is the same groups as $R^{13}$ provided that at least one of the $R^{13b}$ is amidino.

[Reaction Scheme-10B]

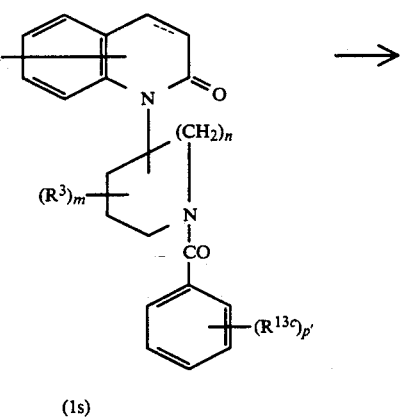

(1s)

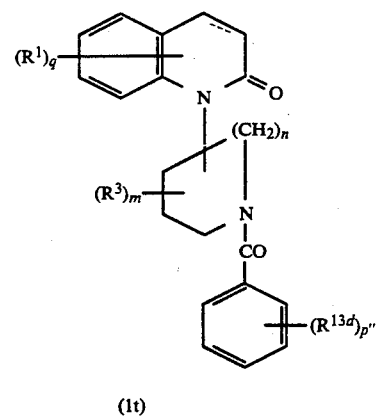

(1t)

wherein $R^1$, q, $R^3$, m, n, p', p", and the bond between 3- and 4-positions of the carbostyril nucleus are the same as defined above, and $R^{13c}$ is the same groups as $R^{13}$ provided that at least one of the $R^{13c}$ is a cyano-substituted lower alkoxy, and $R^{13d}$ is the same groups as $R^{13}$ provided that at least one of the $R^{13d}$ is an amidino-substituted lower alkoxy.

The reaction of converting the compound (1q) to the compound (1r) in the above Reaction Scheme-10A and of converting the compound (1s) to the compound (1t) in the above Reaction Scheme-10B is carried out by reacting the compound (1q) and the compound (1s) with various alcohols, phenols, and thiols, respectively in an appropriate solvent or without solvent in the co-presence of a basic compound and hydrogen chloride, followed by reacting the resultant imidate compound with aqueous ammonia in an appropriate solvent. The solvent used in the reaction for obtaining an imidate compound includes, for example, halogenated hydrocarbons (e.g. dichloromethane, chloroform, etc.), aromatic hydrocarbons (e.g. benzene, toluene, etc.), and the like. The alcohols used therein include, preferably lower alcohols such as methanol, ethanol, etc. These alcohols are usually used in an amount of 1 mole or more, preferably 1 to 2 moles, to 1 mole of the starting compound. The basic compound includes, preferably metal alcoholates such as sodium methylate, sodium ethylate, etc., particularly preferably the alcoholates with the same alcohols as above. The reaction for forming imidate compound is usually carried out at a temperature of about $-10°$ C. to about $50°$ C., preferably about $0°$ C. to room temperature, for about 1 to 200 hours. The imidate compound thus obtained can be used in the subsequent reaction without being isolated from the reaction mixture.

The solvent used in the reaction of converting the imidate compound to the desired amidine compound includes, for example, water soluble solvents such as lower alcohols (e.g. methanol, ethanol, isopropanol, etc.), acetone, dimethylformamide, acetonitrile, and the like. The aqueous ammonium used in the reaction is usually used in an amount of 1 mole or more, preferably 5 to 50 moles, to 1 mole of the imidate compound. The reaction is usually carried out at a temperature of about $0°$ C. to about $100°$ C., preferably $0°$ C. to room temperature, for about 10 minutes to about 15 hours. In the above reaction of converting the imidate compound to the amidine compound, there may occasionally be produced a compound where $R^{13d}$ is the same groups as $R^{13}$ provided that at least one of the $R^{13d}$ is a carbamoyl-substituted lower alkoxy, or $R^{13b}$ is the same groups as $R^{13}$ provided that at least one of $R^{13b}$ is a carbamoyl group, but these compounds can easily be separated from the reaction system.

[Reaction Scheme-11]

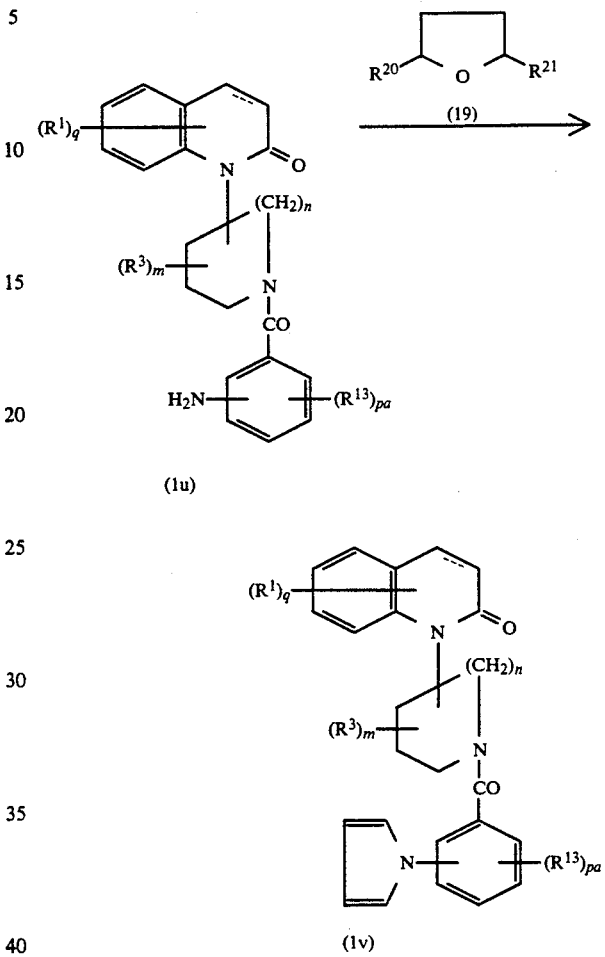

wherein $R^1$, q, $R^3$, m, n, $R^{13}$, and the bond between 3- and 4-positions of the carbostyril nucleus are the same as defined above, and $R^{20}$ and $R^{21}$ are each lower alkoxy, and pa is 0 or an integer of 1 to 2.

The reaction of the compound (1u) and the compound (19) can be carried out in an appropriate solvent in the presence of an acid. The solvent includes, for example, water, lower alcohols (e.g. methanol, ethanol, isopropanol, etc.), ketones (e.g. acetone, methyl ethyl keton, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.), organic acids (e.g. formic acid, acetic acid, aromatic sulfonic acid, etc.). The reaction is usually carried out at a temperature of from room temperature to about $200°$ C., preferably from room temperature to about $150°$ C., for about 0.5 to 5 hours. The compound (19) is usually used in an amount of at least 1 mole, preferably 1 to 2 moles, to 1 mole of the compound (1u).

[Reaction Scheme-12A]

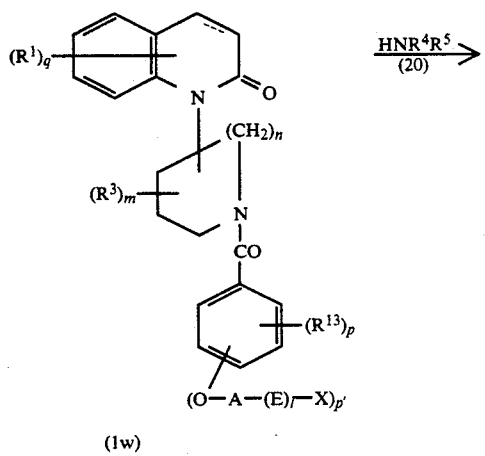

(1w)

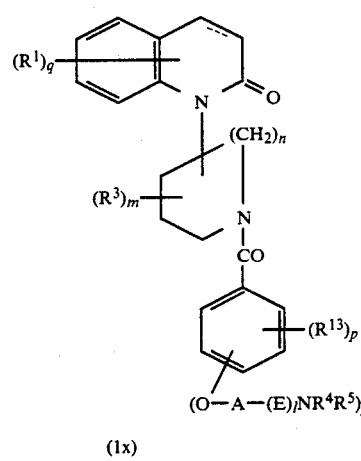

(1x)

wherein $R^1$, q, $R^3$, m, n, $R^4$, $R^5$, $R^{13}$, p, p', p'', X, A, E, l, and the bond between 3- and 4-positions of the carbostyril nucleus are the same as defined above.

[Reaction scheme-12B]

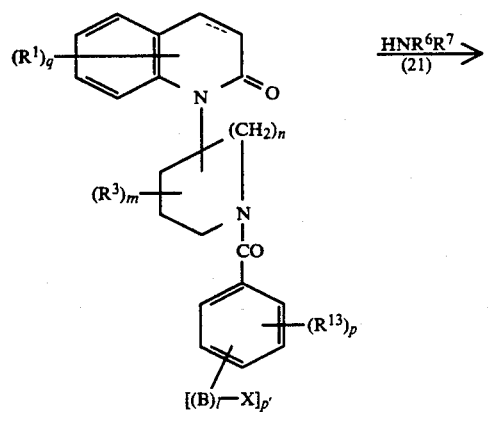

(1y)

-continued

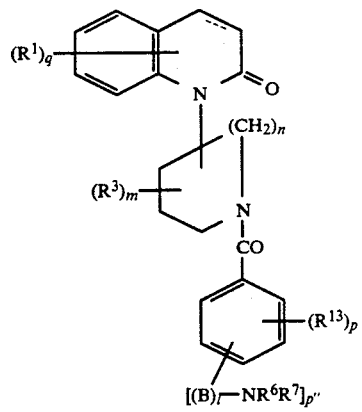

(1z)

wherein $R^1$, q, $R^3$, m, n, $R^6$, $R^7$, $R^{13}$, p, p', p'', X, B, l, and the bond between 3- and 4-positions of the carbostyril nucleus are the same as defined above.

[Reaction Scheme-12C]

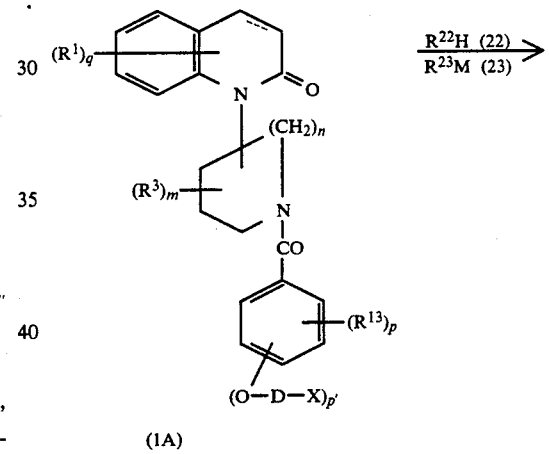

(1A)

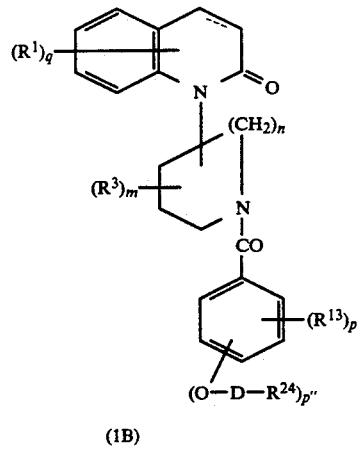

(1B)

wherein $R^1$, q, $R^3$, m, n, $R^{13}$, p, p', p'', X, and the bond between 3- and 4-positions of the carbostyril nucleus are the same as defined above, and D is a lower alkylene, $R^{22}$ is a group of the formula:

$R^{32}$ and $R^{33}$ are the same as defined above), benzoyloxy, a lower alkylsulfonyloxy, a lower alkanoyloxy, a lower alkylthio, benzimidazolylthio, pyrimidylthio, an imidazolylthio having optionally a lower alkyl substituent, a phenylthio having optionally a substituent selected from nitro and amino on the phenyl ring, pyridylthio, or pyrrolyl, $R^{23}$ is hydroxy, a lower alkoxy, benzoyloxy, a lower alkylsulfonyloxy, a lower alkanoyloxy, or a lower alkoxy having one or two substituents selected from cyano, hydroxy and an amino having optionally a lower alkyl substituent, $R^{24}$ is the same as the above $R^{22}$ or $R^{23}$, and M is an alkali metal (e.g. potassium, sodium, etc.).

Scheme-12D]

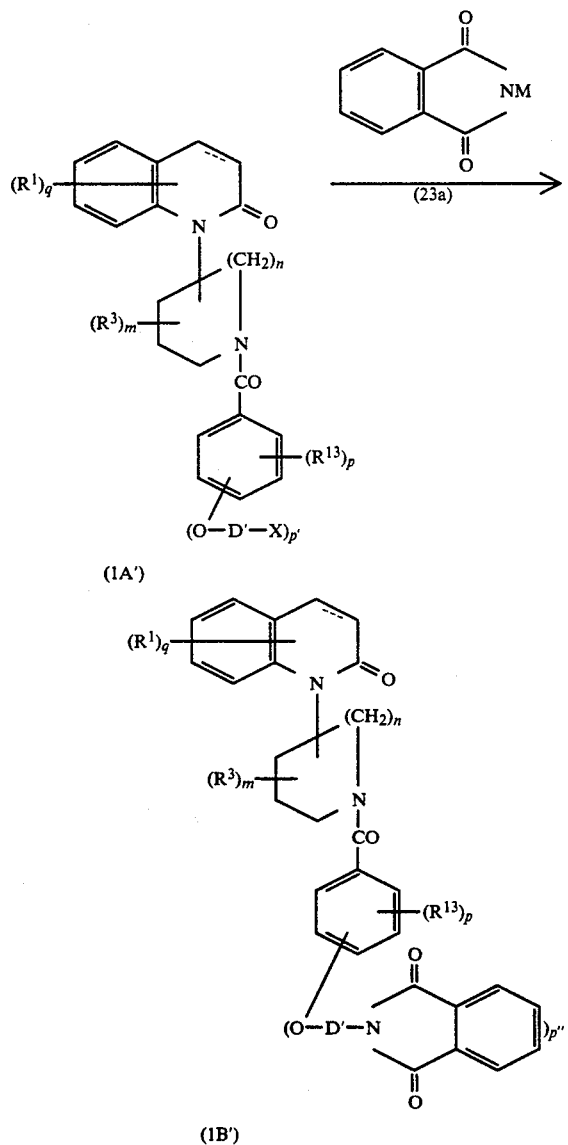

wherein $R^1$, q, $R^3$, m, n, $R^{13}$, p, p', p'', X, M and the bond between 3- and 4-positions of the carbostyril nucleus are the same as defined above, and D' is a lower alkylene.

The reaction of the compound (1w) and the compound (20) in Reaction Scheme-12A, of the compound (1y) and the compound (21) in Reaction Scheme-12B, of the compound (1A) and the compound (22) or (23) in Reaction Scheme-12C., and of the compound (1A') and the compound (23a) in Reaction Scheme-12D is carried out under the same conditions as in the reaction of the compound (1h) and the compound (11) in the above Reaction Scheme-8.

Reaction Scheme-13]

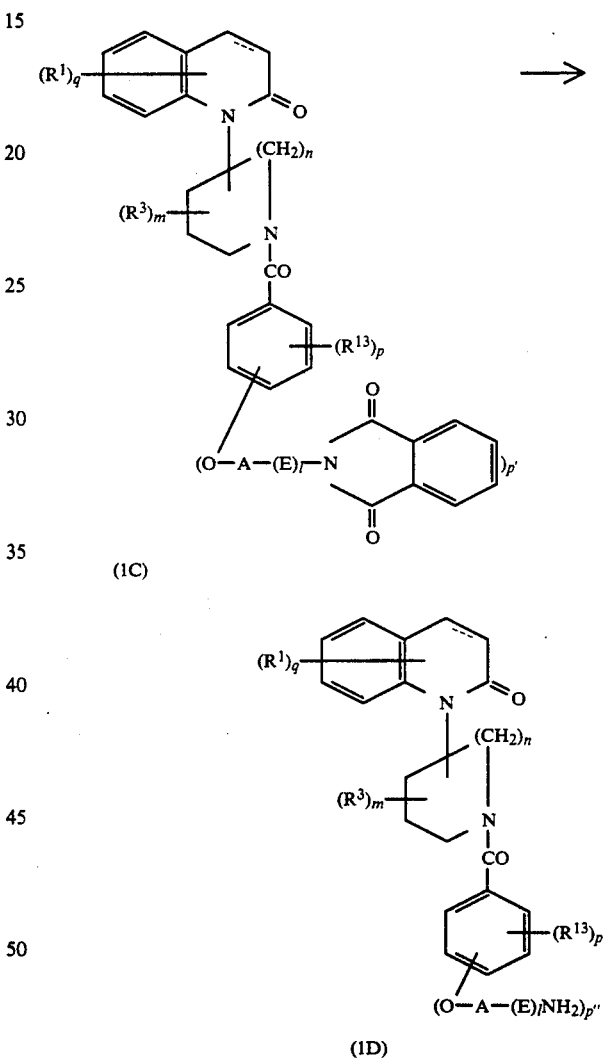

wherein $R^1$, q, $R^3$, m, n, $R^{13}$, p, p', p'', A, E, l, and the bond between 3- and 4-positions of the carbostyril nucleus are the same as defined above.

The reaction of converting the compound (1C) into the compound (1D) can be carried out by reacting the compound (1C) with hydrazine in an appropriate solvent or by hydrolyzing the compound (1C). The solvent used in the reaction with hydrazine includes the same solvent as used in the reaction of the compound (1h) and the compound (11) in the above Reaction Scheme-8. The reaction is usually carried out at a temperature of from room temperature to about 120° C., preferably about 0° C. to about 100° C., for about 0.5 to 5 hours. Hydrazine is usually used in an amount of at least 1 mole, preferably about 1 to 5 moles, to 1 mole of the compound (1C). The hydrolysis is carried out under the same conditions as in the hydrolysis of the compound (1) wherein $R^4$ or $R^5$ is a lower alkoxycarbonyl as described hereinafter.

Reaction Scheme-14]

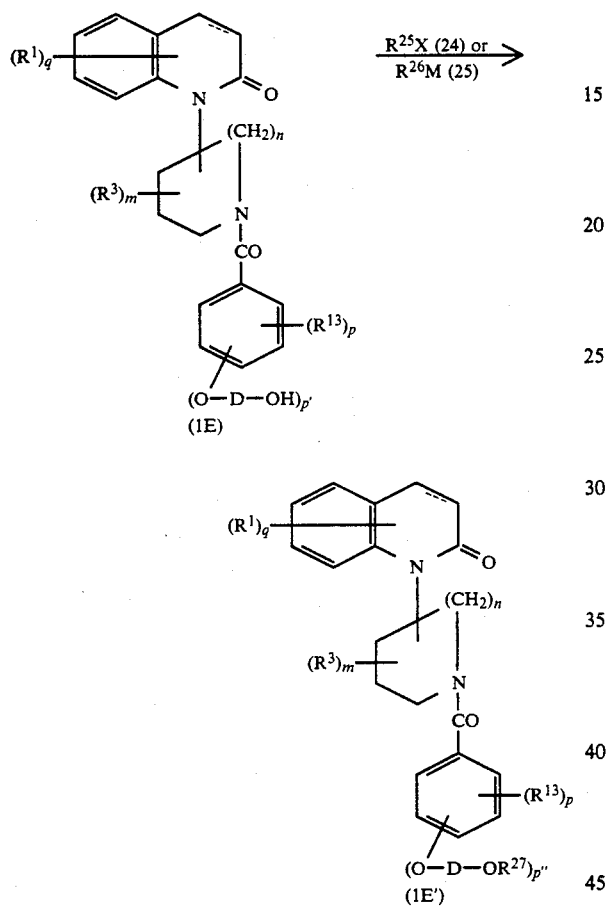

wherein $R^1$, q, $R^3$, m, n, $R^{13}$, p, p', p", X, D, M, and the bond between 3- and 4-positions of the carbostyril nucleus are the same as defined above, and $R^{25}$ is a lower alkanoyl, a lower alkenyl, a lower alkyl, a lower alkylsulfonyl, a lower alkyl having one or two substituents selected from hydroxy and an amino having optionally a lower alkyl substituent, or benzoyl, $R^{26}$ is a group of —OCN, and $R^{27}$ is the same groups as the above $R^{25}$ or a carbamoyl.

The reaction of the compound (1E) and the compound (24) is carried out under the same conditions as in the reaction of the compound (1h) and the compound (11) in the above Reaction Scheme-8. In said reaction, an alkali metal halide (e.g. sodium iodide, potassium iodide, etc.) may be added to the reaction system.

The reaction of the compound (1E) and the compound (25) is carried out in an appropriate solvent in the presence of an acid. The solvent includes the same solvents as used in the reaction of the compound (1h) and the compound (11) in the above Reaction Scheme-8. In addition thereto, there may also be used halogenated hydrocarbons (e.g. methylene chloride, chloroform, carbon tetrachloride, etc.). The acid includes, for example, mineral acids (e.g. hydrochloric acid, sulfuric acid, hydrobromic acid, etc.) and organic acids (e.g. formic acid, acetic acid, trifluroacetic acid, aromatic sulfonic acids, etc.). The reaction is usually carried out at a temperature of about 0° C. to about 150° C., preferably, from room temperature to about 100° C., for about 1 to 15 hours. The compound (25) is usually used in an amount of 1 to 5 moles, preferably 1 to 3 moles, to 1 mole of the compound (1E).

[Reaction scheme-15]

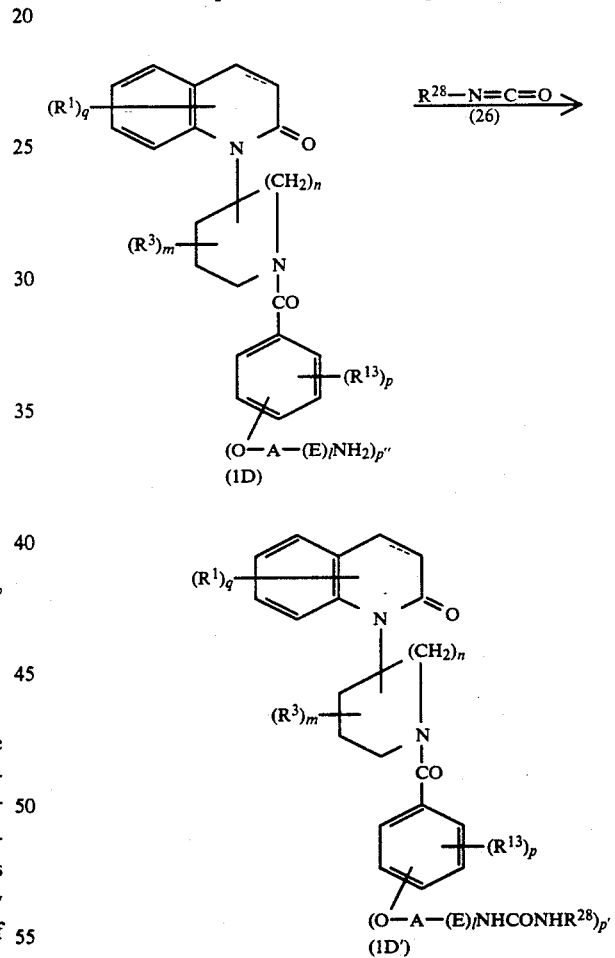

wherein $R^1$, q, $R^3$, m, n, $R^{13}$, p, p', p", A, e, E, l, and the bond between 3- and 4-positions of the carbostyril nucleus are the same as defined above, and $R^{28}$ is hydrogen atom, phenyl or a lower alkyl.

The reaction of the compound (1D) and the compound (26) is carried out under the same conditions as in the reaction of the compound (1d) and the compound (8) in the above Reaction Scheme-6.

Reaction Scheme-16]

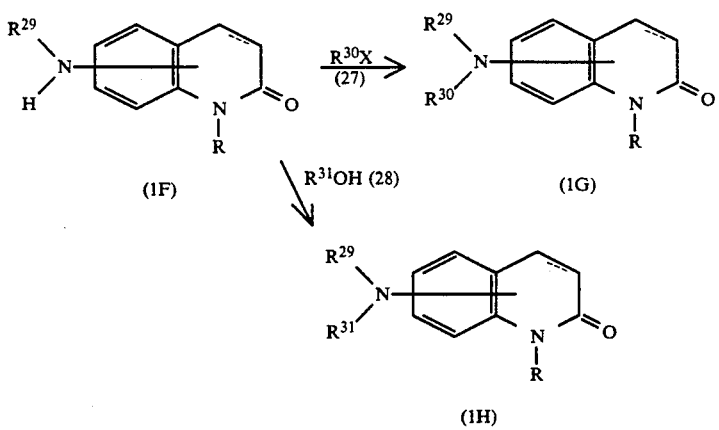

wherein R, X, and the bond between 3- and 4-positions of the carbostyril nucleus are the same as defined above, and $R^{29}$ is hydrogen atom, a lower alkanoyl, a lower alkyl or benzoyl, $R^{30}$ is a lower alkyl, and $R^{31}$ is a lower alkanoyl or benzoyl.

The reaction of the compound (1F) and the compound (27) is carried out under the same conditions as in the reaction of the compound (1k) and the compound (14) in the above Reaction Scheme-9A.

The reaction of the compound (1F) and the compound (28) is carried out under the same conditions as in the reaction of the compound (1k) and the compound (15) in the above Reaction Scheme-9A.

[Reaction Scheme-17]

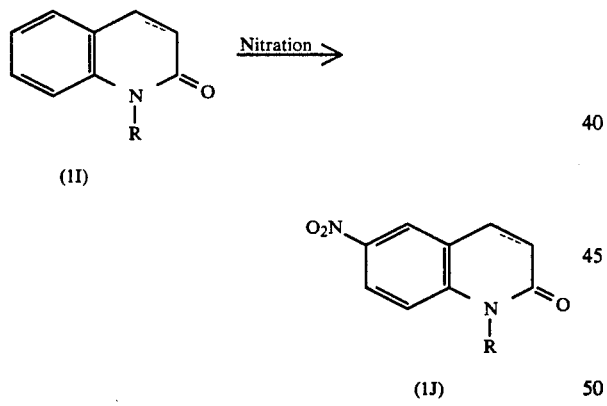

wherein R and the bond between 3- and 4-positions of the carbostyril nucleus are the same as defined above.

The nitration of the compound (1I) can be carried our under the same conditions as used in the conventional nitration reaction of an aromatic compound. That is, it can be carried out by using a nitrating agent in an appropriate inert solvent or without solvent. The inert solvent includes, for example, acetic acid, acetic anhydride, conc. sulfuric acid, and the like. The nitrating agent includes, for example, fuming nitric acid, conc. nitric acid, mixed acid (e.g. a mixture of nitric acid with sulfuric acid, fuming sulfuric acid, phosphoric acid, or acetic anhydride), a mixture of an alkali metal nitrate (e.g. potassium nitrate, sodium nitrate, etc.) with sulfuric acid, and the like. The nitrating agent is used in an equimolar amount or more, usually in an excess amount, to the amount of the starting compound. The reaction is advantageously carried out at a temperature of about 0° C. to room temperature for about 0.5 to 4 hours.

[Reaction Scheme-18]

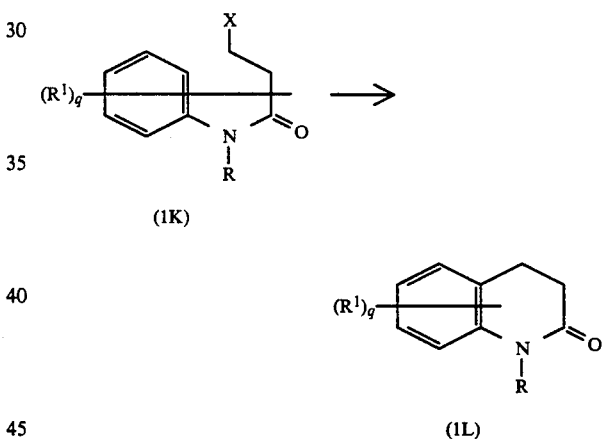

wherein $R^1$, q, R, and X are the same as defined above.

The cyclization reaction of the compound (1K) is so-called Friedel Craft reaction and is usually carried out in an appropriate solvent in the presence of a Lewis acid. The solvent includes any conventional solvent which is usually used in this kind of reaction, for example, carbon disulfide, nitrobenzene, chlorobenzene, dichloromethane, dichloroethane, trichloroethane, tetrachloroethane, and the like. The Lewis acid includes any conventional acid, for example, aluminum chloride, zinc chloride, iron chloride, tin chloride, boron tribromide, boron trifluoride, conc. sulfuric acid, and the like. The amount of Lewis acid is not critical but is usually in the range of about 2 to 6 moles, preferably about 3 to 4 moles, to 1 mole of the compound (1K). The reaction temperature is usually in the range of about 20° C. to 200° C., preferably 40° C. to 180° C. The reaction period of time may vary depending on the kinds of the starting compound, catalyst and reaction temperature, etc., but is usually in the range of about 0.5 to 6 hours. Besides, sodium chloride may be added to the reaction system in order to proceed the reaction advantageously.

[Reaction Scheme-19]

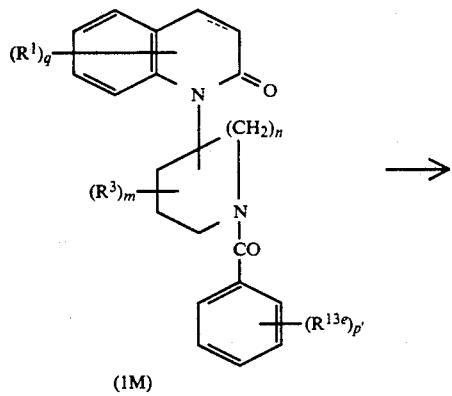

(1M)

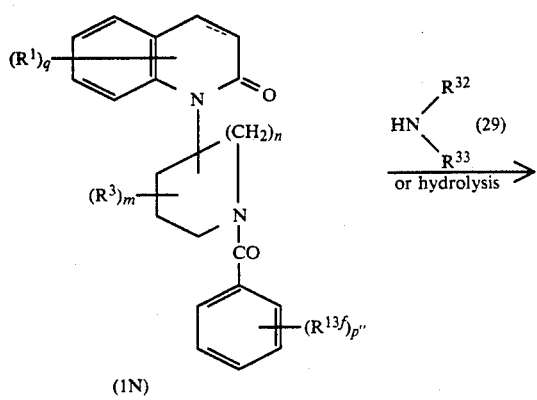

(1N)

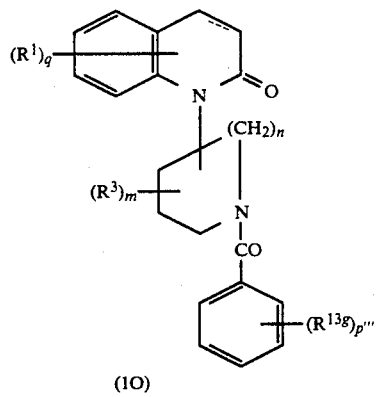

(1O)

wherein $R^1$, q, $R^3$, m, n, p', p'', and the bond between 3- and 4-positions of the carbostyril nucleus are the same as defined above, and $R^{13e}$ is the same groups as $R^{13}$ provided that at least one of the $R^{13e}$ is a lower alkenyloxy, $R^{13f}$ is the same groups as $R^{13}$ provided that at least one of the $R^{13f}$ is an oxilanyl-substituted lower alkoxy, $R^{13g}$ is the same groups as $R^{13}$ provided that at least one of the $R^{13g}$ is a lower alkoxy having a substituent selected from hydroxy and a group of the formula:

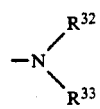

($R^{32}$ and $R^{33}$ are as defined above), and p''' is an integer of 1 to 3.

The reaction of converting the compound (M) into the compound (N) is carried out under the same conditions as in the reaction of oxidizing lower alkylthio into lower alkylsulfonyl as mentioned above. The reaction of the compound (1N) and the compound (29) is carried out under the same conditions as in the reaction of the compound (1h) and the compound (11) in the above Reaction Scheme-8. Besides, the hydrolysis of the compound (1N) can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

[Reaction Scheme-20]

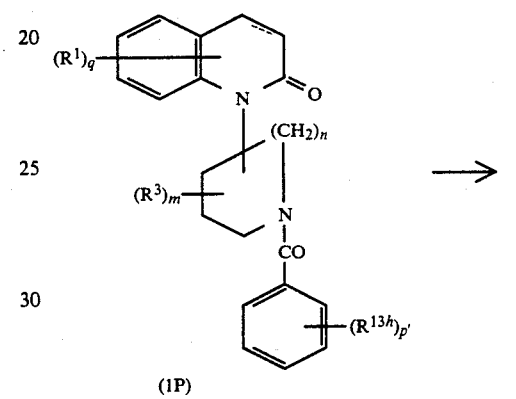

(1P)

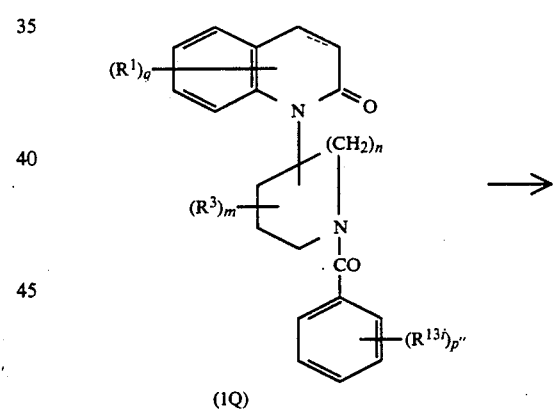

(1Q)

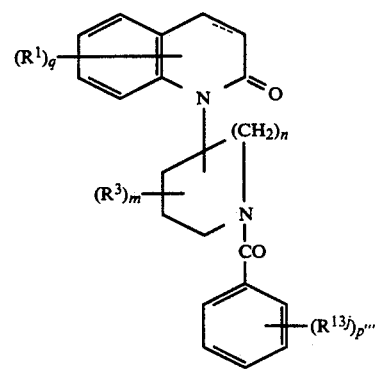

(1R)

wherein $R^1$, q, $R^3$, m, n, p', p'', p''', and the bond between 3- and 4-positions of the carbostyril nucleus are the same as defined above, and $R^{13h}$ is the same groups as $R^{13}$ provided that at least one of the $R^{13h}$ is a lower alkanoyl, $R^{13i}$ is the same groups as $R^{13}$ provided that at least one of the R13i is a lower alkenyl having optionally a substituent selected from a lower alkoxycarbonyl, carboxyl or hydroxy, $R^{13j}$ is the same groups as $R^{13}$ provided that at least one of the $R^{13j}$ is a lower alkyl having optionally a substituent selected from a lower alkoxycarbonyl, carboxyl and hydroxy.

The reaction of converting the compound (1P) into the compound (1Q) is carried out in an appropriate solvent in the presence of a Wittig reagent and a basic compound. The Wittig reagent includes, for example, a phosphoric compound of the formula:

$$[(R^{34})_3P^+—CH_2—R^{35}]X^-  \qquad (A)$$

wherein $R^{34}$ is phenyl, $R^{35}$ is a lower alkyl having optionally a substituent selected from a lower alkoxycarbonyl, carboxyl and hydroxy, and X is a halogen atom, and a phosphoric compound of the formula:

$$(R^{36})_2PCH_2COOR^{37} \qquad (B)$$

wherein $R^{36}$ is a lower alkoxy, and $R^{37}$ is a lower alkyl.

The basic compound includes inorganic bases (e.g. metallic sodium, metallic potassium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about $-80°$ C. to about 150° C., preferably about $-80°$ C. to about 120° C., for about 0.5 to 15 hours.

The reaction of converting the compound (1Q) into the compound (1R) is carried out under the same conditions as in the catalytic hydrogenation as described herebefore.

The starting compound (2) can be prepared, for example, by the processes as shown in the following Reaction Schemes-21 and -22.

Reaction Scheme-21]

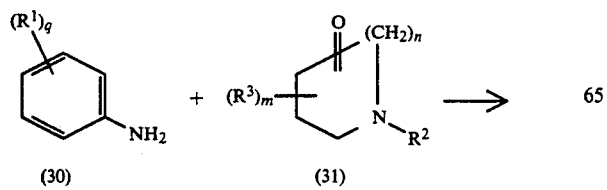

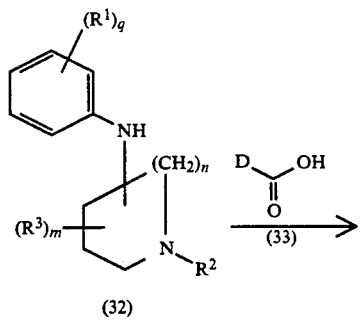

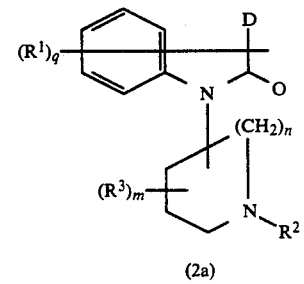

wherein $R^1$, q, $R^2$, $R^3$, m, n and D are the same as defined above, provided that the group $R^1$ may substitute on either of the benzene ring or the group D of the compound (2a).

The reaction of the compound (30) and the compound (31) is carried out under the same conditions as in the reaction of the compound (1k) and the compound (18) in the above Reaction Scheme-9A.

The reaction of the compound (32) and the compound (33) is carried out under the same conditions as in the reaction of the compound (1d) and the compound (7) in the above Reaction Scheme-5.

Reaction Scheme-22]

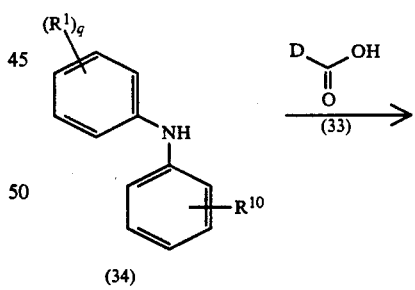

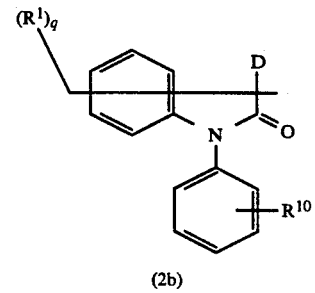

wherein $R^1$, q, $R^{10}$, and D are the same as defined above, provided that the group $R^1$ may substitute on either of the benzene ring or the group D of the compound (2b).

The reaction of the compound (34) and the compound (33) is carried out under the same conditions as the above reaction of the compound (32) and the compound (33).

The starting compound (3) can be prepared, for example, by the process of the following Reaction Scheme-23.

Reaction Scheme-23]

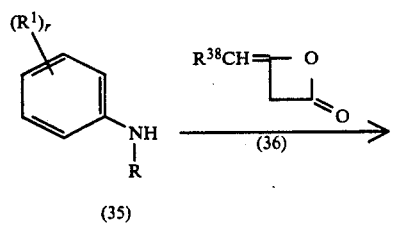

(35)

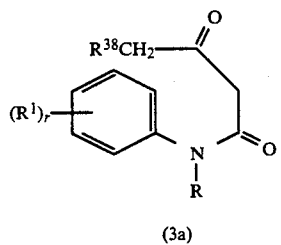

(3a)

wherein $R^1$ and R are the same as defined above, $R^{38}$ is hydrogen atom or a lower alkyl, and r is 1 or 2.

The reaction of the compound (35) and the compound (36) is carried out in a solvent as used in the reaction of the compound (1E) and the compound (25) in the above Reaction Scheme-14. The compound (36) is usually used in an amount of at least 1 mole, preferably 1 to 2 moles, to 1 mole of the compound (35). The reaction is usually carried out at a temperature of 0° C. to 150° C., preferably from room temperature to about 100° C., for about 0.5 to 5 hours.

The starting compound (4) can be prepared, for example, by the process of the following Reaction Scheme-24.

[Reaction Scheme-24]

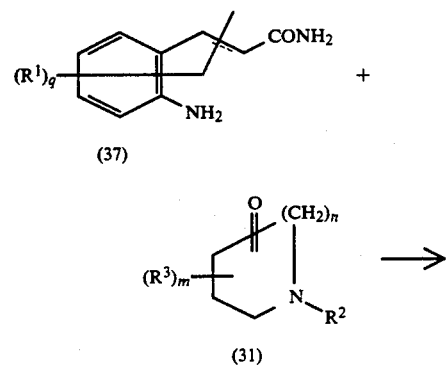

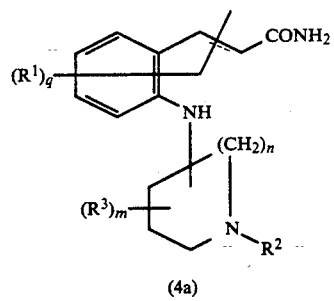

(4a)

wherein $R^1$, q, $R^2$, $R^3$, m, and n are the same as defined above.

The reaction of the compound (37) and the compound (31) is carried out under the same conditions as in the reaction of the compound (30) and the compound (31) in the above Reaction Scheme-21.

The staring compound (1K) can be prepared, for example, by the process of the following Reaction Scheme-25.

[Reaction Scheme-25]

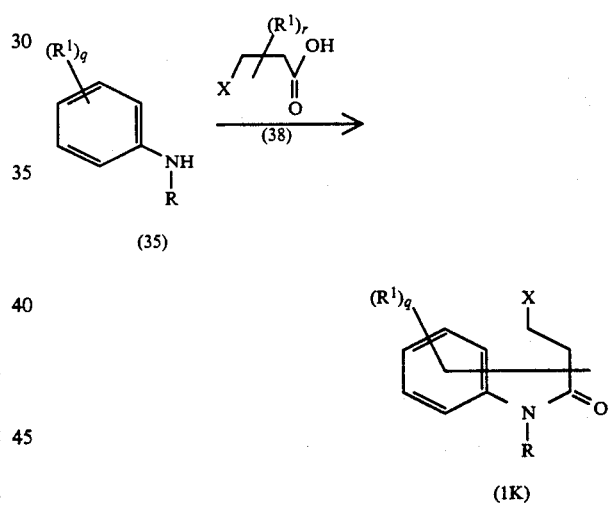

wherein $R^1$, q, r, R and X are as defined above, provided that the total of q and r is not more than 3.

The reaction of the compound (35) and the compound (38) is carried out under the same conditions as in the reaction of the compound (32) and the compound (33) in the above Reaction Scheme-21.

[Reaction Scheme-26]

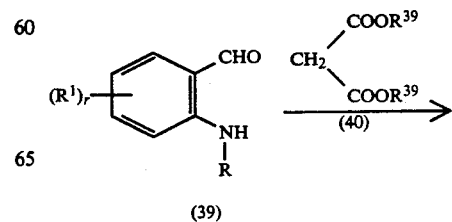

(39)

-continued

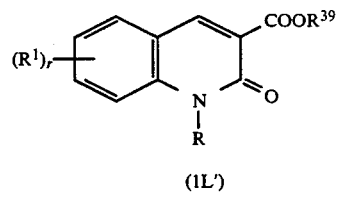

(1L')

wherein $R^1$, r and R are as defined above, and $R^{39}$ is a lower alkyl.

The reaction of the compound (39) and the compound (40) is carried out in an appropriate solvent in the presence of a basic compound. The basic compound includes, inorganic bases (e.g. sodium hydroxide, potassium hydroxide, sodium hydrogen carbonate, potassium hydrogen carbonate, potassium carbonate, sodium carbonate, sodium hydride, etc.), alkali metal alcoholates (e.g. sodium methylate, sodium ethylate, etc.), and organic bases (e.g. triethylamine, pyridine, α-picoline, N,N-dimethylaniline, N-methylmorpholine, piperidine, pyrrolidine, etc.). The solvent includes, for example, ethers (e.g. dioxane, tetrahydrofuran, monoglyme, diglyme, etc.), aromatic hydrocarbons (e.g. benzene, toluene, xylene, etc.), lower alcohols (e.g. methanol, ethanol, isopropanol, etc.), polar solvents (e.g. dimethylsulfoxide, dimethylformamide, etc.), and the like. The reaction is usually carried out at a temperature of form room temperature to 150° C., preferably from 60° C. to 120° C., for about 1 to 24 hours. The compound (40) is usually used in an equimolar to large excess amount, preferably 1 to 5 moles to 1 mole of the compound (39). A lower alkane (e.g. acetic acid, etc.) or molecular sieves may be added to the reaction system to proceed the reaction advantageously.

The compound (39) can be prepared, for example, by the process of the following reaction scheme.

[Reaction Scheme-27]

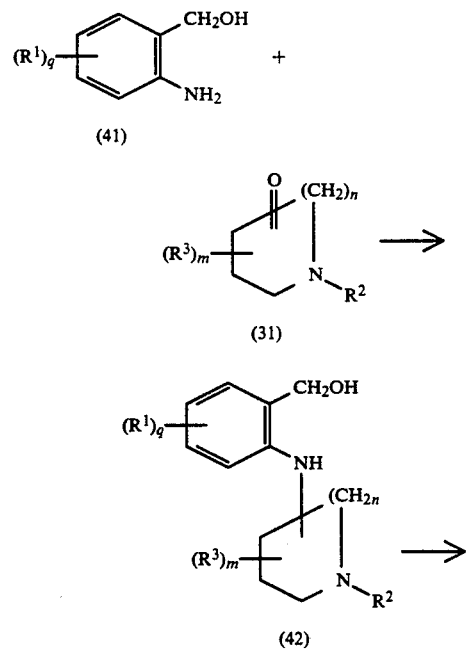

-continued

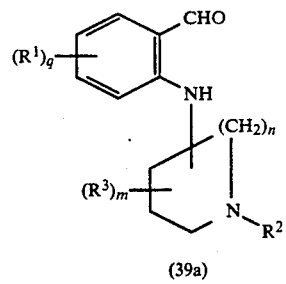

(39a)

wherein $R^1$, q, $R^2$, $R^3$, m and n are as defined above.

The reaction of the compound (41) and the compound (31) is carried out under the same conditions as in the reaction of the compound (30) and the compound (31) in the above Reaction Scheme-21.

The reaction of converting the compound (42) into the compound (39a) is carried out in an appropriate solvent or without solvent in the presence of an oxidizing agent. The solvent includes the above-mentioned aromatic hydrocarbons, lower alcohols, halogenated hydrocarbons, ethers, polar solvents (e.g. dimethylsulfoxide, dimethylformamide, hexamethylphosphoric triamide, etc.). The oxidizing agent includes acetic anhydride-dimethylsulfoxide, phosphorus pentoxide-dimethylsulfoxide, sulfur trioxide.pyridine complex-dimethylsulfoxide, dicyclohexylcarbodiimidedimethylsulfoxide, oxalyl chloride-dimethylsulfoxide, chromic acid, chromic acid complexes (e.g. chromic acidpyridine complex, chromic acid-2-pyridine complex, etc.), manganese dioxide, and the like. When oxayl chloridedimethylsulfoxide is used as the oxidizing agent, there may be added to the reaction system the basic compound as used in the reaction of the compound (1d) and the carboxylic halide in the above Reaction Scheme-5. The reaction is usually carried out at a temperature of 0° C. to 150° C., preferably from room temperature to about 100° C., for about 1 to 30 hours. The oxidizing agent is usually used in an amount of 1 to 20 moles, preferably 1 to 15 moles, to 1 mole of the compound (42).

[Reaction Scheme-28]

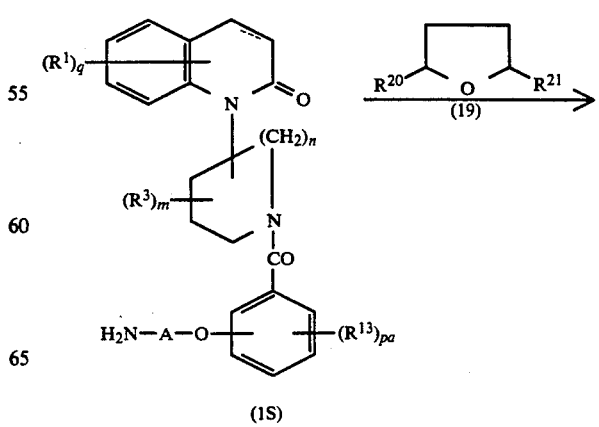

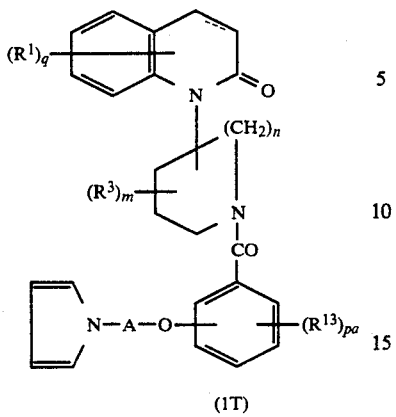

(1T)

wherein $R^1$, q, $R^3$, m, n, $R^{13}$, pa, A, $R^{20}$, $R^{21}$ and the bond between 3- and 4-positions of the carbostyril nucleus are the same as defined above.

The reaction of the compound (1S) and the compound (19) is carried out under the same conditions as in the reaction of the compound (1u) and the compound (19) in the above Reaction Scheme-11.

lower alkanoyl, $R^{43}$ is a lower alkoxy, a halogen atom, an amino having optionally one or two substituents selected from a lower alkyl and a lower alkanoyl, or nitro, t is 0, 1 or 2, s is an integer of 1 to 3, provided that total of t and s is not more than 3.

The reaction of the compound (1U) and the compound (43) is carried out under the same conditions as in the reaction of the compound (1k) and the compound (14) in the above Reaction Scheme-9A.

The reaction of the compound (1U) and the compound (44) is carried out under the same conditions as in the reaction of the compound 1lk) and the compound (15) in the above Reaction Scheme-9A.

[Reaction Scheme-29]

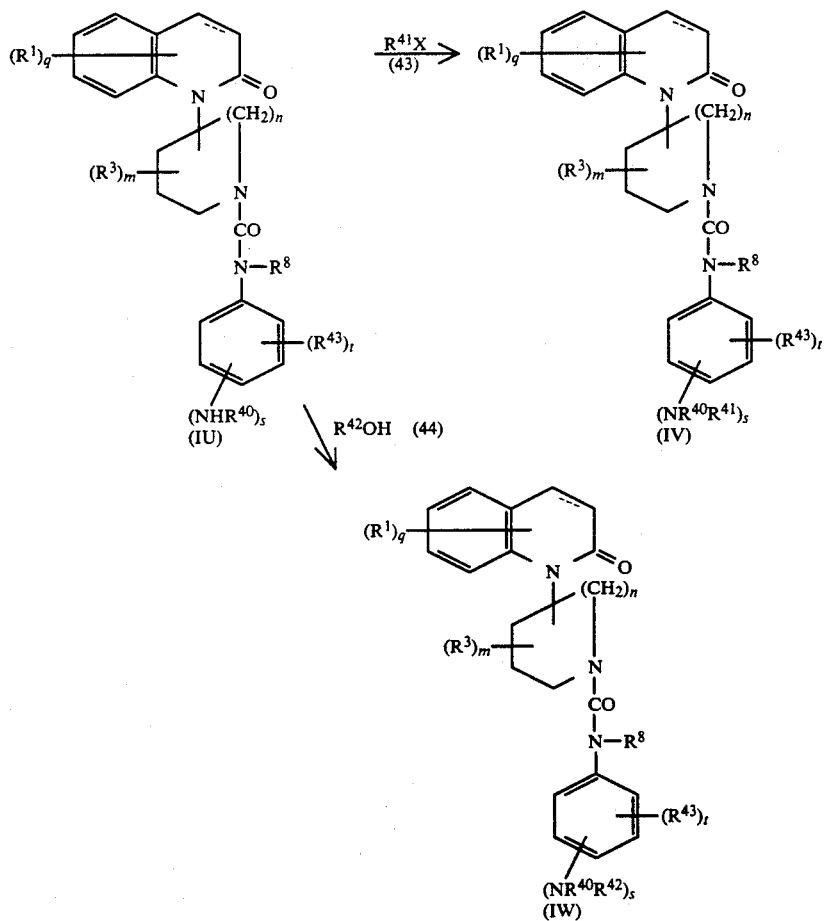

wherein $R^1$, q, $R^3$, m, n, $R^8$, X, and the bond between 3- and 4-positions of the carbostyril nucleus are the same as defined above, and $R^{40}$ is hydrogen atom, a lower alkyl or a lower alkanoyl, $R^{41}$ is a lower alkyl, $R^{42}$ is a Reaction Scheme-30]

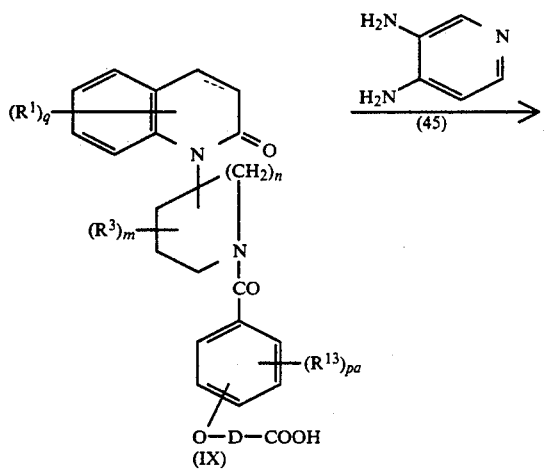

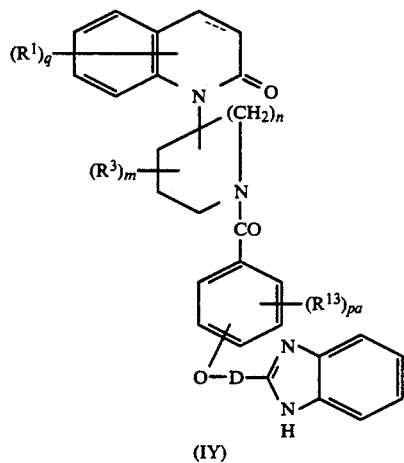

wherein $R^1$, q, $R^3$, m, n, $R^{13}$, pa, D, and the bond between 3-and 4-positions of the carbostyril nucleus are the same as defined above.

The reaction of the compound IX) and the compound (45) is carried out in an appropriate solvent or without solvent in the presence of an acid. The acid includes, for example, inorganic acids (e.g. hydrochloric acid, sulfuric acid, hydrobromic acid, nitric acid, phosphorus pentoxide, polyphosphoric acid, etc,), and organic acids (e.g. p-toluenesulfonic acid, ethanesulfonic acid, methanesulfonic acid, trifluoroacetic acid, etc.), or a mixture of these acids. The solvent includes the same solvents as used in the cyclization reaction of the compound (4) in the above Reaction Scheme-3. The compound (45) is usually used in an amount of at least 1 mole, preferably 1 to 1.5 mole, to 1 mole of the compound (1X). The reaction is usually carried out at a temperature of from room temperature to about 200° C., preferably from room temperature to about 150° C., for about 1 to 5 hours.

[Reaction Scheme-31]

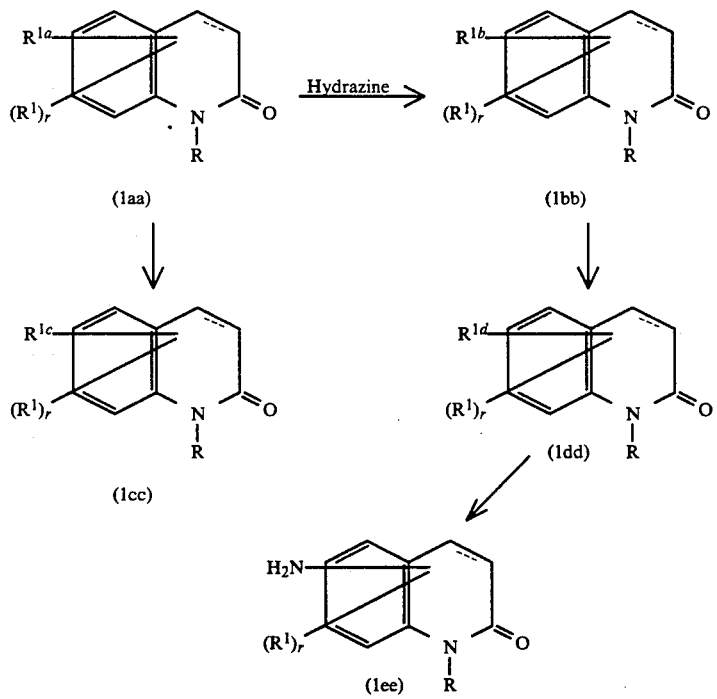

wherein R, $R^1$ and the bond between 3- and 4-positions of the carbostyril nucleus are the same as defined above, and $R^{1a}$ is a lower alkoxycarbonyl, $R^{1b}$ is hydrazinocarbonyl, $R^{1c}$ is carboxyl, $R^{1d}$ is a phenyl(lower)alkoxycarbonyl-substituted amino, and r is 1 or 2.

The reaction of the compound (1aa) and hydrazine is carried out in an appropriate solvent. The solvent includes the same solvents as used in the reaction of the compound (1d) and the halide (7) in the above Reaction Scheme-5. Hydrazine is used in a large excess amount, preferably in 8 to 20 moles to 1 mole of the compound (1aa). The reaction is usually carried out at a temperature of from room temperature to about 150° C., preferably from room temperature to about 100° C., for about 1 to 10 hours.

The reaction of converting the compound (1aa) into the compound (1cc) is carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinafter.

The reaction of converting the compound (1bb) into the compound (1dd) is carried out by reacting the compound (1bb) with a metal nitrite (e.g. sodium nitrite, potassium nitrite, etc.) in an appropriate solvent in the presence of an acid, followed by reacting the resultant with a phenyl lower alcohol (e.g. benzyl alcohol, α-phenethyl alcohol, β-phenethyl alcohol, etc.). The acid used therein includes, for example, hydrochloric acid, hyrobromic acid, sulfuric acid, tetrafluoroboric acid, hexafluorophosphoric acid, and the like. The solvent used in the reaction with a metal nitrite includes, for example, water, dichloromethane, chloroform, carbon tetrachloride or a mixture of these solvents. The reaction is usually carried out at a temperature of about $-20°$ C. to about $10°$ C., preferably about $-5°$ C. to about $5°$ C., for about 5 minutes to about one hour. The nitrite is usually used in an amount of at least 1 mole, preferably 1 to 1.5 mole, to 1 mole of the compound (1bb). The solvent used in the reaction with a phenyl lower alcohol includes, for example, aromatic hydrocarbons (e.g. benzene, toluene, xylene, etc.), ketones (e.g. acetone, methyl ethyl ketone, etc.), ethers (e.g. dioxane, tetrahydrofuran, diethyl ether, ethylene glycol dimethyl ether, etc.), and the like. The reaction is carried out at a temperature of from room temperature to about 200° C., preferably from room temperature to about 150° C., for about 0.5 to 10 hour. The phenyl lower alcohol is usually used in an amount of at least 1 mole, preferably 1 to 2 moles, to 1 mole of the compound (1bb).

The reaction of converting the compound (1dd) into the compound (1ee) is carried out under the same conditions as in the reduction reaction of the compound (1) wherein $R^2$ is a heterocyclic group-substituted carbonyl having a phenyl(lower)alkoxycarbonyl on at least one nitrogen atom thereof as described hereinafter.

wherein $R^1$, q, R, $R^{34}$, and X are the same as defined above, and $R^{44}$ is a lower alkoxycarbonyl.

The reaction of the compound (39) and the compound (46) is carried out under the same conditions as in the reaction of converting the compound (1P) into the compound (1Q) in the above Reaction Scheme-20.

The cyclization reaction of the compound (47) is carried out in the presence of a catalytic reducing agent and in the presence or absence of a basic compound or an acid, preferably in the presence of an acid, in an appropriate solvent. The basic compound includes, for example, organic bases (e.g. triethylamine, trimethylamine, pyridine, dimethylaniline, N-methylmorpholine, DBN, DBU, DABCO, etc.), and inorganic bases (e.g. potassium carbonate, sodium carbonate, sodium hydroxide, potassium hydroxide, sodium hydride, potassium hydride, potassium hydrogen carbonate, sodium hydrogen carbonate, etc.), and the acid includes, for example, inorganic acids (e.g. hydrochloric acid, sulfuric acid, phosphoric acid, etc.), organic acids (e.g. acetic acid, etc.), or a mixture of these acids. The solvent includes, for example, water, alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. tetrahydrofuran, diethyl ether, dimethoxyethane, etc.), esters (e.g. methyl acetate, ethyl acetate, etc.), N,N-dimethylformamide, dimethylsulfoxide, hexamethylphosphoric triamide, or a mixture of these solvents. The catalytic reducing agent includes the same catalysts as used in the reduction reaction of the compound (1a) in the above Reaction Scheme-1. The reaction is usually carried out under atmospheric pressure to about 20 kg/cm², preferably atmospheric pressure to about 10 kg/cm², at a temperature of about 0° C. to about 200° C., preferably from room temperature to about 150° C., for about 1 to 10 hours. The catalytic reducing agent is preferably used in an amount of 0.02 to 1 part by weight to 1 part of the compound (47).

[Reaction Scheme-32]

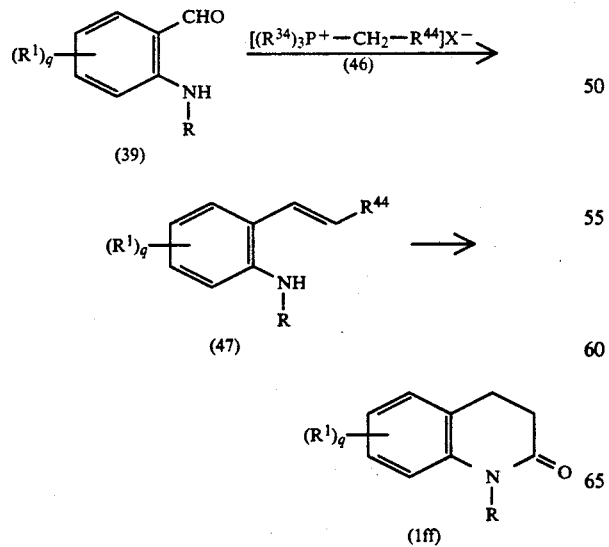

Reaction Scheme-33]

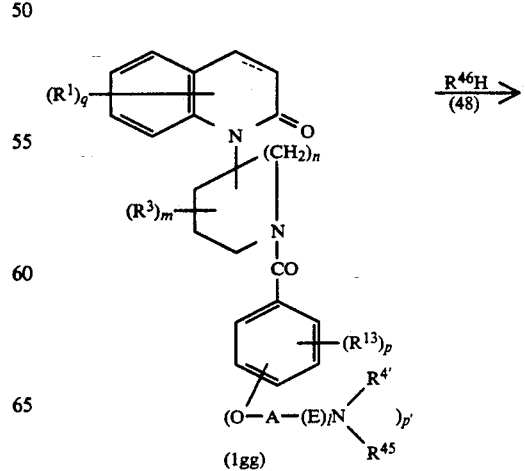

-continued

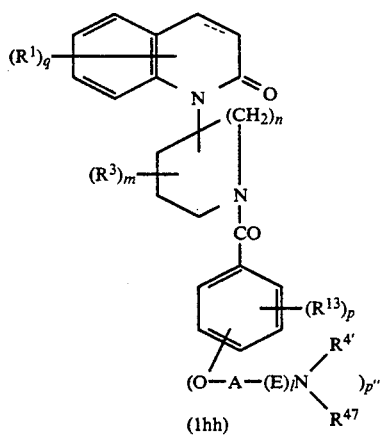

(1hh)

wherein $R^1$, q, $R^3$, m, n, $R^{13}$, $R^{4'}$, p', p'', A, E, l, and the bond between 3- and 4-positions of the carbostyril nucleus are the same as defined above, and $R^{45}$ is a lower alkanoyl which has one halogen substituent and may optionally have a further substituent selected from a phenyl(lower)alkoxycarbonylamino, hydroxy, a phenyl having optionally a hydroxy substituent, carbamoyl, imidazolyl and a lower alkylthio, $R^{46}$ is an amino which may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower)alkoxycarbonyl, and $R^{47}$ is an amino-substituted lower alkanoyl wherein the lower alkanoyl moiety may optionally have a substituent selected from a phenyl(lower)alkoxycarbonylamino, hydroxy, a phenyl having optionally a hydroxy substituent, carbamoyl, imidazolyl, and a lower alkylthio, and the amino group may optionally have a substituent selected from a lower alkyl having optionally a hydroxy substituent, a lower alkenyl, a phenyl(lower)alkyl having optionally a lower alkoxy substituent, a lower alkylsulfonyl, a lower alkanoyl, and a phenyl(lower)alkoxycarbonyl.

The reaction of the compound (1gg) and the compound (48) is carried out under the same conditions as in the reaction of the compound (1h) and the compound (11) in the above Reaction Scheme-8.

Reaction Scheme-34]

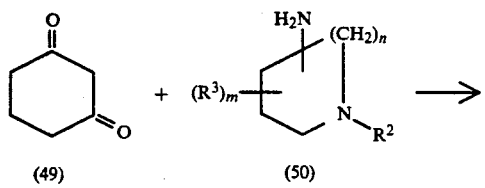

-continued

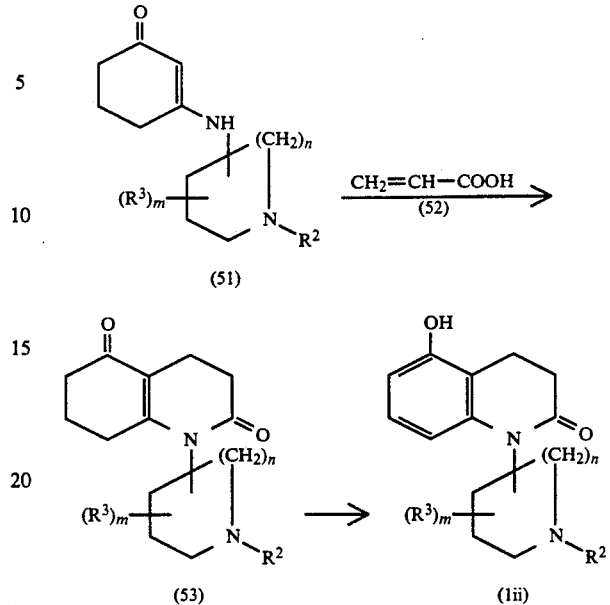

wherein $R^2$, $R^3$, m, and n are the same as defined above.

The reaction of the compound (49) and the compound (50) is carried out by heating them in an appropriate solvent. The solvent includes, for example, alcohols (e.g. methanol, ethanol, isopropanol, etc.), acetonitrile, ethers (e.g. dioxane, diethyl ether, diglyme, tetrahydrofuran, etc.), aromatic hydrocarbons (e.g. benzene, toluene, xylene, etc.), or a mixture of these solvents. The reaction is usually carried out at a temperature of from room temperature to about 200° C., preferably about 50° C. to about 150° C., for about 1 to 10 hours. The compound (50) is usually used in an amount of at least 1 mole, preferably 1 to 1.5 mole, to 1 mole of the compound (49).

The reaction of the compound (51) and the compound (52) is usually carried out without using any solvent at a temperature of about 50° C. to about 200° C., preferably from about 50° C. to about 150° C., for about 1 to 10 hours.

The reaction of converting the compound (53) into the compound (1bb) is carried out in an appropriate solvent in the presence of a halogenating agent and a basic compound. The solvent includes, for example, halogenated hydrocarbons (e.g. dichloromethane, dichloroethane, chloroform, carbon tetrachloride, etc.), alcohols (e.g. methanol, ethanol, propanol, etc.), and the like. The halogenating agent includes N-halogenated succinimides (e.g. N-bromosuccinimide, N-chlorosuccinimide, etc.), halogen molecules (e.g. bromine, chlorine, etc.), N-bromoacetamide, pyrrolidinium bormide perbromide, and the like. The basic compound includes the compounds as used in the reaction of the compound (1h) and the compound (11) in the above Reaction Scheme-8. The reaction is usually carried out at a temperature of about 0° C. to about 150° C., preferably from room temperature to about 100° C., for about 1 to 10 hours. The halogenating agent is usually used in an amount of at least 1 mole, preferably 1 to 3 moles, to 1 mole of the compound (53).

[Reaction Scheme-35]

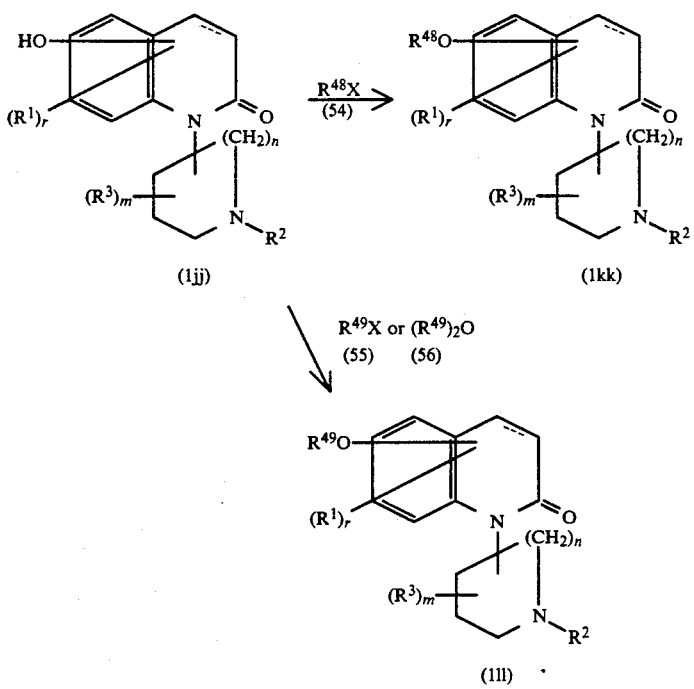

wherein $R^1$, r, $R^2$, $R^3$, m, n, X, and the bond between 3- and 4-positions of the carbostyril nucleus are the same as defined above, and $R^{48}$ is a lower alkyl, and $R^{49}$ is a lower alkanoyl.

The reaction of the compound (1jj) and the compound (54) is carried out under the same conditions as in the reaction of the compound (1h) and the compound (11) in the above Reaction Scheme-8.

The reaction of the compound (1jj) and the compound (55) is carried out under the same conditions as in the reaction of the compound (1h) and the compound (12), wherein a carboxylic halide is used, in the above Reaction Scheme-8, and the reaction of the compound (1jj) and the compound (56) is carried out under the same conditions as in the reaction of the compound (1k) and the compound of the formula: $(R^{5b'})_2O$ in the above Reaction Scheme-9A.

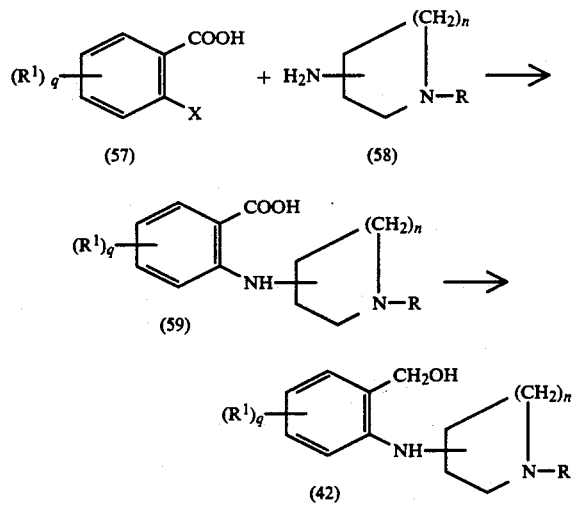

wherein $R^1$, q, n, R and X are as defined above.

The reaction of the compound (57) and the compound (58) is carried out under the same conditions as in the reaction of the compound (5) and the compound (6) in the above Reaction Scheme-4. In this reaction, copper monoxide may be added to the reaction system in order to proceed the reaction advantageously.

The reaction of converting the compound (59) into the compound (42) can be carried out under the same conditions as used in the reduction reaction of the compound (1) wherein $R^{13}$ is a lower alkanoyl or benzoyl as described hereinafter.

In case of the compounds of the formula (1) wherein (a) $R^2$ is a phenyl(lower)alkanoyl wherein the lower alkanoyl moiety is substituted by an amino having a lower alkoxycarbonyl substituent, (b) $R^4$ or $R^5$ is a lower alkoxycarbonyl, (c) $R^6$ or $R^7$ is a lower alkoxycarbonyl, or (d) $R^6$ and $R^7$ form a heterocyclic group which has a lower alkoxycarbonyl substituent on at least one nitrogen atom of the heterocyclic group, these compound can be subjected to hydrolysis to obtain the corresponding compounds of the formula (1) wherein (a) $R^2$ is a phenyl(lower)alkanoyl wherein the lower alkanoyl moiety is substituted by an amino, (b) $R^4$ or $R^5$ is hydrogen atom, (c) $R^6$ or $R^7$ is hydrogen atom, or (d) $R^6$ and $R^7$ form a heterocyclic group where at least one nitrogen has no substituent, respectively.

The hydrolysis can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydoxides (e.g. sodium hydroxide, potassium hydroxide, calcium hydroxide, etc.), and the like. The reaction is usually carried out at a temperature of from room temperature to about 200° C., preferably from room temperature to about 150° C., for about 0.5 to 25 hours.

In the case of the compounds of the formula (1) wherein $R^2$ is a heterocyclic group-substituted carbonyl which has a phenyl(lower)alkoxycarbonyl on at least one nitrogen atom thereof; $R^{13}$ is a benzoyl which is substituted by at least one amino group having at least one phenyl(lower)alkoxycarbonyl substituent on the phenyl ring; $R^4$ or $R^5$ is a pyrrolidinylcarbonyl having at least one phenyl(lower)alkoxycarbonyl substituent on the nitrogen atom of the pyrrolidine ring, or an amino-substituted lower alkanoyl wherein the amino has at least one phenyl(lower)alkoxycarbonyl susbtituent and the lower alkanoyl moiety may optionally have a substituent; or $R^6$ or $R^7$ is a phenyl(lower)alkoxycarbonyl, these compounds can be subjected to a reduction reaction to obtain the corresponding compounds of the formula (1) wherein $R^2$ is a heterocyclic group-substituted carbonyl wherein at least one nitrogen has hydrogen substituent; $R^{13}$ is a benzoyl which has at least one amino group having no phenyl(lower)alkoxycarbonyl substituent; $R^4$ or $R^5$ is a pyrrolidinylcarbonyl having no substituent on the nitrogen atom thereof or an aminosubstituted lower alkanoyl having no substituent on the amino group thereof; or $R^6$ or $R^7$ is hydrogen atom. The reduction is carried out by catalytic reduction in an appropriate solvent in the presence of a catalyst. The solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), or a mixture of these solvents. The catalyst includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 100° C., preferably from about 0° C. to about 80° C., under atmospheric pressure to 10 atm., for about 0.5 to 20 hours.

The compound of the formula (1) wherein $R^{13}$ is a phenyl(lower)alkoxy can be converted into the corresponding compound (1) wherein $R^{13}$ is hydroxy by reduction thereof. The reduction can be carried out under the same conditions as in the reduction of the compound (1) wherein $R^2$ is a heterocyclic group-substituted carbonyl having a phenyl(lower)alkoxycarbonyl substituent on at least one nitrogen atom as described above.

In the case of the compounds of the formula (1) wherein $R^1$ is nitro; $R^2$ is a phenoxycarbonyl having at least one nitro substituent; $R^8$ or $R^9$ is a phenyl having at least one nitro substituent; $R^{13}$ is nitro, a phenylthio-substituted lower alkoxy having at least one nitro substituent on the phenyl ring, or a phenylsulfonyl-substituted lower alkoxy having at least one nitro substituent on the phenyl ring; or $R^4$ or $R^5$ is a benzoyl having at least one nitro susbtituent, or a phenylsulfonyl having at least one nitro substituent on the phenyl ring, these compounds can be subjected to a reduction reaction to obtain the corresponding compounds of the formula (1) wherein $R^1$ is amino; $R^2$ is a phenoxycarbonyl having at least one amino substituent; $R^8$ or $R^9$ is a phenyl having at least one amino substituent; $R^{13}$ is amino, or a phenylthio-substituted lower alkoxy having at least one amino substituent on the phenyl ring, or a phenylsulfonyl-substituted lower alkoxy having at least one amino substituent on the phenyl ring; or $R^4$ or $R^5$ is a benzoyl having at least one amino substituent, or a phenylsulfonyl having at least one amino substituent on the phenyl ring.

The reduction reaction can be carried out, for example, (1) by reducing them in an appropriate solvent with a catalytic reducing agent, or (2) by reducing them in an appropriate inert solvent with a reducing agent, such as a combination of a metal or metal salt and an acid, or a metal or metal salt and an alkali metal hydroxide, sulfide, ammonium salt, and the like.

In the case of reduction using a catalytic reducing agent (1), the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), and the like. The catalytic reducing agent includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 150° C., preferably from about 0° C. to about 100° C., under atmospheric hydrogen pressure to 10 atm., for about 0.5 to 10 hours.

In the case of the reduction (2), the reducing agent includes a combination of iron, zinc, tin or stannous chloride with a mineral acid (e.g. hydrochloric acid, sulfuric acid, etc.), or of iron, ferrous sulfate, zinc or tin with an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example, water, acetic acid, methanol, ethanol, dioxane, and the like. The conditions of the reduction reaction are determined depending on the kinds of the reducing agent, for example, in case of a combination of stannous chloride and hydrochloric acid, it is advantageously carried out at a temperature of about 0° C. to room temperature for about 0.5 to 10 hours. The reducing agent is usually used in an amount of at least 1 mole, preferably 1 to 5 moles, to 1 mole of the starting compound.

The compound of the formula (1) wherein $R^{13}$ is a lower alkanoyl or benzoyl can be converted into the corresponding compound (1) wherein $R^{13}$ is a lower alkyl substituted by hydroxy and/or phenyl by reduction thereof. The reduction reaction can advantageously be carried out by using a hydrogenating reducing agent. The hydrogenating reducing agent includes, for example, lithium aluminum hydride, sodium boro hydride, diborane, and the like. The reducing agent is usually used in an amount of at least 1 mole, preferably 1 to 15 moles, to 1 mole of the starting compound. The reduction reaction is usually carried out in an appropriate solvent such as water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about −60° C. to about 150° C., preferably about −30° C. to about 100° C., for about 10 minutes to about 5 hours. In case of using lithium aluminum hydride or diborane as the reducing agent, it is preferable to proceed the reaction in an anhydrous solvent such as tetrahydrofuran, diethyl ether, diisopropyl ether, diglyme, or the like.

The compound of the formula (1) wherein $R^{13}$ is hydroxy can be converted into the corresponding compound (1) wherein $R^{13}$ is a group of the formula: $-OR^{17}$ (wherein $R^{17}$ is as defined below) by reacting it with a compound of the formula:

$$R^{17}X$$

wherein $R^{17}$ is a carboxy-substituted alkyl, a lower alkoxycarbonyl-substituted alkyl, a lower alkanoyloxysubstituted lower alkyl, a lower alkenyloxy-substituted lower alkyl, a lower alkoxy(lower)alkyl, an alkyl, a lower alkyl having one or two substituents selected from hydroxy, a lower alkanoyloxy, a tri(lower)alkylammonium, a lower alkoxy, or a group of the formula:

wherein $R^{32}$ and $R^{33}$ are as defined above), a halogen-substituted lower alkyl, a lower alkylsulfonyloxy-substituted lower alkyl, a benzoyloxy-substituted lower alkyl, a tricyclo[3.3.1.1]decanyl-substituted lower alkyl, a group of the formula:

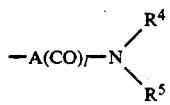

wherein A, l, $R^4$ and $R^5$ are as defined above), a carbamoyloxy-substituted lower alkyl, a lower alkylthiosubstituted lower alkyl, a lower alkylsulfonyl-substituted lower alkyl, a lower alkylsulfinyl-substituted lower alkyl, an alkenyl, a lower alkanoyl, a lower alkylsulfonyl, a lower alkynyl, a phenyl(lower)alkyl, a cycloalkyl, a cycloalkenyl, a cyano-susbtituted lower alkyl, an oxilanyl-substituted lower alkyl, a phthalimido-substituted alkyl, a pyrrolylsubstituted lower alkyl, an amidino-substituted lower alkyl, a lower alkoxy(lower)alkyl having one or two substituents selected from hydroxy and an amino having optionally a lower alkyl-substituent, a morpholino-substituted lower alkyl which may optionally have a substituent selected from a lower alkyl and oxo, a benzimidazolylthio-substituted lower alkyl, a benzimidazolylsulfinyl-substituted lower alkyl, an imidazo[4,5-c]pyridylcarbonyl-substituted lower alkyl, a pyrimidylthio-substituted lower alkyl, a pyrimidylsulfinylsubstituted lower alkyl, a pyrimidylsulfonyl-substituted lower alkyl, an imidazolylthio-substituted lower alkyl which may optionally have a lower alkyl substituent on the imidazole ring, an imidazolylsulfonyl-substituted lower alkyl which may optionally have a lower alkyl substituent on the imidazole ring, a phenylthio-substituted lower alkyl which may optionally have a substituent selected from nitro and amino on the phenyl ring, a phenylsulfonyl-substituted lower alkyl which may optionally have a substituent selected from nitro and an amino having optionally one or two subsitutents selected from a lower alkanoyl and a lower alkyl on the phenyl ring, a pyridylthio-substituted lower alkyl, a pyridylsulfonyl-substituted lower alkyl having optionally an oxo substituent on the pyridine ring, and X is as defined above.

The above reaction is carried out under the same conditions as in the reaction of the compound (1h) and the compound (11) in the above Reaction Scheme-8. Besides, an alkali metal halide (e.g. sodium iodide, potassium iodide, etc.) may be added to the reaction system.

The compounds of the formula (1) wherein $R^{13}$ is a lower alkylthio, a lower alkylthio-susbtituted lower alkoxy, a benzimidazolylthio-substituted lower alkoxy, a pyrimidylthio-substituted lower alkoxy, an imidazolylthio-substituted lower alkoxy having optionally a lower alkyl substituent on the imidazole ring, a phenylthio-substituted lower alkoxy which may optionally have a substituent selected from nitro and amino on the phenyl ring, or a pyridylthio-substituted lower alkoxy can be converted into the corresponding compounds of the formula (1) wherein $R^{13}$ is a lower alkylsulfinyl or a lower alkylsulfonyl; or a lower alkylsulfinylsubstituted lower alkoxy or a lower alkylsulfonylsubstituted lower alkoxy; a benzimidazolylsulfinylsubstituted lower alkoxy; a pyrimidylsulfinyl-substituted lower alkoxy or a pyrimidylsulfonyl-substituted lower alkoxyl; an imidazolylsulfonyl-substituted lower alkoxy which may optionally have a lower alkyl substituent on the imidazole ring; a phenylsulfonyl-substituted lower alkoxy which may optionally have a substituent selected from nitro and amino on the phenyl ring; or pyridylsulfonyl-substituted lower alkoxy, by oxidation thereof.

The oxidation of converting the lower alkylthio into the lower alkylsulfinyl; the oxidation of converting the lower alkylsulfinyl into the lower alkylsulfonyl; the oxidation of converting the lower alkylthio-substituted lower alkoxy into the lower alkylsulfinyl-substituted lower alkoxy; the oxidation of converting the lower alkylsulfinylsubstituted lower alkoxy into the lower alkylsulfonylsubstituted lower alkoxy; the oxidation of converting the pyrimidylthio-substituted lower alkoxy into the pyrimidylsulfinyl-substituted lower alkoxy; and the oxiation of converting the pyrimidylsulfinyl-substituted lower alkoxy into the pyrimidylsulfonyl-substituted lower alkoxy are carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. Besides, in cases of the oxidation of converting the lower alkylthio into the lower alkylsulfonyl; the oxidation of converting the lower alkylthio-substituted lower alkoxy into the lower alkylsulfonyl-substituted lower alkoxy; the oxidation of converting the pyrimidylthio-substituted lower alkoxy into the pyrimidylsulfonyl-substituted lower alkoxy; the oxidation of converting the imidazolylthio-substituted lower alkoxy having optionally a lower alkyl substituent on the imidazole ring into the imidazolylsulfonyl-substituted lower alkoxy having optionally a lower alkyl substituent on the imidazole ring; the oxiation of converting the phenylthiosubstituted lower alkoxy which may optionally have a substituent selected from nitro and amino on the phenyl ring into the phenylsulfonyl-substituted lower alkoxy which may optionally have a substituent selected from nitro and amino on the phenyl ring; and the oxidation of converting the pyridylthio-substituted lower alkoxy into the pyridylsulfonyl-substituted lower alkoxy, the oxidizing agent is usually used at least 2 moles, preferably 2 to 4 moles, to 1 mole of the starting compound. The above reaction is usually carried out at a temperature of about 0° C. to about 40° C., preferably from about 0° C. to room temperature, for about 1 to 15 hours. In the above reaction, in case of the compound wherein $R^{13}$ is a pyridylthio-substituted lower alkoxy, the pyridyl group may occasionally also be oxidized to give the corresponding pyridine N-oxide compound.

The compound of the formula (1) wherein $R^{13}$ is a lower alkenyl, an alkenyloxy or a cycloalkenyloxy can be converted into the corresponding compound (1) wherein $R^{13}$ is a lower alkyl, an alkoxy or a cycloalkyloxy by reduction thereof. The reduction reaction is carried out under the same conditions as in the above-mentioned reaction of converting the compound (1) wherein $R^6$ or $R^7$ is a phenyl(lower)alkoxycarbonyl into the compound (1) wherein $R^6$ or $R^7$ is hydrogen atom.

The compound of the formula (1) wherein $R^{13}$ is a lower alkanoyl can be converted into the corresponding compound (1) wherein $R^{13}$ is a hydroxyimino-substituted lower alkyl by reacting it with hydroxylamine. The reaction is carried out in an inert solvent in the presence or absence of a basic compound. The basic compound includes, for example, inorganic basic compounds (e.g. sodium hydroxide, potassium hyroxide, sodium carbonate, potassium carbonate, etc.), lower alkanic acid alkali metal salts (e.g. sodium acetate, etc.), organic bases (e.g. piperidine, pyridine, 4-dimethylaminopyridine, triethylamine, DBN, DBU, DABCO, etc.), and the like. The solvent includes any solvent which does not affect on the reaction, for example, water, lower alcohols (e.g. methanol, ethanol; isopropanol, etc.), fatty acids (e.g. acetic acid, etc.), ethers (e.g. dioxane, tetrahydrofuran, diethyl ether, ethylene glycol monomethyl ether, etc.), aromatic hyrocarbons (e.g. benzene, toluene, xylene, etc.), halogenated hydrocarbons (e.g. dichloromethane, dichloroethane, chloroform, carbon tetrachloride, etc.), aprotic polar solvents (e.g. dimethylformamide, dimethylsulfoxide, hexamethylphosphoric triamide, etc.), or a mixture of these solvents. The hydroxylamine is usually used in an amount of at least 1 mole, preferably 1 to 5 moles, to 1 mole of the starting compound. The reaction is usually carried out at a temperature of from room temperature to about 200° C., preferably from room temperature to about 150° C., for about 1 to 15 hours.

In case of the compounds of the formula (1) wherein $R^{13}$ is a lower alkoxycarbonyl-substituted alkoxy, a lower alkanoyloxy-substituted lower alkoxy, a lower alkanoyloxysubstituted lower alkyl, a lower alkanoyloxy, a lower alkoxycarbonyl, a lower alkoxycarbonyl(lower)alkyl, $R^6$ or $R^7$ is a lower alkoxycarbonyl(lower)alkyl, $R^4$ or $R^5$ is a lower alkanoyloxy(lower)alkyl, a cycloalkylcarbonyl having at least one substituent of a lower alkanoyloxy on the cycloalkyl group, or a lower alkanoyloxy(lower)alkyl, or $R^1$ is a lower alkanoyloxy, these compounds can be converted by hydrolysis thereof into the corresponding compounds (1) wherein $R^{13}$ is a carboxy-substituted lower alkoxy, a hydroxy-substituted lower alkoxy, a hydroxy-substituted lower alkyl, hydroxy, carboxy, a carboxy-substituted lower alkyl, $R^6$ or $R^7$ is a carboxy-substituted lower alkyl, $R^4$ or $R^5$ is a hydroxy-substituted lower alkanoyl, a cycloalkylcarbonyl having at least one hydroxy substituent on the cycloalkyl group, or a hydroxy-substituted lower alkyl, or $R^1$ is hydroxy. The above hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described herebefore.

In the case of the compounds of the formula (1) wherein $R^1$ is a lower alkanoyl-substituted amino; $R^2$ is a an alkanoyl; $R^2$ is a group of the formula:

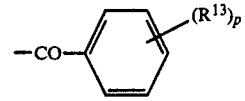

(wherein $R^{13}$ and p are as defined above), or a phenoxycarbonyl having at least one lower alkanoyl-substituted amino on the phenyl ring; $R^4$ or $R^5$ is a lower alkanoyl having optionally one to three substituents of a halogen atom, an amino-substituted lower alkanoyl having a lower alkanoyl substituent, an amino-substituted lower alkyl having a lower alkanoyl substituent, a piperidinylcarbonyl having a lower alkanoyl substituent on the nitrogen atom of the piperidine ring, or a phenylsulfonyl having at least one lower alkanoyl-substituted amino on the phenyl ring; $R^6$ or $R^7$ is a lower alkaonyl having one to three substituents of a halogen atom; or $R^4$ and $R^5$ or $R^{11}$ and $R^{12}$ form a heterocyclic group which has a lower alkanoyl substituent on the nitrogen atom of said heterocyclic group, these compounds can be converted by hydrolysis into the corresponding compounds of the formula (1) wherein $R^1$ is amino; $R^2$ is hydrogen atom; $R^2$ is a phenoxycarbonyl having at least one amino substituent on the phenyl ring; $R^4$ or $R^5$ is hydrogen atom, an amino-substituted lower alkanoyl, an aminosubstituted lower alkyl, unsubstituted piperidinylcarbonyl, or a phenylsulfonyl having at least one amino substituent on the phenyl group; $R^6$ or $R^7$ is hydrogen atom; or $R^4$ and $R^5$ or $R^{11}$ and $R^{12}$ form a heterocyclic group which have no substituent on the nitrogen atom of said heterocyclic group. The hydrolysis can be carried out under the same conditions as in the hydrolysis of the compound (1) where $R^4$ or $R^5$ is a lower alkoxycarbonyl to convert into a compound (1) where $R^4$ or $R^5$ is hydrogen atom as described hereinbefore.

In the case of the compounds of the formula (1) wherein $R^4$ or $R^5$ is a phenyl(lower)alkyl; $R^{11}$ or $R^{12}$ is a phenyl(lower)alkyl; or $R^4$ and $R^5$ or $R^{11}$ and $R^{12}$ form a heterocyclic group which has a phenyl(lower)alkyl substituent on the nitrogen atom of said heterocyclic group, these compounds can be subjected to a reduction reaction to obtain the corresponding compounds of the formula (1) wherein $R^4$ or $R^5$ is hydrogen atom; $R^{11}$ or $R^{12}$ is hydrogen atom; or $R^4$ and $R^5$ or $R^{11}$ and $R^{12}$ form a heterocyclic group which has no substituent on the nitrogen atom of said heterocyclic group. The reduction is carried out under the same conditions as in the above-mentioned reduction of converting a compound (1) wherein $R^6$ or $R^7$ is a phenyl(lower)alkoxycarbonyl into the compound (1) wherein $R^6$ or $R^7$ is hydrogen atom. Besides, the reduction reaction can also be carried out by using the same solvent and catalyst as in the catalytic hydrogenation reaction together with a hydrogen donor (e.g. formic acid, cyclohexene, hydrazine hydrate, ammonium formate, etc.), at a temperature of from room temperature to 150° C., preferably from room temperature to 100° C., for about 1 to 6 hours.

The compound of the formula (1) wherein $R^2$ is a benzoyl having at least one lower alkenyloxy substituent can be converted into the corresponding compound (1) wherein $R^2$ has at least two substituents of hydroxy and a lower alkenyl by subjecting it to Claisen rearrangement. The reaction is carried out by heating said compound in an appropriate solvent. The solvent includes solvents having a high boiling point, such as dimethylformamide, diphenyl ether, dimethylaniline, tetrahydronaphthalene, etc.. The reaction is usually carried out at a temperature of 100° C. to 250° C., preferably from 150° C. to 250° C. for about 1 to 30 hours.

In the case of the compounds of the formula (1) wherein $R^{13}$ is a carboxy-substituted alkoxy, carboxy or a carboxy-substituted lower alkyl; $R^6$ or $R^7$ is a carboxy-substituted lower alkyl; $R^4$ and $R^5$ form a heterocyclic group which has at least one carboxyl substituent on the heterocyclic group, these compounds can be converted by esterification thereof into the corresponding compounds of the formula (1) wherein $R^{13}$ is a lower alkoxycarbonyl-substituted alkoxy, a lower alkoxycarbonyl, or a lower alkoxycarbonyl(lower)alkyl; $R^6$ or $R^7$ is a lower alkoxycarbonyl(lower)alkyl; or $R^4$ and $R^5$ form a heterocyclic group which has at least one lower alkoxycarbonyl substituent on the heterocyclic group. The esterification is usually carried out by reacting the compound with an alochol (e.g. methanol, ethanol, isopropanol, etc.) in the presence of a mineral acid (e.g. hydrochloric acid, sulfuric acid, etc.) and a halogenating agent (e.g. thionyl chloride, phosphorus oxychloride, phosphorus pentoxide, phosphorus trichloride, etc.), at a temperature of 0° C. to about 150° C., preferably from 50° C. to 100° C., for about 1 to 10 hours.

In the case of the compounds of the formula (1) wherein $R^4$ or $R^5$ is a lower alkoxycarbonyl or a lower alkoxycarbonyl(lower)alkyl; $R^6$ or $R^7$ is a lower alkoxycarbonyl(lower)alkyl or a carboxy(lower)alkyl; or $R^4$ and $R^5$ form a heterocyclic group which has at least one substituent of carboxy or a lower alkoxycabonyl on the heterocyclic group, these compounds can be reacted with an amine having optionally a lower alkyl-substituent or an amine having optionally a substituent selected from a lower alkyl and a lower alkanoyl under the same coniditons as in the reaction of the compound (1d) and the compound (7) in the above Reaction Scheme-5 to obtain the corresponding compounds (1) wherein $R^4$ or $R^5$ is an amido having optionally a lower alkyl substituent, or an amido-substituted lower alkyl which has optionally a substituent selected from a lower alkyl and a lower alkanoyl; $R^6$ or $R^7$ is an amido-substituted lower alkyl having optionally a lower alkyl substituent on the amido group; or $R^4$ and $R^5$ form a heterocyclic group being substituted by at least one amido group which has optionally a lower alkyl substituent. In this reaction, when the $R^6$ in the compound (1) is hydrogen atom and the $R^7$ is a carboxy(lower)alkyl, these groups may occasionally form an intermolecular amido bond to give the compound wherein $R^6$ and $R^7$ form a group of the formula:

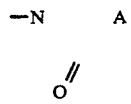

(wherein A is as defined above).

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding compounds (1) wherein $R^4$ or $R^5$ is a benzoyl which has at least one amino having one or two lower alkyl substituents; a phenylsulfonyl which phenyl ring is substituted by at least one amino having one or two lower alkyl substituents; an amino-substituted lower alkyl wherein the amino group has one or two lower alkyl substituents; or $R^{13}$ is a phenylsulfonyl-substituted lower alkoxy which phenyl ring is substituted by at least one amino having one or two lower alkyl substituents by treating them under the same conditions as in the reaction of the compound (1k) and the compound (14) in the above Reaction Scheme-9A.

In case of the compounds of the formula (1) wherein $R^4$ or $R^5$ is a benzoyl which has at least one amino having optionally one lower alkyl substituent; a phenylsulfonyl which phenyl ring is substituted by at least one amino having optionally one lower alkyl substituent; an amino-substituted lower alkyl wherein the amino group may optionally have one lower alkyl substituent; or $R^{13}$ is a phenylsulfonyl-substituted lower alkoxy which phenyl ring is substituted by at least one amino having optionally one lower alkyl substituent, these compounds can be converted into the corresponding compounds (1) wherein $R^4$ or $R^5$ is a benzoyl which has a substituent selected from a lower alkanoyl and a lower alkoxycarbonyl and further at least one amino having optionally one lower alkyl substituent; a phenylsulfonyl which phenyl ring is substituted by a lower alkanoyl and further by at least one amino having optionally one lower alkyl substituent; an amino-substituted lower alkyl wherein the amino group has a lower alkanoyl substituent and further at least one amino having optionally a lower alkyl substituent; or $R^{13}$ is a phenylsulfonyl-substituted lower alkoxy which phenyl ring is substituted by a lower alkanoyl and further by at least one amino having optionally one lower alkyl substituent by treating them under the same conditions as in the reaction of the compound (1k) and the compound (15) in the above Reaction Scheme-9A.

The compound of the formula (1d) can also be prepared by reducing the compound (1) wherein $R^2$ is a phenyl(lower)alkyl under the same conditions as in the above-mentioned reduction of the compound (1) wherein $R^2$ is a heterocyclic group-substituted carbonyl which has at least one phenyl(lower)alkoxycarbonyl on the nitrogen atom. The reduction reaction may be carried out in the presence of an acid (e.g. hydrochloric acid, etc.).

The compound (1) wherein $R^{13}$ is a tri(lower)alkylammonium can also be prepared by reacting a compound (1) wherein $R^{13}$ is a di(lower)alkylamino with a compound of the formula: $R^{50}X$ (wherein $R^{50}$ is a lower alkyl and X is a halogen atom) under the same conditions as in the reaction of the compound (1h) and the compound (11) in the above Reaction Scheme-8.

The compound (1) wherein $R^{13}$ is an ammonium(lower)alkoxy having three substituents selected from a lower alkyl, a lower alkenyl and oxo can also be prepared by reacting a compound (1) wherein $R^{13}$ is an amino-substituted lower alkoxy which has two substituents selected from a lower alkyl and/or a lower alkenyl on the amino group with a compound of the formula: $R^{51}X$ (wherein $R^{51}$ is a lower alkyl or a lower alkenyl, and X is as defined above) under the same conditions as in the reaction of the compound (1h) and the compound (11) of the above Reaction Scheme-8. Besides, said compound can be converted into a compound (1) wherein $R^{13}$ is an ammonium(lower)alkoxy having oxo substituent by oxidizing the compound under the same conditions as in the above-mentioned oxidization reaction for converting the compound (1) wherein $R^{13}$ is a lower alkylthio into the corresponding compound (1) wherein $R^{13}$ is a lower alkylsulfonyl.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, citric acid, succinic acid, benzoic acid, etc. Among the active compounds (1) of the invention, the compounds having an ammonium group can be converted into a salt thereof with a pharmaceutically acceptable halogen anion (e.g. chlorine anion, bromine anion, fluorine anion, or iodine anion). These salts are useful as an active ingredient as like as the compounds (1) in the free form.

In addition, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromtography, preparative thin layer chromatography, extraction with a solvent, and the like.

The compounds and their salts of this invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspendions are sterilized and are preferably made isotonic with the blood. In the preparation of these solutions, emulsions and suspensions, there are used conventional diluents, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the antivasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Components | Amount |
| --- | --- |
| 1-[1-(4-Dimethylaminobenzoyl)-4-piperidinyl]-3,4-dihydrocarbostyril | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 1-[1-(2-Methoxy-4-ethoxybenzoyl)-4-piperidinyl]-3,4-dihydrocarbostyril | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 7-Fluoro-1-[1-(2,4-dimethoxybenzoyl)-4-piperidinyl]-3,4-dihydrocarbostyril | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

Reference Example 1

A mixture of aniline (28.0 g), 1-benzyl-4-piperidone (56.7 g), acetic acid (55 ml), platinum oxide (0.9 g) and ethanol (420 ml) is subjected to catalytic reduction at room temperature at normal pressure for 2 hours. The catalyst is removed by filtration and the filtrate is concentrated.

The resulting residue is made alkaline with a 10% aqueous sodium hydroxide solution and extracted with dichloromethane. After the extract is dried and concentrated, n-hexane is added to the residue and the formed crystals are separated by filtration and recrystallized from n-hexane to give N-(1-benzyl-4-piperidinyl)aniline (63.3 g) as colorless prisms, m.p. 73°–75° C.

Using appropriate starting materials, the same procedure as in Reference Example 1 is repeated to give the following compounds:

N-(1-Benzyl-4-piperidinyl)-4-methoxyaniline, m.p. 75°–76° C. (recrystallized from n-hexane), colorless prisms N-(1-Benzyl-4-piperidinyl)-4-methylaniline, m.p. 95°–96° C. (recrystallized from n-hexane), colorless prisms N-(1-Benzyl-4-piperidinyl)-4-fluoroaniline, m.p. 87°–88° C. (recrystallized from n-hexane), colorless prisms N-(1-Benzyl-4-piperidinyl)-3-methylaniline NMR (CDCl$_3$) δ: 1.38–1.64 (2H, m), 2.00–2.20 (4H, m), 2.26 (3H, s), 2.72–2.94 (2H, m), 3.20–3.40 (1H, m), 3.62 (2H, s), 3.55–3.70 (1H, m), 6.39 (2H, d, J=6.2 Hz), 6.49 (1H, d, J=7.4 Hz), 7.04 (1H, t, J=7.4 Hz), 7.20–7.45 (6H, m)

N-(1-Benzyl-4-piperidinyl)-3-fluoroaniline, m.p. 72°–74° C. (recrystallized from n-hexane), colorless prisms N-(1-Benzyl-4-piperidinyl)-2-methylaniline, m.p. 100°–102° C. (recrystallized from n-hexane), colorless prisms N-(1-Benzyl-4-piperidinyl)-3-acetaminoaniline NMR (CDCl$_3$) δ: 1.34–2.73 (2H, m), 1.82–2.25 (7H, m), 2.68–2.95 (2H, m), 3.28 (1H, brs), 3.51 (2H, s), 3.58–3.80 (1H, m), 6.30–6.60 (2H, m), 7.01–7.53 (7H, m)

N-(1-Benzoyl-4-piperidinyl)aniline, m.p. 161°–163° C. (recrystallized from ethanol), white powders N-(1-Benzyl-3-piperidinyl)aniline NMR (CDCl$_3$) δ: 1.4–1.8 (4H, m), 2.3–2.5 (3H, m), 2.7–2.8 (1H, m), 3.51 (2H, d, J=2.4 Hz), 3.4–3.7 (1H, m), 3.9–4.1 (1H, m), 6.6–6.8 (3H, m), 7.1–7.3 (7H, m)

N-(1-Benzyl-3-pyrrolidinyl)aniline

NMR (CDCl$_3$) δ: 1.6–1.8 (1H, m), 2.2–2.6 (3H, m), 2.7–2.9 (2H, m), 3.62 (2H, s), 3.8–4.2 (1H, m), 6.5–6.8 (3H, m), 7.1–7.4 (7H, m)

N-(1-Benzyl-3-methyl-4-piperidinyl)aniline

NMR (CDCl$_3$) δ: 0.9–1.1 (3H, m), 1.6–2.0 (2H, m), 2.0–2.7 (4H, m), 2.8–3.0 (1H, m), 3.3–3.7 (3H, m), 6.5–6.7 (3H, m), 7.1–7.4 (7H, m)

Reference Example 2

To a mixture of N-(1-benzyl-4-piperidinyl)aniline (0.9 g), diisopropyl ether (30 ml) and triethylamine (0.5 g) is added β-ethoxyacrylic acid chloride (0.7 g) in portions at 60° C. After refluxing for 1 hour, the reaction mixture is poured into ice-water and extracted with ethyl acetate. The extract is dried and concentrated and to the resulting residue is added n-hexane and the formed crystals are separated by filtration and recrystallized from n-hexane to give N-(β-ethoxyacryloyl)-N-(1-benzyl-4-piperidinyl)aniline (1.1 g) as white powders, m.p. 106°–108° C.

Reference Example 3

To a mixture of N-(1-benzyl-4-piperidinyl)aniline (1.8 g), diisopropyl ether (20 ml) and triethylamine (0.87 g) is added dropwise a solution of β-n-butoxyacrylic acid chloride (1.4 g) in diisopropyl ether (5 ml) with stirring and heating at 70° C. After completion of dropwise addition, the mixture is further stirred with heating at the same temperature for 0.5 hour. After cooling, water is added to the reaction mixture and the mixture is subjected to extraction with ethyl acetate. The extract is washed with water and dried over magnesium sulfate. The solvent is distilled off under reduced pressure and the resulting residue is purified by silica gel column chromatography to give N-(β-n-butoxyacryloyl)-N-(1-benzyl-4-piperidinyl)-aniline (2.6 g).

NMR (CDCl$_3$) δ: 0.86 (3H, t, J=7.1 Hz), 1.2–1.4 (1H, m), 1.4–1.6 (2H, m), 1.6–1.9 (2H, m), 2.1–2.3 (1H, m), 2.4–2.6 (3H, m), 2.7–2.9 (1H, m), 3.4–3.7 (4H, m), 4.86 (1H, d, J=12 Hz), 5.1–5.3 (1H, m), 7.1–7.5 (10H, m), 7.47 (1H, d, J=12 Hz)

Using appropriate starting materials, the procedure of the above Reference Examples 2 and 3 is repeated to give the following compounds:

N-(β-n-Butoxyacryloyl)-N-(1-benzyl-3-piperidinyl)-aniline

NMR (CDCl$_3$) δ: 0.85 (3H, t, J=7 Hz), 0.8–2.0 (10H, m), 2.6–2.8 (1H, m), 3.0–3.2 (1H, m), 3.40, 3.53 (2H, AB-q, J=13.2 Hz), 3.62 (2H, t, J=6.3 Hz), 4.7–5.0 (2H, m), 7.0–7.6 (10H, m)

N-(β-n-Butoxyacryloyl)-N-(4-nitrophenyl)aniline

NMR (CDCl$_3$) δ: 0.90 (3H, t, J=7.2 Hz), 1.3–1.6 (2H, m), 1.6–1.8 (2H, m), 3.76 (2H, t, J=6.4 Hz), 5.17 (1H, d, J=11.9 Hz), 7.1–7.6 (7H, m), 7.66 (1H, d, J=11.9 Hz), 8.14 (2H, d, J=9.2 Hz)

Reference Example 4

2-(2-Carbamoylethyl)aniline (37 g) and 1-benzoyl-4-oxopiperidine (67.6 g) are dissolved in ethanol (500 ml) and to the solution is added acetic acid to adjust the pH of the solution to about 5.5. To the solution is further added PtO$_2$ (1 g) and the mixture is stirred under 1 atm. at room temperature under H$_2$ atmosphere. When H$_2$ is absorbed up to 5 liters, the reaction is stopped and the catalyst is separated by filtration. The filtrate is concentrated to give N-(1-benzoyl-4-piperidinyl)-2-(2-carbamoylethyl)aniline.

Reference Example 5

To a concentrated sulfuric acid (15 ml) is added in portions N-(β-ethoxyacryloyl)-N-(1-benzyl-4-piperidinyl)aniline (1.1 g) at 60° C. After stirring the mixture at the same temperature for 15 minutes, the reaction mixture is poured into ice-water, made alkaline with a 10% aqueous sodium hydroxide solution and extracted with dichloromethane. After the extract is concentrated by distilling off the solvent, the resulting residue is purified by silica gel column chromatography (eluent; dichloromethane:methanol=50:1) and recrystallized from ethyl acetate to give 1-(1-benzyl-4-piperidinyl)carbostyril (0.8 g) as white powders, m.p. 97°–99° C.

Using appropriate starting materials, the procedure of Reference Example 5 is repeated to give the following compounds:

6-Methoxy-1-(1-benzyl-4-piperidinyl)carbostyril hydrochloride as white powders, m.p. 227°–230° C. (recrystallized from methanol)

6-Methyl-1-(1-benzyl-4-piperidinyl)carbostyril hydrochloride as white powders, m.p. 259°–261° C. (recrystallized from ethanol)

6-Fluoro-1-(1-benzyl-4-piperidinyl)carbostyril hydrochloride as white powders, m.p. 232°–236° C. (recrystallized from ethanol)

7-Methyl-1-(1-benzyl-4-piperidinyl)carbostyril

NMR (CDCl$_3$) δ: 1.62–1.85 (2H, m), 2.18–2.40 (2H, m), 2.52 (3H, s), 2.75–3.22 (4H, m), 3.61 (2H, s), 5.28 (1H, brs), 6.58 (1H, d, J=9.3 Hz), 7.01 (1H, d, J=7.9 Hz), 7.20–7.48 (6H, m), 7.55 (1H, d, J=9.3 Hz)

7-Fluoro-1-(1-benzyl-4-piperidinyl)carbostyril hydrochloride as white powders, m.p. 254°–257° C. (recrystallized from ethanol)

8-Methyl-1-(1-benzyl-4-piperidinyl)carbostyril hydrochloride as white powders, m.p. 253°–257° C. (recrystallized from ethanol)

7-Acetamido-1-(1-benzyl-4-piperidinyl)carbostyril

NMR (CDCl$_3$) δ: 1.60–1.82 (2H, m), 2.11–2.35 (2H, m), 2.24 (3H, s), 2.72–3.15 (4H, m), 3.55 (2H, s), 5.25 (1H, bs), 6.54 (1H, d, J=8.7 Hz), 7.14–7.60 (9H, m), 8.28 (1H, s), 8.63 (1H, s)

1-(1-Benzyl-3-pyrrolidinyl)carbostyril

NMR (CDCl$_3$) δ: 2.1–2.7 (4H, m), 3.1–3.2 (1H, m), 3.2–3.4 (1H, m), 3.59 (1H, d, J=12.9 Hz), 3.87 (1H, d, J=12.9 Hz), 6.4–6.5 (1H, m), 6.64 (1H, d, J=9.4 Hz), 7.1–7.7 (9H, m), 8.74 (1H, d, J=8.6 Hz)

1-(1-Benzyl-3-methyl-4-piperidinyl)carbostyril

NMR (CDCl$_3$) δ: 1.30 (3H, d, J=7.1 Hz), 1.7–1.8 (1H, m), 2.0–2.2 (1H, m), 2.3–2.5 (2H, m), 2.8–2.9 (1H, m), 3.0–3.2 (1H, m), 3.48 (1H, d, J=13.5 Hz), 3.62 (1H, d, J=13.5 Hz), 3.6–3.9 (1H, m), 4.4–4.6 (1H, m), 6.58 (2H, d, J=9.4 Hz), 7.56 (2H, d, J=9.4 Hz), 7.1–7.6 (9H, m)

1-(1-Benzyl-4-piperidinyl)-7-dimethylaminocarbostyril

NMR (CDCl$_3$) δ: 1.65–1.82 (2H, m), 2.18–2.40 (2H, m), 2.80–3.20 (4H, m), 3.12 (6H, s), 3.61 (2H, s), 5.28 (1H, brs), 6.35 (1H, d, J=9.2 Hz), 6.65 (1H, dd, J=8.8 Hz, 2.2 Hz), 6.80–7.10 (1H, m), 7.15–7.40 (6H, m), 7.48 (1H, d, J=9.2 Hz)

1-(4-Nitrophenyl)carbostyril

NMR (CDCl$_3$) δ: 6.60 (1H, d, J=8.3 Hz), 6.78 (1H, d, J=9.6 Hz), 7.2–7.4 (2H, m), 7.52 (2H, d, J=9.0 Hz), 7.64 (1H, dd, J=1.5 Hz, 6.1 Hz), 7.83 (1H, d, J=9.6 Hz), 8.48 (2H, d, J=9.0 Hz)

Reference Example 6

To N-(1-benzyl-4-piperidinyl)aniline (13.3 g) is added benzene (70 ml) and thereto is added dropwise a solution of diketene (5.0 g) in benzene (10 ml) at room temperature. After refluxing for 1 hour, the reaction mixture is concentrated by distilling off the solvent. To the resulting residue are added ethyl acetate and diethyl ether and the formed crystals are separated by filtration and recrystallized from ethyl acetate/n-hexane to give N-(1-benzyl-4-piperidinyl)-α-acetoacetoanilide (16.0 g) as white powders, m.p. 124°–126° C.

Reference Example 7

N-(1-Benzyl-4-piperidinyl)-α-acetoacetoanilide (13.2 g) is added in portions to concentrated sulfuric acid (80 ml) at 80° C. After stirring at 90° C. for 1 hour, the reaction mixture is poured into ice-water, made alkaline with potassium carbonate and then extracted with ethyl acetate. After the extract is concentrated by distilling off the solvent, the resulting residue is purified by silica gel column chromatography (eluent; ethyl acetate:methanol=100:1) to give 4-methyl-1-(1-benzyl-4-piperidinyl)carbostyril (1.5 g).

NMR (CDCl$_3$) δ: 1.60–1.85 (2H, m), 2.15–2.35 (2H, m), 2.42 (3H, s), 2.65–3.20 (4H, m), 3.59 (2H, s), 5.29 (1H, brs), 7.13–7.95 (9H, m)

Reference Example 8

To 1-(1-benzyl-4-piperidinyl)-7-acetylaminocarbostyril (3.0 g) are added ethanol (32 ml) and an aqueous 10% sodium hydroxide solution (32 ml) and the mixture is refluxed for 1 hour. After the reaction mixture is concentrated by distilling off the solvent, water is added to the residue and the resulting solution is extracted with dichloromethane. The extract is concentrated by distilling off the solvent and recrystallized from ethanol/chloroform to give 1-(1-benzyl-4-piperidinyl)-7-aminocarbostyril (2.4 g) as white powders, m.p. 238°–241° C.

Reference Example 9

To a mixture of 1-(1-benzyl-4-piperidinyl)-7-aminocarbostyril (0.7 g), methanol (10 ml) and 37% formalin (1.4 ml) is added NaBH$_3$CN (0.3 g) in portions. Thereafter, acetic acid (0.7 ml) is added thereto in portions at room temperature and the mixture is stirred at the same temperature for 1 hour. After completion of the reaction, water is added to the reaction mixture and the mixture is neutralized with an aqueous potassium carbonate and then extracted with ethyl acetate. The extract is concentrated by distilling off the solvent to give 1-(1-benzyl-4-piperidinyl)-7-dimethylaminocarbostyril (0.7 g).

NMR (CDCl$_3$) δ: 1.65–1.82 (2H, m), 2.18–2.40 (2H, m), 2.80–3.20 (4H, m), 3.12 (6H, s), 3.61 (2H, s), 5.28 (1H, brs), 6.35 (1H, d, J=9.2 Hz), 6.65 (1H, dd, J=8.8 Hz, 2.2 Hz), 6.80–7.10 (1H, m), 7.15–7.40 (6H, m), 7.48 (1H, d, J=9.2 Hz)

Reference Example 10

To 10% Pd-C (0.1 g) is added acetic acid (20 ml) and then 1-(4-nitrophenyl)carbostyril (0.9 g) and the mixture is subjected to catalytic reduction at 80° C. under normal pressure. After completion of the reaction, 10% Pd-C is removed by filtration and the resulting solution is concentrated under reduced pressure. To the concentrate is added water and the solution is made alkaline with an aqueous sodium hydroxide solution and then extracted with dichloromethane. The extract is washed with water and dried over magnesium sulfate. The solvent is distilled off under reduced pressure and the residue is purified by silica gel column chromatography and recrystallized from ethanol to give 1-(4-aminophenyl)carbostyril (0.66 g) as brown powders, m.p. 225°–230° C.

NMR (CDCl$_3$) δ: 2.7–2.9 (2H, m), 3.0–3.1 (2H, m), 3.8 (2H, brs), 6.50 (1H, dd, J=1.4 Hz, 7.8 Hz), 6.7–6.8 (2H, m), 6.8–7.1 (4H, m), 7.1–7.2 (1H, m)

Reference Example 11

To a solution of 3,4-dihydrocarbostyril (3 g) in N-methylpyrrolidone (30 ml) are added p-iodobenzoic acid (5.58 g), copper (0.3 g) and potassium carbonate (3.03 g) and the mixture is stirred at 150° C. for 4 hours. An aqueous sodium hydroxide solution is added to the reaction mixture and the mixture is washed with dichloromethane. The aqueous layer is made acidic with concentrated hydrochloric acid and then extracted with diethyl ether and the extract is dried over magnesium sulfate. After the solvent is distilled off under reduced pressure, methanol (50 ml) is added to the residue and thionyl chloride (10 ml) is slowly added to the solution while stirring with ice-cooling. After completion of dropwise addition, the mixture is refluxed for 0.5 hour.

After methanol is distilled off under reduced pressure, water is added to the residue and the solution is extracted with dichloromethane and dried over magnesium sulfate. The solvent is distilled off under reduced pressure and the resulting residue is purified by silica gel column chromatography to give 1-(4-methoxycarbonylphenyl)-3,4-dihydrocarbostyril (1.44 g).

NMR (CDCl$_3$) δ: 2.7–2.9 (2H, m), 3.0–3.2 (2H, m), 3.93 (3H, s), 6.3–6.4 (1H, m), 6.9–7.1 (2H, m), 7.2–7.3 (1H, m), 7.34 (2H, d, J=8.6 Hz), 8.17 (2H, d, J=8.6 Hz)

Reference Example 12

To a solution of 1-(4-methoxycarbonylphenyl)-3,4-dihydrocarbostyril (1.84 g) in methanol (40 ml) is added a 5% aqueous sodium hydroxide solution (20 ml) and the mixture is stirred at room temperature overnight. Methanol is distilled off under reduced pressure and to the residue is added water. After the solution is washed with dichloromethane, the aqueous layer is made acidic with concentrated hydrochloric acid and extracted with diethyl ether and dried over magnesium sulfate. The solvent is distilled off under reduced pressure and the resulting residue is purified by silica gel column chromatography, followed by recrystallization from ethanol to give 1-(4-carboxyphenyl)-3,4-dihydrocarbostyril (0.87 g) as pale yellow powders, m.p. 265°–270° C.

NMR (DMSO-d$_6$) δ: 2.7–2.9 (2H, m), 2.9–3.2 (2H, m), 6.21 (1H, d, J=7.4 Hz), 6.9–7.2 (2H, m), 7.29 (1H, d, J=6.3 Hz), 7.38 (2H, d, J=8.3 Hz), 8.08 (2H, d, J=8.3 Hz)

Reference Example 13

Using appropriate starting materials, the procedure of Reference Example 1 is repeated to give the following compounds:

N-(1-Benzyl-4-piperidinyl)-3,4-difluoroaniline

NMR (CDCl$_3$) δ: 1.30–1.65 (2H, m), 1.86–2.25 (4H, m), 2.72–2.97 (2H, m), 3.04–3.30 (1H, m), 3.36–3.60 (3H, m), 6.11–6.46 (2H, m), 6.80–7.00 (1H, m), 7.30 (5H, s)

N-(1-Benzyl-4-piperidinyl)-3,5-difluoroaniline

NMR (CDCl$_3$) δ: 1.45–1.62 (2H, m), 1.95–2.25 (4H, m), 2.75–2.93 (2H, m), 3.10–3.30 (1H, m), 3.52 (2H, s), 3.70–3.87 (1H, m), 5.98–6.15 (3H, m), 7.20–7.48 (5H, m)

Reference Example 14

Using appropriate starting materials, the procedure of Reference Example 5 is repeated to give the following compounds:

6,7-Difluoro-1-(1-benzyl-4-piperidinyl)carbostyril as white powders (recrystallized from ethanol), m.p. 132°–134° C.

5,7-Difluoro-1-(1-benzyl-4-piperidinyl)carbostyril as colorless prisms (recrystallized from ethanol), m.p. 165°–166° C.

Reference Example 15

To a mixture of N-(1-benzyl-4-piperidinyl)aniline (6.4 g), diisopropyl ether (70 ml) and triethylamine (4.8 ml) is added at 70° C. a solution of α-methylcinnamoyl chloride (4.9 g) in diisopropyl ether (10 ml). After stirring at the same temperature for 30 minutes, water is added to the reaction solution and the mixture is extracted with ethyl acetate. The extract is concentrated by distilling off the solvent and to the resulting residue is added diethyl ether and the formed crystals are separated by filtration to give N-(α-methylcinnamoyl)-N-(1-benzyl-4-piperidinyl)aniline (8.9 g), m.p. 150°–152° C.

Reference Example 16

To grinded aluminum chloride (26 g) are added chlorobenzene (26 ml) and N-(α-methylcinnamoyl)-N-(1-benzyl-4-piperidinyl)aniline (8.7 g) and the mixture is heated at 110° C. for 1 hour. After cooling, the reaction mixture is poured into ice-water and made alkaline with an aqueous sodium hydroxide solution. After extraction with dichloromethane, the extract is concentrated and the resulting residue is purified by silica gel column chromatography (eluent; methylene chloride). The purified substance is converted into hydrochloride and then recrystallized from ethanol/water to give 1-(1-benzyl-4-piperidinyl)-3-methylcarbostyril hydrochloride (5.8 g) as colorless needles, m.p. 274°–276° C.

Reference Example 17

A mixture of o-aminobenzyl alcohol (20.4 g), ethanol (300 ml), 1-benzyl-4-piperidone (31.6 g) and acetic acid (40 ml) is refluxed for 30 minutes. After concentrating the reaction mixture, water is added to the resulting residue and the mixture is extracted with dichloromethane. After concentrating the extract to remove the solvent, n-hexane is added to the resulting residue and the formed crystals are separated by filtration to give 1-benzylspiro[piperidin-4,2'-(4H-1',2'-dihydro-3,1-benzoxadine)] (37.7 g), m.p. 114°–115° C.

Reference Example 18

To a mixture of 1-benzylspiro[piperidin-4,2'-(4H-1',2'-dihydro-3,1-benzoxadine)] (10.3 g), methanol (80 ml) and sodium cyanoborohydride (2.2 g) is added acetic acid (4.1 ml) in portions and the mixture is stirred at room temperature overnight. The reaction mixture is diluted with water and made alkaline with an aqueous potassium carbonate solution and the formed crystals are separated by filtration to give N-(1-benzyl-4-piperidinyl)-o-hydroxymethylaniline (9.4 g), m.p. 164°–168° C.

Reference Example 19

A mixture of N-(1-benzyl-4-piperidinyl)-o-hydroxymethylaniline (2.9 g), chloroform (100 ml) and manganese dioxide (12 g) is refluxed for 1 hour. After cooling, the mixture is filtered and the filtrate is concentrated. The resulting residue is purified by silica gel column chromatography (eluent; dichloromethane) to give N-(1-benzyl-4-piperidinyl)-o-formylaniline (2.4 g) as yellow powders, m.p. 87°–90° C.

Reference Example 20

A mixture of N-(1-benzyl-4-piperidinyl)-o-formylaniline (32.0 g), diethyl malonate (35.4 g), piperidine (5 ml), acetic acid (2.5 ml), anhydrous toluene (320 ml) and molecular sieves (32 g) is refluxed for 8 hours. After concentrating the reaction mixture, dichloromethane is added to the residue and the mixture is filtered. Water is added to the filtrate and the mixture is extracted with dichloromethane. After concentrating the extract, the resulting residue is purified by silica gel column chromatography (eluent; dichloromethane/methanol=50/1) to give 3-ethoxycarbonyl-1-(1-benzyl-4-piperidinyl)carbostyril (27.2 g).

NMR (CDCl$_3$) δ: 1.41 (3H, t, J=7.1 Hz), 1.65–1.86 (2H, m), 2.14–2.40 (2H, m), 2.68–3.25 (4H, m), 3.53 (2H, s), 4.41 (2H, q, J=7.1 Hz), 5.28 (1H, brs), 7.16–7.93 (9H, m), 8.30 (1H, s)

Reference Example 21

Using appropriate starting materials, the procedure of Reference Example 1 is repeated to give the following compounds:

N-(1-Benzoyl-4-piperidinyl)-3-fluoroaniline as white powders (recrystallized from ethanol), m.p. 114°–116° C.

N-(1-Benzoyl-4-piperidinyl)-3,5-difluoroaniline as white powders (recrystallized from ethanol), m.p. 175°–176° C.

Reference Example 22

Using appropriate starting materials, the procedure of Reference Examples 17 and 18 is repeated to give the following compound:

N-(1-Benzyl-4-piperidinyl)-2-hydroxymethyl-3-methylaniline as white powders, m.p. 182°–184° C.

Reference Example 23

Using appropriate starting materials, the procedure of Reference Example 19 is repeated to give the following compound:

N-(1-Benzyl-4-piperidinyl)-2-formyl-3-methylaniline as yellow powders, m.p. 114°–116° C.

Reference Example 24

To N-(1-benzyl-4-piperidinyl)-2-formyl-3-methylaniline (7.0 g) are added methanol (100 ml) and methyl (triphenylphosphoranylidene)acetate (15 g) and the mixture is refluxed for 1 hour. After cooling, the formed crystals are separated by filtration to give methyl 2-methyl-5-[(1-benzyl-4-piperidinyl)amino]cinnamate (5.6 g) as pale yellow powders, m.p. 140°–142° C.

EXAMPLE 1

To N-(1-benzoyl-4-piperidinyl)-2-(2-carbamoylethyl)aniline (85 g) prepared in Reference Example 4 is added 5% hydrochloric acid (500 ml) and the mixture is refluxed for 5 hours. After cooling, the reaction mixture is extracted with diethyl ether and the aqueous layer is made alkaline with a 50% aqueous sodium hydroxide solution and extracted with ethyl acetate. The extract is dried over sodium carbonate and concentrated. The concentrate is purified by silica gel column chromatography (eluent; n-hexane/ethyl acetate=1/0–10/1) and recrystallized from ethanol/n-hexane to give 1-(1-benzoyl-4-piperidinyl)-3,4-dihydrocarbostyril (35 g) as white powders, m.p. 108°–111° C.

EXAMPLES 2 TO 383C

Using appropriate starting materials, the procedure of Example 1 is repeated to give the following compounds as shown in Table 1. Table 2 shows the NMR analysis of these compounds.

TABLE 1

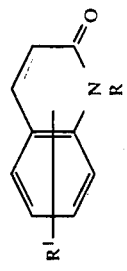

Bond between 3- and 4-positions in the carbostyril ring: single bond

| | Structure | | Crystalline form | Recrystallization solvent | Melting point/ NMR analysis | Form |
|---|---|---|---|---|---|---|
| | R | R¹ | | | | |
| Example 2 | piperidine-N—COCH₂CH₃ (4-methyl) | H | white powders | ethanol/n-hexane | 82–83° C. | Free |
| Example 3 | 4-methylpiperidine-N—CO—C₆H₄—NO₂ | H | pale yellow powders | ethanol/n-hexane | 142–145° C. | Free |
| Example 4 | 4-methylpiperidine-N—CO-(2-furyl) | H | white powders | ethanol/n-hexane | 108–111° C. | Free |
| Example 5 | 4-methylpiperidine-N—CO-(3-pyridyl) | H | white powders | ethanol/n-hexane | 113–116° C. | Free |
| Example 6 | 4-methylpiperidine-N—CO-(4-pyridyl) | H | white powders | ethanol/n-hexane | 105–108° C. | Free |
| Example 7 | 4-methylpiperidine-N—CO-(2-thienyl) | H | white powders | ethanol/n-hexane | 129–132° C. | Free |

TABLE 1-continued

| Example | Structure | | Form | Recrystallization solvent | Melting point | Salt |
|---|---|---|---|---|---|---|
| Example 8 | [piperidine with 4-methyl, N-C(=O)-pyrrole-2-yl (NH)] | H | white powders | ethanol/n-hexane | 161–162° C. (decomposition) | Free |
| Example 9 | [piperidine with 4-methyl, N-C(=O)-NH-phenyl] | H | white powders | ethanol/n-hexane | 194–196° C. | Free |
| Example 10 | [piperidine with 4-methyl, N-C(=O)-(2-OCH$_3$, 4-OC$_2$H$_5$-phenyl)] Bond between 3- and 4-positions in the carbostyril ring: double bond | H | white powders | ethanol/n-hexane | 172–174° C. | Free |
| Example 11 | [piperidine with 4-methyl, N-C(=O)-CH=CH-phenyl] Bond between 3- and 4-positions in the carbostyril ring: single bond | H | white powders | ethanol/n-hexane | 144–147° C. | Free |
| Example 12 | [piperidine with 4-methyl, N-C(=O)-CH$_2$-phenyl] | H | | | 1) | Free |
| Example 13 | [piperidine with 4-methyl, N-C(=O)-pyrrolidine-2-yl-N-COOCH$_2$-phenyl] | H | white powders | ethanol/n-hexane | 143–147° C. | Free |
| Example 14 | [piperidine with 4-methyl, N-C(=O)-CH(phenyl)-NHCOC(CH$_3$)$_3$] | H | white powders | ethanol/n-hexane | 143–146° C. | Free |

TABLE 1-continued

| Example | Structure | R | Form | Solvent | mp | Salt |
|---|---|---|---|---|---|---|
| Example 15 | piperidine-N-C(=O)-O-phenyl | H | white powders | diethyl ether/n-hexane | 138–140° C. | Free |
| Example 16 | piperidine-N-C(=O)-CH₂-adamantyl | H | white powders | n-hexane | 143–145° C. | Free |
| Example 17 | piperidine-N-C(=O)-CH₂-(2-thienyl) | H | | | 2) | Free |
| Example 18 | piperidine-N-C(=O)-(4-chlorophenyl) | H | white powders | n-hexane/ethanol | 111–112° C. | Free |
| Example 19 | piperidine-N-C(=O)-(4-methoxyphenyl) | H | white powders | n-hexane/ethanol | 93–96° C. | Free |
| Example 20 | piperidine-N-C(=O)-pyrazinyl | H | | | 3) | Free |
| Example 21 | piperidine-N-C(=O)-(2-chlorophenyl) | H | white powders | n-hexane/ethanol | 175–178° C. | Free |

TABLE 1-continued

| Example | Structure | | | | |
|---|---|---|---|---|---|
| Example 22 | (3-Cl-C6H4)-C(=O)-N-(4-methylpiperidine) | H | white powders | n-hexane/ethanol | 123–126° C. | Free |
| Example 23 | (2,4-di-OCH3-C6H3)-C(=O)-N-(4-methylpiperidine) | H | white powders | n-hexane/ethanol | 141–143° C. | Free |
| Example 24 | Ph-CH(NH2)-C(=O)-N-(4-methylpiperidine) | H | white powders | diethyl ether | 116–120° C. | Free |
| Example 25 | (3,5-di-C(CH3)3-4-OH-C6H2)-C(=O)-N-(4-methylpiperidine) | H | white powders | n-hexane/ethanol | 134–136° C. | Free |
| Example 26 | (4-O(CH2)3CH3-C6H4)-C(=O)-N-(4-methylpiperidine) | H | | | 4) | Free |
| Example 27 | (4-N(CH3)2-C6H4)-C(=O)-N-(4-methylpiperidine) | H | white powders | n-hexane/ethanol | 153–155° C. | Free |
| Example 28 | acetonide sugar-C(=O)-N-(4-methylpiperidine) | H | | | 5) | Free |
| Example 29 | (4-SCH3-C6H4)-C(=O)-N-(4-methylpiperidine) | H | | | 6) | Free |

TABLE 1-continued

| Example | Structure | R | Form | Solvent | mp | Salt |
|---|---|---|---|---|---|---|
| Example 30 | 3,4-dimethoxyphenyl-C(=O)-N(4-methylpiperidine) | H | white powders | n-hexane/ethanol | 121–124° C. | Free |
| Example 31 | 4-phenoxyphenyl-C(=O)-N(4-methylpiperidine) | H | white powders | n-hexane/ethanol | 205–208° C. | Free |
| Example 32 | 4-(NHCOCH₃)phenyl-C(=O)-N(4-methylpiperidine) | H | white amorphous | n-hexane | 85–90° C. 7) | Free |
| Example 33 | 4-(OCCH₃)phenyl-C(=O)-N(4-methylpiperidine) | H | white powders | n-hexane/ethanol | 170–171° C. | Free |
| Example 34 | (CH₃)₂C=CH-CH₂-CH₂-C(CH₃)=CH-C(=O)-N(4-methylpiperidine) | H | | | 8) | Free |
| Example 35 | 4-bromophenyl-C(=O)-N(4-methylpiperidine) | H | white powders | n-hexane/ethanol | 124–126° C. | Free |
| Example 36 | 4-fluorophenyl-C(=O)-N(4-methylpiperidine) | H | white powders | n-hexane/ethanol | 105–107° C. | Free |
| Example 37 | 4-cyanophenyl-C(=O)-N(4-methylpiperidine) | H | pale yellow powders | n-hexane/ethanol | 169–172° C. | Free |

TABLE 1-continued

| | | | | | |
|---|---|---|---|---|---|
| Example 38 | [structure: piperidine-N-C(=O)-phenyl with NO2 and OCH3 substituents] | H | pale yellow amorphous | n-hexane/ethanol | 85–90° C., 9) Free |
| Example 39 | [structure: piperidine-N-C(=O)-phenyl-C(=O)CH3] | H | | n-hexane/ethanol | 10) Free |
| Example 40 | [structure: piperidine-N-C(=O)-phenyl-CH2N(CH3)2] | H | white powders | n-hexane/ethanol | 83–86° C. Free |
| Example 41 | [structure: piperidine-N-C(=O)-phenyl-N(imidazole-SCH2CH3)] | H | | n-hexane/ethanol | 11) Free |
| Example 42 | [structure: piperidine-N-C(=O)-phenyl-CF3] | H | white powders | n-hexane/ethanol | 161–163° C. Free |
| Example 43 | [structure: piperidine-N-C(=O)-phenyl with NO2, NO2] | H | pale yellow powders | n-hexane/ethanol | 108–111° C. Free |
| Example 44 | [structure: piperidine-N-C(=O)-phenyl with OCH3, OCH3] | H | white powders | n-hexane/ethanol | 202–204° C. Free |

TABLE 1-continued

| Example | Structure | R | Form | Solvent | M.p. | Salt |
|---|---|---|---|---|---|---|
| Example 45 | 4-methylpiperidine-N-C(=O)-(2,3-dimethoxyphenyl) | H | white powders | n-hexane/ethanol | 194–195° C. | Free |
| Example 46 | 4-methylpiperidine-N-C(=O)-(4-t-butylphenyl) | H | white powders | n-hexane/ethanol | 110–112° C. | Free |
| Example 47 | 4-methylpiperidine-N-C(=O)-(2,4,5-trimethoxyphenyl) | H | white powders | n-hexane/ethanol | 123–126° C. | Free |
| Example 48 | 4-methylpiperidine-N-C(=O)-(4-aminophenyl) | H | white powders | n-hexane/ethanol | 198–199° C. | Free |
| Example 49 | 4-methylpiperidine-N-C(=O)-(4-acetylphenyl) | H | white powders | n-hexane/ethanol | 160–162° C. | Free |
| Example 50 | 4-methylpiperidine-N-C(=O)-(4-benzyloxyphenyl) | H | | | 12) | Free |
| Example 51 | 4-methylpiperidine-N-C(=O)-(4-methylsulfonylphenyl) | H | white powders | n-hexane/ethanol | 194–196° C. | Free |
| Example 52 | 4-methylpiperidine-N-C(=O)-(4-hydroxyphenyl) | H | white powders | n-hexane/ethanol | 182–183° C. | Free |

TABLE 1-continued

| Example | Structure | | | | |
|---|---|---|---|---|---|
| Example 53 | 4-COOH-C6H4-C(=O)-N(piperidinyl-4-CH3) | H | white powders | n-hexane/ethanol | 232–235° C. Free |
| Example 54 | 3-OCH3-4-SCH3-C6H3-C(=O)-N(piperidinyl-4-CH3) | H | | | 13) Free |
| Example 55 | 4-[O(CH2)2N(CH3)2]-C6H4-C(=O)-N(piperidinyl-4-CH3) | H | | | 14) Free |
| Example 56 | 4-[OCH2CH(CH3)2]-C6H4-C(=O)-N(piperidinyl-4-CH3) | H | | | 15) Free |
| Example 57 | 4-[N(CH3)(COOC(CH3)3)]-C6H4-C(=O)-N(piperidinyl-4-CH3) | H | | | 16) Free |
| Example 58 | 4-[4-(COOC(CH3)3)-piperazin-1-yl]-C6H4-C(=O)-N(piperidinyl-4-CH3) | H | white powders | n-hexane | 136–138° C. Free |
| Example 59 | 4-[N(COOC(CH3)3)(CH2CH(CH3)2)]-C6H4-C(=O)-N(piperidinyl-4-CH3) | H | | | 17) Free |

TABLE 1-continued

| | Structure | | Recryst. solvent | Form | m.p. | Salt |
|---|---|---|---|---|---|---|
| Example 60 | [4-(piperidin-1-yl-carbonyl)phenyl-piperidine with NH] | H | | | 18) | Free |
| Example 61 | [4-(piperidin-1-yl-carbonyl)phenyl-OCH₂CH=C(CH₃)₂] | H | | | 19) | Free |
| Example 62 | [4-(piperidin-1-yl-carbonyl)phenyl-NHCH₃] | H | n-hexane/ethanol | white powders | 184–186° C. | Free |
| Example 63 | [4-(piperidin-1-yl-carbonyl)phenyl-N(C₂H₅)₂] | H | n-hexane/ethanol | white powders | 139–140° C. | Free |
| Example 64 | [quinolinone-piperidinyl carbonyl] | H | n-hexane/ethanol | white powders | 238–240° C. | Free |
| Example 65 | [2-(N-methyl-acetamido)-benzoyl-piperidine] | H | n-hexane/ethanol | white powders | 224–226° C. | Free |
| Example 66 | [4-(piperidin-1-yl-carbonyl)phenyl-O(CH₂)₂CH₃] | H | n-hexane/ethanol | white powders | 110–111° C. | Free |
| Example 67 | [4-(piperidin-1-yl-carbonyl)phenyl-N(CH₃)(COCH₂Cl)] | H | n-hexane/ethanol | white powders | 220–222° C. (decomposition) | Free |

TABLE 1-continued

| | Structure | R | Notes | Form | Ref |
|---|---|---|---|---|---|
| Example 68 | piperidine-N-C(=O)-C6H4-N(piperazine-N-CH3) | H | | Free | 20) |
| Example 69 | 4-methylpiperidine-N-C(=O)-C6H4-CH(CH3)2 | H | | Free | 21) |
| Example 70 | 4-methylpiperidine-N-C(=O)-C6H4-CHO | H | | Free | 22) |
| Example 71 | 4-methylpiperidine-N-C(=O)-C6H4-SC2H5 | H | white powders, n-hexane/ethanol | | 98–99° C. |
| Example 72 | 4-methylpiperidine-N-C(=O)-C6H3(OCH3)(Cl) | H | white powders, n-hexane/ethanol | | 84–87° C. |
| Example 73 | 4-methylpiperidine-N-C(=O)-C6H4-CH2OH | H | white powders, n-hexane/ethanol | | 138–139° C. |

| Example | Structure | R | Appearance | Solvent | M.P. | Form |
|---|---|---|---|---|---|---|
| Example 74 | 4-methylpiperidine N-C(=O)-phenyl(OCH₃)(S(=O)CH₃) | H | white powders | n-hexane/ethanol | 95–98° C. | Free |
| Example 75 | 4-methylpiperidine N-C(=O)-phenyl-C(=O)-phenyl | H | white powders | n-hexane/ethanol | 240–243° C. (decomposition) | Free |
| Example 76 | 4-methylpiperidine N-C(=O)-phenyl(OCH₃)(N(CH₃)₂) | H | white powders | n-hexane/ethanol | 93–96° C. (decomposition) | Free |
| Example 77 | 4-methylpiperidine N-C(=O)-pyrrolidine-H | H | | | 23) | Free |
| Example 78 | 4-methylpiperidine N-C(=O)-phenyl-NHCOCF₃ | H | pale red powders | n-hexane | 104–107° C. | Free |
| Example 79 | 4-methylpiperidine N-C(=O)-phenyl-NHCH₂CH=CH₂ | H | | | 24) | Free |
| Example 80 | 4-methylpiperidine N-C(=O)-phenyl(NH₂)(NH₂) | H | white powders | n-hexane/ethanol | 113–116° C. | Free |

-continued
| Example | Structure | | | Solvent | mp/Note | Form |
|---|---|---|---|---|---|---|
| Example 81 | 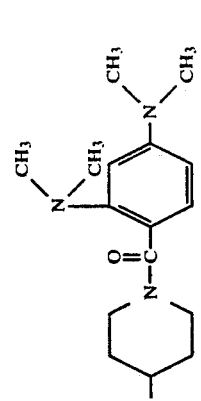 | H | pale grey powders | n-hexane/ethanol | 162–164° C. | Free |
| Example 82 | 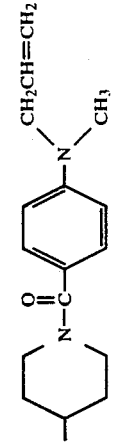 | H | | n-hexane/ethanol | 25) | Free |
| Example 83 | 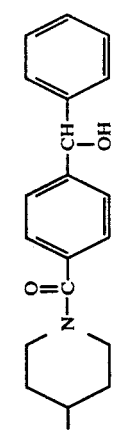 | H | white powders | n-hexane/ethanol | 93–96° C. | Free |
| Example 84 | 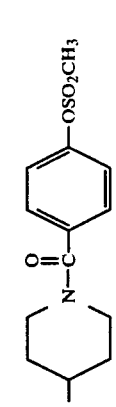 | H | | n-hexane/ethanol | 26) | Free |
| Example 85 | 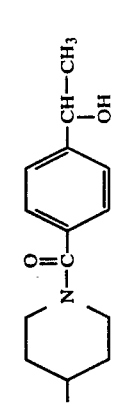 | H | white powders | n-hexane/ethanol | 144–146° C. | Free |
| Example 86 | 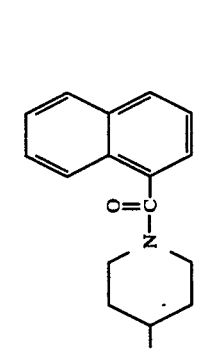 | H | white powders | n-hexane/ethanol | 197–199° C. | Free |
| Example 87 | 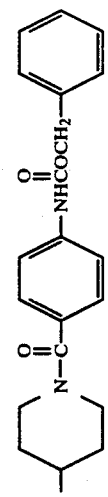 | H | | | 27) | Free |

-continued
| | | | | | |
|---|---|---|---|---|---|
| Example 88 |  | H | | | 28) Free |
| Example 89 | | H | | | 29) Free |
| Example 90 | | H | | | 30) Free |
| Example 91 |  | H | white powders | n-hexane/ethanol | 193–196° C. Free |
| Example 92 | | H | white powders | n-hexane/ethanol | 82–85° C. Free |
| Example 93 |  | H | | | 31) Free |
| Example 94 | | H | | | 32) Free |
| Example 95 | 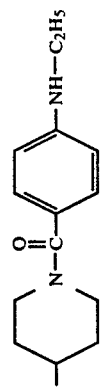 | H | white powders | n-hexane | 122–125° C. Free |

-continued

| Example | Structure | | | mp | Solvent | Form |
|---|---|---|---|---|---|---|
| Example 96 | 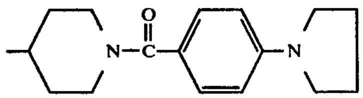 | H | pale yellow powders | n-hexane/ethanol | 168–171° C. | Free |
| Example 97 | 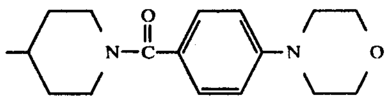 | H | pale yellow powders | n-hexane/ethanol | 213–215° C. | Free |
| Example 98 | 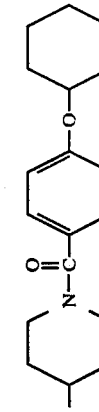 | H | white powders | n-hexane | 111–114° C. | Free |
| Example 99 | 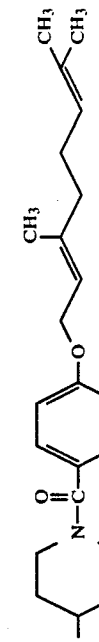 | H | | | 33) | Free |
| Example 100 | 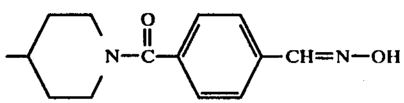 | H | white powders | n-hexane/ethanol | 222–224° C. | Free |
| Example 101 | 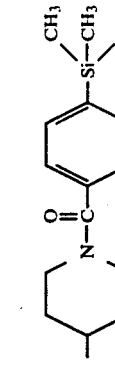 | H | white powders | n-hexane | 149–151° C. | Free |
| Example 102 | 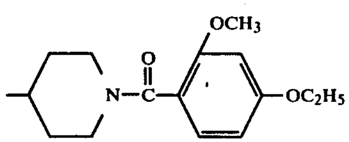 | H | colorless prisms | n-hexane/ethanol | 174–175° C. | Free |
| Example 103 | 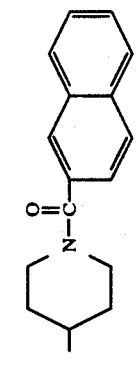 | H | white powders | n-hexane/ethanol | 130–132° C. | Free |

| | | | -continued | | | |
|---|---|---|---|---|---|---|
| Example 104 | 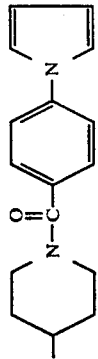 | H | pale grey powders | n-hexane | 153–156° C. | Free |
| Example 105 | 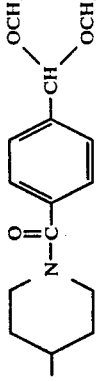 | H | white powders | n-hexane | 134–136° C. | Free |
| Example 106 | 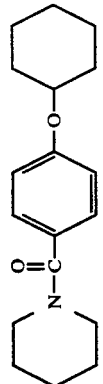 | H | | | 34) | Free |
| Example 107 | 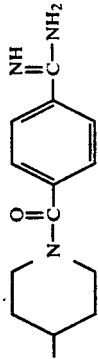 | H | white powders | water | 92–97° C. 35) | Free |
| Example 108 | 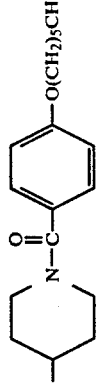 | H | | | 36) | Free |
| Example 109 | 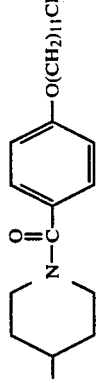 | H | | | 37) | Free |
| Example 110 | 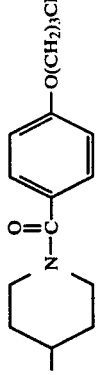 | H | | | 38) | Free |
| Example 111 | 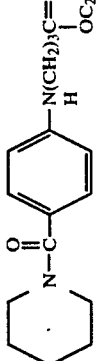 | H | | | 40) | Free |
| Example 112 | 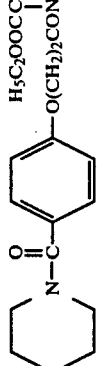 | H | | | 41) | Free |

-continued

| | | | |
|---|---|---|---|
| Example 113 | (structure: 4-methylpiperidine-N-C(=O)-C6H4-O(CH2)3C(=NH)NH2) | H | 42) Free |
| Example 114 | (structure: 4-methylpiperidine-N-C(=O)-C6H4-O(CH2)3-N(piperazine)-C6H4-OCH3) | H | 43) Free |
| Example 115 | (structure: 4-methylpiperidine-N-C(=O)-C6H4-O(CH2)3-N(piperazine)-C6H4-Cl) | H | 44) Free |
| Example 116 | (structure: 4-methylpiperidine-N-C(=O)-C6H4-NHCOOCH3) | H | 45) Free |
| Example 117 | (structure: 4-methylpiperidine-N-C(=O)-C6H4-CH=CHC2H5) | H | 46) Free |
| Example 118 | (structure: 4-methylpiperidine-N-C(=O)-C6H4-O(CH2)3CHCH2N(CH3)2, OH) | H | 47) Free |
| Example 119 | (structure: 4-methylpiperidine-N-C(=O)-C6H4-O(CH2)3CHCH2NH-CH3, OH) | H | 48) Free |
| Example 120 | (structure: 4-methylpiperidine-N-C(=O)-C6H4-N(2-pyrrolidinone)) | H | 49) Free |

-continued
| | | | | |
|---|---|---|---|---|
| Example 121 | 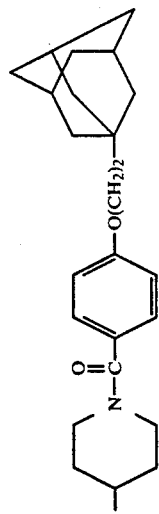 | H | 50) | Free |
| Example 122 | 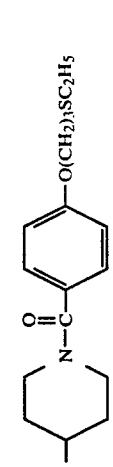 | H | 51) | Free |
| Example 123 | 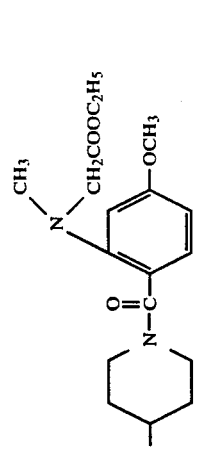 | H | 52) | Free |
| Example 124 | 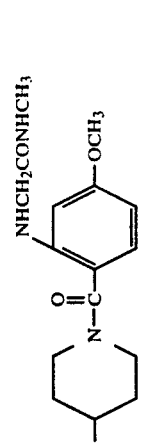 | H | 53) | Free |
| Example 125 | 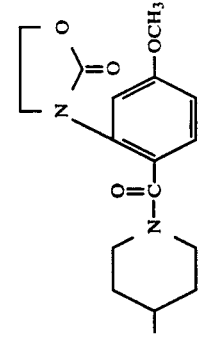 | H | 54) | Free |
| Example 126 | 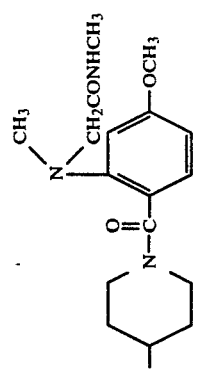 | H | 55) | Free |

-continued
| | | | | |
|---|---|---|---|---|
| Example 127 | 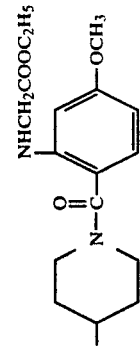 | H | | 56) | Free |
| Example 128 | 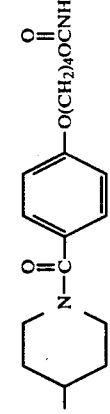 | H | | 57) | Free |
| Example 129 | 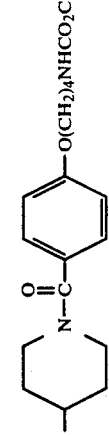 | H | | 58) | Free |
| Example 130 | 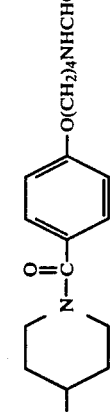 | H | | 59) | Free |
| Example 131 | 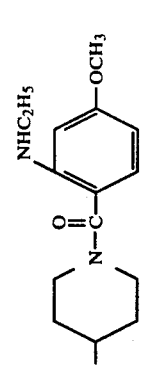 | H | | 60) | Free |
| Example 132 | 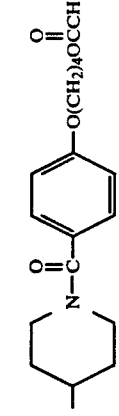 | H | white powders | 67–69° C. diethyl ether/ n-hexane | Free |
| Example 133 | 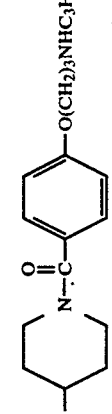 | H | | 61) | Free |
| Example 134 | 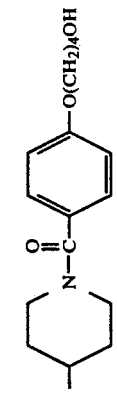 | H | colorless needles | 136–138° C. diethyl ether/ n-hexane | Free |

-continued
| Example | Structure | R | Recryst. solvent | Form | mp |
|---|---|---|---|---|---|
| Example 135 |  | H | colorless needles | ethanol/diethyl ether | 171–173° C. Free |
| Example 136 | 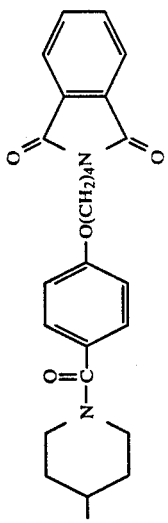 | H | | | Free 62) |
| Example 137 | 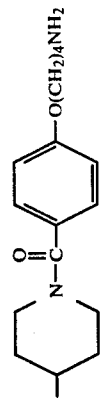 | H | | | Free 63) |
| Example 138 | 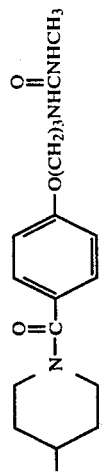 | H | | | Free 64) |
| Example 139 | 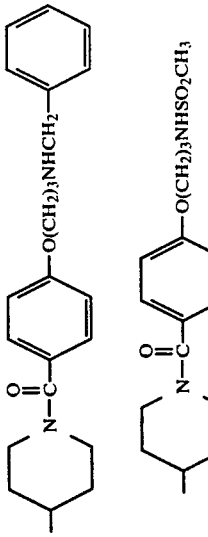 | H | | | Free 65) |
| Example 140 | 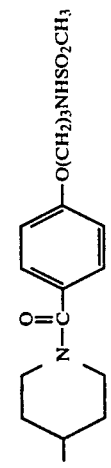 | H | | | Free 66) |
| Example 141 | 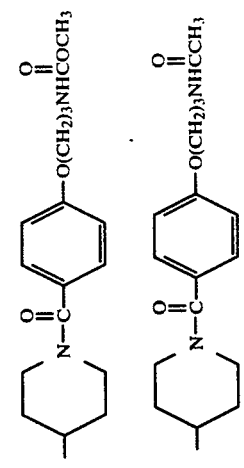 | H | colorless needles | ethanol/diethyl ether | 147.5–149° C. Free 67) |
| Example 142 | 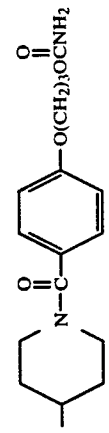 | H | colorless needles | ethanol | 136–138° C. Free 68) |

-continued
| | | | | | | |
|---|---|---|---|---|---|---|
| Example 143 | Example 144 | Example 145 | Example 146 | Example 147 | Example 148 | Example 149 |
| 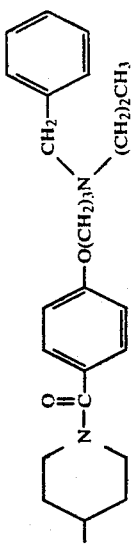 | 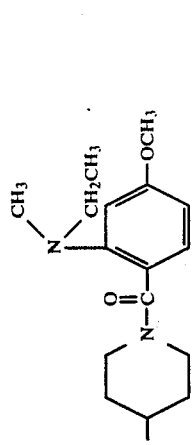 | 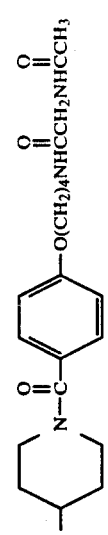 | 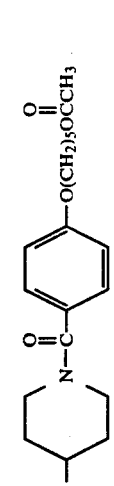 | 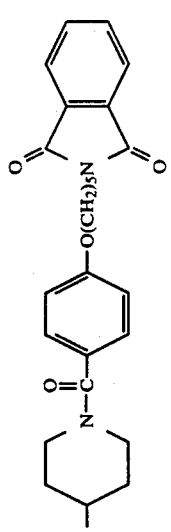 | 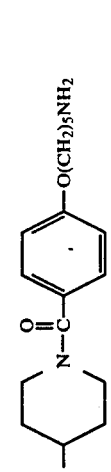 | 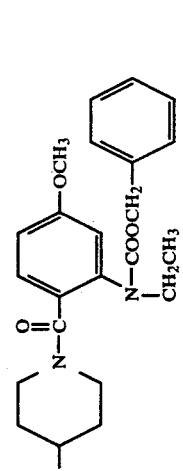 |
| H | H | H | H | H | H | H |
| 69) | 70) | 71) | 72) | 73) | 74) | 75) |
| Free | Free | Free | Free | Free | Free | Free |

-continued
| | | | | |
|---|---|---|---|---|
| Example 150 | 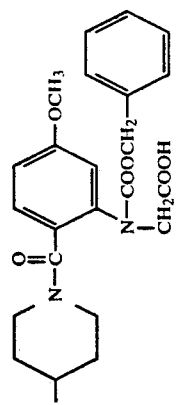 | H | 76) | Free |
| Example 151 | 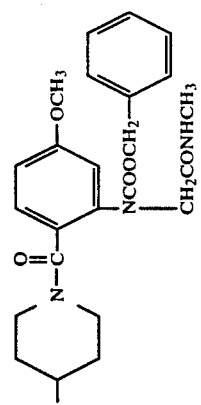 | H | 77) | Free |
| Example 152 | 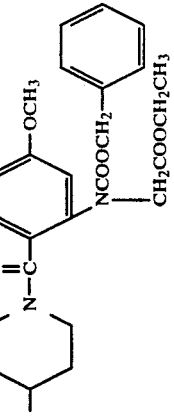 | H | 78) | Free |
| Example 153 | 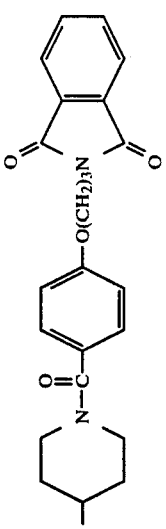 | 7-F | 79) | Free |
| Example 154 | 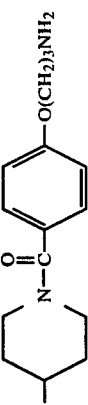 | 7-F | 80) | Free |

| Example | Structure | Substituent | mp/notes | Form |
|---|---|---|---|---|
| Example 155 | (4-piperidinyl-C(O)-C6H4-O(CH2)3NHCCH3=O) | 7-F | | Free 81) |
| Example 156 | (4-methylpiperidine-NH) | 7-C2H5 | | Free 82) |
| Example 157 | (2,4-diOCH3-C6H3-C(O)-N-piperidinyl) | 7-C2H5 | | Free 83) |
| Example 158 | (4-methylpiperidine-NH) | 7-OCH3 | | Free 84) |
| Example 159 | (2,4-diOCH3-C6H3-C(O)-N-(4-methylpiperidinyl)) | 7-OCH3 | | Free 85) |
| Example 160 | (2,4-diOCH3-C6H3-C(O)-N-(4-methylpiperidinyl)) | 6-NHCO-C6H5 | | Free 86) |
| Example 161 | (2,4-diOCH3-C6H3-C(O)-N-(4-methylpiperidinyl)) | 6-NHCOCH3 | 271–272° C. ethanol white powders | Free |
| Example 162 | (2,4-diOCH3-C6H3-C(O)-N-(4-methylpiperidinyl)) | 6-NH2 | | Free 87) |

-continued

| Example | Structure | 6-NO₂ | Color | Solvent | mp | Form |
|---|---|---|---|---|---|---|
| Example 163 | 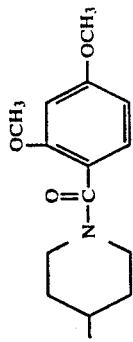 | | pale yellow powders | ethanol | 197–199° C. | Free |
| Example 164 | 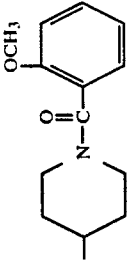 | H | white powders | dichloromethane/ n-hexane | 151.5–152.5° C. | Free |
| Example 165 | 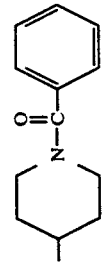 Bond between 3- and 4-positions in the carbostyril ring: double bond | H | | | 88) | Free |
| Example 166 | 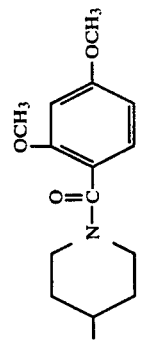 | H | | | 89) | Free |
| Example 167 | 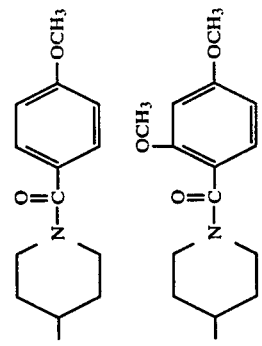 | H | | | 90) | Free |
| Example 168 | 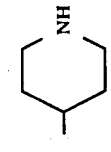 | H | | | 91) | Free |
| Example 169 | 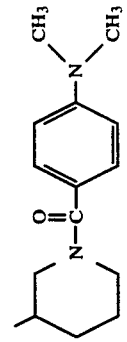 Bond between 3- and 4-positions in the carbostyril ring: single bond | H | white powders | ethanol/diethyl ether/ n-hexane | 181–183° C. | Free |

| | | | | |
|---|---|---|---|---|
| Example 170 | 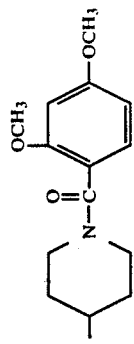 | -continued 6-F | | 92) Free |
| Example 171 | 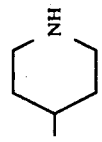 | 6-F | | 93) Free |
| Example 172 | 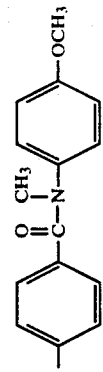 | H | | 94) Free |
| Example 173 | 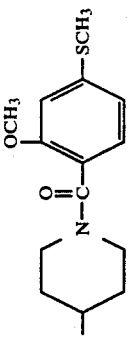 | 7-F | | 95) Free |
| Example 174 | 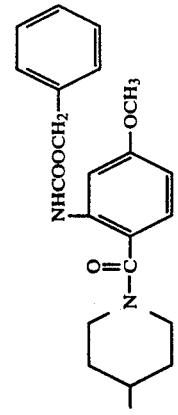 | H | | 96) Free |
| Example 175 | 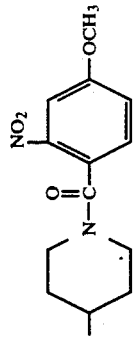 | H | colorless needles | ethanol/diethyl ether | 151–154° C. Free |
| Example 176 | 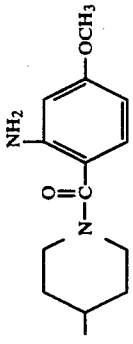 | H | colorless needles | ethanol | 169–171° C. Free |

-continued
| Example | Structure | R | mp / solvent | form | No. |
|---|---|---|---|---|---|
| Example 177 | 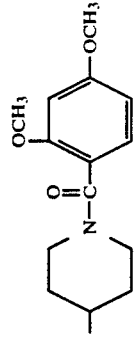 | 7-F | | white powders | 97) |
| Example 178 | 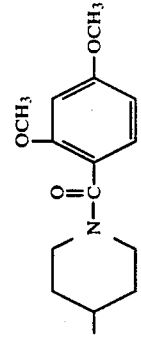 | 6-CH₃ | | | 98) |
| Example 179 | 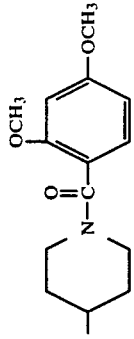 | 8-CH₃ | | | 99) |
| Example 180 | 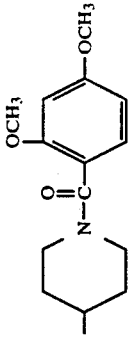 | 7-CH₃ | | | 100) |
| Example 181 | 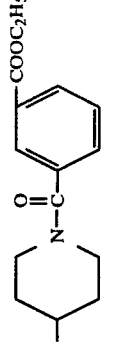 | H | | | 101) |
| Example 182 | 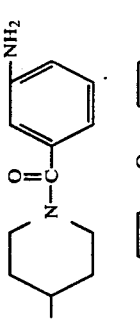 | H | ethanol/n-hexane | white powders, 183–183.5° C. | Free |
| Example 183 | 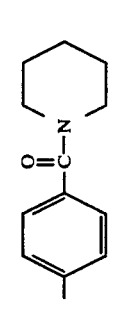 | H | ethanol/diethyl ether/n-hexane | white powders, 175–176° C. | Free |
| Example 184 | 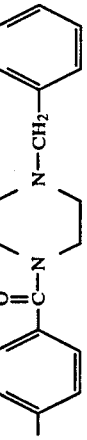 | H | | | 102) Free |

-continued
| | | | | | |
|---|---|---|---|---|---|
| Example 185 | 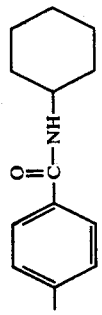 | H | white powders | ethanol/diethyl ether/ n-hexane | 291–292° C. | Free |
| Example 186 | 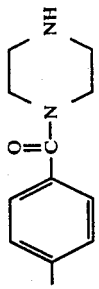 | H | white powders | ethanol/diethyl ether/ n-hexane | 215–216° C. | Free |
| Example 187 | 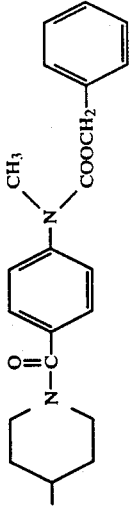 | H | | | 103) | Free |
| Example 188 | 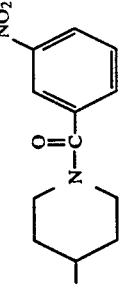 | H | | | 104) | Free |
| Example 189 | 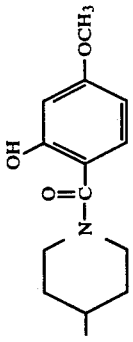 | H | white powders | dichloromethane/ n-hexane | 140.5–142° C. | Free |
| Example 190 | 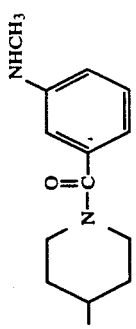 | H | white powders | ethanol/n-hexane | 164–164.5° C. | Free |
| Example 191 | 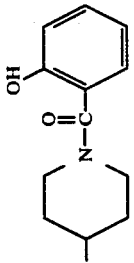 | H | colorless needles | ethanol/methanol/ diethyl ether | 156–158° C. | Free |

-continued

| | | | | | |
|---|---|---|---|---|---|
| Example 192 | 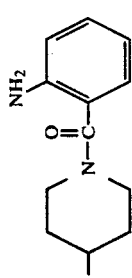 | H | colorless needles | ethanol/diethyl ether | 158–166° C. | Hydrochloride |
| Example 193 | 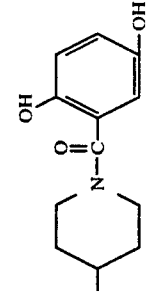 | H | colorless prisms | ethanol/methanol | 245–249° C. | Free |
| Example 194 | 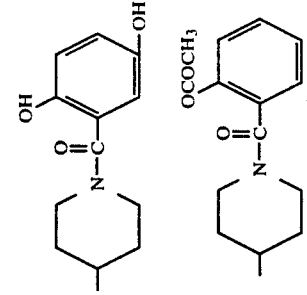 | H | colorless prisms | ethanol/diethyl ether | 159–161° C. | Free |
| Example 195 | 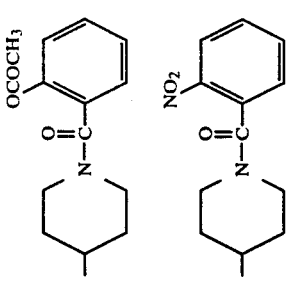 | H | pale yellow needles | methanol/chloroform/ diethyl ether | 207–209° C. | Free |
| Example 196 | 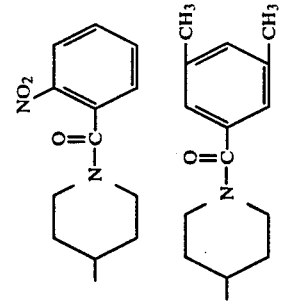 | H | colorless needles | ethanol/diethyl ether/ n-hexane | 177–180° C. | Free |
| Example 197 | 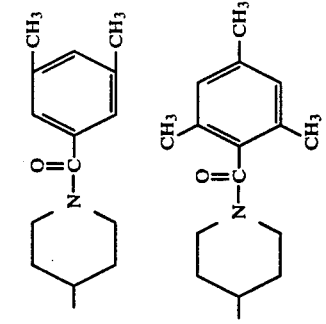 | H | colorless needles | ethyl acetate/diethyl ether/n-hexane | 145–150° C. | Free |
| Example 198 | 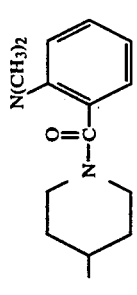 | H | colorless flakes | ethyl acetate/ethanol | 209–211° C. | Free |

-continued
| Example | Structure | | Solvent | m.p. | Form |
|---|---|---|---|---|---|
| Example 199 | 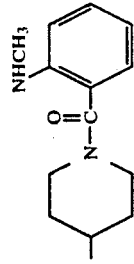 | H | | 105) | Free |
| Example 200 | 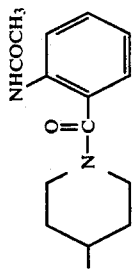 | H | ethyl acetate/ diethyl ether | 141–143° C. | Free |
| Example 201 | 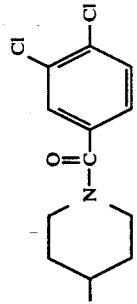 | H | | 106) | Free |
| Example 202 | 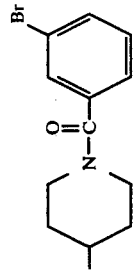 | H | ethyl acetate/diethyl ether/n-hexane | 148–150° C. | Free |
| Example 203 | 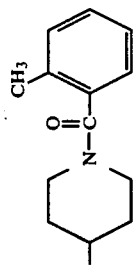 | H | ethanol/diethyl ether/n-hexane | 169–172° C. | Free |
| Example 204 | 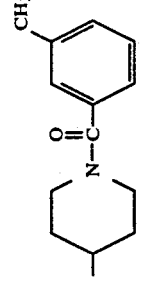 | H | ethyl acetate/diethyl ether/n-hexane | 144–146° C. | Free |
| Example 205 | 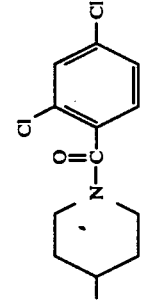 | H | | 107) | Free |

| | | | | | |
|---|---|---|---|---|---|
| Example 206 | 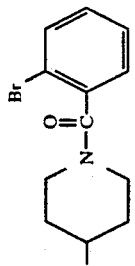 | H | colorless flakes | ethyl acetate/diethyl ether/n-hexane | 181–183° C. | Free |
| Example 207 | 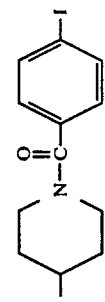 | H | colorless needles | ethyl acetate/diethyl ether/n-hexane | 141–144° C. | Free |
| Example 208 | 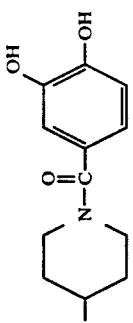 | H | colorless prisms | ethanol/diethyl ether | 234–236° C. | Free |
| Example 209 | 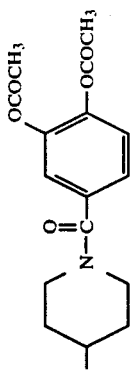 | H | colorless needles | ethyl acetate/diethyl ether | 117–119° C. | Free |
| Example 210 | 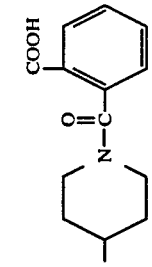 | H | white powders | ethanol/n-hexane | 116–120° C. | Free |
| Example 211 | 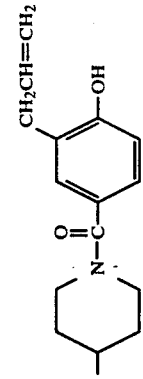 | H | white powders | dichloromethane/n-hexane | 87–90° C. | Free |
| Example 212 | 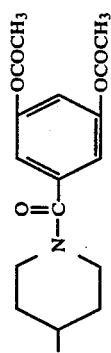 | H | white powders | dichloromethane/n-hexane | 171.5–172.5° C. | Free |

-continued

| | | | | | |
|---|---|---|---|---|---|
| Example 213 | 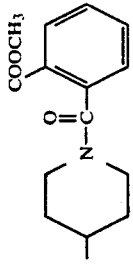 | H | white powders | dichloromethane/ n-hexane | 159.5–160° C. | Free |
| Example 214 | 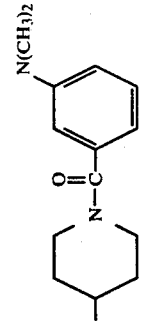 | H | white powders | dichloromethane/ n-hexane | 168–169° C. | Free |
| Example 215 | 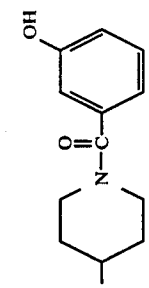 | H | white powders | dichloromethane/ n-hexane | 188–189° C. | Free |
| Example 216 | 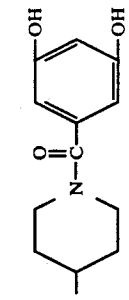 | H | white powders | dichloromethane/ n-hexane | 295° C. (decomposition) | Free |
| Example 217 | 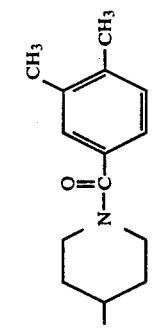 | H | white powders | ethanol/n-hexane | 131.5–132.5° C. | Free |
| Example 218 | 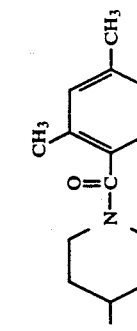 | H | white powders | dichloromethane/ n-hexane | 159–160° C. | Free |
| Example 219 | 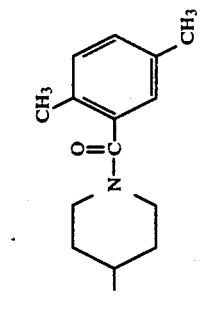 | H | white powders | dichloromethane/ n-hexane | 172–172.5° C. | Free |

-continued

| | | | | | |
|---|---|---|---|---|---|
| Example 220 | [structure: 4-methylpiperidine-N-C(=O)-C6H4-(CH2)2CH3] | H | | | 108) Free |
| Example 221 | [structure: 4-methylpiperidine-N-C(=O)-biphenyl] | H | | | 109) Free |
| Example 222 | [structure: 4-methylpiperidine-N-C(=O)-C6H3(OCH3)2 (3,5-dimethoxy)] | H | white powders | dichloromethane/n-hexane | 154–154.5° C. Free |
| Example 223 | [structure: 4-methylpiperidine-N-C(=O)-C6H4-OCH2CH3] | H | white powders | dichloromethane/n-hexane | 97–99° C. Free |
| Example 224 | [structure: piperidine-N-C(=O)-C6H4-OCH2CH=CH2] | H | | | 110) Free |
| Example 225 | [structure: 4-methylpiperidine-N-C(=O)-C6H3(CH2CH=CH2)(OCH2CH=CH2)] | H | | | 111) Free |
| Example 226 | [structure: 4-methylpiperidine-N-C(=O)-C6H4-CH3] | H | white powders | dichloromethane/n-hexane | 112–113.5° C. Free |
| Example 227 | [structure: 3-methylpiperidine-N-C(=O)-C6H3(OCH3)2] | H | | | 112) Free |

| | | | | |
|---|---|---|---|---|
| Example 228 | 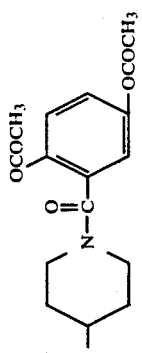 | H | colorless needles | ethyl acetate/ diethyl ether | 134–137° C. | Free (113) |
| Example 229 | 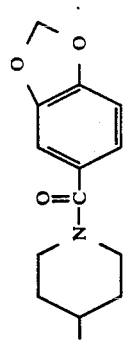 | H | | | | Free (114) |
| Example 230 | 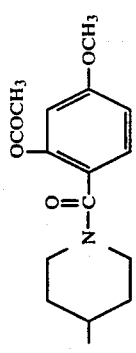 | H | | | | Free (115) |
| Example 231 | 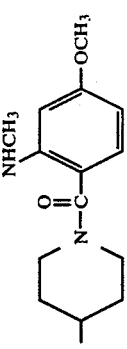 | H | | | | Free (116) |
| Example 232 | 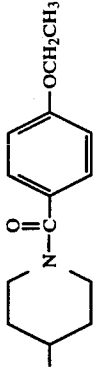 | 7-F | | | | Free |
| Example 233 | 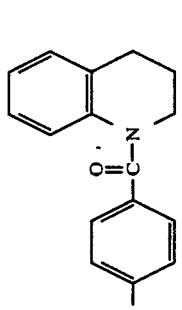 | H | white powders | ethanol/diethyl ether/ n-hexane | 162–163° C. | Free (117) |
| Example 234 | 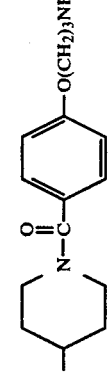 | H | | | | Free |

-continued
| | | | | | | |
|---|---|---|---|---|---|---|
| Example 235 | 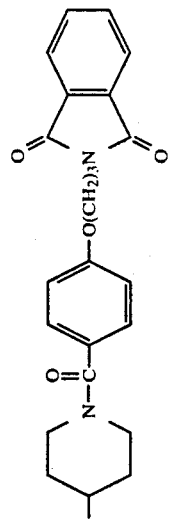 | H | | 118) | | Free |
| Example 236 | 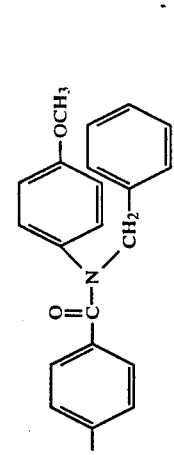 | H | | 119) | | Free |
| Example 237 | 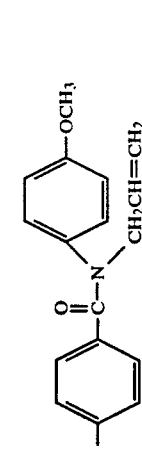 | H | | 120) | | Free |
| Example 238 | 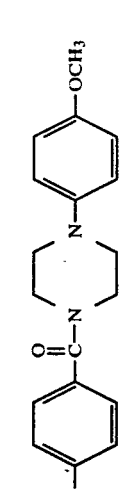 | H | white powders | ethanol/diethyl ether/n-hexane | 179–180° C. | Free |
| Example 239 | 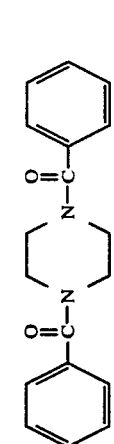 | H | white powders | ethanol/diethyl ether/n-hexane | 188–189° C. | Free |
| Example 240 | 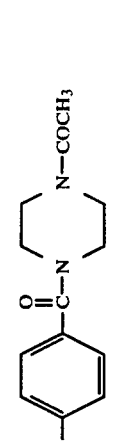 | H | white powders | ethanol/diethyl ether/n-hexane | 217–218° C. | Free |
| Example 241 | 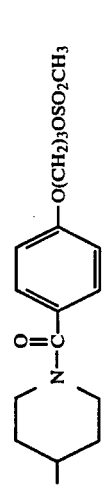 | H | | 121) | | Free |

-continued

| | | | | | |
|---|---|---|---|---|---|
| Example 242 | [structure: 4-methylpiperidine-N-C(=O)-phenyl-O(CH₂)₃N(CH₃)-CH₃] | H | 122) | | Hydrochloride |
| Example 243 | [structure: 4-methylpiperidine-N-C(=O)-phenyl-O(CH₂)₃N(CH₂)₂CH₃-CH₃] | H | 123) | | Free |
| Example 244 | [structure: adamantyl-NH-C(=O)-p-tolyl] | H | white powders | ethanol/diethyl ether/ n-hexane 279–280° C. | Free |
| Example 245 | [structure: p-tolyl-C(=O)-N(CH₂CH₃)-phenyl-OCH₃] | H | white powders | ethanol/diethyl ether/ n-hexane 155–156° C. | Free |
| Example 246 | [structure: 4-methylpiperidine-N-C(=O)-phenyl-O(CH₂)₃N(CH₃)-C(=O)phenyl] | H | 124) | | Free |
| Example 247 | [structure: 4-methylpiperidine-N-C(=O)-phenyl-O(CH₂)₃OCH₂-CH=CH₂] | H | 125) | | Free |
| Example 248 | [structure: 4-methylpiperidine-N-C(=O)-phenyl with NH(CH₂)₂CH₃ and OCH₃ substituents] | H | 126) | | Free |

| | | |
|---|---|---|
| Example 249 | 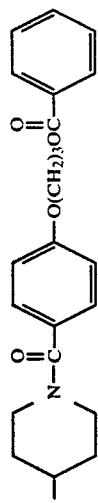 | H | 127) Free |
| Example 250 | 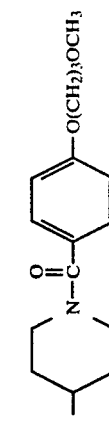 | H | 128) Free |
| Example 251 | 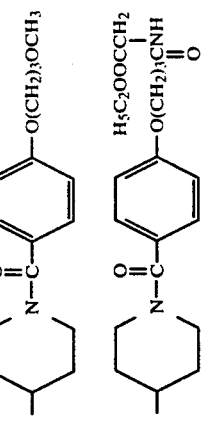 | H | 129) Free |
| Example 252 | 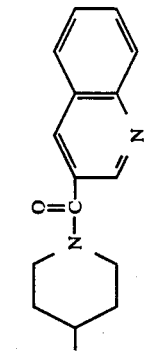 | H | 130) Free |
| Example 253 | 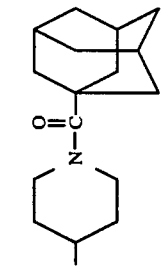 | H | 131) Free |
| Example 254 | 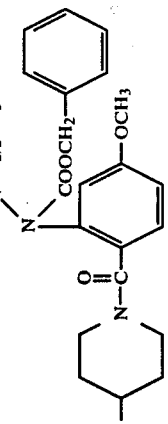 | H | 132) colorless needles ethanol/diethyl ether/ n-hexane 146–148° C. Free |
| Example 255 | 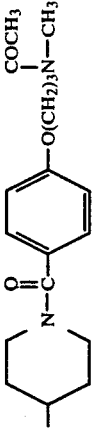 | H | 132) Free |
| Example 256 | 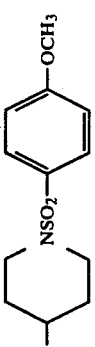 | H | 133) Free |

-continued

| Example | Structure | | | Notes |
|---|---|---|---|---|
| Example 257 | [quinoline-2-carbonyl-(4-methylpiperidine)] | H | (134) | Free |
| Example 258 | [2-oxo-1,2-dihydroquinolin-4-yl-carbonyl-(4-methylpiperidine)] | H | (135) | Free |
| Example 259 | [(CH₃)₃CCH₂C(O)–N(4-methylpiperidine)] | H | (136) | Free |
| Example 260 | [4-(O(CH₂)₃COOH)-C₆H₄-C(O)-N(4-methylpiperidine)] | H | 90–91° C. ethanol/water white powders | Free |
| Example 261 | [4-(OCH₂CONH-CH(CH₂OOCC₂H₅))-C₆H₄-C(O)-N(4-methylpiperidine)] | H | (137) | Free |
| Example 262 | [4-(OCH₂CONH-C₆H₅)-C₆H₄-C(O)-N(4-methylpiperidine)] | H | (138) | Free |
| Example 263 | [4-(OCH₂CON(CH₃)₂)-C₆H₄-C(O)-N(4-methylpiperidine)] | H | (139) | Free |
| Example 264 | [4-(O(CH₂)₃COOC₂H₅)-C₆H₄-C(O)-N(4-methylpiperidine)] | H | (140) | Free |

-continued
| | | | | | | |
|---|---|---|---|---|---|---|
| Example 265 |  | 7-N(CH₃)₂ | | | 141) | Free |
| Example 266 |  | 4-CH₃ | | | 142) | Free |
| Example 267 | 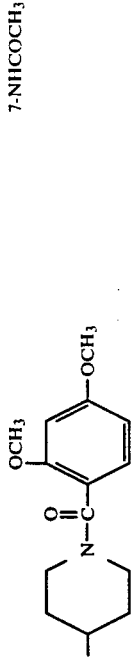 | 7-NHCOCH₃ | white powders | ethanol | 176-178° C. 143) | Free |
| Example 268 | 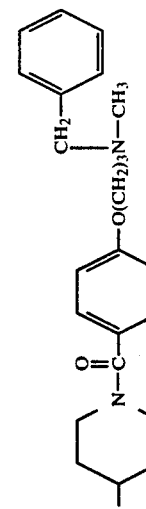 | H | colorless needles | ethanol/acetone/diethyl ether | 222-226° C. | Hydrochloride |
| Example 269 |  | H | | | 143) | Free |
| Example 270 |  | H | colorless needles | ethanol/acetone/diethyl ether | 89-93° C. | Hydrochloride |
| Example 271 | 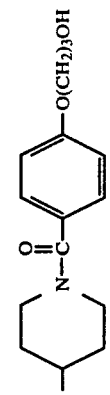 | H | | | 144) | Free |

-continued
| | | | | |
|---|---|---|---|---|
| Example 272 | 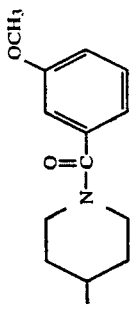 | H | white powders | dichloromethane/n-hexane | 90–92° C. | Free |
| Example 273 | 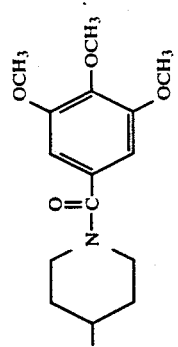 | H | white powders | dichloromethane/n-hexane | 139–139.5° C. | Free |
| Example 274 | 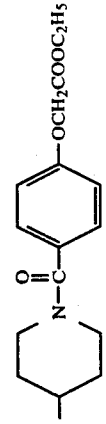 | H | | | 145) | Free |
| Example 275 | 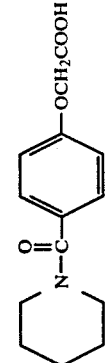 | H | white powders | ethanol | 101.5–103.5° C. | Free |
| Example 276 | 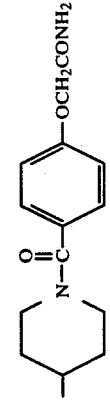 | H | white powders | ethanol | 115–117° C. | Free |
| Example 277 | 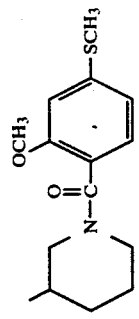 | H | | | 146) | Free |
| Example 278 | 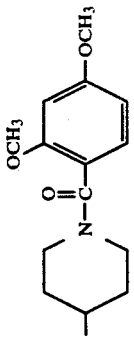 | 6-OCH$_3$ | | | 147) | Free |

-continued
| Example | Structure | R | Description | Solvent | mp | Form |
|---|---|---|---|---|---|---|
| Example 279 | 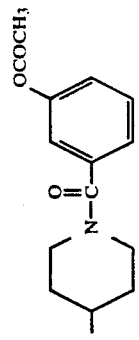 | H | | | 148) | Free |
| Example 280 | 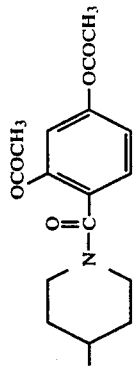 | H | | | 149) | Free |
| Example 281 | 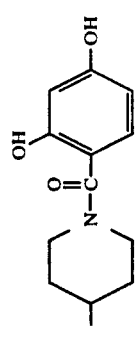 | H | | | 150) | Free |
| Example 282 | 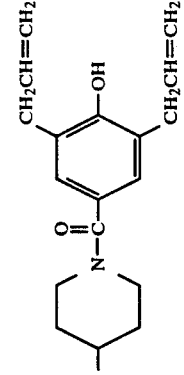 | H | white powders | dichloromethane/n-hexane | 158-160° C. | Free |
| Example 283 | 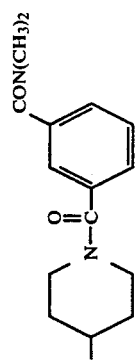 | H | colorless needles | ethyl acetate/diethyl ether | 171-174° C. | Free |
| Example 284 | 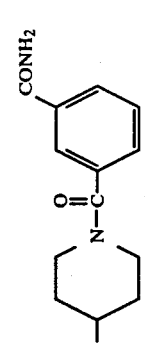 | H | | | 151) | Free |
| Example 285 | 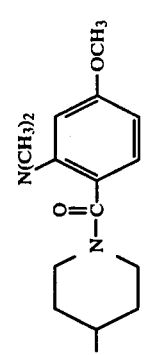 | H | colorless flakes | ethanol | 138-140° C. | Free |

-continued
| | | | | | |
|---|---|---|---|---|---|
| Example 286 | 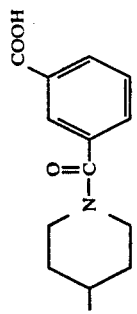 | H | colorless needles | dichloromethane/ethanol | 237–240° C. | Free |
| Example 287 | 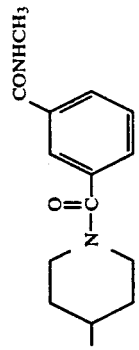 | H | | | 152) | Free |
| Example 288 | 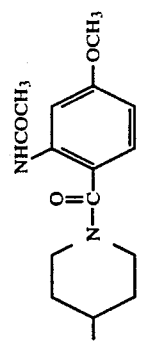 | H | colorless flakes | methanol/water | 169–171° C. | Free |
| Example 289 | 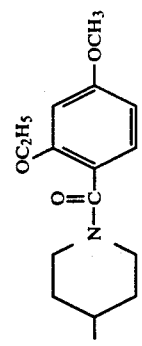 | H | | | 153) | Free |
| Example 290 | 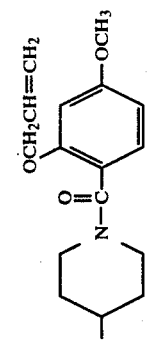 | H | | | 154) | Free |
| Example 291 | 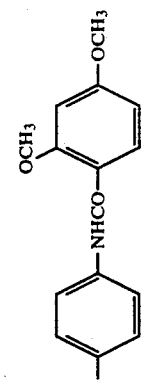 | H | white powders | ethanol/diethyl ether/n-hexane | 226–227° C. | Free |
| Example 292 | 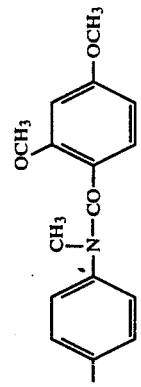 | H | | | 155) | Free |

-continued
| | | | | |
|---|---|---|---|---|
| Example 293 | 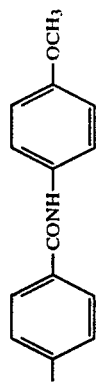 | H | white powders ethanol/diethyl ether/ n-hexane | 254–255° C. | Free |
| Example 294 | 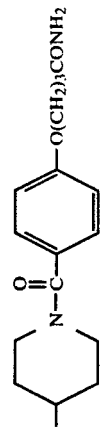 | H | | 156) | Free |
| Example 295 | 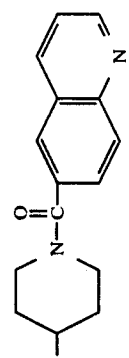 | H | | 157) | Free |
| Example 296 | 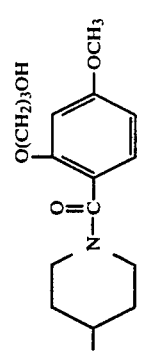 | H | | 158) | Free |
| Example 297 | 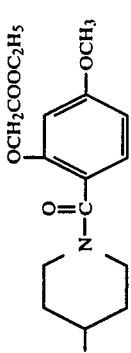 | H | | 159) | Free |
| Example 298 | 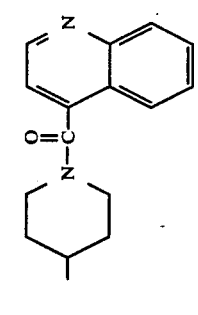 | H | | 160) | Free |
| Example 299 | 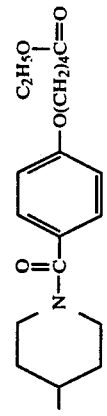 | H | | 161) | Free |

-continued

| | Structure (Ar group) | R | Crystal form | Solvent | m.p. | Salt |
|---|---|---|---|---|---|---|
| Example 300 | 4-(O(CH₂)₄CONH₂)-C₆H₄-C(=O)-N(4-methylpiperidine) | H | colorless prisms | ethanol/n-hexane | 156–157° C. | Free |
| Example 301 | 4-(O(CH₂)₄COOH)-C₆H₄-C(=O)-N(4-methylpiperidine) | H | colorless needles | ethanol/water | 175–176° C. | Free |
| Example 302 | 3-CH₃O,4-(O(CH₂)₅C(=O)-)-C₆H₃-C(=O)-N(4-methylpiperidine) | H | | | 162) | Free |
| Example 303 | 2-OCH₂COOH,4-OCH₃-C₆H₃-C(=O)-N(4-methylpiperidine) | H | white powders | ethanol/water | 229.5–231° C. | Free |
| Example 304 | 4-(O(CH₂)₁₀COOH)-C₆H₄-C(=O)-N(4-methylpiperidine) | H | white powders | ethanol/water | 132–133° C. | Free |
| Example 305 | 4-(O(CH₂)₄CONH-CH₂CONH₂)-C₆H₄-C(=O)-N(4-methylpiperidine) | H | | | 163) | Free |
| Example 306 | 4-(O(CH₂)₄CONH-CH₂COOC₂H₅)-C₆H₄-C(=O)-N(4-methylpiperidine) | H | | | 164) | Free |
| Example 307 | 4-(O(CH₂)₅CONH₂)-C₆H₄-C(=O)-N(4-methylpiperidine) | H | | | 165) | Free |
| Example 308 | 4-(O(CH₂)₅COOH)-C₆H₄-C(=O)-N(4-methylpiperidine) | H | colorless needles | ethanol/water | 146–148° C. | Free |

| | | | | | |
|---|---|---|---|---|---|
| Example 309 | 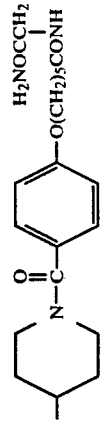 | H | | 166) | Free |
| Example 310 | 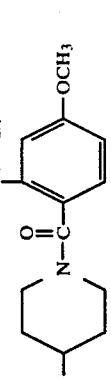 | H | white powders | 179.5-181.5° C. ethanol/water | Free |
| Example 311 | 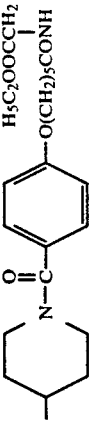 | H | | 166A) | Free |

| | | | | |
|---|---|---|---|---|
| Example 312 | 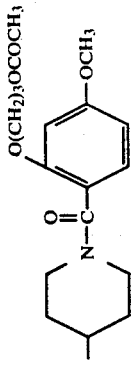 | H | | 167) Free |
| Example 313 | 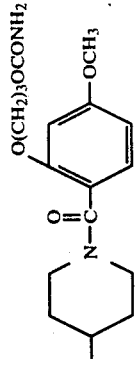 | H | | 168) Free |
| Example 314 | 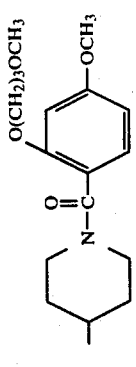 | H | | 169) Free |
| Example 315 | 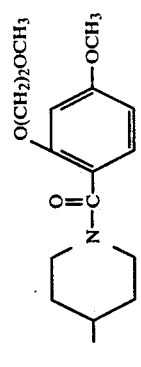 | H | | 170) Free |
| Example 316 | 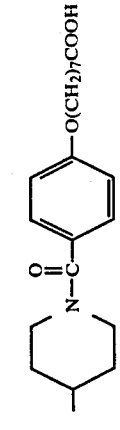 | H | colorless needles ethanol/water | 110–112° C. Free |
| Example 317 | 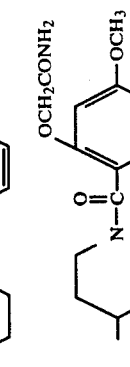 | H | white powders ethanol/n-hexane | 175.5–176.5° C. Free |
| Example 318 | 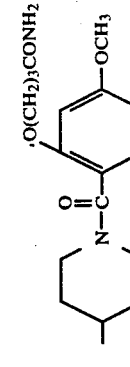 | H | | 171) Free |
| Example 319 | 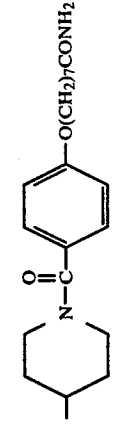 | H | | 172) Free |

| | | | |
|---|---|---|---|
| Example 320 | [structure: 4-methylpiperidine-N-C(=O)-phenyl with O(CH₂)₃COOC₂H₅ and OCH₃] | H | 173) Free |
| Example 321 | [structure: 4-methylpiperidine-N-C(=O)-phenyl-O(CH₂)₇CONH-CH₂-CONH₂ (H₂NOCCH₂)] | H | 174) Free |
| Example 322 | [structure: 4-methylpiperidine-N-C(=O)-phenyl-O(CH₂)₃CONH-CH(CH₃)-COOC₂H₅ (H₅C₂OOC)] | H | 175) Free |
| Example 323 | [structure: 4-methylpiperidine-N-C(=O)-phenyl-O(CH₂)₇COOCH₃] | H | 176) Free |
| Example 324 | [structure: 4-methylpiperidine-N-C(=O)-phenyl with OCH₂CH₂OH and OCH₃] | H | 177) Free |
| Example 325 | [structure: 4-methylpiperidine-N-C(=O)-phenyl with OCH₂OCOCH₃ and OCH₃] | H | 178) Free |
| Example 326 | [structure: 4-methylpiperidine-N-C(=O)-phenyl-O(CH₂)₃CONH-CH₂-CONH₂ (H₂NOCCH₂)] | H | 179) Free |

-continued

| | | | | | |
|---|---|---|---|---|---|
| Example 327 | 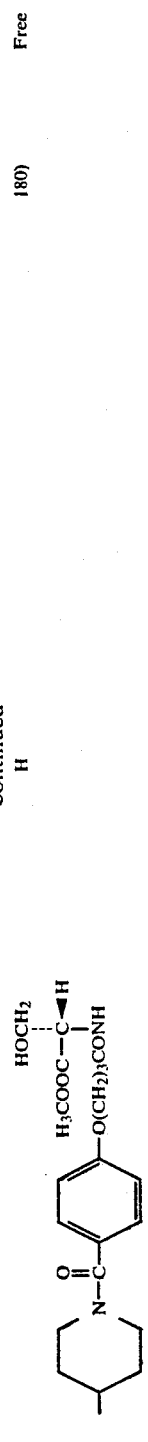 | H | | | Free |
| Example 328 |  | H | | 180) | Free |
| Example 329 |  | H | white powders | diethyl ether/n-hexane | 181) 101–104° C. | Free |
| Example 330 | 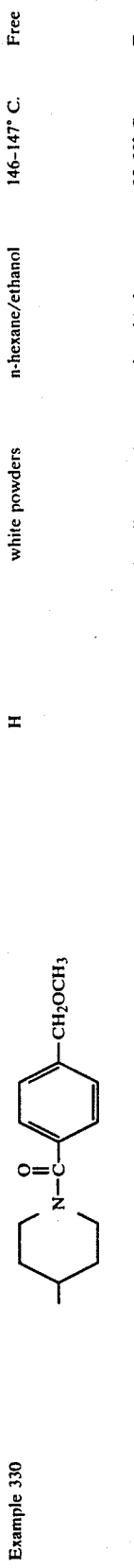 | H | white powders | n-hexane/ethanol | 146–147° C. | Free |
| Example 331 |  | H | pale yellow powders | ethanol/n-hexane | 95–98° C. | Free |
| Example 332 | 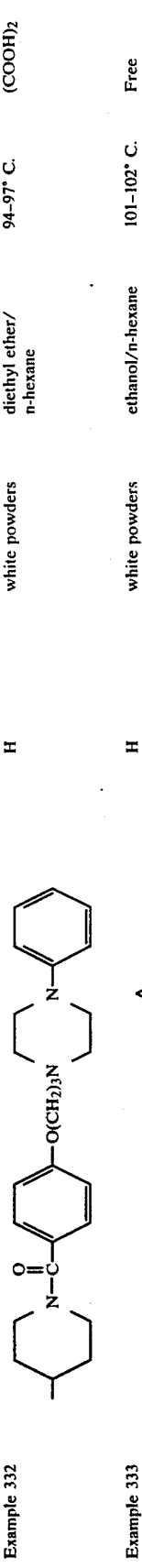 | H | white powders | diethyl ether/n-hexane | 94–97° C. | (COOH)$_2$ |
| Example 333 |  | H | white powders | ethanol/n-hexane | 101–102° C. | Free |
| Example 334 |  | H | white powders | diethyl ether | 72–76° C. | $\begin{array}{c} CH_2COOH \\ \mid \\ OH-C-COOH \\ \mid \\ CH_2COOH \end{array}$ |

-continued

| | | | | | |
|---|---|---|---|---|---|
| Example 335 | 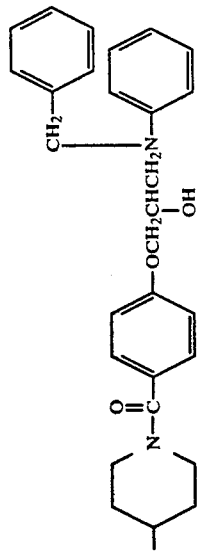 | H | white powders | ethanol/n-hexane | 87–89° C. | Free |
| Example 336 | 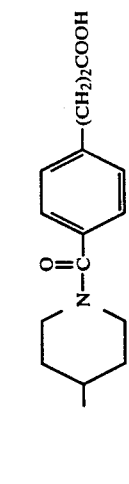 | H | white powders | diethyl ether/n-hexane | 70–72° C. | Free |
| Example 337 | 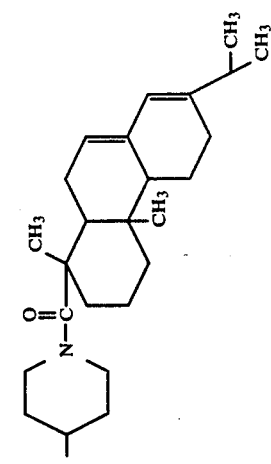 | H | white powders | ethanol/n-hexane | 94–96° C. | Free |
| Example 338 | 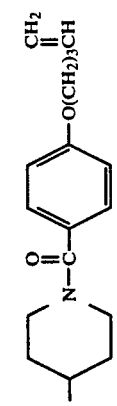 | H | white powders | ethanol/n-hexane | 108–109° C. | Free |
| Example 339 | 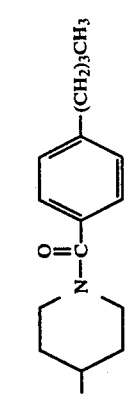 | H | white powders | n-hexane/ethanol | 103–104° C. | Free |
| Example 340 | 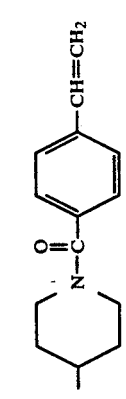 | H | white powders | ethanol/n-hexane | 114–116° C. | Free |
| Example 341 | 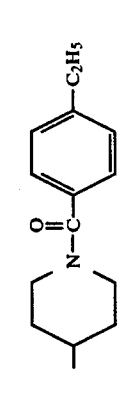 | H | white powders | ethanol/n-hexane | 133–134° C. | Free |

-continued
| | | | | | |
|---|---|---|---|---|---|
| Example 342 | 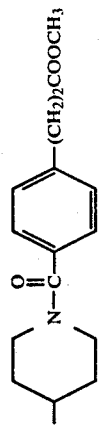 | H | white powders | n-hexane | 85–86° C. | Free |
| Example 343 | 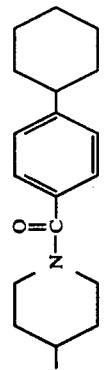 | H | white powders | n-hexane | 121–122° C. | Free |
| Example 344 | 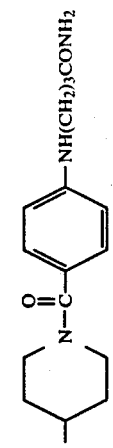 | H | white powders | ethanol/n-hexane | 71–73° C. | Free |
| Example 345 | 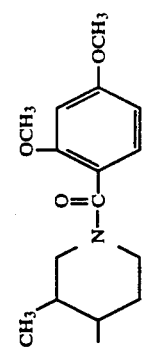 | H | | | 182) | Free |
| Example 346 | 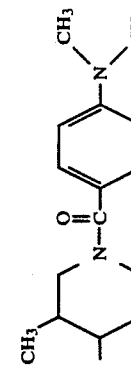 | H | | | 183) | Free |
| Example 347 | 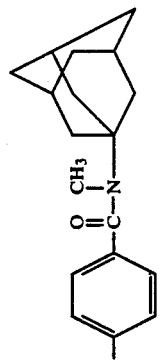 | H | | | 184) | Free |
| Example 348 | 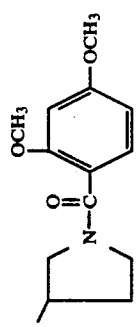 | H | | | 185) | Free |

-continued
| Example | Structure | R | # | Salt |
|---|---|---|---|---|
| Example 349 | 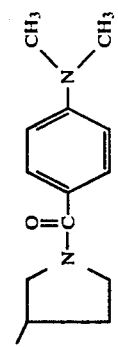 | H | 186) | Free |
| Example 350 | 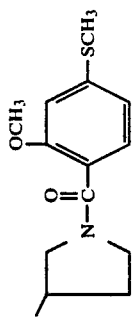 | H | 187) | Free |
| Example 351 | 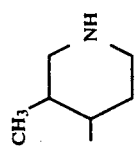 | H | 188) | Free |
| Example 352 | 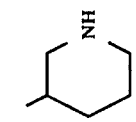 | H | 189) | Free |
| Example 353 | 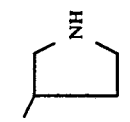 | H | 190) | Free |
| Example 354 | 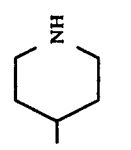 | 6-OCH$_3$ | 191) | Free |
| Example 355 | 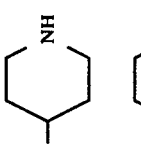 | 6-CH$_3$ | 192) | Free |
| Example 356 | 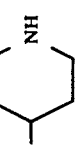 | 7-CH$_3$ | 193) | Free |

-continued
| | | | | |
|---|---|---|---|---|
| Example 357 | 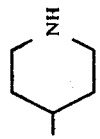 | 7-F | (194) | Free |
| Example 358 | 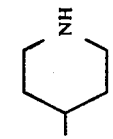 | 8-CH₃ | (195) | Free |
| Example 359 | 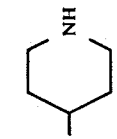 | 7-NHCOCH₃ | (196) | Free |
| Example 360 | 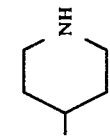 | 4-CH₃ | (197) | Free |
| Example 361 | 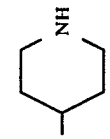 | 7-N(CH₃)₂ | (198) | Free |
| Example 362 | 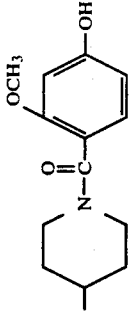 | H | (199) | Free |
| Example 363 | 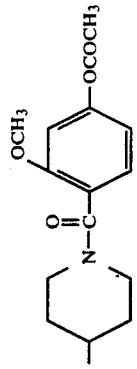 | H | (200) | Free |
| Example 364 | 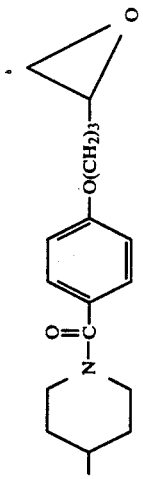 | H | (201) | Free |

-continued

| Example | Structure | R | Crystal form | Solvent | mp | Form |
|---|---|---|---|---|---|---|
| Example 365 | piperidine-N-C(=O)-C6H4-O(CH2)5COOH | H | colorless needles | ethanol/water | 146–148° C. | Free |
| Example 366 | piperidine-N-C(=O)-C6H4-N(CH3)2 | H | white powders | ethanol/diethyl ether/n-hexane | 181–183° C. | Free |
| Example 367 | piperidine-N-C(=O)-C6H4-O(CH2)4NH-SO2CH3 | H | colorless prisms | ethanol | 99–101° C. | Free |
| Example 368 | piperidine-N-C(=O)-C6H3(OCH3)-SOCH3 | H | white powders | ethanol/n-hexane | 83–86° C. | Free |
| Example 369 | piperidine-N-C(=O)-C6H3(OCH3)-OCH3 | 7-C2H5 | | | 202) | Free |
| Example 370 | piperidine-N-C(=O)-C6H3(OCH3)-OCH3 | 7-OCH3 | | | 203) | Free |
| Example 371 | piperidine-N-C(=O)-C6H3(OCH3)-SCH3 | 7-F | | | 204) | Free |
| Example 372 | piperidine-N-C(=O)-C6H3(OCH3)-OC2H5 | 7-F | white powders | ethanol/water | 159–161° C. | Free |

-continued
| | | | | |
|---|---|---|---|---|
| Example 373 | 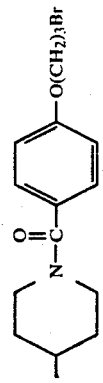 | H | | 205) | Free |
| Example 374 | 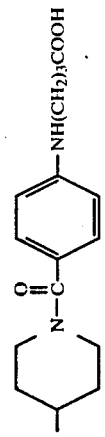 | H | | 206) | Free |
| Example 375 | 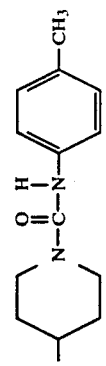 | H | colorless flakes | diethyl ether | 175–176° C. | Free |
| Example 376 | 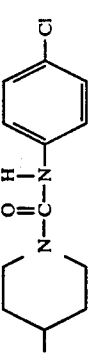 | H | white powders | diethyl ether | 199–200° C. | Free |
| Example 377 | 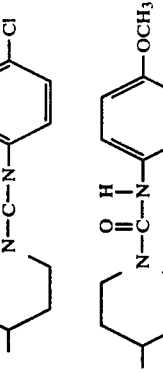 | H | white powders | diethyl ether | 167–168° C. | Free |
| Example 378 | 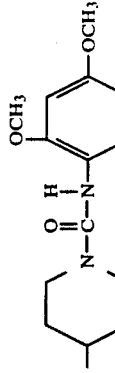 | H | white powders | diethyl ether/n-hexane | 136–137° C. | Free |
| Example 379 | 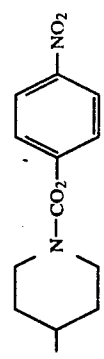 | H | white powders | diethyl ether/n-hexane | 154–155° C. | Free |
| Example 380 | 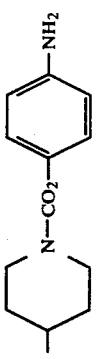 | H | white powders | diethyl ether/n-hexane | 167–168° C. | Free |

-continued
| | | | | | |
|---|---|---|---|---|---|
| Example 381 | 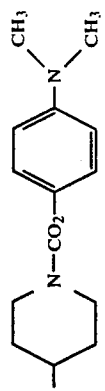 | H | white powders | diethyl ether/n-hexane | 189–191° C. Free |
| Example 382 | 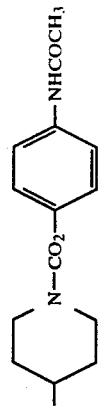 | H | white powders | diethyl ether/n-hexane | 215–216° C. Free |
| Example 383 | 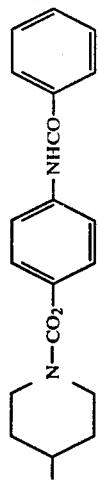 | H | white powders | diethyl ether/n-hexane | 199–200° C. Free |
| Example 383A | 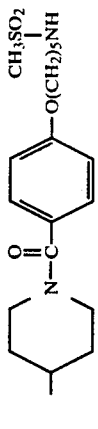 | H | | | 207) Free |
| Example 383B | 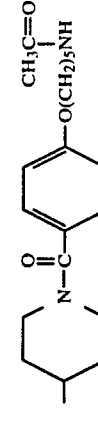 | H | colorless prisms | ethanol/ethyl acetate | 141–142° C. 208) Free |
| Example 383C | 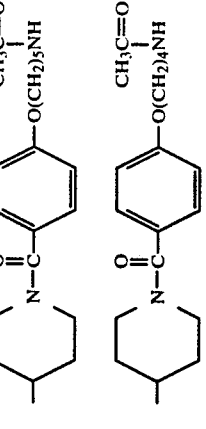 | H | | | 209) Free |

TABLE 2

| No. | NMR (CDCl$_3$) δ value |
|---|---|
| 1 | 1.55-1.82 (2H, m), 2.08-2.87 (7H, m), 2.95-3.17 (1H, m), 3.79 (2H, s), 3.90-4.08 (1H, m), 4.35-4.58 (1H, m), 4.73-4.92 (1H, m), 6.86-7.48 (9H, m) |
| 2 | 1.65-1.84 (2H, m), 2.25-2.88 (7H, m), 3.05-3.24 (1H, m), 3.97 (2H, s), 4.00-4.13 (1H, m), 4.38-4.58 (1H, m), 4.73-4.92 (1H, m), 6.92-7.28 (7H, m) |
| 3 | 1.72-2.01 (2H, m), 2.53-3.01 (7H, m), 3.13-3.33 (1H, m), 4.09-4.23 (1H, m), 4.43-4.62 (1H, m), 4.87-5.04 (1H, m), 6.97-7.33 (4H, m), 8.55 (1H, dd, J=2.5, 1.4 Hz) 8.64 (1H, d, J=2.5 Hz), 8.99 (1H, d, J=1.4 Hz) |
| 4 | 0.98 (3H, t, J=7.3 Hz), 1.40-1.93 (6H, m), 2.50-3.15 (8H, m), 3.99 (2H, t, J=6.4 Hz), 3.13-5.10 (3H, m), 6.83-7.48 (4H, m) |
| 5 | 1.46-1.86 (8H, m), 2.33-3.04 (8H, m), 3.95-5.10 (8H, m), 6.02-6.20 (1H, m), 6.96-7.40 (9H, m) |
| 6 | 1.65-1.93 (2H, m), 2.50 (3H, s), 2.52-3.24 (8H, m), 3.56-5.25 (3H, m), 6.95-7.46 (8H, m) |
| 7 | 1.65-1.96 (2H, m), 2.18 (3H, s), 2.46-3.18 (8H, m), 3.72-5.13 (3H, m), 6.95-7.32 (4H, m), 7.32-7.56 (4H, m), 7.95 (1H, brs) |
| 8 | 1.20-3.33 (20H, m), 3.85-5.85 (8H, m), 6.96-7.29 (4H, m) |
| 9 | 1.12-1.93 (2H, m), 2.52-3.30 (8H, m), 4.00 (3H, s), 3.73-5.15 (3H, m) 7.00-7.34 (5H, m), 7.72 (1H, dd, j=8.6, 2.1 Hz), 7.99 (1H, d, j=2.1 Hz) |
| 10 | 1.63-2.04 (2H, m), 2.52-3.24 (8H, m), 2.63 (3H, s), 3.71-3.89 (1H, m), 4.26-4.44 (1H, m), 4.80-5.04 (1H, m). 7.00-7.33 (4H, m), 7.56 (2H, d, J=8.0 Hz), 8.01 (2H, d, J=8.0 Hz) |
| 11 | 1.33 (3H, t, J=7.3 Hz), 1.68-2.06 (2H, m), 2.50-3.30 (8H, m), 3.13 (2H, q, J=7.3 Hz), 3.72-5.13 (3H, m), 6.97-7.34 (6H, m), 7.44 (2H, d, J=8.5 Hz), 7.58 (2H, d, J=8.5 Hz) |
| 12 | 1.72-1.98 (2H, m), 2.54-3.20 (8H, m), 3.84-5.08 (3H, m), 5.13 (2H, s), 6.98-7.52 (13H, m) |
| 13 | 1.58-1.73 (1H, m), 1.78-1.96 (1H, m), 2.50 (3H, s), 2.42-3.26 (8H, m), 3.56-3.73 (1H, m), 3.28-3.97 (3H, m), 4.20-4.73 (1H, m), 4.88-5.05 (1H, m), 6.78-6.92 (2H, m), 6.98-7.36 (4H, m) |
| 14 | 1.72-1.94 (2H, m), 2.48-3.26 (10H, m), 2.66 (6H, s), 2.77-5.28 (5H, m), 6.94-7.45 (6H, m) |
| 15 | 1.03 (6H, d, J=6.7 Hz), 1.70-1.90 92H, m), 1.95-2.22 (1H, m), 2.47-3.18 (8H, m), 3.74 (2H, d, J=6.5 Hz), 3.66-5.10 93H, m), 6.84-7.49 (8H, m) |
| 16 | 1.47 (9H, s), 1.68-1.97 (2H, m), 2.50-3.22 (8H, m), 3.28 (3H, s), 3.66-5.10 (3H, m), 6.96-7.52 (8H, m) |
| 17 | 1.45 (9H, s), 1.55 (3H, s), 1.69 (3H, s), 1.60-1.94 (2H, m), 2.50-3.23 (8H, m), 3.72-5.14 (3H, m), 4.22 (2H, d, J=6.4 Hz), 5.20-5.33 (1H, m), 6.98-7.44 (8H, m) |
| 18 | 1.68-1.93 (2H, m), 2.50-3.34 (16H, m), 3.90-4.97 (3H, m), 6.89 (2H, d, J=8.8 Hz), 6.98-7.31 (4H, m), 7.41 (2H, d, j=8.8 Hz), |
| 19 | 1.56-1.79 (2H, m), 1.75 (3H, s), 1.80 (3H, s), 2.47-3.14 (8H, m), 3.93-5.05 (3H, m), 4.53 (2H, d, J=6.8 Hz), 5.40-5.57 (1H, m), 6.83-7.53 (8H m) |
| 20 | 1.70-1.90 (2H, m),2.36 (3H, s), 2.43-3.12 (12H, m), 3.22-3.35 (4H, m), 3.92-4.86 (3H, m), 6.89 (2H, d, J=8.7 Hz), 6.96-7.32 (4H, m), 7.41 (2H, d, J=8.8 Hz) |
| 21 | 1.25 (6H, d, J=6.9 Hz), 1.63-2.00 (2H, m), 2.49-3.27 (9H, m), 3.70-5.20 (3H, m), 6.97-7.47 (8H, m) |
| 22 | 1.68-2.07 (2H, m), 2.50-3.30 (8H, m), 3.70-3.93 (1H, m), 4.28-4.45 (1H, m), 4.83-4.58 (1H, m), 7.02-7.33 (4H, m), 7.62-7.69 (2H, m), 7.93-8.01 (2H, m), 10.08 (1H, s) |
| 23 | 1.72-2.29 (6H. m), 2.39-2.92 (7H, m), 3.10-3.32 91H, m), 3.35-3.65 (2H, m), 3.82-4.25 (2H, m), 4.52-4.90 (2H, m), 6.39-7.35 (5H, m) |
| 24 | 1.72-1.92 (2H, m), 2.52-3.12 (8H, m), 3.72-3.88 (2H, m), 4.07 (1H, brs), 4.15-4.76 (3H, m), 5.14-5.35 (2H, m), 5.83-6.04 (1H, m), 6.56-6.62 (2H, m), 6.98-7.37 (6H, m) |
| 25 | 1.72-1.90 (2H, m), 2.52-3.10 (8H, m), 2.99 (3H, s), 3.93-4.02 (2H, m), 4.23-4.68 (3H, m), 5.08-5.21 (2H, m), 5.72-5.94 (1H, m), 6.61-6.75 (2H, m), 6.96-7.32 (4H, m), 7.35-7.46 (2H, m) |
| 26 | 1.63-2.05 (2H, m), 2.52-3.23 (8H, m), 3.18 (3H, s), 3.59-5.18 (3H, m), 6.98-7.42 (6H, m), 7.52-7.62 (2H, m) |
| 27 | 1.65-1.97 (2H, m), 2.48-3.22 (8H, m), 3.73-5.15 (3H, m), 5.20 (2H, s), 6.98-7.45 (13H, m) |
| 28 | 1.61-1.95 (2H, m), 2.44-3.22 (8H, m), 3.33 (3H, s), 3.59-3.74 (1H, m), 3.75-3.92 (3H, m), 4.29-4.72 (1H, m), 4.89-5.08 (1H, m), 5.18 (2H, s), 6.80-7.42 (12H, m) |
| 29 | 1.56-1.95 (2H, m), 2.45-3.28 (8H, m), 2.85 (3H, s),2.63-4.03 (5H, m), 4.32-5.12 (2H, m), 6.10 (1H, d J=2.0 Hz), 6.20 (1H, dd, J=8.2, 2.0 Hz), 6.95-7.31 (4H, m) |
| 30 | 0.77-1.98 (23H, m), 2.28-3.22 (10H, m), 3.90-4.08 (1H, m), 4.32-4.53 (1H, m). 4.73-4.94 (1H, m), 6.93-7.33 (4H, m) |
| 31 | 1.33 (9H, s), 1.58-2.01 (2H, m), 2.48-3.21 (8H, m), 3.77-5.11 (3H, m), 6.99-7.31 (4H, m), 7.41 (4H, s) |
| 32 | 1.68-1.96 (2H, m), 2.48-3.22 (8H, m), 2.54 (1H, s), 3.82-5.32 (3H, m), 4.72 (2H, d, J=2.4 Hz), 6.92-7.33 (6H, m), 7.38-7.52 (2H, m) |
| 33 | 1.60-1.92 (2H, m), 1.61 (3H, s), 1.68 (3H, s), 1.75 (3H, s), 1.95-2.22 (4H, m), 2.51-3.15 (8H, m), 3.88-4.93 (3H, m), 4.56 92H, d, J=6.6 Hz), 5.04-5.18 (1H, m), 5.42-5.56 (1H, m), 6.88-7.32 (6H, m), 7.38-7.48 (2H, m) |
| 34 | 1.20-2.10 (12H, m), 2.44-3.13 (8H, m), 3.78-5.08 (4H, m), 6.90 (2H, d, J=8.7 Hz), 6.97-7.32 (4H, m), 7.40 (2H, d, J=8.7 Hz) |

DMSO-d$_6$

| 35 | 1.55-1.92 (2H, m), 2.32-3.05 (7H, m), 3.12-3.62 (2H, m), 4.22-4.72 (2H, m), 6.92-7.38 (4H, m), 7.63 (2H, d, J=8.2 Hz), 7.92 (2H, d, J=8.2 Hz), 9.48 (3H, brs) Ms (m/e) = 377 (m$^+$) |

CDCl$_3$

| 36 | 0.85-1.02 (3H, m), 1.25-1.60 (6H, m), 1.70-1.92 (4H, m), 2.52-3.16 (8H, m), 3.98 (2H, t, J=6.5 Hz), 3.86-5.06 (3H, m), 6.84-6.96 (2H, m), 6.98-7.33 (4H, m), 7.38-7.50 (2H, m) |
| 37 | 0.80-0.96 (3H, m),1.18-1.55 (18H, m), 1.68-1.92 (4H, m), 2.51-3.11 (8H, m), 3.78-5.05 (3H, m), 3.97 (2H, t, J=6.5 Hz), 6.84-6.98 (2H, m), 7.00-7.32 (4H, m), 7.38-7.50 (2H, m) |
| 38 | 1.68-1.94(2H, m), 2.08-2.26 (2H, m), 2.48-3.21 (10H, m), 3.81-5.10 (3H, m), 4.11 (2H, t, J=5.7 Hz), 6.91 (2H, d, J=8.8 Hz), 6.98-8.30 (4H, m), 7.44 (2H, d, J=8.8 Hz) |
| 40 | 1.26 (3H, t, J=7.1 Hz), 1.70-2.10 (4H, m), 2.42 (2H, t, J=7.0 Hz), 2.49-3.31 (10H, m), 4.14 (2H, q, J=7.1 Hz), 3.93-4.28 (4H, m), 6.57 (2H, d, J=8.6 Hz), 6.95-7.33 (4H, m), 7.34 (2H, d, J=8.6 Hz) |
| 41 | 1.21 (3H, t, J=7.1 Hz), 1.55-1.95 (2H, m), 2.42-3.05 (10H, m), 2.94 (2H, t, J=7.3 Hz), 3.70-5.02 (5H, m), 4.14 (2H, q, J=7.1 Hz), 5.28-5.95 (1H, m), 6.90-7.25 (6H, m), 7.32 (2H, d, J=8.1 Hz) |

TABLE 2-continued

| No. | NMR (CDCl$_3$) δvalue |
|---|---|
| 42 | 1.43-1.70 (2H, m), 1.71-1.96 (2H, m), 2.09-2.35 (2H, m), 2.45-3.18 (8H, m), 3.76-5.04 (5H, m), 6.84-7.43 (8H, m), 8.42-9.13 (3H, m) |
| 43 | 1.56-1.83 (2H, m), 2.01-2.21 (2H, m), 2.43-3.11 (12H, m), 3.49-3.61 (4H, m), 3.70 (3H, s), 3.62-4.95 (7H, m), 6.71-6.90 (6H, m), 6.92-7.25 (4H, m), 7.30-7.45 (2H, m) |
| 44 | 1.63-1.86 (2H, m), 2.02-2.22 (2H, m), 2.44-3.21 (12H, m), 3.42-3.70 (4H, m), 3.68-4.97 (7H, m), 6.72-7.43 (12H, m) |
| 45 | 1.65-1.98 (2H, m), 2.49-3.22 (8H, m), 3.78 (3H, s), 3.75-5.07 (3H, m), 6.96-7.32 (5H, m), 7.43 (4H, m) |
| 46 | 1.05-1.33 (3H, m), 1.66-2.02 (2H, m), 2.30-3.26 (10H, m), 3.83-5.13 (3H, m), 5.69-5.83, 6.35-6.75 (2H, m), 7.02-7.54 (8H, m) |
| 47 | 1.42-2.16 (6H, m), 2.18-2.45 (8H, m), 2.52-3.18 (8H, m), 3.28-5.12 (7H, m), 6.90 (2H, d, J=8.6 Hz), 6.97-7.30 (4H, m), 7.42 (2H, d, J=8.6 Hz) |
| 48 | 1.48-2.14 (6H, m), 2.35-3.18 (13H, m), 3.53-5.02 (8H, m), 6.90 (2H, d, J=8.7 Hz), 6.98-7.29 (4H, m), 7.41 (2H, d, J=8.7 Hz) |
| 49 | 1.58-1.88 (2H, m), 2.03-2.25 (2H, m), 2.45-3.13 (10H, m), 3.67-5.03 (5H, m), 6.86-7.25 (4H, m), 7.35-7.68 (4H, m) |
| 50 | 1.49-1.89 (16H, m), 1.90-2.07 (2H, m), 2.48-3.12 (8H, m), 3.79-4.99 (3H, m), 4.05 (2H, t, J=7.2 Hz), 6.89 (2H, d, J=8.7 Hz), 6.97-7.31 (4H, m), 7.41 (2H, d, J=8.7 Hz) |
| 51 | 1.27 (3H, t, J=7.4 Hz), 1.68-1.92 (2H, m), 1.98-2.18 (2H, m), 2.45-3.14 (10H, m), 3.70-5.15 (3H, m), 4.10 (2H, t, J=6.1 Hz), 6.91 (2H, d, J=8.6 Hz), 6.99-7.32 (4H, m), 7.43 (2H, d, J=8.6 Hz) |
| 52 | 1.18-1.37 (3H, m), 1.50-2.02 (2H, m), 2.32-3.35 (11H, m), 4.45-4.51 (9H, m), 4.78-5.09 (1H, m), 6.39-6.60 (2H, m), 6.94-7.35 (5H, m) |
| 53 | 1.65-1.97 (2H, m), 2.49-3.10 (11H, m), 3.78 (3H, s), 3.85 (2H, d, J=6.1 Hz), 4.13-4.62 (3H, m), 6.02 (1H, t, J=6.1 Hz), 6.14 (1H, d, J=2.3 Hz), 6.30 (2H, dd, J=2.3, 8.5 Hz), 6.84-7.35 (6H, m) |
| 54 | 1.62-2.05 (2H, m), 2.48-3.28 (8H, m), 3.47 (1H, d, J=5.1 Hz), 3.75-4.94 (6H, m), 3.83 (3H, s), 6.75-7.47 (7H, m) |
| 55 | 1.64-2.06 (2H, m), 2.48-3.69 (15H, m), 3.80 (3H, m), 3.81-4.52 (3H, m), 4.79-5.09 (2H, m), 6.44-6.70 (2H, m), 6.92-7.38 (5H, m), 7.85-8.21 (1H, m) |
| 56 | 1.30 (3H, t, J=7.1 Hz), 1.71-1.92 (2H, m), 2.47-3.11 (8H, m), 3.79 (3H, s), 3.91 (2H, d, J=5.4 Hz), 4.25 (2H, q, J=7.1 Hz), 4.31-4.61 (2H, m), 5.91 (1H, t, J=5.3 Hz), 6.07 (1H, d, J=2.3 Hz), 6.26 (1H, dd, J=2.3, 8.4 Hz), 6.94-7.36 (5H, m) |
| 57 | 1.67-2.01 (6H, m), 2.47-3.14 (8H, m), 3.95-4.91 (9H, m), 6.84-7.52 (8H, m) |
| 58 | 1.54-2.00 (6H, m), 2.45-3.36 (10H, m), 3.67 (3H, s), 3.84-5.08 (4H, m), 4.00 (2H, t, J=5.9 Hz), 6.89 (2H, d, J=8.7 Hz), 6.94-7.48 (4H, m), 7.42 (2H, d, J=8.7 Hz) |
| 59 | 1.55-2.00 (6H, m), 2.45-3.48 (10H, m), 3.76-5.10 (3H, m), 3.99 (2H, t, J=5.7 Hz), 5.74-6.25 (1H, m), 6.78-7.53 (8H, m), 8.15 (1H, s) |
| 60 | 1.30 (3H, t, J=7.1 Hz), 1.67-1.90 (2H, m), 2.49-3.26 (10H, m), 3.81 (3H, s), 4.27-4.56 (3H, m), 5.33-5.49 (1H, m), 6.09-6.27 (2H, m), 6.91-7.31 (5H, m) |
| 61 | 0.97 (3H, t, J=7.5 Hz), 1.55-2.01 (4H, m), 2.09-2.35 (2H, m), 2.41-5.13 (18H, m), 6.90 (2H, d, J=8.7 Hz), 6.95-7.38 (4H, m), 7.42 (2H, d, J=8.7 Hz) |
| 62 | 1.51-2.02 (8H, m), 2.48-3.20 (10H, m), 3.72-5.08 (3H, m), 4.01 (2H, t, J=6.2 Hz), 6.80-7.55 (8H, m) |
| 63 | 1.55-2.20 (4H, m), 2.49-3.50 (10H, m), 2.96 (3H, m), 3.90-5.13 (4H, m), 4.09 (2H, t, J=5.7 Hz), 6.90 (2H, d, J=8.7 Hz), 6.95-7.38 (4H, m), 7.43 (2H, d, J=8.7 Hz) |
| 64 | 1.60-2.15 (5H, m), 2.47-3.18 (10H, m), 3.82 (2H, s), 3.95-5.11 (3H, m), 4.08 (3H, t, J=6.2 Hz), 6.89 (2H, d, J=8.5 Hz), 6.95-7.50 (9H, m), 7.42 (2H, d, J=8.5 Hz) |
| 65 | 1.59-2.20 (4H, m), 2.50-3.49 (10H, m), 2.96 (3H, s), 3.91-5.11 (4H, m), 4.09 (2H, t, J=5.7 Hz), 6.90 (2H, d, J=8.7 Hz), 6.94-7.40 (4H, m), 7.43 (2H, d, J=8.7 Hz) |
| 66 | 1.60-2.10(4H, m), 2.45-3.49 (13H, m), 3.80-5.01 (7H, m), 6.88 (2H, d, J=8.6 Hz), 6.95-7.45 (4H, m), 7.40 (2H, d, J=8.6 Hz) |
| 67 | 1.63-2.15 (4H, m), 1.99 (3H, s), 2.49-3.20 (8H, m), 3.35-3.60 (2H, m), 3.90-5.10 (3H, m), 4.06 (2H, t, J=5.9 Hz), 5.89 (1H, brs), 6.89 (2H, d, J=8.7 Hz), 6.95-7.37 (4H, m), 7.43 (2H, d, J=8.7 Hz) |
| 68 | 1.60-2.32 (4H, m), 2.41-3.27 (8H, m), 3.71-5.15 (5H, m), 4.07 (2H, t, J=6.2 Hz), 4.26 (2H, t, J=6.2 Hz), 6.96 (2H, d, J=8.6 Hz), 6.99-7.40 (4H, m), 7.43 (2H, d, J=8.6 Hz) |
| 69 | 0.86 (3H, t, J=7.3 Hz),1.35-2.04 (6H, m), 2.40 (2H, t, J=7 Hz), 2.50-3.17 (10H, m), 3.57 (2H, s),3.90-5.05 (3H, m), 4.00 (2H, t, J=6.5 Hz), 6.85 (2H, d, J=8.8 Hz), 6.94-7.38 (9H, m), 7.42 (2H, d, J=8.8 Hz) |
| 70 | 0.99-1.23 (3H, m),1.54-2.00 (2H, m), 2.35-3.40 (13H, m),3.52-3.77 (1H, m), 3.80 (3H, s), 4.15-4.52 (1H, m), 4.83-5.04 (1H, m), 6.49-6.57 (2H, m), 6.90-7.35 (4H, m) |
| 71 | 1.50-2.12 (6H, m), 2.03 (3H, m), 2.45-3.44 (10H, m), 3.88 (2H, d, J=5.1 Hz), 3.98 (2H, t, J=6.0 Hz), 4.01-5.05 (3H, m), 6.50-7.52 (10H, m) |
| 72 | 1.45-2.01 (8H, m), 2.06 (3H, s), 2.48-3.25 (8H, m), 3.70-5.12 (3H, m), 3.99 (2H, t, J=6.3 Hz), 4.10 (2H, t, J=6.3 Hz), 6.89 (2H, d, J=8.8 Hz), 6.97-7.35 (4H, m), 7.43 (2H, d, J=8.8 Hz) |
| 73 | 1.40-2.02(8H, m), 2.48-3.15 (8H, m), 3.60-5.12 (3H, m), 3.72 (2H, t, J=7.0 Hz), 3.97 (2H, t, J=6.3 Hz), 6.87 (2H, d, J=8.7 Hz), 6.92-7.32 (4H, m), 7.41 (2H, d, J=8.7 Hz), 7.61-7.93 (4H, m) |
| 74 | 1.35-2.02 (10H, m), 2.47-3.25 (10H, m), 3.71-5.16 (3H, m), 3.99 (2H, t, J=6.4 Hz), 6.89 (2H, d, J=8.7 Hz), 6.93-7.35 (4H, m), 7.42 (2H, d, J=8.7 Hz) |
| 75 | 1.01-5.60 (20H, m), 3.82 (3H, s), 6.55-7.60 (12H, m) |
| 76 | 1.52-5.51 (17H, m), 3.83 (3H, s), 6.75-7.55 (12 H, m) |
| 77 | 1.50-5.52 (20H, m), 3.82 (3H, s), 6.69-7.55 (12H, m), 9.20-9.75 (1H, m) |
| 78 | 1.09-5.45 (25H, m), 6.77-7.48 (12H, m) |
| 79 | 1.65-1.97 (2H, m), 2.10-2.30 (2H, m), 2.48-3.01 (8H, m), 3.82-4.78 (7H, m), 6.62-6.93 (4H, m), 7.11 (1H, dd, J=6.2, 7.3 Hz), 7.38 (2H, d, J=8.5 Hz), 7.66-7.86 (4H, m) |
| 80 | 1.55-2.10 (4H, m), 2.43-3.18 (10H, m), 3.74-5.18 (5H, m), 6.65-7.00 (4H, m), 7.10 (1H, dd, J=6.4, 7.3 Hz), 7.41 (2H, d, J=8.7 Hz) |
| 81 | 1.60-1.90 (2H, m), 1.98 (3H, s), 1.90-2.10 (2H, m), 2.43-3.10 (8H, m), 3.45 (2H, q, J=6.4 Hz), 4.05 (2H, t, J=5.9 Hz), 3.82-5.04 (3H, m),5.92 (1H, brs), 6.65-6.97 (4H, m), 7.11 (1H, dd, J=6.4, 7.3 Hz), 7.43 (2H, d, J=8.7 Hz) |
| 82 | 1.25 (3H, t, J=7.5 Hz), 1.64-1.82 (2H, m), 1.91 (1H, brs), 2.35-2.87 (10H, m), 3.15-3.35 (2H, m), 4.16-4.50 (1H, m), 6.85 (1H, d, J=7.7 Hz), 7.00 (1H, s), 7.10 (1H, d, J=7.7 Hz) |
| 83 | 1.26 (3H, t, J=7.5 Hz), 1.58-1.98 (2H, m), 2.45-3.22 (10H, m), 3.58-3.98 (7H, m), 4.23-4.61 (1H, m), 4.87-5.05 (1H, m), 6.40-6.57 (2H, m), 6.80-7.38 (3H, m) |

TABLE 2-continued

| No. | NMR (CDCl₃) δ value |
|---|---|
| 84 | 1.62–1.95 (2H, m), 2.50–2.93 (9H, m), 3.15–3.50 (2H, m), 3.84 (3H, s), 4.15–4.48 (1H, m), 6.50–6.60 (1H, m), 6.70–6.82 (1H, m), 7.06 (1H, d, J=8.2 Hz) |
| 85 | 1.55–1.98 (2H, m), 2.44–3.25 (8H, m), 3.60–4.10 (10H, m), 4.20–4.75 (1H, m), 4.86–5.05 (1H, m), 6.44–6.85 (4H, m), 7.07 (1H, d, J=8.2 Hz), 7.17–7.36 (1H, m) |
| 86 | 1.54–1.92 (2H, m), 2.32–3.22 (8H, m), 3.50–3.90 (7H, m), 4.23–4.71 (1H, m), 4.82–5.00 (1H, m), 6.34–6.60 (2H, m), 6.95–7.72 (5H, m), 7.90 (2H, d, J=7.0 Hz), 8.40–8.65 (1H, m) |
| 87 | 1.50–1.93 (2H, m), 2.34–3.20 (8H, m), 3.30–4.15 (9H, m), 4.22–4.75 (1H, m), 4.85–5.03 (1H, m), 6.42–6.63 (4H, m), 6.82–7.33 (2H, m) |
| 88 | 1.60–2.02 (2H, m), 2.62–3.41 (4H, m), 3.73–4.26 (1H, m), 4.50–5.72 (2H, m), 6.64 (1H, d, J=9.4 Hz), 7.15–7.70 (10H, m) |
| 89 | 1.55–1.96 (2H, m), 2.72–3.30 (4H, m), 3.84 (3H, s), 3.82–5.55 (3H, m), 6.65 (1H, d, J=9.4 Hz), 6.93 (2H, d, J=8.7 Hz), 7.23 (1H, t, J=7.6 Hz), 7.48–7.75 (6H, m) |
| 90 | 1.55–1.95 (2H, m), 2.63–3.34 (4H, m), 3.66–4.00 (7H, m), 4.95–5.16 (1H, m), 6.42–6.77 (3H, m), 7.13–7.40 (2H, m), 7.45–7.86 (4H, m) |
| 91 | 1.62–2.03 (3H, m), 2.55–3.03 (4H, m), 3.14–3.50 92H, m), 4.68–5.85 (1H, br), 6.65 (1H, d, J=9.4 Hz), 7.19 (1H, t, J=7.4 Hz) |
| 92 | 1.55–1.98 (2H, m), 2.38–3.26 (8H, m), 3.57–4.00 (7H, m), 4.24–4.71 (1H, m), 4.85–5.07 (1H, m), 6.50–6.61 (2H, m), 6.83–7.39 (4H, m) |
| 93 | 1.60–2.05 (3H, m), 2.31–3.00 (8H, m), 3.10–3.48 (2H, m), 4.21–5.42 (1H, m), 6.76–7.38 (3H, m) |
| 94 | 2.76 (3H, t, J=8.1 Hz), 3.0 (3H, t, J=8 Hz), 3.48 (3H, s), 3.75 (3H, s), 6.19 (1H, dd, J=3.1, 6 Hz), 6.78 (2H, d, J=8.3 Hz), 6.9–7.2 (7H, m), 7.43 (2H, d, J=8.4 Hz) |
| 95 | 1.57–1.95 (2H, m), 2.50 (3H, s), 2.45–3.25 (7H, m), 3.57–4.00 (4H, m), 4.15–4.77 (1H, m), 4.88–5.07 (1H, m), 6.63–7.36 (6H, m) |
| 96 | 1.73–1.95 (2H, m), 2.49–3.11 (8H, m), 3.84 (3H, s), 4.24–4.58 (3H, m), 5.21 (2H, s), 6.57 (1H, dd, J=2.5, 8.5 Hz), 6.96–7.52 (10H, m), 7.87 (1H, d, J=2.5 Hz), 8.81 (1H, s) |
| 97 | 1.54–1.72 (1H, m), 1.77–1.92 (1H, m), 2.40–3.23 (8H, m), 3.58–3.73 (1H, m), 3.73–3.95 (6H, m), 4.20–4.77 (1H, m), 4.88–5.07 (1H, m), 6.43–6.60 (2H, m), 6.65–7.00 (2H, m), 7.05–7.37 (2H, m) |
| 98 | 1.55–1.93 (2H, m), 2.30 (3H, s), 2.40–3.24 (8H, m), 3.56–3.72 (1H, m), 3.73–3.85 (6H, m), 4.27–4.73 (1H, m), 4.85–5.02 (1H, m), 6.41–6.57 (2H, m), 6.90–7.37 (4H, m) |
| 99 | 1.58–2.00 (2H, m), 2.35 (3H, s), 2.32–3.14 (8H, m), 3.27–3.48 (1H, m), 3.53–4.00 (7H, m), 4.78–5.01 (1H, m), 6.37–6.64 (2H, m), 6.87–7.48 (4H, m) |
| 100 | 1.57–1.97 (2H, m), 2.37 (3H, s), 2.43–3.26 (8H, m), 3.48–3.98 (7H, m), 4.21–4.63 (1H, m), 4.84–5.07 (1H, m), 6.42–6.60 (2H, m), 6.78–7.37 (4H, m) |
| 101 | 1.40 (3H, t, J=7.1 Hz), 1.55–2.09 (2H, m), 2.43–3.34 (8H, m), 3.66–4.07 (1H, m), 4.25–4.58 (1H, m), 4.39 (2H, q, J=7.1 Hz), 4.75–5.12 (1H, m), 6.96–7.74 (6H, m), 8.01–8.23 (2H, m) |
| 102 | 2.3–2.7 (4H, br), 2.8 (2H, t, J=8 Hz), 3.1 (2H, t, J=8 Hz), 3.4–3.9 (4H, m), 3.55 (2H, s), 6.36 (1H, dd, J=2.2, 6.9 Hz), 6.9–7.1 (2H, m), 7.1–7.4 (8H, m), 7.54 (2H, d, J=8.4 Hz) |
| 103 | 1.60–2.08 (2H, m), 2.45–3.10 (8H, m), 3.35 (3H, s), 3.62–4.05 (1H, br), 4.34 (1H, m), 4.60–5.07 (1H, br), 5.16 (2H, s), 6.76–7.53 (13H, m) |
| 104 | 1.82 (2H, m), 2.54–3.32 (8H, m), 3.77 (1H, brs), 4.35 (1H, m), 4.89 (1H, brs), 7.00–7.30 (4H, m), 7.59–7.67 (1H, m), 7.80–7.84 (1H, m), 8.27–8.33 (2H, m) |
| 105 | 1.68–2.01 (2H, m), 2.50–3.09 (11H, m), 4.19–4.73 (3H, m), 4.88–5.33 (1H, m), 6.60–6.75 92H, m), 4.96–7.39 (6H, m) |
| 106 | 1.60–2.03 (2H, m), 2.45–3.32 (8H, m), 3.67–4.07 (1H, m), 4.15–4.44 (1H, m), 4.61–5.04 (1H, m), 6.96–7.68 (7H, m) |
| 107 | 1.51–2.08 (2H, m), 2.42–3.67 (9H, m), 4.15–5.09 (2H, m), 6.90–7.62 (7H, m) |
| 108 | 0.94 (3H, t, J=7.3 Hz), 1.50–1.97 (4H, m), 2.50–3.20 (10H, m), 3.74–4.20 (1H, br), 4.41 (1H, m), 4.50–5.08 (1H, br), 6.98–7.34 (6H, m), 7.38 (2H, d, J=8.1 Hz) |
| 109 | 1.85 (2H, m), 2.55–3.30 (8H, m), 3.78–4.38 (1H, br), 4.41 (1H, m), 4.66–5.17 (1H, br), 6.99–7.66 (13H, m) |
| 110 | 1.84 (2H, m), 2.55–3.10 (8H, m), 4.00–5.00 92H, m), 4.40 (1H, m), 4.57 (2H, d, J=5.3 Hz), 5.31 (1H, d, J=10.5 Hz), 5.42 (1H, d, J=16.6 Hz), 6.06 (1H, ddt, J=16.6, 10.5, 5.3 Hz), 6.93 (2H, d, J=8.7 Hz), 6.99–7.32 (4H, m), 7.43 (2H, d, J=8.7 Hz) |
| 111 | 1.82 (2H, m), 2.51–3.12 (8H, m), 3.43 (2H, m, J=6.8 Hz), 4.12–4.70 (2H, m), 4.43 (1H, m), 4.58 (2H, d, J=5.0 Hz), 5.06 (1H, d, J=10.0 Hz), 5.08 (2H, d, J=17.0 Hz), 5.29 91H, d, J=9.0 Hz), 5.43 91H, d, J=18.9 Hz), 5.92–6.16 (2H, m), 6.84 (1H, d, J=8.5 Hz), 7.00–7.37 (6H, m) |
| 112 | 1.6–2.1 (3H, m), 2.4–2.7 (2H, m), 2.7–3.2 (4H, m), 3.4–4.2 (3H, m), 3.8 (6H, s), 4.7–5.0 (1H, br), 6.4–6.6 (2H, m), 6.9–7.4 (5H, m) |
| 113 | 1.66–1.97 (2H, m), 2.44–3.10 (8H, m), 3.90–5.00 (2H, m), 4.39 (1H, m), 6.00 (2H, s), 6.83 (1H, d, J=8.2 Hz), 6.96–7.32 (6H, m) |
| 114 | 1.83 (2H, m), 2.31 (3H, s), 2.48–3.17 (8H, m), 3.82 (3H, s), 4.13–4.63 (2H, m), 4.70–5.02 (1H, m), 6.67–6.88 (2H, m), 6.97–7.49 (5H, m) |
| 115 | 1.70–1.92 (2H, m), 2.47–3.08 (11H, m), 3.82 (3H, s), 4.26–4.61 (3H, m), 5.55 (1H, brs), 6.12–6.29 (2H, m), 6.95–7.36 (5H, m) |
| 116 | 1.42 (3H, t, J=6.9 Hz), 1.64–1.90 (2H, m), 2.44–3.17 (8H, m), 4.05 92H, q, J=6.9 Hz), 3.90–5.00 (3H, m), 6.65–6.98 (4H, m), 7.03–7.17 (1H, m), 7.41 (2H, d, J=8.7 Hz) |
| 117 | 1.64–2.10 (4H, m), 2.97–3.18 (8H, m), 2.92 (2H, t, J=6.8 Hz), 4.08 (2H, t, J=6.1 Hz), 4.10–5.15 (3H, m), 6.82–7.58 (8H, m), MS (m/e): 407 (m⁺), 333, 260, 229, 121, 82 |
| 118 | 1.62–1.95 (2H, m), 2.07–2.33 (2H, m), 2.43–3.16 (8H, m), 3.92 (2H, t, J=6.8 Hz), 4.06 (2H, t, J=6.1 Hz), 3.95–5.05 (3H, m), 6.80 (2H, d, J=8.7 Hz), 6.95–7.39 (4H, m), 7.38 92H, d, J=8.7 Hz), 7.65–8.00 (4H, m) |
| 119 | 2.76 (2H, t, J=8.1 Hz), 3.02 (2H, t, J=7.8 Hz), 3.72 (3H, s), 5.10 (2H, s), 6.17 (1H, dd, J=2.6, 6.5 Hz), 6.68 (2H, d, J=9.0 Hz), 6.85 (2H, d, J=8.8 Hz), 6.9–7.4 (10H, m), 7.46 (2H, d, J=8.5 Hz) |
| 120 | 2.76 (2H, t, J=8.1), 3.02 (2H, t, J=7.9 Hz), 3.75 (3H, s), 4.50 (2H, d, J=6 Hz), 5.20 91H, d, J=1.62 Hz), 5.19 (1H, d, J=11.0 Hz), 5.9–6.1 (1H, m), 6.18 (1H, dd, J=2.6, 6.5 Hz), 6.76 (2H, d, J=8.9 Hz), 6.9–7.3 (7H, m), 7.45 (2H, d, J=8.3 Hz) |
| 121 | 1.64–1.96 (2H, m), 2.15–2.87 (2H, m), 2.49–3.20 (8H, m), 3.01 (3H, s), 4.02–5.03 (3H, m), 4.12 (2H, t, J=5.9 Hz), 4.53 (2H, t, J=6.1 Hz), 6.91 (2H, d, J=8.7 Hz), 6.95–7.46 (4H, m), 7.44 (2H, d, J=8.7 Hz) |

TABLE 2-continued

| No. | NMR (CDCl₃) δ value |
|---|---|
| 122 | 1.55–3.26 (14H, m), 2.72 (6H, s), 3.90–5.18 (3H, m),4.05 (2H, t, J=5.7 Hz), 6.90 (2H, d, J=8.7 Hz), 6.93–7.38 (4H, m), 7.43 (2H, d, J=8.7 Hz) |
| 123 | 0.91 (3H, t, J=5.8 Hz), 1.42–3.31 (21H, m), 2.33 (3H, s), 3.88–5.15 (3H, m), 4.05 (2H, t, J=5 Hz), 6.91 (2H, d, J=7 Hz), 6.95–7.38 (4H, m), 7.42 (2H, d, J=7 Hz) |
| 124 | 1.65–5.12 (22H, m), 6.67–7.60 (13H, m) |
| 125 | 1.65–1.99 (2H, m), 2.07 (2H, quint, J=6.2 Hz), 2.49–3.24 (8H, m), 3.62 (2H, t, J=6.2 Hz), 3.87–4.93 (5H, m), 4.10 (2H, t, J=6.2 Hz), 5.11–5.38 (2H, m), 5.80–6.07 (1H, m), 6.80–7.53 (8H, m) |
| 126 | 1.02 (3H, t, J=7.3 Hz), 1.60–2.07 (4H, m), 2.47–3.18 (10H, m), 3.80 (3H, s), 4.30–4.58 (3H, m), 5.53 (1H, t, J=5.2 Hz), 6.07–6.28 (2H, m), 6.94–7.34 (5H, m) |
| 127 | 1.64–1.92 (2H, m), 2.28 (2H, quint, J=6.1 Hz), 2.45–3.27 (8H, m), 4.02–5.22 (3H, m), 4.16 (2H, t, J=6.1 Hz), 4.53 (2H, t, J=6.1 Hz), 6.83–7.69 (11H, m), 7.98–8.18 (2H, m) |
| 128 | 1.69–1.97 (2H, m), 2.06 (2H, quint, J=6.2 Hz), 2.48–3.16 (8H, m), 3.36 (3H, s), 3.56 (2H, t, J=6.2 Hz), 4.09 (2H, t, J=6.2 Hz), 4.12–5.04 (3H, m), 6.91 (2H, t, J=8.7 Hz), 6.94–7.35 (4H, m), 7.43 (2H, d, J=8.7 Hz) |
| 129 | 1.28 (3H, t, J=7.1 Hz), 1.83 (2H, m), 2.15 (2H, quint, J=6.7 Hz), 2.47 (2H, t, J=6.7 Hz), 2.50–3.20 (8H, m), 3.60–5.10 (2H, m), 4.02 (2H, s), 4.05 (2H, t, J=6.7 Hz), 4.21 (2H, q, J=7.1 Hz), 4.39 (1H, m), 6.12 (1H, brs), 6.91 (2H, d, J=8.6 Hz), 6.99–7.29 (4H, m), 7.42 (2H, d, J=8.6 Hz) |
| 130 | 1.87 (2H, m), 2.50–3.43 (8H, m), 3.94 (1H, m), 4.38 (1H, m), 4.96 (1H, m), 6.99–7.30 (4H, m), 7.58–7.65 (1H, m), 7.75–7.98 (2H, m), 8.12–8.16 (1H, m), 8.31 (1H, m), 9.01 (1H, m) |
| 131 | 1.73 (6H, m), 1.82 (2H, m), 2.04 (9H, m), 2.43–3.00 (8H, m), 4.46 (1H, m), 4.67 (1H, m), 4.73 (1H, m), 6.98–7.30 (4H, m) |
| 132 | 1.65–2.28 (7H, m), 2.44–3.20 (11H, m), 3.42–5.11 (7H, m), 6.83–7.60 (8H, m) |
| 133 | 1.40–1.90 (2H, m), 2.30–2.95 (8H, m), 3.90 (3H, s), 3.98 (2H, m), 4.32 (1H, m), 6.90–7.27 (6H, m), 7.73 (2H, m) |
| 134 | 1.55–2.05 (2H, m), 2.54–3.33 (8H, m), 4.05–4.24 (1H, m), 4.47–4.65 (1H, m), 4.93–5.10 (1H, m), 6.98–7.31 (4H, m), 7.64 (1H, m), 7.74–7.80 (2H, m), 7.86 (1H, m), 8.11 (1H, d, J=8.4 Hz), 8.28 (1H, d, J=8.4 Hz) |
| 135 | 1.56–1.86 (1H, m), 1.86–2.30 (1H, m), 2.44–3.35 (8H, m), 3.60–3.86 (1H, m), 4.12–4.62 (1H, m), 4.91–5.20 (1H, m), 6.63–7.78 (9H, m) |
| 136 | 1.08 (9H, s), 1.80 (2H, m), 2.32 (2H, s), 2.45–2.76 (5H, m), 2.76–2.92 (2H, m), 3.05–3.18 (1H, m), 4.03–4.18 (1H, m), 4.40 (1H, m), 4.78–4.98 (1H, m), 6.97–7.28 (4H, m) |
| 137 | 1.30 93H, t, J=7.1 Hz), 1.84 (2H, m), 2.50–3.22 (8H, m), 3.90 (1H, t, J=5.4 Hz), 3.43–5.20 (2H, m), 4.13 (2H, d, J=5.4 Hz), 4.24 (2H, q, J=7.1 Hz), 4.57 (2H, s), 4.38 (1H, m), 6.97 (2H, d, J=8.7 Hz), 7.03–7.32 (4H, m), 7.47 (2H, d, J=8.7 Hz) |
| 138 | 1.75 (2H, m), 2.51–3.31 (8H, m), 3.80–5.28 (2H, m), 4.37 (1H, m), 4.64 (2H, s), 6.90–7.67 (13H, m) |
| 139 | 1.83 (2H, m), 2.54–3.23 (8H, m), 2.94 (3H, s), 3.09 (3H, m), 3.76–5.17 (2H, m), 4.39 (1H, m), 4.73 (2H, s), 6.97 (2H, d, J=8.6 Hz), 7.02–7.27 (4H, m), 7.43 (2H, d, J=8.6 Hz) |
| 140 | 1.26 (3H, t, J=7.1 Hz), 1.83 (2H, m), 2.12 (2H, quint, J=6.2 Hz), 2.40–3.20 (10H, m), 3.40–5.10 (2H, m), 4.04 (2H, t, J=6.2 Hz), 4.15 (2H, q, J=7.1 Hz), 4.39 (1H, m), 6.90 (2H, d, J=8.6 Hz), 6.98–7.28 (4H, m), 7.43 (2H, d, J=8.6 Hz) |
| 141 | 1.54–1.98 (2H, m), 2.40–3.22 (9H, m), 2.95 (6H, s), 3.58–3.90 (7H, m), 4.85–5.06 (1H, m), 6.33–6.62 (4H, m), 6.70 (1H, d, J=8.2 Hz), 7.12–7.30 (1H, m) |
| 142 | 1.27 (3H, d, J=6.8 Hz), 1.55–1.95 (2H, m), 2.28–3.24 (7H, m), 3.55–3.97 (7H, m), 4.27–4.73 (1H, m), 4.75–5.07 (1H, m), 6.38–6.60 (2H, m), 6.97–7.38 (5H, m) |
| 143 | 1.67–3.23 (12H, m), 2.06 (3H, s), 3.94–5.15 (3H, m), 4.08 (2H, t, J=6.2 Hz), 4.26 (2H, t, J=6.2 Hz), 6.77–7.75 (8H, m) |
| 144 | 1.54–2.23 (5H, m), 2.51–3.20 (8H, m), 3.77–5.08 (5H, m), 4.15 (2H, t, J=6 Hz), 6.83–7.59 (8H, m) |
| 145 | 1.31 (3H, t, J=7.1 Hz), 1.83 (2H, m), 2.54–3.26 (8H, m), 3.70–5.20 (2H, m), 4.30 (2H, q, J=7.1 Hz), 4.38 (1H, m), 4.65 (2H, s), 6.93 (2H, d, J=8.7 Hz), 6.99–7.36 (4H, m), 7.44 (2H, d, J=8.7 Hz) |
| 146 | 1.6–2.1 (3H, m), 2.4–2.6 (2H, m), 2.5 (3H, s), 2.6–3.2 (4H, m), 3.4–4.1 (6H, m), 4.8–5.0 (1H, br), 6.6–7.4 (7H, m) |
| 147 | 1.55–1.93 (2H, m), 2.30–3.24 (8H, m), 3.56–4.05 (10H, m), 4.27–4.72 (1H, m), 4.84–5.07 (1H, m), 6.40–6.60 (2H, m), 6.64–6.82 (2H, m), 6.93–7.38 (2H, m) |
| 148 | 1.80 (2H, m), 2.31 (3H, s), 2.52–3.25 (8H, m), 3.68–4.20 (1H, br), 4.34 (1H, m), 4.65–5.13 (1H, br), 6.88–7.52 (8H, m) |
| 149 | 1.56–2.00 (2H, m), 2.30 (6H, s), 2.50–3.15 (8H, m), 3.20–3.90 (1H, m), 4.27 (1H, m), 4.90 (1H, m), 6.95–7.33 (7H, m) |
| 150 | 1.70–2.00 (2H, m), 2.55–3.15 (8H, m), 4.33 (1H, m), 4.47 (1H, m), 4.54 (1H, m), 6.36–6.49 (2H, m), 7.02–7.35 (5H, m) |
| 151 | 1.59∝2.11 (2H, m), 2.48–3.33 (8H, m), 3.70–5.15 (3H, m), 5.58–6.60 (2H, m), 6.97–8.05 (8H, m) |
| 152 | 1.56–3.35 (13H, m), 3.60–5.08 (3H, m), 6.75–7.98 (8H, m) |
| 153 | 1.31–1.78 (5H, m), 2.32–3.28 (8H, m), 3.68 (1H, m), 3.81 (3H, s), 4.06 (2H, m), 4.43 (1H, m), 4.96 (1H, m), 6.49–6.62 (2H, m), 6.97–7.44 (5H, m) |
| 154 | 1.53–1.90 (2H, m), 2.35–3.27 (8H, m), 3.60–3.77 (1H, m), 3.81 (3H, s), 4.29–4.60 (1H, br), 4.58 (2H, m), 4.88–5.06 (1H, m), 5.18–5.51 (2H, m), 6.08 (1H, m), 6.42–6.60 (2H, m), 6.93–7.48 (5H, m) |
| 155 | 2.78 (3H, t, J=8 Hz), 3.04 (3H, t, J=8 Hz), 3.50 (3H, s), 3.59 (3H, s), 3.76 (3H, s), 6.0–6.1 (1H, br), 6.2 (1H, brs), 6.41 (1H, dd, J=2.3, 8.4 Hz), 6.9–7.1 (4H, m), 7.1–7.3 (4H, m) |
| 156 | 1.66–2.03 (2H, m), 2.14 (2H, m), 2.44 (2H, t, J=7.2 Hz), 2.51–3.32 (8H, m), 3.70–5.30 (2H, m), 4.04 (2H, t, J=6.0 Hz), 4.38 (1H, m), 5.75 (1H, brs),5.90 (1H, brs), 6.90 (2H, d, J=8.6 Hz), 6.99–7.29 (4H, m), 7.42 (2H, d, J=8.6 Hz) |
| 157 | 1.55–2.10 (2H, m), 2.22–3.36 (8H, m), 3.78–4.20 (1H, m), 4.23–4.56 (1H, m), 4.70–5.18 (1H, m), 6.95–7.34 (4H, m), 7.46 (1H, dd, J=8.3, 4.2 Hz), 7.67 (1H, dd, J=8.3, 1.3 Hz), 7.90 (1H, d, J=8.3 Hz), 8.20 (2H, m), 8.96 (1H, dd, J=4.2, 1.3 Hz) |
| 158 | 1.58–2.31 (4H, m), 2.44–3.30 (8H, m), 3.60–4.50 (6H, m), 3.81 (3H, s), 4.70–5.15 (1H, m), 6.43–6.60 (2H, m), 6.99–7.33 (5H, m), |
| 159 | 1.29 (3H, t, J=7.1 Hz), 1.58–1.98 (2H, m), 2.53–3.37 (8H, m), 3.80 (3H, s), 4.21 (2H, q, J=7.1 Hz), 4.22–4.47 (1H, m), 4.62 (2H, s), 4.63–4.80 (1H, m), 4.87–5.07 (1H, m), 6.28–6.37 (1H, m), 6.52–6.66 (1H, m), 6.95–7.46 (5H, m) |
| 160 | 1.46–2.12 (2H, m), 2.45–3.22 (8H, m), 3.36–3.55 (1H, m), 4.22–4.53 (1H, m), 5.02–5.17 (1H, m), 6.98–7.74 (7H, m), |

TABLE 2-continued

| No. | NMR (CDCl$_3$) δvalue |
|---|---|
|  | 8.03-8.26 (2H, m), 8.94-9.05 (1H, m) |
| 161 | 1.26 (3H, t, J=7.1 Hz), 1.63-2.00 (6H, m), |
|  | 2.32-2.44 (2H, m), 2.54-3.03 (8H, m), |
|  | 3.75-5.03 (2H, m), 3.95-4.09 (2H, m), |
|  | 4.14 (2H, q, J=7.1 Hz), 4.40 (1H, m), |
|  | 6.90 (2H, d, J=8.7 Hz), 6.98-7.27 (4H, m), |
|  | 7.43 (2H, d, J=8.7 Hz) |
| 162 | 1.42-1.62 (2H, m), 1.62-1.93 (6H, m), |
|  | 2.36 (2H, t, J=7.1 Hz), 2.45-3.12 (8H, m), |
|  | 3.67 (3H, s), 3.74-5.03 (2H, m), |
|  | 3.98 (2H, t, J=6.3 Hz), 4.39 (1H, m), |
|  | 6.90 (2H, d, J=8.7 Hz), 6.99-7.28 (4H, m), |
|  | 7.43 (2H, d, J=8.7 Hz) |
| 163 | 1.63-2.10 (6H, m), 2.33 (2H, m), |
|  | 2.46-3.18 (8H, m), 3.50-5.00 (2H, m), |
|  | 3.89 (2H, d, J=4.8 Hz), 4.00 (2H, m), |
|  | 4.37 (1H, m), 5.76 (1H, brs), 6.50 (1H, brs), |
|  | 6.74 (1H, brs), 6.89 92H, d, J=8.6 Hz), |
|  | 6.99-7.27 (4H, m), 7.41 (2H, d, J=8.6 Hz) |
| 164 | 1.28 (3H, t, J=7.1 Hz), 1.83 (6H, m), |
|  | 2.17 (2H, m), 2.43-3.18 (8H, m), |
|  | 3.55-5.00 (2H, m), 3.98 (2H, m), 3.99 (2H, d, J=5.1 Hz), |
|  | 4.20 (2H, q, J=7.1 Hz), 4.37 (1H, m), |
|  | 6.66 (1H, brs), 6.89 92H, d, J=8.6 Hz), |
|  | 6.99-7.32 (4H, m), 7.42 (2H, d, J=8.6 Hz) |
| 165 | 1.41-2.10 (8H, m), 2.26 (2H, t, J=7.3 Hz), |
|  | 2.54-3.24 (8H, m), 3.80-5.10 (2H, m), |
|  | 3.99 (2H, t, J=6.3 Hz), 4.39 (1H, m), |
|  | 5.22-5.86 (2H, m), 6.89 (2H, d, J=8.7 Hz), |
|  | 6.99-7.29 (4H, m), 7.42 (2H, d, J=8.7 Hz) |
| 166 | 1.48-1.62 (2H, m), 1.62-2.17 (6H, m), |
|  | 2.27 (2H, t, J=7.3 Hz), 2.54-3.30 (8H, m), |
|  | 3.30-5.10 (2H, m), 3.91 (2H, d, J=5.0 Hz), |
|  | 3.98 (2H, t, J=6.3 Hz), 4.37 (1H, m), |
|  | 5.75 (1H, brs), 6.51 (1H, brs), 6.66 (1H, brs), |
|  | 6.89 (2H, d, J=8.7 Hz), 6.99-7.27 (4H, m), |
|  | 7.41 (2H, d, J=8.7 Hz) |
| 166A | 1.28 (3H, t, J=7.1 Hz), 1.46-1.63 (2H, m), |
|  | 1.63-1.96 (6H, m), 2.28 (2H, t, J=7.3 Hz), |
|  | 2.54-3.12 (8H, m), 3.62-5.07 (2H, m), |
|  | 3.98 (2H, t, J=6.4 Hz), 4.01 (2H, d, J=5.3 Hz), |
|  | 4.20 (2H, q, J=7.1 Hz), 4.48 (1H, m), |
|  | 6.45 (1H, brs), 6.89 (2H, d, J=8.7 Hz), |
|  | 6.99-7.31 (4H, m), 7.42 (2H, d, J=8.7 Hz) |
| 167 | 1.57-1.94 (2H, m), 2.02-2.35 (2H, m), |
|  | 2.06 (3H, s), 2.45-3.24 (8H, m), |
|  | 3.64 (1H, m), 3.82 (3H, s), 3.98-4.50 (5H, m), |
|  | 4.85-5.06 (1H, m), 6.38-6.63 (2H, m), |
|  | 6.97-7.33 (5H, m) |
| 168 | 1.67 (1H, m), 1.75-1.94 (1H, m), |
|  | 2.00-2.37 (2H, m), 2.45-3.26 (8H, m), |
|  | 3.56-3.80 (1H, m), 3.81 (3H, s), |
|  | 3.94-4.47 (5H, m), 4.66-5.27 (3H, m), |
|  | 6.44-6.55 (2H, m), 6.98-7.32 (5H, m) |
| 169 | 1.55-1.77 (1H, m), 1.77-1.94 (1H, m), |
|  | 1.94-2.33 (2H, m), 2.33-3.24 (8H, m), |
|  | 3.35 (3H, s), 3.42-3.77 (3H, m), 3.81 (3H, s), |
|  | 3.95-4.27 (2H, m), 4.40 (1H, m), |
|  | 4.87-5.07 (1H, m), 6.42-6.62 (2H, m), |
|  | 6.98-7.32 (5H, m) |
| 170 | 1.53-1.77 (1H, m), 1.77-1.98 (1H, m), |
|  | 2.32-3.33 (8H, m), 3.43 (3H, m), |
|  | 3.56-3.99 (3H, m), 3.81 (3H, s), |
|  | 3.99-4.30 (2H, m), 4.40 (1H, m), |
|  | 4.85-5.06 (1H, m), 6.49-6.66 (2H, m), |
|  | 6.97-7.43 (5H, m) |
| 171 | 1.62-1.82 (1H, m), 1.82-2.02 (1H, m), |
|  | 2.03-2.40 (2H, m), 2.40-3.26 (10H, m), |
|  | 3.68-3.90 (1H, m), 3.81 (3H, s), 3.97 (1H, m), |
|  | 4.02-4.26 (2H, m), 4.36-5.10 (2H, m), |
|  | 6.43-6.57 (2H, m), 7.00-7.29 (5H, m) |
| 172 | 1.26-1.98 (12H, m), 2.20 (2H, t, J=7.5 Hz), |
|  | 2.53-3.27 (8H, m), 3.77-5.05 (2H, m), |
|  | 3.97 (2H, t, J=6.4 Hz), 4.37 (1H, m), |
|  | 6.01 (1H, brs), 6.05 (1H, brs), |
|  | 6.90 92H, d, J=8.6 Hz), 6.99-7.29 (4H, m), |
|  | 7.42 (2H, d, J=8.6 Hz) |
| 173 | 1.26 (3H, t, J=7.1 Hz), 1.54-1.75 (1H, m), |
|  | 1.75-1.96 (1H, m), 2.03-2.33 (2H, m), |
|  | 2.44-3.24 (10H, m), 3.57-3.78 (1H, m), |
|  | 3.80 (3H, s), 4.01 (2H, t, J=6.3 Hz), |
|  | 4.14 (2H, q, J=7.1 Hz), 4.39 (1H, m), |
|  | 4.82-5.04 (1H, m), 6.40-6.59 (2H, m), |
|  | 6.98-7.33 (5H, m) |
| 174 | 1.10-2.06 (12H, m), 2.23 (2H, t, J=7.5 Hz), |
|  | 2.42-3.24 (8H, m), 3.67-5.15 (2H, m), |
|  | 3.90 (2H, d, J=5.2 Hz), 3.97 92H, t, J=6.4 Hz), |
|  | 4.37 (1H, m), 6.09 (1H, brs), |
|  | 6.90 (2H, d, J=8.6 Hz), 6.97-7.30 (4H, m), |
|  | 7.41 (2H, d, J=8.6 Hz) |
| 175 | 1.27 (3H, t, J=7.1 Hz), 1.39 (3H, d, J=7.2 Hz), |
|  | 1.63-1.95 (2H, m), 2.14 (2H, quint, J=6.5 Hz), |
|  | 2.43 (2H, t, J=6.5 Hz), 2.54-3.10 (8H, m), |
|  | 3.80-5.15 (2H, m), 4.04 (2H, t, J=6.5 Hz), |
|  | 4.19(2H, q, J=7.1 Hz), 4.39 (1H, m), |
|  | 4.57 (1H, qunit, J=7.2 Hz), 6.29 (1H, d, J=7.2 Hz), |
|  | 6.90 (2H, d, J=8.7 Hz), 6.99-7.29 (4H, m), |
|  | 7.42 (2H, d, J=8.7 Hz) |
| 176 | 1.18-1.54 (6H, m), 1.54-1.93 (6H, m), |
|  | 2.32 (2H, t, J=7.4 Hz), 2.54-3.10 (8H, m), |
|  | 3.67 (3H, s), 3.80-5.05 (2H, m), |
|  | 3.97 (2H, t, J=6.5 Hz), 4.40 (1H, m), |
|  | 6.70 (2H, d, J=8.6 Hz), 6.99-7.27 (4H, m), |
|  | 7.43 (2H, d, J=8.6 Hz) |
| 177 | 1.62-1.96 (2H, m), 2.52-3.18 (8H, m), |
|  | 3.68-4.42 (6H, m), 3.81 (3H, s), |
|  | 4.80-5.05 (1H, m), 6.47-6.64 (2H, m), |
|  | 6.99-7.29 (5H, m) |
| 178 | 1.54-1.93 (2H, m), 2.04 (3H, s), |
|  | 2.27-3.28 (8H, m), 3.56-3.80 (1H, m), |
|  | 3.81 (3H, s), 4.00-4.73 (5H, m), |
|  | 4.83-5.05 (1H, m), 6.49-6.65 (2H, m), |
|  | 6.98-7.36 (4H, m) |
| 179 | 1.52-1.98 (2H, m), 2.12 (2H, quint, J=6.5 Hz), |
|  | 2.45 (2H, t, J=6.5 Hz), 2.54-3.24 (8H, m), |
|  | 3.65-5.18 (2H, m), 3.89 (2H, d, J=5.2 Hz), |
|  | 4.02 (2H, t, J=6.5 Hz), 4.36 (1H, m), |
|  | 6.00 (1H, brs), 6.61 (1H, brs), |
|  | 6.89 (2H, d, J=8.6 Hz), 6.99-7.29 (5H, m), |
|  | 7.40 (2H, d, J=8.6 Hz) |
| 180 | 1.57-1.94 (2H, m), 2.12 (2H, quint, J=6.6 Hz), |
|  | 2.43 (2H, t, J=6.6 Hz), 2.54-3.14 (8H, m), |
|  | 3.28 (1H, m), 3.76 (3H, s), 4.00 (2H, d, J=3.8 Hz), |
|  | 4.01 (2H, t, J=6.6 Hz), 4.10-5.00 (1H, m), |
|  | 4.37 (1H, m), 4.65 (1H, dt, J=7.6, 3.8 Hz), |
|  | 6.74 (1H, d, J=7.6 Hz), 6.91 (2H, d, J=8.7 Hz), |
|  | 6.99-7.29 (4H, m), 7.42 (2H, d, J=8.7 Hz) |
| 181 | 1.22-1.94 (18H, m), 2.31 (2H, t, J=7.5 Hz), |
|  | 2.42-3.17 (8H, m), 3.66 (3H, s), |
|  | 3.80-5.10 (2H, m), 3.97 (2H, t, J=6.5 Hz), |
|  | 4.40 (1H, m), 6.90 (2H, d, J=8.6 Hz), |
|  | 6.99-7.28 (4H, m), 7.43 (2H, d, J=8.6 Hz) |
| 182 | 0.9-1.4 (3H, s), 1.5-1.8 (1H, m), |
|  | 2.3-2.7 (3H, m), 2.8-3.3 (4H, m), |
|  | 3.3-4.0 (8H, m), 4.2-4.5 (1H, m), |
|  | 4.6-4.9 (1H, br), 6.4-6.6 (2H, m), |
|  | 7.0-7.4 (5H, m) |
| 183 | 1.12 (3H, d, J=6.9 Hz), 1.6-1.8 (1H, m), |
|  | 2.4-2.7 (3H, m), 2.8-2.9 (2H, m), |
|  | 3.00 (6H, s),2.9-3.4 (3H, m), |
|  | 4.1-4.5 (3H, m), 6.68 (2H, d, J=8.8 Hz), |
|  | 7.0"7.3 (4H, m), 7.40 (2H, d, J=8.8 Hz) |
| 184 | 1.6-1.8 (6H, m), 2.1-2.3 (3H, br), |
|  | 2.3-2.4 (6H, br), 2.7-2.9 (2H, m), |
|  | 2.92 (3H, s), 3.0-3.2 (2H, m), |
|  | 6.3-6.5 (2H, m), 6.9-7.1 (2H, m), |
|  | 7.2-7.3 (1H, m), 7.25 (2H, d, J=8.5 Hz), |
|  | 7.56 (2H, d, J=8.5 Hz) |
| 185 | 2.1-2.3 (1H, m), 2.5-2.9 (5H, m), |
|  | 3.3-4.2 (10H, m), 5.0-5.2 (1H, m), |
|  | 6.4-6.6 (2H, m), 7.0-7.2 (2H, m) |
| 186 | 2.1-2.3 (1H, m), 2.5-2.9 (5H, m), |
|  | 2.99 (6H, s), 3.6-4.3 (4H, m), |
|  | 4.8-5.0 (1H, br), 6.6-6.7 (2H, m) |
| 187 | 2.1-2.4 (1H, m), 2.5-3.0 (8H, m), |
|  | 3.3-4.2 (7H, m), 5.0-5.2 (1H, m), |
|  | 6.7-7.1 (4H, m), 7.1-7.3 (3H, m) |
| 188 | 1.22 (3H, d, J=7.1 Hz), 1.5-1.7 (1H, m), |
|  | 2.3-2.5 (2H, m), 2.5-3.3 (9H, m), |
|  | 4.1-4.3 (1H, m), 6.9-7.1 (1H, m), |
|  | 7.1-7.3 (3H, m), |
| 189 | 1.6-2.0 (3H, m), 2.5-2.6 (8H, m), |

TABLE 2-continued

| No. | NMR (CDCl₃) δ value |
|---|---|
|  | 3.6–3.9 (2H, m), 4.0–4.3 (1H, m), 6.9–7.1 (1H, m), 7.1–7.3 (3H, m) |
| 190 | 2.1–2.4 (2H, m), 2.5–2.7 (2H, m), 2.7–3.1 (3H, m), 3.1–3.3 (1H, m), 3.3–3.6 (2H, m), 3.9 (1H, s), 4.6–4.8 (1H, m), 7.0–7.3 (4H, m) |
| 191 | 1.65–1.97 (2H, m), 2.40–2.92 (9H, m), 3.15–3.34 (2H, m), 3.78 (3H, s), 4.25–4.49 (1H, m), 6.67–6.72 (2H, m), 7.16 (1H, d, J=8.1 Hz) |
| 192 | 1.55–1.85 (3H, m), 2.30 (3H, s), 2.36–2.90 (8H, m), 3.15–3.32 (2H, m), 4.23–4.48 (1H, m), 6.90–7.06 (2H, m), 7.11 (1H, d, J=8.1 Hz) |
| 193 | 1.63–1.95 (3H, m), 2.36 (3H, s), 2.43–2.90 (8H, m), 3.13–3.31 (2H, m), 4.18–4.40 (1H, m), 6.81 (1H, d, J=7.5 Hz), 6.95–7.10 (2H, m) |
| 194 | 1.65–1.86 (2H, m), 1.98 (2H, brs), 2.40–2.90 (8H, m), 3.15–3.38 (2H, m), 4.14–4.48 (1H, m), 6.70 (1H, dt, J=8.2, 2.3 Hz), 6.94 (1H, dd, J−11.0, 2.3 Hz), 7.09 (1H, t, J=8.1 Hz) |
| 195 | 1.62–1.95 (3H, m), 2.35 (3H, s), 2.38–2.90 (8H, m), 3.10–3.48 (3H, m), 6.88–7.20 (3H, m) |
| 196 | 1.64–1.83 (2H, m), 2.19 (3H, s), 2.40–2.86 (8H, m), 4.42–4.62 (1H, m), 7.08 (2H, s), 7.67 (1H, s), 7.81 (1H, brs) |
| 197 | 1.27 (3H, t, J=7.0 Hz), 1.62–1.83 (2H, m), 1.91 (1H, brs), 2.30–3.32 (9H, m), 4.23–4.45 (1H, m), 6.96–7.30 (4H, m) |
| 198 | 1.67–1.86 (2H, m), 2.21 (1H, brs), 2.43–2.83 (8H, m), 2.95 (6H, s), 3.15–3.32 (2H, m), 4.16–4.40 (1H, m), 6.41 (1H, dd, J=8.3, 2.3 Hz), 6.57 (1H, d, J=2.3 Hz), 7.01 (1H, d, J=8.3 Hz) |
| 199 | 1.56–1.95 (2H, m), 2.43–3.23 (8H, m), 3.56–3.83 (1H, m), 3.67 (3H, d, J=9.3 Hz), 4.23–4.67 (1H, m), 4.86–5.05 (1H, m), 6.26–6.42 (2H, m), 6.96–7.35 (5H, m), 8.57–8.73 (1H, m) |
| 200 | 1.60–1.74 (1H, m), 1.80–1.93 (1H, m), 2.31 (3H, s), 2.47–3.38 (8H, m), 3.58–3.75 (1H, m), 3.91 (3H, d, J=8.9 Hz), 4.27–4.69 (1H, m), 4.88–5.03 (1H, m), 6.67–6.91 (2H, m), 6.96–7.30 (5H, m) |
| 201 | 1.52–2.10 (6H, m), 2.45–3.10 (11H, m), 3.72–5.10 (5H, m), 6.90 (2H, d, J=8.7 Hz), 6.97–7.32 (4H, m), 7.43 (2H, d, J=8.7 Hz) |
| 202 | 1.26 (3H, t, J=7.5 Hz), 1.62–1.98 (2H, m), 2.35–3.28 (10H, m), 3.57–3.98 (7H, m), 4.41 (1H, brs), 4.85–5.05 (1H, m), 6.40–6.60 (2H, m), 6.82–7.00 (2H, m), 7.08 (1H, d, J=7.5 Hz), 7.16–7.35 (1H, m) |
| 203 | 1.58–2.00 (2H, m), 2.42–3.25 (8H, m), 3.60–4.02 (10H, m), 4.20–4.70 (1H, m), 4.86–5.05 91H, m), 6.42–6.80 (4H, m), 7.07 (1H, d, J=8.2 Hz), 7.13–7.38 (1H, m) |
| 204 | 1.58–2.02 (2H, m), 2.50 (3H, s), 2.40–3.28 (8H, m), 3.57–4.00 (4H, m), 4.15–4.78 (1H, m), 4.87–5.08 (1H, m), 6.65–7.38 (6H, m) |
| 205 | 1.67–1.93 (2H, m), 2.33 (2H, quint, J=6.1 Hz), 2.48–3.15 (8H, m), 3.61 (2H, t, J=6.4 Hz), 3.78–5.28 (3H, m), 4.14 (2H, t, J=5.8 Hz), 6.92 (2H, d, J=8.7 Hz), 6.98–7.32 (4H, m), 7.44 (2H, d, J=8.7 Hz) |
| 206 | 1.72–2.13 (4H, m), 2.45 (2H, t, J=7.0 Hz), 2.47–3.35 (10H, m), 3.90–4.35 (4H, m), 6.55 (2H, d, J=8.6 Hz), 6.93–7.30 (6H, m), 7.33 (2H, d, J=8.6 Hz), 8.95 (1H, brs) |
| 207 | 1.44–1.97 (8H, m), 2.48–3.30 (10H, m), 2.96 (3H, s), 3.83–5.02 (4H, m), 3.98 (2H, t, J=6.1 Hz), 6.89 (2H, d, J=8.7 Hz), 6.98–7.35 (4H, m), 7.42 (2H, d, J=8.7 Hz) |
| 208 | 1.46–2.02 (8H, m), 1.97 (3H, s), 2.48–3.37 (10H, m), 3.80–5.09 (3H, m), 3.97 (2H, t, J=6.2 Hz), 5.87 (1H, brs), 6.89 (2H, d, J=8.8 Hz), 6.95–7.39 (4H, m), 7.42 (2H, d, J=8.8 Hz) |
| 209 | 1.52–2.03 (6H, m), 1.97 (3H, s), 2.47–3.40 (10H, m), 3.81–4.96 (3H, m), 3.99 (2H, t, J=6.1 Hz), 5.86 (1H, brs), 6.88 (2H, d, J=8.7 Hz), 6.94–7.38 (4H, m), 7.42 (2H, d, J=8.7 Hz) |

EXAMPLE 384

Acetic acid (30 ml) and 1-(1-benzyl-3-methyl-4-piperidinyl)carbostyril (2.1 g) are added to 10% palladiumcarbon (0.5 g) and the mixture is subjected to catalytic reduction at 80° C. under atmospheric pressure. After the catalytic reduction, 10% palladium-carbon is filtered off and the filtrate is concentrated under reduced pressure. Water is added to the residue and the mixture is basified with aqueous sodium hydroxide solution and then extracted with dichloromethane. After washed with water, the extract is dried with magnesium sulfate and the solvent is distilled off under reduced pressure to give 1-(3-methyl-4-piperidinyl)-3,4-dihydrocarbostyril (1.01 g).

NMR (CDCl₃) δ ppm: 1.22 (3H, d, J=7.1 Hz), 1.5–1.7 (1H, m), 2.3–2.5 (1H, m), 2.5–3.3 (9H, m), 4.1–4.3 (1H, m), 6.9–7.1 (1H, m), 7.1–7.3 (3H, m)

The compounds of the above Examples 1–9, 11–164, 169–350, 352–383C are obtained in the same manners as in Example 384.

EXAMPLE 385

Conc. sulfuric acid (8 ml) is added to N-(β-ethoxyacryloyl)-N-(1-benzoyl-4-piperidinyl)aniline (0.8 g) and the mixture is reacted at 60° C. for 30 minutes. The reaction mixture is poured into ice-water and then extracted with dichloromethane. The solvent is concentrated and the resulting residue is purified by silica gel column chromatography (solvent; dichloromethane:methanol=50:1) to give 1-(1-benzoyl-4-piperidinyl)carbostyril (0.53 g).

NMR (CDCl₃) δ ppm: 1.60–2.02 (2H, m), 2.62–3.41 (4H, m), 3.73–4.26 (1H, m), 4.50–5.72 (2H, m), 6.64 (1H, d, J=9.4 Hz), 7.15–7.70 (10H, m)

The compounds of the above Examples 10 and 166–168 are obtained in the same manners as in Example 385.

EXAMPLE 386

Ethanol (10 ml) and 10% aqueous sodium hydroxide solution (12 ml) are added to 1-(1-benzoyl-4-piperidinyl)carbostyril (1.0 g) and the mixture is refluxed with heating for 7 hours. After concentration, water is added thereto and the mixture is extracted with dichloromethane. The dichloromethane layer is collected by filtration and water is added thereto. The mixture is acidified with diluted hydrochloric acid. The aqueous layer is basified with diluted aqueous sodium hydroxide solution, extracted with dichloromethane and then concentrated to give 1-(4piperidinyl)carbostyril (0.58 g).

NMR (CDCl₃) δ ppm: 1.62–2.03 (3H, m), 2.55–3.03 (4H, m), 3.14–3.50 (2H, m), 4.68–5.85 (1H, br), 6.65 (1H, d, J=9.4 Hz), 7.19 (1H, t, J=7.4 Hz), 7.35–8.00 (4H, m)

Using the suitable starting materials, the compounds of the above Examples 156, 158, 171, 186, 351–361 and the following Examples 580, 581 and 577A are obtained in the same manners as in Example 386.

EXAMPLE 387

1-(4-Piperidinyl)-3,4-dihydrocarbostyril (0.2 g) is added to conc. sulfuric acid (5 ml) and thereto is added fuming nitric acid (0.1 ml) under ice cooling. The mixture is stirred at room temperature for 30 minutes, and then the reaction mixture is poured into ice-water. The mixture is basified and extracted with dichloromethane. The solvent is concentrated to give 6-nitro-1-(4-piperidinyl)-3,4-dihydrocarbostyril (0.2 g).

NMR (CDCl$_3$) δ ppm: 1.65-2.10 (3H, m), 2.44-3.45 (10H, m), 4.26-4.55 (1H, m), 7.34 (1H, d, J=8.9 Hz), 8.00-8.22 (2H, m)

Using the suitable starting materials, the compounds of the above Examples 3, 38, 43, 163, 175, 188, 195, 379 and the following Example 510 are obtained in the same manners as in Example 387.

EXAMPLE 388

A mixture of 10% palladium-carbon (0.4 g) and acetic acid (50 ml) is added to 6-nitro-1-[1-(2,4-dimethoxybenzoyl)-4-piperidinyl]-3,4-dihydrocarbostyril (4.0 g) and the mixture is subjected to catalytic reduction at 70° C. for 1 hour. The catalyst is filtered off and the filtrate is concentrated. The resulting residue is basified with 10% aqueous sodium hydroxide solution and extracted with dichloromethane. The solvent is concentrated and the resulting residue is purified by silica gel column chromatography (solvent; dichloromethane:methanol=20:1) to give 6-amino-1-[1-(2,4-dimethoxybenzoyl)-4-piperidinyl]-3,4-dihydrocarbostyril (1.9 g).

NMR (CDCl$_3$) δ ppm: 1.50-1.93 (2H, m), 2.34-3.20 (8H, m), 3.30-4.15 (9H, m), 4.22-4.75 (1H, m), 4.85-5.03 (1H, m), 6.42-6.63 (4H, m), 6.82-7.33 (2H, m)

Using the suitable starting materials, the compounds of the above Examples 48, 80, 182, 176, 192, 380 and the following Examples 485, 511 are obtained in the same manners as in Example 388 and in following Example 401.

EXAMPLE 389

Dichloromethane (10 ml) and triethylamine (0.15 ml) are added to 6-amino-1-[1-(2,4-dimethoxybenzoyl)-4-piperidinyl]-3,4-dihydrocarbostyril (0.3 g). Acetic anhydride (0.2 ml) is added thereto and the mixture is stirred at room temperature for 1 hour. Water is added to the reaction mixture and extracted with dichloromethane. After concentration, the residue is purified by silica gel column chromatography (solvent; chloroform:methanol=20:1) and further recrystallized from ethanol to give 6-acetylamino-1-[1-(2,4-dimethoxybenzoyl)-4-piperidinyl]-3,4-dihydrocarbostyril (0.25 g) as white powder, m.p. 271°-272° C.

The compounds of the above Examples 160, 267, 359 and the following Examples 484 and 486 are obtained in the same manners as in Example 389.

EXAMPLE 390

7-Fluoro-1-(4-piperidinyl)-3,4-dihydrocarobstyril (2.37 g), 2-methoxy-4-ethoxybenzoic acid (2.43 g) and bis(2-oxo-oxazolydinyl)phosphinyl chloride (3.65 g) are dissolved in dichloromethane (50 ml) and thereto is added dropwise triethylamine (4 ml). The mixture is stirred at room temperature overnight and poured into water. The mixture is extracted with dichloromethane, dried with sodium carbonate and then purified by silica gel column chromatography (solvent; n-hexane:ethyl acetate=1:1). The resultant is recrystallized from ethanol/water to give 7-fluoro-1-[1-(2-methoxy-4-ethoxybenzoyl)-4-piperidinyl]-3,4-dihydrocarbostyril (2.5 g) as white powder, m.p. 159°-161° C.

EXAMPLE 391

1-(4-Piperidinyl)-3,4-dihydrocarbostyril (500 mg) and triethylamine (0.6 ml) are dissolved in dichloromethane (10 ml) and thereto is added dropwise ethyl chlorocarbonate (0.31 ml) gradually. The mixture is stirred at room temperature for 2 hours and poured into water. The mixture is extracted with chloroform, dried with sodium carbonate and purified by silica gel column chromatography (solvent; n-hexane:ethyl acetate=3:1). The resultant is recrystallized from ethanol/n-hexane to give 1-(1-ethoxycarbonyl-4-piperidinyl)-3,4-dihydrocarbostyril (0.1 g) as white powder, m.p. 82°-83° C.

EXAMPLE 392

1-(4-Piperidinyl)-3,4-dihydrocarbostyril (500 mg), triethylamine (1.2 ml) and pyrrole-2-carboxylic acid (314 mg) are dissolved in dichloromethane (10 ml) and thereto is added dropwise diethyl cyanophosphate (0.82 ml) under ice cooling. The mixture is stirred with ice cooling for 1 hour and then stirred at room temperature for 2 hours. The mixture is poured into water, extracted with chlorform, dried with sodium carbonate and purified by silica gel column chromatography (solvent; dichloromethane:methanol=20:1). The resultant is recrystallized from n-hexane/diethyl ether to give 1-[1-(2-pyrrolylcarbonyl)-4-piperidinyl]-3,4-dihyrocarbostyril (0.2 g), as white powder, m.p. 161°-162° C. (decomposed).

EXAMPLE 393

1-(4-Piperidinyl)-3,4-dihydrocarbostyril (0.8 g) is dissolved in dichloromethane (20 ml) and thereto is added phenylisocyanate (0.57 ml) and the mixture is stirred at room temperature for 4 hours. The solvent is concentrated and the residue is purified by silica gel column chromatography (solvent; n-hexane:ethyl acetate=5:1) and recrystallized from n-hexane/ethanol to give 1-(1-anilinocarbonyl-4-piperidinyl)-3,4-dihydrocarbostyril (0.8 g), as white powder, m.p. 194°-196° C.

The compounds of the above Examples 1-155, 157, 159-167, 169-170, 173-182, 187-232, 234-235, 241-243, 246-290, 294-346, 348-350, 362-383C and the following Examples 436, 438, 440, 442, 443-460, 465-475, 482-579 and 582-587 are obtained in the same manners as in Examples 390-393.

EXAMPLE 394

1-[1-(4-α-t-Butoxycarbonylaminophenylacetyl)-4-piperidinyl]-3,4-dihydrocarbostyril (400 mg) is dissolved in formic acid (5 ml) and the mixture is stirred at room temperature overnight. The solvent is distilled off under reduced pressure and the resulting oily product is purified by silica gel column chromatography (solvent; dichloromethane:methanol=8:1). The resultant is recrystallized from diethyl ether to give 1-[1-(4-α-aminophenylacetyl)-4-piperidinyl)-3,4-dihydrocarbostyril (0.22 g), as white powder, m.p. 116°-120° C.

EXAMPLE 395

A mixture (5 ml) of hydrobromic acid and acetic acid (35% solution) is added to 1-{1-[4-(N-t-butoxycarbonyl-N-methylamino)benzoyl]-4-piperidinyl}-3,4-dihyrocarbostyril (1.8 g) and the mixture is stirred at room temperature overnight. The reaction mixture is poured into water and the pH value thereof is adjusted to pH 12–14 by adding potassium carbonate. The mixture is extracted with chloroform, dried with sodium carbonate and then purified by silica gel column chromatography (solvent; n-hexane:ethyl acetate=1:1). The resultant is recrystallized from n-hexane/ethanol to give 1-{1-[4-(N-methylamino)benzoyl]-4-piperidinyl}-3,4-dihydrocarbostyril (1.2 g), as white powder, m.p. 184°–186° C.

EXAMPLE 396

1-[1-(1-Benzyloxycarbonyl-2-pyrrolidinylcarbonyl)-4-piperidinyl]-3,4-dihydrocarbostyril (0.87 g) is dissolved in ethanol (20 ml) and thereto is added 5% palladium-carbon (0.1 g). The mixture is stirred at room temperature under 1 atm. under hydrogen atmosphere. After the completion of the reaction, the catalyst is filtered off and the filtrate is concentrated. The resultant is purified by silica gel column chromatography (solvent; dichloromethane:methanol=8:1) to give 1-[1-(2-pyrrolidinylcarbonyl)-4-piperidinyl]-3,4-dihydrocarbostyril (205 mg).

NMR (CDCl$_3$) $\delta$ ppn: 1.72–2.29 (6H, m), 2.39–2.92 (7H, m), 3.10–3.32 (1H, m), 3.35–3.65 (2H, m), 3.82–4.25 (2H, m), 4.52–4.90 (2H, m), 6.30–7.35 (5H, m)

EXAMPLE 397

1-[1-(4-Benzyloxybenzoyl)-4-piperidinyl]-3,4-dihyrocarbostyril (4.76 g) is dissolved in methanol (100 ml) and thereto is added 5% palladium-carbon (1 g). The mixture is stirred at room temperature under 1 atm. under hydrogen atmosphere. After the completion of the reaction, the catalyst is filetered off and the filtrate is concentrated. The resultant is purified by silica gel column chromatography (solvent; n-hexane:ethyl acetate=1:1) and further recrystallized from n-hexane/ethanol to give 1-[1-(4-hydroxybenzoyl)-4-piperidinyl]-3,4-dihydrocarbostyril (2.5 g) as white powder, m.p. 182°–183° C.

EXAMPLE 398

60% Sodium hydride (0.34 g) is washed with n-hexane and thereto is added dimethylformamide (20 ml). Thereto are added 1-[1-(4-hydroxybenzoyl)-4-piperidinyl]-3,4-dihydrocarbostyril (1 g), 2-chloroethyldimethylamine hydrochloride (0.66 g) and sodium iodide (1.7 g) and the mixture is stirred at 50°–60° C. under argon atmosphere for 2 hours. Then, the mixture is further stirred at room temperature overnight. The reaction mixture is poured into water and extracted with ethyl acetate/toluene, dried with sodium carbonate. The resultant is purified by silica gel column chromatography (solvent; n-hexane:ethyl acetate=1:1) to give 1-{1-[1-(2-dimethylaminoethoxy)benzoyl]-4-piperidinyl}-3,4-dihydrocarbostyril (0.362 g).

NMR (DMSO-d$_6$) $\delta$ ppm: 1.72–1.94 (2H, m), 2.48–3.26 (10H, m), 2.66 (6H, s), 3.77–5.28 (5H, m), 6.94–7.45 (6H, m)

EXAMPLE 399

1-[1-(4-Hydroxybenzoyl)-4-piperidinyl]-3,4-dihydrocarbostyril (500 mg), prenyl bromide (0.5 ml) and 1,8-diazabicyclo[5.4.0]-undecene-7 (0.65 ml) are dissolved in isopropanol (10 ml) and the mixture is refluxed with heating for 4 hours. The solvent is distilled off under reduced pressure and the residue is purified by silica gel column chromatography (solvent; n-hexane:ethyl acetate=2:1) to give 1-{1-[4-(2-isopentenyloxy)benzoyl]-4-piperidinyl} -3,4-dihydrocarbostyril (0.159 g).

NMR (CDCl$_3$) $\delta$ ppm: 1.56–1.79 (2H, m), 1.75 (3H, s), 1.80 (3H, s), 2.47–3.14 (8H, m), 3.93–5.05 (3H, m), 4.53 (2H, d, J=6.8 Hz), 5.40–5.57 (1H, m), 6.83–7.53 (8H, m)

The compounds of the above Examples 10, 19, 23, 26, 30, 31, 33, 38, 44, 45, 47, 50, 54, 55, 56, 61, 66, 72, 74, 76, 84, 89, 91, 94, 95, 98, 99, 102, 106, 108–110, 113–115, 118–119, 121–155, 157, 159–164, 166, 167, 170, 172–180, 189, 194, 209, 212, 222–225, 227, 228, 230–232, 234–235, 241–243, 246–251, 254–256, 260–280, 285, 288–294, 296, 297, 299–328, 332–335, 338, 345, 348, 350, 362–365, 367–373, 377–378, 383A–383C and the following Examples 436, 438, 440, 442, 445, 472, 475, 482–577, 582–587 are obtained in the same manners as in Examples 398 and 399.

EXAMPLE 400

Trifluoroacetic acid (0.21 ml) is added dropwise with stirring to a mixture of 1-{1-[4-(3-hydroxypropoxy)benzoyl]-4-piperidinyl}-3,4-dihydrocarbostyril (0.51 g), NaOCN (0.16 g), toluene (5 ml) and chloroform (5 ml) at room temperature. After adding, the mixture is stirred at room temperature overnight. Ethyl acetate is added to the reaction mixture and the mixture-is washed with saturated aqueous sodium hydrogen carbonate solution, water and saline solution successively and then dried with sodium sulfate. The solvent is distilled off and the resulting residue is purified by silica gel column chromatography (solvent; dichloromethane:methanol=100:1) to give 1-{1-[4-(3-carbamoyloxypropoxy)benzoyl-4-piperidinyl}-3,4-dihydrocarbostyril (0.15 g).

NMR (CDCl$_3$) $\delta$ ppm: 1.60–2.32 (4H, m), 2.41–3.27 (8H, m), 3.71–5.15 (5H, m), 4.07 (2H, t, J=6.2 Hz), 4.26 (2H, t, J=6.2 Hz), 6.96 (2H, d, J=8.6 Hz), 6.99–7.40 (4H, m), 7.43 (2H, d, J=8.6 Hz)

The compounds of the above Examples 128, 313 and the following Examples 470, 569 are obtained in the same manners as in Example 400.

EXAMPLE 401

1-[1-(4-Nitrobenzoyl)-4-piperidinyl-3,4-dihydrocarbostyril (4.21 g) is dissolved in ethanol (100 ml) and thereto is added 5% palladium-carbon (1 g) and the mixture is stirred at room temperature under 1 atm. under hydrogen atomsphere. After the reaction, the catalyst is removed by fileration. The filtrate is concentrated and the residue is purified by silica gel column chromatography (solvent: dichloromethane:methanol=20:1) and recrystallized from n-hexane/ethanol to give 1-[1-(4-aminobenzoyl)-4-piperidinyl]-3,4-dihydrocarbostyril (2.1 g) as white powder, m.p.: 198°–199° C.

EXAMPLE 402

1-[1-(4-Methoxycarbonylbenzoyl)-4-piperidinyl]-3,4-dihydrocarbostyril (6.33 g) and sodium hydroxide (1.94 g) are dissolved in methanol (100 ml) and the mixture is stirred at room temperature overnight. After the solvent is concentrated, water is added to the residue and the mixture is extracted with diethyl ether. The aqueous layer is adjusted to pH 1 by adding conc. hydrochloric acid and extracted with ethyl acetate. The extract is dried with magnesium sulfate, concentrated and recrystallized from n-hexane/ethanol to give 1-[1-(4-carboxybenzoyl)-4-piperidinyl]-3,4-dihydrocarbostyril (4.5 g) as white powder, m.p.: 232°–235° C.

Using the suitable starting materials, the compounds of the above Examples 260, 275, 301, 303, 304, 308, 310, 316, 336, 365, 374 and the following Example 482 are obtained in the same manners as in Example 402.

EXAMPLE 403

1-{1-[4-(N-methylamino)benzoyl]-4-piperidinyl}-3,4-dihydrocarbostyril (200 mg) is dissolved in dichloromethane (5 ml) and thereto is added α-chloroacetyl chloride (55 μl) under ice cooling. Continually thereto is added triethylamine (0.23 ml) and the mixture is stirred at room temperature overnight. After the solvent is concentrated, the residue is purified by silica gel column chromatography (solvent: n-hexane:ethyl acetate=1:1) and recrystallized from n-hexane/ethanol to give 1-{1-[4-(N-α-chloroacetyl-N-methylamino)benzoyl}-4-piperidinyl]-3,4-dihydrocarbostyril (0.18 g) as white powder, m.p.: 220°–222° C. (decomposed).

EXAMPLE 404

1-[1-(4-Aminobenzoyl)-1-piperidinyl]-3,4-dihydrocarbostyril (4 g) is dissolved in dichloromethane (100 ml) and thereto is added trifluoroacetic anhydride (2.1 ml). Under ice cooling, thereto is added dropwise triethylamine (4.78 ml) and the mixture is stirred at the same temperature for 2 hours and then at room temperature overnight. The reaction mixture is poured into water and extracted with chloroform and dried with magnesium sulfate. The resulting residue is purified by silica gel column chromatography (solvent: n-hexane:ethyl acetate=1:1) and recrystallized from n-hexane to give 1-[1-(4-trifluoroacetylamino)-4-piperidinyl]-3,4-dihydrocarbostyril (3.8 g) as light red powder, m.p.: 104°–107° C.

EXAMPLE 405

A mixture of 1-[1-(2-aminobenzoyl)-4-piperidinyl]-3,4-dihydrocarbostyril (0.96 g), acetic anhydride (10 ml) and conc. sulfuric acid (0.1 ml) is stirred at room temperature for 2 hours. The reaction mixture is basified with 1N aqueous sodium hydroxide solution and extracted with ethyl acetate. The extract is washed successively with saturated aqueous sodium hydrogen carbonate solution, 1N hydrochloric acid and saturated saline solution and dried with sodium sulfate. After the solvent is distilled off, the residue is recrystallized from ethyl acetate/diethyl ether to give 1-[1-(2-acetylaminobenzoly)-4-piperidinyl]- 3,4-dihydrocarbostyril (0.55 g) as colorless needles, m.p.: 141°–143° C.

Using the suitable starting materials, the compounds of the above Examples 32, 57–59, 67, 78, 87, 88, 116, 129, 130, 137, 140–141, 145, 149–152, 155, 174, 187, 200, 246, 254, 255, 288, 291, 292, 382, 383, 383B, 383C and the following Examples 451, 452, 463, 467, 468, 469, 488, 500–503, 506–508, 510, 511, 513–515, 519–521, 523, 536, 537, 587 are obtained in the same manners as in Examples 403–405.

EXAMPLE 406

1-[1-(3-Ethoxycarbonylbenzoyl)-4-piperidinyl]-3,4-dihydrocarbostyril (0.5 g), aqueous ammonia (10 ml) and ammonium chloride (the effective amount as a catalyst) are dissolved in ethanol (10 ml) and the mixture is stirred at 110°–130° C. for 10 hours in an autoclave. Ethanol is distilled off under reduced pressure and the residue is extracted with methylene chloride. The organic layer is washed with water and saturated saline solution, dried with sodium sulfate and concentrated. The solvent is distilled off and the resulting residue is purified by silica gel column chromatography (solvent: methylene chloride:methanol=10:1) to give 1-[1-(3-carbamoylbenzoyl)-4-piperidinyl]-3,4-dihydrocarbostyril (0.15 g).

NMR (CDCl$_3$) δ ppm: 1.59–2.11 (2H, m), 2.48–3.33 (8H, m), 3.70–5.15 (3H, m), 5.58–6.60 (2H, m), 6.97–8.05 (8H, m)

Using the suitable starting materials, the compounds of the above Examples 276, 294, 300, 305, 307, 309, 313, 317–319, 321, 326, 329 and 344 are obtained in the same manners as in Example 406.

EXAMPLE 407

A mixture of 1-{1-[4-3-methylaminopropoxy)benzoyl]-4-piperidinyl}-3,4-dihydrocarbostyril (0.5 g), propyl bromide (0.13 ml), sodium hydrogen carbonate (0.15 g) and acetonitrile (10 ml) is stirred at room temperature for 8 hours. Further thereto are added propyl bromide (0.13 ml) and sodium hydrogen carbonate (0.15 g) and the mixture is stirred with heating at 60° C. for 8 hours. The solvent is distilled off and the resulting residue is extracted with ethyl acetate. The extract is washed successively with saturated sodium hydrogen carbonate, water and saline solution and dried with sodium sulfate. The solvent is distilled off and the resulting residue is purified by silica gel column chromatography (solvent: dichloromethane:methanol=20:1) to give 1-[1-{4-[3-(N-methyl-N-propylamino)propoxy]benzoyl}-4-piperidinyl]-3,4-dihydrocarbostyril (0.15 g).

NMR (CDCl$_3$) δ ppm: 0.91 (3H, t, J=5.8 Hz), 1.42–3.31 (21H, m), 2.33 (3H, s), 3.88–5.15 (3H, m), 4.05 (2H, t, J=5 Hz), 6.91 (2H, d, J=7 Hz), 6.95–7.38 (4H, m), 7.42 (2H, d, J=7 Hz)

EXAMPLE 408

A mixture of 1-{1-[4-(3-aminopropoxy)benzoyl]-4-piperidinyl}-3,4-dihydrocarbostyril (1.4 g), benzaldehyde (0.42 ml) and methanol (15 ml) is stirred at room temperature for 3 hours and cooled with ice. Thereto is added sodium boron hydride (0.21 g) and the mixture is stirred under ice cooling for 2 hours and then allowed to stand at room temperature overnight. The solvent is distilled off and water is added to the resulting residue and the mixture is extracted with ethyl acetate. The extract is washed successively with saturated sodium hydrogen carbonate, water and saline solution, dried with sodium sulfate and then the solvent is distilled off. The resulting residue is purified by silica gel column chromatography (solvent: methanol:dichloromethane=1:100) to give 1-{1-[4-benzylaminopropoxy)-benzoyl]-4-piperidinyl}-3,4-dihydrocarbostyril (1.02 g).

NMR (CDCl$_3$) δ ppm: 1.60–2.15 (5H, m), 2.47–3.18 (10H, m), 3.82 (2H, s), 3.95–5.11 (3H, m), 4.08 (3H, t, J=6.2 Hz), 6.89 (2H, d, J=8.5 Hz), 6.95–7.50 (9H, m), 7.42 (2H, d, J=8.5 Hz)

EXAMPLE 409

1-[1-(2-Methoxy-4-methylaminobenzoyl)-4-piperidinyl]-3,4-dihydrocarbostyril (500 mg) is dissolved in methanol (10 ml) and thereto is added formaldehyde (0.54 ml) and then thereto is added NaBH$_3$CN (86.4 mg) under ice cooling. The mixture is stirred under ice cooling for 2 hours and further stirred at room temperature. The reaction mixture is concentrated and to the residue is added saturated aqueous sodium hydrogen carbonate solution. The mixture is extracted with chloroform and dried with sodium sulfate. The solvent is distilled off and the resulting residue is purified by silica gel column chromatography (solvent: n-hexane:ethyl acetate=1:1) and recrystallized from n-hexane/ethanol to give 1-[1-(2-methoxy-4-dimethylaminobenzoyl)-4-piperazinyl]-3,4-dihydrocarbostyril (0.263 g) as white powder, m.p.: 93°–96° C.

Using the suitable starting materials, the compounds of the above Examples 27, 40, 55, 57, 59, 62, 63, 65, 67, 68, 76, 79, 81, 82, 88, 89, 92, 114, 115, 118, 119, 123, 124, 126, 127, 131, 133, 138, 139, 143, 144, 149, 150–152, 169, 184, 185, 187, 190, 198, 199, 214, 231, 236–238, 242–246, 248, 251, 254, 255, 261–263, 265, 268, 270, 283, 285, 287, 291–293, 305, 306, 309, 311, 321, 322, 326, 327, 332, 334, 335, 344, 346, 349, 361, 366, 367, 374, 381, 383A and the following Examples 448, 449, 454, 455, 456, 458, 459, 464, 466, 474A, 489–496, 498, 499, 504, 505, 509, 516–518, 522, 532, 539–546, 550–552, 554–556, 559, 562–565 and 567 are obtained in the same manners as in Examples 407–409.

EXAMPLE 410

A mixture of 1-[1-{4-[3-(N-benzyl-N-methylamino)propoxy]benzoyl}-4-piperidinyl]-3,4-dihydrocarbostyril (5.3 g), 5% palladium-carbon (0.8 g), ammonium formate (2.6 g) and ethanol (300 ml) is refluxed with heating for 2 hours. The catalyst is filtered off and ethanol is distilled off under reduced pressure. To the residue is added chloroform and the mixture is washed successively with saturated sodium hydrogen carbonate, water and saline solution. Further the mixture is dried with sodium sulfate and the solvent is distilled off. The resulting residue is purified by silica gel column chromatography (solvent: dichloromethane:methanol=20:1→5:1) to give 1-[1-{4-[3-(N-methylamino)propoxy]benzoyl}-4-piperidinyl]-3,4-dihydrocarbostyril (4.37 g).

This product is dissolved in acetone and converted into hydrochloride salt thereof in hydrochloric acid/ethanol. The precipitated crystal is collected by filtration and recrystallized from ethanol/acetone/diethyl ether to give 1-[1-{4-[3-(N-methylamino)propoxy]benzoyl}-4-piperidinyl]-3,4-dihydrocarbostyril hydrochloride as colorless needles, m.p.: 89°–93° C.

EXAMPLE 411

1-[1-{4-[3-(Phthalimido-1-yl)propoxy]benzoyl}-4-piperidinyl]-3,4-dihydrocarbostyril (9.5 g), hydrazine hydrate (1.03 ml) and ethanol (100 ml) are refluxed with heating for 2.5 hours. After cooling, the mixture is adjusted to pH 1 by adding conc. hydrochloric acid and the precipitated materials are filtered off. Most of ethanol is distilled off from the filtrate and water is added to the residue. The insoluble materials are filtered off and the mother liquid is basified with 5N sodium hydroxide, extracted with ethyl acetate. The organic layer is washed with saturated saline solution and dried with sodium sulfate, concentrated. The residue is purified by silica gel column chromatography (solvent: methylene chloride:methanol=15:1) to give 1-{1-[4-(3-aminopropoxy)benzoyl]-4-piperidinyl}-3,4-dihydrocarbostyril (5.18 g).

NMR (CDCl$_3$) δ ppm: 1.64–2.10 (4H, m), 2.97–3.18 (8H, m), 2.92 (2H, t, J=6.8 Hz), 4.08 (2H, t, J=6.1 Hz), 4.10–5.15 (3H, m), 6.82–7.58 (8H, m)

Using the suitable starting materials, the compounds of the above Examples 136, 148, 154 and the following Examples 473 and 586 are obtained in the same manners as in Example 411.

EXAMPLE 412

1-{1-[4-(3-Aminopropoxy)benzoyl]-4-piperidinyl}-3,4-dihydrocarbostyril (0.5 g), methylisocyanate (0.15 ml) and acetone (10 ml) are heated at 100° C. for 18 hours in an autoclave. Acetone is distilled off and the residue is purified by silica gel column chromatography (solvent: methylene chloride:methanol=100–50:1) to give 1-{1-[4-(3-(3-methylureido)propoxy)benzoyl]-4-piperidinyl}-3,4-dihydrocarbostyril (0.19 g).

NMR (CDCl$_3$) δ ppm: 1.55–2.20 (4H, m), 2.49–3.50 (10H, m), 2.96 (3H, m), 3.90–5.13 (4H, m), 4.09 (2H, t, J=5.7 Hz), 6.90 (2H, d, J=8.7 Hz), 6.95–7.38 (4H, m), 7.43 (2H, d, J=8.7 Hz)

EXAMPLE 413

A mixture of formic acid (0.19 ml) and acetic anhydride (0.4 ml) is stirred with heating at 50°–60° C. for 1.5 hour. Thereto is added 1-{1-[4-(4-aminobutoxy)benzoyl]-4-piperidinyl}-3,4-dihydrocarbostyril (0.6 g) at room temperature and the mixture is stirred at room temperature for 13 hours. The reaction mixture is poured into ice-water and extracted with ethyl acetate. The extract is washed with aqueous sodium hydrogen carbonate, water and saline solution and dried with sodium sulfate. The solvent is distilled off and the resulting residue is purified by silica gel column chromatography (solvent: dichloromethane:methanol=50:1→25:1) to give 1-{1-[4-(4-formylaminobutoxy)benzoyl]-4-piperidinyl}-3,4-dihydrocarbostyril (0.49 g).

NMR (CDCl$_3$) δ ppm: 1.55–2.00 (6H, m), 2.45–3.48 (10H, m), 3.76–5.10 (3H, m), 3.99 (2H, t, J=5.7 Hz), 5.74–6.25 (1H, m), 6.78–7.53 (8H, m), 8.15 (1H, s)

Using the suitable starting materials, the compounds of the above Example 130 and the following Examples 488 and 508 are obtained in the same manners as in Example 413.

EXAMPLE 414

1-[1-(4-Formylbenzoyl)-4-piperidinyl]-3,4-dihydrocarbostyril (500 mg) is dissolved in methanol (10 ml) and thereto is added sodium boron hydride (63 mg) under ice cooling and the mixture is stirred for 2 hours. The solvent is concentrated and the resulting residue is purified by silica gel column chromatography (solvent: n-hexane:ethyl acetate=2:1) and recrystallized from n-hexane/ethanol to give 1-[1-(4-hydroxymethylbenzoyl)-4-piperidinyl]-3,4-dihydrocarbostyril (390 mg) as white powder, m.p.: 138°–139° C.

Using the suitable starting materials, the compounds of the above Examples 83, 85 and the following Examples 444 and 456 are obtained in the same manners as in Example 414.

EXAMPLE 415

60% Sodium hydride (147 mg) is washed with n-hexane and thereto is added dimethylformamide (10 ml) under argon atmosphere. To the mixture is added 1-[1-(4-trifluoroacetylaminobenzoyl)-4-piperidinyl]-3,4-dihydrocarbostyril (1 g) under ice cooling, and the mixture is stirred for a while and then thereto is added dropwise allyl bromide (0.32 ml). The mixture is stirred under ice cooling for 1 hour and then at room temperature overnight to give 1-{1-[4-(N-trifluoroacetyl-N-allylamino)benzoyl]-4-piperidinyl}-3,4-dihydrocarbostyril. To this product are added water (20 ml) and sodium hydroxide (0.1 g) and the mixture is stirred for 4 hours. The reaction mixture is poured into water and extracted with ethyl acetate/toluene (1:1), dried with sodium carbonate. The solvent is distilled off and the resulting residue is purified by silica gel column chromatography (solvent: n-hexane:ethyl acetate=1:1) to give 1-[1-(4-allylaminobenzoyl)-4-piperidinyl]-3,4-dihydrocarbostyril (0.5 g).

NMR (CDCl$_3$) δ ppm: 1.72–1.92 (2H, m), 2.52–3.12 (8H, m), 3.72–3.88 (2H, m), 4.07 (1H, brs), 4.15–4.76 (3H, m), 5.14–5.35 (2H, m), 5.83–6.04 (1H, m), 6.56–6.62 (2H, m), 6.98–7.37 (6H, m)

EXAMPLE 416

1-[1-(2-Methoxy-4-methylthiobenzoyl)-4-piperidinyl]-3,4-dihydrocarbostyril (500 mg) is dissolved in methanol (10 ml) and thereto is added a solution of NaIO$_4$ (391 mg) in water (4 ml) and the mixture is stirred at room temperature overnight. The solvent is distilled off under reduced pressure, and water is added to the resulting residue. The mixture is extracted with chloroform, dried with magnesium sulfate. The solvent is distilled off and the resulting residue is purified by silica gel column chromatography (solvent: n-hexane:ethyl acetate=2:1) and recrystallized from n-hexane/ethanol to give 1-[1-(2-methoxy-4-methylsulfinylbenzoyl)-4-piperidinyl]-3,4-dihydrocarbostyril (0.31 g) as white powder, m.p.: 95°–98° C.

Using the suitable starting meterials, the compounds of the above Examples 51, 368 and the following Example 570 are obtained in the same manners as in Example 416.

EXAMPLE 417

1-[1-(2-Methoxy-4-acetyloxybenzoyl)-4-piperidinyl]-3,4-dihydrocarbostyril (0.4 g) and sodium hydroxide (0.5 g) are dissolved in methanol (20 ml) and the mixture is stirred at room temperature for 1 hour. The solvent is concentrated and water is added to the residue, then the mixture is extracted with chloroform, dried with magnesium sulfate. The solvent is ditilled off and the resulting residue is purified by silica gel column chromatography (solvent: n-hexane:ethyl acetate=1:1) to give 1-[1-(2-methoxy-4-hydroxybenzoyl)-4-piperidinyl]-3,4-dihydrocarbostyril (0.3 g).

NMR (CDCl$_3$) δ ppm: 1.56–1.95 (2H, m), 2.43–3.23 (8H, m), 3.56–3.83 (1H, m), 3.67 (3H, d, J=9.3 Hz), 4.23–4.67 (1H, m), 4.86–5.05 (1H, m), 6.26–6.42 (2H, m), 6.96–7.35 (5H, m), 8.57–8.73 (1H, m)

EXAMPLE 418

1-{1-[4-(2-Cyclohexenyloxy)benzoyl]-4-piperidinyl}-3,4-dihydrocarbostyril (200 mg) is dissolved in ethanol (5 ml) and thereto is added 10% palladium-carbon (50 mg). The mixture is stirred at room temperature under atmospheric pressure under hydrogen atmosphere. After the completion of the reaction, the catalyst is removed by filtration. The resulting filtrate is concentrated and purified by silica gel column chromatography (solvent: n-hexane:ethyl acetate=1:1) to give 1-[1-(4-cyclohexyloxybenzoyl)-4-piperidinyl]-3,4-dihydrocarbostyril (174 mg).

NMR (CDCl$_3$) δ ppm: 1.20–2.10 (12H, m), 2.44–3.13 (8H, m), 3.78–5.08 (4H, m), 6.90 (2H, d, J=8.7 Hz), 6.97–7.32 (4H, m), 7.40 (2H, d, J=8.7 Hz)

EXAMPLE 419

1-[1-(4-Formylbenzoyl)-4-piperidinyl]-3,4-dihydrocarbostyril (1 g), hydroxylamine hydrochloride (580 mg) and sodium acetate (1.6 g) are dissolved in ethanol (20 ml) and water (10 ml) and the mixture is stirred at room temperature overnight. The solvent is concentrated and water is added to the residue. The mixture is extracted with chloroform, dried with sodium carbonate. The solvent is distilled off and the resulting residue is purified by silica gel column chromatography (solvent: n-hexane:ethyl acetate=1:2) and recrystallized from n-hexane/ethanol to give 1-[1-(4-hydroxyiminomethylbenzoyl)-4-piperidinyl]-3,4-dihydrocarbostyril (1 g) as white powder, m.p.: 222°–224° C.

EXAMPLE 420

1-[1-(4-Aminobenzoyl)-4-piperidinyl]-3,4-dihydrocarbostyril (500 mg) and 2,5-dimethoxytetrahydrofuran (0.19 ml) are refluxed with heating for 2 hours in acetic acid. The solvent is concentrated and the residue is purified by silica gel column chromatography (solvent: n-hexane:ethyl acetate=1:1) and recrystallized from n-hexane to give 1-{1-[4-(1-pyrrolyl)benzoyl]-4-piperidinyl}-3,4-dihydrocarbostyril (228 mg) as light gray powder, m.p.: 153°–156° C.

EXAMPLE 421

1-[1-(4-Glycidoxybenzoyl)-4-piperidinyl]-3,4-dihydrocarbostyril (200 mg) is dissolved in methanol (4 ml) and thereto is added diethylamine (0.26 ml) and the mixture is stirred at room temperature overnight, and then refluxed with heating for 3 hours. The solvent is concentrated and the residue is purified by silica gel column chromatography (solvent: n-hexane:ethyl acetate=1:1→dichloromethane: methanol=10:1) to give 1-{1-[4-(3-diethylamino-2-hydroxypropoxy)benzoyl]-4-piperidinyl}-3,4-dihydrocarbostyril (0.18 g).

This product is stirred with the equivalent amount of citric acid in diethyl ether to give citrate salt thereof as white powder, m.p.: 72°–76° C. (recrystallized from diethyl ether).

Using the suitable starting materials, the compounds of the above Examples 118, 119, 335 and the following Examples 448, 474A, 489, 532–535, 537, 538, 541–558, 562–567 are obtained in the same manners as in Example 421.

EXAMPLE 422

1-[1-(4-Cyanobenzoyl)-4-piperidinyl]-3,4-dihydrocarbostyril (1 g) is dissolved in chloroform (10 ml) and thereto is added ethanol (0.18 ml). Under ice cooling, hydrochloric acid gas is passed through the mixture to saturate and further the mixture is stirred at 5°–7° C. for 4 days. After the reaction, the solvent is concentrated to give 1-{1-[4-(1-ethoxy-1-iminomethyl)benzoyl]-4-piperidinyl}-3,4-dihydrocarbostyril (1 g). This product is used for the subsequent reaction.

1-{1-[4-(1-Ethoxy-1-iminomethyl)benzoyl]-4piperidinyl{-3,4-dihydrocarbostyril (1 g) is dissolved in methanol (10 ml) and thereto is added aqueous ammonia (10 ml) and the mixture is stirred at room temperature overnight. The solvent is concentrated and water is added to the residue. The mixture is extracted with chloroform, dried with sodium carbonate, concentrated and then purified by silica gel column chromatography (solvent: chloroform: methanol=10:1) and recrystallized from ethanol/n-hexane to give 1-[1-(4-carbamoyl-4-piperidinyl]-3,4-dihydrocarbostyril (0.2 g) as white powder, m.p.: 101°–104° C.

Further, the aqueous layer is concentrated and the resulting residue is recrystallized from water to give 1-[1-(4-amidinobenzoyl)-4-piperidinyl]-3,4-dihydrocarbostyril (0.4 g) as white powder, m.p.: 92°–97° C.

NMR (CDCl₃) δppm: 1.55–1.92 (2H, m), 2.32–3.05 (7H, m), 3.12–3.62 (2H, m), 4.22–4.72 (2H, m), 6.92–7.38 (4H, m), 7.63 (2H, d, J=8.2 Hz), 7.92 (2H, d, J=8.2 Hz), 9.48 (3H, brs)

Using the suitable starting materials, the compound of the above Example 113 is obtained in the same manners as in Example 422.

EXAMPLE 423

1-{1-[4-(4-Pentenyloxy)benzoyl]-4-piperidinyl}-3,4-dihydrocarbostyril (2 g) is dissolved in dichloromethane (50 ml) and thereto is added gradually m-chloroperbenzoic acid (1.6 g) at room temperature. The mixture is stirred under the same conditions overnight and the reaction mixture is poured into aqueous sodium hydrogen carbonate solution and the mixture is extracted with chloroform and dried with magnesium sulfate. The solvent is distilled off and the resulting residue is purified by silica gel column chromatography (solvent: n-hexane:ethyl acetate=1:1) to give 1-{1-[4-(3-oxiranylpropoxy)benzoyl]-4-piperidinyl)-3,4-hydrocarbostyril (1.5 g).

NMR (CDCl₃) δppm: 1.52–2.10 (6H, m), 2.45–3.10 (11H, m), 3.72–5.10 (5H, m), 6.90 (2H, d, J=8.7 Hz), 6.97–7.32 (4H, m), 7.43 (2H, d, J=8.7 Hz)

Using the suitable starting materials, the compounds of the above Example 333 and the following Example 572 are obtained in the same manners as in Example 423.

EXAMPLE 424

1-[1-(4-Formylbenzoyl)-4-piperidinyl]-3,4-dihydrocarbostyril (4.77 g) is dissolved in methanol (100 ml) and thereto is added carbomethoxymethylenetriphenylphosphorane (5.3 g) and the mixture is stirred at room temperature for 1 hour. The solvent is concentrated and the residue is purified roughly by silica gel column chromatography (solvent: n-hexane:ethyl acetate=1:1) to give a mixture (8 g) of 1-{1-[4-(2-methoxycarbonylvinyl)benzoyl]-4-piperidinyl]-3,4-dihydrocarbostyril and triphenylphosphineoxide.

This mixture is dissolved in ethanol (100 ml) and thereto is added 10% palladium-carbon (1 g). The mixture is stirred at room temperature under 1 atm. under hydrogen atmosphere. After the reaction, the catalyst is removed by filtration and the resulting filtrate is concentrated. The resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl}-3,4-dihydrocarbostyril (3 g) as white powder, m.p.: 85°–86° C.

Using the suitable starting materials, the compounds of the above Examples 220, 336 and 339 are obtained in the same manners as in Example 424.

EXAMPLE 425

To a mixture of propyltriphenylphosphonium bromide (2.34 g), potassium-t-butoxide (62 mg) and sodium amide powder (0.3 g) is added tetrahydrofuran (110 ml) under argon atmosphere and the mixture is stirred at room temperature for 3 hours. To the resulting yellowish red solution is added 1-[1-(4-formylbenzoyl)-4-piperidinyl]-3,4-dihydrocarbostyril (2 g) gradually under ice cooling and the mixture is stirred under the same conditions for 3 hours. The reaction mixture is poured into water and extracted with ethyl acetate/toluene and then dried over sodium carbonate. The resultant is purified by silica gel column chromatography (solvent: n-hexane:ethyl acetate=1:1) to give 1-{1-[4-(1-butenyl)benzoyl]-4-piperidinyl}-3,4-dihydrocarbostyril (2 g).

NMR (CDCl₃) δppm: 1.05–1.33 (3H, m), 1.66–2.02 (2H, m), 2.30–3.26 (10H, m), 3.85–5.13 (3H, m), 5.69–5.83, 6.35–6.75 (2H, m), 7.02–7.54 (8H, m)

EXAMPLE 426

Ethanethiol (0.125 ml) is dissolved in methanol (10 ml) and thereto is added sodium methoxide (0.11 g). The mixture is stirred at room temperature for 30 minutes. Thereto is added a solution of 1-{1-[4-(3-bromopropoxy)benzoyl]-4-piperidinyl}-3,4-dihydrocarbostyril (0.59 g) in methanol (2 ml) and the mixture is stirred at room temperature overnight. The solvent is concentrated and water is added to the residue, extracted with chloroform, dried with sodium carbonate. The solvent is distilled off and the resulting residue is purified by silica gel column chromatography (solvent: n-hexane:ethyl acetate=1:1) to give 1-{1-[4-(3-ethylthiopropoxy)benzoyl]-4-piperidinyl}-3,4-dihydrocarbostyril (0.2 g).

NMR (CDCl₃) δppm: 1.27 (3H, t, J=7.4 Hz), 1.68–1.92 (2H, m), 1.98–2.18 (2H, m), 2.45–3.14 (10H, m), 3.70–5.15 (3H, m), 4.10 (2H, t, J=6.1 Hz), 6.91 (2H, d, J=8.6 Hz), 6.99–7.32 (4H, m), 7.43 (2H, d, J=8.6 Hz)

Using the suitable starting materials, the compounds of the above Example 40, 55, 56, 66, 114, 115, 129, 132, 133, 135, 136, 137–141, 143, 145, 146, 147, 148, 153–155, 234, 235, 241–243, 246, 249, 250, 251, 255, 261, 262, 268–270, 276, 294, 300, 305–307, 309, 311, 317–319, 321, 322, 325–327, 332, 367, 383A–383C and the following Examples 445, 449–459, 466–469, 471–473, 488–496, 498–531, 539–540, 559–560, 569, 585–587 are obtained in the same manners as in Example 426.

EXAMPLE 427

1-[1-(4-Vinylbenzoyl)-4-piperidinyl]-3,4-dihydrocarbostyril (0.6 g) is dissolved in ethanol (10 ml) and thereto is added 10% palladium-carbon (0.1 g) and the mixture is stirred under hydrogen atmosphere. After the reaction, the catalyst is removed by filtration and the filtrate is concentrated. The resultant is purified by silica gel column chromatography-(solvent: n-hexane:ethyl acetate=1:1) and recrystallized from n-hexane/ethanol to give 1-[1-(4-ethylbenzoyl)-4-piperidinyl]-3,4-dihydrocarbostyril (0.5 g) as white powder, m.p.: 133°–134° C.

Using the suitable starting materials, the compounds of the above Examples 69, 220 and 339 are obtained in the same manners as in Example 427.

EXAMPLE 428

1-[1-(4-Allyloxybenzoyl)-4-piperidinyl]-3,4-dihydrocarbostyril (1.15 g) is dissolved in N,N-dimethylaniline (5 ml) and the mixture is heated at 180°–190° C. for 8 hours. After cooling, the reaction mixture is adjusted to around pH 4 by adding hydrochloric acid thereto. The mixture is extracted with dichloromethane and dried with magnesium sulfate. The solvent is distilled off and the residue is purified by silica gel column chromatography (solvent: n-hexane:ethyl acetate=3:1→1:3) and further purified by silica gel column chromatography (solvent: dichloromethane:methanol=100:1) and recrystallized from dichloromethane/n-hexane to give 1-[1-(4-hydroxy-3-allylbenzoyl)-4-piperidinyl]-3,4-dihydrocarbostyril (0.22 g) as white powder, m.p.: 87°–90° C.

Using the suitable starting materials, the compound of the above Example 282 is obtained in the same manners as in Example 428.

EXAMPLE 429

To a solution of 1-(4-aminophenyl)-3,4-dihydrocarbostyril (0.45 g) in dichloromethane (15 ml) is added triethylamine (0.29 g). Thereto is added 2,4-dimethoxybenzoyl chloride (0.42 g) with stirring under ice cooling. The mixture is refluxed with heating for 0.5 hour. After cooling, water is added thereto and the mixture is extracted with dichloromethane, washed with water and then dried with magnesium sulfate. The solvent is distilled off under reduced pressure and the residue is purified by silica gel column chromatography and recrystallized from ethanol/diethyl ether/n-hexane to give 1-[4-(2,4-dimethoxybenzoylamino)phenyl]-3,4-dihydrocarbostyril (0.44 g) as white powder, m.p.: 226°–227° C.

Using the suitable starting materials, the compound of the above Example 292 is obtained in the same manners as in Example 429.

Example 430

To a solution of 1-[4-(4-methoxyanilinocarbonyl)-phenyl]-3,4-dihydrocarbostyril (0.2 g) in dimethylformamide (15 ml) is added 60% sodium hydride (24 mg) with stirring under ice cooling and the mixture is stirred at room temperature for 0.5 hour. Then, thereto is added a solution of ethyl bromide (64 mg) in dimethylformamide (DMF, 1 ml) and the mixture is refluxed with heating for 1 hour. DMF is distilled off under reduced pressure and water is added to the residue and the mixture is extracted with dichloromethane. The extract is washed with water and dried with magnesium sulfate. The solvent is distilled off under reduced pressure and the resulting residue is purified by silica gel column chromatography to give 1-[4-(N-ethyl-4-methoxyanilinocarbonyl)phenyl]-3,4-dihydrocarbostyril (0.12 g).

NMR (CDCl$_3$) δppm: 2.76 (3H, t, J=8.1 Hz), 3.0 (3H, t, J=8 Hz), 3.48 (3H, s), 3.75 (3H, s), 6.19 (1H, dd, J=3.1 Hz, 6 Hz), 6.78 (2H, d, J=8.3 Hz), 6.9–7.2 (7H, m), 7.43 (2H, d, J=8.4 Hz)

EXAMPLE 431

To a solution of 1-[4-(2,4-dimethoxybenzoylamino)-phenyl]-3,4-dihydrocarbostyril (0.19 g) in dimethylformamide (8 ml) is added with stirring 60% sodium hydride (0.02 g) under ice cooling. The mixture is stirred at room temperature for 0.5 hour and thereto is added a solution of methyl iodide (0.08 g) in dimethylformamide (6 ml). The mixture is stirred at room temperature for 3 hours. The solvent is distilled off under reduced pressure and water is added to the residue. The mixture is extracted with dichloromethane, washed with water and dried with magnesium sulfate. The solvent is distilled off under reduced pressure and the resulting residue is purified by silica gel column chromatography to give 1-{4-[N-(2,4-dimethoxybenzoyl)-N-methylamino]phenyl}-3,4-dihydrocarbostyril (70 mg).

NMR (CDCl$_3$) δppm: 2.78 (3H, t, J=8 Hz), 3.04 (3H, t, J=8 Hz), 3.50 (3H, s), 3.59 (3H, s), 3.76 (3H, s), 6.0–6.1 (1H, m), 6.2 (1H, brs), 6.41 (1H, dd, J=2.3 Hz, 8.4 Hz), 6.9–7.1 (4H, m), 7.1–7.3 (4H, m)

Using the suitable starting materials, the compounds of the above Examples 245, 236, 237, 172, 292 and 347 are obtained in the same manners as in Examples 430 and 431.

EXAMPLE 432

To a solution of 1-(4-carboxyphenyl)-3,4-dihydrocarbostyril (0.2 g) in chloroform (5 ml) is added thionyl chloride (0.8 ml) and the mixture is refluxed with heating for 1 hour. Then, chloroform and thionyl chloride are distilled off under reduced pressure to give 4-(3,4-dihydrocarbostyril-1-yl)benzoic acid chloride.

To a solution of p-anisidine (0.11 g) in chloroform (5 ml) is added triethylamine (0.15 g) and thereto is added with stirring a solution of 4-(3,4-dihydrocarbostyril-1-yl)benzoic acid chloride obtained above in chloroform (2 ml) under ice cooling. The mixture is stirred at room temperature overnight. Water is added to the reaction mixture and the mixture is extracted with dichloromethane, washed with water and dried with magnesium sulfate. The solvent is distilled off under reduced pressure and the resulting residue is crystallized from diethyl ether and further recrystallized from ethanol/diethyl ether/n-hexane to give 1-[4-(4-methoxyanilinocarbonyl)phenyl]-3,4-dihydrocarbostyril (240 mg) as white powder, m.p.: 254°–255° C.

Using the suitable starting materials, the compounds of the above Examples 172, 183–186, 233, 236–240, 244, 245 and 347 are obtained in the same manners as in Example 432.

EXAMPLE 433

To a solution of 1-[4-(1-piperazinylcarbonyl)phenyl]-3,4-dihydrocarbostyril (0.15 g) in dichloromethane (20 ml) is added triethylamine (91 mg), and further thereto is added with stirring a solution of benzoyl chloride (69 mg) in dichloromethane (2 ml) under ice cooling and the mixture is stirred at room temperature for 1 hour. Water is added thereto and the mixture is extracted with dichloromethane, dried with magnesium sulfate. The solvent is distilled off under reduced pressure and the resulting residue is crystallized by adding diethyl ether and n-hexane. The precipitated crystal is recrystallized from ethanol/diethyl ether/n-hexane to give 1-[4-(4-benzoyl-1-piperazinyl)phenyl]-3,4-dihydrocarbostyril (0.16 g) as white powder, m.p.: 188°–189° C.

Using the suitable starting materials, the compound of the above Example 240 is obtained in the same manners as in Example 433.

EXAMPLE 434

1-{1-[4-(2-Carboxyethyl)benzoyl]-4-piperidinyl}-3,4-dihydrocarbostyril (2 g) is dissolved in methanol (50 ml) and thereto is added dropwise thionyl chloride (1.1 ml) under ice cooling. After adding, the mixture is stirred at 0°–5° C. for 1 hour and further at room temperature overnight. The solvent is concentrated and the resulting residue is purified by silica gel column chromatography (solvent: n-hexane:ethyl acetate=1:1) and recrystallized from n-hexane to give 1-{1-[4-(2-methoxycarbonylethyl)benzoyl]-4-piperidinyl56 -3,4-dihyrocarbostyril (1.46 g) as white powder, m.p.: 85°–86° C.

Using the suitable starting materials, the compounds of the above Examples 49, 111, 112, 123, 127, 181, 213, 264, 274, 297, 299, 302, 306, 311, 320, 322, 323, 327, 328 and 342 are obtained in the same manners as in Example 434.

Using the suitable starting materials, the following compounds are obtained in the same manners as in Examples 1 and 384.

TABLE 3

Structure:

![structure: carbostyril with (R¹)q on benzene ring and N-R]

Bond between 3- and 4-positions in the carbostyril ring: Single bond

| | R | R¹ | q | Crystalline form | Recrystallization solvent | Melting Point/ NMR analysis | Form |
|---|---|---|---|---|---|---|---|
| Example 435 | ![NH-cyclohexyl-CH3] | F (6-, 7-positions) | 2 | | | 210) | Free |
| Example 436 | ![structure with OC2H5, OCH3, N-piperidyl-CH3, C=O] | F (6-, 7-positions) | 2 | White powders | Ethanol | 135–136° C. | Free |
| Example 437 | ![NH-cyclohexyl-CH3] | F (5-, 7-positions) | 2 | White powders | Ethanol | 137–140° C. | Free |
| Example 438 | ![structure with OC2H5, OCH3, N-piperidyl-CH3, C=O] | F (5-, 7-positions) | 2 | White powders | Ethanol | 178–180° C. | Free |
| Example 439 | ![NH-cyclohexyl-CH3] | CH3 (3-position) | 1 | | | 211) | Free |
| Example 440 | ![structure with OC2H5, OCH3, N-piperidyl-CH3, C=O] | CH3 (3-position) | 1 | | | 212) | Free |

TABLE 3-continued

| | Structure | | | Crystalline form | Recrystallization solvent | Melting Point/ NMR analysis | Form |
|---|---|---|---|---|---|---|---|
| | R | R¹ | q | | | | |
| Example 441 | 4-methylpiperidin-1-yl (NH linker) | CO$_2$C$_2$H$_5$ (3-position) | 1 | | | 213) | Free |
| Example 442 | 2,4-disubstituted benzoyl piperidine (OC$_2$H$_5$, OCH$_3$) | CO$_2$C$_2$H$_5$ (3-position) | 1 | | | 214) | Free |
| Example 443 | 4-(CH=CH-CH(OH)-CH$_2$OH)phenyl-carbonyl piperidine; Bond between 3- and 4-positions in the carbostyril ring: Double bond | H | 1 | | | 215) | Free |
| Example 444 | 4-((CH$_2$)$_4$OH)phenylcarbonyl piperidine; Bond between 3- and 4-positions in the carbostyril ring: Single bond | H | 1 | White powders | Ethanol/n-hexane | 140–143° C. | Free |
| Example 445 | 4-(H$_3$C-C(=O)-(CH$_2$)$_4$O)phenylcarbonyl piperidine | H | 1 | | | 216) | Free |
| Example 446 | 4-(H$_5$C$_2$-O(CH$_2$)$_3$SO)phenylcarbonyl piperidine | H | 1 | | | 217) | Free |

TABLE 3-continued

| | Structure | | | Crystalline form | Recrystallization solvent | Melting Point/ NMR analysis | Form |
|---|---|---|---|---|---|---|---|
| | R | R¹ | q | | | | |
| Example 447 | (piperidine-N-C(=O)-phenyl-O(CH₂)₃SO₂C₂H₅) | H | 1 | | | 218) | Free |
| Example 448 | (piperidine-N-C(=O)-phenyl-O(CH₂)₄CHOH-N(CH₃)₂) | H | 1 | | | 219) | Free |
| Example 449 | (piperidine-N-C(=O)-phenyl-O(CH₂)₃N-piperazine-N-CH₂-phenyl) | H | 1 | White powders | Ethanol/water | 208–210° C. | Dioxalate |
| Example 450 | (piperidine-N-C(=O)-phenyl-O(CH₂)₃N-piperazine-NH) | H | 1 | Light yellow powders | n-Hexane/diethyl ether | 64–68° C. | Dihydrochloride.trihydrate |
| Example 451 | (piperidine-N-C(=O)-phenyl-O(CH₂)₃N-piperazine-N-CO-CH₃) | H | 1 | | | 220) | Free |
| Example 452 | (piperidine-N-C(=O)-phenyl-O(CH₂)₃N-piperazine-N-CO-phenyl) | H | 1 | | | 221) | Free |

TABLE 3-continued

| | Structure | | | | | Melting Point/ | |
|---|---|---|---|---|---|---|---|
| | R | R¹ | q | Crystalline form | Recrystallization solvent | NMR analysis | Form |
| Example 453 | [structure: phenyl-NH-CO-piperazine-(CH₂)₃O-C₆H₄-C(=O)-N-(4-methylcyclohexyl)] | H | 1 | | | 222) | Free |
| Example 454 | [structure: H₃C-piperazine-(CH₂)₃O-C₆H₄-C(=O)-N-(4-methylcyclohexyl)] | H | 1 | White powders | Ethanol/water | 214–217° C. | Dioxalate |
| Example 455 | [structure: PhCH₂-piperazine-(CH₂)₃O-C₆H₄-C(=O)-N-(4-methylcyclohexyl)] | H | 1 | White powders | Ethanol/water | 208–211° C. (decomposed) | Dioxalate |
| Example 456 | [structure: (HO)HCH₂C-piperazine-(CH₂)₃O-C₆H₄-C(=O)-N-(4-methylcyclohexyl)] | H | 1 | White powders | Ethanol/water | 206–210° C. | Dioxalate |
| Example 457 | [structure: pyrrolidine-(CH₂)₄O-C₆H₄-C(=O)-N-(4-methylcyclohexyl)] | H | 1 | | | 223) | Free |

TABLE 3-continued

| | Structure | | | | | Melting Point/ | |
|---|---|---|---|---|---|---|---|
| | R | R¹ | q | Crystalline form | Recrystallization solvent | NMR analysis | Form |
| Example 458 | 4-(H₃CHN-O(CH₂)₃CO-O-)C₆H₄-N(C=O)- cyclohexyl | H | 1 | | | 224) | Free |
| Example 459 | 4-(H₅C₂HN-O(CH₂)₃CO-O-)C₆H₄-N(C=O)- cyclohexyl | H | 1 | | | 225) | Free |
| Example 460 | 4-(O(CH₂)₅OH)C₆H₄-N(C=O)-cyclohexyl | H | 1 | Colorless needles | Ethanol/diethyl ether | 123–125° C. | Free |
| Example 461 | 4-NO₂-C₆H₄-NH-C(=O)-cyclohexyl | H | 1 | Light yellow needles | Ethanol/chloroform | 194–196° C. | Free |
| Example 462 | 4-NH₂-C₆H₄-NH-C(=O)-cyclohexyl | H | 1 | | | 226) | Free |
| Example 463 | 4-NHCOCH₃-C₆H₄-NH-C(=O)-cyclohexyl | H | 1 | Colorless prisms | Ethanol | 249–252° C. | Free |
| Example 464 | 4-N(CH₃)₂-C₆H₄-NH-C(=O)-cyclohexyl | H | 1 | Colorless prisms | Methanol | 107–110° C. | Free |

TABLE 3-continued

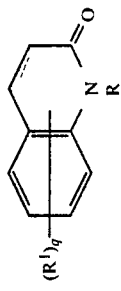

| | Structure | | | | | Melting Point/ | |
|---|---|---|---|---|---|---|---|
| | R | R¹ | q | Crystalline form | Recrystallization solvent | NMR analysis | Form |
| Example 465 | [4-methylcyclohexyl-N(C=O)-C6H4-O(CH2)6OH] | H | 1 | Colorless needles | Ethanol/diethyl ether | 120–122° C. | Free |
| Example 466 | [4-methylcyclohexyl-N(C=O)-C6H4-O(CH2)6NH-SO2CH3] | H | 1 | | | 227) | Free |
| Example 467 | [4-methylcyclohexyl-N(C=O)-C6H4-O(CH2)6NH-COCH3] | H | 1 | | | 228) | Free |
| Example 468 | [4-methylcyclohexyl-N(C=O)-C6H4-O(CH2)4NH-CO-C6H4-N(CH3)CO2CH2C6H5] | H | 1 | | | 229) | Free |
| Example 469 | [4-methylcyclohexyl-N(C=O)-C6H4-O(CH2)4NH-CO-C6H4-NHCH3] | H | 1 | | | 230) | Free |

TABLE 3-continued

| | Structure | | | | | Melting Point/ | |
|---|---|---|---|---|---|---|---|
| | R | R¹ | q | Crystalline form | Recrystallization solvent | NMR analysis | Form |
| Example 470 | [4-(H₂N(CH₂)₅OCO)-phenyl-C(=O)-N-(4-methylpiperidine)] | H | 1 | | | 231) | Free |
| Example 471 | [4-(phthalimido-(CH₂)₆O)-phenyl-C(=O)-N-(4-methylpiperidine)] | H | 1 | | | 232) | Free |
| Example 472 | [4-(H₃C(CH₂)₆OCO)-phenyl-C(=O)-N-(4-methylpiperidine)] | H | 1 | | | 233) | Free |
| Example 473 | [4-(H₂N(CH₂)₆O)-phenyl-C(=O)-N-(4-methylpiperidine)] | H | 1 | | | 234) | Free |
| Example 474 | [4-(Br(CH₂)₄O)-phenyl-C(=O)-N-(4-methylpiperidine)] | H | 1 | | | 235) | Free |
| Example 474A | [4-((H₅C₂)(H₅C₂)C(NH₂)CH(OH)(CH₂)₄O)-phenyl-C(=O)-N-(4-methylpiperidine)] | H | 1 | | | 236) | Free |

TABLE 4

| No. | NMR (CDCl₃) δ value |
|---|---|
| 210 | 1.60 (1H, s), 1.68–1.85 (2H, m), 2.35–2.92 (8H, m) 3.15–3.32 (2H, m), 4.18–4.40 (1H, m), 6.86–7.18 (2H, m) |
| 211 | 1.21 (3H, d, J=6.5 Hz), 1.60–2.00 (3H, m), 2.35–2.95 (8H, m), 3.14–3.37 (2H, m), 4.28–4.50 (1H, m) 6.95–7.32 (4H, m) |
| 212 | 1.21 (3H, d, J=6.5 Hz), 1.42 (3H, t, J=7.0 Hz), 1.62–2.04 (2H, m), 2.30–3.28 (7H, m), 3.55–3.95 (4H, m), 4.04 (2H, q, J=7.0 Hz), 4.25–5.10 (2H, m) 6.38–6.60 (2H, m), 6.98–7.40 (5H, m) |
| 213 | 1.18 (3H, t, J=7.1 Hz), 1.50–1.88 (3H, m), 2.50–3.46 (9H, m), 3.60–3.62 (2H, m), 4.03–4.28 (2H, m), 4.47–4.60 (1H, m), 6.95–7.30 (4H, m) |
| 214 | 1.17 (3H, t, J=7.1 Hz), 1.42 (3H, t, J=7.0 Hz), 1.56–2.00 (2H, m), 2.38–3.35 (6H, m), 3.42–5.10 (11H, m), 6.37–6.60 (2H, m), 6.95–7.40 (5H, m) |
| 215 | 1.58–1.97 (2H, m), 2.43–3.22 (10H, m), 3.65–5.12 (5H, m), 5.68–5.84, 6.18–6.36 (total: 1H, m), 6.51 (1H, d, J=15.9 Hz), 6.46–7.49 (8H, m) |
| 216 | 1.56–1.98 (6H, m), 2.05 (3H, s), 2.52–3.21 (10H, m) 3.76–5.08 (5H, m), 6.98–7.43 (8H, m) |
| 217 | 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m) |
| 218 | 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m) |
| 219 | 1.34–1.93 (8H, m), 2.17–2.42 (2H, m), 2.31 (6H, s), 2.51–3.04 (9H, m), 3.62–5.07 (6H, m), 6.86–6.95 (2H, m), 6.97–7.32 (4H, m), 7.36–7.48 (2H, m) |
| 220 | 1.68–2.18 (4H, m), 2.09 (3H, s), 3.28–3.13 (14H, m), 3.43–3.72 (4H, m), 3.86–5.08 (5H, m), 6.85–7.50 (8H, m) |
| 221 | 1.70–2.08 (4H, m), 2.34–3.12 (14H, m), 3.34–5.04 (9H, m), 6.88–7.52 (8H, m), 7.40 (5H, s) |
| 222 | 1.72–2.14 (4H, m), 2.40—3.14 (14H, m), 3.43–3.60 (4H, m), 3.73–5.13 (5H, m), 6.47 (1H, brs), 6.88–7.48 (13H, m) |
| 223 | 1.71–2.15 (6H, m), 2.46–3.20 (8H, m), 3.80–5.15 (2H, m), 3.96 (4H, t, J=6.8 Hz), 4.39 (1H, m), 6.15 (2H, t, J=2.1 Hz), 6.67 (2H, t, J=2.1 Hz), 6.88 (2H, d, J=8.7 Hz), 6.99–7.28 (4H, m), 7.42 (2H, d, J=8.7 Hz) |
| 224 | 1.60–1.98 (2H, m), 2.11 (2H, quint, J=6.5 Hz), 2.36 (2H, t, J=6.5 Hz), 2.53–3.15 (8H, m), 2.78 (3H, d, J=4.8 Hz), 3.60–5.10 (2H, brs), 4.00 (2H, t, J=6.5 Hz), 4.36 (1H, m), 6.16 (1H, brs), 6.88 (2H, d, J=8.7 Hz), 6.99–7.29 (4H, m), 7.41 (2H, d, J=8.7 Hz) |
| 225 | 1.33 (3H, t, J=6.8 Hz), 1.65–1.94 (2H, m), 2.14 (2H, quint, J=6.6 Hz), 2.37 (2H, t, J=6.6 Hz), 2.46–3.12 (8H, m), 3.80–5.00 (2H, m), 4.03 (2H, t, J=6.6 Hz), 4.05 (2H, q, J=6.8 Hz), 4.38 (1H, m), 5.69 (1H, brs), 6.90 (2H, d, J=8.6 Hz), 6.98–7.30 (4H, m), 7.42 (2H, d, J=8.6 Hz) |
| 226 | 1.63–1.92 (2H, m), 2.40–3.80 (10H, m), 4.08–4.55 (3H, m), 6.41 (1H, brs), 6.52–6.75 (2H, m), 6.92–7.35 (6H, m), |
| 227 | 1.31–2.02 (10H, m), 2.47–3.25 (10H, m), 2.95 (3H, s), 3.98 (2H, t, J=6.3 Hz), 4.04–5.05 (4H, m), 6.89 (2H, d, J=8.8 Hz), 6.95–7.37 (4H, m), 7.42 (2H, d, J=8.8 Hz), |
| 228 | 1.25–2.18 (13H, m), 2.45–3.40 (10H, m), 3.97 (2H, t, J=6.4 Hz), 4.05–5.07 (3H, m), 5.79 (1H, brs), 6.89 (2H, d, J=8.7 Hz), 6.95–7.37 (4H, m), 7.42 (2H, d, J=8.7 Hz) |
| 229 | 1.60–2.05 (6H, m), 2.43–3.15 (8H, m), 3.34 (3H, s), 3.49–3.63 (2H, m), 3.82–5.05 (5H, m), 5.17 (2H, s), 6.50 (1H, brs), 6.88 (2H, d, J=8.6 Hz), 6.94–7.49 (13H, m), 7.74 (2H, d, J=8.6 Hz) |
| 230 | 1.60–2.07 (6H, m), 2.42–3.18 (11H, m), 3.35–3.62 (2H, m), 3.80–5.09 (6H, m), 6.20–6.45 (1H, m), 6.54 (2H, d, J=8.7 Hz), 6.88 (2H, d, J=8.7 Hz), 6.94–7.35 (4H, m), 7.40 (2H, d, J=8.7 Hz), 7.63 (2H, d, J=8.7 Hz) |
| 231 | 1.45–1.99 (8H, m), 2.48–3.18 (8H, m), 3.99 (2H, t, J=6.3 Hz), 4.10 (2H, t, J=6.3 Hz), 4.17–5.08 (5H, m), 6.82–7.54 (8H, m) |
| 232 | 1.27–1.99 (10H, m), 2.40–3.15 (8H, m), 3.70 (2H, t, J=7 Hz), 3.97 (2H, t, J=6.3 Hz), 4.08–5.10 (3H, m), 6.29–7.96 (12H, m) |
| 233 | 1.26–1.95 (10H, m), 2.05 (3H, s), 2.45–3.18 (8H, m), 3.87–5.08 (7H, m), 6.82–7.52 (8H, m) |
| 234 | 1.25–2.03 (12H, m), 2.45–3.26 (10H, m), 3.98 (2H, t, J=6.4 Hz), 4.08–5.11 (3H, m), 6.90 (2H, d, J=8.8 Hz), 6.90–7.39 (4H, m), 7.42 (2H, d, J=8.8 Hz) |
| 235 | 1.63–2.22 (6H, m), 2.47–3.18 (8H, m), 3.63 (2H, t, J=6.6 Hz), 3.94–5.04 (5H, m), 6.82–7.52 (8H, m) |
| 236 | 1.11 (6H, t, J=7.2 Hz), 1.35–1.96 (8H, m), 2.32–3.13 (14H, m), 3.58–5.07 (5H, m), 4.00 (2H, t, J=6.3 Hz), 6.83–6.95 (2H, m), 6.98–7.32 (4H, m), 7.35–7.48 (2H, m), |

The following compound is obtained in the same manner as in Examples 1 and 385.

TABLE 5

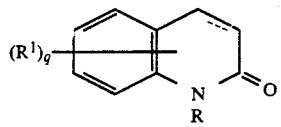

| | Structure | | | Crystalline | Recrystallization | | |
|---|---|---|---|---|---|---|---|
| | R | R¹ | q | form | solvent | Melting point | Form |
| | Bond between 3- and 4-positions in the carbostyril ring: Double bond | | | | | | |
| Example 475 | -N◯-N-C(=O)-◯-OC₂H₅ | H | 1 | Colorless needles | Ethanol/diethyl ether | 144–146° C. | Free |

EXAMPLE 476

To a solution of 1-{1-[4-(3-ethylthiopropoxy)benzoyl]-4-piperidinyl}-3,4-dihydrocarbostyril (0.44 g) in dichloromethane (10 ml) is added m-chloroperbenzoic acid (0.52 g) under ice cooling. The mixture is stirred at room temperature overnight, and the reaction mixture is poured into aqueous sodium carbonate solution. The mixture is extracted with chloroform and dried with sodium carbonate. The solvent is distilled off and the resulting residue is purified by silica gel column chromatography (solvent: n-hexane:ethyl acetate=1:2) to give 1-{1-[4-(3-ethylsulfonylpropoxy)benzoyl]-4-piperidinyl}-3,4-dihydrocarbostyril (0.19 g.).

NMR (CDCl₃) δppm: 1.44 (3H, t, J=7.5 Hz), 1.68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

EXAMPLE 478

A mixture of 1-{1-[4-(4-aminobutoxy)benzoyl]-4-piperidinyl}-3,4-dihydrocarbostyril (0.50 g), acetic acid (10 ml) and 2,5-dimethoxytetrahydrofuran (0.17 ml) is refluxed with stirring under heating for 1 hour. The reaction solution is concentrated under reduced pressure and the resulting residue is purified by silica gel column chromatography (solvent: dichloromethane:methanol=100:1) to give 1-[1-{4-[4-(1-pyrrolyl)butoxy]benzoyl}-4-piperidinyl]-3,4-dihydrocarbostyril (0.30 g).

NMR (CDCl$_3$) δppm: 1.71–2.15 (6H, m), 2.46–3.20 (8H, m), 3.80–5.15 (2H, m), 3.96 (4H, t, J=6.8 Hz), 4.39 (1H, m), 6.15 (2H, t, J=2.1 Hz), 6.67 (2H, t, J=2:1 Hz), 6.88 (2H, d, J=8.7 Hz), 6.99–7.28 (4H, m), 7.42 (2H, d, J=8.7 Hz)

EXAMPLE 479

Sodium metaperiodate (0.28 g) is dissolved in water (4 ml) and thereto is added a solution of 1-{1-[4-(3-ethylthiopropoxy)benzoyl]-4-piperidinyl}-3,4-dihydrocarbostyril (0.4 g) in methanol (15 ml) and the mixture is stirred at room temperature overnight. The reaction mixture is concentrated and the residue is extracted with chloroform. The extract is dried with magnesium sulfate and the solvent is distilled off. The resulting residue is purified by silica gel column chromatography (solvent n-hexane ethyl acetate=1:2→ethyl acetate:methanol=20:1) to give 1-{1-[4-(3-ethylsulfinylpropoxy)benzoyl]-4-piperidinyl}-3,4-dihydrocarbostyril (0.12 g).

MNR (CDCl$_3$) δppm: 1.44 (3H, t, J=7.5 Hz), 1,68–1.97 (2H, m), 2.28–3.17 (10H, m), 3.05 (2H, q, J=7.5 Hz), 3.20 (2H, t, J=7.4 Hz), 3.78–5.13 (3H, m), 4.15 (2H, t, J=5.7 Hz), 6.86–7.49 (8H, m)

EXAMPLE 480

4-Hydroxypropyltriphenylphosphonium bromide (2.4 g) is dispersed into tetrahydrofuran (50 ml) and thereto is added dropwise lithium diisopropylamide (a solution in 1.99 N tetrahydrofuran) (6.1 ml) at 0°–5° C. After adding, the mixture is stirred at 0°–5° C. for 1 hour and thereto is added 1-[1-(4-formylbenzoyl)-4-piperidinyl]-3,4-dihydrocarbostyril (2 g). The mixture is stirred at room temperature overnight. The reaction mixture is poured into ice-water and adjusted to pH 4–5 by adding conc. hydrochloric acid. The mixture is extracted with ethyl acetate and dried with magnesium sulfate. The solvent is distilled off and the resulting residue is purified by silica gel column chromatography (solvent: n-hexane:ethyl acetate=1:1→ ethyl acetate:methanol=20:1) to give 1-{1-[4-(4-hydroxy-1-butenyl)benzoyl]-4-piperidinyl}-3,4-dihydrocarbostyril (1 g).

NMR (CDCl$_3$) δppm: 1.58–1.97 (2H, m), 2.43–3.22 (10H, m), 3.65–5.12 (5H, m), 5.68–5.84, 6.18–6.36 (total; 1H, m), 6.51 (1H, d, J=15.9 Hz), 6.96–7.49 (8H, m)

EXAMPLE 481

To crushed aluminum chloride (26 g) are added chlorobenzene (26 ml) and N-cinnamoyl-N-(1-benzoyl-4-piperidinyl)aniline (8.7 g) and the mixture is reacted at 110° C. for 1 hour. After cooling, the reaction mixture is poured into ice-water and the mixture is basified with aqueous sodium hydroxide solution. The mixture is extracted with dichloromethane and the solvent is concentrated. The residue is purified by silica gel column chromatography (solvent: methylene chloride) to give 1-(1-benzoyl-4-piperidinyl)carbostyril (5.9 g).

Using the suitable starting materials, the compounds of the above Examples 10, 166–168, 475 and the following Examples 578–587 are obtained in the same manners as in Example 481.

Using the suitable materials, the following compounds are obtained in the same manners as in Exampels 1 and 384.

TABLE 6

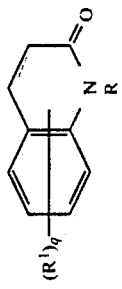

Bond between 3- and 4-positions in the carbostyril ring: Single bond

| | Structure R | R¹ | q | Crystalline form | Recrystallization solvent | Melting point/ NMR analysis | Form |
|---|---|---|---|---|---|---|---|
| Example 482 | 4-OC₂H₅, 2-OCH₃ benzoyl-piperidine | —COOH (3-position), | 1 | White amorphous form | | 237) | Free |
| Example 483 | 4-OC₂H₅, 2-OCH₃ benzoyl-piperidine | —CONHNH₂ (3-position), | 1 | White amorphous form | | 238) | Free |
| Example 484 | 4-OC₂H₅, 2-OCH₃ benzoyl-piperidine | —NHCO₂CH₂—C₆H₅ (3-position) | 1 | White amorphous form | | 239) | Free |
| Example 485 | 4-OC₂H₅, 2-OCH₃ benzoyl-piperidine | —NH₂ (3-position), | 1 | White powders | Ethanol | 257–260° C. | Hydrochloride |
| Example 486 | 4-OC₂H₅, 2-OCH₃ benzoyl-piperidine | —NHCOCH₃ (3-position), | 1 | White amorphous form | | 240) | Free |

TABLE 6-continued

| | | | | | |
|---|---|---|---|---|---|
| Example 487 | ![structure] | —N(CH₃)₂ (3-position), $-OC_2H_5$, $OCH_3$ | 1 | White amorphous form | 241) Free |
| Example 488 | ![structure] $O(CH_2)_3NHCH$ | F (7-position), | 1 | White amorphous form | 242) Free |
| Example 489 | ![structure] $O(CH_2)_4CHCH_2N(C_2H_5)_2$, OH, OCH₃ | F (5-, 7-positions), | 2 | White amorphous form | 245) Free |
| Example 490 | ![structure] $O(CH_2)_5CONH-CH(CONH_2)-$-C₆H₄-OH | H | 1 | White amorphous form | 246) Free |
| Example 491 | ![structure] $O(CH_2)_5CONH-CH(CONH_2)-CH(CH_3)_2$ | H | 1 | White amorphous form | 247) Free |
| Example 492 | ![structure] $O(CH_2)_3CON(CH_3)_2$ | H | 1 | | 248) Free |
| Example 493 | ![structure] $O(CH_2)_3CONHCH_2C_6H_5$ | H | 1 | | 249) Free |

TABLE 6-continued

| | | | | | |
|---|---|---|---|---|---|
| Example 494 | [structure] | H | — | White amorphous form | 250) Free |
| Example 495 | [structure] | H | — | White amorphous form | 251) Free |
| Example 496 | [structure] | H | — | White amorphous form | 252) Free |
| Example 497 | [structure] | H | — | White amorphous form | 253) Free |
| Example 498 | [structure] | H | — | | 254) Free |
| Example 499 | [structure] | H | — | | 255) Free |
| Example 500 | [structure] | H | — | | 256) Free |

TABLE 6-continued

| | Structure | | | |
|---|---|---|---|---|
| Example 501 | 4-methylpiperidine-N-C(=O)-C6H4-O(CH2)3NHCOCH2CH(CH3)CH3 | H | — | 257) Free |
| Example 502 | 4-methylpiperidine-N-C(=O)-C6H4-O(CH2)3NHCO2C2H5 | H | White amorphous form | 258) Free |
| Example 503 | 4-methylpiperidine-N-C(=O)-C6H4-O(CH2)3NHCO2CH2CH(CH3)CH3 | H | White amorphous form | 259) Free |
| Example 504 | 4-methylpiperidine-N-C(=O)-C6H4-O(CH2)3NHSO2-C6H5 | H | White amorphous form | 260) Free |
| Example 505 | 4-methylpiperidine-N-C(=O)-C6H4-O(CH2)3NHSO2-C6H4-CH3 | H | White amorphous form | 261) Free |
| Example 506 | 4-methylpiperidine-N-C(=O)-C6H4-O(CH2)3NHCOCH2NHCOCH3 | H | White amorphous form | 262) Free |
| Example 507 | 4-methylpiperidine-N-C(=O)-C6H4-O(CH2)3NHCO-CH(CH3)(NHCOCH3) (H) | H | White amorphous form | 263) Free |
| Example 508 | 4-methylpiperidine-N-C(=O)-C6H4-O(CH2)3NHCHO | H | White amorphous form | 264) Free |
| Example 509 | 4-methylpiperidine-N-C(=O)-C6H4-O(CH2)5CONH(CH2)3N(CH3)2 | H | White amorphous form | 265) Free |

TABLE 6-continued

| | Structure | R | Form | No. | Recrystallization solvent | Melting point | Salt |
|---|---|---|---|---|---|---|---|
| Example 510 | 4-methylpiperidine-N-CO-C₆H₄-O(CH₂)₃NHCO-C₆H₄-NO₂ | H | 1 | 266) | | Light yellow amorphous form | Free |
| Example 511 | 4-methylpiperidine-N-CO-C₆H₄-O(CH₂)₃NHCO-C₆H₄-NH₂ | H | 1 | 267) | | White amorphous form | Free |
| Example 512 | 4-methylpiperidine-N-CO-C₆H₄-O(CH₂)₃NHCONH-C₆H₅ | H | 1 | 268) | Ethyl acetate/n-hexane | 121–126° C. White powders | Free |
| Example 513 | 4-methylpiperidine-N-CO-C₆H₄-O(CH₂)₃NHCO-C*H(NHCOCH₃)(CH₂)₂CONH₂ | H | 1 | 269) | | White amorphous form | Free |
| Example 514 | 4-methylpiperidine-N-CO-C₆H₄-O(CH₂)₃NHCO-C₆H₄-NHCOCH₃ | H | 1 | 270) | | White amorphous form | Free |
| Example 515 | 4-methylpiperidine-N-CO-C₆H₄-O(CH₂)₃NHCO-C₆H₄-N(CH₃)₂ | H | 1 | 271) | Ethyl acetate/n-hexane | 175.5–177° C. White powder | Free |
| Example 516 | 4-methylpiperidine-N-CO-C₆H₄-O(CH₂)₂NHCONHC₂H₅ | H | 1 | 272) | | White amorphous form | Free |
| Example 517 | 4-methylpiperidine-N-CO-C₆H₄-O(CH₂)₅CONH(CH₂)₂N(CH₃)₂ | H | 1 | | | | Free |

TABLE 6-continued

| Example | Structure | | | | |
|---|---|---|---|---|---|
| Example 518 | [structure] | H | 1 | White amorphous form | | Free 273) |
| Example 519 | [structure] | H | 1 | White amorphous form | | Free 274) |
| Example 520 | [structure] | H | 1 | White amorphous form | | Free 275) |
| Example 521 | [structure] | H | 1 | White amorphous form | | Free 276) |
| Example 522 | [structure] | H | 1 | White amorphous form | | Free 277) |
| Example 523 | [structure] | H | 1 | White amorphous form | | Free 278) |
| Example 524 | [structure] | H | 1 | | | Free 279) |
| Example 525 | [structure] | H | 1 | White powders | Ethanol/water 196–198° C. | Dioxalate |

TABLE 6-continued

| Example | Structure | | | | | Dioxalate |
|---|---|---|---|---|---|---|
| | | H | White powders | — | 214-215° C. | |
| Example 526 | 4-methylpiperidine-C(=O)-C6H4-O(CH2)4N-piperazine-N-CH3 | H | — | — | 280) | Free |
| Example 527 | 4-methylpiperidine-C(=O)-C6H4-O(CH2)4N-piperazine-N-SO2CH3 | H | — | — | 281) | Free |
| Example 528 | 4-methylpiperidine-C(=O)-C6H4-O(CH2)4N-piperazine-N-CO2CH3 | H | — | — | 282) | Free |
| Example 529 | phenyl-C(=O)N-piperidine-C6H4-O(CH2)4OCON-piperazine-N-CH2-phenyl | H | — | — | 283) | Free |
| Example 530 | 4-methylpiperidine-C(=O)-C6H4-O(CH2)4N-piperazine-N-COCH3 | H | — | — | 284) | Free |
| Example 531 | 4-methylpiperidine-C(=O)-C6H4-O(CH2)4OCON-piperidine-NH | H | — | — | 285) | Free |
| Example 532 | 4-methylpiperidine-C(=O)-C6H4-O(CH2)4CH(OH)CH2NHCH2-phenyl | H | — | — | 286) | Free |
| Example 533 | 4-methylpiperidine-N-C(=O)-C6H4-O(CH2)4CH(OH)CH2NH2 | H | — | — | | Free |

TABLE 6-continued

| Example | Structure | | | | | |
|---------|-----------|---|---|---|---|---|
| Example 534 | [piperidine-N-C(=O)-C6H4-O(CH2)4CH(OH)CH2N-piperidine-N-CH2-phenyl], H | White powders | Ethanol/water | 196–198° C. | Dioxalate |
| Example 535 | [piperidine(4-Me)-N-C(=O)-C6H4-O(CH2)4CH(OH)CH2N-piperidine-NH], H | White powders | Ethanol/water | 198–199° C. | Dioxalate |
| Example 536 | [piperidine(4-Me)-N-C(=O)-C6H4-O(CH2)4CH(OCOCH3)CH2NHCOCH3], H | | | 287) | Free |

| | | | | |
|---|---|---|---|---|
| Example 537 | 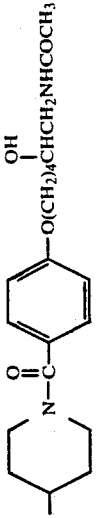 | H | — | 288) | Free |
| Example 538 | 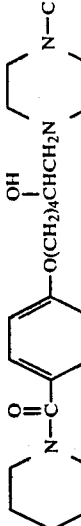 | H | — | 289) | Free |
| Example 539 | 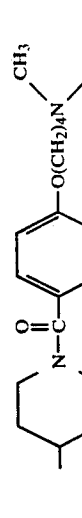 | H | — | 290) | Free |
| Example 540 | 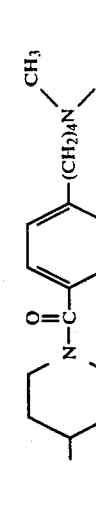 | H | — | 291) | Free |
| Example 541 | 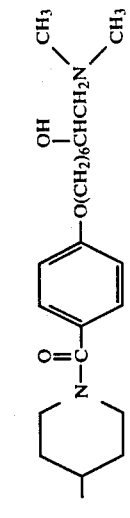 | H | — | 292) | Free |
| Example 542 | 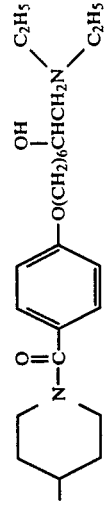 | H | — | 293) | Free |
| Example 543 | 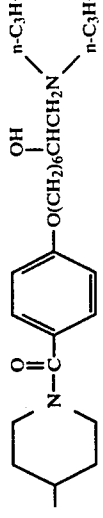 | H | — | 294) | Free |
| Example 544 | 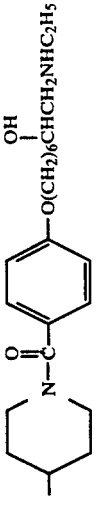 | H | — | 295) | Free |

-continued
| | | | | |
|---|---|---|---|---|
| Example 545 | 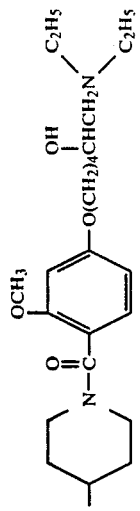 | H | — | 296) | Free |
| Example 546 | 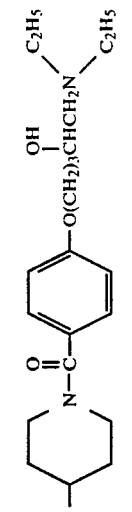 | H | — | 297) | Free |
| Example 547 | 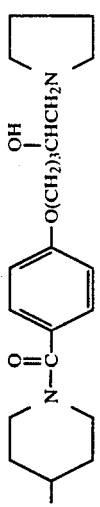 | H | — | 298) | Free |
| Example 548 | 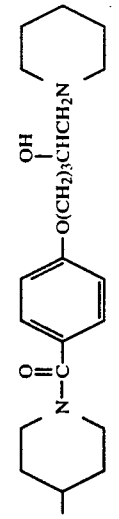 | H | — | 299) | Free |
| Example 549 | 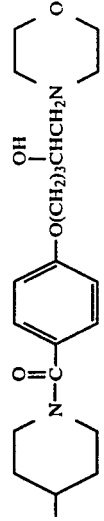 | H | — | 300) | Free |
| Example 550 | 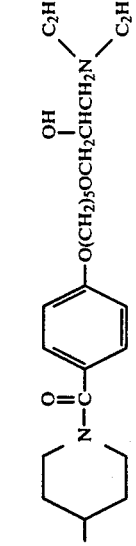 | H | — | 301) | Free |
| Example 551 | 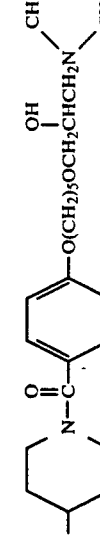 | H | — | 302) | Free |
| Example 552 | 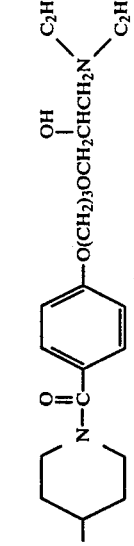 | H | — | 303) | Free |

| | | | | |
|---|---|---|---|---|
| Example 553 | 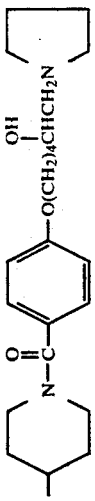 | H | — | 304) | Free |
| Example 554 | 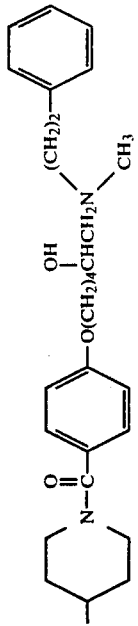 | H | — | 305) | Free |
| Example 555 | 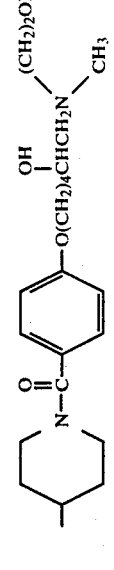 | H | — | 306) | Free |
| Example 556 | 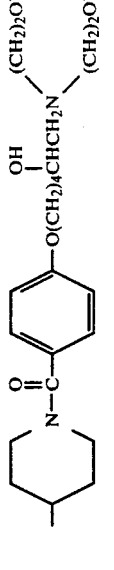 | H | — | 307) | Free |
| Example 557 |  | H | — | 308) | Free |
| Example 558 | 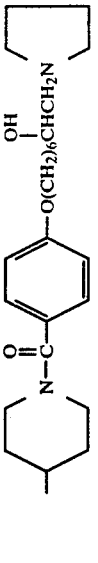 | H | — | 309) | Free |
| Example 559 | 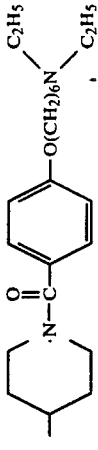 | H | — | 310) | Free |
| Example 560 | 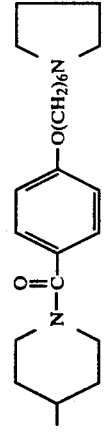 | H | — | 311) | Free |

-continued
| | | | | |
|---|---|---|---|---|
| Example 561 | 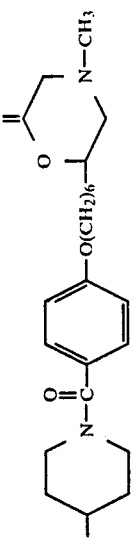 | H | — | 312) Free |
| Example 562 | 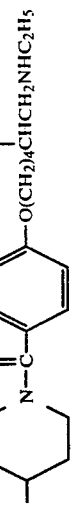 | H | — | 313) Free |
| Example 563 | 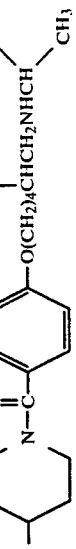 | H | — | 314) Free |
| Example 564 | 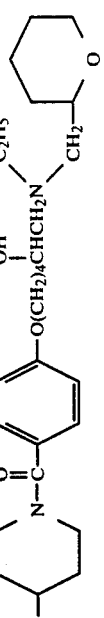 | H | — | 315) Free |
| Example 565 | 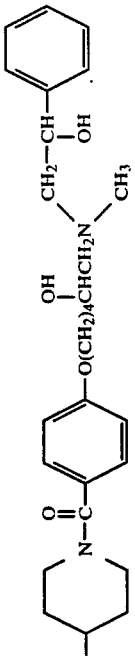 | H | — | 316) Free |
| Example 566 | 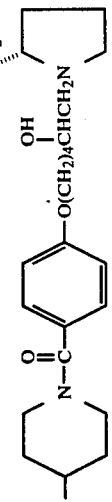 | H | — | 317) Free |
| Example 567 | 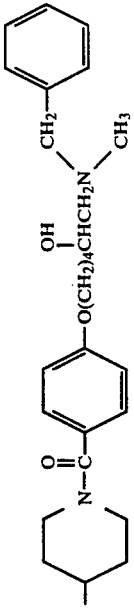 | H | — | 318) Free |

-continued
| | | | | | |
|---|---|---|---|---|---|
| Example 568 | 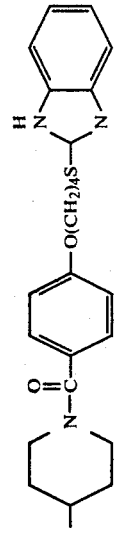 | H | 1 | White amorphous form | 319) Free |
| Example 569 | 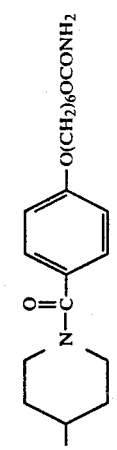 | H | 1 | White amorphous form | 320) Free |
| Example 570 | 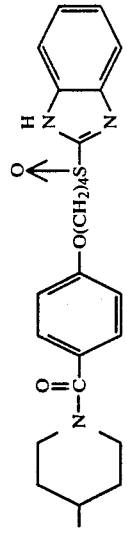 | H | 1 | White amorphous form | 321) Free |
| Example 571 | 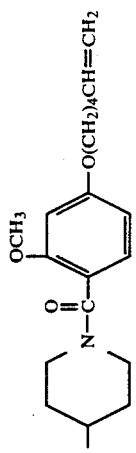 | F (5-, 7-position), | 2 | White amorphous form | 325) Free |
| Example 572 | 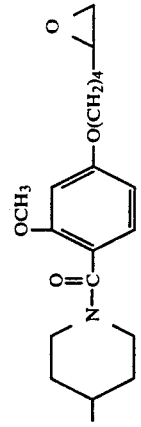 | F (5-, 7-position), | 2 | White amorphous form | 326) Free |
| Example 573 | 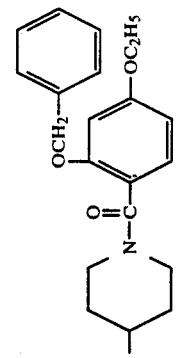 | H | 1 | White powders | Ethanol 63–65° C. |
| Example 574 | 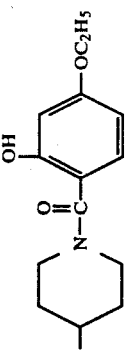 | H | 1 | White powders | Ethanol 138–140° C. |

-continued
| | | | | | |
|---|---|---|---|---|---|
| Example 575 | 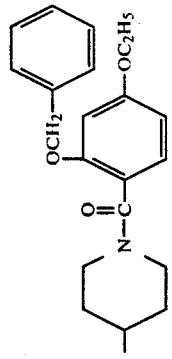 | F (7-position), | — | White powders | Ethanol | 83–86° C. | Free |
| Example 576 | 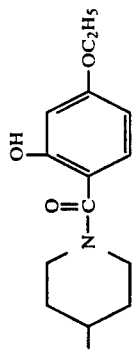 | F (7-position), | — | White powders | Ethanol | 140–142° C. | Free |
| Example 577 | 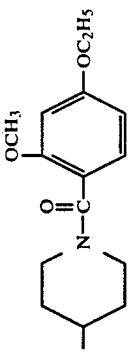 | CH₃ (5-position), | — | White amorphous form | | 327) | Free |
| Example 577A | 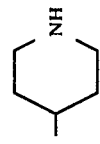 | CH₃ (5-position), | — | White amorphous form | | 328) | Free |

The following compounds are obtained in the same manners as in Examples 1 and 385.

TABLE 7

| | Structure | | | Crystalline form | Recrystallization solvent | Melting point/ NMR analysis | Form |
|---|---|---|---|---|---|---|---|
| | R | R¹ | q | | | | |
| | Bond between 3- and 4-positions in the carbostyril ring: Double bond | | | | | | |
| Example 578 | (4-methylpiperidinyl)-C(=O)- | F (7-position), | 1 | White powders | Ethanol | 182–185° C. | Free |
| Example 579 | (4-methylpiperidinyl)-C(=O)- | F (5-, 7-positions), | 2 | White powders | Ethanol | 183–185° C. | Free |
| Example 580 | 4-methylpiperidinyl-NH | F (7-position), | 1 | White amorphous form | | 243) | Free |
| Example 581 | 4-methylpiperidinyl-NH | F (5-, 7-positions), | 2 | White powders | Ethanol/n-hexane | 186–187° C. | Free |
| Example 582 | (4-methylpiperidinyl)-C(=O)-(2-OCH₃, 4-OC₂H₅-phenyl) | F (7-position), | 1 | White powders | Ethanol/diethyl ether | 187–188° C. | Free |
| Example 583 | (4-methylpiperidinyl)-C(=O)-(2-OCH₃, 4-OCH₃-phenyl) | F (7-position), | 1 | White amorphous form | | 244) | Free |

TABLE 7-continued

| | Structure | | | | Crystalline form | Recrystallization solvent | Melting point/ NMR analysis | Form |
| --- | --- | --- | --- | --- | --- | --- | --- | --- |
| | R | R¹ | q | | | | | |
| Example 584 | OCH₃, OC₂H₅ piperidine benzamide structure | F (5-, 7-positions) | 2 | | White powders | Ethanol/diethyl ether | 150–152° C. | Free |
| Example 585 | phthalimide-O(CH₂)₃N, piperidine benzamide structure | H | 1 | | White amorphous form | | 322) | Free |
| Example 586 | O(CH₂)₃NH₂, piperidine benzamide structure | H | 1 | | White amorphous form | | 323) | Free |
| Example 587 | O(CH₂)₃NHCOCH₃, piperidine benzamide structure | H | 1 | | White amorphous form | | 324) | Free |

TABLE 8

| No. | NMR (CDCl$_3$) δ value |
|---|---|
| 237 | 1.42 (3H, t, J=7.0 Hz), 1.58-2.05 (2H, m), 2.35-3.47 (7H, m), 3.55-3.95 (4H, m), 4.04 (2H, q, J=7 Hz), 4.38 (1H, brs), 2.94 (1H, brs), 6.37-6.56 (2H, m), 7.00-7.40 (5H, m) |
| 238 | 1.42 (3H, t, J=7 Hz), 1.52-1.95 (2H, m), 2.30-3.93 (13H, m), 4.04 92H, q, J=7 Hz), 4.15-5.06 (3H, m), 6.40-6.62 (2H, m), 6.97-7.50 (5H, m) |
| 239 | 1.40 (3H, t, J=7 Hz), 1.55-2.00 (2H, m), 2.30-5.05 (15H, m), 5.30 (2H, s), 5.95 (1H, brs), 6.50-6.60 (2H, m), 7.02-7.942 (10H, m) |
| 240 | 1.42 (3H, t, J=7 Hz), 1.55-1.98 (2H, m), 2.08 (3H, s), 2.40-3.95 (7H, m), 4.05 92H, q, J=7 Hz), 4.20-4.65 (2H, m), 4.90-5.11 (1H, m), 6.42-6.73 (3H, m), 7.02-7.40 (5H, m) |
| 241 | 1.42 (3H, t, J=7 Hz), 1.50-1.96 (2H, m), 2.43 (6H, s), 2.51-3.28 (7H, m), 3.57-3.95 (4H, m), 4.04 (2H, q, J=7 Hz), 4.33-4.75 (1H, m), 4.84-5.06 (1H, m), 6.40-6.60 (2H, m), 6.99-7.32 (5H, m) |
| 242 | 1.68-2.15 (4H, m), 2.45-3.20 (8H, m), 3.40-3.62 92H, m), 4.06 (2H, t, J=5.9 Hz), 4.10-5.10 (3H, m), 6.26 (1H, brs), 6.68-7.25 (5H, m), 7.42 (2H, d, J=8.7 Hz), 8.15 (1H, s) |
| 243 | 1.65-1.88 (2H, m), 2.20 (1H, brs), 2.60-3.05 (4H, m), 3.18-3.42 (2H, m), 5.15 (1H, brs), 6.59 (1H, d, J=9.4 Hz), 6.94 (1H, m), 7.35-7.65 (3H, m) |
| 244 | 1.60-1.97 (2H, m), 2.50-3.33 (4H, m), 3.54-4.02 (7H, m), 4.95-5.12 (1H, m), 6.40-6.65 (3H, m), 6.90-7.13 (1H, m), 7.15-7.67 (4H, m) |
| 245 | 1.08 (6H, t, J=7.1 Hz), 1.32-1.90 (8H, m), 2.25-3.20 (15H, m), 3.60-5.10 (9H, m), 6.40-6.85 (4H, m), 7.15-7.30 (1H, m) |
| 246 | 1.45-1.97 (6H, m), 2.16 (2H, m), 2.36-3.32 (8H, m), 2.56 (2H, m), 3.60-5.15 (2H, m), 3.87 (2H, m), 4.32 (2H, m), 4.68 (2H, m), 6.19 (1H, brs), 6.64 (2H, d, J=8.0 Hz), 6.83 (2H, d, j=8.3 Hz), 6.92-7.23 (8H, m), 7.36 (2H, d, J=8.3 Hz) |
| 247 | 0.95 (3H, d, J=6.0 Hz), 0.98 (3H, d, J=6.0 Hz), 1.38-1.61 (2H, m), 1.62-1.96 (6H, m), 2.08 (1H, m), 2.27 (2H, t, J=7.3 Hz), 2.53-3.15 (8H, m), 3.77-4.85 (2H, m), 3.97 (2H, t, J=6.2 Hz), 4.32 (2H, m), 5.79 (1H, brs), 6.50 92H, m), 6.89 (2H, d, J=8.6 Hz), 6.99-7.27 (4H, m), 7.42 (2H, d, J=8.6 Hz) |
| 248 | 1.67-1.96 (2H, m), 2.14 (2H, quint, J=6.3 Hz), 2.40-3.10 (8H, m), 2.52 (2H, t, J=6.3 Hz), 2.96 (3H, s), 3.02 (3H, s), 3.85-5.10 (2H, m), 4.07 (2H, t, J=6.3 Hz), 4.37 (1H, m), 6.92 (2H, d, J=8.6 Hz), 6.98-7.33 (4H, m), 7.43 (2H, d, J=8.6 Hz), |
| 249 | 1.65-1.95 (2H, m), 2.12 (2H, quint, J=6.4 Hz), 2.41 (2H, t, J=6.4 Hz), 2.54-2.85 (8H, m), 3.80-5.10 (2H, m), 3.98 92H, t, J=6.4 Hz), 4.35 (1H, m), 4.40 (2H, t, J=5.5 Hz), 6.54-6.92 (1H, brs), 6.83 (2H, d, J=8.6 Hz), 6.99-7.31 (9H, m), 7.37 (2H, d, J=8.6 Hz) |

| No. | NMR (DMSO-d$_6$) δ value |
|---|---|
| 250 | 1.21-1.82 (8H, m), 2.08 (2H, t, J=7.1 Hz), 2.26-3.20 (8H, m), 3.39 (2H, m), 3.60-4.66 (2H, brs), 3.93 (2H, t, J=6.4 Hz), 4.32 (2H, m), 6.71 (1H, s), 6.84-7.01 (2H, brs), 6.94 (2H, d, J=8.7 Hz), 7.16-7.31 (4H, m), 7.32 (2H, d, J=8.7 Hz), 7.47 (1H, s), 7.88 (1H, d, J=8.2 Hz), |
| 251 | 1.10-1.97 (10H, m), 2.07 (2H, t, J=7.6 Hz), 2.16 (2H, t, J=7.3 Hz), 2.32-3.40 (8H, m), 3.60-4.80 (2H, brs), 3.99 (2H, t, J=6.4 Hz), 4.15 (1H, m), 4.28 (1H, m), 6.74 (1H, brs), 6.98 (2H, d, J=8.6 Hz), 7.05 (1H, brs), 7.20-7.29 (4H, m), 7.36 (2H, d, J=8.6 Hz), 7.85 (1H, d, J=7.7 Hz) |

| No. | NMR (CDCl$_3$) δ value |
|---|---|
| 252 | 1.38-1.59 (2H, m), 1.60-2.18 (8H, m), 2.09 (3H, s), 2.25 (2H, t, J=7.2 Hz), 2.44-3.17 (8H, m), 2.57 (2H, t, J=6.1 Hz), 3.55-5.10 (2H, brs), 3.97 (2H, t, J=6.1 Hz), 4.38 (1H, m), 4.64 (1H, q, J=7.2 Hz), 5.95 (1H, brs), 6.78 (1H, brs), 6.82 (1H, brs), 6.89 (2H, d, J=8.7 Hz), 6.91-7.28 (4H, m), 7.41 (2H, d, J=8.7 Hz) |
| 253 | 1.42-1.64 (2H, m), 1.64-2.06 (6H, m), 2.57 (2H, t, J=6.1 Hz), 2.64-3.24 (8H, m), 3.67-5.15 (2H, m), 3.92 (2H, t, J=6.1 Hz), 4.34 (1H, m), 6.84 (2H, d, J=8.7 Hz), 7.00-7.36 (5H, m), 7.40 (2H, d, J=8.7 Hz), 8.28 (1H, d, J=5.6 Hz), 8.80 (1H, s) |
| 254 | 1.13-1.96 (14H, m), 2.25 (2H, t, J=7.3 Hz), 2.46-3.08 (8H, m), 3.16 (2H, m), 3.72 (3H, s), 3.96 (2H, t, J=6.2 Hz), 4.05-4.97 (2H, m), 4.37 (1H, m), 4.57 (1H, m), 5.07 (1H, brs), 5.08 (2H, s), 6.34 (1H, d, J=5.7 Hz), 6.88 (2H, d, J=8.6 Hz), 6.98-7.30 (4H, m), 7.34 (5H, s), 7.41 (2H, d, J=8.6 Hz) |
| 255 | 1.30-1.93 (14H, m), 2.27 (2H, t, J=7.3 Hz), 2.53-3.11 (10H, m), 3.73 (3H, s), 3.98 (2H, t, J=6.3 Hz), 4.13-5.06 (2H, m), 4.38 (1H, m), 4.59 (1H, m), 6.46 (1H, d, J=7.8 Hz), 6.89 (2H, d, J=8.6 Hz), 6.98-7.30 (4H, m), 7.42 (2H, d, J=8.6 Hz) |
| 256 | 1.14 (3H, t, J=7.6 Hz), 1.84 (2H, m), 2.00 (2H, quint, J=6.1 Hz), 2.21 (2H, q, J=7.6 Hz), 2.43-3.23 (8H, m), 3.42 (2H, q, J=6.1 Hz), 3.65-5.14 (2H, m), 4.03 (2H, t, J=6.1 Hz), 4.36 (1H, m), 6.52 (1H, brs), 6.89 (2H, d, J=8.4 Hz), 6.98-7.32 (4H, m), 7.42 (2H, d, J=8.4 Hz) |
| 257 | 0.95 (6H, t, J=6.3 Hz), 1.84 (2H, m), 1.94-2.22 (5H, m), 2.53-3.17 (8H, m), 3.46 (2H, q, J=6.1 Hz), 3.66-5.05 (2H, m), 4.05 (2H, t, J=6.1 Hz), 4.38 (1H, m), 6.00 (1H, brs), 6.90 (2H, d, J=8.7 Hz), 6.99-7.29 (4H, m), 7.43 (2H, d, J=8.7 Hz) |
| 258 | 1.24 (3H, t, J=7.1 Hz), 1.66-1.93 (2H, m), 2.01 (2H, quint, J=6.2 Hz), 2.53-3.15 (8H, m), 3.39 (2H, q, J=6.2 Hz), 3.60-5.10 (2H, m), 4.05 (2H, t, J=6.2 Hz), 4.11 (2H, q, J=7.1 Hz), 4.39 (1H, m), 4.94 (1H, brs), 6.91 (2H, d, J=8.7 Hz), 6.98-7.29 (4H, m), 7.43 (2H, d, J=8.7 Hz) |
| 259 | 0.92 (6H, d, J=6.7 Hz), 1.60-1.94 (3H, m), 2.02 (2H, quint, J=6.2 Hz), 2.53-3.15 (8H, m), d.39 (2H, q, J=6.2 Hz), 3.60-5.20 (2H, m), 3.84 (2H, d, J=6.7 Hz), 4.06 (2H, t, J=6.2 Hz), 4.39 (1H, m), 4.95 (1H, brs), 6.91 (2H, d, J=8.7 Hz), 6.98-7.29 (4H, m), 7.43 (2H, d, J=8.7 Hz) |
| 260 | 1.55-1.87 (2H, m), 1.95 (2H, quint, J=6.0 Hz), 2.52-3.10 (8H, m), 3.12 (2H, q, J=6.0 Hz), 3.66-5.10 (2H, m), 3.96 (2H, t, J=6.0 Hz), 4.37 (1H, m), 5.51 (1H, brs), 6.81 (2H, d, J=8.6 Hz), 6.98-7.30 (4H, m), 7.36-7.60 (5H, m), 7.85 (2H, d, J=8.6 Hz) |
| 261 | 1.60-1.90 (2H, m), 1.95 (2H, quint, J=6.1 Hz), 2.40 (3H, s), 2.50-3.10 (8H, m), 3.15 (2H, q, J=6.1 Hz), 3.70-5.05 (2H, m), 3.97 (2H, t, J=6.1 Hz), 4.38 (1H, m), 5.19 (1H, t, J=6.1 Hz), 6.82 (2H, d, J=8.7 Hz), 6.98-7.28 (4H, m), 7.27 (2H, d, J=8.7 Hz), 7.40 (2H, d, J=8.7 Hz), 7.74 (2H, d, J=8.1 Hz), |
| 262 | 1.68-1.93 (2H, m), 1.93-2.14 (2H, m), 2.02 (3H, s), 2.53-3.25 (8H, m), 3.46 (2H, q, J=5.9 Hz), 3.70-5.15 (2H, m), 3.86 (2H, d, J=4.6 Hz), 4.04 (2H, t, J=5.9 Hz), 4.37 (1H, m), 6.65 (1H, brs), 6.77 (1H, brs), 6.90 (2H, d, J=8.6 Hz), 6.98-7.33 (4H, m), 7.42 (2H, d, J=8.6 Hz) |
| 263 | 0.93 (6H, d, J=6.7 Hz), 1.60-1.92 (2H, m), 1.93-2.15 (3H, m), 2.00 (3H, s), 2.33-3.24 (3H, m), 3.45 (2H, m), 3.70-5.10 (2H, m), 4.03 (2H, t, J=5.9 Hz), 4.24 (1H, t, J=8.5 Hz), 4.38 (1H, m), 6.63 (1H, d, J=8.5 Hz), 6.89 (2H, d, J=8.6 Hz), 6.98-7.29 (5H, m), 7.42 (2H, d, J=8.6 Hz) |
| 264 | 1.67-1.94 (2H, m), 2.04 (2H, quint, J=6.2 Hz), 2.53-3.20 (8H, m), 3.51 (2H, q, J=6.2 Hz), 3.65-5.15 (2H, m), 4.06 (2H, t, J=6.2 Hz), 4.37 (1H, m), 6.29 (1H, brs), 6.91 (2H, d, J=8.7 Hz), 6.98-7.29 (4H, m), 7.43 92H, d, J=8.7 Hz), 8.14 (1H, s) |
| 265 | 1.39-1.62 (2H, m), 1.62-1.95 (8H, m), 2.20 (2H, t, J=7.4 Hz), 2.33 (6H, s), 2.50 (2H, t, J=6.5 Hz), 2.56-3.20 (8H, m), 3.34 (2H, q, J=5.9 Hz), 3.66 (1H, brs), 3.86-5.20 (1H, m), 3.98 (2H, t, J=6.3 Hz), 4.39 (1H, m), 6.89 (2H, d, J=8.6 Hz), 6.98-7.30 (5H, m), 7.42 (2H, d, J=8.6 Hz) |
| 266 | 1.82 (2H, m), 2.13 (2H, quint, J=5.9 Hz), 2.52-3.20 (8H, m), 3.66 92H, q, J=5.9 Hz), 3.80-5.10 (2H, m), 4.08 (2H, t, J=5.9 Hz), 4.31 (1H, m), 6.86 (2H, d, J=8.7 Hz), 6.99-7.12 (2H, m), 7.16-7.29 (2H, m), 7.38 (2H, d, J=8.7 Hz), 7.59 (1H, t, J=5.9 Hz), 7.98 (2H, dd, J=7.0, 1.9 Hz), 8.20 (2H, dd, J=7.0, 1.9 Hz) |
| 267 | 1.67-1.94 (2H, m), 2.09 (2H, quint, J=6.0 Hz), 2.53-3.20 (8H, m), 3.46-5.00 (4H, m), 3.60 (2H, q, J=6.0 Hz), 4.08 92H, t, J=6.0 Hz), 4.34 (1H, m), 6.63 (2H, d, J=8.6 Hz), 6.77 (1H, t, J=6.0 Hz), 6.88 (2H, d, J=8.7 Hz), 6.98-7.29 (4H, m), 7.39 (2H, d, J=8.7 Hz), 7.60 (2H, d, J=8.6 Hz) |
| 268 | 1.60-2.33 (4H, m), 2.53-3.20 (8H, m), 3.30 (2H, m), 3.70-5.17 (2H, m), 3.92 (2H, t, J=5.9 Hz), 4.33 (2H, m), 5.83 (2H, brs), 6.82 (2H, d, J=8.6 Hz), 6.92-7.50 (9H, m), 7.37 (2H, d, J=8.6 Hz), 7.67 (1H, s) |
| 269 | 1.70-2.12 (4H, m), 2.00 (3H, s), 2.14-2.50 (4H, m), |

TABLE 8-continued

| | |
|---|---|
| | 2.53–3.20 (8H, m), 3.44 (2H, q, J=5.9 Hz), 3.80–5.10 (2H, brs), 4.03 (2H, t, J=5.9 Hz), 4.41 (2H, m), 6.05 (1H, brs), 6.70 (1H, brs), 6.91 (2H, d, J=8.6 Hz), 6.98–7.32 (5H, m), 7.41 (2H, d, J=8.6 Hz), 7.51 (1H, t, J=5.9 Hz) |
| 570 | 1.66–1.97 (2H, m), 2.04–2.30 (2H, m), 2.15 (3H, s), 2.44–3.20 (8H, m), 3.60 (2H, q, J=5.7 Hz), 4.05 (2H, t, J=5.7 Hz), 4.31 (1H, m), 3.80–5.14 (2H, m), 6.82 (2H, d, J=8.7 Hz), 6.99–7.42 (5H, m), 7.31 (2H, d, J=8.7 Hz), 7.54 (2H, d, J=8.6 Hz), 7.69 (2H, d, J=8.6 Hz), 8.96 (1H, brs) |
| 271 | 1.06 (3H, t, J=6.8 Hz), 1.84 (2H, m), 1.92 (2H, quint, J=5.9 Hz), 2.25–3.20 (8H, m), 3.15 (2H, quint, J=6.8 Hz), 3.30 (2H, q, J=5.9 Hz), 3.56–5.10 (2H, m), 4.00 (2H, t, J=5.9 Hz), 4.33 (1H, m), 5.29 (1H, t, J=6.8 Hz), 5.67 (1H, t, J=5.9 Hz), 6.89 (2H, d, J=8.4 Hz), 6.98–7.32 (4H, m), 7.39 (2H, d, J=8.4 Hz) |
| 272 | 1.40–1.62 (2H, m), 1.62–1.94 (6H, m), 2.23 (2H, t, J=7.6 Hz), 2.27 (6H, s), 2.46 (2H, t, J=5.8 Hz), 2.52–3.10 (8H, m), 3.34 (2H, q, J=5.8 Hz), 3.75–5.10 (2H, m), 3.98 (2H, t, J=6.3 Hz), 4.38 (1H, m), 6.33 (1h, brs), 6.94 (2H, d, J=8.7 Hz), 6.98–7.30 (4H, m), 7.42 (2H, d, J=8.7 Hz), |
| 273 | 1.35–1.60 (4H, m), 1.61–2.00 (8H, m), 2.03–2.21 (4H, m), 2.53–3.14 (10H, m), 3.50 (2H, s), 3.60–5.20 (2H, m), 3.83 (1H, m), 3.97 (2H, t, J=6.3 Hz), 4.39 91H, m), 5.41 (1H, d, J=8.0 Hz), 6.88 (2H, d, J=8.7 Hz), 6.99–7.32 (4H, m), 7.30 (5H, m), 7.42 (2H, d, J=8.7 Hz) |
| 274 | 1.70–2.20 (6H, m), 1.99 (3H, s), 2.08 (3H, s), 2.35–3.20 (10H, m), 3.45 (2H, q, J=6.0 Hz), 3.70–5.20 (2H, m), 4.03 (2H, t, J=6.0 Hz), 4.38 (1H, m), 4.57 (1H, q, J=7.2 Hz), 6.58 (1H, d, J=6.0 Hz), 6.80–6.98 (1H, brs), 6.91 (2H, d, J=8.6 Hz), 6.99–7.29 (4H, m), 7.43 (2H, d, J=8.6 Hz) |
| 275 | 1.70–2.03 (4H, m), 2.05 (3H, s), 2.58–3.22 (8H, m), 2.99 (2H, d, J=7.0 Hz), 3.44 (2H, d, J=5.9 Hz), 3.55–5.30 (2H, m), 3.96 (2H, t, J=5.9 Hz), 4.40 (1H, m), 4.72 (1H, q, J=7.0 Hz), 6.75 (1H, s), 6.92 (2H, d, J=8.6 Hz), 7.04–7.60 (7H, m), 7.44 (2H, d, J=8.6 Hz) |
| 276 | 1.33 (3H, d, J=7.0 Hz), 1.65–1.93 (2H, m), 1.93–2.12 (2H, m), 1.97 (3H, s), 2.53–3.20 (8H, m), 3.43 (2H, q, J=6.1 Hz), 3.80–5.20 (2H, m), 4.02 (2H, t, J=6.1 Hz), 4.37 (1H, m), 4.46 (1H, quint, J=7.0 Hz), 6.64 (1H, brs), 6.90 (2H, d, J=8.7 Hz), 6.98–7.29 (5H, m), 7.42 (2H, d, J=8.7 Hz) |
| 277 | 1.38–1.64 (4H, m), 1.65–2.10 (8H, m), 2.20 (2H, t, J=7.3 Hz), 2.53–3.10 (10H, m), 3.10–3.39 (2H, m), 3.45–5.20 (2H, m), 3.94 (1H, m), 3.98 (2H, t, J=6.3 Hz), 4.37 (1H, m), 5.82 (1H, d, J=7.8 Hz), 6.90 (2H, d, J=8.7 Hz), 6.98–7.28 (4H, m), 7.41 (2H, d, J=8.7 Hz) |
| 278 | 1.85 (4H, m), 2.54–3.24 (10H, m), 3.35 (2H, m), 3.63–5.00 (2H, m), 3.85 (2H, m), 4.31 (1H, m), 5.11 (2H, s), 5.41 (1H, brs), 6.15 (1H, brs), 6.45 (2H, d, J=8.3 Hz), 6.77 (2H, d, J=8.6 Hz), 6.84 (2H, d, J=8.3 Hz), 7.00–7.30 (4H, m), 7.34 (5H, s), 7.37 (2H, d, J=8.6 Hz), 8.12 (1H, s) |
| 279 | 1.57–1.92 (6H, m), 2.19–3.15 (18H, m), 3.51–3.61 (2H, m), 3.84–5.22 (3H, m), 3.99 (2H, t, J=6.3 Hz), 6.83–7.46 (13H, m) |
| 280 | 1.57–2.05 (6H, m), 2.40–3.56 (21H, m), 3.75–5.12 (3H, m), 4.02 (2H, t, J=5.9 Hz), 6.83–7.52 (8H, m) |
| 281 | 1.59–1.98 (6H, m), 2.32–3.16 (14H, m), 3.35–5.18 (7H, m), 3.70 (3H, s), 4.01 (2H, t, J=6.2 Hz), 6.83–7.48 (8H, m) |
| 282 | 1.66–2.12 (6H, m), 2.32–3.13 (12H, m), 3.33–5.10 (13H, m), 6.84–7.49 (13H, m) |
| 283 | 1.57–1.95 (6H, m), 2.09 (3H, s), 2.28–3.28 (14H, m), 3.48–5.07 (7H, m), 4.01 (2H, t, J=6.2 Hz), 6.87–7.49 (8H, m) |
| 284 | 1.71–1.98 (6H, m), 2.15 (1H, brs), 2.49–3.16 (12H, m), 3.32–5.12 (11H, m), 6.85–7.48 (8H, m) |
| 285 | 1.34–2.01 (8H, m), 2.41–3.23 (12H, m), 3.56–5.18 (8H, m), 6.82–7.48 (11H, m) |
| 286 | 1.39–1.96 (8H, m), 2.03 (2H, brs), 2.43–3.18 (10H, m), 3.35–5.15 (4H, m), 3.99 (2H, t, J=6.3 Hz), 6.84–7.47 (8H, m) |
| 287 | 1.42–1.94 (8H, m), 1.98 (3H, s), 2.08 93H, s), 2.50–3.18 (8H, m), 3.30–3.58 (2H, m), 3.71–5.07 (4H, m), 3.97 (2H, t, J=6.2 Hz), 5.90–6.03 (1H, m), 6.87–7.49 (8H, m) |
| 288 | 1.38–2.08 (8H, m), 1.99 (3H, s), 2.39–3.56 (11H, m), 3.58–5.11 (6H, m), 6.17–6.42 (1H, m), 6.82–7.48 (8H, m) |
| 289 | 1.37–1.94 (8H, m), 2.14–3.15 (19H, m), 2.32 (3H, s), 3.58–5.07 (4H, m), 3.99 (2H, t, J=6.4 Hz), 6.82–7.48 (8H, m) |
| 290 | 1.65–1.98 (6H, m), 2.33–3.13 (10H, m), 2.39 (6H, s), 3.88–4.99 (3H, m), 4.02 (2H, t, J=5.9 Hz), 6.83–7.50 (8H, m) |
| 291 | 1.44–2.03 (6H, m), 2.21 (6H, s), 2.28 (2H, t, J=7.2 Hz), 2.52–3.28 (10H, m), 3.76–5.13 (3H, m), 6.98–7.42 (8H, m) |
| 292 | 1.36–1.98 (10H, m), 2.12–2.39 (2H, m), 2.28 (6H, s), 2.52–3.12 (10H, m), 3.55–5.13 (5H, m), 3.99 (2H, t, J=6.3 Hz), 6.86–7.48 (8H, m) |
| 293 | 1.04 (6H, t, J=7.1 Hz), 1.32–1.95 (10H, m), 2.20–3.16 (16H, m), 3.43–5.13 (5H, m), 4.00 (2H, t, J=6.4 Hz), 6.86–7.49 (8H, m) |
| 294 | 0.89 (6H, t, J=7.4 Hz), 1.32–1.94 (16H, m), 2.26–3.12 (14H, m), 3.45–4.98 (5H, m), 3.99 (2H, t, J=6.3 Hz), 6.34–7.49 (8H, m) |
| 295 | 1.12 (3H, t, J=7.1 Hz), 1.38–1.96 (10H, m), 2.26–3.12 (15H, m), 3.46–5.06 (5H, m), 3.99 (2H, t, J=6.0 Hz), 6.89 (2H, d, J=8.7 Hz), 6.99–7.32 (4H, m), 7.42 (2H, d, J=8.7 Hz) |
| 296 | 1.07 (6H, t, J=7.2 Hz), 1.28–1.94 (8H, m), 2.25–3.17 (15H, m), 3.55–5.08 (7H, m), 3.96 (2H, t, J=6.5 Hz), 6.42–7.33 (8H, m) |
| 297 | 1.04 (6H, t, J=7.1 Hz), 1.42–2.14 (6H, m), 2.23–3.13 (14H, m), 3.56–5.02 (7H, m), 6.87–7.49 (8H, m) |
| 298 | 1.51–2.13 (10H, m), 2.52–3.40 (15H, m), 3.78–5.03 (6H, m), 6.83–7.48 (8H, m) |
| 299 | 1.35–2.10 (12H, m), 2.13–3.12 (15H, m), 3.57–4.83 (6H, m), 6.82–7.53 (8H, m) |
| 300 | 1.44–2.12 (6H, m), 2.20–3.13 (15H, m), 3.15–4.86 (10H, m), 6.88–7.57 (8H, m) |
| 301 | 1.08 (6H, t, J=7.9 Hz), 1.43–1.93 (8H, m), 2.40–3.16 (14H, m), 3.28–5.17 (4H, m), 3.45 (2H, t, J=5.1 Hz), 3.51 (2H, t, J=8.0 Hz), 3.99 (2H, t, J=6.4 Hz), 6.84–7.48 (4H, m) |
| 302 | 1.48–1.93 (8H, m), 2.27–3.13 (10H, m), 2.45 (6H, s), 3.36–3.67 (5H, m), 3.73–5.17 (4H, m), 3.99 (2H, t, J=6.3 Hz), 6.86–7.50 (8H, m) |
| 303 | 1.23 (6H, t, J=7.2 Hz), 1.67–1.94 (2H, m), 2.06 (2H, quint, J=6.2 Hz), 2.43–3.14 (14H, m), 3.38–3.62 (4H, m), 3.66 (2H, t, J=6.1 Hz), 3.87–5.22 (4H, m), 4.08 (2H, t, J=6.1 Hz), 6.85–7.48 (8H, m) |
| 304 | 1.38–1.98 (12H, m), 2.25–3.18 (14H, m), 3.33–5.13 (7H, m), 6.80–7.50 (8H, m) |
| 305 | 1.26–1.92 (8H, m), 2.15–3.13 (14H, m), 2.32 (3H, s), 3.20–5.03 (5H, m), 3.98 (2H, t, J=6.4 Hz), 6.82–7.47 (3H, m) |
| 306 | 1.37–1.94 (8H, m), 2.28–3.23 (14H, m), 2.36 (3H, s), 3.54–5.15 (4H, m), 3.68 (2H, t, J=4.8 Hz), 4.00 (2H, t, J=6.3 Hz), 6.83–7.52 (8H, m) |
| 307 | 1.33–1.98 (8H, m), 2.28–3.18 (14H, m), 3.38–5.18 (11H, m), 3.98 (2H, t, J=6.2 Hz), 6.78–7.48 (8H, m) |
| 308 | 1.35–1.98 (8H, m), 2.25–3.32 (18H, m), 3.38–5.10 (7H, m), 6.78–7.48 (13H, m) |
| 309 | 1.38–1.98 (16H, m), 2.23–3.15 (14H, m), 3.32–5.05 (5H, m), 4.00 (2H, t, J=6.3 Hz), 6.32–7.50 (8H, m) |
| 310 | 1.43 (6H, t, J=7.3 Hz), 1.35–1.65 (4H, m), 1.70–1.98 (6H, m), 2.51–3.23 (4H, m), 3.77–5.23 (3H, m), 3.99 (2H, t, J=6.2 Hz), 6.85–7.51 (8H, m) |
| 311 | 1.34–2.31 (14H, m), 2.51–3.65 (14H, m), 3.70–5.14 (3H, m), 3.98 (2H, t, J=6.2 Hz), 6.83–7.50 (8H, m) |
| 312 | 1.46–2.06 (12H, m), 2.16–3.13 (14H, m), 3.33–5.07 (5H, m), 4.00 (2H, t, J=6.0 Hz), 6.83–7.48 (8H, m) |
| 313 | 1.13 (3H, t, J=7.2 Hz), 1.38–2.02 (9H, m), 2.37–3.13 (12H, m), 3.53–5.12 (3H, m), 3.99 (2H, t, J=6.3 Hz), 6.82–7.52 (8H, m) |
| 314 | 1.11 (6H, dd, J=6.3, 1.0 Hz), 1.38–1.95 (8H, m), 2.35–3.12 (13H, m), 3.46–5.09 (4H, m), 3.99 (2H, t, J=6.3 Hz), 6.32–7.49 (8H, m) |
| 315 | 1.02 (3H, t, J=7.1 Hz), 1.28–2.03 (14H, m), 2.21–3.12 (14H, m), 3.28–5.12 (8H, m), 3.99 (2H, t, J=6.4 Hz), 6.82–7.48 (8H, m) |
| 316 | 1.38–1.96 (8H, m), 2.28–3.13 (17H, m), 3.62–5.08 (5H, m), 3.99 (2H, t, J=6.3 Hz), 6.82–7.48 (13H, m) |
| 317 | 1.37–2.00 (12H, m), 2.18–3.30 (15H, m), 3.40–5.16 (4H, m), 3.47 (1H, dd, J=11.1, 4.1 Hz), 3.62 (1H, dd, J=11.1, 4.1 Hz), 3.99 (2H, t, J=6.4 Hz), |

TABLE 8-continued

| | |
|---|---|
| | 6.82–7.48 (8H, m) |
| 318 | 1.35–1.95 (8H, m), 2.18–3.13 (10H, m), 2.24 (3H, s), 3.46 (1H, d, J=13.0 Hz), 3.69 (1H, d, J=13.0 Hz), 3.55–5.14 (4H, m), 3.99 (2H, t, J=6.3 Hz), 6.82–7.48 (13H, m) |
| 319 | 1.65–2.08 (6H, m), 2.46–3.49 (10H, m), 3.78–5.08 (5H, m), 6.81 (2H, d, J=8.7 Hz), 6.95–7.75 (10H, m), 11.40 (1H, brs) |
| 320 | 1.30–1.99 (10H, m), 2.45–3.20 (8H, m), 3.74–5.20 (5H, m), 3.98 (2H, t, J=6.4 Hz), 4.06 (2H, t, J=6.6 Hz), 6.90 (2H, d, J=8.7 Hz), 6.93–7.57 (6H, m) |
| 321 | 1.68–2.32 (6H, m), 2.49–3.64 (10H, m), 3.77–5.10 (5H, m), 6.80 (2H, d, J=9.1 Hz), 6.96–7.91 (10H, m), 12.03 (1H, s) |
| 322 | 1.55–1.97 (2H, m), 2.07–2.32 (2H, m), 2.55–5.17 (7H, m), 3.92 (2H, t, J=6.8 Hz), 4.06 (2H, t, J=6 Hz), 6.65 (1H, d, J=9.4 Hz), 6.82 (2H, d, J=8.7 Hz), 7.10–8.05 (11H, m), |
| 323 | 1.61–2.08 (6H, m), 2.65–3.34 (4H, m), 2.93 (2H, t, J=6.8 Hz), 3.88–5.20 (3H, m), 4.09 (2H, t, J=6 Hz), 6.65 (1H, d, J=9.4 Hz), 6.93 (2H, d, J=8.8 Hz), 7.11–7.77 (7H, m) |
| 324 | 1.62–2.09 (4H, m), 1.93 (3H, s), 2.60–3.49 (6H, m), 3.85–5.15 (3H, m), 4.00 (2H, t, J=5.9 Hz), 6.00 (1H, brs), 6.59 (1H, d, J=9.4 Hz), 6.85 (2H, d, J=8.7 Hz), 7.08–7.66 (7H, m) |
| 325 | 1.30–2.15 (8H, m), 2.32–3.20 (8H, m), 3.53–4.05 (6H, m), 4.20–4.78 (1H, m), 4.80–5.15 (3H, m), 5.70–5.93 (1H, m), 6.38–6.88 (4H, m), 7.10–7.35 (1H, m) |
| 326 | 1.28–1.96 (8H, m), 2.30–3.21 (11H, m), 3.56–4.10 (6H, m), 4.12–4.78 (1H, m), 4.83–5.10 (1H, m), 6.40–6.85 (4H, m), 7.12–7.32 (1H, m) |
| 327 | 1.41 (3H, t, J=6.9 Hz), 1.52–1.90 (2H, m), 2.30 (3H, s), 2.38–3.27 (8H, m), 3.55–3.93 (4H, m), 4.04 (2H, q, J=6.9 Hz), 4.20–4.68 (1H, m), 4.80–5.08 (1H, m), 6.35–6.64 (2H, m), 6.78–7.37 (4H, m) |
| 328 | 1.64–1.86 (3H, m), 2.30 (3H, s), 2.40–2.90 (8H, m), 3.12–3.31 (2H, m), 4.20–4.40 (1H, m), 6.82–7.20 (3H, m) |

EXAMPLE 588

To 1-[1-(2-methoxy-4-ethoxybenzoyl)-4-piperidinyl]-3-ethoxycarbonyl-3,4-dihydrocarbostyril (0.48 g) are added sodium hydroxide (0.2 g), water (4 ml) and ethanol (10 ml) and the mixture is stirred at room temperature for 30 minutes. Water is added to the reaction mixture and the mixture is extracted with ethyl acetate. The aqueous layer is neutralized with acetic acid and extracted with dichloromethane. The extract is concentrated to give 1-[1-(2-methoxy-4-ethoxybenzoyl)-4-piperidinyl]-3-carboxy-3,4-dihydrocarbostyril (0.38 g) as white amorphous form.

NMR (CDCl$_3$) δppm: 1.42 (3H, t, J=7.0 Hz), 1.58–2.05 (2H, m), 2.35–3.47 (7H, m), 3.55–3.95 (4H, m), 4.04 (2H, q, J=7 Hz), 4.38 (1H, brs), 4.94 (1H, brs), 6.37–6.56 (2H, m), 7.00–7.40 (5H, m)

EXAMPLE 589

To 1-[1-(2-methoxy-4-ethoxybenzoyl)4-piperidinyl]-3-ethoxycarbonyl-3,4-dihydrocarbstyril (1,1 g) are added hydrazine monohydrate (1.1 g) and ethanol (15 ml) and the mixture is refluxed with heating for 7 hours. The reaction mixture is concentrated and the residue is purified by silica gel column chromatography (solvent: dichloromethane→dichloromethane:methanol=20:1) to give 1-[1-(2-methoxy-4-ethoxybenzoyl)4-piperidinyl]-3-hydrazinocarbonyl-3,4-dihydrocarbostyril (0.9 g) as white amorphous form.

NMR (CDCl$_3$) δppm: 1.42 (3H, t, J=7.0 Hz), 1.52–1.95 (2H, m), 2.30–3.93 (13H, m), 4.04 (2H, q, J=7 Hz), 4.15–5.06 (3H, m), 6.40–6.62 (2H, m), 6.97–7.50 (5H, m)

EXAMPLE 590

To 1-[1-(2-methoxy-4-ethoxybenzoyl)-4-piperidinyl]-3-hydrazinocarbonyl-3,4-dihydrocarbostyril (1.4 g) are added dichloromethane (14 ml), 10% hydrochloric acid (5.5 ml) and water (14 ml). To the mixture is added dropwise a solution of sodium nitrite (0.25 g) in water (3 ml) at a temperature below 5° C. The mixture is stirred at 5° C. for 15 minutes. The dichloromethane layer is separated, dried and concentrated. To the resulting residue are added benzyl alcohol (0.5 g) and toluene (7 ml) and the mixture is refluxed with heating for 2 hours. After cocentration, the resulting residue is purified by silica gel column chromatography (solvent: dichloromethane) to give 1-[1-(2-methoxy-4-ethoxybenzoyl)-4-piperidinyl]-3-benzyloxycarbonylamino-3,4-dihydrocarbostyril (0.9 g) as white amorphous form.

NMR (CDCl$_3$) δppm: 1.40 (3H, t, J=7.0 Hz), 1.55–2.00 (2H, m), 2.30–5.05 (15H, m), 5.30 (2H, s), 5.95 (1H, brs), 6.50–6.60 (2H, m), 7.02–7.42 (10H, m)

EXAMPLE 591

To 1-[1-(2-methoxy-4-ethoxybenzoyl)-4-piperidinyl]-3-benzyloxycarbonylamino-3,4-dihydrocarbostyril (0.8 g) are added ethanol (20 ml) and 10% palladium-carbon (0.15 g) and the mixture is subjected to catalytic reduction at room temperature for 4 hours. After the catalyst is removed by filtration, the resulting filtrate is concentrated. To the residue are added ethanol (5 ml) and conc. hydrochloric acid (0.2 ml) and the mixture is concentrated again. Diethyl ether is added to the residue and the precipitated crystal is collected by filtration and recrystallized from ethanol to give 1-[1-(2-methoxy-4-ethoxybenzoyl)-4-piperidinyl]-3-amino-3,4-dihydrocarbostyril hydrochloride (0.52 g) as white powder, m.p.: 257°–260° C.

EXAMPLE 592

To 1-{1-[4-(5-carboxypentyloxy)benzoyl]-4-piperidinyl}-3,4-dihydrocarbostyril (2.00 g) are added 3,4-diaminopyridine (0.47 g), phosphorus pentoxide (1.00 g) and methanesulfonic acid (7.0 ml) and the mixture is stirred with heating at 100°–120° C. for 3 hours. After cooling, the reaction solution is poured into ice-water (30 ml) and the mixture is adjusted to around pH 11 with aqueous sodium hydroxide solution and extracted with dichloromethane. The extract is dried with magnesium sulfate and the solvent is distilled off. The resulting residue is purified by silica gel column chromatography (solvent: dichloromethane:methanol =20:1→9:1) to give 1-{1-[4-(5-(imidazo[4,5-c]pyridine-2-yl)carboxypentyloxy)benzoyl]-4-piperidinyl}-3,4-dihydrocarbostyril (1.32 g) as white amorphous form.

NMR (CDCl$_3$) δppm: 1.42–1.64 (2H, m), 1.64–2.06 (6H, m), 2,57 (2H, t, J=6.1 Hz), 2,64–3.24 (8H, m), 3.67–5.15 (2H, m), 3.92 (2H, t, J=6.1 Hz), 4.34 (1H, m), 6.84 (2H, d, J=8.7 Hz), 7.00–7.36 (5H, m), 7.40 (2H, d, J=8.7 Hz), 8.28 (1H, d, J=5.6 Hz), 8.80 (1H, s)

EXAMPLE 593

To methyl 2-methyl-5-[(1-benzyl-4-piperidinyl)amino]cinnamate (1.0 g) are added acetic acid (10 ml), conc. hydrochloric acid (3 ml), water (3 ml) and 10% palladiumcarbon (0.2 g) and the mixture is subjected to catalytic reduction at 90° C. for 2 hours under atmospheric pressure. After cooling, the catalyst is removed by filtration and the filtrate is concentrated. Water is added to the resulting residue and the mixture is basified with potassium carbonate and then extracted with dichloromethane. The solvent is concentrated to give 5-methyl-1-(4-piperidinyl)-3,4-dihydrocarbostyril (0.6 g) as colorless amorphous form.

NMR (CDCl$_3$) δppm: 1.64–1.86 (3H, m), 2.30 (3H, s), 2.40–2.90 (8H, m), 3.12–3.31 (2H, m), 4.20–4.40 (1H, m), 6.82–7.20 (3H, m)

Using the suitable starting materials, the compounds of the above Examples 1-9, 11-164, 169-383C, 435-474A and 482-577A are obtained in the same manners as Example 593.

Using the suitable starting materials, the following compounds are obtained in the same manners as in Examples 1, 384 and 593.

TABLE 9

| | Structure | | | Crystalline form | q | Recrystallization solvent | Melting point/NMR analysis | FAB-MS (Pos.) (m/z) | Form |
|---|---|---|---|---|---|---|---|---|---|
| | R | | R¹ | | | | | | |

Bond between 3- and 4-positions in the carbostyril ring: Single bond

| | R | R¹ | q | Crystalline form | Recrystallization solvent | Melting point/NMR analysis | Form |
|---|---|---|---|---|---|---|---|
| Example 594 | (structure with O(CH₂)₅Br) | H | 1 | | | 491) | Free |
| Example 595 | (structure with O(CH₂)₆Br) | H | 1 | | | 492) | Free |
| Example 596 | (structure with O(CH₂)₃NHCO, N—CO₂CH₂-phenyl) | H | 1 | Colorless amorphous form | | 329) | Free |
| Example 597 | (structure with O(CH₂)₃NHCO, NHCOCH₂-biphenyl, (CH₂)₄—NHCOCH₂) | H | 1 | Colorless amorphous form | | 330) | Free |
| Example 598 | (structure with O(CH₂)₃NHCO, NH₂, phenol-OH) | H | 1 | Colorless amorphous form | | 331) | Free |

TABLE 9-continued

| | | | | |
|---|---|---|---|---|
| Example 599 | [structure] | H | — | Colorless amorphous form | 332) Free |
| Example 600 | [structure] | H | — | | 333) Free |
| Example 601 | [structure] | H | — | Colorless amorphous form | 334) Free |
| Example 602 | [structure] | H | — | Colorless amorphous form | 335) Free |
| Example 603 | [structure] | H | — | Colorless amorphous form | 336) Free |
| Example 604 | [structure] | H | — | | 337) Free |
| Example 605 | [structure] | H | — | Colorless amorphous form | 338) Free |
| Example 606 | [structure] | H | — | Colorless amorphous form | 339) Free |

TABLE 9-continued

| | | | | | |
|---|---|---|---|---|---|
| Example 607 | [structure with O(CH$_2$)$_5$CON-piperazine-NH] | H | Colorless amorphous form | 340) | Free |
| Example 608 | [structure with O(CH$_2$)$_5$CON-piperazine-N—COCH$_3$] | H | Colorless amorphous form | 341) | Free |
| Example 609 | [structure with O(CH$_2$)$_5$CON-piperazine-N—CH$_3$] | H | Colorless amorphous form | 342) | Free |
| Example 610 | [structure with O(CH$_2$)$_5$CON-piperazine-NCH$_2$CH=CH$_2$] | H | | 343) | Free |
| Example 611 | [structure with O(CH$_2$)$_5$NHCO(CH$_2$)$_3$NH$_2$] | H | | 344) | Free |
| Example 612 | [structure with O(CH$_2$)$_3$NHCO(CH$_2$)$_3$NHCO$_2$CH$_2$-phenyl] | H | | 345) | Free |
| Example 613 | [structure with O(CH$_2$)$_5$NHCO(CH$_2$)$_3$NHCO$_2$CH$_2$-phenyl] | H | | 346) | Free |
| Example 614 | [structure with O(CH$_2$)$_5$NHCOCH$_2$Cl] | H | | 347) | Free |

TABLE 9-continued

| Example | Structure | | | | Notes |
|---|---|---|---|---|---|
| Example 615 | [piperidine-C(=O)-C6H4-O(CH2)5NHCO(CH2)3NH2] | H | — | 348) | Free |
| Example 616 | [piperidine-C(=O)-C6H4-O(CH2)5NHCOCH2N(CH3)2] | H | — | 349) | Free |
| Example 617 | [piperidine-C(=O)-C6H4-O(CH2)5CON(piperidine-CO2C2H5)] | H | — | 350) | Free |
| Example 618 | [piperidine-C(=O)-C6H4-O(CH2)5NHCOCH2N(C2H5)2] | H | — | 351) | Free |
| Example 619 | [piperidine-C(=O)-C6H4-O(CH2)5NHCO(CH2)3NHCOCH3] | H | — | 352) | Free |
| Example 620 | [piperidine-C(=O)-C6H4-O(CH2)5NHCO(CH2)3N(CH3)2] | H | — | 353) | Free |
| Example 621 | [piperidine-C(=O)-C6H4-O(CH2)5NHCOCH2OCOCH3] | H | — | 354) | Colorless amorphous form |
| Example 622 | [piperidine-C(=O)-C6H4-O(CH2)5NHCOCH2OH] | H | — | 355) | Colorless amorphous form |
| Example 623 | [piperidine-C(=O)-C6H4-O(CH2)5NHCOCH2NHC2H5] | H | — | 356) | Free |

TABLE 9-continued

| | Structure | | | | |
|---|---|---|---|---|---|
| Example 624 | [piperidine-N-C(=O)-C6H4-O(CH2)5CON-(4-CO2H-cyclohexyl)] | H | 1 | Colorless amorphous form | 357) Free |
| Example 625 | [piperidine-N-C(=O)-C6H4-O(CH2)5NHCOCH2NHCH2CH=CH2] | H | 1 | | 358) Free |
| Example 626 | [piperidine-N-C(=O)-C6H4-O(CH2)4NHCOCH2Cl] | H | 1 | | 359) Free |
| Example 627 | [piperidine-N-C(=O)-C6H4-O(CH2)4NHCOCH2N(CH3)2] | H | 1 | | 360) Free |
| Example 628 | [piperidine-N-C(=O)-C6H4-O(CH2)4NHCOCH2N(C2H5)2] | H | 1 | | 361) Free |
| Example 629 | [piperidine-N-C(=O)-C6H4-O(CH2)4NHCOCH2OCOCH3] | H | 1 | Colorless amorphous form | 362) Free |
| Example 630 | [piperidine-N-C(=O)-C6H4-O(CH2)5NHCOCH2N(4-CH3-piperazine)] | H | 1 | | 363) Free |
| Example 631 | [piperidine-N-C(=O)-C6H4-O(CH2)5NHCOCH2N(4-phenyl-piperazine)] | H | 1 | Colorless amorphous form | 364) Free |

TABLE 9-continued

| Example | Structure | | | | |
|---|---|---|---|---|---|
| Example 632 | [piperidine-N-C(=O)-C6H4-O(CH2)4NHCOCH2OH] | H | 1 | Colorless amorphous form | 365) Free |
| Example 633 | [piperidine-N-C(=O)-C6H4-O(CH2)5NHCOCH2NHCH(CH3)2] | H | 1 | | 366) Free |
| Example 634 | [piperidine-N-C(=O)-C6H4-O(CH2)5NHCOCH2NHCH2-phenyl] | H | 1 | | 367) Free |
| Example 635 | [piperidine-N-C(=O)-C6H4-O(CH2)5NHCOCH2N(pyrrolidine)] | H | 1 | | 368) Free |
| Example 636 | [piperidine-N-C(=O)-C6H4-O(CH2)5NHCOCH2N(morpholine)] | H | 1 | | 369) Free |
| Example 637 | [piperidine-N-C(=O)-C6H4-O(CH2)5NHCOCH2N(CH3)(CH2-phenyl)] | H | 1 | | 370) Free |
| Example 638 | [piperidine-N-C(=O)-C6H4-O(CH2)5NHCOCH2N(CH3)(CH2)2OH] | H | 1 | | 371) Free |
| Example 639 | [piperidine-N-C(=O)-C6H4-O(CH2)5NHCOCH2N(CH3)(CH2-C6H4-OC2H5)] | H | 1 | | 372) Free |

TABLE 9-continued

| Example | Structure | | | | |
|---|---|---|---|---|---|
| Example 640 | 4-methylpiperidine-N-C(=O)-C6H4-O(CH2)5NHCOCH2NHCO2CH2-C6H5 | H | 1 | Colorless amorphous form | 373) Free |
| Example 641 | 4-methylpiperidine-N-C(=O)-C6H4-O(CH2)5CON(4-CONH2-piperidine) | H | 1 | Colorless amorphous form | 374) Free |
| Example 642 | 4-methylpiperidine-N-C(=O)-C6H4-O(CH2)4NHCO-(4-NH-piperidine) | H | 1 | Colorless amorphous form | 375) Free |
| Example 643 | 4-methylpiperidine-N-C(=O)-C6H4-O(CH2)4NHCO-(4-(N-COCH3)-piperidine) | H | 1 | Colorless amorphous form | 376) Free |
| Example 644 | 4-methylpiperidine-N-C(=O)-C6H4-O(CH2)5CON(4-(N(CH3)2)-piperidine) | H | 1 | Colorless amorphous form | 377) Free |
| Example 645 | 4-methylpiperidine-N-C(=O)-C6H4-O(CH2)5NHCOCH2NH2 | H | 1 | | 378) Free |
| Example 646 | 4-methylpiperidine-N-C(=O)-C6H4-O(CH2)5NHCOCH2NHSO2CH3 | H | 1 | Colorless amorphous form | 379) Free |
| Example 647 | 4-methylpiperidine-N-C(=O)-C6H4-O(CH2)5NHCO-C6H4-NO2 | H | 1 | Colorless amorphous form | 380) Free |
| Example 648 | 4-methylpiperidine-N-C(=O)-C6H4-O(CH2)5NHCO-C6H4-NH2 | H | 1 | Colorless amorphous form | 381) Free |

TABLE 9-continued

| | | | | | |
|---|---|---|---|---|---|
| Example 649 | ![structure with piperidine-C(=O)-phenyl-O(CH₂)₅NHSO₂-phenyl-NO₂] | H | 1 | Colorless amorphous form | 382) Free |
| Example 650 | ![structure with piperidine-C(=O)-phenyl-O(CH₂)₅NHCO-phenyl-NHCOCH₃] | H | 1 | Colorless amorphous form | 383) Free |
| Example 651 | ![structure with piperidine-C(=O)-phenyl-O(CH₂)₅NHCO-phenyl-N(CH₃)₂] | H | 1 | Colorless amorphous form | 384) Free |
| Example 652 | ![structure with piperidine-C(=O)-phenyl-O(CH₂)₅NHSO₂-phenyl-NH₂] | H | 1 | Colorless amorphous form | 385) Free |

| | | | | | |
|---|---|---|---|---|---|
| Example 653 | 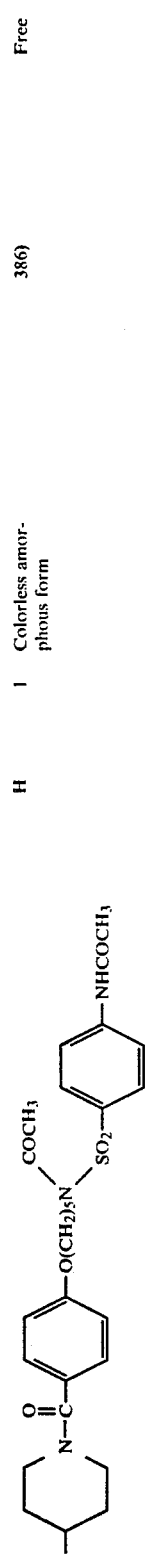 | H | 1 | Colorless amorphous form | 386) Free |
| Example 654 |  | H | 1 | Colorless amorphous form | 387) Free |
| Example 655 |  | H | 1 | — | 388) Free |
| Example 656 | 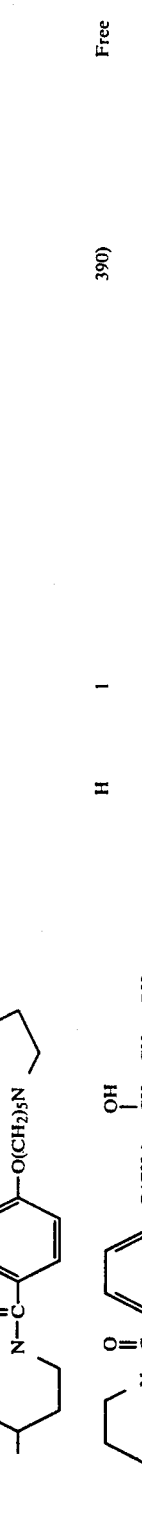 | H | 1 | — | 389) Free |
| Example 657 | 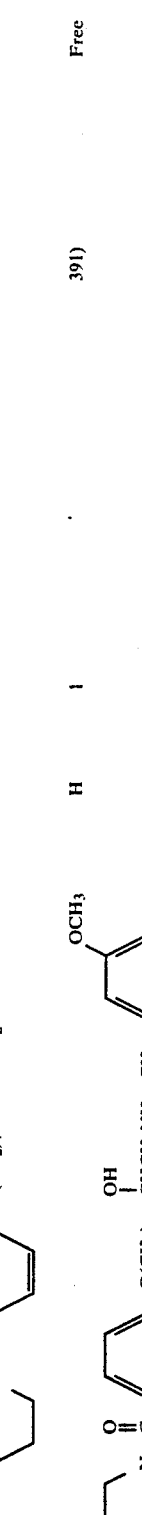 | H | 1 | — | 390) Free |
| Example 658 | 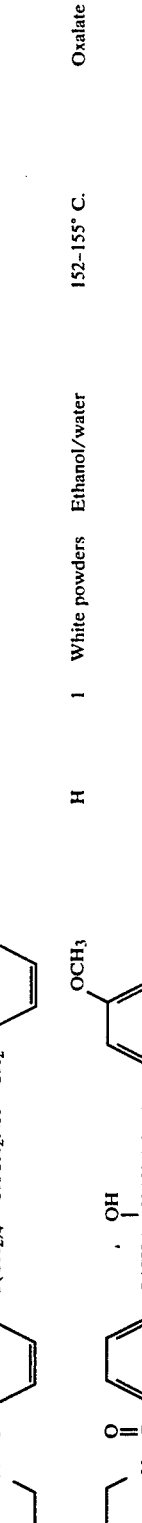 | H | 1 | — | 391) Free |
| Example 659 | 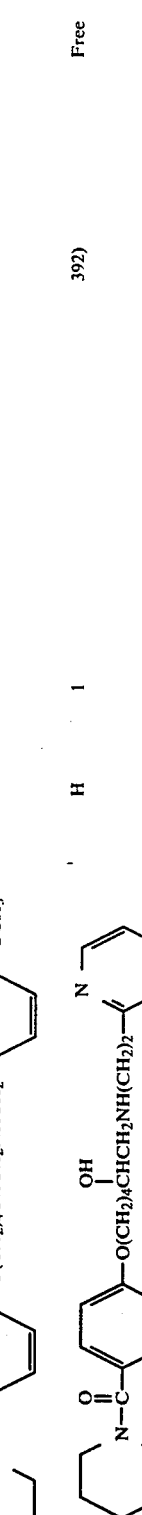 | H | 1 | White powders Ethanol/water | 152–155° C. Oxalate |
| Example 660 |  | H | 1 | — | 392) Free |

-continued

| | | | | |
|---|---|---|---|---|
| Example 661 | [structure: piperidine-N-C(=O)-C6H4-O(CH2)4CH(OH)CH2N(piperidine-4-CH2-phenyl)] | H | — | 393) Free |
| Example 662 | [structure: 4-Me-piperidine-N-C(=O)-C6H4-O(CH2)4N(piperazine)N-CH2CH=CH2] | H | — | 394) Free |
| Example 663 | [structure: 4-Me-piperidine-N-C(=O)-C6H4-O(CH2)4-CH(OH)-CH2-N(CH3)(CH2)2-(2-pyridyl)] | H | — | 395) Free |
| Example 664 | [structure: 4-Me-piperidine-N-C(=O)-C6H4-O(CH2)4-CH(OH)-CH2-N(C2H5)-CH2-(3-pyridyl)] | H | — | 396) Free |
| Example 665 | [structure: 4-Me-piperidine-N-C(=O)-C6H4-O(CH2)7-N(pyrrolidine)] | H | — | 397) Free |
| Example 666 | [structure: 4-Me-piperidine-N-C(=O)-C6H4-O(CH2)7-N(C2H5)2] | H | — | 398) Free |
| Example 667 | [structure: 4-Me-piperidine-N-C(=O)-C6H4-O(CH2)4-N(pyrrolidine)] | H | — | 399) Free |
| Example 668 | [structure: 4-Me-piperidine-N-C(=O)-C6H4-O(CH2)4-N(C2H5)2] | H | — | 400) Free |

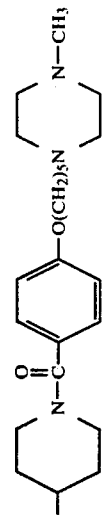

| | | | | |
|---|---|---|---|---|
| Example 677 | 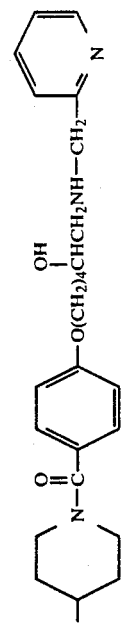 | H | — | 405) | Free |
| Example 678 | 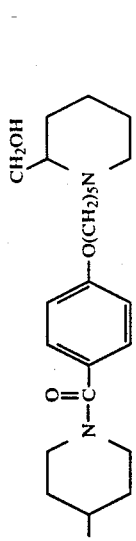 | H | — | 406) | Free |
| Example 679 | 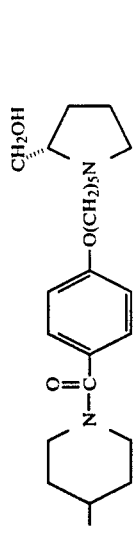 | H | — | 407) | Free |
| Example 680 | 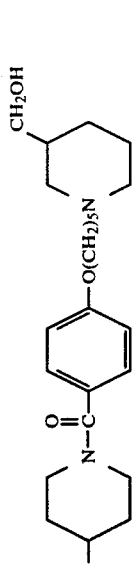 | H | — | 408) | Free |
| Example 681 | 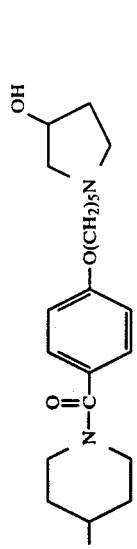 | H | — | 409) | Free |
| Example 682 | 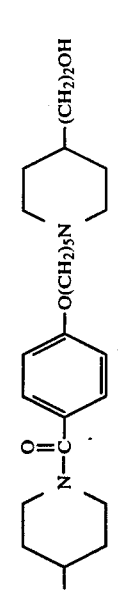 | H | Colorless amorphous form | 410) | Hydrochloride |
| Example 683 | 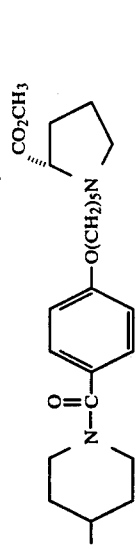 | H | — | 411) | Free |

| | | | | | |
|---|---|---|---|---|---|
| Example 684 | 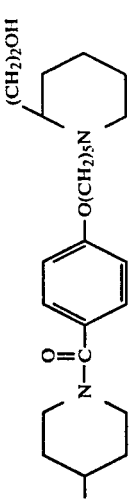 | -continued H | — | 412) | Hydrochloride |
| Example 685 | 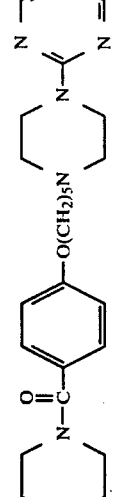 | H | Light yellow amorphous form | 413) | Free |
| Example 686 | 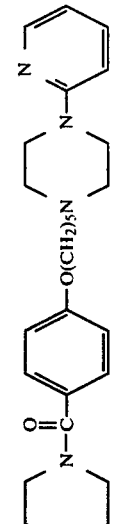 | H | — | 414) | Free |
| Example 687 | 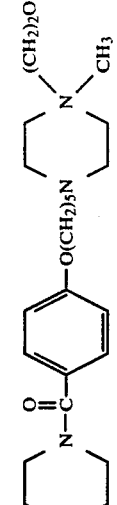 | H | — | 415) | Free |
| Example 688 | 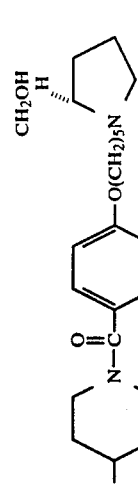 | H | — | 416) | Free |
| Example 689 | 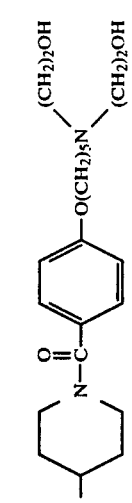 | H | — | 417) | Free |
| Example 690 | 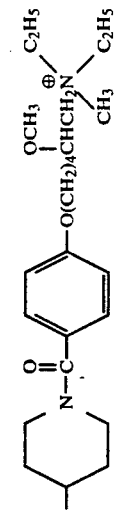 | H | Colorless amorphous form | 418) 551 | I⊖ |
| Example 691 | 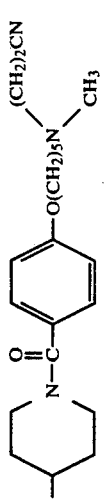 | H | — | 419) | Free |

| | | | | |
|---|---|---|---|---|
| Example 692 | 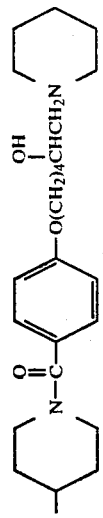 | H | — | Free | 420) |
| Example 693 | 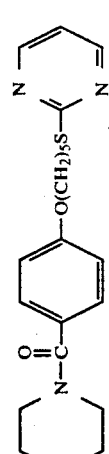 | H | — | Free | 421) |
| Example 694 | 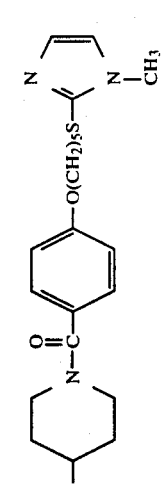 | H | — | Free | 422) |
| Example 695 | 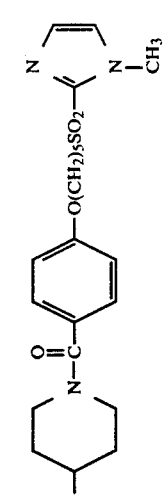 | H | — | Colorless amorphous form | 423) |
| Example 696 | 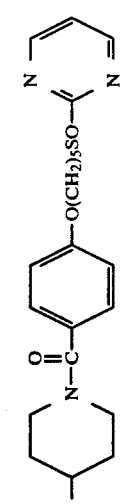 | H | — | Free | 424) |
| Example 697 | 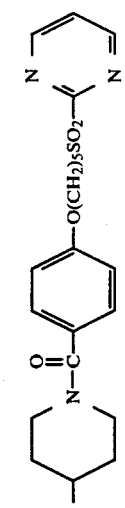 | H | — | Colorless amorphous form | 425) |
| Example 698 | 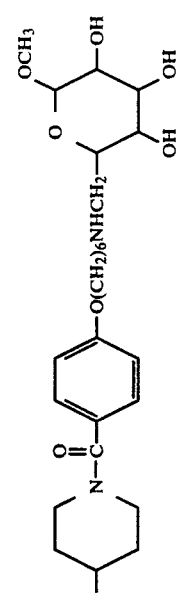 | H | — | Free | 426) |

| | | -continued | | | |
|---|---|---|---|---|---|
| Example 699 | 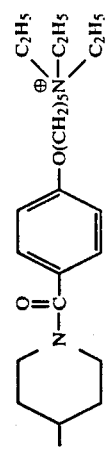 | H | — | 427) | Br⊖ |
| Example 700 | 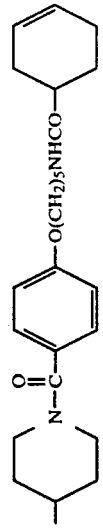 | H | — | 428) | Free |
| Example 701 | 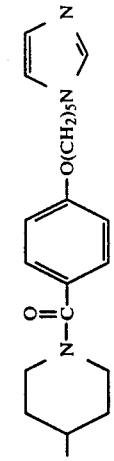 | H | — | 429) | Free |
| Example 702 | 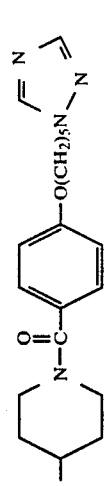 | H | — | 430) Colorless amorphous form | Free |
| Example 703 | 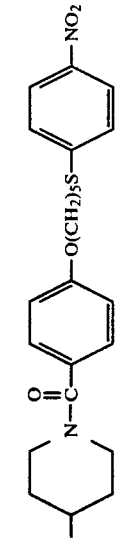 | H | — | 431) Colorless amorphous form | Free |
| Example 704 | 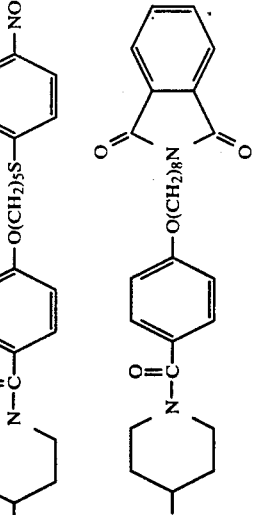 | H | — | 432) | Free |
| Example 705 | 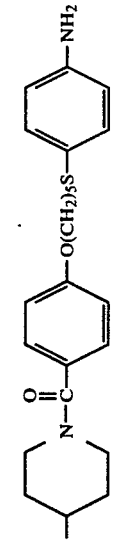 | H | — | 433) | Free |
| Example 706 | 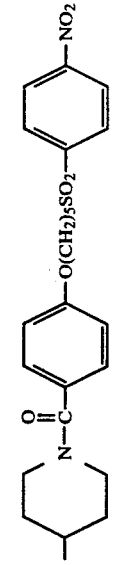 | H | — | 434) | Free |

-continued
| Example 707 | 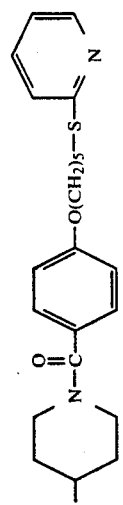 | H | — | 435) | Free |
| Example 708 | 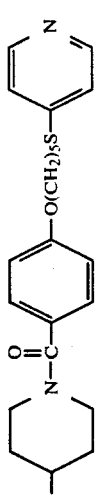 | H | — | 436) | Free |
| Example 709 | 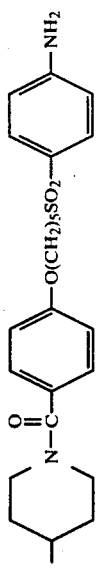 | H | Colorless amorphous form | 437) | Free |
| Example 710 | 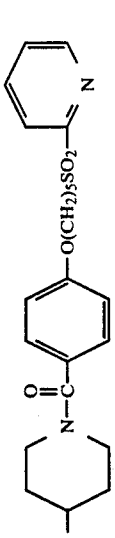 | H | — | 438) | Free |
| Example 711 |  | H | Colorless amorphous form | 439) | Free |
| Example 712 |  | H | Colorless amorphous form | 440) | Free |

| Example | Structure | | | | | |
|---|---|---|---|---|---|---|
| Example 713 |  | H | 1 | | 441) | Free |
| Example 714 |  | H | 1 | | 442) | Free |
| Example 715 |  | H | 1 | Colorless amorphous form | 443) | Free |
| Example 716 |  | H | 1 | Colorless amorphous form | 444) | Free |
| Example 717 | 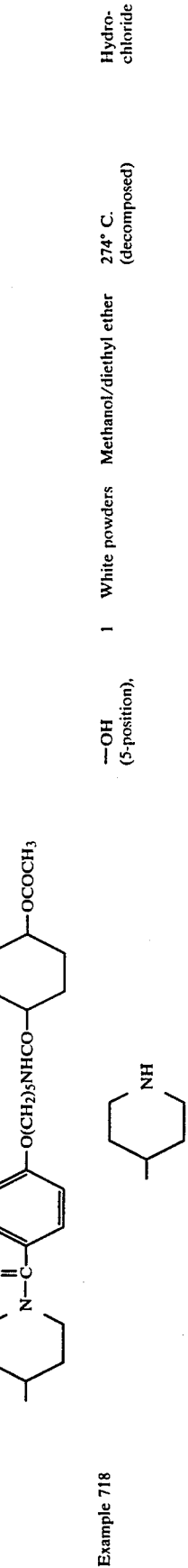 | H | 1 | Colorless amorphous form | 445) | Free |
| Example 718 |  | —OH (5-position), | 1 | White powders | Methanol/diethyl ether | 274° C. (decomposed) | Hydrochloride |
| Example 719 |  | —OC$_2$H$_5$ (5-position), | 1 | White powders | Methanol/diethyl ether | 250° C. (decomposed) | Hydrochloride |
| Example 720 |  | —OH (5-position), | 1 | Colorless amorphous form | 446) | Free |

| | | -continued | | |
|---|---|---|---|---|
| Example 721 | 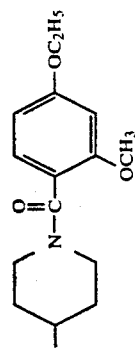 | —OH (5-position), | Colorless amorphous form | 447) Free |
| Example 722 | 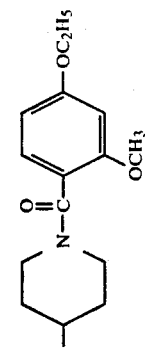 | —OCH₃ (5-position), | Colorless amorphous form | 448) Free |
| Example 723 | 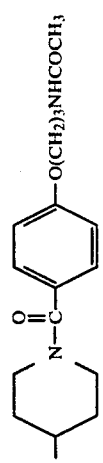 | —OC₂H₅ (5-position), | Colorless amorphous form | 449) Free |
| Example 724 | 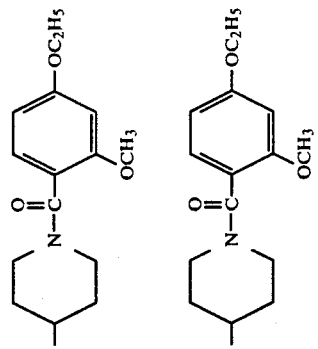 | —OC₂H₅ (5-position), | Colorless amorphous form | 450) Free |
| Example 725 | | —OC₂H₅ (5-position), | Colorless amorphous form | 451) Free |
| Example 726 | 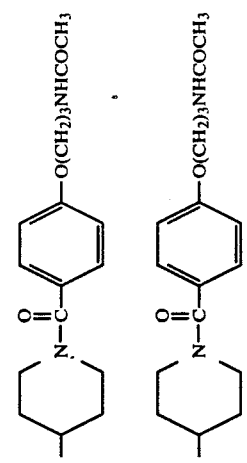 | —OCOCH₃ (5-position), | Colorless amorphous form | 452) Free |
| Example 727 | | —OCOCH₃, | Colorless amorphous form | 453) Free |

| Example | Structure | | | | Melting point | Salt form |
|---|---|---|---|---|---|---|
| Example 728 | 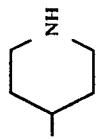 | —CH₃ (5-, 7-position) | 2 | White powders | 278–282° C. | Hydrochloride |
| Example 729 | 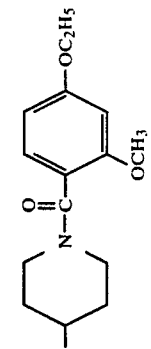 | —CH₃ (5-, 7-positions), | 2 | White powders | 165–167° C. | Free |
| Example 730 | 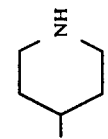 | F (5-position), | 1 | | 454) | Free |
| Example 731 | 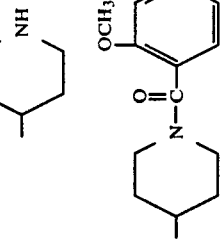 | F (5-position), | 1 | Colorless amorphous form | 455) | Free |
| Example 732 | 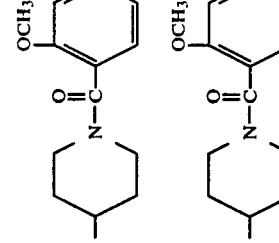 | F (5-position), | 1 | Colorless amorphous form | 456) | Free |
| Example 733 | 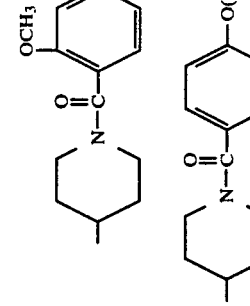 | —CH₃ (5-position), | 1 | Colorless amorphous form | 457) | Free |
| Example 734 | 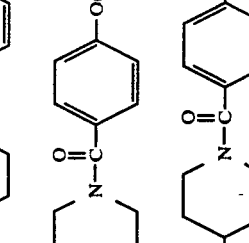 | —CH₃ (5-position), | 1 | Colorless amorphous form | 458) | Free |
| Example 735 | 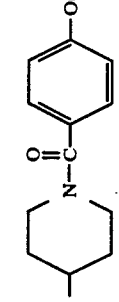 | —CH₃ (5-position), | 1 | Colorless amorphous form | 459) | Free |

| | | | | |
|---|---|---|---|---|
| Example 736 | 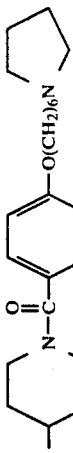 | —CH₃ (5-position), | Colorless amorphous form | 460) Free |
| Example 737 | 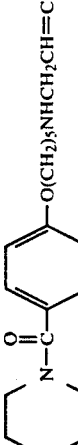 | H | — | 461) Free |
| Example 738 |  | H | — | 462) Free |
| Example 739 | 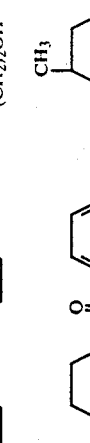 | H | — | 463) Free |
| Example 740 | 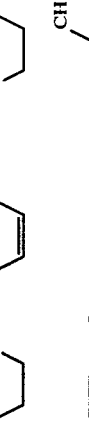 | H | — | 464) Free |
| Example 741 | 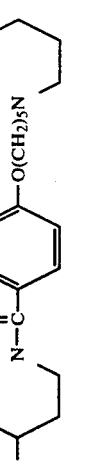 | H | — | 465) Free |
| Example 742 | 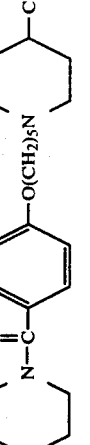 | H | — | 466) Free |
| Example 743 | 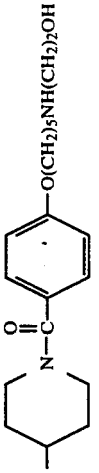 | H | — | 467) Free |

| | | | |
|---|---|---|---|
| Example 744 | 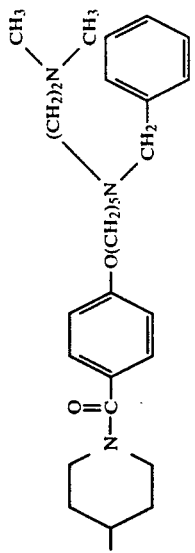 | H | 468) Free |
| Example 745 | 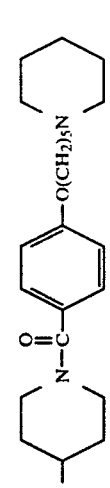 | H | 469) Free |
| Example 746 | 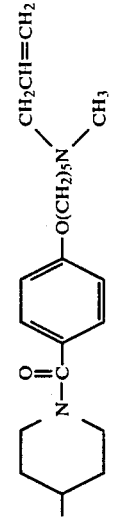 | H | 470) Free |
| Example 747 | 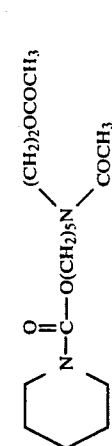 | H | 471) Free |
| Example 748 | 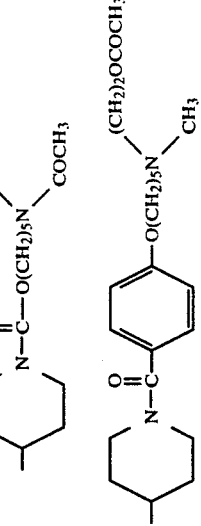 | H | 472) Free |
| Example 749 | 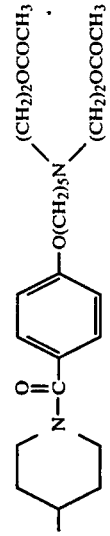 | H | 473) Free |
| Example 750 | 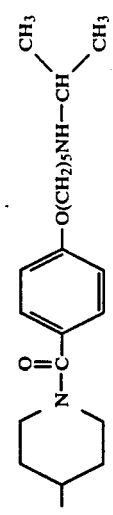 | H | 474) Free |
| Example 751 | 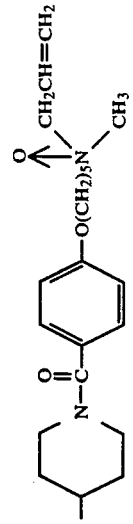 | H | 475) Free |

-continued
| | | | | |
|---|---|---|---|---|
| Example 752 | 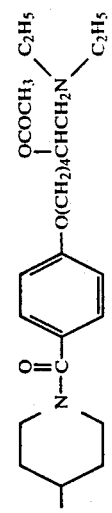 | H | | 476) Free |
| Example 753 | 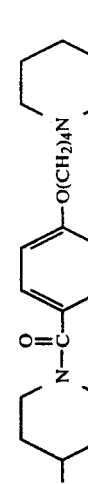 | H | | 477) Free |
| Example 754 | 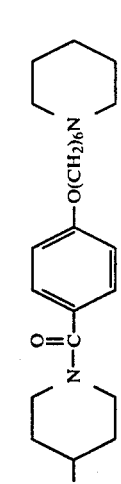 | H | | 478) Free |
| Example 755 | 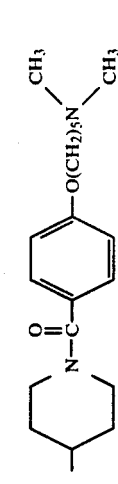 | H | | 479) Free |
| Example 756 | 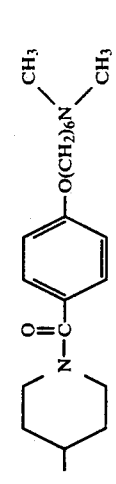 | H | | 480) Free |
| Example 757 | 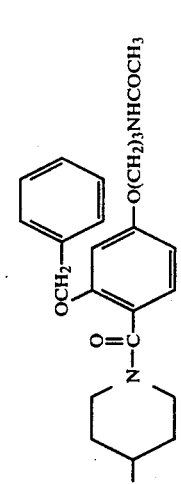 | H | Colorless amorphous form | 481) Free |
| Example 758 | 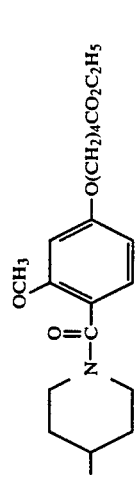 | H | | 482) Free |
| Example 759 | 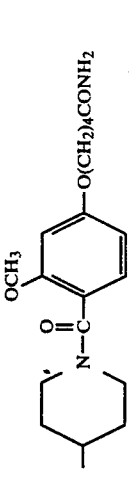 | H | Colorless amorphous form | 483) Free |

-continued
| | | | | | |
|---|---|---|---|---|---|
| Example 760 | 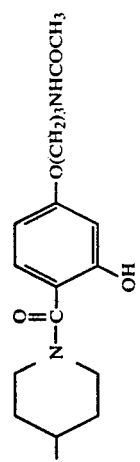 | H | Colorless needles | Ethanol/diethyl ether | 155-157° C. | Free |
| Example 761 | 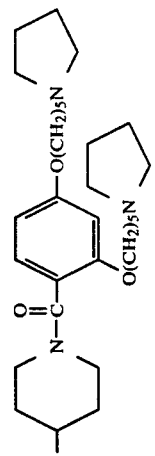 | H | Colorless amorphous form | | 484) | Free |
| Example 762 | 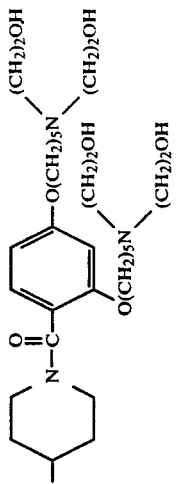 | H | | | 485) | Free |
| Example 763 | 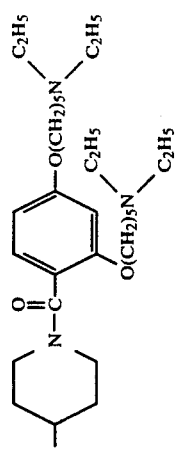 | H | | | 486) | Dihydrochloride |
| Example 764 | 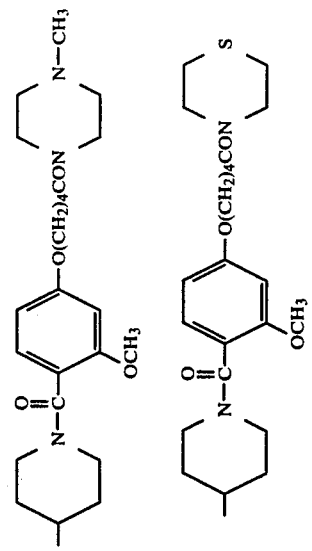 | H | Colorless amorphous form | | 487) | Free |
| Example 765 | 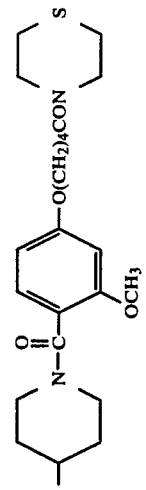 | H | Colorless amorphous form | | 488) | Free |

-continued

| | | | | | |
|---|---|---|---|---|---|
| Example 766 | ![structure with O(CH2)4CON-thiomorpholine S-oxide, OCH3] | H | 489) | Colorless amorphous form | Free |
| Example 767 | ![structure with O(CH2)4CON-thiomorpholine SO2] | H | 490) | Colorless amorphous form | Free |
| Example 768 | ![structure with O(CH2)5NH-cyclohexyl] | H | 493) | — | Free |
| Example 769 | ![structure with O(CH2)5NHCH2C≡CH] | H | 494) | — | Free |

EXAMPLE 770

1-{1-[4-(4-Oxiranylbutoxy)benzoyl]-4-piperidinyl}-3,4-dihydrocarbostyril (1.6 g) is dissolved in a mixture of dioxane (30 ml) and water (10 ml). Thereto is added conc. sulfuric acid (0.1 ml) and the mixture is stirred at room temperature overnight. The mixture is neutralized with sodium hydrogen carbonate and then extracted with chloroform. The extract is dried with magnesium sulfate and the solvent is evaporated off. The resulting residue is purified by silica gel column chromatography (solvent: dichloromethane:methanol=50:1) to give 1-{1-[4-(5,6-dihydroxyhexyloxy)benzoyl]-4-piperidinyl}-3,4-dihydrocarbostyril (0.6 g).

NMR (CDCl$_3$) δppm: 1.35-1.93 (8H, m), 2.15-3.15 (10H, m), 3.32-3.78 (3H, m), 3.83-5.22 (3H, m), 3.97 (2H, t, J=6.3 Hz), 6.79-7.48 (8H, m)

EXAMPLE 771

Using the suitable starting materials, the compounds of the above Examples 718, 719, 728 and 730 are obtained in the same manners as Example 386.

EXAMPLE 772

Using the suitable starting materials, the compounds of the above Examples 594-717, 720-727, 729, 731-769 are obtained in the same manners as in Examples 390-393.

EXAMPLE 773

Using the suitable starting materials, the compounds of the above Examples 594-717, 720-727, 729, 731-769 are obtained in the same manners as in Examples 398 and 399.

EXAMPLE 774

Using the suitable starting materials, the compounds of the above Examples 596-648, 650-651, 653, 700, 712, 714, 716, 717, 720, 723, 726, 727, 733, 747, 757, and 760 are obtained in the same manners as in Examples 403-405.

EXAMPLE 775

Using the suitable starting materials, the compounds of the above Examples 600, 604, 609, 610, 616, 618, 620, 623, 625, 627, 628, 630, 631, 633, 634, 637-639, 646, 649, 651, 652-655, 658-660, 662, 663, 666, 668-671, 673, 677, 685-687, 689-691, 698, 699, 715, 735-738, 742-744, 746-752, 755, 756, 762-764, 768-769 are obtained in the same manners as in Examples 407-409.

EXAMPLE 776

Using the suitable starting materials, the compounds of the above Examples 695, 696, 697, 706, 709-712, 715, 751, 766 and 767 are obtained in the same manners as in Example 416.

EXAMPLE 777

Using the suitable starting materials, the compounds of the above Examples 657-661, 663, 664, 674, 676, 677 and 692 are obtained in the same manners as in Example 421.

EXAMPLE 778

Using the suitable starting materials, the compounds of the above Examples 596-603, 605, 606, 611-616, 618-623, 625-640, 642, 643, 645-656, 662, 665-673, 675, 678-689, 691, 693, 694, 698, 700-705, 707, 708, 713, 714, 716, 717, 720, 723, 726, 727, 733, 735-750, 753-757, 760-763, 768 and 769 are obtained in the same manners as in Example 426.

TABLE 10

| No. | NMR (CDCl$_3$) δ value |
|---|---|
| 329 | 1.64-2.44(8H, m), 2.50-3.20(8H, m), 3.25-3.70 (4H, m), 3.80-5.00(2H, brs), 3.99(2H, m), 4.33 (2H, m), 5.07(1H, d, J=12.5Hz), 5.19(1H, d, J=12.5Hz), 6.38(1H, brs), 6.89(2H, d, J=8.4Hz), 6.99-7.28(4H, m), 7.33(5H, m), 7.42(2H, d, J=8.4Hz) |
| 330 | 1.25-2.20(6H, m), 1.80(2H, m), 1.95(2H, m), 2.52-3.04(8H, m), 3.12(2H, m), 3.41(2H, q, J=5.4Hz), 3.80-4.90(2H, brs), 3.98(2H, t, J=5.4Hz), 4.10(1H, m), 4.35(1H, m), 5.29(4H, s), 5.31(1H, brs), 5.70(1H, brs), 6.72(1H, brs), 6.87(2H, d, J=8.6Hz), 6.98-7.27(4H, m), 7.30(10H, s), 7.39(2H, d, J=8.6Hz) |
| 331 | 1.84(2H, m), 2.40-3.15(10H, m), 3.23-3.50(2H, m), 3.56(2H, t, J=6.1Hz), 3.70-5.15(2H, brs), 3.94(2H, t, J=5.6Hz), 4.35(2H, m), 6.61(2H, d, J=8.0Hz), 6.84(2H, d, J=8.6Hz), 6.92(2H, d, J=8.0Hz), 6.99-7.29(4H, m), 7.40(2H, d, J=8.6Hz), 7.50(1H, brs) |
| 332 | 1.65-2.50(8H, m), 2.50-3.10(10H, m), 3.45(2H, q, J=6.4Hz), 3.60-5.10(2H, brs), 3.81(1H, dd, J=9.0, 5.3Hz), 4.06(2H, t, J=5.9Hz), 4.38(1H, m), 6.92(2H, d, J=8.7Hz), 6.99-7.29(4H, m), 7.43 (2H, d, J=8.7Hz), 8.00(1H, brs) |
| 333 | 1.70-1.93(2H, m), 2.04(2H, quint, J=6.2Hz), 2.30 (6H, s), 2.53-3.20(8H, m), 2.96(2H, s), 3.50(2H, q, J=6.2Hz), 3.80-5.10(2H, brs), 4.08(2H, t, J=6.2Hz), 4.37(1H, m), 6.92(2H, d, J=8.7Hz), 6.99-7.29(4H, m), 7.44(2H, d, J=8.7Hz), 7.53 (1H, brs) |
| 334 | 1.60-1.89(2H, m), 1.97(2H, quint, J=6.0Hz), 2.53-3.20(8H, m), 3.44(2H, q, J=6.0Hz), 3.64 (1H, dd, J=11.2, 5.2Hz), 3.80-5.10(2H, brs), 4.00 (2H, t, J=6.0Hz), 4.12(1H, dd, J=11.2, 5.2Hz), 4.17(1H, m), 4.35(1H, m), 5.10(2H, s), 5.97(1H, d, J=6.0Hz), 6.89(2H, d, J=8.7Hz), 6.99-7.30 (4H, m), 7.33(5H, s), 7.39(2H, d, J=8.7Hz) |
| 335 | 1.37(3H, d, J=7.0Hz), 1.64-1.90(2H, m), 1.97 (2H, m), 2.53-3.20(8H, m), 3.43(2H, q, J=6.2Hz), 3.65-5.00(2H, brs), 4.00(2H, t, J=5.8Hz), 4.21 (1H, quint, J=7.0Hz), 4.37(1H, m), 5.05(1H, d, J=12.1Hz), 5.18(1H, d, J=12.1Hz), 5.55(1H, d, J=7.0Hz), 6.70(1H, brs), 6.88(2H, d, J=8.7Hz), 6.99-7.36(4H, m), 7.33(5H, s), 7.40(2H, d, J=8.7Hz) |
| 336 | 1.33(3H, d, J=6.9Hz), 1.63-1.95(2H, m), 2.03 (2H, quint, J=6.0Hz), 2.53-3.20(8H, m), 3.41-3.55 (3H, m), 3.80-5.20(2H, brs), 4.06(2H, t, J=6.0Hz), 4.37(1H, m), 6.93(2H, d, J=8.6Hz), 6.99-7.89(4H, m), 7.43(2H, d, J=8.6Hz), 7.68(1H, t, J=6.0Hz) |
| 337 | 1.42-1.62(2H, m), 1.62-1.90(6H, m), 2.31-2.44 (6H, m), 2.54-3.10(8H, m), 3.46(2H, m), 3.51(2H, s), 3.63(2H, m), 3.83-5.15(2H, brs), 3.98(2H, t, J=6.4Hz), 4.39(1H, m), 6.89(2H, d, J=8.7Hz), 6.99-7.33(4H, m), 7.31(5H, s), 7.42(2H, d, J=8.7Hz) |
| 338 | 0.82(3H, d, J=6.9Hz), 0.99(3H, d, J=6.9Hz), 1.64-1.90(2H, m), 2.04(2H, m), 2.10-2.41(1H, m), 2.54-3.08(8H, m), 3.24(1H, d, J=3.8Hz), 3.48 (2H, q, J=6.5Hz), 3.67-5.50(2H, brs), 4.06(2H, t, J=5.9Hz), 4.38(1H, m), 6.92(2H, d, J=8.7Hz), 6.99-7.28(4H, m), 7.43(2H, d, J=8.7Hz), 7.67 (1H, brs) |
| 339 | 0.82(3H, d, J=6.9Hz), 0.99(3H, d, J=6.9Hz), 1.68-1.93(2H, m), 2.03(2H, quint, J=6.1Hz), 2.33 (1H, m), 2.54-3.17(8H, m), 3.25(1H, d, J=3.7Hz), 3.49(2H, q, J=6.1Hz), 3.80-5.20(2H, brs), 4.07 (2H, t, J=6.1Hz), 4.39(1H, m), 6.92(2H, d, J=8.7Hz), 7.03-7.30(4H, m), 7.43(2H, d, J=8.7Hz), 7.64(1H, brs) |
| 340 | 1.41-1.60(2H, m), 1.61-1.98(6H, m), 2.35(2H, t, J=7.4Hz), 2.54-3.10(12H, m), 3.44(2H, t, J=4.9Hz), 3.59(2H, t, J=4.9Hz), 3.80-5.20(2H, brs), 3.99(2H, t, J=6.3Hz), 4.39(1H, m), 6.89(2H, d, J=8.6Hz), 6.99-7.28(4H, m), 7.42(2H, d, J=8.6Hz) |
| 341 | 1.40-1.65(2H, m), 1.65-2.00(6H, m), 1.76(3H, s), 2.39(2H, t, J=7.4Hz), 2.54-3.20(8H, m), 3.49 (4H, m), 3.61(4H, m), 3.85-5.20(2H, brs), 4.00 (2H, t, J=6.3Hz), 4.39(1H, m), 6.89(2H, d, J=8.7Hz), |

TABLE 10-continued 342   6.99-7.25(4H, m), 7.42(2H, d, J=8.7Hz)
342   1.40-1.65(2H, m), 1.65-2.02(6H, m), 2.37(2H, t, J=7.3Hz), 2.54-3.30(12H, m), 2.81(3H, s). 3.46-4.10(4H, m), 4.00(2H, t, J=6.2Hz), 4.10-5.20 (2H, brs), 4.37(1H, m), 6.90(2H, d, J=8.7Hz), 7.00-7.26(4H, m), 7.42(2H, d, J=8.7Hz)
343   1.42-1.63(2H, m), 1.64-2.00(6H, m), 2.32-2.52 (6H, m). 2.54-3.10(8H, m), 3.01(2H, d, J=6.6Hz), 3.48(2H, m), 3.64(2H, m), 3.80-5.10(2H, brs), 3.99(2H, t, J=6.3Hz), 4.40(1H, m), 5.18(1H, d, J=10.3Hz), 5.20(1H, d, J=16.8Hz), 5.85(1H, ddt, J=16.8, 10.3, 6.6Hz), 6.89(2H, d, J=8.7Hz), 6.99-7.26(4H, m), 7.42(2H, d, J=8.7Hz)
344   1.60-1.90(2H, m), 1.81(2H, quint, J=7.0Hz), 1.98 (2H, quint, J=6.2Hz), 2.25(2H, t, J=7.0Hz), 2.52-3.17(10H, m), 3.39(2H, q, J=6.2Hz), 3.65-5.15(2H, br), 3.90(2H, brs), 4.03(2H, t, J=6.2Hz), 4.33(1H, m), 6.91(2H, d, J=8.5Hz), 6.98-7.28(5H, m), 7.40(2H, d, J=8.5Hz)
345   1.70-1.93(2H, m), 1.81(2H, quint, J=6.6Hz), 1.98 (2H, quint, J=6.1Hz), 2.22(2H, t, J=6.6Hz), 2.46-3.10(8H, m), 3.21(2H, q, J=6.6Hz), 3.40 (2H, q, J=6.1Hz), 3.80-5.10(2H, brs), 4.01(2H, t, J=6.1Hz), 4.34(1H, m), 5.07(2H, s). 5.73(1H, brs), 6.89(2H, d, J=8.7Hz), 6.91(1H, brs), 6.99-7.25(4H, m), 7.32(5H, s). 7.40(2H, d, J=8.7Hz)
346   1.52(4H, m). 1.66-1.97(6H, m), 2.20(2H, t, J=6.8Hz), 2.53-3.05(8H, m), 3.10-3.32(4H, m), 3.70-5.10(2H, br), 3.96(2H, t, J=6.3Hz), 4.37(1H, m). 5.08(2H, s), 5.31(1H, brs), 6.30(1H, brs), 6.88(2H, d, J=8.7Hz), 6.99-7.27(4H, m), 7.33 (5H, s), 7.41(2H, d, J=8.7Hz)
347   1.41-1.71(4H, m), 1.71-1.90(4H, m), 2.54-3.20 (8H, m), 3.34(2H, q, J=6.5Hz), 3.60-5.15(2H, brs), 3.99(2H, t, J=6.2Hz), 4.04(2H, s). 4.38 (1H, m), 6.72(1H, brs), 6.90(2H, d, J=8.7Hz), 6.99-7.28(4H, m), 7.43(2H, d, J=8.7Hz)
348   1.32-1.67(4H, m), 1.67-2.00(6H, m), 2.25(2H, t, J=7.3Hz), 2.53-3.10(10H, m), 3.24(2H, q, J=6.2Hz), 3.70-5.20(2H, brs), 3.97(2H, t, J=6.2Hz), 4.36(1H, m), 6.54(1H, m), 6.89(1H, d, J=8.7Hz), 6.99-7.23(4H, m), 7.41(2H, d, J=8.7Hz)
349   1.25-1.72(4H, m), 1.73-1.94(4H, m), 2.29(6H, s), 2.54-3.10(8H, m), 2.94(2H, s), 3.31(2H, q, J=6.3Hz), 3.74-5.10(2H, br), 3.99(2H, t, J=6.3Hz), 4.39(1H, m), 6.89(2H, d, J=8.7Hz), 6.99-7.28 (5H, m), 7.43(2H, d, J=8.7Hz)
350   1.26(3H, t, J=7.1Hz), 1.42-2.05(12H, m), 2.37 (2H, t, J=7.4Hz), 2.44-3.25(11H, m), 3.50-5.10 (2H, brs), 3.73-3.94(1H, m), 3.99(2H, t, J=6.3Hz), 4.15(2H, q, J=7.1Hz), 4.23-4.53(2H, m), 6.90(2H, d, J=8.7Hz), 6.99-7.29(4H, m), 7.42 (2H, d, J=8.7Hz)
351   1.02(6H, t, J=7.1Hz), 1.39-1.71(4H, m), 1.71-2.05(4H, m), 2.38-3.14(8H, m), 2.55(4H, q, J=7.1Hz), 3.01(2H, s), 3.30(2H, q, J=6.3Hz), 3.70-5.15(2H, brs), 3.98(2H, t, J=6.3Hz), 4.39(1H, m), 6.89(2H, d, J=8.7Hz), 6.99-7.27(4H, m), 7.43 (2H, d, J=8.7Hz), 7.45(1H, brs)
352   1.37-1.68(4H, m), 1.68-1.90(6H, m), 1.96(3H, s), 2.16(2H, t, J=6.7Hz), 2.54-3.15(8H, m), 3.15-3.33(4H, m), 3.75-5.20(2H, brs), 3.98(2H, t, J=6.2Hz), 4.36(1H, m), 6.90(2H, d, J=8.5Hz), 6.92(1H, brs), 6.99-7.31(4H, m), 7.41(2H, d, J=8.5Hz)
353   1.48-1.64(4H, m), 1.69-1.91(4H, m), 1.91-2.13 (2H, m), 2.21(2H, t, J=6.7Hz), 2.54-3.11(10H, m), 2.66(6H, s), 3.25(2H, q, J=6.2Hz), 3.70-5.10 (2H, brs), 3.98(2H, t, J=6.2Hz), 4.35(1H, m), 6.15(1H, brs), 6.90(2H, d, J=8.7Hz), 6.99-7.28 (4H, m), 7.41(2H, d, J=8.7Hz)
354   1.37-1.69(4H, m), 1.69-1.94(4H, m), 2.16(3H, s), 2.53-3.20(8H, m), 3.32(2H, q, J=6.5Hz), 3.65-5.15(2H, br), 3.98(2H, t, J=6.2Hz), 4.54(1H, m), 4.65(2H, s), 6.51(1H, brs), 6.90(2H, d, J=8.7Hz), 6.99-7.30(4H, m), 7.42(2H, d, J=8.7Hz)
355   1.49-1.69(4H, m), 1.69-1.98(4H, m), 2.54-3.18 (8H, m), 3.31(2H, q, J=6.3Hz), 3.67(1H, t, J=5.1Hz), 3.80-5.15(2H, brs). 4.00(2H, t, J=6.2Hz), 4.03(2H, d, J=5.1Hz), 4.37(1H, m). 6.64(1H, brs), 6.90(2H, d, J=8.7Hz), 6.99-7.28(4H, m), 7.41(2H, d, J=8.7Hz)
356   (1.10(3H, t, J=7.1Hz), 1.42-1.70(4H, m), 1.70-1.95(4H, m), 2.54-3.17(8H, m), 2.61(2H, q, J=7.1Hz), 3.24(2H, s), 3.30(2H, q, J=6.5Hz), 3.60-5.20(2H, brs), 3.99(2H, t, J=6.3Hz), 4.37(1H, m), 6.90(2H, d, J=8.6Hz), 6.99-7.30(4H, m), 7.42 (2H, d, J=8.6Hz), 7.45(1H, brs)
357   1.30-2.00(12H, m), 2.36(2H, m), 2.52-3.20(11H, m), 3.50-5.15(2H, brs), 3.60-3.84(1H, m), 3.98 (2H, t, J=6.1Hz), 4.22-4.60(2H, m), 6.88(2H, d, J=8.6Hz), 6.99-7.25(4H, m), 7.40(2H, d, J=8.6Hz)
358   1.49-1.68(4H, m), 1.68-1.95(4H, m), 2.54-3.10 (8H, m), 3.23(2H, d, J=5.1Hz), 3.27(2H, s), 3.31 (2H, q, J=6.3Hz), 3.70-5.10(2H, brs), 3.98(2H, t, J=6.3Hz), 4.39(1H, m), 5.12(1H, d, J=10.2Hz), 5.19(1H, d, J=17.2Hz), 5.85(1H, ddt, J=17.2, 10.2, 5.1Hz), 6.89(2H, d, J=8.7Hz), 6.99-7.38(5H, m), 7.42(2H, d, J=8.7Hz),
359   1.63-1.96(6H, m), 2.54-3.20(8H, m), 3.39(2H, q, J=6.4Hz), 3.65-5.20(2H, brs), 4.01(2H, t, J=5.8Hz), 4.05(2H, s), 4.38(1H, m), 6.80(1H, brs), 6.90(2H, d, J=8.7Hz), 6.99-7.25(4H, m), 7.43 (2H, d, J=8.7Hz)
360   1.62-1.98(6H, m), 2.28(6H, s), 2.54-3.14(8H, m), 2.94(2H, s), 3.36(2H, q, J=6.5Hz), 3.70-5.10 (2H, brs), 4.01(2H, t, J=5.9Hz), 4.39(1H, m), 6.90(2H, d, J=8.7Hz), 6.99-7.25(4H, m), 7.27 (1H, brs), 7.43(2H, d, J=8.7Hz)
361   1.03(6H, t, J=7.2Hz), 1.59-1.98(6H, m), 2.43-3.20(8H, m), 2.55(4H, q, J=7.2Hz). 3.02(2H, s), 3.35(2H, q, J=6.5Hz), 3.70-5.10(2H, brs), 4.02 (2H, t, J=5.9Hz), 4.39(1H, m), 6.90(2H, d, J=8.7Hz), 6.99-7.29(4H, m), 7.43(2H, d, J=8.7Hz), 7.51(1H, brs)
362   1.60-1.94(6H, m), 2.15(3H, s), 2.54-3.20(8H, m), 3.37(2H, q, J=6.5Hz), 3.80-5.20(2H, brs), 4.00 (2H, t, J=5.8Hz), 4.37(1H, m), 4.55(2H, s), 6.60 (1H, bs). 6.90(2H, d, J=8.5Hz), 7.00-7.28(4H, m), 7.42(2H, d, J=8.5Hz)
363   1.38-1.72(4H, m), 1.72-1.97(4H, m), 2.30(3H, s), 2.36-3.20(16H, m), 3.01(2H, s), 3.31(2H, q, J=6.4Hz), 3.70-5.15(2H, brs), 3.99(2H, t, J=6.2Hz), 4.36(1H, m), 6.90(2H, d, J=8.7Hz), 6.99-7.30(5H, m), 7.43(2H, d, J=8.7Hz)
364   1.36-1.70(4H, m), 1.70-1.97(4H, m), 2.52-3.15 (8H, m), 2.66(4H, m), 3.06(2H, s), 3.20(4H, m), 3.33(2H, q, J=6.4Hz), 3.75-5.10(2H, brs), 3.98 (2H, t, J=6.1Hz), 4.34(1H, m), 6.60-7.36(11H, m), 7.40(2H, d, J=8.5Hz)
365   1.56-1.97(6H, m), 2.54-3.22(8H, m), 3.34(2H, q, J=6.4Hz), 3.70-5.10(2H, brs), 3.98(2H, d, J=5.2Hz), 4.00(2H, t, J=5.9Hz), 4.35(1H, m), 4.51 (1H, t, J=5.2Hz), 6.89(1H, brs), 6.90(2H, d, J=8.7Hz), 7.00-7.29(4H, m), 7.40(2H, d, J=8.7Hz)
366   1.05(6H, d, J=6.2Hz), 1.38-1.72(4H, m), 1.72-1.95(4H, m), 2.54-3.16(9H, m), 3.24(2H, s), 3.30 (2H, q, J=6.3Hz), 3.70-5.20(2H, brs), 3.98(2H, t, J=6.3Hz), 4.38(1H, m), 6.90(2H, d, J=8.6Hz), 6.99-7.32 94H, m), 7.42(2H, d, J=8.6Hz), 7.49 (1H, brs)
367   1.40-1.69(4H, m), 1.69-1.96(4H, m), 2.54-3.16 (8H, m), 3.29(2H, s), 3.29(2H, q, J=6.3Hz), 3.67-5.20(2H, brs), 3.76(2H, t, J=6.3Hz), 4.38(1H, m), 6.88(2H, d, J=8.7Hz), 7.00-7.39(10H, m), 7.41(2H, d, J=8.7Hz)
368   1.37-1.68(4H, m), 1.68-1.98(4H, m), 1.79(4H, m), 2.40-3.15(8H, m), 2.59(4H, m), 3.14(2H, s), 3.31 (2H, q, J=6.4Hz), 3.66-5.20(2H, brs), 3.99(2H, t, J=6.2Hz), 4.37(1H, m), 6.89(2H, d, J=8.6Hz), 6.98-7.29(5H, m), 7.42(2H, d, J=8.6Hz)
369   1.37-1.71(4H, m), 1.71-1.94(4H, m), 2.35-3.15 (8H, m), 2.52(4H, m), 3.00(2H, s), 3.31(2H, q, J=6.4Hz), 3.69(4H, m), 3.80-5.20(2H, brs), 3.99 (2H, t, J=6.1Hz), 4.36(1H, m), 6.89(2H, d, J=8.6Hz), 6.99-7.29(5H, m), 7.42(2H, d, J=8.6Hz)
370   1.36-1.69(4H, m), 169-1.95(4H, m), 2.28(3H, s), 2.52-3.13(8H, m), 3.02(2H, s), 3.30(2H, q, J=6.4Hz), 3.56(2H, s), 3.80-5.20(2H, brs), 3.96(2H, t, J=6.2Hz), 4.36(1H, m), 6.88(2H, d, J=8.7Hz), 6.98-7.35(5H, m), 7.29(5H, m), 7.42(2H, d, J=8.7Hz)
371   1.38-1.69(4H, m), 1.69-1.94(4H, m), 2.33(3H, s), 2.54-3.17(8H, m), 2.58(2H, t, J=5.2Hz), 3.07 2H, s), 3.29(2H, q, J=6.4Hz), 3.65(2H, t, J=5.2Hz),

TABLE 10-continued

| | |
|---|---|
| | 3.80–5.20(2H, br), 3.98(2H, t, J=6.2Hz), 4.38(1H, m), 6.89(2H, d, J=8.7Hz), 6.99–7.28 (4H, m), 7.39(1H, bs), 7.42(2H, d, J=8.7Hz) |
| 372 | 1.40(3H, t, J=7.0Hz), 1.43–1.68(4H, m), 1.68–1.93(4H, m), 2.26(3H, s), 2.54–3.10(8H, m), 3.01 (2H, s), 3.30(2H, q, J=6.4Hz), 3.49(2H, s), 3.75–5.10(2H, br), 3.97(2H, t, J=6.2Hz), 4.00 (2H, q, J=7.0Hz), 4.39(1H, m), 6.84(2H, d, J=8.5Hz), 6.89(2H, d, J=8.6H), 6.99–7.28(5H, m), 7.18(2H, d, J=8.5Hz), 7.42(2H, d, J=8.6Hz) |
| 373 | 1.32–1.65(4H, m), 1.65–1.93(4H, m), 2.53–3.14 (8H, m), 3.24(2H, q, J=6.2Hz), 3.60–5.10(2H, brs), 3.82(2H, d, J=5.7Hz), 3.94(2H, t, J=6.2Hz), 4.37(1H, m), 5.11(2H, s), 5.79(1H, brs), 6.48(1H, brs), 6.88(2H, d, J=8.7Hz), 6.99–7.36 (4H, m), 7.33(5H, s), 7.41(2H, d, J=8.7Hz) |
| 374 | 1.42–2.02(12H, m), 2.36(2H, t, J=7.4Hz), 2.38 (1H, m), 2.54–3.16(10H, m), 3.53–5.15(2H, brs), 3.76–3.97(1H, m), 4.00(2H, t, J=6.3Hz), 4.38 (1H, m), 4.48–4.67(1H, m), 5.58(1H, brs), 5.81 (1H, brs), 6.90(2H, d, J=8.7Hz), 6.99–7.29(4H, m), 7.42(2H, d, J=8.7Hz) |
| 375 | 1.45–1.98(10H, m), 2.23(1H, m), 2.54–3.10(10H, m), 3.12(1H, m), 3.18(1H, m), 3.32(2H, q, J=6.4Hz), 3.70–5.20(2H, brs), 4.00(2H, t, J=5.8Hz), 4.37(1H, m), 5.95(1H, brs), 6.90(2H, d, J=8.7Hz), 6.99–7.28(4H, m), 7.42(2H, d, J=8.7Hz) |
| 376 | 1.44–2.02(10H, m), 2.09(3H, s), 2.29(1H, m), 2.54–3.20(10H, m), 3.32(2H, q, J=6.4Hz), 3.70–5.20(2H, brs), 3.78–3.94(1H, m), 4.00(2H, t, J=5.8Hz), 4.36(1H, m), 4.52–4.69(1H, m), 5.87 (1H, brs), 6.89(2H, d, J=8.7Hz), 6.99–7.28(4H, m), 7.42(2H, d, J=8.7Hz) |
| 377 | 1.42–2.01(12H, m), 2.38(2H, t, J=7.3Hz), 2.52–3.26(11H, m), 2.94(3H, s), 3.09(3H, s), 3.65–5.20(2H, brs), 3.82–4.14(1H, m), 4.00(2H, t, J=6.2Hz), 4.36(1H, m), 4.53–4.74(1H, m), 6.91 (2H, d, J=8.6Hz), 6.98–7.29(4H, m), 7.42(2H, d, J=8.6Hz) |
| 378 | 1.37–1.71(4H, m), 1.71–1.90(4H, m), 2.53–3.16 (8H, m), 3.30(2H, q, J=6.3Hz), 3.32(2H, s), 3.70–5.20(2H, brs), 3.98(2H, t, J=6.1Hz), 4.35 (1H, m), 6.90(2H, d, J=8.5Hz), 6.99–7.29(4H, m), 7.42(2H, d, J=8.5Hz), 7.44(1H, bs) |
| 379 | 1.33–1.67(4H, m), 1.67–2.00(4H, m), 2.53–3.15 (8H, m), 2.96(3H, s), 3.24(2H, q, J=6.2Hz), 3.50–5.30(2H, brs), 3.71(2H, d, J=5.8Hz), 3.97 (2H, t, J=6.2Hz), 4.36(1H, m), 6.11(1H, t, J=5.8Hz), 6.88(1H, brs), 6.90(2H, d, J=8.7Hz), 6.99–7.29(4H, m), 7.41(2H, d, J=8.7Hz) |
| 380 | 1.41–2.10(8H, m), 2.53–3.30(8H, m), 3.47(2H, q, J=6.2Hz), 3.70–5.20(2H, brs), 3.97(2H, t, J=6.2Hz), 4.34(1H, m), 6.87(2H, d, J=8.7Hz), 6.99–7.29(5H, m), 7.39(2H, d, J=8.7Hz), 7.96(2H, dd, J=6.9, 2.0Hz), 8.22(2H, dd, J=6.9, 2.0Hz) |
| 381 | 1.41–1.73(4H, m), 1.73–2.02(4H, m), 2.53–3.20 (8H, m), 3.43(2H, q, J=6.4Hz), 3.70–5.20(2H, br), 3.97(2H, t, J=6.2Hz), 4.36(1H, m), 6.40 (1H, brs), 6.62(2H, d, J=8.5Hz), 6.87(2H, d, J=8.5Hz), 6.99–7.28(4H, m), 7.40(2H, d, J=8.5Hz), 7.60(2H, d, J=8.5Hz) |
| 382 | 1.30–1.63(4H, m), 1.63–2.05(4H, m), 2.55–3.30 (8H, m), 3.00(2H, q, J=6.2Hz), 3.70–5.20(2H, brs), 3.90(2H, t, J=6.2Hz), 4.37(1H, m), 5.50 (1H, t, J=6.2Hz), 6.86(2H, d, J=8.7Hz), 7.00–7.29(4H, m), 7.41(2H, d, J=8.7Hz), 8.04(2H, dd, J=6.9, 2.0Hz), 8.33(2H, dd, J=6.9, 2.0Hz), |
| 383 | 1.40–1.95(8H, m), 2.15(3H, s), 2.54–3.20(8H, m), 3.44(2H, q, J=6.1Hz), 3.70–5.20(2H, brs), 3.95 (2H, t, J=6.1Hz), 4.33(1H, m), 6.76(1H, brs), 6.83(2H, d, J=8.7Hz), 7.00–7.30(4H, m), 7.34 (2H, d, J=8.7Hz), 7.53(2H, d, J=8.7Hz), 7.68 (2H, d, J=8.7Hz), 8.73(1H, brs) |
| 384 | 1.40–1.95(8H, m), 2.54–3.11(8H, m), 3.01(6H, s), 3.46(2H, q, J=6.5Hz), 3.80–5.30(2H, brs), 3.98(2H, t, J=6.3Hz), 4.39(1H, m), 6.14(1H, brs), 6.65(2H, dd, J=6.9, 2.1Hz), 6.89(2H, d, J=8.8Hz), 6.99–7.28(4H, m), 7.42(2H, d, J=8.8Hz), 7.67(2H, dd, J=6.9, 2.1Hz) |
| 385 | 1.26–1.61(4H, m), 1.61–2.00(4H, m), 2.54–3.30 (8H, m), 2.91(2H, q, J=6.0Hz), 3.70–5.20(2H, brs), 3.90(2H, t, J=6.2Hz), 4.34(1H, m), 4.91 (1H, brs), 6.60(2H, d, J=8.6Hz), 6.85(2H, d, J=8.6Hz), 6.99–7.29(4H, m), 7.40(2H, d, J=8.6Hz), 7.58(2H, d, J=8.6Hz) |
| 386 | 1.48–1.74(4H, m), 1.74–2.02(4H, m), 2.23(3H, s), 2.28(3H, s), 2.54–3.30(8H, m), 3.65–5.20(2H, brs), 3.79(2H, t, J=7.4Hz), 4.00(2H, t, J=5.9Hz), 4.35(1H, m), 6.91(2H, d, J=8.7Hz), 7.00–7.30(4H, m), 7.41(2H, d, J=8.7Hz), 7.46(2H, d, J=8.4Hz), 7.65(2H, d, J=8.4Hz), 9.23(1H, s) |
| 387 | 1.33–1.64(4H, m), 1.64–1.93(4H, m), 2.54–3.15 (8H, m), 2.92(2H, q, J=6.5Hz), 3.02(6H, s), 3.70–5.20(2H, brs), 3.90(2H, t, J=6.3Hz), 4.38 (1H, m), 4.81(1H, t, J=6.5Hz), 6.66(2H, d, J=9.1Hz), 6.86(2H, d, J=8.7Hz), 6.99–7.28(4H, m), 7.41(2H, d, J=8.7Hz), 7.69(2H, d, J=9.1Hz) |
| 388 | 1.02(6H, t, J=7.1Hz), 1.34–1.93(8H, m), 2.37–3.12(10H, m), 2.52(4H, q, J=7.1Hz), 3.86–5.08 (3H, m), 3.98(2H, t, J=6.5Hz), 7.83–7.49(8H, m) |
| 389 | 1.42–1.96(12H, m), 2.35–3.15(14H, m), 3.78–5.13 (3H, m), 3.98(2H, t, J=6.4Hz), 6.82–7.50(8H, m) |
| 390 | 1.35–1.93(8H, m), 2.15–3.15(10H, m), 3.32–3.78 (3H, m), 3.83–5.22(3H, m), 3.97(2H, t, J=6.3Hz), 6.79–7.48(8H, m) |
| 391 | 1.38–1.93(8H, m), 2.43–3.40(12H, m), 3.65–5.15 (4H, m), 3.81(3H, s), 3.84(2H, s), 3.97(2H, t, J=6.2Hz), 6.75–7.48(12H, m) |
| 392 | 1.30–1.96(6H, m), 2.49–3.62(16H, m), 3.68–5.05 (4H, m), 3.98(2H, t, J=6.2Hz), 6.78–7.52(8H, m), 7.62(1H, dt, J=7.7, 1.8Hz), 8.43–8.59(1H, m) |
| 393 | 1.18–1.95(14H, m), 2.13–3.10(16H, m), 3.56–5.14 (4H, m), 3.99(2H, t, J=6.3Hz), 6.83–7.48(13H, m), |
| 394 | 1.60–1.93(6H, m), 2.27–3.14(18H, m), 3.02(2H, d, J=6.6Hz), 3.75–5.05(3H, m), 4.00(2H, t, J=6.2Hz), 5.12–5.26(2H, m), 5.78–5.98(1H, m), 6.81–7.47(8H, m) |
| 395 | 1.32–2.03(8H, m), 2.33(3H, s), 2.28–3.13(15H, m), 3.52–5.15(4H, m), 3.98(2H, t, J=6.3Hz), 6.83–7.48(10H, m), 7.60(1H, dt, J=7.6, 1.8Hz), 8.50–8.57(1H, m) |
| 396 | 1.06(3H, t, J=6.7Hz), 1.20–1.96(8H, m), 2.28–3.15(12H, m), 3.22–5.08(5H, m), 3.46(1H, d, J=14.4Hz), 3.83(1H, d, J=14.4Hz), 3.99(2H, t, J=6.7Hz), 6.83–7.52(10H, m), 8.52–8.62(1H, m) |
| 397 | 1.25–1.62(8H, m), 1.65–1.93(8H, m), 2.36–3.13 (14H, m), 3.80–5.05(3H, m), 3.97(2H, t, J=6.5 Hz), 6.83–7.49(8H, m) |
| 398 | 1.09(6H, t, J=7.2Hz), 1.22–1.93(12H, m), 2.4–3.12(10H, m), 2.63(4H, q, J=7.2Hz), 3.12–5.11 (3H, m), 3.98(2H, t, J=6.6Hz), 6.84–7.48(8H, m) |
| 399 | 1.63–2.03(10H, m), 2.48–3.13(14H, m), 3.82–5.03 (3H, m), 4.01(2H, t, J=5.9Hz), 6.81–7.49(8H, m) |
| 400 | 1.05(6H, t, J=7.2Hz), 1.57–1.90(6H, m), 2.42–3.15(14H, m), 3.83–5.04(3H, m), 4.01(2H, t, J=6.4Hz), 6.83–7.48(8H, m) |
| 401 | 1.25–1.93(10H, m), 2.36(3H, s), 2.43–3.12(17H, m), 3.82–5.16(3H, m), 3.97(2H, t, J=6.4Hz), 6.85–7.48(10H, m), 7.60(1H, dt, J=7.6, 1.9Hz), 8.49–8.55(1H, m) |
| 402 | 1.35–3.35(26H, m), 3.62–4.42(5H, m), 3.99(2H, t, J=6.6Hz), 5.57(1H, brs), 6.83–7.47(8H, m), |
| 403 | 1.42–2.08(12H, m), 2.43–3.44(15H, m), 3.82–5.04 (4H, m), 3.99(2H, t, J=6.2Hz), 6.83–7.49(8H, m) |
| 404 | 1.32–1.93(8H, m), 2.25(2H, brs), 2.50–3.13(10H, m), 3.80–5.00(4H, m), 3.92(2H, s), 3.97(2H, t, J=6.5Hz), 6.82–7.48(10H, m), 7.65(1H, dt, J=7.6, 1.8Hz), 8.51–8.59(1H, m) |
| 405 | 1.32–1.92(10H, m), 2.48–3.17(10H, m), 3.72–5.18 (4H, m), 3.82(2H, s), 3.97(2H, t, J=6.4Hz), 6.83–7.49(9H, m), 7.65–7.75(1H, m), 8.50(1H, dd, J=4.8, 1.6Hz), 8.56(1H, d, J=1.8Hz) |
| 406 | 1.13–1.92(14H, m), 2.18–3.12(14H, m), 3.47(1H, dd, J=10.7, 4.1Hz), 3.75(1H, dd, J=10.7, 3.8Hz), 3.81–5.08(3H, m), 3.98(2H, t, J=6.4Hz), 6.83–7.48(8H, m) |
| 407 | 1.40–2.03(12H, m), 2.25–3.15(13H, m), 3.20–3.31 (1H, m), 3.45(1H, dd, J=11.0, 3.0Hz), 3.67(1H, dd, J=11.0, 3.6Hz), 3.75–5.13(3H, m), 3.99(2H, t, J=6.3Hz), 6.83–7.50(8H, m) |
| 408 | 1.07–1.93(13H, m), 1.96–3.13(15H, m), 3.53(1H, dd, J=10.5, 5.8Hz), 3.66(1H, dd, J=10.5, 5.0Hz), 3.74–5.13(3H, m), 3.98(2H, t, J=6.4Hz), 6.83–7.47(8H, m) |

TABLE 10-continued

| No. | NMR (DMSO-d$_6$) δ value |
|---|---|
| 409 | 1.42-1.93(8H, m), 2.12-3.14(17H, m), 3.83-5.14 (4H, m), 3.99(2H, t, J=6.4Hz), 6.83-6.96(2H, m), 6.96-7.32(4H, m), 7.33-7.48(2H, m) |

| No. | NMR (DMSO-d$_6$) δ value |
|---|---|
| 410 | 1.33-1.97(15H, m), 2.38-3.28(14H, m), 3.48(2H, t, J=6.3Hz), 3.90-4.83(3H, m), 4.07(2H, t, J=6.2 Hz), 6.95-7.49(8H, m), 10.30(1H, brs) |

| No. | NMR (CDCl$_3$) δ value |
|---|---|
| 411 | 1.40-1.66(4H, m), 1.68-2.22(8H, m), 2.26-3.28 (13H, m), 3.72(3H, s), 3.78-5.10(3H, m), 3.97 (2H, t, J=6.4Hz), 6.83-7.48(8H, m) |

| No. | NMR (DMSO-d$_6$) δ value |
|---|---|
| 412 | 1.30-2.13(16H, m), 2.33-3.60(16H, m), 3.62-4.93 (3H, m), 4.02(2H, t, J=6.2Hz), 6.87-7.05(3H, m), 7.18-7.42(5H, m), 10.03(1H, brs) |

| No. | NMR (CDCl$_3$) δ value |
|---|---|
| 413 | 1.43-1.93(8H, m), 2.35-3.12(14H, m), 3.67-5.24 (3H, m), 3.84(4H, t, J=5.3Hz), 4.00(2H, t, J=6.4 Hz), 6.47(1H, t, J=4.7Hz), 6.84-7.50(8H, m), 8.30(2H, d, J=4.7Hz) |
| 412 | 1.40-1.96(8H, m), 2.34-3.13(14H, m), 3.55(4H, t, J=4.8Hz), 3.75-5.21(3H, m), 4.00(2H, t, J=6.4 Hz), 6.55-6.67(2H, m), 6.85-7.53(9H, m), 8.12-8.22(1H, m) |
| 415 | 1.40-1.93(8H, m), 2.28(3H, s), 2.41-3.12(13H, m), 3.61(2H, t, J=5.5Hz), 3.75-5.25(3H, m), 3.99 (2H, t, J=6.4Hz), 6.85-7.49(8H, m) |
| 416 | 1.37-2.04(12H, m), 2.22-3.16(13H, m), 3.18-3.34 (1H, m), 3.45(1H, dd, J=11.0, 2.8Hz), 3.67(1H, dd, J=11.0, 3.5Hz), 3.85-5.23(3H, m), 3.99(2H, t, J=6.3Hz), 6.83-7.50(8H, m) |
| 417 | 1.38-1.93(8H, m), 2.28-3.13(16H, m), 3.63(4H, t, J=5.4Hz), 3.77-5.08(3H, m), 3.99(2H, t, J=6.3 Hz), 6.85-7.50(8H, m) |
| 418 | 1.38(6H, dt, J=7.1, 2.5Hz), 1.42-1.98(8H, m), 2.49-3.14(8H, m), 3.22-3.41(1H, m), 3.27(3H, s), 3.39(3H, s), 3.48-5.13(9H, m), 4.04(2H, t, J=6.2 Hz), 6.83-7.47(8H, m) |
| 419 | 1.38-1.95(8H, m), 2.27(3H, s), 2.36-3.19(14H, m), 3.78-5.06(3H, m), 3.99(2H, t, J=6.4Hz), 6.85-6.95(2H, m), 6.97-7.32(4H, m), 7.37-7.48 (2H, m) |
| 420 | 1.32-1.97(14H, m), 1.12-3.21(15H, m), 3.58-5.06 (4H, m), 3.99(2H, t, J=6.4Hz), 6.83-7.54(8H, m) |
| 421 | 1.51-2.00(8H, m), 2.47-3.28(8H, m), 3.18(2H, t, J=6.8Hz), 3.79-5.15(3H, m), 4.00(2H, t, J=6.1 Hz), 6.78-3.37(7H, m), 7.42(2H, d, J=8.7Hz), 8.50(2H, d, J=4.8Hz) |
| 422 | 1.45-2.17(8H, m), 2.44-3.24(10H, m), 3.61(3H, s), 3.80-5.12(3H, m), 3.97(2H, t, J=6.3Hz), 6.80-7.38(8H, m), 7.42(2H, d, J=8.7Hz) |
| 423 | 1.52-2.04(8H, m), 2.49-3.15(8H, m), 3.38-3.57 (2H, m), 3.75-5.12(8H, m), 6.88(2H, d, J=8.7Hz), 6.93-7.36(6H, m), 7.42(2H, d, J=8.7Hz) |
| 424 | 1.47-2.20(8H, m), 2.48-3.33(10H, m), 3.75-5.14 (5H, m), 6.87(2H, d, J=8.7Hz), 6.93-7.54(7H, m), 8.88(2H, d, J=4.9Hz) |
| 425 | 1.52-2.13(8H, m), 2.49-3.14(8H, m), 3.47-3.68 (2H, m), 3.85-5.11(3H, m), 3.99(2H, t, J=6.1Hz), 6.87(2H, d, J=8.8Hz), 6.93-7.38(4H, m), 7.42 (2H, d, J=8.8Hz), 7.57(1H, d, J=4.9Hz), 8.95 (1H, d, J=4.9Hz) |
| 426 | 1.09-2.02(10H, m), 2.42-5.21(29H, m), 6.89(2H, d, J=8.7Hz), 6.94-7.36(4H, m), 7.40(2H, d, J=8.7 Hz) |
| 427 | 1.38(9H, t, J=7.1Hz), 1.48-2.19(8H, m), 2.49-3.16(8H, m), 3.27-3.45(2H, m), 3.50(6H, q, J=7.1 Hz), 3.80-5.11(3H, m), 4.03(2H, t, J=4.7Hz), 6.90(2H, d, J=8.6Hz), 6.97-3.38(4H, m), 7.41 (2H, d, J=8.6Hz) |
| 428 | 1.34-3.39(25H, m), 3.77-5.12(3H, m), 3.97(2H, t, J=6.3Hz), 5.57-5.92(3H, m), 6.88(2H, d, J=8.8 Hz), 6.94-7.36(4H, m), 7.42(2H, d, J=8.8Hz) |
| 429 | 1.35-1.99(8H, m), 2.42-3.20(8H, m), 3.72-5.15 (3H, m), 3.97(4H, t like, J=6.9Hz), 6.81-7.62 (11H, m) |
| 430 | 1.37-2.14(8H, m), 2.45-3.16(8H, m), 3.71-5.15 (3H, m), 3.98(2H, t, J=6.2Hz), 4.21(2H, t, J=7.0 Hz), 6.78-7.52(8H, m), 7.94(1H, s), 8.07(1H, s) |
| 431 | 1.53-2.01(8H, m), 2.48-3.17(10H, m), 3.80-5.12 (3H, m), 4.00(2H, t, J=6Hz), 6.89(2H, d, J=8.8 Hz), 6.92-7.55(8H, m), 6.05-8.22(2H, m) |
| 432 | 1.22-1.96(14H, m), 2.46-3.16(8H, m), 3.75-5.18 (3H, m), 3.68(2H, t, J=7.2Hz), 3.96(2H, t, J=6.5 Hz), 6.89(2H, d, J=8.7Hz), 6.94-7.36(4H, m), 7.42(2H, d, J=8.7Hz), 7.63-7.92(4H, m) |
| 433 | 1.40-2.02(8H, m), 2.41-3.22(10H, m), 3.50-5.15 (3H, m), 3.76(2H, brs), 3.95(2H, t, J=6.2Hz), 6.48-6.68(2H, m), 6.87(2H, d, J=8.8Hz), 6.94-7.37(6H, m), 7.42(2H, d, J=8.8Hz) |
| 434 | 1.44-2.11(8H, m), 2.50-3.32(10H, m), 3.83-5.10 (3H, m), 3.96(2H, t, J=5.8Hz), 6.85(2H, d, J=8.7 Hz), 6.90-7.38(4H, m), 7.41(2H, d, J=8.7Hz), 8.05-8.21(2H, m), 8.36-8.52(2H, m) |
| 435 | 1.41-2.12(8H, m), 2.45-3.41(8H, m), 3.20(2H, t, J=6.9Hz), 3.70-5.11(3H, m), 3.99(3H, t, J=6.3 Hz), 6.75-7.17(11H, m), 8.37-8.52(2H, m) |
| 436 | 1.51-2.05(8H, m), 2.37-3.22(10H, m), 3.76-5.14 (3H, m), 4.00(2H, t, J=6.1Hz), 6.89(2H, d, J=8.7 Hz), 6.95-7.38(6H, m), 7.43(2H, d, J=8.7Hz), 8.30-8.49(2H, m) |
| 437 | 1.41-1.92(8H, m), 2.47-3.19(10H, m), 3.70-5.10 (5H, m), 3.93(2H, t, J=6Hz), 6.56-7.70(12H, m) |
| 438 | 1.46-2.02(8H, m), 2.43-3.19(10H, m), 3.31-3.56 (2H, m), 3.70-5.11(3H, m), 3.96(2H, t, J=5.9Hz), 6.75-7.51(8H, m), 7.56(1H, ddd, J=1.3, 4.7, 7.6 Hz), 7.89-8.18(2H, m), 8.68-8.81(1H, m) |
| 439 | 1.48-1.97(8H, m), 2.47-3.30(10H, m), 3.78-5.12 (5H, m), 6.87(2H, d, J=8.7Hz), 6.94-7.36(4H, m), 7.43(2H, d, J=8.7Hz), 7.68-7.88(2H, m), 8.23-8.39(2H, m) |
| 440 | 1.41-2.01(8H, m), 2.25(3H, s), 2.48-3.16(10H, m), 3.71-5.18(3H, m), 3.90(2H, d, J=5.5Hz), 6.78 (2H, d, J=8.7Hz), 6.98-7.54(8H, m), 7.63(2H, d, J=8.7Hz), 9.03(1H, brs) |
| 441 | 1.15-2.16(16H, m), 2.44-3.13(10H, m), 3.75-5.20 (3H, m), 3.98(2H, t, J=6.5Hz), 6.90(2H, d, J=8.7 Hz), 6.94-7.37(4H, m), 7.42(2H, d, J=8.7Hz) |
| 442 | 1.22-5.20(34H, m), 5.92-6.19(1H, m), 6.90(2H, d, J=8.5Hz), 6.95-7.34(4H, m), 7.42(2H, d, J=8.5 Hz), |
| 443 | 1.42-1.96(8H, m), 2.50-3.19(10H, m), 3.06(6H, s), 3.74-5.11(3H, m), 3.94(2H, t, J=6.2Hz), 6.69 (2H, d, J=9.1Hz), 6.85(2H, d, J=8.8Hz), 6.92-7.34(4H, m), 7.40(2H, d, J=8.8Hz), 7.69(2H, d, J=9.1Hz) |
| 444 | 1.20-2.02(14H, m), 1.97(3H, m), 2.48-3.32(10H, m), 3.77-5.15(3H, m), 3.98(2H, t, J=6.4Hz), 5.61 (1H, brs), 6.90(2H, d, J=8.7Hz), 6.98-7.38(4H, m), 7.42(2H, d, J=8.7Hz) |
| 445 | 1.29-3.40(25H, m), 2.03(3H, s), 2.07(3H, s), 3.81-5.15(7H, m), 5.76(brs), 6.89(2H, d, J=8.4 Hz), 6.96-7.51(6H, m) |
| 446 | 1.62-1.94(2H, m), 1.99(3H, s), 2.01(2H, m), 2.46-3.20(8H, m), 3.45(2H, q, J=6.3Hz), 3.70-5.20(2H, brs), 4.05(2H, t, J=5.9Hz), 4.34(1H, m), 6.00(1H, brs), 6.60(1H, d, J=8.1Hz), 6.67 (1H, d, J=8.1Hz), 6.89(2H, d, J=8.7Hz), 7.10 (1H, t, J=8.1Hz), 7.42(2H, d, J=8.7Hz) |
| 447 | 1.42(3H, t, J=7.0Hz), 1.57-1.75(1H, m), 1.75-1.93(1H, m), 2.40-3.24(8H, m), 3.56-3.92(4H, m), 4.04(2H, q, J=7.0Hz), 4.19-4.66(1H, m), 4.80-5.04(1H, m), 6.37-6.67(1H, m), 6.48(1H, d, J=8.1 Hz), 6.60-6.78(1H, m), 6.61(1H, d, J=8.1Hz), 7.01(1H, t, J=8.1Hz), 7.10-7.46(1H, m), 8.36 (1H, brs) |
| 448 | 1.42(3H, t, J=7.0Hz), 1.57-1.75(1H, m), 1.75-1.94(1H, m), 2.35-3.20(8H, m), 3.57-3.73(1H, m), 3.73-3.92(3H, m), 3.84(3H, s), 4.02(2H, q, J=7.0 Hz), 4.25-4.75(1H, m), 4.86-5.04(1H, m), 6.43-6.57(1H, m), 6.50(1H, d, J=8.2Hz), 6.64(1H, m), J=8.2Hz), 6.68-6.91(1H, m), 7.12-7.33(1H, m), 7.18(1H, t, J=8.2Hz) |
| 449 | 1.42(3H, t, J=6.9Hz), 1.66-1.91(2H, m), 1.91-2.13(2H, m), 1.97(3H, s), 2.47-3.20(8H, m), 3.42 (2H, q, J=6.3Hz), 3.80-5.20(2H, brs), 4.03(2H, t, J=6.9Hz), 4.05(2H, q, J=6.9Hz), 4.35(1H, m), 6.37(1H, brs), 6.64(1H, d, J=8.2Hz), 6.74(1H, d, J=8.2Hz), 6.89(2H, d, J=8.7Hz), 7.17(1H, t, J=8.2Hz), 7.42(2H, d, J=8.7Hz) |

TABLE 10-continued

| | |
|---|---|
| 450 | 1.42(6H, t, J=7.0Hz), 1.55–1.76(1H, m), 1.76–1.93(1H, m), 2.35–3.22(8H, m), 3.50–3.75(1H, m), 3.75–3.94(3H, m), 4.04(4H, q, J=7.0Hz), 4.26–4.72(1H, m), 4.82–5.05(1H, m), 6.49–6.58(1H, m), 6.51(1H, d, J=8.2Hz), 6.63(1H, d, J=8.2Hz), 6.68–6.92(1H, m), 7.15(1H, t, J=8.2Hz), 7.20–7.35(1H, m) |
| 451 | 1.42(3H, t, J=7.0Hz), 1.55–1.75(1H, m), 1.75–1.98(1H, m), 2.33(3H, s), 2.41–3.23(8H, m), 3.53–3.96(4H, m), 4.05(2H, q, J=7.0Hz), 4.18–4.68(1H, m), 4.86–5.08(1H, m), 6.46–6.60(1H, m), 6.49(1H, d, J=8.0Hz), 6.81(1H, d, J=8.0Hz), 6.94–7.32(2H, m), 7.24(1H, t, J=8.0Hz) |
| 452 | 1.55–1.88(2H, m), 1.88–2.10(2H, m), 1.97(3H, s), 2.47–3.20(8H, m), 3.42(2H, q, J=6.3Hz), 3.60–5.20(2H, brs), 3.84(3H, s), 4.03(2H, t, J=6.0 Hz), 4.34(1H, m), 6.30(1H, brs), 6.65(1H, d, J=8.3Hz), 6.75(1H, d, J=8.3Hz), 6.89(2H, d, J=8.7Hz), 7.20(1H, t, J=8.3Hz), 7.41(2H, d, J=8.7Hz) |
| 453 | 1.67–1.93(2H, m), 1.93–2.11(2H, m), 1.98(3H, s), 2.33(3H, s), 2.50–3.15(8H, m), 3.43(2H, q, J=6.4 Hz), 3.80–5.20(2H, br), 4.04(2H, t, J=5.9Hz), 4.33(1H, m), 6.13(1H, brs), 6.82(1H, d, J=8.1 Hz), 6.90(2H, d, J=8.7Hz), 7.01(1H, d, J=8.1 Hz), 7.26(1H, t, J=8.1Hz), 7.42(2H, d, J=8.7Hz) |
| 454 | 1.60–1.90(3H, m), 2.40–2.95(8H, m), 3.10–3.36 (2H, m), 4.23–4.48(1H, m), 6.70–7.22(3H, m) |
| 455 | 1.55–1.93(2H, m), 2.35–3.27(8H, m), 3.58–4.00 (7H, m), 4.25–4.74(1H, m), 4.86–5.07(1H, m), 6.44–6.60(2H, m), 6.73–7.37(4H, m) |
| 456 | 1.42(3H, t, J=7.0Hz), 1.55–1.90(2H, m), 2.35–3.20(8H, m), 3.60–3.93(4H, m), 4.01(2H, q, J=7.0 Hz), 4.25–4.70(1H, m), 4.85–5.05(1H, m), 6.40–6.59(2H, m), 6.72–7.35(4H, m) |
| 457 | 1.70–2.12(4H, m), 1.95(3H, s), 2.31(3H, s), 2.42–3.15(8H, m), 3.35–3.50(2H, m), 3.80–5.10 (5H, m), 6.17(1H, brs), 6.80–7.20(5H, m), 7.42 (2H, d, J=8.5Hz) |
| 458 | 1.40–2.05(10H, m), 2.31(3H, s), 2.42–3.20(8H, m), 3.43(2H, t, J=6.7Hz), 3.70–5.05(5H, m), 6.80–7.22(5H, m), 7.42(2H, d, J=8.7Hz) |
| 459 | 1.03(6H, t, J=7.1Hz), 1.22–2.00(10H, m), 2.31 (3H, s), 2.40–3.23(14H, m), 3.80–5.21(5H, m), 6.85–7.20(5H, m), 7.42(2H, d, J=8.7Hz) |
| 460 | 1.30–2.15(14H, m), 2.31(3H, s), 2.38–3.20(14H, m), 3.80–5.05(5H, m), 6.80–7.22(5H, m), 7.42(2H, d, J=8.7Hz) |
| 461 | 1.42–1.96(8H, m), 2.42–3.13(12H, m), 3.30(2H, d, J=6.1Hz), 3.98(2H, t, J=6.3Hz), 3.80–4.97(3H, m), 4.98–5.28(2H, m), 5.83–6.04(1H, m), 6.82–7.48 (8H, m) |
| 462 | 1.34–1.95(9H, m), 2.45–3.15(12H, m), 3.57(2H, t J=5.4Hz), 3.63(2H, s), 3.95(2H, t, J=6.3Hz), 3.78–5.14(3H, m), 6.84–7.50(13H, m) |
| 463 | 1.07(3H, d, J=6.3Hz), 1.24–1.93(14H, m), 2.07–2.48(3H, m), 2.53–3.13(10H, m), 3.98(2H, t, J=6.4Hz), 3.82–5.10(3H, m), 6.84–7.50(8H, m) |
| 464 | 0.76–0.95(1H, m), 0.87(3H, d, J=6.1Hz), 1.38–1.93(14H, m), 2.27–2.41(2H, m), 2.52–3.12(10H, m), 3.98(2H, t, J=6.4Hz), 3.83–5.07(3H, m), 6.83–7.49(8H, m) |
| 465 | 0.92(3H, d, J=5.8Hz), 1.14–2.02(15H, m), 2.26–2.42(2H, m), 2.52–3.13(10H, m), 3.98(2H, t, J=6.4Hz), 3.86–5.06(3H, m), 6.83–7.52(8H, m) |
| 466 | 1.43–1.93(8H, m), 2.52–3.13(14H, m), 3.69(2H, t, J=5.3Hz), 3.99(2H, t, J=6.3Hz), 3.80–5.05(3H, m), 6.83–7.49(8H, m) |
| 467 | 1.04(6H, t, J=7.2Hz), 1.33–2.05(8H, m), 2.30–3.22(14H, m), 3.54–3.75(1H, m), 3.93–4.20(2H, m), 4.30–4.42(1H, m), 4.93–5.07(1H, m), 6.83–7.42 (8H, m) |
| 468 | 1.36–1.92(8H, m), 2.28(6H, s), 2.42–3.13(14H, m), 3.60(2H, s), 3.72–5.07(3H, m), 3.96(2H, t, J=6.4Hz), 6.85–7.48(13H, m) |
| 469 | 1.45–1.98(14H, m), 2.49–3.14(14H, m), 3.82–5.13 (3H, m), 3.99(2H, t, J=6.2Hz), 6.82–7.49(8H, m) |
| 470 | 1.38–1.94(8H, m), 2.22(3H, s), 2.28–2.44(2H, m), 2.49–3.10(8H, m), 3.00(2H, d, J=6.5Hz), 3.88–4.96(3H, m), 3.98(2H, t, J=6.4Hz), 5.08–5.24 (2H, m), 5.87(1H, ddt, J=17.1, 10.2, 6.5Hz), 6.83–7.49(8H, m) |
| 471 | 1.40–1.92(8H, m), 2.05, 2.07, 2.12, 2.14(total: 6H, s), 2.52–3.14(8H, m), 3.28–3.43(2H, m), 3.55 (2H, dt, J=8.5, 5.9Hz), 3.99(2H, dt, J=6.1, 6.1 Hz), 4.20(2H, dt, J=6.0, 6.0Hz), 3.84–4.98(3H, m), 6.85–7.50(8H, m) |
| 472 | 1.38–1.93(8H, m), 2.07(3H, s), 2.31(3H, s), 2.37–3.13(12H, m), 3.87–5.04(3H, m), 3.98(2H, t, J=6.4Hz), 4.18(2H, t, J=5.9Hz), 6.84–7.49(8H, m) |
| 473 | 1.37–1.94(8H, m), 2.05(6H, s), 2.49–3.12(10H, m), 2.77(4H, t, J=6.2Hz), 3.83–5.05(3H, m), 3.98 (2H, t, J=6.3Hz), 4.12(4H, t, J=6.1Hz), 6.85–7.48(8H, m) |
| 474 | 1.13(6H, d, J=6.3Hz), 1.40–1.93(8H, m), 2.49–3.13(12H, m), 3.84–5.03(3H, m), 3.98(2H, t, J=6.4Hz), 6.84–7.48(8H, m) |
| 475 | 1.44–2.08(8H, m), 2.02–3.30(10H, m), 3.09(3H, s), 3.77–5.02(3H, m), 3.87(2H, d, J=7.1Hz), 4.00 (2H, d, J=6.1Hz), 5.41–5.08(2H, m), 6.03–6.27 (1H, m), 6.83–7.48(8H, m) |
| 476 | 1.00(6H, t, J=7.1Hz), 1.41–1.93(8H, m), 2.05 (3H, s), 2.32–3.13(14H, m), 3.86–5.05(3H, m), 3.98(2H, t, J=6.3Hz), 4.90–5.03(1H, m), 6.85–7.48(8H, m) |
| 477 | 1.38–1.93(12H, m), 2.37–3.13(14H, m), 3.87–5.05 (3H, m), 4.01(2H, t, J=6.4Hz), 6.83–7.49(8H, m) |
| 478 | 1.28–1.93(16H, m), 2.32–3.11(14H, m), 3.83–5.07 (3H, m), 3.97(2H, t, J=6.4Hz), 6.85–7.51(8H, m) |
| 479 | 1.43–1.96(8H, m), 2.26(6H, s), 2.26–2.42(2H, m), 2.53–3.07(8H, m), 3.91–5.04(3H, m), 3.99(2H, t, J=6.4Hz), 6.86–7.47(8H, m) |
| 480 | 1.30–1.92(10H, m), 2.30(6H, s), 2.27–2.43(2H, m), 2.53–3.12(8H, m), 3.87–4.87(3H, m), 3.98(2H, t, J=6.4Hz), 6.85–7.48(8H, m) |
| 481 | 1.55–2.16(7H, m), 2.37–5.37(17H, m), 6.38–7.59 (13H, m) |
| 482 | 1.26(3H, t, J=7.2Hz), 1.52–2.01(6H, m), 2.32–3.33(10H, m), 3.53–5.10(8H, m), 4.14(2H, q, J=7.2Hz), 6.40–6.58(2H, m), 6.96–7.33(5H, m) |
| 483 | 1.58–3.32(16H, m), 3.56–5.12(8H, m), 5.52–6.00 (2H, m), 6.48–6.60(2H, m), 6.95–7.48(5H, m) |
| 484 | 1.35–5.15(49H, m), 6.36–6.60(2H, m), 6.92–7.38 (5H, m) |
| 485 | 1.27–4.61(52H, m), 4.78–5.06(1H, m), 6.34–6.60 (2H, m), 6.93–7.40(5H, m) |

| No. | NMR (DMSO-d$_6$) δ value |
|---|---|
| 486 | 1.24(12H, t, J=7.2Hz), 1.31–2.12(14H, m), 2.25–4.43(26H, m), 4.55–4.79(1H, m), 6.48–6.72(2H, m), 6.94–7.43(5H, m), 10.49–10.97(2H, m) |

| No. | NMR (CDCl$_3$) δ value |
|---|---|
| 487 | 1.51–2.02(6H, m), 2.18–4.13(27H, m), 4.28–4.72 (1H, m), 4.88–5.08(1H, m), 6.37–6.59(2H, m), 6.92–7.38(5H, m) |
| 488 | 1.53–1.99(6H, m), 2.30–3.24(14H, m), 3.55–4.12 (10H, m), 4.22–4.75(1H, m), 4.86–5.08(1H, m), 6.39–6.58(2H, m), 6.92–7.38(5H, m) |
| 489 | 1.51–2.10(6H, m), 2.12–3.29(14H, m), 3.52–4.68 (11H, m), 4.77–5.07(1H, m), 6.35–6.62(2H, m), 6.92–7.48(5H, m) |
| 490 | 1.55–2.00(6H, m), 2.34–3.25(14H, m), 3.53–4.72 (11H, m), 4.81–5.07(1H, m), 6.39–6.58(2H, m), 6.92–7.37(5H, m) |
| 491 | 1.49–2.08(8H, m), 2.48–3.13(8H, m), 3.44(2H, t, J=6.7Hz), 3.76–5.08(3H, m), 4.00(2H, t, J=6.3 Hz), 6.83–7.48(8H, m) |
| 492 | 1.42–1.63(4H, m), 1.68–2.02(6H, m), 2.48–3.18 (8H, m), 3.43(2H, t, J=6.7Hz), 3.86–5.13(3H, m), 3.99(2H, t, J=6.3Hz), 6.84–7.52(8H, m) |
| 493 | 0.98–2.02(18H, m), 2.23–3.13(12H, m), 3.85–4.97 (3H, m), 3.98(2H, t, J=6.4Hz), 6.83–7.47(8H, m) |
| 494 | 1.42–1.95(9H, m), 2.22(1H, t, J=2.4Hz), 2.48–3.13(10H, m), 3.43(2H, d, J=2.4Hz), 3.84–5.13 (3H, m), 3.99(2H, t, J=6.4Hz), 6.84–7.51(8H, m) |

Using the suitable starting materials, the following compounds are obtained in the same manners as in Examples 1, 384, 390–393, 398, 399, 407–409, 426 and 593.

TABLE 11

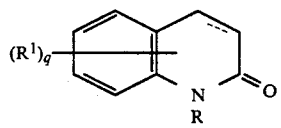

| | Structure | | | | |
|---|---|---|---|---|---|
| | R | R¹ | q | NMR analysis | Form |
| | Bond between 3- and 4-positions in the carbostyril ring: Single bond | | | | |
| Example 779 | [piperidine]-N-C(O)-[phenyl]-O(CH₂)₅NHC(CH₃)₃ | H | 1 | 495) | Free |
| Example 780 | [piperidine]-N-C(O)-[phenyl]-O(CH₂)₅NHCH₂CH(CH₃)₂ | H | 1 | 496) | Free |
| Example 781 | [piperidine]-N-C(O)-[phenyl]-O(CH₂)₅NHCH₂C(CH₃)₃ | H | 1 | 497) | Free |
| Example 782 | [piperidine]-N-C(O)-[phenyl]-O(CH₂)₅NHCH₂C(CH₃)=CH₂ | H | 1 | 498) | Free |
| Example 783 | [piperidine]-N-C(O)-[phenyl]-O(CH₂)₅NH-cyclopropyl | H | 1 | 499) | Free |
| Example 784 | [piperidine]-N-C(O)-[phenyl]-O(CH₂)₅NH(CH₂)₂C(CH₃)₃ | H | 1 | 500) | Free |
| Example 785 | [piperidine]-N-C(O)-[phenyl]-O(CH₂)₅NH(CH₂)₃CH₃ | H | 1 | 501) | Free |
| Example 786 | [piperidine]-N-C(O)-[phenyl]-O(CH₂)₅N((CH₂)₂N(CH₃)₂)(COCH₃) | H | 1 | 502) | Free |
| Example 787 | [piperidine]-N-C(O)-[phenyl]-O(CH₂)₅NHCH(CH₃)(CH₂CH₃) | H | 1 | 503) | Free |

Using the suitable starting materials, the following compound is obtained in the same manners as in Examples 1, 384, 390–393, 398, 399, 407–409, 421 and 593.

TABLE 12

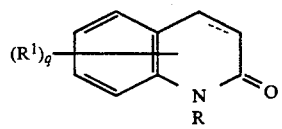

| | Structure | | | | |
|---|---|---|---|---|---|
| | R | R¹ | q | NMR analysis | Form |
| | Bond between 3- and 4-positions in the carbostyril ring: Single bond | | | | |
| Example 788 | ![piperidine-CO-phenyl-O(CH2)5CHCH2N(C2H5)2 with OH] | H | 1 | 504) | Free |

TABLE 13

| No. | NMR (CDCl₃) δ value |
|---|---|
| 495 | 1.66 (9H, s), 1.42–1.93 (8H, m), 2.51–3.22 (11H, m), 3.83–5.15 (3H, m), 3.98 (2H, t, J=6.4 Hz), 6.83–7.48 (8H, m) |
| 496 | 0.93 (6H, d, J=6.6 Hz), 1.42–1.94 (9H, m), 2.33–3.14 (11H, m), 2.46 (2H, d, J=6.9 Hz), 3.83–5.18 (3H, m), 3.98 (2H, t, J=6.4 Hz), 6.85–7.48 (8H, m) |
| 497 | 0.93 (9H, s), 1.43–2.01 (9H, m), 2.37 (2H, s), 2.50–3.13 (10H, m), 3.82–5.03 (3H, m), 3.99 (2H, t, J=6.4 Hz), 6.86–6.94 (2H, m), 6.98–7.30 (4H, m), 7.38–7.47 (2H, m) |
| 498 | 1.43–1.96 (9H, m), 1.75 (3H, s), 2.52–3.13 (10H, m), 3.19 (2H, s), 3.88–5.05 (3H, m), 3.99 (2H, t, J=6.4 Hz), 4.85 (2H, d, J=6.5 Hz), 6.85–7.52 (8H, m) |
| 499 | 0.28–0.51 (4H, m), 1.41–1.94 (9H, m), 2.06–2.21 (1H, m), 2.51–3.17 (10H, m), 3.82–5.08 (3H, m), 3.98 (2H, t, J=6.4 Hz), 6.86–7.51 (8H, m) |
| 500 | 0.91 (9H, s), 1.34–1.94 (10H, m), 2.11 (1H, brs), 2.49–3.12 (12H, m), 3.84–5.03 (3H, m), 3.98 (2H, t, J=3.4 Hz), 6.83–7.48 (8H, m) |
| 501 | 0.91 (3H, t, J=7.2 Hz), 1.24–1.93 (12H, m), 2.13 (1H, brs), 2.44–3.15 (12H. m), 3.78–5.14 (3H, m), 3.98 (2H, t, J=6.4 Hz), 6.84–7.48 (8H, m) |
| 502 | 1.39–1.95 (8H, m), 2.11 (3H, d, J=1.5 Hz), 2.27 (3H, s), 2.33 (3H, s), 2.48–3.13 (16H, m), 3.26–3.67 (4H, m), 3.87–5.10 (5H, m), 6.85–7.53 (8H, m) |
| 503 | 0.90 (3H, t, J=7.4 Hz), 1.07 (3H, d, J=6.3 Hz), 1.20–1.92 (10H, m), 2.22 (1H, brs), 2.49–3.12 (11H, m), 3.85–5.04 (3H, m), 3.98 (2H, t, J=6.4 Hz), 6.83–7.48 (8H, m) |
| 504 | 1.02 (6H, t, J=7.1 Hz), 1.31–1.93 (10H, m), 2.16–3.13 (15H, m), 3.49–3.67 (1H, m), 3.85–4.93 (3H, m), 3.98 (2H, t, J=6.4 Hz), 6.83–7.48 (8H, m) |

Reference Example 25

1,3-Cyclohexanedione (10.0 g) is dissolved in toluene (100 ml) with heating and thereto is added 4-amino-1-benzylpiperidine (18.6 ml). The mixture is refluxed for 2 hours by using Dean-Stark apparatus. After cooling, the precipitated crystal is washed with diethyl ether, and recrystallized from toluene to give 1-(1-benzyl-4-piperidinylamino)-1-cyclohexen-3-on (24.2 g) as light yellow prisms, m.p.: 171°–172° C.

Reference Example 26

Acrylic acid (28.9 ml) is added to 1-(1-benzyl-4-piperidinylamino)-1-cyclohexen-3-on (100 g) and the mixture is refluxed with stirring for 6 hours. After cooling, the reaction mixture is dissolved in chloroform containing 10% methanol and purified by silica gel column chromatography (solvent; dichloromethane:-methanol=40:1). The resultant is recrystallized from ethanol/water to give 1-(1-benzyl-4-piperidinyl)-5-oxo-3,4,5,6,7,8-hexahydrocarbostyril (23.98 g) as colorless needles, m.p.: 102°–103° C.

Reference Example 27

1-(1-Benzyl-4-piperidinyl)-5-oxo-3,4,5,6,7,8-hexahydrocarbostyril (10.0 g) is dissolved in chloroform (500 ml) and thereto is added N-bromosuccinimide (5.78 g). The mixture is refluxed with stirring for 2 hours. Thereto are added N-bromosuccinimide (5.00 g) and triethylamine (50 ml) and the mixture is refluxed with stirring for 3 hours. After cooling, the reaction mixture is washed twice with 30% aqueous sodium thiosulfate solution (200 ml) and once with saline solution (500 ml) and then dried with magnesium sulfate. The solvent is evaporated off and the resulting residue is purified by silica gel column chromatography (solvent: dichloromethane:methanol=40:1) and recrystallized from ethanol/water to give 1-(1-benzyl-4-piperidinyl)-5-hydroxy-3,4-dihydrocarbostyril (2.13 g) as colorless needles, m.p.: 183°–184° C.

Reference Example 28

1-(1-Benzyl-4-piperidinyl)-5-hydroxy-3,4-dihydrocarbostyril (500 mg) is dissolved in acetone (20 ml) and thereto are added potassium carbonate (246 mg) and ethyl iodide (0.18 ml). The mixture is refluxed with stirring for 6.5 hours. After the reaction, the insoluble materials are removed by filtration, and the filtrate is concentrated under reduced pressure. Dichloromethane is added to the resulting residue and the mixture is washed with 5% aqueous sodium hydroxide solution and then dried with magnesium sulfate. The solvent is evaporated and the resulting residue is purified by silica gel column chromatography (solvent; dichloromethane:methanol=50:1) to give 1-(1-benzyl-4-piperidinyl)-5-ethoxy-3,4-dihydrocarbostyril (0.27 g).

NMR (CDCl₃) δppm: 1.41 (3H, t, J=7.0 Hz), 1.58–1.82 (2H, m), 2.03–2.24 (2H, m), 2.47–3.10 (8H, m), 3.54 (2H, s), 4.03 (2H, q, J=7.0 Hz), 4.19–4.36 (1H, m), 6.60 (1H, d, J=8.2 Hz), 6.85 (1H, d, J=8.2 Hz), 7.14 (1H, t, J=8.2 Hz), 7.22–7.37 (5H, m)

Reference Example 29

Using the suitable starting materials, N-(1-benzyl-4-piperidinyl)-3,5-dimethylaniline is obtained in the same manner as in the above Reference Example 1.

NMR (CDCl₃) δppm: 1.35–1.60 (2H, m), 1.95–2.20 (4H, m), 2.22 (6H, s), 2.70–2.94 (2H, m), 3.15–3.40 (1H, m), 3.52 (2H, s), 6.22 (2H, s), 6.33 (1H, s), 7.20–7.40 (5H, m)

Reference Example 30

Using the suitable starting materials, N-cinnamoyl-N-(1-benzyl-4-piperidinyl)-3,5-dimethylaniline is obtained in the same manners as in the above Reference Example 15 as white powders, m.p.: 151°-154° C.

Reference Example 31

Using the suitable starting materials, 1-(1-benzyl-4-piperidinyl)-5,7-dimethylcarbostyril hydrochloride is obtained in the same manner as in the above Reference Example 16 as white powders, m.p.: 241°-244° C.

Reference Example 32

Using the suitable starting materials, N-(1-benzyl-4-piperidinyl)-2-formyl-3-fluoroaniline is obtained in the same manner as in the above Reference Example 19 as yellow powders, m.p.: 108°-109° C.

Reference Example 33

Using the suitable starting materials, methyl 2-fluoro-5-[(1-benzyl-4-piperidinyl)amino]cinnamate is obtained in the same manner as in the above Reference Example 24 as white powders, m.p.: 130°-133° C.

Reference Example 34

Potassium carbonate (8.9 g), 4-amino-1-benzylpiperidine (18.5 g), cupric oxide (0.6 g) and dimethylformamide (25 ml) are added to 2-chloro-6-fluorobenzoic acid (11.3 g) and the mixture is reacted with heating at 140° C. for 6 hours. After the reaction, the solvent is concentrated and to the resulting residue are added water (200 ml) and active carbon (1 g). The mixture is refluxed for 30 minutes. After filtration, the filtrate is cooled and then adjusted to pH 8.0 with diluted hydrochloric acid. The precipitated crystal is collected by filtration and washed successively with water and methanol to give 2-(1-benzyl-4-piperidinylamino)-6-fluorobenzoic acid (7.6 g) as white powders, m.p.: 233°-236° C.

Reference Example 35

To a solution of lithium aluminium hydride (0.9 g) in anhydrous tetrahydrofuran (160 ml) is added 2-(1-benzyl-4-piperidinylamino)-6-fluorobenzoic acid (8.0 g) and the mixture is refluxed for 1 hour. After cooling, the reaction solution is poured into ice-water and then extracted with dichloromethane. The solvent is concentrated and to the resulting residue is added diethyl ether/n-hexane. The precipitated crystal is collected by filtration to give N-(1-benzyl-4-piperidinyl)-2-hydroxymethyl-3-fluoroaniline (4.6 g) as light yellow powders, m.p.: 167°-170° C.

Pharmacological Test

Experiment 1 : $V_1$ receptor binding assay

Using rat liver plasma membrane preparations prepared according to Ichihara's method [cf: Akira Ichihara, J. Bio. Chem., 258 9283 (1983)], the plasma membrane (50000 dpm, $2 \times 10^{-10}$M) of $[H]^3$-Arg-vasopressin and a test compound (100 ng, $10^{-7}-10^{-4}$M) are incubated at 37° C. for 10 minutes in 100 mM Tris-HCl buffer pH: 8.0 (250 μl) containing 5 mM MgCl$_2$, 1 mM EDTA and 0.1% BSA. After incubation, the mixture is filtered three times using the glass filter (GF/F) so as to separate the membrane preparation combining with vasopressin and then washed with the buffer (5 ml). This glass filter is taken out and mixed with liquid scintillation cocktail. The amount of $[H]^3$-vasopressin combining with the membrane is measured by liquid scintillation counter and the rate of the inhibitory effect of the test compound is estimated according to the following equation.

$$\text{Rate of the inhibitory effect (\%)} = 100 - \frac{C_1 - B_1}{C_0 - B_0} \times 100$$

$C^1$: The amount of $[H]^3$-vasopressin combining with the membrane in the presence of the test compound (known amount).

$C^0$: The amount of $[H]^3$-vasopressin combining with the membrane in the absence of the test compound.

$B^1$: The amount of $[H]^3$-vasopressin combining with the membrane in the presence of the excess amount of vasopressin ($10^{-6}$M).

The results are espressed as IC$_{50}$ values, which is the concentration of the test compound required to achieve the inhibitory effect in the rate of 50%.

The results are shown in the following Table 14.

Test Compounds 1. 1-[1-(4-Methylaminobenzoyl)-4-piperidinyl]-3,4-dihydrocarbostyril
2. 1-[1-(4-Dimethylaminobenzoyl)-4-piperidinyl]-3,4-dihydrocarbostyril
3. 1-{1-[4-(4-Carbamoylbutoxy)benzoyl]-4-piperidinyl}-3,4-dihydrocarbostyril
4. 1-{1-[4-(4-Carbamoylmethylaminocarbonylbutoxy)benzoyl]-4-piperidinyl}-3,4-dihydrocarbostyril
5. 1-{1-[4-(3-Cyanopropoxy)benzoyl]-4-piperidinyl}-3,4-dihydrocarbostyril
6. 1-{1-[4-(3-Amidinopropoxy)benzoyl]-4-piperidinyl}-3,4-dihydrocarbostyril
7. 1-{1-[4-(3-Carbamoylpropoxy)benzoyl]-4piperidinyl}-3,4-dihydrocarbostyril
8. 1-{1-[4-(3-Ethoxycarbonylmethylaminocarbonylpropoxy)benzoyl]-4-piperidinyl}-3,4-dihydrocarbostyril
9. 1-{1-[4-(3-Carbamoylmethylaminocarbonylpropoxy)benzoyl]-4-piperidinyl}-3,4-dihydrocarbostyril
10. Methyl N-[4-{4-[4-(1,2,3,4-tetrahydro-2-oxo-1-quinolyl)-1-piperidinylcarbonyl]phenoxy}]butanoyl-L-serinate
11. Methyl N-[4-{4-[4-(1,2,3,4-tetrahydro-2-oxo-1-quinolyl)-1-piperidinylcarbonyl]phenoxy}]butanoyl-L-alanate
12. 1-{1-[4-(5-Carbamoylpentyloxy)benzoyl]-4-piperidinyl}-3,4-dihydrocarbostyril
13. 1-{1-[4-(5-Ethoxycarbonylmethylaminocarbonylpentyloxy)benzoyl]-4-piperidinyl]-3,4-dihydrocarbostyril
14. 1-{1-[4-(5-Carbamoylmethylaminocarbonylpentyloxy)benzoyl]-4-piperidinyl}-3,4-dihydrocarbostyril
15. 1-{1-[4-(7-Carbamoylheptyloxy)benzoyl]-4-piperidinyl}-3,4-dihydrocarbostyril
16. 1-{1-[4-(7-Carbamoylmethylaminocarbonylheptyloxy)benzoyl]-4-piperidinyl}-3,4-dihydrocarbostyril
17. 1-[1-[4-(3-Dimethylaminopropoxy)benzoyl]-4-piperidinyl}-3,4-dihydrocarbostyril
18. 1-{1-[4-(3-Benzylaminopropoxy)benzoyl]-4-piperidinyl}-3,4-dihydrocarbostyril
19. 1-{1-[4-[3-(Phthalimido-1-yl)propoxy]benzoyl]-4-piperidinyl}-3,4-dihydrocarbostyril
20. 1-{1-[4-(3-Acetylaminopropoxy)benzoyl]-4-piperidinyl}-3,4-dihydrocarbostyril 21. 1-{1-[4-(3-Methoxycarbonylaminopropoxy)benzoyl]-4-piperidinyl}-3,4-dihydrocarbostyril
22. 1-{1-[4-(3-Methylsulfonylaminopropoxy)benzoyl]-4-piperidinyl}-3,4-dihydrocarbostyril
23. 1-[1-{4-[3-(3-Methylureido)propoxy)benzoyl}-4-piperidinyl]-3,4-dihydrocarbostyril
24. 1-{1-[4-(4-Aminobutoxy)benzoyl]-4-piperidinyl}-3,4-dihydrocarbostyril
25. 1-{1-[4-(4-(N-Acetylglycylaminobutoxy)benzoyl]-4-piperidinyl}-3,4-dihydrocarbostyril
26. 1-{1-[4-(4-Formylaminobutoxy)benzoyl]-4-piperidinyl}-3,4-dihydrocarbostyril
27. 1-{1-[4-(4-Methoxycarbonylaminobutoxy)benzoyl]-4-piperidinyl}-3,4-dihydrocarbostyril
28. 1-{1-[4-(4-Methylsulfonylaminobutoxy)benzoyl]-4-piperidinyl}-3,4-dihydrocarbostyril
29. 1-{1-[4-(5-Aminopentyloxy)benzoyl]-4-piperidinyl}-3,4-dihydrocarbostyril
30. 1-{1-[4-(5-Methylamino-4-hydroxypentyloxy)benzoyl]-4-piperidinyl}-3,4-dihydrocarbostyril
31. 1-{1-[4-(5-Dimethylamino-4-hydroxypentyloxy)benzoyl]-4-piperidinyl}-3,4-dihydrocarbostyril
32. 1-{1-[4-(3-Hydroxypropoxy)benzoyl]-4-piperidinyl}-3,4-dihydrocarbostyril
33. 1-{1-[4-(3-Acetoxypropoxy)benzoyl]-4-piperidinyl}-3,4-dihydrocarbostyril
34. 1-{1-[4-(3-Methylsulfonyloxypropoxy)benzoyl]-4-piperidinyl}-3,4-dihydrocarbostyril
35. 1-{1-[4-(3-Carbamoyloxypropoxy)benzoyl]-4-piperidinyl}-3,4-dihydrocarbostyril
36. 1-{1-[4-(4-Hydroxybutoxy)benzoyl]-4-piperidinyl}-3,4-dihydrocarbostyril
37. 1-{1-[4-(4-Acetoxybutoxy)benzoyl]-4-piperidinyl}-3,4-dihydrocarbostyril
38. 1-{1-[4-(4-Carbamoyloxybutoxy)benzoyl]-4-piperidinyl}-3,4-dihydrocarbostyril
39. 1-{1-[4-(5-Acetoxypentyloxy)benzoyl]-4-piperidinyl}-3,4-dihydrocarbostyril
40. 1-[1-(4-Methoxybenzoyl)-4-piperidinyl]-3,4-dihydrocarbostyril
41. 1-[1-(4-Ethoxybenzoyl)-4-piperidinyl]-3,4-dihydrocarbostyril
42. 1-[1-(4-Propoxybenzoyl)-4-piperidinyl]-3,4-dihydrocarbostyril
43. 1-[1-(4-Butoxybenzoyl)-4-piperidinyl]-3,4-dihydrocarbostyril
44. 1-[1-(4-Allyloxybenzoyl)-4-piperidinyl]-3,4-dihydrocarbostyril
45. 1-[1-(4-Phenyloxybenzoyl)-4-piperidinyl]-3,4-dihydrocarbostyril
46. 1-[1-(4-Acetoxybenzoyl)-4-piperidinyl]-3,4-dihydrocarbostyril
47. 1-[1-(2,4-Dimethoxybenzoyl)-4-piperidinyl]-3,4-dihydrocarbostyril
48. 1-[1-(2-Methoxy-4-methylaminobenzoyl)-4-piperidinyl]-3,4-dihydrocarbostyril
49. 1-[1-(2-Methoxy-4-dimethylaminobenzoyl)-4-piperidinyl]-3,4-dihydrocarbostyril
50. 1-{1-[2,4-Bis(N,N-dimethylamino)benzoyl]-4-piperidinyl}-3,4-dihydrocarbostyril
51. 1-{1-[2-(2-Oxooxazolydine-3-yl)-4-methoxybenzoyl]-4-piperidinyl}-3,4-dihydrocarbostyril
52. 1-[1-(2-Methoxy-4-ethoxybenzoyl)-4-piperidinyl]-3,4-dihydrocarbostyril
53. 1-[1-(2-Methoxy-4-methylthiobenzoyl)-4-piperidinyl]-3,4-dihydrocarbostyril
54. 1-[1-(2-Methoxy-4-chlorobenzoyl)-4-piperidinyl]-3,4-dihydrocarbostyril
55. 1-[1-(2-Dimethylamino-4-methoxybenzoyl)-4-piperidinyl]-3,4-dihydrocarbostyril
56. 1-[1-(2-Ethylamino-4-methoxybenzoyl)-4-piperidinyl]-3,4-dihydrocarbostyril
57. 1-[1-(2-Propylamino-4-methoxybenzoyl)-4-piperidinyl]-3,4-dihydrocarbostyril
58. 1-{1-[2-(N-Methyl-N-ethylamino)-4-methoxybenzoyl]-4-piperidinyl}-3,4-dihydrocarbostyril
59. 1-[1-(2-Ethoxy-4-methoxybenzoyl)-4-piperidinyl]-3,4-dihydrocarbostyril
60. 1-[1-(2-Hydroxy-4-methoxybenzoyl)-4-piperidinyl]-3,4-dihydrocarbostyril
61. 1-[1-(2-Acetoxy-4-methoxybenzoyl)-4-piperidinyl]-3,4-dihydrocarbostyril
62. 1-[1-(2-Allyloxy-4-methoxybenzoyl)-4-piperidinyl]-3,4-dihydrocarbostyril
63. 1-{1-[2-(3-Hydroxypropoxy)-4-methoxybenzoyl]-4-piperidinyl}-3,4-dihydrocarbostyril
64. 1-{1-[2-(3-Acetoxypropoxy)-4-methoxybenzoyl]-4-piperidinyl}-3,4-dihydrocarbostyril
65. 1-{1-[2-(3-Carbamoyloxypropoxy)-4-methoxybenzoyl]-4-piperidinyl}-3,4-dihydrocarbostyril
66. 1-{1-[2-(3-Methoxypropoxy)-4-methoxybenzoyl]-4-piperidinyl}-3,4-dihydrocarbostyril
67. 1-{1-[2-(3-Carbamoylpropoxy)-4-methoxybenzoyl]-4-piperidinyl}-3,4-dihydrocarbostyril
68. 1-{1-[2-(2-Hydroxyethoxy)-4-methoxybenzoyl]-4-piperidinyl}-3,4-dihydrocarbostyril
69. 1-{1-[2-(2-Acetoxyethoxy)-4-methoxybenzoyl]-4-piperidinyl}-3,4-dihydrocarbostyril
70. 1-{1-[2-(2-Methoxyethoxy)-4-methoxybenzoyl]-4-piperidinyl}-3,4-dihydrocarbostyril
71. 1-[1-(4-Bromobenzoyl)-4-piperidinyl]-3,4-dihydrocarbostyril
72. 1-[1-(4-Benzoylbenzoyl)-4-piperidinyl]-3,4-dihydrocarbostyril
73. 1-[1-(4-Methylthiobenzoyl)-4-piperidinyl]-3,4-dihydrocarbostyril
74. 1-[1-(4-Ethylthiobenzoyl)-4-piperidinyl]-3,4-dihydrocarbostyril
75. 1-[1-(4-Methylbenzoyl)-4-piperidinyl]-3,4-dihydrocarbostyril
76. 1-[1-(4-Propylbenzoyl)-4-piperidinyl]-3,4-dihydrocarbostyril
77. 1-[1-(4-Butylbenzoyl)-4-piperidinyl]-3,4-dihydrocarbostyril
78. 1-[1-(3,4-Dimethylbenzoyl)-4-piperidinyl]-3,4-dihydrocarbostyril
79. 6-Fluoro-1-[1-(2,4-dimethoxybenzoyl)-4-piperidinyl]-3,4-dihydrocarbostyril
80. 7-Fluoro-1-[1-(2-methoxy-4-methylthiobenzoyl)-4-piperidinyl]-3,4-dihydrocarbostyril
81. 7-Methyl-1-[1-(2,4-dimethoxybenzoyl)-4-piperidinyl]-3,4-dihydrocarbostyril
82. 1-[1-(2-Methoxy-4-ethoxybenzoyl)-4-piperidinyl]carbostyril
83. 1-(1-Tricyclo[3.3.1.1$^{3,7}$]decanylcarbonyl-4-piperidinyl)-3,4-dihydrocarbostyril
84. 1-[1-(2-Methoxy-4-methylthiobenzoyl)-3-pyrrolidinyl]-3,4-dihydrocarbostyril
85. 1-{4-[N-(4-Methoxyphenyl)-N-benzylamidophenyl]-3,4-dihydrocarbostyril
86. 1-{1-[4-(3-[4-(4-Methoxyphenyl)-1-piperazinyl]propoxy)benzoyl]-4-piperidinyl}-3,4-dihydrocarbostyril
87. 1-{1-[4-(3-Allyloxypropoxy)benzoyl]-4-piperidinyl}-3,4-dihydrocarbostyril 88. 1-{1-[4-(3-Carbamoylpropylamino)benzoyl]-4-piperidinyl}-3,4-dihydrocarbostyril
89. 1-{1-[4-(2-Ethylthioimidazol-1-yl)benzoyl]-4-piperidinyl}-3,4-dihydrocarbostyril
90. 1-{1-[4-(N-Allyl-N-methylamino)benzoyl]-4-piperidinyl}-3,4-dihydrocarbostyril
91. 1-{1-[4-(1-Pyrrolidinyl)benzoyl]-4-piperidinyl}-3,4-dihydrocarbostyril
92. 1-[1-{4-[3-(N-Methyl-N-benzoylamino)propoxy]benzoyl}-4-piperidinyl]-3,4-dihydrocarbostyril
93. 1-[1-{4-[3-(4-Phenyl-1-piperazinyl)propoxy]-benzoyl}-4-piperidinyl]-3,4-dihydrocarbostyril
94. 1-{1-[4-(3-Benzoyloxypropoxy)benzoyl]-4-piperidinyl}-3,4-dihydrocarbostyril
95. 1-{1-[4-(3-Ethylthiopropoxy)benzoyl]-4-piperidinyl}-3,4-dihydrocarbostyril
96. 1-[1-(4-Propargylbenzoyl)-4-piperidinyl]-3,4-dihydrocarbostyril
97. 1-[1-(4-Benzyloxybenzoyl)-4-piperidinyl]-3,4-dihydrocarbostyril
98. 1-{1-[4-(2-Cyclohexenyloxy)benzoyl]-4-piperidinyl}-3,4-dihydrocarbostyril
99. 1-[1-(4-Cyclohexyloxybenzoyl)-4-piperidinyl]-3,4-dihydrocarbostyril
100. 1-[1-(4-Methylsulfonyloxybenzoyl)-4-piperidinyl]-3,4-dihydrocarbostyril
101. 1-[1-(4-Glycidoxybenzoyl)-4-piperidinyl]-3,4-dihydrocarbostyril
102. 1-{1-[4-Methoxy-2-(N-methyl-N-ethoxycarbonylmethylamino)benzoyl]-4-piperidinyl}-3,4-dihydrocarbostyril
103. 1-[1-(4-Methoxy-2-benzyloxycarbonylaminobenzoyl)-4-piperidinyl]-3,4-dihydrocarbostyril
104. 1-[1-(4-Methoxy-2-acetylaminobenzoyl)-4-piperidinyl]-3,4-dihydrocarbostyril
105. 1-[1-(4-Methoxy-2-methylaminocarbonylmethylamino)-4-piperidinyl]-3,4-dihydrocarbostyril
106. 1-[1-(4-Trifluoromethylbenzoyl)-4-piperidinyl]-3,4-dihydrocarbostyril
107. 1-[1-(4-Acetylbenzoyl)-4-piperidinyl]-3,4-dihydrocarbostyril
108. 1-[1-(4-Hydroxyiminomethylbenzoyl)-4-piperidinyl]-3,4-dihydrocarbostyril
109. 1-[1-(4-Methoxymethylbenzoyl)-4-piperidinyl]-3,4-dihydrocarbostyril
110. 1-[1-(4-Trimethylsilylbenzoyl)-4-piperidinyl]-3,4-dihydrocarbostyril
111. 1-[1-(4-Allylbenzoyl)-4-piperidinyl]-3,4-dihydrocarbostyril
112. 1-[1-(4-Cyclohexylbenzoyl)-4-piperidinyl]-3,4-dihydrocarbostyril
113. 1-[1-(3,4-Methylenedioxybenzoyl)-4-piperidinyl]-3,4-dihydrocarbostyril
114. 1-[1-(2,6-Dimethyl-1,5-heptadiene-1-carbonyl)-4-piperidinyl]-3,4-dihydrocarbostyril
115. 1-{1-(Tricyclo[3.3.1.1$^{3,7}$]decanylacetyl-4-piperidinyl}-3,4-dihydrocarbostyril
116. 1-[1-(2-Naphthylcarbonyl)-4-piperidinyl]-3,4-dihydrocarbostyril
117. 1-[1-(3-quinolylcarbonyl)-4-piperidinyl]-3,4-dihydrocarbostyril
118. 1-[3-Methyl-1-(2,4-dimethoxycarbonyl)-4-piperidinyl]-3,4-dihydrocarbostyril
119. 1-[1-(3-Nitro-4-methoxybenzoyl)-4-piperidinyl]-3,4-dihydrocarbostyril
120. 6,7-Difluoro-1-[1-(2-methoxy-4-ethoxybenzoyl)-4-piperidinyl]-3,4-dihydrocarbostyril
121. 1-{1-[4-(3-Methylaminocarbonylpropoxy)benzoyl]-4-piperidinyl}-3,4-dihydrocarbostyril
122. 1-{1-[4-(4-Hydroxy-1-butenyl)benzoyl]-4-piperidinyl}-3,4-dihydrocarbostyril
123. 1-{1-[4-(4-Hydroxybutyl)benzoyl]-4-piperidinyl}-3,4-dihydrocarbostyril
124. 1-{1-[4-(4-Acetoxybutyl)benzoyl]-4-piperidinyl}-3,4-dihydrocarbostyril
125. 1-[1-{4-[4-(1-pyrrolyl)butoxy]benzoyl}-4-piperidinyl]-3,4-dihydrocarbostyril
126. 1-[1-{4-[(4-Methylaminobenzoyl)aminobutoxy]benzoyl}-4-piperidinyl]-3,4-dihydrocarbostyril
127. 1-{1-[4-(Ethylsulfinylpropoxy)benzoyl]-4-piperidinyl}-3,4-dihydrocarbostyril
128. 1-{1-[4-(6-Hydroxyhexyloxy)benzoyl]-4-piperidinyl}-3,4-dihydrocarbostyril
129. 1-{1-[4-(5-Carbamoyloxypentyloxy)benzoyl]-4-piperidinyl}-3,4-dihydrocarbostyril
130. 1-{1-[4-(6-Acetoxyhexyloxy)benzoyl]-4-piperidinyl}-3,4-dihydrocarbostyril
131. 1-{1-[4-(6-Dimethylamino-5-hydroxyhexyloxy)benzoyl]-4-piperidinyl}-3,4-dihydrocarbostyril
132. 1-[1-{4-[3-(1-piperazinyl)propoxy]benzoyl}-4-piperidinyl]-3,4-dihyrocarbostyril dihydrochloride trihydrate
133. 1-[1-{4-[3-(4-Benzyl-1-piperazinyl)propoxy]benzoyl}-4-piperidinyl]-3,4-dihydrocarbostyril dioxalate
134. 1-[1-{4-[3-(4-Acetyl-1-piperazinyl)propoxy]-benzoyl}-4-piperidinyl]-3,4-dihydrocarbostyril
135. 1-[1-{4-[3-(4-Anilinocarbonyl-1-piperazinyl)propoxy]benzoyl}-4-piperidinyl]-3,4-dihydrocarbostyril
136. 1-[1-{4-[3-(4-Methyl-1-piperazinyl)propoxy]benzoyl}-4-piperidinyl]-3,4-dihydrocarbostyril dioxalate
137. 1-[1-{4-[3-(4-Benzoylmethyl-1-piperazinyl)propoxy]benzoyl}-4-piperidinyl]-3,4-dihydrocarbostyril dioxalate
138. 1-{1-[4-{3-[4-(2-Phenyl-2-hydroxyethyl)-1-piperazinyl]propoxy}benzoyl]-4-piperidinyl}-3,4-dihydrocarbostyril dioxalate
139. 5,7-Difluoro-1-[1-(2-methoxy-4-ethoxybenzoyl)-4-piperidinyl]-3,4-dihydrocarbostyril
140. 1-{1-[4-(6-Aminohexyloxy)benzoyl]-4-piperidinyl}-3,4-dihydrocarbostyril
141. 1-{1-[4-(6-Acetylaminohexyloxy)benzoyl]-4-piperidinyl}-3,4-dihydrocarbostyril
142. 1-{1-[4-(6-Methylsulfonylaminohexyloxy)benzoyl]-4-piperidinyl}-3,4-dihydrocarbostyril
143. 1-{1-[4-(3-Ethylsulfonylpropoxy)benzoyl]-4-piperidinyl}-3,4-dihydrocarbostyril
144. 1-{1-[4-(6-Diethylamino-5-hydroxyhexyloxy)benzoyl]-4-piperidinyl}-3,4-dihydrocarbostyril
145. 1-{1-[4-(3-Formylaminopropoxy)benzoyl]-4-piperidinyl}-7-fluoro-3,4-dihydrocarbostyril
146. 1-{1-[4-{5-[1-(S)-Carbamoyl-2-(4-hydroxyphenyl)]ethylaminocarbonylpentyloxy}benzoyl]-4-piperidinyl}-3,4-dihydrocarbostyril
147. 1-{1-[4-{5-[1-(S)-Carbamoyl-2-methyl]propylaminocarbonylpentyloxy}benzoyl]-4-piperidinyl}-3,4dihydrocarbostyril
148. 1-{1-[4-(3-Dimethylaminocarbonylpropoxy)benzoyl]-4-piperidinyl}-3,4-dihydrocarbostyril
149. 1-{1-[4-{5-[1-(S)-Carbamoyl-2{4(1H)imidazoyl}]ethylaminocarbonylpentyloxy)benzoyl]-4-piperidinyl}-3,4-dihydrocarbostyril 150. 1-{1-[4-(5-[1-(S),3-Dicarbamoyl]-propylaminocarbonylpentyloxy)benzoyl]-4-piperidinyl}-3,4-dihydrocarboxtyril
151. 1-[1-(2-Methoxy-4-ethoxybenzoyl)-4-piperidinyl]-7-fluorocarbostyril
152. 1-[1-(2-Methoxy-4-ethoxybenzoyl)-4-piperidinyl]-3-carboxy-3,4-dihydrocarbostyril
153. 1-{1-[4-(5-[1-(S)-Carbamoyl-3-(methylthio)]-propylaminocarbonylpentyloxy)benzoyl]-4-piperidinyl}-3,4-dihydrocarbostyril
154. 1-{1-[4-(5-(Imidazo[4,5-c]pyridine-2-yl)carbonylpentyloxy)benzoyl]-4-piperidinyl}-3,4--dihydrocarbostyril
155. 1-[1-(2-Hydroxy-4-ethoxybenzoyl)-4-piperidinyl]-7-fluoro-3,4-dihydrocarbostyril
156. 1-{1-[4-[(4-Benzyl-1-piperazinyl)butoxy]-benzoyl]-4-piperidinyl}-3,4-dihydrocarbostyril
157. 1-{1-[4-[4-(1-Piperazinyl)butoxy]benzoyl]-4-piperidinyl}-3,4-dihydrocarbostyril
158. 1-{1-[4-[4-(4-Methyl-1-piperazinyl)butoxy]benzoyl]-4-piperidinyl}-3,4-dihydrocarbostyril
159. 1-{1-[4-[4-(4-Methylsulfonyl-1-piperazinyl)butoxy]benzoyl]-4-piperidinyl}-3,4-dihydrocarbostyril
160. 1-{1-[4-[4-(4-Methoxycarbonyl-1-piperazinyl)butoxy]benzoyl]-4-piperidinyl}-3,4-dihydrocarbostyril
161. 1-{1-[4-[4-(4-Benzyl-1-piperazinyl)carbonyloxybutoxy]benzoyl]-4-piperidinyl}-3,4-dihydrocarbostyril
162. 1-{1-[4-[4-(4-Acetyl-1-piperazinyl)butoxy]benzoyl]-4-piperidinyl}-3,4-dihydrocarbostyril
163. 1-{1-[4-[4-(1-Piperazinyl)carbonyloxybutoxy]benzoyl]-4-piperidinyl}-3,4-dihydrocarbostyril
164. 1-{1-[4-[4-(Benzimidazol-1-yl)thiobutoxy]benzoyl]-4-piperidinyl}-3,4-dihydrocarbostyril
165. 1-{1-[4-{5-[(5-Benzyloxycarbonylamino)-1-(S)-methoxycarbonyl]pentylaminocarbonylpentyloxy}benzoyl]-4-piperidinyl}-3,4-dihydrocarbostyril
166. 1-{1-[4-{5-[5-Amino-1-(S)-methoxycarbonyl]pentylaminocarbonylpentyloxy}benzoyl]-4-piperidinyl}-3,4-dihydrocarbostyril
167. 1-{1-[4-(3-Isopentylaminopropoxy)benzoyl]-4-piperidinyl}-3,4-dihydrocarbostyril
168. 1-{1-[4-(3-Ethoxycarbonylaminopropoxy)benzoyl]-4-piperidinyl}-3,4-dihydrocarbostyril
169. 1-{1-[4-(3-Phenylsulfonylaminopropoxy)benzoyl]-4-piperidinyl}-3,4-dihydrocarbostyril
170. 1-{1-[4-(5-Hydroxy-6-benzylaminohexyloxy)benzoyl]-4-piperidinyl}-3,4-dihydrocarbostyril
171. 1-{1-[4-(5-Hydroxy-6-aminohexyloxy)benzoyl]-4-piperidinyl}-3,4-dihydrocarbostyril
172. 1-{1-[4-(5-Hydroxy-6-(4-benzyl-1-piperazinyl)hexyloxy]benzoyl]-4-piperidinyl}-3,4-dihydrocarbostyril dioxalate
173. 1-{1-[4-(5-Hydroxy-6-(1-piperazinyl)hexyloxy]benzoyl]-4-piperidinyl}-3,4-dihydrocarbostyril dioxalate
174. 1-{1-[4-(3-p-Toluenesulfonylaminopropoxy)benzoyl]-4-piperidinyl}-3,4-dihydrocarbostyril
175. 5,7-Difluoro-1-[1-(2-Methoxy-4-ethoxybenzoyl)-4-piperidinyl]carbostyril
176. 1-{1-[4-(5-Acetoxy-6-acetylaminohexyloxy)benzoyl]-4-piperidinyl}-3,4-dihydrocarbostyril
177. 1-{1-[4-(5-Hydroxy-6-acetylaminohexyloxy)benzoyl]-4-piperidinyl}-3,4-dihydrocarbostyril
178. 1-{1-[4-(5-Hydroxy-6-(4-methyl-1-piperazinyl)hexyloxy]benzoyl]-4-piperidinyl}-3,4-dihydrocarbostyril
179. 1-{1-[4-(4-Dimethylaminobutoxy)benzoyl]-4-piperidinyl}-3,4-dihydrocarbostyril
180. 1-{1-[4-(4-Dimethylaminobutyl)benzoyl]-4-piperidinyl}-3,4 -dihydrocarbostyril
181. 1-{1-[4-(3-Acetylaminoacetylaminopropoxy)benzoyl]-4-piperidinyl}-3,4-dihydrocarbostyril
182. 1-{1-[4-(3-[2-(Acetylamino)valerylamino]-propoxy)benzoyl]-4-piperidinyl}-3,4-dihydrocarbostyril
183. 1-{1-[4-(3-Formylaminopropoxy)benzoyl]-4-piperidinyl}-3,4-dihydrocarbostyril
184. 1-{1-[4-(7-Hydroxy-8-diethylaminooctyloxy)benzoyl]-4-piperidinyl}-3,4-dihydrocarbostyril
185. 7-Fluoro-1-{1-[4-(5-Hydroxy-6-diethylaminohexyloxy)--2-methoxybenzoyl]-4-piperidinyl}-3,4--dihydrocarbostyril
186. 1-{1-[4-(4-Hydroxy-5-(1-pyrrolidinyl)pentyloxy)benzoyl]-4-piperidinyl}-3,4-dihydrocarbostyril
187. 1-{1-[4-(7-Hydroxy-8-dimethylaminooctyloxy)benzoyl]-4-piperidinyl}-3,4-dihydrocarbostyril
188. 1-{1-[4-(4-(Hydroxy-5-(1-piperidinyl)pentyloxy)benzoyl]-4-piperidinyl}-3,4-dihydrocarbostyril
189. 1-{1-[4-(4-Hydroxy-5-morpholinopentyloxy)benzoyl]-4-piperidinyl}-3,4-dihydrocarbostyril
190. 1-{1-[4-(5-(2-Hydroxy-3-diethylaminopropoxy)pentyloxy)benzoyl]-4-piperidinyl}-3,4-dihydrocarbostyril
191. 1-{1-[4-(5-(2-Hydroxy-3-dimethylaminopropoxy)pentyloxy)benzoyl]-4-piperidinyl}-3,4-dihydrocarbostyril
192. 1-{1-[4-(3-(2-Hydroxy-3-diethylaminopropoxy)propoxy)benzoyl]-4-piperidinyl}-3,4-dihydrocarbostyril
193. 1-{1-[4-(3-(4-Aminobenzoylamino)propoxy)benzoyl]-4-piperidinyl}-3,4-dihydrocarbostyril
194. 1-{1-[4-(4-(Benzimidazol-2-yl)sulfinylbutoxy)benzoyl]-4-piperidinyl}-3,4-dihydrocarbostyril
195. 1-{1-[4-(3-(α-N-Acetyl-(L)-glutaminyl)aminopropoxy)benzoyl]-4-piperidinyl}-3,4-dihydrocarbostyril
196. 1-{1-[4-(3-(4-Acetylaminobenzoyl)aminopropoxy)benzoyl]-4-piperidinyl}-3,4-dihydrocarbostyril
197. 1-{1-[4-(5-(3-Dimethylaminopropyl)aminocarbonylpentyloxy)benzoyl]-4-piperidinyl}-3,4-dihydrocarbostyril
198. 1-{1-[4-(3-Ethylaminocarbonylaminopropoxy)benzoyl]-4-piperidinyl}-3,4-dihydrocarbostyril
199. 1-{1-[4-(5-(2-Dimethylaminoethyl)aminocarbonylpentyloxy)benzoyl]-4-piperidinyl}-3,4-dihydrocarbostyril
200. 1-{1-[4-(5-(1-Benzyl-4-piperidinyl)aminocarbonylpentyloxy)benzoyl]-4-piperidinyl}-3,4-dihydrocarbostyril
201. 5,7-Difluoro-1-{1-[2-methoxy-4-(5-hydroxy-6-diethylaminohexyloxy)benzoyl]-4-piperidinyl}3,4-dihydrocarbostyril
202. 1-{1-[4-(5-Hydroxy-6-(1-pyrrolidinyl)hexyloxy)benzoyl]-4-piperidinyl}-3,4-dihydrocarbostyril
203. 1-{1-[4-(5-Hydroxy-6-[N-(2-phenylethyl)-N-methylamino]hexyloxy)benzoyl]-4-piperidinyl}-3,4-dihydrocarbostyril
204. 1-{1-[4-(5-Hydroxy-6-[N-(2-hydroxyethyl)-N-methylamino]hexyloxy)benzoyl]-4-piperidinyl}-3,4--dihydrocarbostyril
205. 1-{1-[4-(5-Hydroxy-6-(4-phenyl-1-piperazinyl)hexyloxy)benzoyl]-4-piperidinyl}-3,4-dihydrocarbostyril 206. 1-{1-[4-(7-Hydroxy-8-(1-pyrrolidinyl)octyloxy)-benzoyl]-4-piperidinyl}-3,4-dihydrocarbostyril 207. 1-{1-[4-(3-(2-Acetylamino-4-methylthiobutyrylamino)propoxy)benzoyl]-4-piperidinyl}-3,4-dihydrocarbostyril 208. 1-{1-[4-(3-[2-(R)-Acetylamino-2-(4(1H)imidazolyl)methylacetylamino]propoxy) benzoyl]-4-piperidinyl}-3,4-dihydrocarbostyril 209. 1-{1-[4-(3-(2-Acetylaminopropanoylamino)-propoxy)benzoyl]-4-piperidinyl}-3,4-dihydrocarbostyril 210. 1-{1-[4-(5-(4-Piperidinyl)aminocarbonylpentyloxy)benzoyl]-4-piperidinyl}-3,4-dihydrocarbostyril 211. 1-{1-[4-(3-[2-Benzyloxycarbonylamino-2α-(4-hydroxybenzyl)acetylamino)propoxy) benzoyl]-4-piperidinyl}-3,4-dihydrocarbostyril 212. 1-{1-[4-(6-Carbamoyloxyhexyloxy)benzoyl]-4-piperidinyl}-3,4-dihydrocarbostyril 213. 1-{1-[4-(6-Diethylaminohexyloxy)benzoyl]-4-piperidinyl}-3,4-dihydrocarbostyril 214. 1-{1-[4-(6-(1-Pyrrolidinyl)hexyloxy)benzoyl]-4-piperidinyl}-3,4-dihydrocarbostyril 215. 1-{1-[4-(6-(1-Methyl-5-oxo-3-morpholino)hexyloxy)benzoyl]-4-piperidinyl}-3,4-dihydrocarbostyril 216. 5-Methyl-1-[1-(2-methoxy-4-ethoxybenzoyl)-4-piperidinyl]-3,4-dihydrocarbostyril 217. 1-{1-[4-(5-Hydroxy-6-isopropylaminohexyloxy)-benzoyl]-4-piperidinyl}-3,4-dihydrocarbostyril 218. 1-{1-[4-(5-Hydroxy-6-[N-ethyl-N-(2-tetrahydropyranylmethyl)amino]hexyloxy)benzoyl]-4-piperidinyl}-3,4-dihydrocarbostyril 219. 1-{1-[4-(5-Hydroxy-6-[N-methyl-N-(2-hydroxy-2-phenylethyl)amino]hexyloxy)benzoyl]-4-piperidinyl}-3,4-dihydrocarbostyril 220. 1-{1-[4-(6-[2(S)-Hydroxymethyl-1-pyrrolidinyl]-5-hydroxy)hexyloxy)benzoyl]-4-piperidinyl}-3,4-dihydrocarbostyril 221. 1-{1-[4-(3-(S)-{N-(Bezyloxycarbonyl)prolyl}-aminopropoxy)benzoyl]-4-piperidinyl}-3,4-dihydrocarbostyril 222. 1-[1-{4-[3-(S)-(N,N'-Di(benzyloxycarbonyl)-lysyl}aminopropoxy]benzoyl}-4-piperidinyl]-3,4-dihydrocarbostyril 223. 1-[1-{4-[3-(S)-Tyrosylaminopropoxy]benzoyl}-4-piperidinyl]-3,4-dihydrocarbostyril 224. 1-{1-[4-(3-(S)-Prolylaminopropoxy)benzoyl]-4-piperidinyl}-3,4-dihydrocarbostyril 225. 1-[1-{4-(3-(R)-Valylaminopropoxy]benzoyl}-4-piperidinyl]-3,4-dihydrocarbostyril 226. 1-[1-{4-(3-(S)-{N-(Benzyloxycarbonyl)seryl}-aminopropoxy]benzoyl}-4-piperidinyl]-3,4-dihydrocarbostyril 227. 1-{1-(4-[4-(4-Allyl-1-piperazinyl)butoxy]benzoyl)-4-piperidinyl}-3,4-dihydrocarbostyril 228. 1-{1-(4-[4-(2-Chloroacetylamino)butoxy]benzoyl)-4-piperidinyl}-3,4-dihydrocarbostyril 229. 1-{1-(4-[5-(2-Acetoxyacetylamino)pentyloxy]-benzoyl)-4-piperidinyl}-3,4-dihydrocarbostyril 230. 1-{1-(4-[5-(2-Hydroxyacetylamino)pentyloxy]-benzoyl)-4-piperidinyl}-3,4-dihydrocarbostyril 231. 1-{1-(4-[4-(4-Piperidinylcarbonylamino)butoxy]-benzoyl)-4-piperidinyl}-3,4-dihydrocarbostyril 232. 1-{1-(4-[4-(1-Acetyl-4-piperidinylcarbonylamino)butoxy]benzoyl)-4-piperidinyl}-3,4-dihydrocarbostyril 233. 1-{1-(4-[5-(4-[2-Pyrimidyl]-1-piperazinyl)pentyloxy]benzoyl)-4-piperidinyl}-3,4-dihydrocarbostyril 234. 1-{1-(4-[5-(4-[2-Pyridyl]-1-piperazinyl)pentyloxy]benzoyl)-4-piperidinyl}-3,4-dihydrocarbostyril 235. 1-{1-[4-(5-Triethylammouniumpentyloxy)benzoyl]-4-piperidinyl}-3,4-dihydrocarbostyril bromide 236. 1-{1-(4-[5-(4-(1-Imidazolyl)pentyloxy]benzoyl)-4-piperidinyl}-3,4-dihydrocarbostyril 237. 1-{1-(4-[5-(4-(1,2,4-Triazol-1-yl)pentyloxy]benzoyl)-4-piperidinyl}-3,4-dihydrocarbostyril 238. 1-{1-(4-[5-(2-(S)-Hydroxymethyl-1-pyrrolidinyl)pentyloxy]benzoyl)-4-piperidinyl}-3,4-dihydrocarbostyril 239. 1-{1-(4-[5-(2-(S)-Methoxycarbonyl-1-pyrrolidinyl)pentyloxy]benzoyl)-4-piperidinyl}-3,4-dihydrocarbostyril 240. 1-{1-(4-[5-(3-Hydroxy-1-piperidinyl)pentyloxy]-benzoyl)-4-piperidinyl}-3,4-dihydrocarbostyril 241. 1-{1-(4-[5-(2-Hydroxymethyl-1-piperidinyl)pentyloxy]benzoyl)-4-piperidinyl}-3,4-dihydrocarbostyril 242. 1-{1-(4-[5-(4-Methyl-1-piperidinyl)pentyloxy]-benzoyl)-4-piperidinyl}-3,4-dihydrocarbostyril 243. 1-{1-(4-[6-(1-Piperidinyl)hexyloxy]benzoyl)-4-piperidinyl}-3,4-dihydrocarbostyril 244. 1-{1-(4-[5-(N-(2-Hydroxyethyl)-N-methylamino)pentyloxy]benzoyl)-4-piperidinyl}-3,4-dihydrocarbostyril 245. 1-{1-(4-[5-(N-Allyl-N-methylamino)pentyloxy]-benzoyl)-4-piperidinyl}-3,4-dihydrocarbostyril 246. N-{5-[4-(4-(3,4-Dihydrocarbostyril-1-yl)-1-piperidinylcarbonyl)phenoxy]pentyl}, N-methyl, N-allylamine oxide 247. 1-{1-(4-[5-(N-(2-Cyanoethyl)-N-methylamino)-pentyloxy]benzoyl)-4-piperidinyl}-3,4-dihydrocarbostyril 248. 1-{1-(4-[5-(N-(2-Dimethylaminoethyl)-N-benzylamino)pentyloxy]benzoyl)-4-piperidinyl}-3,4-dihydrocarbostyril 249. 1-{1-(4-[5-(N,N-Di(2-acetoxyethyl)amino)pentyloxy]benzoyl)-4-piperidinyl}-3,4-dihydrocarbostyril 250. 1-{1-(4-[5-(4-Benzyloxycarbonylaminobutyrylamino)pentyloxy]benzoyl)-4-piperidinyl}-3,4-dihydrocarbostyril 251. 1-{1-(4-[5-(2-Allylaminoacetylamino)pentyloxy]benzoyl)-4-piperidinyl}-3,4-dihydrocarbostyril 252. 1-{1-(4-[5-(2-(1-Pyrrolidinyl)acetylamino)pentyloxy]benzoyl)-4-piperidinyl}-3,4-dihydrocarbostyril 253. 1-{1-(4-[5-(2-Morpholinoacetylamino)pentyloxy]benzoyl)-4-piperidinyl}-3,4-dihydrocarbostyril 254. 1-{1-(4-[5-(2-(4-Methyl-1-piperazinyl)acetylamino)pentyloxy]benzoyl)-4-piperidinyl}-3,4-dihydrocarbostyril 255. 1-{1-(4-[5-(2-(4-Phenyl-1-piperazinyl)acetylamino)pentyloxy]benzoyl)-4-piperidinyl}-3,4-dihydrocarbostyril 256. 1-{1-(4-[5-(2-Benzylaminoacetylamino)pentyloxy]benzoyl)-4-piperidinyl}-3,4-dihydrocarbostyril 257. 1-{1-(4-[5-(2-(N-(2-Hydroxyethyl)-N-methylamino)acetylamino)pentyloxy]benzoyl)-4-piperidinyl}-3,4-dihydrocarbostyril 258. 1-{1-(4-[5-(4-Dimethylaminophenylsulfonylamino)pentyloxy]benzoyl)-4-piperidinyl}-3,4-dihydrocarbostyril 259. 1-{1-(4-[5-(4-Acetylaminobenzoyl)aminopentyloxy]benzoyl)-4-piperidinyl}-3,4-dihydrocarbostyril 260. 1-{1-(4-[5-(3,4-Dihydroxycyclohexylcarbonylaminopentyloxy]benzoyl)-4-piperidinyl} -3,4-dihydrocarbostyril 261. 1-{1-(4-[5-(3,4-Diacetoxycyclohexylcarbonyl)aminopentyloxy]benzoyl)-4-piperidinyl}-3,4-dihydrocarbostyril 262. 1-{1-(4-[5-(4-Aminobenzoyl)aminopentyloxy]benzoyl)-4-piperidinyl}-3,4-dihydrocarbostyril 263. 1-{1-(4-[5-(4-Nitrophenylsulfonyl)aminopentyloxy]benzoyl)-4-piperidinyl}-3,4-dihydrocarbostyril 264. 1-{1-(4-[5-(4-Aminophenylsulfonyl)aminopentyloxy]benzoyl)-4-piperidinyl}-3,4-dihydrocarbostyril 265. 1-{1-(4-[6-(4-(1-Piperidinyl)-1-piperidinyl)hexyloxy]benzoyl)-4-piperidinyl}-3,4-dihydrocarbostyril dioxalate 266. 1-{1-(4-[6-(N-(2-(2-Pyridyl)ethyl)-N-methylamino)hexyloxy]benzoyl)-4-piperidinyl}-3,4-dihydrocarbostyril 267. 1-{1-(4-[6-(N-(2-Methoxy-3,4,5-trihydroxytetrahydropyran-2-yl)methylamino)hexyloxy]benzoyl)-4-piperidinyl}-3,4-dihydrocarbostyril 268. 1-{1-(4-[7-(Diethylamino)heptyloxy]benzoyl)-4-piperidinyl}-3,4-dihydrocarbostyril 269. 1-{1-(4-[5-(4-Benzyl-1-piperazinylcarbonyl)pentyloxy]benzoyl)-4-piperidinyl}-3,4-dihydrocarbostyril 270. 1-{1-(4-[5-(1-Piperazinylcarbonyl)pentyloxy]benzoyl)-4-piperidinyl}-3,4-dihydrocarbostyril 271. 1-{1-(4-[5-(4-Acetyl-1-piperazinylcarbonyl)pentyloxy]benzoyl)-4-piperidinyl}-3,4-dihydrocarbostyril 272. 1-{1-(4-[5-(4-Methyl-1-piperazinylcarbonyl)pentyloxy]benzoyl)-4-piperidinyl}-3,4-dihydrocarbostyril 273. 1-{1-(4-[5-(4-Allyl-1-piperazinylcarbonyl)pentyloxy]benzoyl)-4-piperidinyl}-3,4-dihydrocarbostyril 274. 1-{1-(4-[5-(4-Carboxy-1-piperidinylcabonyl)pentyloxy]benzoyl)-4-piperidinyl}-3,4-dihydrocarbostyril 275. 1-{1-(4-[5-(4-Carbamoyl-1-piperidinylcarbonyl)pentyloxy]benzoyl)-4-piperidinyl}-3,4-dihydrocarbostyril 276. 1-{1-(4-[5-(4-Dimethylaminocarbonyl-1-piperidinylcarbonyl)pentyloxy]benzoyl)-4-piperidinyl}-3,4-dihydrocarbostyril 277. 1-{1-[4-(8-Acetylaminooctyloxy)benzoyl]-4-piperidinyl}-3,4-dihydrocarbostyril 278. 1-{1-(4-[5-(1-Methyl-2-imidazolylthio)pentyloxy]benzoyl)-4-piperidinyl}-3,4-dihydrocarbostyril 279. 1-{1-(4-[5-(2-Pyrimidylthio)pentyloxy]benzoyl)-4-piperidinyl}-3,4-dihydrocarbostyril 280. 1-{1-(4-[5-(2-Pyrimidylsufinyl)pentyloxy]benzoyl)-4-piperidinyl}-3,4-dihydrocarbostyril 281. 1-{1-(4-[5-(2-Pyrimidylsulfonyl)pentyloxy]benzoyl)-4-piperidinyl}-3,4-dihydrocarbostyril 282. 1-{1-(4-[5-(1-Methyl-2-imidazolylsulfonyl)pentyloxy)benzoyl)-4-piperidinyl}-3,4-dihydrocarbostyril 283. 1-{1-(4-[5-(4-Pyridylthio)pentyloxy]benzoyl)-4-piperidinyl}-3,4-dihydrocarbostyril 284. 1-{1-(4-[5-(4-Aminophenylthio)pentyloxy]benzoyl)-4-piperidinyl}-3,4-dihydrocarbostyril 285. 1-{1-(4-[5-(4-Nitrophenylsulfonyl)pentyloxy]benzoyl)-4-piperidinyl}-3,4-dihydrocarbostyril 286. 1-{1-(4-[5-(4-Aminophenylsulfonyl)pentyloxy]benzoyl)-4-piperidinyl}-3,4-dihydrocarbostyril 287. 1-{1-(4-[5-(2-Pyridylsulfonyl)pentyloxy]benzoyl)-4-piperidinyl}-3,4-dihydrocarbostyril 288. 1-{1-(4-[5-(Pyridine-N-oxide-4-ylsulfonyl)pentyloxy]benzoyl)-4-piperidinyl}-3,4-dihydrocarbostyril 289. 1-{1-(4-[5-(4-Acetylaminophenylsulfonyl)pentyloxy]benzoyl)-4-piperidinyl}-3,4-dihydrocarbostyril 290. 1-{1-(4-[5-(4-Dimethylaminophenylsulfonyl)pentyloxy]benzoyl)-4-piperidinyl}-3,4-dihydrocarbostyril 291. 1-{1-(4-[2,4-Di(5-(1-pyrrolidinyl)pentyloxy]benzoyl)-4-piperidinyl}-3,4-dihydrocarbostyril 292. 1-{1-[2,4-Di(5-diethylaminopentyloxy]benzoyl)-4-piperidinyl}-3,4-dihydrocarbostyril 293. 1-{1-[2-Methoxy-4-(4-thiomorpholinocarbonylbutyloxy)benzoyl]-4-piperidinyl}-3,4-dihydrocarbostyril 294. 1-{1-[2-Methoxy-4-(4-carbamoylbutoxy)benzoyl]-4-piperidinyl}-3,4-dihydrocarbostyril 295. 1-{1-(2-Methoxy-4-[4-(4-oxothiomorpholino)carbonylbutyloxy)benzoyl]-4-piperidinyl}-3,4-dihydrocarbostyril 296. 1-{1-(2-Methoxy-4-[4-(4,4-dioxothiomorpholino)carbonylbutyloxy]benzoyl]-4-piperidinyl}-3,4-dihydrocarbostyril 297. 1-{1-[4-(5,6-Dihydroxyhexyloxy)benzoyl]-piperidinyl}-3,4-dihydrocarbostyril 298. 1-{1-(4-[5-Hydroxy-6-(3-methoxybenzylamino)hexyloxy]benzoyl)-4-piperidinyl}-3,4-dihydrocarbostyril 299. 1-{1-(4-[5-Hydroxy-6-(3,4-dimethoxybenzylamino)hexyloxy]benzoyl)-4-piperidinyl}-3,4-dihydrocarbostyril oxalate 300. 1-{1-(4-[5-Hydroxy-6-(N-methyl-N-(2-(2-pyridyl)ethyl)amino)hexyloxy]benzoyl)-4-piperidinyl}-3,4-dihydrocarbostyril 301. 1-{1-[4-(5-Methoxy-6-diethylmethylammoniumhexyloxy)benzoyl]-4-piperidinyl}-3,4-dihydrocarbostyril iodine 302. 1-{1-[4-(5-Hydroxy-6-(2-(S)-carbamoyl-1-pyrrolidinylhexyloxy)benzoyl]-4-piperidinyl}-3,4-dihydrocarbostyril 303. 1-{1-[4-(5-Hydroxy-6-(1-piperidinyl)hexyloxy)benzoyl]-4-piperidinyl}-3,4-dihydrocarbostyril 304. 1-{1-(4-[5-Hydroxy-6-(4-benzyl-1-piperidinyl)hexyloxy]benzoyl]-piperidinyl}-3,4-dihydrocarbostyril 305. 1-{1-[4-(5-Acetoxy-6-diethylaminohexyloxy)benzoyl]-4-piperidinyl}-3,4-dihydrocarbostyril 306. 5-Fluoro-1-[1-(2-methoxy-4-ethoxybenzoyl)-4-piperidinyl}-3,4-dihydrocarbostyril 307. 5-Methyl-1-{1-[4-(6-diethylaminohexyloxy)benzoyl]-4-piperidinyl}-3,4-dihydrocarbostyril 308. 5-Hydroxy-1-[1-(2-methoxy-4-ethoxybenzoyl)-4-piperidinyl}-3,4-dihydrocarbostyril 309. 5-Acetoxy-1-[1-(2-Methoxy-4-ethoxybenzoyl)-4-piperidinyl}-3,4-dihydrocarbostyril 310. 1-{1-(4-[5-(2-Methanesulfonylaminoacetylamino)pentyloxy]benzoyl)-4-piperidinyl}-3,4-dihydrocarbostyril 311. 7-Fluoro-1-[1-(2,4-dimethoxybenzoyl)-4-piperidinyl}-3,4-dihydrocarbostyril 312. 1-{1-[4-(5-Acetylaminopentyloxy)benzoyl]-4-piperidinyl}-3,4-dihydrocarbostyril 313. 1-{1-[4-(4-Acetylaminobutoxy)benzoyl]-4-piperidinyl}-3,4-dihydrocarbostyril

TABLE 14

| Test Comp. No. | IC$_{50}$ (μM) |
|---|---|
| 1 | 0.4 |
| 2 | 0.5 |
| 3 | 0.33 |
| 4 | 0.24 |
| 5 | 0.49 |
| 6 | 0.47 |
| 7 | 0.31 |
| 8 | 0.3 |
| 9 | 0.35 |
| 10 | 0.32 |
| 11 | 0.30 |
| 12 | 0.23 |

TABLE 14-continued

| Test Comp. No. | IC$_{50}$ ($\mu$M) |
|---|---|
| 13 | 0.28 |
| 14 | 0.16 |
| 15 | 0.26 |
| 16 | 0.15 |
| 17 | 0.43 |
| 18 | 0.27 |
| 19 | 0.5 |
| 20 | 0.44 |
| 21 | 0.36 |
| 22 | 0.34 |
| 23 | 0.24 |
| 24 | 0.33 |
| 25 | 0.24 |
| 26 | 0.25 |
| 27 | 0.27 |
| 28 | 0.16 |
| 29 | 0.28 |
| 30 | 0.33 |
| 31 | 0.25 |
| 32 | 0.46 |
| 33 | 0.45 |
| 34 | 0.25 |
| 35 | 0.15 |
| 36 | 0.37 |
| 37 | 0.36 |
| 38 | 0.27 |
| 39 | 0.15 |
| 40 | 0.5 |
| 41 | 0.2 |
| 42 | 0.3 |
| 43 | 0.4 |
| 44 | 0.3 |
| 45 | 0.2 |
| 46 | 0.5 |
| 47 | 0.1 |
| 48 | 0.4 |
| 49 | 0.2 |
| 50 | 0.4 |
| 51 | 0.49 |
| 52 | 0.08 |
| 53 | 0.08 |
| 54 | 0.27 |
| 55 | 0.2 |
| 56 | 0.33 |
| 57 | 0.27 |
| 58 | 0.45 |
| 59 | 0.2 |
| 60 | 0.2 |
| 61 | 0.3 |
| 62 | 0.15 |
| 63 | 0.27 |
| 64 | 0.46 |
| 65 | 0.27 |
| 66 | 0.41 |
| 67 | 0.47 |
| 68 | 0.36 |
| 69 | 0.42 |
| 70 | 0.32 |
| 71 | 0.5 |
| 72 | 0.48 |
| 73 | 0.2 |
| 74 | 0.18 |
| 75 | 0.5 |
| 76 | 0.3 |
| 77 | 0.35 |
| 78 | 0.4 |
| 79 | 0.5 |
| 80 | 0.08 |
| 81 | 0.21 |
| 82 | 0.33 |
| 83 | 0.5 |
| 84 | 7.1 |
| 85 | 3 |
| 86 | 0.57 |
| 87 | 0.53 |
| 88 | 1.0 |
| 89 | 1.6 |
| 90 | 1.1 |
| 91 | 0.72 |
| 92 | 1.2 |
| 93 | 0.64 |
| 94 | 0.63 |
| 95 | 0.96 |
| 96 | 0.6 |
| 97 | 1.1 |
| 98 | 0.77 |
| 99 | 0.96 |
| 100 | 0.9 |
| 101 | 1.6 |
| 102 | 1.1 |
| 103 | 0.7 |
| 104 | 1.0 |
| 105 | 1.2 |
| 106 | 0.7 |
| 107 | 0.75 |
| 108 | 1.4 |
| 109 | 0.75 |
| 110 | 1.3 |
| 111 | 0.73 |
| 112 | 0.97 |
| 113 | 0.98 |
| 114 | 1.5 |
| 115 | 0.7 |
| 116 | 0.76 |
| 117 | 1.5 |
| 118 | 0.26 |
| 119 | 1.4 |
| 120 | 0.2 |
| 121 | 0.46 |
| 122 | 0.71 |
| 123 | 0.35 |
| 124 | 0.32 |
| 125 | 0.59 |
| 126 | 0.36 |
| 127 | 0.61 |
| 128 | 0.23 |
| 129 | 0.18 |
| 130 | 0.39 |
| 131 | 0.066 |
| 132 | 0.16 |
| 133 | 0.33 |
| 134 | 0.16 |
| 135 | 0.2 |
| 136 | 0.18 |
| 137 | 0.12 |
| 138 | 0.24 |
| 139 | 0.051 |
| 140 | 0.1 |
| 141 | 0.12 |
| 142 | 0.1 |
| 143 | 0.55 |
| 144 | 0.022 |
| 145 | 0.17 |
| 146 | 0.073 |
| 147 | 0.098 |
| 148 | 0.36 |
| 149 | 0.15 |
| 150 | 0.096 |
| 151 | 0.16 |
| 152 | 1.6 |
| 153 | 0.084 |
| 154 | 0.2 |
| 155 | 0.057 |
| 156 | 0.18 |
| 157 | 0.09 |
| 158 | 0.10 |
| 159 | 0.098 |
| 160 | 0.22 |
| 161 | 0.45 |
| 162 | 0.11 |
| 163 | 0.075 |
| 164 | 0.78 |
| 165 | 0.54 |
| 166 | 0.044 |
| 167 | 0.28 |
| 168 | 0.19 |
| 169 | 0.17 |
| 170 | 0.039 |

TABLE 14-continued

| Test Comp. No. | IC$_{50}$ ($\mu$M) |
|---|---|
| 171 | 0.24 |
| 172 | 0.043 |
| 173 | 0.039 |
| 174 | 0.49 |
| 175 | 0.32 |
| 176 | 0.13 |
| 177 | 0.13 |
| 178 | 0.045 |
| 179 | 0.25 |
| 180 | 0.40 |
| 181 | 0.23 |
| 182 | 0.12 |
| 183 | 0.24 |
| 184 | 0.039 |
| 185 | 0.01 |
| 186 | 0.063 |
| 187 | 0.040 |
| 188 | 0.068 |
| 189 | 0.13 |
| 190 | 0.033 |
| 191 | 0.034 |
| 192 | 0.061 |
| 193 | 0.12 |
| 194 | 0.35 |
| 195 | 0.19 |
| 196 | 0.17 |
| 197 | 0.035 |
| 198 | 0.32 |
| 199 | 0.055 |
| 200 | 0.034 |
| 201 | 0.008 |
| 202 | 0.027 |
| 203 | 0.049 |
| 204 | 0.059 |
| 205 | 0.12 |
| 206 | 0.03 |
| 207 | 0.07 |
| 208 | 0.10 |
| 209 | 0.25 |
| 210 | 0.023 |
| 211 | 0.25 |
| 212 | 0.16 |
| 213 | 0.059 |
| 214 | 0.058 |
| 215 | 0.17 |
| 216 | 0.041 |
| 217 | 0.053 |
| 218 | 0.044 |
| 219 | 0.060 |
| 220 | 0.020 |
| 221 | 0.25 |
| 222 | 0.65 |
| 223 | 0.072 |
| 224 | 0.094 |
| 225 | 0.099 |
| 226 | 0.48 |
| 227 | 0.13 |
| 228 | 0.20 |
| 229 | 0.20 |
| 230 | 0.18 |
| 231 | 0.041 |
| 232 | 0.12 |
| 233 | 0.21 |
| 234 | 0.18 |
| 235 | 0.066 |
| 236 | 0.26 |
| 237 | 0.075 |
| 238 | 0.033 |
| 239 | 0.15 |
| 240 | 0.048 |
| 241 | 0.021 |
| 242 | 0.059 |
| 243 | 0.039 |
| 244 | 0.034 |
| 245 | 0.054 |
| 246 | 0.29 |
| 247 | 0.17 |
| 248 | 0.034 |
| 249 | 0.045 |
| 250 | 0.32 |
| 251 | 0.098 |
| 252 | 0.086 |
| 253 | 0.18 |
| 254 | 0.060 |
| 255 | 0.38 |
| 256 | 0.19 |
| 257 | 0.20 |
| 258 | 0.47 |
| 259 | 0.11 |
| 260 | 0.15 |
| 261 | 0.12 |
| 262 | 0.093 |
| 263 | 0.36 |
| 264 | 0.16 |
| 265 | 0.019 |
| 266 | 0.035 |
| 267 | 0.082 |
| 268 | 0.027 |
| 269 | 0.16 |
| 270 | 0.044 |
| 271 | 0.042 |
| 272 | 0.038 |
| 273 | 0.057 |
| 274 | 0.49 |
| 275 | 0.046 |
| 276 | 0.11 |
| 277 | 0.30 |
| 278 | 0.11 |
| 279 | 0.18 |
| 280 | 0.087 |
| 281 | 0.054 |
| 282 | 0.075 |
| 283 | 0.61 |
| 284 | 0.40 |
| 285 | 0.23 |
| 286 | 0.15 |
| 287 | 0.10 |
| 288 | 0.048 |
| 289 | 0.10 |
| 290 | 0.30 |
| 291 | 0.098 |
| 292 | 0.077 |
| 293 | 0.22 |
| 294 | 0.17 |
| 295 | 0.077 |
| 296 | 0.073 |
| 297 | 0.52 |
| 298 | 0.065 |
| 299 | 0.065 |
| 300 | 0.034 |
| 301 | 0.047 |
| 302 | 0.088 |
| 303 | 0.038 |
| 304 | 0.037 |
| 305 | 0.065 |
| 306 | 0.084 |
| 307 | 0.023 |
| 308 | 0.095 |
| 309 | 0.073 |
| 310 | 0.16 |

Experiment 2: Anti-vasopressor activity in vivo

The spinal cord of male SD rat (weighing 300–400 g) is broken to give a pith rat. The blood pressure of the pith rat is measured through the cannula inserted into the femoral artery thereof by using a pressure transducer. The test compound and Arg-vasopressin are administered to the pith rat through the cannula inserted into the femoral vein. Anti-vasopressor activity of the test compound in vivo is determined according to the following equation.

$$\text{Anti-vasopressor activity } (\%) = \frac{P}{P_0} \times 100$$

$P_0$: The increase of diastolic pressure when Arg-vasopressin (30 mU/kg) is administered intravenously.

P: The increase of diastolic pressure when Arg-vasopressin (30 mU/kg) is administered intravenouly 3 minutes after the intravenous administration of the test compound.

The results are expressed as $ED_{50}$ value, which is the dose of the test compound required to reduce the increase of diastolic pressure caused by the intravenous administration of Arg-vasopressin (30 mU/kg) to 50% of its control value: $P^0$.

The results are shown in the following Table 15.

TABLE 15

| Test Comp. No. | $ED_{50}$ (mg/kg) |
| --- | --- |
| 2 | 1.0 |
| 20 | 0.2 |
| 40 | 0.8 |
| 41 | 0.5 |
| 47 | 0.4 |
| 311 | 0.3 |
| 312 | 0.8 |
| 313 | 0.3 |

What is claimed is:

1. A carbostyril derivative of the following formula:

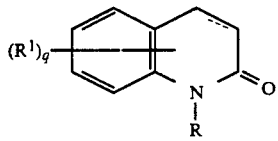
(1)

wherein $R^1$ is hydrogen; nitro; a lower alkoxy; a lower alkoxycarbonyl; a lower alkyl; a halogen; an amino having optionally one or two substituents selected from a lower alkanoyl, a lower alkyl, benzoyl and a phenyl(lower)alkoxycarbonyl; hydroxy; cyano; carboxyl; a lower alkanoyloxy; or a hydrazinocarbonyl, q is an integer of 1 to 3 and q is 1 when $R^1$ is hydrogen and R is a group of the formula:

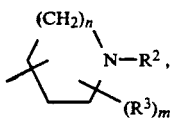

wherein $R^2$ is hydrogen; a lower alkoxycarbonyl; phenoxycarbonyl which phenyl ring may optionally be substituted by one to three substituents selected from nitro and an amino having optionally one or two substituents selected from a lower alkanoyl, a lower alkyl and benzoyl; a phenyl(lower)alkenylcarbonyl; a phenyl(lower)alkanoyl which lower alkanoyl moiety may optionally be substituted by an amino having optionally a lower alkoxycarbonyl substituent; an alkanoyl; an alkenylcarbonyl; a phenylsulfonyl which phenyl ring may optionally be substituted by a lower alkoxy; a group of the formula:

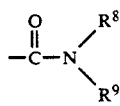

wherein $R^8$ and $R^9$ are the same or different and are each hydrogen; a phenyl which may optionally have one to three substituents selected from a lower alkoxy, a lower alkyl, a halogen, an amino having optionally one or two substituents selected from a lower alkyl and a lower alkanoyl, and nitro; a heterocyclic group-substituted carbonyl with the heterocyclic group being selected from pyrrolidinyl, piperidinyl, piperazinyl morpholino, imidazolyl, thiazolyl, thiomorpholino, pyrrolyl, oxazolyl, pyridyl, tetrahydrofuryl, thienyl, furoyl, pyridazyl, pyrimidyl, pyradyl, quinolyl, indolyl, isoquinolyl, cinnolyl, quinoxalyl, phthalazyl, quinazolyl, benzo(b)furanyl and benzo(b)thiophenyl, which heterocyclic group may optionally have one to three substituents selected from a phenyl(lower)alkoxycarbonyl, a phenyl(lower)alkoxy, oxo, a lower alkyl, and a lower alkylenedioxy; a group of the formula:

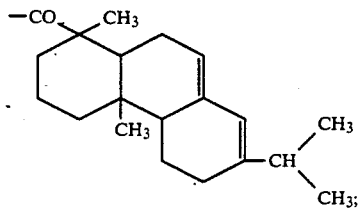

naphthylcarbonyl; thienyl(lower)alkanoyl; tricyclo(3.3.1.1)-decanyl(lower)alkanoyl; tricyclo(3.3.1.1)decanylcarbonyl; or a group of the formula:

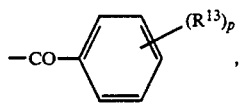

wherein p is 0 or an integer of 1 to 3, and $R^{13}$ is hydroxy; an alkoxy; an alkoxy which has one or two substituents selected from hydroxy, a lower alkanoyloxy, a tri(-lower)alkylammonium, a lower alkoxy, and a group of the formula:

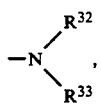

wherein $R^{32}$ and $R^{33}$ are the same or different and are each hydrogen, a lower alkyl, a hydroxy-substituted lower alkyl, a lower alkanoyl, a tetrahydropyranyl(lower)alkyl, a phenyl, a phenyl(lower)alkyl, wherein the alkyl moiety may optionally be substituted by hydroxy and the phenyl ring may optionally be substituted by a lower alkoxy, or a pyridyl(lower)alkyl; or $R^{32}$ and $R^{33}$ may bind with the nitrogen to which they bond to form a 5- or 6-membered, saturated heterocyclic group selected from pyrrolidinyl, piperidinyl, piperazinyl, morpholino, thiomorpholino, and a salt thereof, wherein the heterocyclic group may optionally be substituted by a member selected from a carbamoyl, a lower alkyl, a penyl(lower)alkyl, phenyl and a hydroxy-substituted lower alkyl; a carboxyl-substituted alkoxy; a halogen-substituted lower alkoxy; a lower alkoxycarbonyl-substituted alkoxy; a lower alkanoyloxy-substituted lower alkoxy; a lower alkenyloxy-substituted lower alkoxy; a lower alkoxy(lower)alkoxy; a lower alkylsulfonyloxy-substituted lower alkoxy; a benzoyloxy-substituted lower alkoxy; tricyclo(3.3.1.1)decanyl-substituted lower alkoxy; a lower alkoxy(lower)alkoxy which is substituted by one or two substituents selected from hydroxy and an amino being optionally substituted by a lower alkyl; a morpholinyl-substituted lower alkoxy which may optionally be substituted by a lower alkyl or oxo; a benzimidazolylthio-substituted lower alkoxy; a benzimidazolyl-sulfinyl-substituted lower alkoxy; a group of the formula:

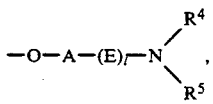

wherein A is an alkylene, I is an integer of 0 or 1, E is —CO— or —OCO—, $R^4$ and $R^5$ are the same or different and are each hydrogen; a lower alkyl which may optionally be substituted by hydroxy cyano; a lower alkenyl; a lower alkynyl; a phenyl(lower)alkyl; a lower alkanoyl which may optionally have one to three halogen substituents; benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower)alkoxycarbonyl substituent; an amido having optionally a lower alkyl substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, phenyl having optionally hydroxy, carbamoyl, imidazolyl or a lower alkylthio substituent, and the amino group may optionally have a substituent selected from a lower alkyl having optionally hydroxy, a lower alkenyl, a phenyl(lower)alkyl having optionally a lower alkoxy substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by a lower alkyl nitro or an amino having optionally one or two substituents selected from a lower alkyl and a lower alkanoyl; an amido-substituted lower alkyl wherein the lower alkyl moiety may have optionally a substituent selected from a phenyl having optionally hydroxy, imidazolyl, carbamoyl or a lower alkylthio substituent, and the amido group may optionally have a lower alkyl substituent; an amino-substituted lower alkyl which may be optionally substituted by a lower alkyl or a lower alkanoyl; anilinocarbonyl; piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyrant-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholinyl, wherein the heterocyclic group has optionally a substituent selected from a lower alkyl and phenyl; a piperidinyl-substituted carbonyl which may optionally be substituted by a lower alkanoyl; a lower alkanoyloxy(lower)alkyl; a pyridyl-substituted lower alkyl; or an amino acid residue which can form an amido group with the amino group thereof, or $R^4$ and $R^5$ may bind together with the nitrogen to which they are bound to form a 5- or 6-membered saturated or unsaturated heterocyclic group selected from pyrrolidinyl, piperidinyl, piperazinyl, morpholino, thiomorpholino, pyrrolyl, pyrazolyl, imidazolyl, imidazolidinyl, 1,2,4-triazolyl, 1,2,3,4-tetrazolyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl and a salt thereof wherein the heterocyclic group may optionally be substituted by a member selected from phenyl having optionally a substituent selected from a lower alkoxy, a halogen, oxo, hydroxy, a lower alkenyl, carboxyl, a phenyl(lower)alkyl having optionally hydroxy on the lower alkyl moiety, a lower alkanoyl, a lower alkyl having optionally hydroxy as a substituent, benzoyl, an amido having optionally a lower alkyl substituent, anilinocarbonyl, a benzoyl(lower)alkyl, a lower alkylsulfonyl, pyrimidinyl, pyridyl, and a lower alkoxycarbonyl; a carbamoyloxysubstituted lower alkoxy, a lower alkylthio-substituted lower alkoxy; a lower alkylsulfonyl-substituted a lower alkoxy; a lower alkylsulfinyl-substituted lower alkoxy; an alkenyloxy; phenoxy; a lower alkanoyloxy; a lower alkylsulfonyloxy; a lower alkynyloxy; a phenyl(lower)alkoxy; a cycloalkyl; a cycloalkyloxy;acycloalkenyloxy; imidazo(4,5-c)pyridyl-carbonyl(lower)alkoxy; a group of the formula:

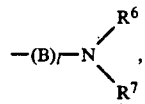

wherein I is as defined above, B is a lower alkylene or a —CO— group, and $R^6$ and $R^7$ are the same or different and are each hydrogen, a lower alkyl, a lower alkanoyl having optionally one to three halogens as substituents, a carboxyl(lower)alkyl, a lower alkoxycarbonyl, a lower alkoxycarbonyl(lower)alkyl, a lower alkenyl, an amido-substituted lower alkyl having optionally a lower alkyl as a substituent, or a phenyl(lower)alkoxycarbonyl; or $R^6$ and $R^7$ may bind together with the nitrogen to which they are bound to form a 5- or 6-membered, saturated or unsaturated, heterocyclic group selected from pyrrolidinyl, piperidinyl, piperazinyl, morpholino, thiomorpholino, pyrrolyl, pyrazolyl, imidazolyl, imidazolidinyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl, and a salt thereof wherein the heterocyclic group may optionally have a substituent selected from a lower alkoxycarbonyl, a lower alkyl, a lower alkylthio, or oxo; nitro; a halogen; a lower alkylsulfonyl; a lower alkyl which may optionally have one to three substituents selected from a halogen, hydroxy, phenyl and a lower alkoxy; a cyano-substituted lower alkoxy; an oxilanyl-substituted lower alkoxy; a phthalimido-substituted alkoxy; an amidino-substituted lower alkoxy; a pyrrolyl-substituted lower alkoxy; cyano; a lower alkoxycarbonyl; amidino; carbamoyl; carboxyl; a lower alkanoyl; benzoyl; a lower alkoxycarbonyl(lower)alkyl; a carboxyl(lower)alkyl; a lower alkoxy(lower)alkyl; a lower alkanoyloxy(lower)alkyl; a hydroxyimino-substituted lower alkyl; phenyl; a lower alkylthio; a lower alkylsulfinyl; a lower alkenyl having optionally hydroxy as a substituent; a lower alkylenedioxy, a lower alkylsilyl; a pyrimidylthio-substituted lower alkoxy; a pyrimidylsulfinyl-substituted lower alkoxy; a pyrmidylsufonyl-substituted lower alkoxy; an imidazolylthio-substituted lower alkoxy which may optionally have a lower alkyl as a substituent; an imidazolylsulfonyl-substituted lower alkoxy which may optionally have a lower alkyl as a substituent; an ammonium-lower alkoxy having three substituents selected from a lower alkoxy, a lower alkenyl and oxo; a phenylthio-substituted lower alkoxy which phenyl ring may optionally have a substituent selected from nitro and an amino; a phenylsulfonyl-substituted lower alkoxy which phenyl ring may optionally have a substituent selected from nitro and an amino having optionally one or two substituents selected from a lower alkanoyl and a lower alkyl; a pyridylthio-substituted lower alkoxy; or a pyridylsulfonyl-substituted lower alkoxy which pyridyl ring may optionally be substituted by oxo; n is an integer of 1 or 2; m is 0 or an integer of 1 to 3; $R^3$ is a lower alkyl; and the bond between the 3-position and the 4-position of the carbostyril ring is a single bond or double bond, or a salt thereof.

2. The compound according to claim 1, wherein $R^2$ is a group of the formula:

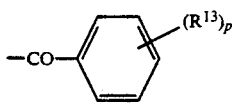

and wherein $R^{13}$ and p are as defined in claim 68, or a salt thereof.

3. The compound according to claim 1, wherein $R^2$ is hydrogen; a lower alkoxycarbonyl; a phenoxycarbonyl which phenyl ring may optionally be substituted by one to three substituents selected from nitro and an amino having optionally one or two substituents selected from a lower alkanoyl, a lower alkyl and benzoyl; a phenyl(lower)alkenyl-carbonyl; a phenyl(lower)alkanoyl which lower alkanoyl moiety may optionally be substituted by an amino having optionally a lower alkoxycarbonyl as a substituent; an alkanoyl; an alkenylcarbonyl; a phenylsulfonyl which phenyl ring may optionally be substituted by a lower alkoxy; a group of the formula:

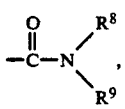

wherein $R^8$ and $R^9$ are the same or different and are each hydrogen or a phenyl which may optionally have one to three substituents selected from a lower alkoxy, a lower alkyl, a halogen, an amino having optionally one or two substituents selected from a lower alkyl and a lower alkanoyl, and nitro; a heterocyclic group-substituted carbonyl which heterocyclic group may optionally have one to three substituents selected from a phenyl(lower)alkoxycarbonyl, a phenyl(lower)alkoxy, oxo, a lower alkyl, and a lower alkylenedioxy; a group of the formula:

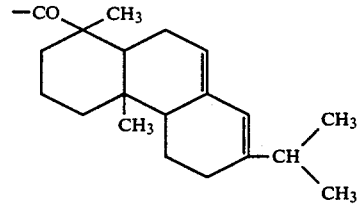

naphthylcarbonyl; thienyl(lower)alkanoyl; tricyclo(3.3.1.1)-decanyl(lower)alkanoyl; or tricyclo(3.3.1.1-)dencantylcarbonyl, or a salt thereof.

4. The compound according to claim 2, wherein $R^{13}$ is a group of the formula:

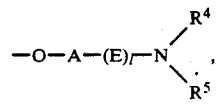

wherein A, E, I, $R^4$ and $R^5$ are as defined in claim 69, and p is an integer of 1 to 3, and a salt thereof.

5. The compound according to claim 2, wherein $R^{13}$ is an alkoxy which has one or two substituents selected from hydroxy, a lower alkanoyloxy, a tri(lower)alkylammonium, a lower alkoxy, and a group of the formula:

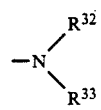

wherein $R^{32}$ and $R^{33}$ are the same or different and are each hydrogen, a lower alkyl, a hydroxy-substituted lower alkyl, a lower alkanoyl, a tetrahydropyranyl(lower)alkyl, phenyl, a phenyl(lower)alkyl, wherein the alkyl moiety may optionally be substituted by hydroxy and the phenyl ring may optionally be substituted by a lower alkoxy, or a pyridyl(lower)alkyl.

6. The compound according to claim 2, wherein $R^{13}$ is a carbamoyloxy-substituted lower alkoxy, and p is an integer of 1 to 3, or a salt thereof.

7. The compound according to claim 2, wherein $R^{13}$ is hydroxy; an alkoxy; a carboxyl-substituted alkoxy; a halogen-substituted lower alkoxy; a lower alkoxycarbonyl-substituted alkoxy; a lower alkanoyloxy-substituted lower alkoxy; a lower alkenyloxy-substituted lower alkoxy; a lower alkoxy(lower)alkoxy; a lower alkylsulfonyloxy-substituted lower alkoxy; a benzoyloxy-substituted lower alkoxy; tricyclo(3.3.1.1)decanyl-substituted lower alkoxy; a lower alkoxy(lower)alkoxy which is substituted by one or two substituents selected from hydroxy and an amino being optionally substituted by a lower alkyl; a morpholinyl-substituted lower alkoxy which may optionally be substituted by a lower alkyl or oxo; a benzimidazolylthio-substituted lower alkyl; a benzimidazolylsulfinyl-substituted lower alkoxy; a lower alkylthio-substituted lower alkoxy; a lower alkylsulfonyl-substituted lower alkoxy; a lower alkylsulfinyl-substituted lower alkoxy; an alkenyloxy; phenoxy; a lower alkanoyloxy; a lower alkylsulfonyloxy; a lower alkynyloxy; a phenyl(lower)alkoxy; a cycloalkyl; a cycloalkyloxy; a cycloalkenyloxy; imidazo-(4,5-c)pyridyl-carbonyl(lower) alkoxy; a group of the formula:

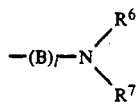

wherein I is as defined above, B is a lower alkylene or a group of —CO—, and $R^6$ and $R^7$ are the same or different and are each hydrogen, a lower alkyl, a lower alkanoyl having optionally one to three halogens as substituents, a carboxyl(lower)alkyl, a lower alkoxycarbonyl, a lower alkoxylcarbonyl(lower)alkyl, a lower alkenyl, an amido-substituted lower alkyl having optionally a lower alkyl as a substituent, or a phenyl(lower)alkoxycarbonyl, or $R^6$ and $R^7$ may bind together with the nitrogen to which they bond to form a 5- or 6-membered, saturated or unsaturated heterocyclic group selected from pyrrolidinyl, piperidinyl, piperazinyl, morpholino, thiomorpholino, pyrrolyl, pyrazolyl, imidazolyl, imidazolidinyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl, isothiazolinyl, isothiazolidinyl and a salt thereof, wherein the heterocyclic group may optionally have a substituent selected from a lower alkoxy-carbonyl, a lower alkyl, a lower alkylthio, or oxo; nitro; a halogen; a lower alkylsulfonyl; a lower alkyl which may optionally have one to three substituents selected from a halogen, hydroxy, phenyl and a lower alkoxy; a cyano-substituted lower alkoxy; an oxilanyl-substituted lower alkoxy; a phthalimido-substituted alkoxy; an amidino-substituted lower alkoxy, a pyrrolyl-substituted lower alkoxy; cyano; a lower alkoxycarbonyl; amidino; carbamoyl; carboxyl; a lower alkanoyl; benzoyl; a lower alkoxycarbonyl(lower)alkyl; a carboxyl(lower)alkyl; a lower alkoxy(lower)alkyl; a lower alkanoyloxy(lower)alkyl; hydroxyimino-substituted lower alkyl; phenyl; a lower alkylthio; a lower alkylsulfinyl; a lower alkenyl having optionally hydroxy as a substituent; a lower alkylenedioxy, a lower alkylsilyl; a pyrimidylthio-substituted lower alkoxy; a pyrimidylsulfinyl-substituted lower alkoxy; a pyrimidylsufonyl-substituted lower alkoxy; an imidazolylthio-substituted lower alkoxy which may optionally have a lower alkyl as a substituent; an imidazolylsulfonyl-substituted lower alkoxy which may optionally have a lower alkyl as a substituent; an ammonium-lower alkoxy having three substituents selected from a lower alkyl, a lower alkenyl and oxo; a phenylthio-substituted lower alkoxy which phenyl ring may optionally have a substituent selected from nitro and an amino; a phenylsulfonyl-substituted lower alkoxy which phenyl ring may optionally have a substituent selected from nitro and an amino having optionally one or two substituents selected from a lower alkanoyl and lower alkyl; a pyridylthio-substituted lower alkoxy; or a pyridylsufonyl-substituted lower alkoxy which pyridyl ring may optionally be substituted by oxo, or a salt thereof.

8. The compound according to claim 4, wherein I is 1, or a salt thereof.

9. The compound according to claim 4, wherein I is 0, and $R^4$ and $R^5$ are the same or different and are each hydrogen; a lower alkyl which may optionally be substituted by hydroxy or cyano; a lower alkenyl; a lower alkynyl; a phenyl(lower)alkyl; a lower alkanoyl which may optionally have one to three halogens as substituents; benzoyl which phenyl ring may optionally be substituted by a member selected from nitro and an amino having optionally one or two substituents selected from a lower alkyl, a lower alkanoyl and a phenyl(lower)alkoxycarbonyl; phenyl; a lower alkoxycarbonyl; a lower alkoxycarbonyl(lower)alkyl wherein the lower alkyl moiety may optionally be substituted by hydroxy or an amino having optionally a phenyl(lower)alkoxycarbonyl as a substituent; an amido having optionally a lower alkyl as a substituent; a pyrrolidinyl-substituted carbonyl which pyrrolidinyl ring may optionally be substituted by a phenyl(lower)alkoxycarbonyl; an amino-substituted lower alkanoyl wherein the lower alkanoyl moiety may optionally be substituted by a member selected from phenyl(lower)alkoxycarbonylamino, hydroxy, phenyl having optionally hydroxy as a substituent, carbamoyl, imidazolyl or a lower alkylthio, and the amino group may optionally have a substituent selected from a lower alkyl having optionally hydroxy as a substituent, a lower alkenyl, a phenyl(lower)alkyl having optionally a lower alkoxy as a substituent on the phenyl ring, a lower alkylsulfonyl, a lower alkanoyl, or a phenyl(lower)alkoxycarbonyl; a hydroxy-substituted lower alkanoyl; a lower alkanoyloxy(lower)alkanoyl; a lower alkylsulfonyl; a phenylsulfonyl which phenyl ring may optionally be substituted by a lower alkyl, nitro or an amino having optionally one or two substituents selected from a lower alkyl and a lower alkanoyl; an amido-substituted lower alkyl wherein the lower alkyl moiety may have optionally a substituent selected from phenyl having optionally hydroxy, imidazolyl, carbamoyl or a lower alkylthio substituent, and the amido group may optionally have a lower alkyl as a substituent; an amino-substituted lower alkyl which may optionally be substituted by a lower alkyl or a lower alkanoyl; anilinocarbonyl; a piperidinyl which may optionally be substituted by a phenyl(lower)alkyl; a cycloalkyl, a cycloalkenylcarbonyl; a cycloalkylcarbonyl which may optionally have one to three substituents selected from hydroxy and a lower alkanoyloxy; a tetrahydropyranyl-substituted lower alkyl wherein the tetrahydropyranyl ring may optionally have one to four substituents selected from hydroxy and a lower alkoxy; a lower alkanoyl which is substituted by a 5- or 6-membered saturated heterocyclic group selected from pyrrolidinyl, piperazinyl, piperidinyl and morpholinyl wherein the heterocyclic group may have optionally a substituent selected from a lower alkyl and a phenyl; a piperidinyl-substituted carbonyl which may optionally be substituted by a lower alkanoyl; a lower alkanoyloxy(lower)alkyl; a pyridyl-substituted lower alkyl; or an amino acid residue which can form an amido group with an amino group thereof, or a salt thereof.

10. The compound according to claim 4, wherein l is 0, and $R^4$ and $R^5$ bind together with the nitrogen to which they bond to form a 5- or 6-membered, saturated or unsaturated heterocyclic group selected from pyrrolidinyl, piperidinyl, piperazinyl, morpholino, thiomorpholino, pyrrolyl, pyrazolyl, imidazolyl, imidazolidinyl, 1,2,4-triazolyl, 1,2,3,4-tetrazolyl, pyrrolinyl, imidazolinyl, pyrazolinyl, pyrazolidinyl, oxazolinyl, oxazolidinyl, isoxazolinyl, isoxazolidinyl, thiazolinyl, thiazolidinyl isothiazolinyl, isothiazolidinyl and a salt thereof,, wherein the heterocyclic group may optionally be substituted by a member selected from a phenyl having optionally a substituent selected from a lower alkoxy and a halogen, oxo, hydroxy, a lower alkenyl, carboxy, a phenyl(lower)alkyl having optionally a hydroxy as a substituent on the lower alkyl moiety, a lower alkanoyl, a lower alkyl having optionally hydroxy as a substituent, benzoyl, an amido having optionally a lower alkyl as a substituent, anilinocarbonyl, a benzoyl(lower)alkyl, a lower alkylsulfonyl, piperidinyl, pyrimidinyl, pyridyl, or a lower alkoxycarbonyl, or a salt thereof.

11. The compound according to claim 5, wherein $R^{32}$ and $R^{33}$ are the same or different and are each hydrogen, a lower alkyl, a hydroxy-substituted lower alkyl, a lower alkanoyl, a tetrahydropyranyl(lower)alkyl, phenyl, a phenyl(lower)alkyl wherein the alkyl moiety may optionally be substituted by hydroxy and the phenyl ring may optionally be substituted by a lower alkoxy, or a pyridyl(lower)alkyl, and a salt thereof.

12. The compound according to claim 9, wherein $R^4$ and $R^5$ are the same or different and are each hydrogen, or a lower alkanoyl which may optionally have one or three halogens as substituents or a salt thereof.

13. The compound according to claim 5, wherein the heterocyclic group to be formed is a 5- or 6-membered saturated heterocyclic group selected from pyrrolidinyl, piperidinyl, piperazinyl, morpholino, thiomorpholino, imidazolidinyl, pyrazolidinyl, oxazolidinyl, isoxazolidinyl, thiazolidinyl, and isothiazolidinyl, or a salt thereof.

14. The compound according to claim 5, wherein the heterocyclic group to be formed is a 5- to 6-membered unsaturated heterocyclic group selected from pyrrolyl, pyrazolyl, imidazolyl, 1,2,4-triazolyl, 1,2,3,4-tetrazolyl, pyrrolinyl, imidazolinyl, pyrazolinyl, oxazolinyl, isoxazolinyl, thiazolinyl, and isothiazolinyl, or a salt thereof.

15. The compound according to claim 11, wherein $R^{32}$ and $R^{33}$ are the same or different and are each hydrogen or a lower alkyl, or a salt thereof.

16. The compound according to claim 12, wherein $R^1$ is hydrogen and the bond between the 3- and 4-positions of the carbostyril nucleus is a single bond, or a salt thereof.

17. The compound according to claim 12, wherein $R^1$ is a halogen and the bond between the 3- and 4-positions of the carbostyril nucleus is a single bond, or a salt thereof.

18. The compound according to claim 12, wherein $R^1$ is nitro; a lower alkoxy; a lower alkoxycarbonyl; a lower alkyl; an amino having optionally one or two substituents selected from a lower alkanoyl, a lower alkyl, benzoyl and a phenyl(lower)alkoxycarbonyl; hydroxy; cyano; carboxy; a lower alkanoyloxy; or hydrazinocarbonyl, and the bond between the 3- and 4-positions of the carbostyril nucleus is a single bond, or a salt thereof.

19. The compound according to claim 13, wherein $R^1$ is hydrogen and the bond between the 3- and 4-positions of the carbostyril nucleus is a single bond, or a salt thereof.

20. The compound according to claim 13, wherein $R^1$ is a halogen and the bond between the 3- and 4-positions of the carbostyril nucleus is a single bond, or a salt thereof.

21. The compound according to claim 13, wherein $R^1$ is nitro; a lower alkoxy; a lower alkoxycarbonyl; a lower alkyl; an amino having optionally one or two substituents selected from a lower alkanoyl, a lower alkyl, benzoyl and a phenyl(lower)alkoxycarbonyl; hydroxy; cyano; carboxy; a lower alkanoyloxy; or hydrazinocarbonyl, and the bond between the 3- and 4-positions of the carbostyril nucleus is a single bond, or a salt thereof.

22. The compound according to claim 13, wherein the bond between the 3-and 4-positions of the carbostyril nucleus is a double bond, or a salt thereof.

23. The compound according to claim 15, wherein $R^1$ is hydrogen and the bond between the 3- and 4-positions of the carbostyril nucleus is a single bond, or a salt thereof.

24. The compound according to claim 15, wherein $R^1$ is a halogen and the bond between the 3- and 4-positions of the carbostyril nucleus is a single bond, or a salt thereof.

25. The compound according to claim 15, wherein $R^1$ is nitro; a lower alkoxy; a lower alkoxycarbonyl; a lower alkyl; an amino having optionally one or two substituents selected from a lower alkanoyl, a lower alkyl, benzoyl and a phenyl(lower)alkoxycarbonyl; hydroxy; cyano; carboxy; a lower alkanoyloxy; or hydrazinocarbonyl, and the bond between the 3- and 4-positions of the carbostyril nucleus is a single bond, or a salt thereof.

26. The compound according to claim 15, wherein the bond between the 3-and 4-positions of the carbostyril nucleus is a double bond, or a salt thereof.

27. The compound according to claim 6, wherein $R^1$ is hydrogen and the bond between the 3- and 4-positions of the carbostyril nucleus is a single bond, or a salt thereof.

28. The compound according to claim 6, wherein $R^1$ is a halogen and the bond between the 3- and 4-positions of the carbostyril nucleus is a single bond, or a salt thereof.

29. The compound according to claim 6, wherein $R^1$ is nitro; a lower alkoxy; a lower alkoxycarbonyl; a lower alkyl; an amino having optionally one or two substituents selected from a lower alkanoyl, a lower alkyl, a benzoyl and a phenyl(lower)alkoxycarbonyl; hydroxy; cyano; carboxy; a lower alkanoyloxy; or hydrazinocarbonyl, and the bond between the 3- and 4-positions of the carbostyril nucleus is a single bond, or a salt thereof.

30. The compound according to claim 6, wherein the bond between the 3-and 4-positions of the carbostyril nucleus is a double bond, or a salt thereof.

31. The compound according to claim 7, wherein $R^1$ is hydrogen and the bond between the 3- and 4-positions of the carbostyril nucleus is a single bond, or a salt thereof.

32. The compound according to claim 7, wherein $R^1$ is halogen and the bond between the 3- and 4-positions of the carbostyril nucleus is a single bond, or a salt thereof.

33. The compound according to claim 7, wherein $R^1$ is nitro; a lower alkoxy; a lower alkoxycarbonyl; a lower alkyl; an amino having optionally one or two substituents selected from a lower alkanoyl, a lower alkyl, benzoyl and a phenyl(lower)alkoxycarbonyl; hydroxy; cyano; carboxy; a lower alkanoyloxy; or hydrazinocarbonyl, and the bond between the 3- and 4-positions of the carbostyril nucleus is a single bond, or a salt thereof.

34. The compound according to claim 1, wherein the bond between the 3-and 4-positions of the carbostyril nucleus is a double bond, or a salt thereof.

35. The compound according to claim 2, wherein p is 1 and $R^{13}$ is substituted at the 4-position of the phenyl ring, or a salt thereof.

36. 1-{1-[4-(3-Acetylaminopropoxy)benzoyl]-4-piperidinyl}-3,4-dihydrocarbostyril.

37. 1-{1-[4-(4-Acetylaminobutoxy)benzoyl]-4-piperidinyl}-3,4-dihydrocarbostyril.

38. 1-{1-[4-(5-Acetylaminopentyloxy)benzoyl]-4-piperidinyl}3,4-dihydrocarbostyril.

39. 1-{1-[4-(3-Carbamoyloxypropoxy)benzoyl]-4-piperidinyl}-3,4-dihydrocarbostyril.

40. 7-Fluoro-1-{1-[4-(3-acetylaminopropoxy)-benzoyl]-4-piperidinyl}-3,4-dihydrocarbostyril.

41. 1-{1-(4-[5-(1-Pyrrolidinyl)pentyloxy]benzoyl)-4-piperidinyl}-3,4-dihydrocarbostyril.

42. 1-{1-[4-(6-Diethylamino-5-hydroxyhexyloxy)-benzoyl]-4-piperidinyl}-3,4-dihydrocarbostyril.

43. 1-{1-(4-[5-Hydroxy-6-(1-pyrrolidinyl)hexyloxy]-benzoyl)-4-piperidinyl}-3,4-dihydrocarbostyril.

44. 1-{1-[4-(5-Hydroxy-6-dimethylaminohexyloxy)-benzoyl]-4-piperidinyl}-3,4-dihydrocarbostyril.

45. 1-{1-[4-(4-Hydroxy-5-dimethylaminopentyloxy)-benzoyl]-4-piperidinyl}-3,4-dihydrocarbostyril.

46. 1-{1-[4-(7-Hydroxy-8-diethylaminooctyloxy)-benzoyl]4-piperidinyl}-3,4-dihydrocarbostyril.

47. 1-{1-[4-(5-Diethylaminopentyloxy)benzoyl]-4-piperidinyl}-3,4-dihydrocarbostyril.

48. The compound according to claim 5, wherein the heterocyclic group to be formed is a 5- or 6-membered, saturated heterocyclic group selected from pyrrolyinyl, piperidinyl, piperazinyl, morpholino, thiomorpholino or a salt thereof.

49. The compound according to claim 5, wherein $R^{32}$ and $R^{33}$ may bind with the nitrogen to which they bond to form a 5- or 6-membered, saturated heterocyclic group selected from pyrrolidinyl, piperidinyl, piperazinyl, morpholino, and thiomorpholino, and wherein the heterocyclic group may optionally be substituted by a member selected from a carbamoyl, a lower alkyl, a phenyl(lower)alkyl, phenyl and a hydroxy-substituted lower alkyl, or a salt thereof.

50. The compound according to claim 12, wherein the bond between the 3- and 4-positions of the carbostyril nucleus is a double bond, or a salt thereof.

51. The compound according to claim 49, wherein $R^1$ is a halogen and the bond between the 3- and 4-positions of the carbostyril nucleus is a single bond, or a salt thereof.

52. The compound according to claim 49, wherein $R^1$ is nitro; a lower alkoxy; a lower alkoxycarbonyl; a lower alkyl; an amino having optionally one or two substituents selected from a lower alkanoyl, a lower alkyl, benzoyl and a phenyl(lower)alkoxycarbonyl; hydroxy; cyano, carboxy; a lower alkanoyloxy; or hydrazinocarbonyl, and the bond between the 3- and 4-positions of the carbostyril nucleus is a single bond, or a salt thereof.

53. The compound according to claim 49, wherein the bond between the 3- and 4-positions of the carbostyril nucleus is a double bond, or a salt thereof.

54. The compound according to claim 49, wherein $R^1$ is hydrogen and the bond between the 3- and 4-positions of the carbostyril nucleus is a single bond, or a salt thereof.

55. A vasopressin antagonistic composition which comprises, as an active ingredient, a compound of the formula (1) as set forth in claim 1, or a pharmaceutically acceptable salt thereof in admixture with a pharmaceutically acceptable carrier or diluent. 999999

* * * * *